United States Patent
Lançois et al.

(10) Patent No.: US 10,611,769 B2
(45) Date of Patent: *Apr. 7, 2020

(54) RSV ANTIVIRAL PYRAZOLO- AND TRIAZOLO-PYRIMIDINE COMPOUNDS

(71) Applicant: Janssen Sciences Ireland Unlimited Company, Co Cork (IE)

(72) Inventors: David Francis Alain Lançois, Issy-les-Moulineaux (FR); Jérôme Émile Georges Guillemont, Issy-les-Moulineaux (FR); Pierre Jean-Marie Bernard Raboisson, Wavre (BE); Dirk André Emmy Roymans, Beerse (BE); Boris Rogovoy, San Diego, CA (US); Vadim Bichko, San Diego, CA (US); Delphine Yvonne Raymonde Lardeau, Issy-les-Moulineaux (FR); Antoine Benjamin Michaut, Illkirch (FR); Anil Koul, Beerse (BE)

(73) Assignee: Janssen Sciences Ireland Unlimited Company, Co Cork (IE)

( * ) Notice: Subject to any disclaimer, the term of this patent is extended or adjusted under 35 U.S.C. 154(b) by 0 days.

This patent is subject to a terminal disclaimer.

(21) Appl. No.: 16/272,934

(22) Filed: Feb. 11, 2019

(65) Prior Publication Data

US 2019/0248793 A1    Aug. 15, 2019

Related U.S. Application Data

(63) Continuation of application No. 15/570,054, filed as application No. PCT/EP2016/059392 on Apr. 27, 2016, now Pat. No. 10,208,048.

(60) Provisional application No. 62/204,390, filed on Aug. 12, 2015, provisional application No. 62/153,753, filed on Apr. 28, 2015.

(51) Int. Cl.
| | |
|---|---|
| *C07D 487/04* | (2006.01) |
| *C07D 519/00* | (2006.01) |
| *A61K 31/437* | (2006.01) |
| *A61K 31/16* | (2006.01) |
| *A61P 31/14* | (2006.01) |

(52) U.S. Cl.
CPC .......... *C07D 487/04* (2013.01); *A61K 31/16* (2013.01); *A61K 31/437* (2013.01); *A61P 31/14* (2018.01); *C07D 519/00* (2013.01)

(58) Field of Classification Search
CPC .... C07D 487/04; C07D 519/00; A61K 31/16; A61K 31/437; A61P 31/14
USPC .......... 544/263, 281, 283; 514/259.3, 259.31
See application file for complete search history.

(56) References Cited

U.S. PATENT DOCUMENTS

| | | | |
|---|---|---|---|
| 5,972,966 A | 10/1999 | deSolms | |
| 5,977,134 A | 11/1999 | Ciccarone et al. | |
| 6,177,443 B1 | 1/2001 | Madsen et al. | |
| 6,218,404 B1 | 4/2001 | Bigge et al. | |
| 6,608,203 B2 | 8/2003 | Cameron et al. | |
| 6,765,096 B1 | 7/2004 | Aono et al. | |
| 6,919,376 B2 | 7/2005 | Llompart et al. | |
| 7,507,842 B2 | 3/2009 | Oehler et al. | |
| 7,642,272 B2 | 1/2010 | Shankar et al. | |
| 7,662,826 B2 | 2/2010 | Seno et al. | |
| 7,893,096 B2 | 2/2011 | Valiante, Jr. | |
| 8,450,343 B2 | 5/2013 | Huang et al. | |
| 8,691,938 B2 | 4/2014 | DeGoey et al. | |
| 8,829,027 B2 | 9/2014 | Eckhardt et al. | |
| 10,208,048 B2 * | 2/2019 | Lancois | C07D 487/04 |
| 2003/0073681 A1 | 4/2003 | Hauske et al. | |
| 2010/0063047 A1 | 3/2010 | Borchardt et al. | |
| 2010/0204265 A1 | 8/2010 | Baskaran et al. | |

FOREIGN PATENT DOCUMENTS

| | | |
|---|---|---|
| CN | 105777632 A | 7/2016 |
| WO | 199619483 A1 | 6/1996 |
| WO | 199701275 A1 | 1/1997 |
| WO | 2004029042 A1 | 4/2004 |
| WO | 2004037817 A1 | 6/2004 |
| WO | 2005000315 A1 | 1/2005 |
| WO | 2005035516 A1 | 4/2005 |
| WO | 2005042530 A1 | 5/2005 |
| WO | 2006030925 A1 | 3/2006 |
| WO | 2006034341 A2 | 3/2006 |
| WO | 2007/044085 A2 | 4/2007 |
| WO | 2007060409 A1 | 5/2007 |
| WO | 2008063671 A2 | 5/2008 |
| WO | 2009/023179 A2 | 2/2009 |
| WO | 2010104306 A2 | 9/2010 |
| WO | 2010111058 A1 | 9/2010 |
| WO | 2011163518 A1 | 12/2011 |
| WO | 2012051361 A1 | 4/2012 |
| WO | 2015042297 A1 | 3/2015 |
| WO | 2015106025 A1 | 7/2015 |
| WO | 2016017980 A1 | 2/2016 |
| WO | 2016071293 A2 | 5/2016 |
| WO | 2016/174079 A1 | 11/2016 |

OTHER PUBLICATIONS

Wyde, et al., "CL387626 exhibits marked and unusual antiviral activity against respiratory syncytial virus in tissue culture and in cotton rats", Antiviral Research, vol. 38: pp. 31-42.

* cited by examiner

*Primary Examiner* — Venkataraman Balasubramanian

(57) ABSTRACT

The invention concerns novel substituted pyrazolo- and triazolo-pyrimidine compounds of formula (I) having antiviral activity, in particular, having an inhibitory activity on the replication of the respiratory syncytial virus (RSV). The invention further concerns pharmaceutical compositions comprising these compounds and the compounds for use in the treatment of respiratory syncytial virus infection.

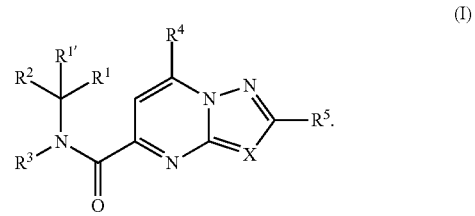

16 Claims, No Drawings

RSV ANTIVIRAL PYRAZOLO- AND TRIAZOLO-PYRIMIDINE COMPOUNDS

CROSS-REFERENCE TO RELATED APPLICATIONS

This application is a continuation of U.S. patent application Ser. No. 15/570,054 filed on Oct. 27, 2017, which is a national phase entry of International Application No. PCT/EP2016/059392, filed on Apr. 27, 2016, which claims priority to U.S. Provisional Patent Application No. 62/153,753, filed Apr. 28, 2015 and to U.S. Provisional Patent Application No. 62/204,390 filed Aug. 12, 2015, each of which is incorporated herein in its entirety.

FIELD OF THE INVENTION

The invention concerns novel substituted pyrazolo- and triazolo-pyrimidine compounds having antiviral activity, in particular, having an inhibitory activity on the replication of the respiratory syncytial virus (RSV). The invention further concerns pharmaceutical compositions comprising these compounds and the compounds for use in the treatment of respiratory syncytial virus infection.

BACKGROUND

Human RSV or Respiratory Syncytial Virus is a large RNA virus, member of the family of Paramyxoviridae, subfamily pneumoviridae together with bovine RSV virus. Human RSV is responsible for a spectrum of respiratory tract diseases in people of all ages throughout the world. It is the major cause of lower respiratory tract illness during infancy and childhood. Over half of all infants encounter RSV in their first year of life, and almost all within their first two years. The infection in young children can cause lung damage that persists for years and may contribute to chronic lung disease in later life (chronic wheezing, asthma). Older children and adults often suffer from a (bad) common cold upon RSV infection. In old age, susceptibility again increases, and RSV has been implicated in a number of outbreaks of pneumonia in the aged resulting in significant mortality.

Infection with a virus from a given subgroup does not protect against a subsequent infection with an RSV isolate from the same subgroup in the following winter season. Re-infection with RSV is thus common, despite the existence of only two subtypes, A and B.

Today only three drugs have been approved for use against RSV infection. A first one is ribavirin, a nucleoside analogue that provides an aerosol treatment for serious RSV infection in hospitalized children. The aerosol route of administration, the toxicity (risk of teratogenicity), the cost and the highly variable efficacy limit its use. The other two drugs, RespiGam® (RSV-IG) and Synagis® (palivizumab), polyclonal and monoclonal antibody immunostimulants, are intended to be used in a preventive way. Both are very expensive, and require parenteral administration.

Clearly there is a need for an efficacious non-toxic and easy to administer drug against RSV replication. It would be particularly preferred to provide drugs against RSV replication that could be administered perorally.

Compounds that exhibit anti-RSV activity are disclosed in WO-2005/042530.

DETAILED DESCRIPTION OF THE INVENTION

The present invention relates to compounds of formula (I)

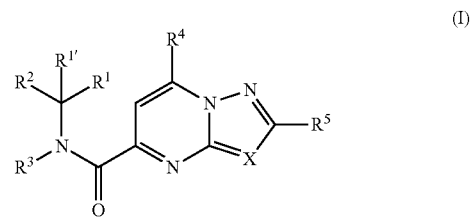

(I)

including any stereochemically isomeric form thereof, wherein

X is N or $CR^6$ wherein $R^6$ is hydrogen, halo or $C_{1-4}$alkyl;
$R^1$ is $CH_3$ or $CH_2CH_3$, and $R^{1'}$ is hydrogen; or $R^1$ and $R^{1'}$ are taken together with the carbon atom to which they are attached to form cyclopropyl; and $R^2$ is $C_{3-6}$alkyl and $R^3$ is $C_{1-4}$alkyl;

or the

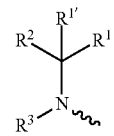

moiety is a radical of formula:

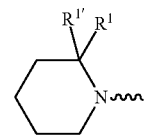
(a-1)

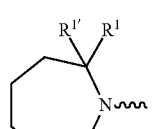
(a-2)

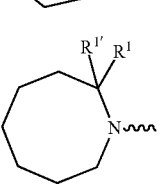
(a-3)

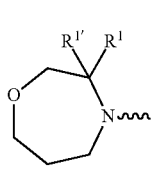
(a-4)

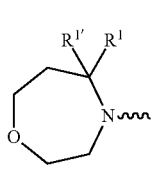
(a-5)

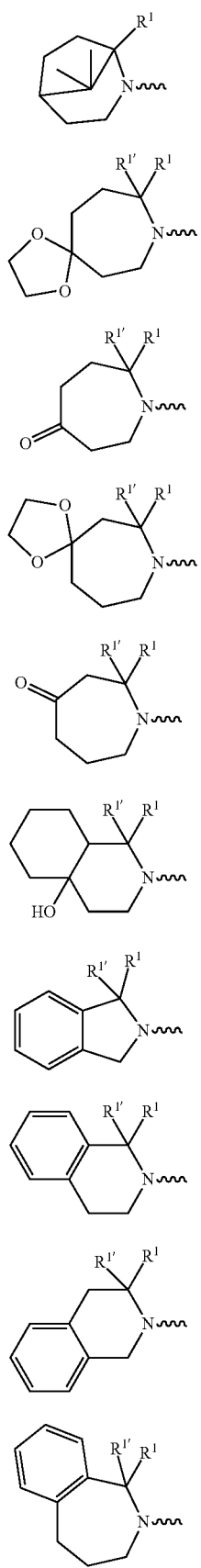
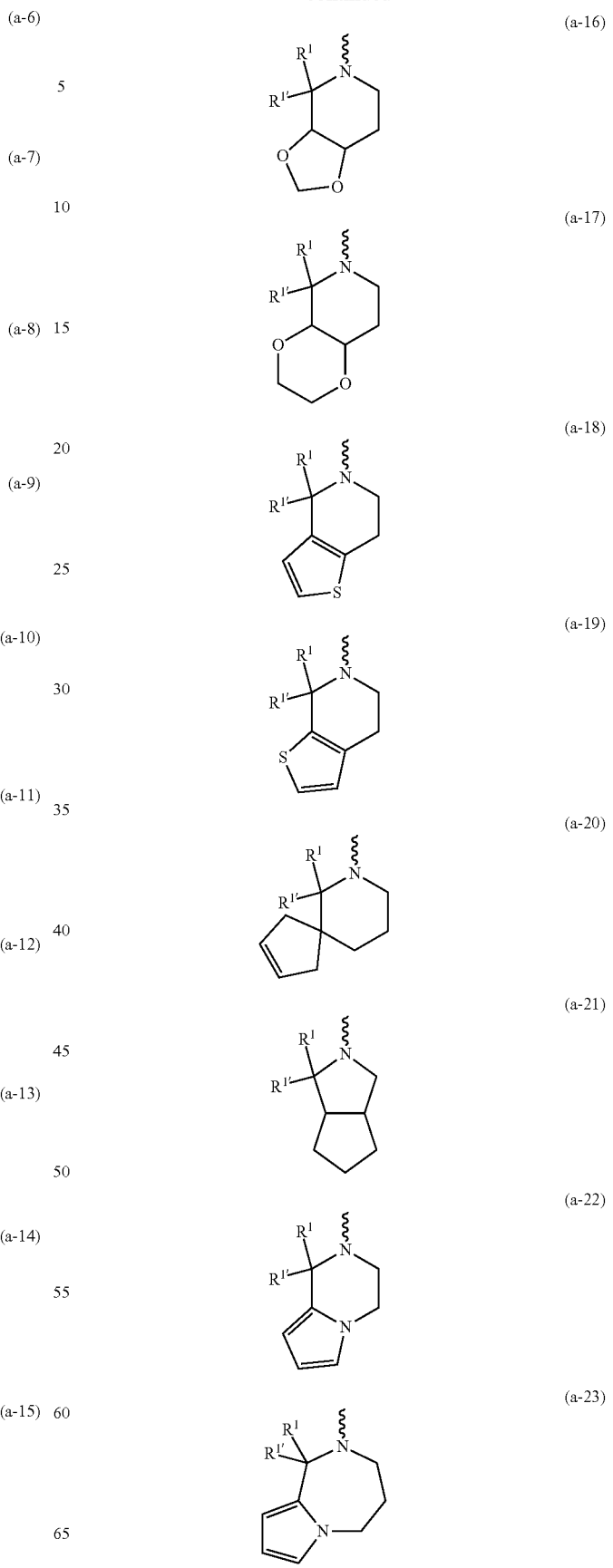

-continued (a-24) 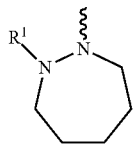

(a-25) 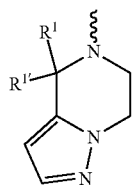

(a-26) 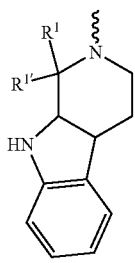

(a-27) 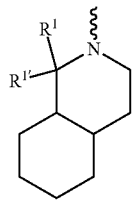

(a-28) 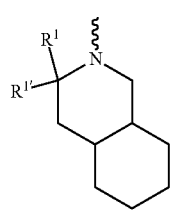

(a-29) 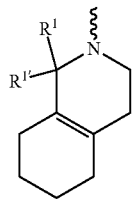

(a-30) 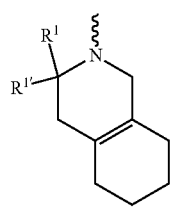

wherein $R^1$ is $CH_3$ or $CH_2CH_3$, and $R^{1'}$ is hydrogen; or $R^{1'}$ is absent in radical (a-6); or $R^1$ and $R^{1'}$ are taken together with the carbon atom to which they are attached to form cyclopropyl; and radical (a-1) to (a-30) are optionally substituted with one or two substituents each independently selected from $C_{1-2}$alkyl and halo;

$R^4$ is $C_{1-6}$alkyl; $C_{3-6}$alkenyl, polyhalo$C_{1-4}$alkyl; $C_{1-4}$alkyl substituted with one $C_{3-6}$cycloalkyl; aminocarbonyl, mono- or di($C_{1-4}$alkyl)aminocarbonyl; oxetanyl optionally substituted with $C_{1-4}$alkyl; Heteroaryl$^1$; $C_{3-6}$cycloalkyl; $C_{3-6}$cycloalkyl substituted with one or two substituents each individually selected from hydroxy, halo, cyano, $C_{1-4}$alkyl, $C_{1-4}$alkyloxy, polyhalo$C_{1-4}$alkyl, and polyhalo$C_{1-4}$alkyloxy; or NR$^7$R$^8$ wherein R$^7$ is selected from hydrogen and $C_{1-4}$alkyl;

R$^8$ is $C_{1-4}$alkyl or $C_{3-6}$cycloalkyl;

or R$^7$ and R$^8$ are taken together with the nitrogen to which they are attached to form azetidinyl, pyrrolidinyl or piperidinyl;

$R^5$ is $C_{3-6}$cycloalkyl;

Heteroaryl;

Bicycle;

naphthyl substituted with 1, 2 or 3 substituents each independently selected from halo and hydroxycarbonyl;

phenyl substituted with 1, 2 or 3 substituents each independently selected from hydroxy;

halo;

$C_{1-6}$alkyl;

$C_{1-6}$alkyl substituted with one, two or three substituents each independently selected from halo, hydroxy, hydroxycarbonyl, aminocarbonyl, Heterocycle, $C_{3-6}$cycloalkyl, $C_{3-6}$cycloalkyl substituted with one or two substituents each independently selected from $C_{1-4}$alkyl, halo, hydroxycarbonyl, and $C_{1-4}$alkyl substituted with hydroxycarbonyl;

$C_{3-6}$alkenyl;

$C_{3-6}$alkenyl substituted with one or two substituents selected from $C_{1-6}$alkyl, hydroxy, hydroxycarbonyl and aminocarbonyl;

$C_{3-6}$alkynyl;

$C_{3-6}$alkynyl substituted with one hydroxycarbonyl;

$C_{3-6}$cycloalkyl;

$C_{3-6}$cycloalkyl substituted with one, two or three substituents each independently selected from $C_{1-4}$alkyl, halo, hydroxycarbonyl, and $C_{1-4}$alkyl substituted with hydroxycarbonyl;

$C_{3-6}$cycloalkenyl;

$C_{3-6}$cycloalkenyl substituted with one hydroxycarbonyl;

$C_{1-6}$alkyloxy optionally substituted with hydroxycarbonyl;

polyhalo$C_{1-4}$alkyl;

polyhalo$C_{1-4}$alkyloxy;

cyano;

nitro;

B(OH)$_2$;

hydroxycarbonyl;

CO—NHOH;

CO—NR$^9$R$^{10}$;

CO—NH—NR$^9$R$^{10}$;

NR$^9$R$^{10}$;

NH—CO—R$^{11}$;

NH—CO—O—R$^1$;

NH—CO—NH—R$^{11}$;

NH—CS—NH—R$^{11}$;

NH—C=(N—CN)—NH—R$^{11}$;

aminosulfonyl; mono- or di($C_{1-4}$alkyl)aminosulfonyl;

Heterocycle; and spiro[3.3]heptanyl optionally substituted with hydroxycarbonyl;

wherein

R$^9$ and R$^{10}$ are each independently selected from hydrogen; $C_{1-6}$alkyl; SO$_2$—R$^{12}$; and $C_{1-6}$alkyl substituted with one or two substituents each independently selected from hydroxy, hydroxycarbonyl, $C_{3-6}$cycloalkyl, $C_{3-6}$cycloalkyl substituted with hydroxycarbonyl, $C_{1-4}$alkylcarbonylamino, mono- or di($C_{1-4}$alkyl)amino, and Heterocycle;

$R^{11}$ is $C_{1-6}$alkyl; $C_{3-6}$alkenyl; $C_{3-6}$cycloalkyl; Aryl; Heterocycle; or $C_{1-6}$alkyl substituted with one substituent selected from $C_{3-6}$cycloalkyl, $C_{1-4}$alkyloxy, hydroxy, cyano, hydroxycarbonyl, aminocarbonyl, mono- or di($C_{1-4}$alkyl)aminocarbonyl, $C_{1-4}$alkylcarbonylamino, and Heterocycle;

$R^{12}$ is $C_{1-4}$alkyl, $C_{3-6}$cycloalkyl, or $C_{1-4}$alkyl substituted with one $C_{3-6}$cycloalkyl, Heteroaryl is thienyl, imidazolyl, pyrazolyl, thiazolyl, pyridinyl, 1-benzopyrazolyl, 2,3-dihydro-1H-indolyl, 2-oxo-2,3-dihydro-1H-indolyl, quinolinyl, 2-oxo-quinolinyl, benzimidazolyl, cinnolinyl, or 2H-chromenyl, wherein each Heteroaryl is optionally substituted with one or two substituents each independently selected from $C_{1-4}$alkyl, halo, amino, aminocarbonyl, and NH—CO—$C_{3-6}$cycloalkyl;

Heteroaryl$^1$ is imidazolyl or pyrazolyl; wherein each Heteroaryl$^1$ is optionally substituted with one or two substituents each independently selected from $C_{1-4}$alkyl, halo and hydroxycarbonyl;

Heterocycle is azetidinyl, tetrahydrofuranyl, pyrrolidinyl, furanyl, thienyl, imidazolyl, pyrazolyl, thiazolyl, oxazolyl, isoxazolyl, 1,2,4-oxadiazolyl, 2,5-dihydro-1H-pyrrolyl, pyridinyl, pyrimidinyl, pyrazinyl, 2-oxo-azepanyl, 2,5-dioxopyrrolidinyl, or 3-oxo-2,3-dihydro-1,2-oxazolyl; wherein each Heterocycle is optionally substituted with one or two substituents each independently selected from $C_{1-4}$alkyl, $C_{3-6}$cycloalkyl, halo, hydroxy$C_{1-4}$alkyl, polyhalo$C_{1-4}$alkyl, hydroxycarbonyl, and $C_{1-4}$alkyl substituted with hydroxycarbonyl;

Aryl is phenyl substituted with one or two substituents each independently selected from hydrogen, halogen, $C_{1-4}$alkyl, $C_{1-4}$alkyloxy, and trifluoromethyl;

Bicycle is 1,2,3,4-tetrahydronaphthalenyl, chromanyl or 2,3-dihydrobenzofuranyl; wherein each Bicycle is optionally substituted with one or two substituents each independently selected from $C_{1-4}$alkyl, halo and hydroxycarbonyl;

with the proviso that [7-ethyl-2-(3-thienyl)pyrazolo[1,5-a]pyrimidin-5-yl](2-methyl-1-piperidinyl)-methanone and [7-ethyl-2-(2-pyridinyl)pyrazolo[1,5-a]pyrimidin-5-yl](2-methyl-1-piperidinyl)-methanone are not included;

or a pharmaceutically acceptable acid addition salt thereof.

As used in the foregoing definitions:

halo is generic to fluoro, chloro, bromo and iodo;

$C_{1-2}$alkyl defines saturated hydrocarbon radicals having from 1 to 2 carbon atoms such as methyl and ethyl;

$C_{1-4}$alkyl defines straight and branched chain saturated hydrocarbon radicals having from 1 to 4 carbon atoms such as, for example, methyl, ethyl, propyl, butyl, 1-methylethyl, 2-methylpropyl and the like;

$C_{1-6}$alkyl is meant to include $C_{1-4}$alkyl and the higher homologues thereof having 5 or 6 carbon atoms, such as, for example, 2 methylbutyl, pentyl, hexyl and the like;

$C_{3-6}$alkenyl defines straight and branched chain unsaturated hydrocarbon radicals having from 3 to 6 carbon atoms, such as propenyl, butenyl, pentenyl or hexenyl;

$C_{3-6}$alkynyl defines straight and branched chain unsaturated hydrocarbon radicals having from 3 to 6 carbon atoms, such as propynyl, butynyl, pentynyl or hexynyl;

$C_{3-6}$cycloalkyl is generic to cyclopropyl, cyclobutyl, cyclopentyl, and cyclohexyl;

$C_{3-6}$cycloalkenyl is generic to cyclopropenyl, cyclobutenyl, cyclopentenyl, and cyclohexenyl;

polyhalo$C_{1-4}$alkyl is defined as polyhalosubstituted $C_{1-4}$alkyl, in particular $C_{1-4}$alkyl (as hereinabove defined) substituted with 2 to 6 halogen atoms such as difluoromethyl, trifluoromethyl, trifluoroethyl, and the like.

The term "compounds of the invention" as used herein, is meant to include the compounds of formula (I), and the salts and solvates thereof.

As used herein, any chemical formula with bonds shown only as solid lines and not as solid wedged or hashed wedged bonds, or otherwise indicated as having a particular configuration (e.g. R, S) around one or more atoms, contemplates each possible stereoisomer, or mixture of two or more stereoisomers.

Hereinbefore and hereinafter, the terms "compound of formula (I)" and "intermediates of synthesis of formula (I)" are meant to include the stereoisomers thereof and the tautomeric forms thereof.

The terms "stereoisomers", "stereoisomeric forms" or "stereochemically isomeric forms" hereinbefore or hereinafter are used interchangeably.

The invention includes all stereoisomers of the compounds of the invention either as a pure stereoisomer or as a mixture of two or more stereoisomers. Enantiomers are stereoisomers that are non-superimposable mirror images of each other. A 1:1 mixture of a pair of enantiomers is a racemate or racemic mixture. Diastereomers (or diastereoisomers) are stereoisomers that are not enantiomers, i.e. they are not related as mirror images. If a compound contains a double bond, the substituents may be in the E or the Z configuration. Substituents on bivalent cyclic (partially) saturated radicals may have either the cis- or trans-configuration; for example if a compound contains a disubstituted cycloalkyl group, the substituents may be in the cis or trans configuration.

The term "stereoisomers" also includes any rotamers, also called conformational isomers, the compounds of formula (I) may form.

Therefore, the invention includes enantiomers, diastereomers, racemates, E isomers, Z isomers, cis isomers, trans isomers, rotamers, and mixtures thereof, whenever chemically possible.

The meaning of all those terms, i.e. enantiomers, diastereomers, racemates, E isomers, Z isomers, cis isomers, trans isomers and mixtures thereof are known to the skilled person.

The absolute configuration is specified according to the Cahn-Ingold-Prelog system. The configuration at an asymmetric atom is specified by either R or S. Resolved stereoisomers whose absolute configuration is not known can be designated by (+) or ( ) depending on the direction in which they rotate plane polarized light. For instance, resolved enantiomers whose absolute configuration is not known can be designated by (+) or (−) depending on the direction in which they rotate plane polarized light.

When a specific stereoisomer is identified, this means that said stereoisomer is substantially free, i.e. associated with less than 50%, preferably less than 20%, more preferably less than 10%, even more preferably less than 5%, in particular less than 2% and most preferably less than 1%, of the other stereoisomers. Thus, when a compound of formula (I) is for instance specified as (R), this means that the compound is substantially free of the (S) isomer; when a compound of formula (I) is for instance specified as E, this means that the compound is substantially free of the Z isomer; when a compound of formula (I) is for instance specified as cis, this means that the compound is substantially free of the trans isomer.

Some of the compounds according to formula (I) may also exist in their tautomeric form. Such forms in so far as they may exist, although not explicitly indicated in the above formula (I) are intended to be included within the scope of the present invention.

It follows that a single compound may exist in both stereoisomeric and tautomeric form.

The pharmaceutically acceptable acid addition salts as mentioned hereinabove are meant to comprise the therapeutically active non-toxic acid addition salt forms that the compounds of formula (I) are able to form. These pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butane-dioic acid), maleic, fumaric, malic, tartaric, citric, methanesulfonic, ethanesulfonic, benzenesulfonic, p toluenesulfonic, cyclamic, salicylic, p aminosalicylic, pamoic and the like acids.

Conversely said salt forms can be converted by treatment with an appropriate base into the free base form.

The compounds of formula (I) may exist in both unsolvated and solvated forms. The term 'solvate' is used herein to describe a molecular association comprising a compound of the invention and one or more pharmaceutically acceptable solvent molecules, e.g. water or ethanol. The term 'hydrate' is used when said solvent is water.

For the avoidance of doubt, compounds of formula (I) may contain the stated atoms in any of their natural or non-natural isotopic forms. In this respect, embodiments of the invention that may be mentioned include those in which (a) the compound of formula (I) is not isotopically enriched or labelled with respect to any atoms of the compound; and (b) the compound of formula (I) is isotopically enriched or labelled with respect to one or more atoms of the compound. Compounds of formula (I) that are isotopically enriched or labelled (with respect to one or more atoms of the compound) with one or more stable isotopes include, for example, compounds of formula (I) that are isotopically enriched or labelled with one or more atoms such as deuterium, $^{13}C$, $^{14}C$, $^{14}N$, 15O or the like. Particular compounds of formula (I) that are isotopically enriched are the compounds of formula (I) wherein $R^6$ is deuterium.

In a first embodiment the invention concerns compounds of formula (I), including any stereochemically isomeric forms thereof, wherein $R^1$ is $CH_3$ or $CH_2CH_3$, and $R^{1'}$ is hydrogen; or $R^{1'}$ is absent in radical (a-6);

or $R^1$ and $R^{1'}$ are taken together with the carbon atom to which they are attached to form cyclopropyl; and radical (a-1) to (a-15) are optionally substituted with one or two substituents each independently selected from $C_{1-2}$alkyl and halo;

$R^4$ is $C_{1-6}$alkyl; polyhalo$C_{1-4}$alkyl; $C_{1-4}$alkyl substituted with one $C_{3-6}$cycloalkyl; or $NR^7R^8$ wherein $R^7$ is selected from hydrogen and $C_{1-4}$alkyl;

$R^8$ is $C_{1-4}$alkyl or $C_{3-6}$cycloalkyl;

or $R^7$ and $R^8$ are taken together with the nitrogen to which they are attached to form azetidinyl, pyrrolidinyl or piperidinyl;

$R^5$ is $C_{3-6}$cycloalkyl;

Heteroaryl;

naphthyl substituted with 1, 2 or 3 substituents each independently selected from halo and hydroxycarbonyl;

phenyl substituted with 1, 2 or 3 substituents each independently selected from hydroxy;

halo;

$C_{1-6}$alkyl;

$C_{1-6}$alkyl substituted with one substituent selected from hydroxy, hydroxycarbonyl and aminocarbonyl;

$C_{3-6}$alkenyl;

$C_{3-6}$alkenyl substituted with one or two substituents selected from $C_{1-6}$alkyl, hydroxy, hydroxycarbonyl and aminocarbonyl;

$C_{3-6}$alkynyl;

$C_{3-6}$alkynyl substituted with one hydroxycarbonyl;

$C_{3-6}$cycloalkyl;

$C_{3-6}$cycloalkyl substituted with one hydroxycarbonyl;

$C_{3-6}$cycloalkenyl;

$C_{3-6}$cycloalkenyl substituted with one hydroxycarbonyl;

$C_{1-6}$alkyloxy;

polyhalo$C_{1-4}$alkyl;

cyano;

nitro;

$B(OH)_2$;

hydroxycarbonyl;

CO—NHOH;

CO—$NR^9R^{10}$;

CO—NH—$NR^9R^{10}$;

$NR^9R^{10}$;

NH—CO—$R^{11}$;

NH—CO—O—$R^{11}$;

NH—CO—NH—$R^{11}$;

NH—CS—NH—$R^{11}$;

NH—C=(N—CN)—NH—$R^{11}$;

aminosulfonyl; mono- or di($C_{1-4}$alkyl)aminosulfonyl; and

Heterocycle;

wherein $R^9$ and $R^{10}$ are each independently selected from hydrogen; $C_{1-6}$alkyl; $SO_2$—$R^{12}$; and $C_{1-6}$alkyl substituted with hydroxy, hydroxycarbonyl, $C_{3-6}$cycloalkyl, $C_{1-4}$alkylcarbonylamino, mono- or di($C_{1-4}$alkyl)amino, or Heterocycle;

$R^{11}$ is $C_{1-6}$alkyl; $C_{3-6}$alkenyl; $C_{3-6}$cycloalkyl; Aryl; Heterocycle; or $C_{1-6}$alkyl substituted with one substituent selected from $C_{3-6}$cycloalkyl, $C_{1-4}$alkyloxy, hydroxy, cyano, hydroxycarbonyl, aminocarbonyl, mono- or di($C_{1-4}$alkyl)aminocarbonyl, $C_{1-4}$alkylcarbonylamino, and Heterocycle;

$R^{12}$ is $C_{1-4}$alkyl, $C_{3-6}$cycloalkyl, or $C_{1-4}$alkyl substituted with one $C_{3-6}$cycloalkyl, Heteroaryl is thienyl, imidazolyl, pyrazolyl, thiazolyl, pyridinyl, 1-benzopyrazolyl, 2,3-dihydro-1H-indolyl, 2-oxo-2,3-dihydro-1H-indolyl, quinolinyl, 2-oxo-quinolinyl, benzimidazolyl, or cinnolinyl, wherein each Heteroaryl is optionally substituted with one or two substituents each independently selected from $C_{1-4}$alkyl, halo, amino, aminocarbonyl, and NH—CO—$C_{3-6}$cycloalkyl;

Heterocycle is tetrahydrofuranyl, pyrrolidinyl, furanyl, thienyl, imidazolyl, pyrazolyl, thiazolyl, pyridinyl, pyrimidinyl, pyrazinyl, 2-oxo-azepanyl, or 2,5-dioxopyrrolidinyl; wherein each Heterocycle is optionally substituted with one or two substituents each independently selected from $C_{1-4}$alkyl, $C_{3-6}$cycloalkyl, halo and hydroxycarbonyl;

Aryl is phenyl substituted with one or two substituents each independently selected from hydrogen, halogen, $C_{1-4}$alkyl, $C_{1-4}$alkyloxy, and trifluoromethyl;

with the proviso that [7-ethyl-2-(3-thienyl)pyrazolo[1,5-a]pyrimidin-5-yl](2-methyl-1-piperidinyl)-methanone and [7-ethyl-2-(2-pyridinyl)pyrazolo[1,5-a]pyrimidin-5-yl](2-methyl-1-piperidinyl)-methanone are not included;

or a pharmaceutically acceptable acid addition salt thereof.

In a second embodiment the invention concerns compounds of formula (I), including any stereochemically isomeric forms thereof, wherein X is N or $CR^6$ wherein $R^6$ is hydrogen or halo;

$R^1$ is $CH_3$ or $CH_2CH_3$, and $R^{1'}$ is hydrogen; or $R^1$ and $R^{1'}$ are taken together with the carbon atom to which they are attached to form cyclopropyl; and $R^2$ is $C_{3-6}$alkyl and $R^3$ is $CH_3$;

or the

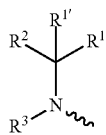

moiety is a radical of formula:

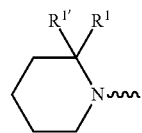 (a-1)

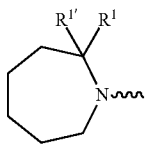 (a-2)

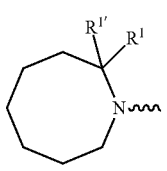 (a-3)

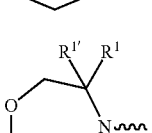 (a-4)

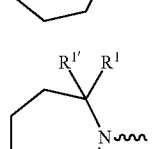 (a-5)

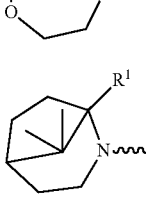 (a-6)

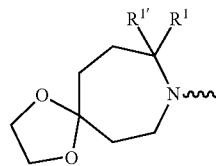 (a-7)

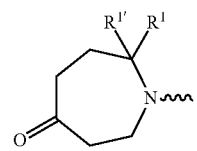 (a-8)

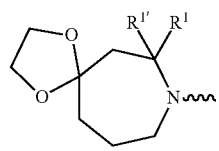 (a-9)

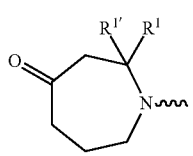 (a-10)

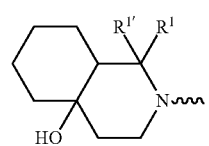 (a-11)

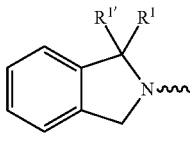 (a-12)

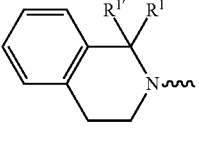 (a-13)

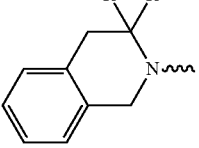 (a-14)

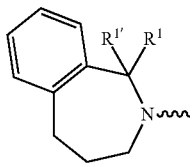 (a-15)

wherein $R^1$ is $CH_3$ or $CH_2CH_3$, and $R^{1'}$ is hydrogen; or $R^{1'}$ is absent in radical (a-6); or $R^1$ and $R^{1'}$ are taken together with the carbon atom to which they are attached to form cyclopropyl; and radical (a-1) to (a-15) are optionally substituted with one or two substituents each independently selected from $C_{1-2}$alkyl and halo;

$R^4$ is $C_{1-6}$alkyl; polyhalo$C_{1-4}$alkyl; $C_{3-6}$cycloalkyl; $C_{1-4}$alkyl substituted with one $C_{3-6}$cycloalkyl; or NR$^7$R$^8$ wherein R$^7$ is selected from hydrogen and C$_{1-4}$alkyl;
R$^8$ is C$_{1-4}$alkyl or C$_{3-6}$cycloalkyl;
or R$^7$ and R$^8$ are taken together with the nitrogen to which they are attached to form pyrrolidinyl or piperidinyl;
R$^5$ is C$_{3-6}$cycloalkyl;
Heteroaryl;
phenyl substituted with 1, 2 or 3 substituents each independently selected from hydroxy;
halo;
C$_{1-6}$alkyl;
C$_{1-6}$alkyl substituted with one substituent selected from hydroxy, hydroxycarbonyl and aminocarbonyl;
C$_{3-6}$alkenyl substituted with one or two substituents selected from C$_{1-6}$alkyl, hydroxy, hydroxycarbonyl and aminocarbonyl;
C$_{3-6}$cycloalkyl substituted with one hydroxycarbonyl;
C$_{1-6}$alkyloxy;
cyano;
B(OH)$_2$;
hydroxycarbonyl;
CO—NHOH;
CO—NR$^9$R$^{10}$;
CO—NH—NR$^9$R$^{10}$;
NR$^9$R$^{10}$;
NH—CO—R$^{11}$;
NH—CO—O—R$^{11}$;
NH—CO—NH—R$^{11}$;
NH—CS—NH—R$^{11}$;
NH—C=(N—CN)—NH—R$^{11}$;
aminosulfonyl; mono- or di(C$_{1-4}$alkyl)aminosulfonyl; and
Heterocycle;
wherein
R$^9$ and R$^{10}$ are each independently selected from hydrogen; C$_{1-6}$alkyl; SO$_2$—R$^{12}$; and C$_{1-6}$alkyl substituted with C$_{3-6}$cycloalkyl, mono- or di(C$_{1-4}$alkyl)amino, or Heterocycle;
R$^{11}$ is C$_{1-6}$alkyl; C$_{3-6}$alkenyl; C$_{3-6}$cycloalkyl; Aryl; Heterocycle; or C$_{1-6}$alkyl substituted with one substituent selected from C$_{3-6}$cycloalkyl, C$_{1-4}$alkyloxy, hydroxy, cyano, hydroxycarbonyl, aminocarbonyl, mono- or di(C$_{1-4}$alkyl)aminocarbonyl, C$_{1-4}$alkylcarbonylamino, and Heterocycle;
R$^{12}$ is C$_{1-4}$alkyl, or C$_{3-6}$cycloalkyl;
Heteroaryl is thienyl, pyridinyl, 1-benzopyrazolyl, 2,3-dihydro-1H-indolyl, 2-oxo-2,3-dihydro-1H-indolyl, quinolinyl, 2-oxo-quinolinyl, benzimidazolyl, cinnolinyl, or 2H-chromenyl;
wherein each Heteroaryl is optionally substituted with one or two substituents each independently selected from C$_{1-4}$alkyl, halo, aminocarbonyl, and NH—CO—C$_{3-6}$cycloalkyl;
Heterocycle is azetidinyl, tetrahydrofuranyl, pyrrolidinyl, furanyl, thienyl, imidazolyl, pyrazolyl, thiazolyl, pyridinyl, pyrimidinyl, pyrazinyl, 2-oxo-azepanyl, 2,5-dioxopyrrolidinyl, or 3-oxo-2,3-dihydro-1,2-oxazolyl; wherein each Heterocycle is optionally substituted with one or two substituents each independently selected from C$_{1-4}$alkyl, C$_{3-6}$cycloalkyl, halo and hydroxycarbonyl;
Aryl is phenyl substituted with one or two substituents each independently selected from hydrogen and halogen;
with the proviso that [7-ethyl-2-(3-thienyl)pyrazolo[1,5-a]pyrimidin-5-yl](2-methyl-1-piperidinyl)-methanone and [7-ethyl-2-(2-pyridinyl)pyrazolo[1,5-a]pyrimidin-5-yl](2-methyl-1-piperidinyl)-methanone are not included;

or a pharmaceutically acceptable acid addition salt thereof.

In a third embodiment the invention concerns compounds of formula (I), including any stereochemically isomeric forms thereof, wherein
X is N or CR$^6$ wherein R$^6$ is hydrogen, halo or C$_{1-4}$alkyl;
R$^1$ is CH$_3$ or CH$_2$CH$_3$, and R$^{1'}$ is hydrogen; or R$^1$ and R$^{1'}$ are taken together with the carbon atom to which they are attached to form cyclopropyl; and R$^2$ is C$_{3-6}$alkyl and R$^3$ is C$_{1-4}$alkyl;
or the

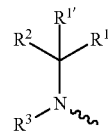

moiety is a radical of formula:

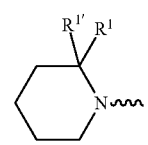
(a-1)

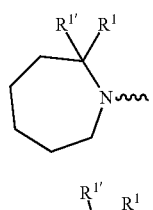
(a-2)

(a-3)

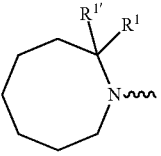
(a-4)

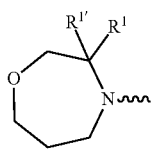
(a-5)

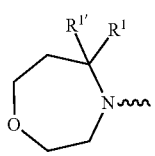
(a-6)

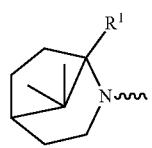

-continued

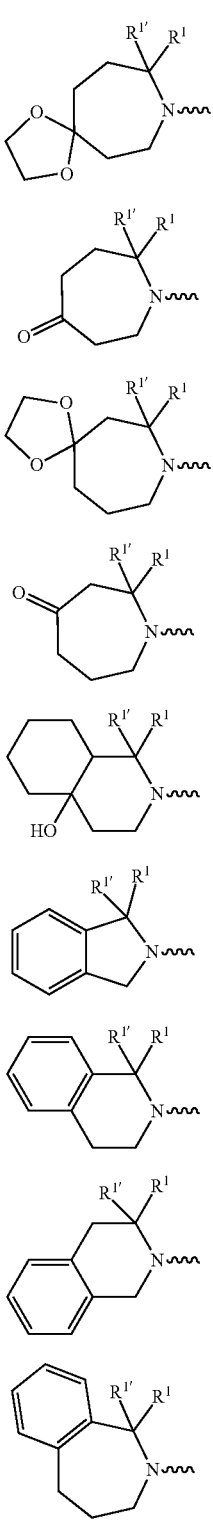

wherein $R^1$ is $CH_3$ or $CH_2CH_3$, and $R^{1'}$ is hydrogen; or $R^{1'}$ is absent in radical (a-6);
or $R^1$ and $R^{1'}$ are taken together with the carbon atom to which they are attached to form cyclopropyl; and radical (a-1) to (a-15) are optionally substituted with one or two substituents each independently selected from $C_{1-2}$alkyl and halo;

$R^4$ is $C_{1-6}$alkyl; polyhalo$C_{1-4}$alkyl; $C_{3-6}$cycloalkyl; $C_{1-4}$alkyl substituted with one $C_{3-6}$cycloalkyl; or
$NR^7R^8$ wherein $R^7$ is selected from hydrogen and $C_{1-4}$alkyl;
$R^8$ is $C_{1-4}$alkyl or $C_{3-6}$cycloalkyl;
or $R^7$ and $R^8$ are taken together with the nitrogen to which they are attached to form azetidinyl, pyrrolidinyl or piperidinyl;
$R^5$ is $C_{3-6}$cycloalkyl;
Heteroaryl;
naphthyl substituted with 1, 2 or 3 substituents each independently selected from halo and hydroxycarbonyl;
phenyl substituted with 1, 2 or 3 substituents each independently selected from hydroxy;
halo;
$C_{1-6}$alkyl;
$C_{1-6}$alkyl substituted with one substituent selected from hydroxy, hydroxycarbonyl and aminocarbonyl;
$C_{3-6}$alkenyl;
$C_{3-6}$alkenyl substituted with one or two substituents selected from $C_{1-6}$alkyl, hydroxy, hydroxycarbonyl and aminocarbonyl;
$C_{3-6}$alkynyl;
$C_{3-6}$alkynyl substituted with one hydroxycarbonyl;
$C_{3-6}$cycloalkyl;
$C_{3-6}$cycloalkyl substituted with one hydroxycarbonyl;
$C_{3-6}$cycloalkenyl;
$C_{3-6}$cycloalkenyl substituted with one hydroxycarbonyl;
$C_{1-6}$alkyloxy;
polyhalo$C_{1-4}$alkyl;
cyano;
nitro;
$B(OH)_2$;
hydroxycarbonyl;
CO—NHOH;
CO—$NR^9R^{10}$;
CO—NH—$NR^9R^{10}$;
$NR^9R^{10}$;
NH—CO—$R^{11}$;
NH—CO—O—$R^{11}$;
NH—CO—NH—$R^{11}$;
NH—CS—NH—$R^{11}$;
NH—C=(N—CN)—NH—$R^{11}$;
aminosulfonyl; mono- or di($C_{1-4}$alkyl)aminosulfonyl; and
Heterocycle;
wherein
$R^9$ and $R^{10}$ are each independently selected from hydrogen; $C_{1-6}$alkyl; $SO_2$—$R^{12}$; and $C_{1-6}$alkyl substituted with hydroxy, hydroxycarbonyl, $C_{3-6}$cycloalkyl, $C_{1-4}$alkylcarbonylamino, mono- or di($C_{1-4}$alkyl)amino, or Heterocycle;
$R^{11}$ is $C_{1-6}$alkyl; $C_{3-6}$alkenyl; $C_{3-6}$cycloalkyl; Aryl; Heterocycle; or $C_{1-6}$alkyl substituted with one substituent selected from $C_{3-6}$cycloalkyl, $C_{1-4}$alkyloxy, hydroxy, cyano, hydroxycarbonyl, aminocarbonyl, mono- or di($C_{1-4}$alkyl)aminocarbonyl, $C_{1-4}$alkylcarbonylamino, and Heterocycle;
$R^{12}$ is $C_{1-4}$alkyl, $C_{3-6}$cycloalkyl, or $C_{1-4}$alkyl substituted with one $C_{3-6}$cycloalkyl,
Heteroaryl is thienyl, imidazolyl, pyrazolyl, thiazolyl, pyridinyl, 1-benzopyrazolyl, 2,3-dihydro-1H-indolyl, 2-oxo-2,3-dihydro-1H-indolyl, quinolinyl, 2-oxo-quinolinyl, benzimidazolyl, cinnolinyl, or 2H-chromenyl, wherein each Heteroaryl is optionally substituted with one or two substituents each independently selected from $C_{1-4}$alkyl, halo, amino, aminocarbonyl, and NH—CO—$C_{3-6}$cycloalkyl;

Heterocycle is azetidinyl, tetrahydrofuranyl, pyrrolidinyl, furanyl, thienyl, imidazolyl, pyrazolyl, thiazolyl, pyridinyl, pyrimidinyl, pyrazinyl, 2-oxo-azepanyl, 2,5-dioxopyrrolidinyl, or 3-oxo-2,3-dihydro-1,2-oxazolyl; wherein each Heterocycle is optionally substituted with one or two substituents each independently selected from $C_{1-4}$alkyl, $C_{3-6}$cycloalkyl, halo and hydroxycarbonyl;

Aryl is phenyl substituted with one or two substituents each independently selected from hydrogen, halogen, $C_{1-4}$alkyl, $C_{1-4}$alkyloxy, and trifluoromethyl;

with the proviso that [7-ethyl-2-(3-thienyl)pyrazolo[1,5-a]pyrimidin-5-yl](2-methyl-1-piperidinyl)-methanone and [7-ethyl-2-(2-pyridinyl)pyrazolo[1,5-a]pyrimidin-5-yl](2-methyl-1-piperidinyl)-methanone are not included;

or a pharmaceutically acceptable acid addition salt thereof.

A first group of compounds are compounds of formula (I-a)

(I-a)

including any stereochemically isomeric form thereof, wherein $R^6$ is hydrogen, halo or $C_{1-4}$alkyl;

$R^1$ is $CH_3$ or $CH_2CH_3$, and $R^{1'}$ is hydrogen; or $R^1$ and $R^{1'}$ are taken together with the carbon atom to which they are attached to form cyclopropyl; and $R^2$ is $C_{3-6}$alkyl and $R^3$ is $C_{1-4}$alkyl;

$R^4$ is $C_{1-6}$alkyl; polyhalo$C_{1-4}$alkyl; $C_{3-6}$cycloalkyl; $C_{1-4}$alkyl substituted with one $C_{3-6}$cycloalkyl; or $NR^7R^8$ wherein $R^7$ is selected from hydrogen and $C_{1-4}$alkyl; $R^8$ is $C_{1-4}$alkyl or $C_{3-6}$cycloalkyl; or $R^7$ and $R^8$ are taken together with the nitrogen to which they are attached to form azetidinyl, pyrrolidinyl or piperidinyl;

$R^5$ is $C_{3-6}$cycloalkyl; Heteroaryl; naphthyl substituted with 1, 2 or 3 substituents each independently selected from halo and hydroxycarbonyl; phenyl substituted with 1, 2 or 3 substituents each independently selected from hydroxy; halo; $C_{1-6}$alkyl; $C_{1-6}$alkyl substituted with one substituent selected from hydroxy, hydroxycarbonyl and aminocarbonyl; $C_{3-6}$alkenyl; $C_{3-6}$alkenyl substituted with one or two substituents selected from $C_{1-6}$alkyl, hydroxy, hydroxycarbonyl and aminocarbonyl; $C_{3-6}$alkynyl; $C_{3-6}$alkynyl substituted with one hydroxycarbonyl; $C_{3-6}$cycloalkyl; $C_{3-6}$cycloalkyl substituted with one hydroxycarbonyl; $C_{3-6}$cycloalkenyl; $C_{3-6}$cycloalkenyl substituted with one hydroxycarbonyl; $C_{1-6}$alkyloxy; polyhalo$C_{1-4}$alkyl; cyano; nitro; $B(OH)_2$; hydroxycarbonyl; CO—NHOH; CO—$NR^9R^{10}$; CO—NH—$NR^9R^{10}$; $NR^9R^{10}$; NH—CO—$R^{11}$; NH—CO—O—$R^{11}$; NH—CO—NH—$R^{11}$; NH—CS—NH—$R^{11}$; NH—C═(N—CN)—NH—$R^1$; aminosulfonyl; mono- or di($C_{1-4}$alkyl)aminosulfonyl; and Heterocycle;

wherein $R^9$ and $R^{10}$ are each independently selected from hydrogen; $C_{1-6}$alkyl; $SO_2$—$R^{12}$; and $C_{1-6}$alkyl substituted with hydroxy, hydroxycarbonyl, $C_{3-6}$cycloalkyl, $C_{1-4}$alkylcarbonylamino, mono- or di($C_{1-4}$alkyl)amino, or Heterocycle;

$R^{11}$ is $C_{1-6}$alkyl; $C_{3-6}$alkenyl; $C_{3-6}$cycloalkyl; Aryl; Heterocycle; or $C_{1-6}$alkyl substituted with one substituent selected from $C_{3-6}$cycloalkyl, $C_{1-4}$alkyloxy, hydroxy, cyano, hydroxycarbonyl, aminocarbonyl, mono- or di($C_{1-4}$alkyl)aminocarbonyl, $C_{1-4}$alkylcarbonylamino, and Heterocycle;

$R^{12}$ is $C_{1-4}$alkyl, $C_{3-6}$cycloalkyl, or $C_{1-4}$alkyl substituted with one $C_{3-6}$cycloalkyl, Heteroaryl is thienyl, imidazolyl, pyrazolyl, thiazolyl, pyridinyl, 1-benzopyrazolyl, 2,3-dihydro-1H-indolyl, 2-oxo-2,3-dihydro-1H-indolyl, quinolinyl, 2-oxo-quinolinyl, benzimidazolyl, cinnolinyl, or 2H-chromenyl, wherein each Heteroaryl is optionally substituted with one or two substituents each independently selected from $C_{1-4}$alkyl, halo, amino, aminocarbonyl, and NH—CO—$C_{3-6}$cycloalkyl;

Heterocycle is azetidinyl, tetrahydrofuranyl, pyrrolidinyl, furanyl, thienyl, imidazolyl, pyrazolyl, thiazolyl, pyridinyl, pyrimidinyl, pyrazinyl, 2-oxo-azepanyl, 2,5-dioxopyrrolidinyl or 3-oxo-2,3-dihydro-1,2-oxazolyl; wherein each Heterocycle is optionally substituted with one or two substituents each independently selected from $C_{1-4}$alkyl, $C_{3-6}$cycloalkyl, halo and hydroxycarbonyl;

Aryl is phenyl substituted with one or two substituents each independently selected from hydrogen, halogen, $C_{1-4}$alkyl, $C_{1-4}$alkyloxy, and trifluoromethyl;

or a pharmaceutically acceptable acid addition salt thereof.

A second group of compounds are compounds of formula (I-b)

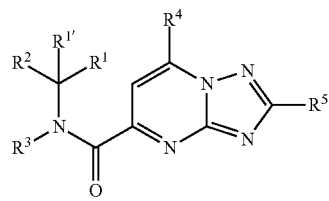

(I-b)

including any stereochemically isomeric form thereof, wherein $R^1$ is $CH_3$ or $CH_2CH_3$, and $R^{1'}$ is hydrogen; or $R^1$ and $R^{1'}$ are taken together with the carbon atom to which they are attached to form cyclopropyl; and $R^2$ is $C_{3-6}$alkyl and $R^3$ is $C_{1-4}$alkyl;

$R^4$ is $C_{1-6}$alkyl; polyhalo$C_{1-4}$alkyl; $C_{3-6}$cycloalkyl; $C_{1-4}$alkyl substituted with one $C_{3-6}$cycloalkyl; or $NR^7R^8$ wherein $R^7$ is selected from hydrogen and $C_{1-4}$alkyl; $R^8$ is $C_{1-4}$alkyl or $C_{3-6}$cycloalkyl; or $R^7$ and $R^8$ are taken together with the nitrogen to which they are attached to form azetidinyl, pyrrolidinyl or piperidinyl;

$R^5$ is $C_{3-6}$cycloalkyl; Heteroaryl; naphthyl substituted with 1, 2 or 3 substituents each independently selected from halo and hydroxycarbonyl; phenyl substituted with 1, 2 or 3 substituents each independently selected from hydroxy; halo; $C_{1-6}$alkyl; $C_{1-6}$alkyl substituted with one substituent selected from hydroxy, hydroxycarbonyl and aminocarbonyl; $C_{3-6}$alkenyl; $C_{3-6}$alkenyl substituted with one or two substituents selected from $C_{1-6}$alkyl, hydroxy, hydroxycarbonyl and aminocarbonyl; $C_{3-6}$alkynyl; $C_{3-6}$alkynyl substituted with one hydroxycarbonyl; $C_{3-6}$cycloalkyl; $C_{3-6}$cycloalkyl substituted with one hydroxycarbonyl; $C_{3-6}$cycloalkenyl; $C_{3-6}$cycloalkenyl substituted with one hydroxycarbonyl; $C_{1-6}$alkyloxy; polyhalo$C_{1-4}$alkyl; cyano; nitro; $B(OH)_2$; hydroxycarbonyl; CO—NHOH; CO—NR$^9$R$^{10}$; CO—NH—NR$^9$R$^{10}$; NR$^9$R$^{10}$; NH—CO—R$^1$; NH—CO—O—R$^{11}$; NH—CO—NH—R$^{11}$; NH—CS—NH—R$^{11}$; NH—C=(N—CN)—NH—R$^1$; aminosulfonyl; mono- or di($C_{1-4}$alkyl)aminosulfonyl; and Heterocycle;

wherein

R$^9$ and R$^{10}$ are each independently selected from hydrogen; $C_{1-6}$alkyl; SO$_2$—R$^{12}$; and $C_{1-6}$alkyl substituted with hydroxy, hydroxycarbonyl, $C_{3-6}$cycloalkyl, $C_{1-4}$alkylcarbonylamino, mono- or di($C_{1-4}$alkyl)amino, or Heterocycle;

R$^{11}$ is $C_{1-6}$alkyl; $C_{3-6}$alkenyl; $C_{3-6}$cycloalkyl; Aryl; Heterocycle; or $C_{1-6}$alkyl substituted with one substituent selected from $C_{3-6}$cycloalkyl, $C_{1-4}$alkyloxy, hydroxy, cyano, hydroxycarbonyl, aminocarbonyl, mono- or di($C_{1-4}$alkyl)aminocarbonyl, $C_{1-4}$alkylcarbonylamino, and Heterocycle;

R$^{12}$ is $C_{1-4}$alkyl, $C_{3-6}$cycloalkyl, or $C_{1-4}$alkyl substituted with one $C_{3-6}$cycloalkyl, Heteroaryl is thienyl, imidazolyl, pyrazolyl, thiazolyl, pyridinyl, 1-benzopyrazolyl, 2,3-dihydro-1H-indolyl, 2-oxo-2,3-dihydro-1H-indolyl, quinolinyl, 2-oxo-quinolinyl, benzimidazolyl, cinnolinyl, or 2H-chromenyl, wherein each Heteroaryl is optionally substituted with one or two substituents each independently selected from $C_{1-4}$alkyl, halo, amino, aminocarbonyl, and NH—CO—$C_{3-6}$cycloalkyl;

Heterocycle is azetidinyl, tetrahydrofuranyl, pyrrolidinyl, furanyl, thienyl, imidazolyl, pyrazolyl, thiazolyl, pyridinyl, pyrimidinyl, pyrazinyl, 2-oxo-azepanyl, 2,5-dioxopyrrolidinyl, or 3-oxo-2,3-dihydro-1,2-oxazolyl; wherein each Heterocycle is optionally substituted with one or two substituents each independently selected from $C_{1-4}$alkyl, $C_{3-6}$cycloalkyl, halo and hydroxycarbonyl;

Aryl is phenyl substituted with one or two substituents each independently selected from hydrogen, halogen, $C_{1-4}$alkyl, $C_{1-4}$alkyloxy, and trifluoromethyl;

or a pharmaceutically acceptable acid addition salt thereof.

A third group of compounds are compounds of formula (I-c)

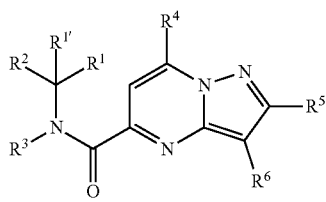

(I-c)

including any stereochemically isomeric form thereof, wherein

R$^6$ is hydrogen, halo or $C_{1-4}$alkyl;

the

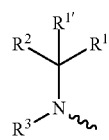

moiety is a radical of formula:

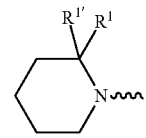 (a-1)

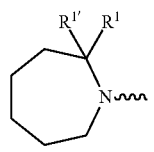 (a-2)

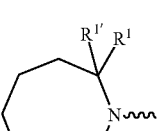 (a-3)

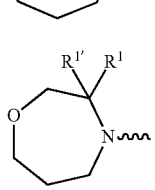 (a-4)

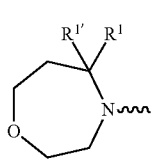 (a-5)

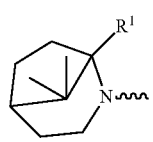 (a-6)

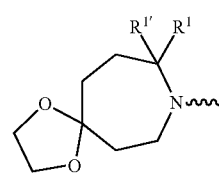 (a-7)

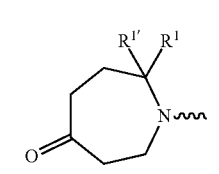 (a-8)

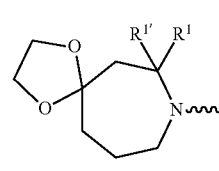 (a-9)

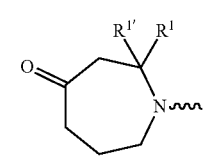 (a-10)

-continued

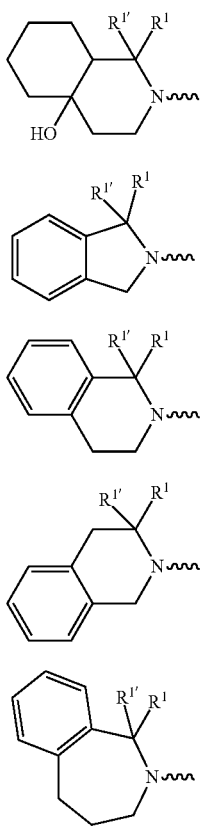

(a-11)

(a-12)

(a-13)

(a-14)

(a-15)

wherein $R^1$ is $CH_3$ or $CH_2CH_3$, and $R^{1'}$ is hydrogen; or $R^{1'}$ is absent in radical (a-6); or $R^1$ and $R^{1'}$ are taken together with the carbon atom to which they are attached to form cyclopropyl; and radical (a-1) to (a-15) are optionally substituted with one or two substituents each independently selected from $C_{1-2}$alkyl and halo;

$R^4$ is $C_{1-6}$alkyl; polyhalo$C_{1-4}$alkyl; $C_{3-6}$cycloalkyl; $C_{1-4}$alkyl substituted with one $C_{3-6}$cycloalkyl; or $NR^7R^8$ wherein $R^7$ is selected from hydrogen and $C_{1-4}$alkyl; $R^8$ is $C_{1-4}$alkyl or $C_{3-6}$cycloalkyl; or $R^7$ and $R^8$ are taken together with the nitrogen to which they are attached to form azetidinyl, pyrrolidinyl or piperidinyl;

$R^5$ is $C_{3-6}$cycloalkyl; Heteroaryl; naphthyl substituted with 1, 2 or 3 substituents each independently selected from halo and hydroxycarbonyl; phenyl substituted with 1, 2 or 3 substituents each independently selected from hydroxy; halo; $C_{1-6}$alkyl; $C_{1-6}$alkyl substituted with one substituent selected from hydroxy, hydroxycarbonyl and aminocarbonyl; $C_{3-6}$alkenyl; $C_{3-6}$alkenyl substituted with one or two substituents selected from $C_{1-6}$alkyl, hydroxy, hydroxycarbonyl and aminocarbonyl; $C_{3-6}$alkynyl; $C_{3-6}$alkynyl substituted with one hydroxycarbonyl; $C_{3-6}$cycloalkyl; $C_{3-6}$cycloalkyl substituted with one hydroxycarbonyl; $C_{3-6}$cycloalkenyl; $C_{3-6}$cycloalkenyl substituted with one hydroxycarbonyl; $C_{1-6}$alkyloxy; polyhalo$C_{1-4}$alkyl; cyano; nitro; $B(OH)_2$; hydroxycarbonyl; CO—NHOH; CO—$NR^9R^{10}$; CO—NH—$NR^9R^{10}$; $NR^9R^{10}$; NH—CO—$R^1$; NH—CO—O—$R^{11}$; NH—CO—NH—$R^{11}$; NH—CS—NH—$R^{11}$; NH—C=(N—CN)—NH—$R^1$; aminosulfonyl; mono- or di($C_{1-4}$alkyl)aminosulfonyl; and Heterocycle; wherein $R^9$ and $R^{10}$ are each independently selected from hydrogen; $C_{1-6}$alkyl; $SO_2$—$R^{12}$; and $C_{1-6}$alkyl substituted with hydroxy, hydroxycarbonyl, $C_{3-6}$cycloalkyl, $C_{1-4}$alkylcarbonylamino, mono- or di($C_{1-4}$alkyl)amino, or Heterocycle;

$R^{11}$ is $C_{1-6}$alkyl; $C_{3-6}$alkenyl; $C_{3-6}$cycloalkyl; Aryl; Heterocycle; or $C_{1-6}$alkyl substituted with one substituent selected from $C_{3-6}$cycloalkyl, $C_{1-4}$alkyloxy, hydroxy, cyano, hydroxycarbonyl, aminocarbonyl, mono- or di($C_{1-4}$alkyl)aminocarbonyl, $C_{1-4}$alkylcarbonylamino, and Heterocycle;

$R^{12}$ is $C_{1-4}$alkyl, $C_{3-6}$cycloalkyl, or $C_{1-4}$alkyl substituted with one $C_{3-6}$cycloalkyl, Heteroaryl is thienyl, imidazolyl, pyrazolyl, thiazolyl, pyridinyl, 1-benzopyrazolyl, 2,3-dihydro-1H-indolyl, 2-oxo-2,3-dihydro-1H-indolyl, quinolinyl, 2-oxo-quinolinyl, benzimidazolyl, cinnolinyl, or 2H-chromenyl, wherein each Heteroaryl is optionally substituted with one or two substituents each independently selected from $C_{1-4}$alkyl, halo, amino, aminocarbonyl, and NH—CO—$C_{3-6}$cycloalkyl;

Heterocycle is azetidinyl, tetrahydrofuranyl, pyrrolidinyl, furanyl, thienyl, imidazolyl, pyrazolyl, thiazolyl, pyridinyl, pyrimidinyl, pyrazinyl, 2-oxo-azepanyl, 2,5-dioxopyrrolidinyl or 3-oxo-2,3-dihydro-1,2-oxazolyl; wherein each Heterocycle is optionally substituted with one or two substituents each independently selected from $C_{1-4}$alkyl, $C_{3-6}$cycloalkyl, halo and hydroxycarbonyl;

Aryl is phenyl substituted with one or two substituents each independently selected from hydrogen, halogen, $C_{1-4}$alkyl, $C_{1-4}$alkyloxy, and trifluoromethyl;

with the proviso that [7-ethyl-2-(3-thienyl)pyrazolo[1,5-a]pyrimidin-5-yl](2-methyl-1-piperidinyl)-methanone and [7-ethyl-2-(2-pyridinyl)pyrazolo[1,5-a]pyrimidin-5-yl](2-methyl-1-piperidinyl)-methanone are not included;

or a pharmaceutically acceptable acid addition salt thereof.

A fourth group of compounds are compounds of formula (I-d)

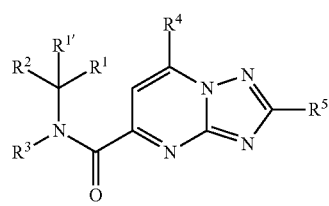

(I-d)

including any stereochemically isomeric form thereof, wherein
the

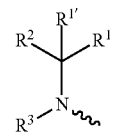

moiety is a radical of formula:

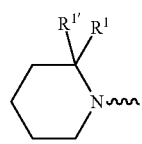

(a-1)

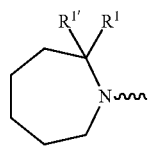
(a-2)

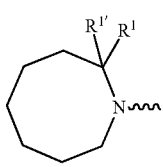
(a-3)

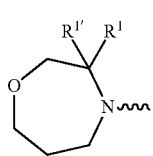
(a-4)

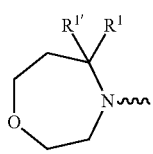
(a-5)

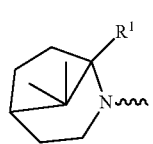
(a-6)

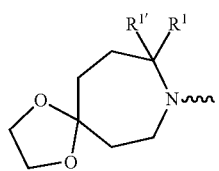
(a-7)

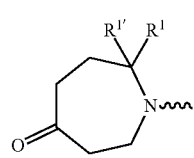
(a-8)

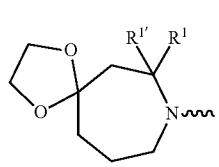
(a-9)

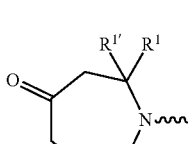
(a-10)

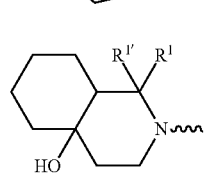
(a-11)

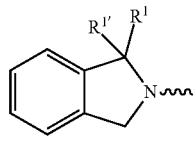
(a-12)

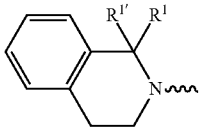
(a-13)

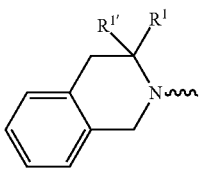
(a-14)

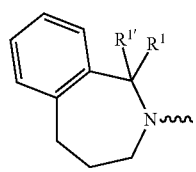
(a-15)

wherein $R^1$ is $CH_3$ or $CH_2CH_3$, and $R^{1'}$ is hydrogen; or $R^{1'}$ is absent in radical (a-6); or $R^1$ and $R^{1'}$ are taken together with the carbon atom to which they are attached to form cyclopropyl; and radical (a-1) to (a-15) are optionally substituted with one or two substituents each independently selected from $C_{1-2}$alkyl and halo;

$R^4$ is $C_{1-6}$alkyl; polyhalo$C_{1-4}$alkyl; $C_{3-6}$cycloalkyl; $C_{1-4}$alkyl substituted with one $C_{3-6}$cycloalkyl; or $NR^7R^8$ wherein $R^7$ is selected from hydrogen and $C_{1-4}$alkyl; $R^8$ is $C_{1-4}$alkyl or $C_{3-6}$cycloalkyl; or $R^7$ and $R^8$ are taken together with the nitrogen to which they are attached to form azetidinyl, pyrrolidinyl or piperidinyl;

$R^5$ is $C_{3-6}$cycloalkyl; Heteroaryl; naphthyl substituted with 1, 2 or 3 substituents each independently selected from halo and hydroxycarbonyl; phenyl substituted with 1, 2 or 3 substituents each independently selected from hydroxy; halo; $C_{1-6}$alkyl; $C_{1-6}$alkyl substituted with one substituent selected from hydroxy, hydroxycarbonyl and aminocarbonyl; $C_{3-6}$alkenyl; $C_{3-6}$alkenyl substituted with one or two substituents selected from $C_{1-6}$alkyl, hydroxy, hydroxycarbonyl and aminocarbonyl; $C_{3-6}$alkynyl; $C_{3-6}$alkynyl substituted with one hydroxycarbonyl; $C_{3-6}$cycloalkyl; $C_{3-6}$cycloalkyl substituted with one hydroxycarbonyl; $C_{3-6}$cycloalkenyl; $C_{3-6}$cycloalkenyl substituted with one hydroxycarbonyl; $C_{1-6}$alkyloxy; polyhalo$C_{1-4}$alkyl; cyano; nitro; $B(OH)_2$; hydroxycarbonyl; CO—NHOH; CO—$NR^9R^{10}$; CO—NH—$NR^9R^{10}$; $NR^9R^{10}$; NH—CO—$R^1$; NH—CO—O—$R^{11}$; NH—CO—NH—$R^{11}$; NH—CS—NH—$R^{11}$; NH—C=(N—CN)—NH—$R^1$; aminosulfonyl; mono- or di($C_{1-4}$alkyl)aminosulfonyl; and Heterocycle;

wherein $R^9$ and $R^{10}$ are each independently selected from hydrogen; $C_{1-6}$alkyl; $SO_2$—$R^{12}$; and $C_{1-6}$alkyl substituted with hydroxy, hydroxycarbonyl, $C_{3-6}$cycloalkyl, $C_{1-4}$alkylcarbonylamino, mono- or di($C_{1-4}$alkyl)amino, or Heterocycle;

$R^{11}$ is $C_{1-6}$alkyl; $C_{3-6}$alkenyl; $C_{3-6}$cycloalkyl; Aryl; Heterocycle; or $C_{1-6}$alkyl substituted with one substituent selected from $C_{3-6}$cycloalkyl, $C_{1-4}$alkyloxy, hydroxy, cyano, hydroxycarbonyl, aminocarbonyl, mono- or di($C_{1-4}$alkyl)aminocarbonyl, $C_{1-4}$alkylcarbonylamino, and Heterocycle;

$R^{12}$ is $C_{1-4}$alkyl, $C_{3-6}$cycloalkyl, or $C_{1-4}$alkyl substituted with one $C_{3-6}$cycloalkyl, Heteroaryl is thienyl, imidazolyl, pyrazolyl, thiazolyl, pyridinyl, 1-benzopyrazolyl, 2,3-dihydro-1H-indolyl, 2-oxo-2,3-dihydro-1H-indolyl, quinolinyl, 2-oxo-quinolinyl, benzimidazolyl, cinnolinyl, or 2H-chromenyl, wherein each Heteroaryl is optionally substituted with one or two substituents each independently selected from $C_{1-4}$alkyl, halo, amino, aminocarbonyl, and NH—CO—$C_{3-6}$cycloalkyl;

Heterocycle is azetidinyl, tetrahydrofuranyl, pyrrolidinyl, furanyl, thienyl, imidazolyl, pyrazolyl, thiazolyl, pyridinyl, pyrimidinyl, pyrazinyl, 2-oxo-azepanyl, 2,5-dioxopyrrolidinyl, or 3-oxo-2,3-dihydro-1,2-oxazolyl; wherein each Heterocycle is optionally substituted with one or two substituents each independently selected from $C_{1-4}$alkyl, $C_{3-6}$cycloalkyl, halo and hydroxycarbonyl;

Aryl is phenyl substituted with one or two substituents each independently selected from hydrogen, halogen, $C_{1-4}$alkyl, $C_{1-4}$alkyloxy, and trifluoromethyl;

or a pharmaceutically acceptable acid addition salt thereof.

A fifth group of compounds are those compounds of formula (I),
including any stereochemically isomeric form thereof, wherein
X is $CR^6$ wherein $R^6$ is hydrogen;
the

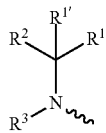

(a-2)

moiety is a radical of formula:

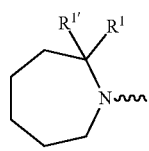

wherein $R^1$ is $CH_3$, and $R^{1'}$ is hydrogen;

$R^4$ is $C_{1-6}$alkyl; $C_{3-6}$alkenyl, polyhalo$C_{1-4}$alkyl; $C_{1-4}$alkyl substituted with one $C_{3-6}$cycloalkyl; $C_{3-6}$cycloalkyl; $C_{3-6}$cycloalkyl substituted with one or two substituents each individually selected from hydroxy, halo, cyano, $C_{1-4}$alkyl, $C_{1-4}$alkyloxy, polyhalo$C_{1-4}$alkyl, and polyhalo$C_{1-4}$alkyloxy;

$R^5$ is naphthyl substituted with 1, 2 or 3 substituents each independently selected from halo and hydroxycarbonyl; or
phenyl substituted with 1, 2 or 3 substituents each independently selected from hydroxy;
halo;
$C_{1-6}$alkyl;
$C_{1-6}$alkyl substituted with one, two or three substituents each independently selected from halo, hydroxy, hydroxycarbonyl, aminocarbonyl, Heterocycle, $C_{3-6}$cycloalkyl, $C_{3-6}$cycloalkyl substituted with one or two substituents each independently selected from $C_{1-4}$alkyl, halo, hydroxycarbonyl, and $C_{1-4}$alkyl substituted with hydroxycarbonyl;
$C_{3-6}$alkenyl;
$C_{3-6}$alkenyl substituted with one or two substituents selected from $C_{1-6}$alkyl, hydroxy, hydroxycarbonyl and aminocarbonyl;
$C_{3-6}$alkynyl;
$C_{3-6}$alkynyl substituted with one hydroxycarbonyl;
$C_{3-6}$cycloalkyl;
$C_{3-6}$cycloalkyl substituted with one, two or three substituents each independently selected from $C_{1-4}$alkyl, halo, hydroxycarbonyl, and $C_{1-4}$alkyl substituted with hydroxycarbonyl;
$C_{3-6}$cycloalkenyl;
$C_{3-6}$cycloalkenyl substituted with one hydroxycarbonyl;
$C_{1-6}$alkyloxy optionally substituted with hydroxycarbonyl;
polyhalo$C_{1-4}$alkyl;
polyhalo$C_{1-4}$alkyloxy; or
Heterocycle;
wherein
Heterocycle is azetidinyl, tetrahydrofuranyl, pyrrolidinyl, furanyl, thienyl, imidazolyl, pyrazolyl, thiazolyl, oxazolyl, isoxazolyl, 1,2,4-oxadiazolyl, 2,5-dihydro-1H-pyrrolyl, pyridinyl, pyrimidinyl, pyrazinyl, 2-oxo-azepanyl, 2,5-dioxopyrrolidinyl, or 3-oxo-2,3-dihydro-1,2-oxazolyl; wherein each Heterocycle is optionally substituted with one or two substituents each independently selected from $C_{1-4}$alkyl, $C_{3-6}$cycloalkyl, halo, hydroxy$C_{1-4}$alkyl, polyhalo$C_{1-4}$alkyl, hydroxycarbonyl, and $C_{1-4}$alkyl substituted with hydroxycarbonyl;

or a pharmaceutically acceptable acid addition salt thereof.

A sixth group of compounds are those compounds of formula (I),
including any stereochemically isomeric form thereof, wherein
X is $CR^6$ wherein $R^6$ is hydrogen;
the

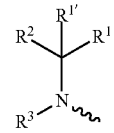

moiety is a radical of formula:

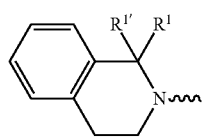

(a-13)

wherein $R^1$ is $CH_3$, and $R^{1'}$ is hydrogen;

$R^4$ is $C_{1-6}$alkyl; $C_{3-6}$alkenyl, polyhalo$C_{1-4}$alkyl; $C_{1-4}$alkyl substituted with one $C_{3-6}$cycloalkyl; $C_{3-6}$cycloalkyl; $C_{3-6}$cycloalkyl substituted with one or two substituents each individually selected from hydroxy, halo, cyano, $C_{1-4}$alkyl, $C_{1-4}$alkyloxy, polyhalo$C_{1-4}$alkyl, and polyhalo$C_{1-4}$alkyloxy; or $NR^7R^8$ wherein $R^7$ and $R^8$ are taken together with the nitrogen to which they are attached to form azetidinyl, pyrrolidinyl or piperidinyl;

$R^5$ is phenyl substituted with 1, 2 or 3 substituents each independently selected from hydroxy;

halo;

$C_{1-6}$alkyl;

$C_{1-6}$alkyl substituted with one, two or three substituents each independently selected from halo, hydroxy, hydroxycarbonyl, aminocarbonyl, Heterocycle, $C_{3-6}$cycloalkyl, $C_{3-6}$cycloalkyl substituted with one or two substituents each independently selected from $C_{1-4}$alkyl, halo, hydroxycarbonyl, and $C_{1-4}$alkyl substituted with hydroxycarbonyl;

$C_{3-6}$alkenyl;

$C_{3-6}$alkenyl substituted with one or two substituents selected from $C_{1-6}$alkyl, hydroxy, hydroxycarbonyl and aminocarbonyl;

$C_{3-6}$alkynyl;

$C_{3-6}$alkynyl substituted with one hydroxycarbonyl;

$C_{3-6}$cycloalkyl;

$C_{3-6}$cycloalkyl substituted with one, two or three substituents each independently selected from $C_{1-4}$alkyl, halo, hydroxycarbonyl, and $C_{1-4}$alkyl substituted with hydroxycarbonyl;

$C_{3-6}$cycloalkenyl;

$C_{3-6}$cycloalkenyl substituted with one hydroxycarbonyl;

$C_{1-6}$alkyloxy optionally substituted with hydroxycarbonyl;

polyhalo$C_{1-4}$alkyl; or polyhalo$C_{1-4}$alkyloxy;

Heterocycle;

wherein

Heterocycle is azetidinyl, tetrahydrofuranyl, pyrrolidinyl, furanyl, thienyl, imidazolyl, pyrazolyl, thiazolyl, oxazolyl, isoxazolyl, 1,2,4-oxadiazolyl, 2,5-dihydro-1H-pyrrolyl, pyridinyl, pyrimidinyl, pyrazinyl, 2-oxo-azepanyl, 2,5-dioxopyrrolidinyl, or 3-oxo-2,3-dihydro-1,2-oxazolyl; wherein each Heterocycle is optionally substituted with one or two substituents each independently selected from $C_{1-4}$alkyl, $C_{3-6}$cycloalkyl, halo, hydroxy$C_{1-4}$alkyl, polyhalo$C_{1-4}$alkyl, hydroxycarbonyl, and $C_{1-4}$alkyl substituted with hydroxycarbonyl;

or a pharmaceutically acceptable acid addition salt thereof.

A seventh group of compounds are those compounds of formula (I), including any stereochemically isomeric form thereof, wherein X is $CR^6$ wherein $R^6$ is hydrogen;

the

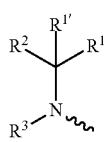

moiety is a radical of formula:

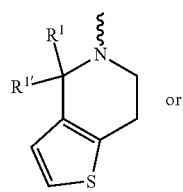

(a-18)

or

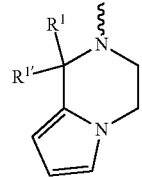

(a-22)

wherein $R^1$ is $CH_3$, and $R^{1'}$ is hydrogen;

$R^4$ is $C_{1-6}$alkyl; $C_{3-6}$alkenyl, polyhalo$C_{1-4}$alkyl; $C_{1-4}$alkyl substituted with one $C_{3-6}$cycloalkyl; $C_{3-6}$cycloalkyl; $C_{3-6}$cycloalkyl substituted with one or two substituents each individually selected from hydroxy, halo, cyano, $C_{1-4}$alkyl, $C_{1-4}$alkyloxy, polyhalo$C_{1-4}$alkyl, and polyhalo$C_{1-4}$alkyloxy;

$R^5$ is phenyl substituted with 1, 2 or 3 substituents each independently selected from hydroxy;

halo;

$C_{1-6}$alkyl;

$C_{1-6}$alkyl substituted with one, two or three substituents each independently selected from halo, hydroxy, hydroxycarbonyl, aminocarbonyl, Heterocycle, $C_{3-6}$cycloalkyl, $C_{3-6}$cycloalkyl substituted with one or two substituents each independently selected from $C_{1-4}$alkyl, halo, hydroxycarbonyl, and $C_{1-4}$alkyl substituted with hydroxycarbonyl;

$C_{3-6}$alkenyl;

$C_{3-6}$alkenyl substituted with one or two substituents selected from $C_{1-6}$alkyl, hydroxy, hydroxycarbonyl and aminocarbonyl;

$C_{3-6}$alkynyl;

$C_{3-6}$alkynyl substituted with one hydroxycarbonyl;

$C_{3-6}$cycloalkyl;

$C_{3-6}$cycloalkyl substituted with one, two or three substituents each independently selected from $C_{1-4}$alkyl, halo, hydroxycarbonyl, and $C_{1-4}$alkyl substituted with hydroxycarbonyl;

$C_{3-6}$cycloalkenyl;

$C_{3-6}$cycloalkenyl substituted with one hydroxycarbonyl;

$C_{1-6}$alkyloxy optionally substituted with hydroxycarbonyl;

polyhalo$C_{1-4}$alkyl; or polyhalo$C_{1-4}$alkyloxy;

or a pharmaceutically acceptable acid addition salt thereof.

An eight group of compounds are compounds of formula (I-e)

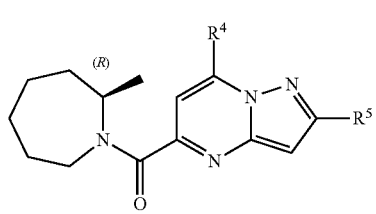

(I-e)

including any stereochemically isomeric form thereof, wherein $R^4$ is $C_{1-6}$alkyl; $C_{3-6}$alkenyl, polyhalo$C_{1-4}$alkyl; $C_{1-4}$alkyl substituted with one $C_{3-6}$cycloalkyl; $C_{3-6}$cycloalkyl; $C_{3-6}$cycloalkyl substituted with one or two substituents each individually selected from hydroxy, halo, cyano, C$_{1-4}$alkyl, C$_{1-4}$alkyloxy, polyhaloC$_{1-4}$alkyl, and polyhaloC$_{1-4}$alkyloxy R$^5$ is naphthyl substituted with 1, 2 or 3 substituents each independently selected from halo and hydroxycarbonyl; or phenyl substituted with 1, 2 or 3 substituents each independently selected from hydroxy;
halo;
C$_{1-6}$alkyl;
C$_{1-6}$alkyl substituted with one, two or three substituents each independently selected from halo, hydroxy, hydroxycarbonyl, aminocarbonyl, Heterocycle, C$_{3-6}$cycloalkyl, C$_{3-6}$cycloalkyl substituted with one or two substituents each independently selected from C$_{1-4}$alkyl, halo, hydroxycarbonyl, and C$_{1-4}$alkyl substituted with hydroxycarbonyl;
C$_{3-6}$alkenyl;
C$_{3-6}$alkenyl substituted with one or two substituents selected from C$_{1-6}$alkyl, hydroxy, hydroxycarbonyl and aminocarbonyl;
C$_{3-6}$alkynyl;
C$_{3-6}$alkynyl substituted with one hydroxycarbonyl;
C$_{3-6}$cycloalkyl;
C$_{3-6}$cycloalkyl substituted with one, two or three substituents each independently selected from C$_{1-4}$alkyl, halo, hydroxycarbonyl, and C$_{1-4}$alkyl substituted with hydroxycarbonyl;
C$_{3-6}$cycloalkenyl;
C$_{3-6}$cycloalkenyl substituted with one hydroxycarbonyl;
C$_{1-6}$alkyloxy optionally substituted with hydroxycarbonyl;
polyhaloC$_{1-4}$alkyl;
polyhaloC$_{1-4}$alkyloxy; or
Heterocycle;
wherein
Heterocycle is azetidinyl, pyrrolidinyl, pyrazolyl or pyridinyl; wherein each Heterocycle is optionally substituted with one or two substituents each independently selected from C$_{1-4}$alkyl, C$_{3-6}$cycloalkyl, halo, hydroxyC$_{1-4}$alkyl, polyhaloC$_{1-4}$alkyl, hydroxycarbonyl, and C$_{1-4}$alkyl substituted with hydroxycarbonyl;
or a pharmaceutically acceptable acid addition salt thereof.

A ninth group of compounds are compounds of formula (I-f)

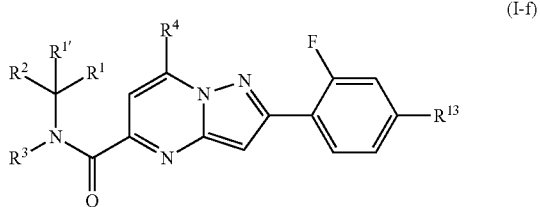

(I-f)

including any stereochemically isomeric form thereof, wherein
the

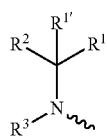

moiety is a radical of formula

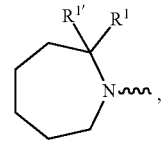

(a-2)

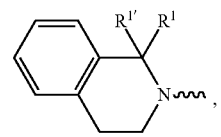

(a-13)

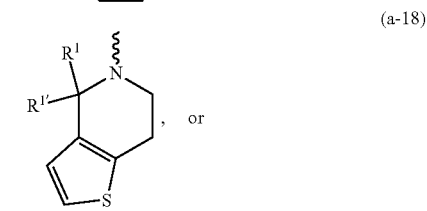

(a-18), or

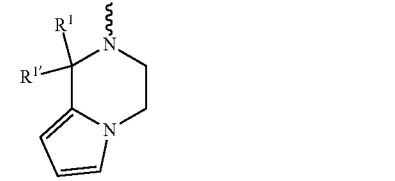

(a-22)

wherein R$^1$ is CH$_3$, and R$^{1'}$ is hydrogen;

R$^4$ is C$_{1-6}$alkyl; C$_{3-6}$alkenyl, polyhaloC$_{1-4}$alkyl; C$_{1-4}$alkyl substituted with one C$_{3-6}$cycloalkyl; C$_{3-6}$cycloalkyl; C$_{3-6}$cycloalkyl substituted with one or two substituents each individually selected from hydroxy, halo, cyano, C$_{1-4}$alkyl, C$_{1-4}$alkyloxy, polyhaloC$_{1-4}$alkyl, and polyhaloC$_{1-4}$alkyloxy R$^{13}$ is C$_{3-6}$alkenyl substituted with one or two substituents selected from C$_{1-6}$alkyl, hydroxy, hydroxycarbonyl and aminocarbonyl;
C$_{3-6}$cycloalkyl substituted with one, two or three substituents each independently selected from C$_{1-4}$alkyl, halo, hydroxycarbonyl, and C$_{1-4}$alkyl substituted with hydroxycarbonyl; or
Heterocycle;
wherein
Heterocycle is azetidinyl, pyrrolidinyl, pyrazolyl or pyridinyl; wherein each Heterocycle is optionally substituted with one or two substituents each independently selected from C$_{1-4}$alkyl, C$_{3-6}$cycloalkyl, halo, hydroxyC$_{1-4}$alkyl, polyhaloC$_{1-4}$alkyl, hydroxycarbonyl, and C$_{1-4}$alkyl substituted with hydroxycarbonyl;
or a pharmaceutically acceptable acid addition salt thereof.

Interesting compounds of formula (I) are those compounds of formula (I) wherein one or more of the following restrictions apply:
a) X is N; or
b) X is CR$^6$ wherein R$^6$ is hydrogen or halo; or
c) R$^1$ is CH$_3$, and R$^{1'}$ is hydrogen; or
d) R$^1$ and R$^{1'}$ are taken together with the carbon atom to which they are attached to form cyclopropyl; or
e) R$^3$ is CH$_3$ or CH$_2$CH$_3$; or
f) R$^4$ is C$_{1-6}$alkyl in particular ethyl; or
g) R$^4$ is C$_{3-6}$cycloalkyl in particular cyclopropyl; or
h) R$^5$ is phenyl substituted with 1, 2 or 3 substituents each independently selected from hydroxy; halo; C$_{1-6}$alkyl; C$_{1-6}$alkyl substituted with one substituent selected from hydroxy, hydroxycarbonyl and aminocarbonyl; C$_{3-6}$alkenyl; C$_{3-6}$alkenyl substituted with one or two substituents selected from C₁₋₆alkyl, hydroxy, hydroxycarbonyl and aminocarbonyl; C₃₋₆alkynyl; C₃₋₆alkynyl substituted with one hydroxycarbonyl; C₃₋₆cycloalkyl; C₃₋₆cycloalkyl substituted with one hydroxycarbonyl; C₃₋₆cycloalkenyl; C₃₋₆cycloalkenyl substituted with one hydroxycarbonyl; C₁₋₆alkyloxy; polyhaloC₁₋₄alkyl; cyano; nitro; B(OH)₂; hydroxycarbonyl; CO—NHOH; CO—NR⁹R¹⁰; CO—NH—NR⁹R¹⁰; NR⁹R¹⁰; NH—CO—R¹¹; NH—CO—O—R¹¹; NH—CO—NH—R¹¹; NH—CS—NH—R¹¹; NH—C=(N—CN)—NH—R¹¹; aminosulfonyl; mono- or di(C₁₋₄alkyl)aminosulfonyl; and Heterocycle; or i) R⁵ is phenyl substituted with 1, 2 or 3 substituents each independently selected from halo; or C₁₋₆alkyl substituted with one substituent selected from hydroxy, hydroxycarbonyl and aminocarbonyl; or j) R⁵ is phenyl substituted with 1, 2 or 3 substituents each independently selected from halo, or C₃₋₆alkenyl substituted with one or two substituents selected from C₁₋₆alkyl, hydroxy, hydroxycarbonyl and aminocarbonyl; and k) R⁵ is phenyl substituted with 1, 2 or 3 substituents each independently selected from halo, or C₃₋₆cycloalkyl substituted with hydroxycarbonyl.

Specific examples of compounds of formula (I) are:

Co. No. (F15)

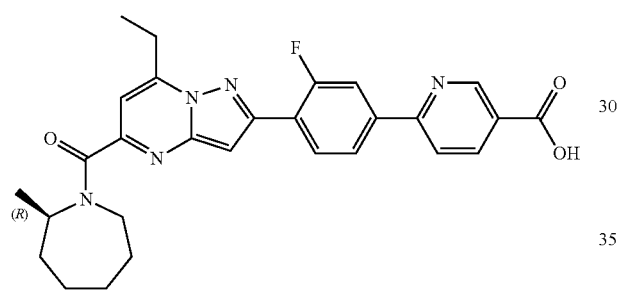

Co. No. (F36)

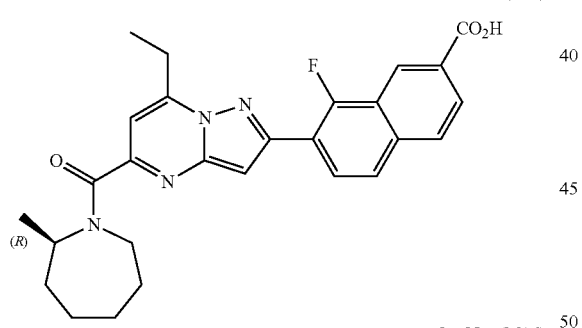

Co. No. (M16)

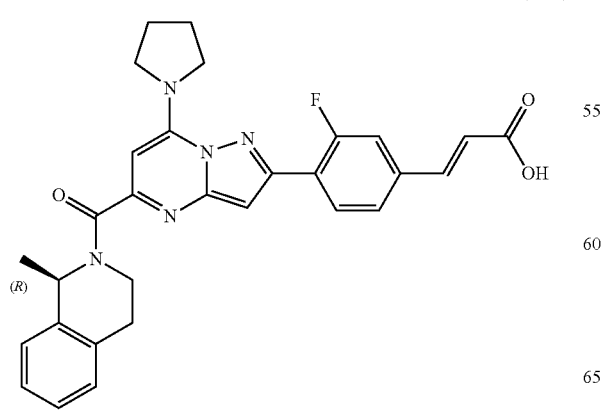

Co. No. (M27)

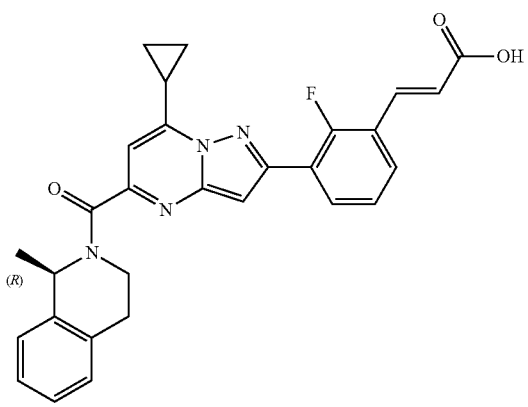

Co. No. (M44)

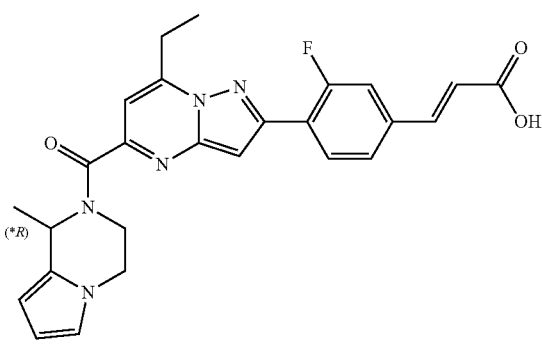

Co. No. (M46)

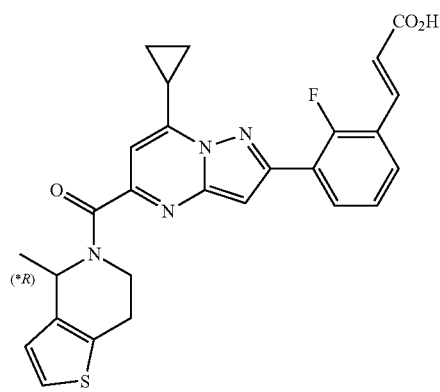

Co. No. (O2)

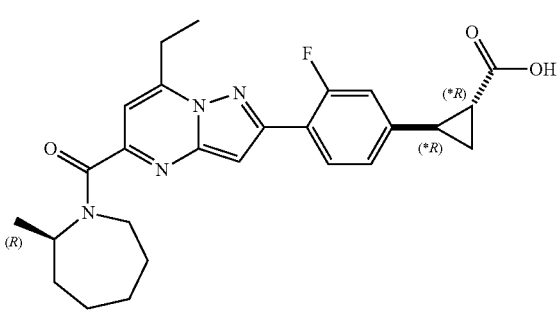

Co. No. (O5)
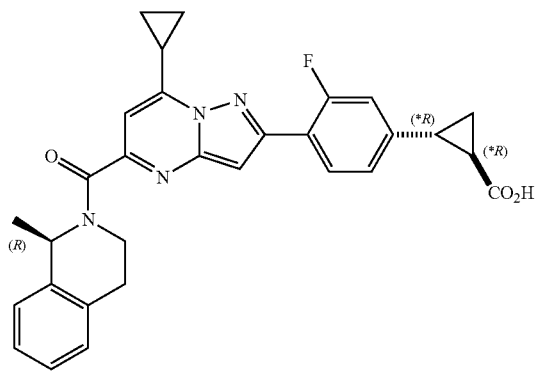
Co. No. (W1)
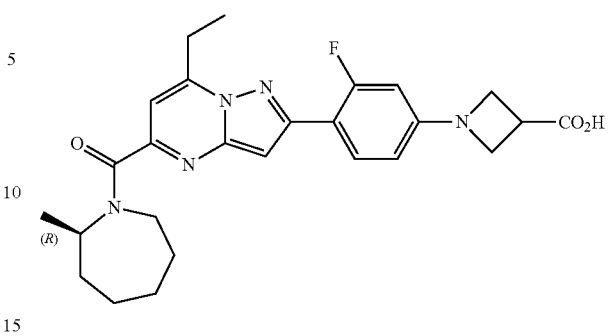
Co. No. (O7)
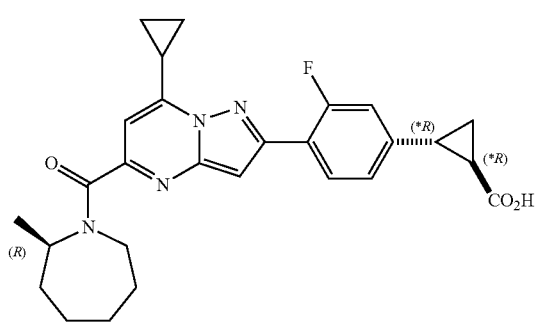
Co. No. (W2)
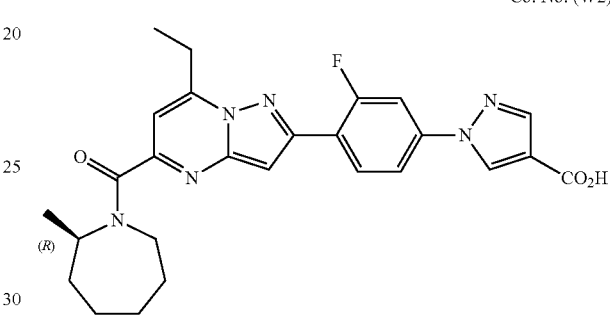
Co. No. (O20)
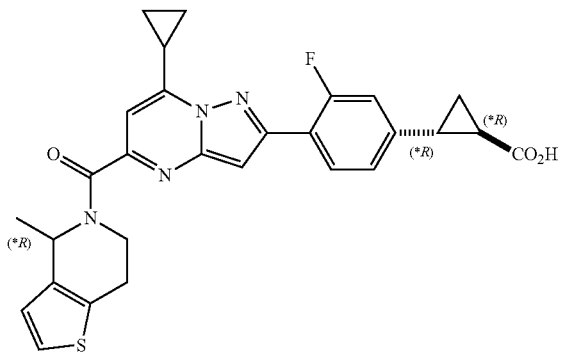
Co. No. (W7)
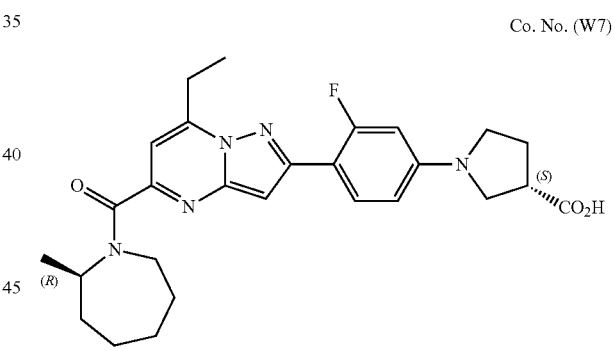
Co. No. (O22)
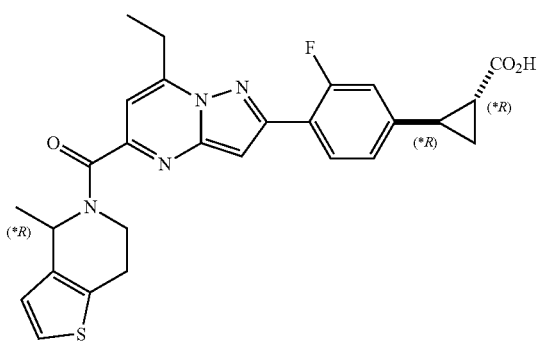
Co. No. (W33)
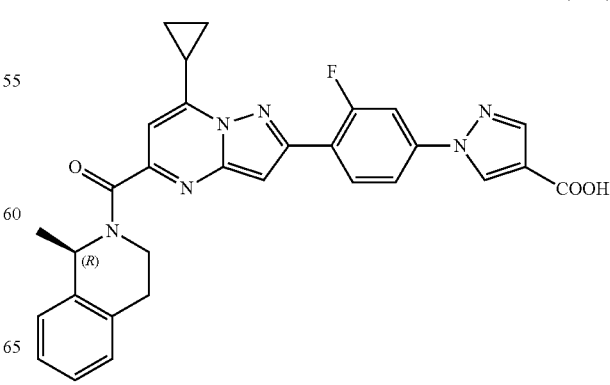

-continued

Co. No. (W37)

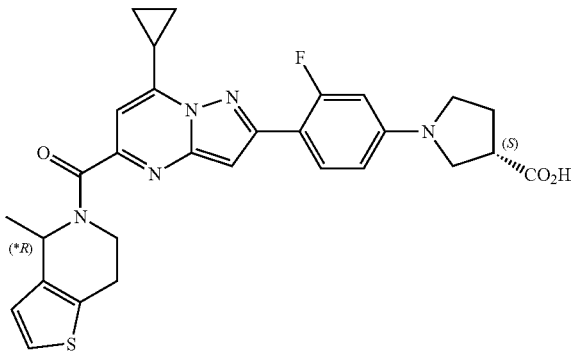

Co. No. (W38)

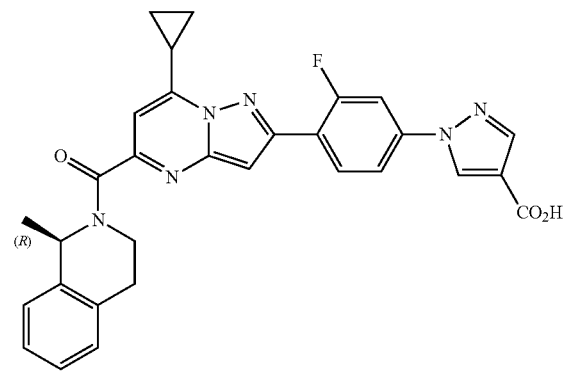

Co. No. (W43)

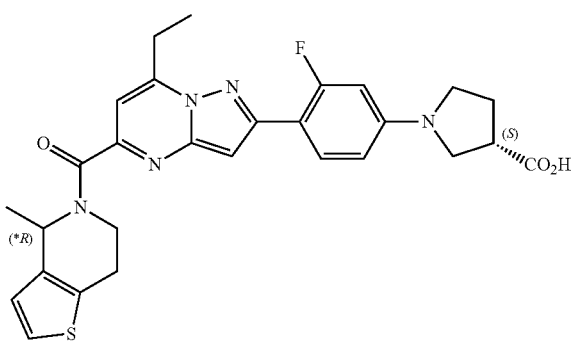

Co. No. (W41)

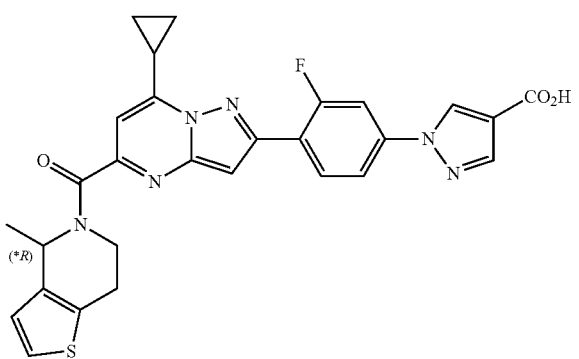

-continued

Co. No. (W51)

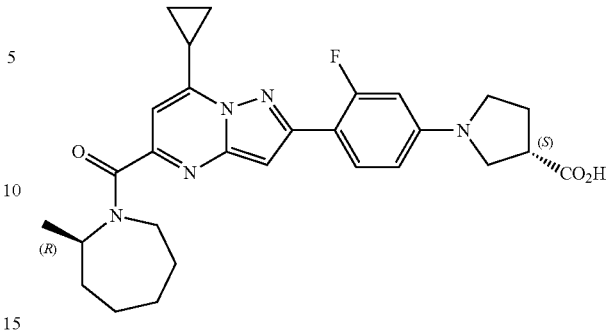

Compounds of formula (I) can generally be prepared by reacting an intermediate of formula (II) with an intermediate of formula (III) in a reaction-inert solvent, such as dichloromethane or DMF, in the present of a suitable reagent, such as BOP ((benzotriazol-1-yloxy)tris(dimethylamino)phosphonium hexafluorophosphate), and a base such as diisopropylethylamine or triethylamine.

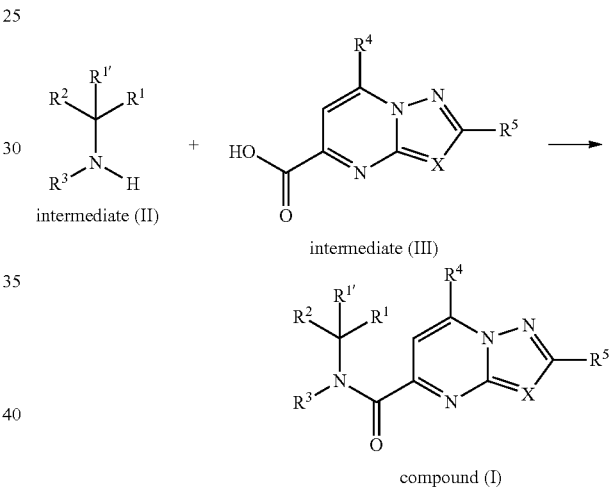

Other synthetic pathways for preparing compounds of formula (I) have been described in the experimental party as general methods of preparation and specific working examples.

The compounds of formula (I) may further be prepared by converting compounds of formula (I) into each other according to art-known group transformation reactions.

The starting materials and some of the intermediates are known compounds and are commercially available or may be prepared according to conventional reaction procedures generally known in the art.

The compounds of formula (I) as prepared in the hereinabove described processes may be synthesized in the form of racemic mixtures of enantiomers which can be separated from one another following art-known resolution procedures. Those compounds of formula (I) that are obtained in racemic form may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The compounds of formula (I) show antiviral properties. Viral infections treatable using the compounds and methods of the present invention include those infections brought on by ortho- and paramyxoviruses and in particular by human and bovine respiratory syncytial virus (RSV). A number of the compounds of this invention moreover are active against mutated strains of RSV. Additionally, many of the compounds of this invention show a favorable pharmacokinetic profile and have attractive properties in terms of bioavailabilty, including an acceptable half-life, AUC and peak values and lacking unfavourable phenomena such as insufficient quick onset and tissue retention.

The in vitro antiviral activity against RSV of the present compounds was tested in a test as described in the experimental part of the description, and may also be demonstrated in a virus yield reduction assay. The in vivo antiviral activity against RSV of the present compounds may be demonstrated in a test model using cotton rats as described in Wyde et al. in Antiviral Research, 38, p. 31-42(1998).

Additionally the present invention provides pharmaceutical compositions comprising at least one pharmaceutically acceptable carrier and a therapeutically effective amount of a compound of formula (I). Also provided are pharmaceutical compositions comprising a pharmaceutically acceptable carrier, a therapeutically active amount of a compound of formula (I), and another antiviral agent, in particular a RSV inhibiting compound.

In order to prepare the pharmaceutical compositions of this invention, an effective amount of the particular compound, in base or acid addition salt form, as the active ingredient is combined in intimate admixture with at least one pharmaceutically acceptable carrier, which carrier may take a wide variety of forms depending on the form of preparation desired for administration. These pharmaceutical compositions are desirably in unitary dosage form suitable, preferably, for oral administration, rectal administration, percutaneous administration or parenteral injection.

For example in preparing the compositions in oral dosage form, any of the usual liquid pharmaceutical carriers may be employed, such as for instance water, glycols, oils, alcohols and the like in the case of oral liquid preparations such as suspensions, syrups, elixirs and solutions; or solid pharmaceutical carriers such as starches, sugars, kaolin, lubricants, binders, disintegrating agents and the like in the case of powders, pills, capsules and tablets. Because of their easy administration, tablets and capsules represent the most advantageous oral dosage unit form, in which case solid pharmaceutical carriers are obviously employed. For parenteral injection compositions, the pharmaceutical carrier will mainly comprise sterile water, although other ingredients may be included in order to improve solubility of the active ingredient. Injectable solutions may be prepared for instance by using a pharmaceutical carrier comprising a saline solution, a glucose solution or a mixture of both. Injectable suspensions may also be prepared by using appropriate liquid carriers, suspending agents and the like. In compositions suitable for percutaneous administration, the pharmaceutical carrier may optionally comprise a penetration enhancing agent and/or a suitable wetting agent, optionally combined with minor proportions of suitable additives which do not cause a significant deleterious effect to the skin. Said additives may be selected in order to facilitate administration of the active ingredient to the skin and/or be helpful for preparing the desired compositions. These topical compositions may be administered in various ways, e.g., as a transdermal patch, a spot-on or an ointment. Addition salts of the compounds of formula (I), due to their increased water solubility over the corresponding base form, are obviously more suitable in the preparation of aqueous compositions.

It is especially advantageous to formulate the pharmaceutical compositions of the invention in dosage unit form for ease of administration and uniformity of dosage. "Dosage unit form" as used herein refers to physically discrete units suitable as unitary dosages, each unit containing a predetermined amount of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

For oral administration, the pharmaceutical compositions of the present invention may take the form of solid dose forms, for example, tablets (both swallowable and chewable forms), capsules or gelcaps, prepared by conventional means with pharmaceutically acceptable excipients and carriers such as binding agents (e.g. pregelatinised maize starch, polyvinylpyrrolidone, hydroxypropylmethylcellulose and the like), fillers (e.g. lactose, microcrystalline cellulose, calcium phosphate and the like), lubricants (e.g. magnesium stearate, talc, silica and the like), disintegrating agents (e.g. potato starch, sodium starch glycollate and the like), wetting agents (e.g. sodium laurylsulphate) and the like. Such tablets may also be coated by methods well known in the art.

Liquid preparations for oral administration may take the form of e.g. solutions, syrups or suspensions, or they may be formulated as a dry product for admixture with water and/or another suitable liquid carrier before use. Such liquid preparations may be prepared by conventional means, optionally with other pharmaceutically acceptable additives such as suspending agents (e.g. sorbitol syrup, methylcellulose, hydroxypropylmethylcellulose or hydrogenated edible fats), emulsifying agents (e.g. lecithin or acacia), non aqueous carriers (e.g. almond oil, oily esters or ethyl alcohol), sweeteners, flavours, masking agents and preservatives (e.g. methyl or propyl p-hydroxybenzoates or sorbic acid).

Pharmaceutically acceptable sweeteners useful in the pharmaceutical compositions of the invention comprise preferably at least one intense sweetener such as aspartame, acesulfame potassium, sodium cyclamate, alitame, a dihydrochalcone sweetener, monellin, stevioside sucralose (4,1', 6'-trichloro-4,1',6'-trideoxygalactosucrose) or, preferably, saccharin, sodium or calcium saccharin, and optionally at least one bulk sweetener such as sorbitol, mannitol, fructose, sucrose, maltose, isomalt, glucose, hydrogenated glucose syrup, xylitol, caramel or honey. Intense sweeteners are conveniently used in low concentrations. For example, in the case of sodium saccharin, the said concentration may range from about 0.04% to 0.1% (weight/volume) of the final formulation. The bulk sweetener can effectively be used in larger concentrations ranging from about 10% to about 35%, preferably from about 10% to 15% (weight/volume).

The pharmaceutically acceptable flavours which can mask the bitter tasting ingredients in the low-dosage formulations are preferably fruit flavours such as cherry, raspberry, black currant or strawberry flavour. A combination of two flavours may yield very good results. In the high-dosage formulations, stronger pharmaceutically acceptable flavours may be required such as Caramel Chocolate, Mint Cool, Fantasy and the like. Each flavour may be present in the final composition in a concentration ranging from about 0.05% to 1% (weight/volume). Combinations of said strong flavours are advantageously used. Preferably a flavour is used that does not undergo any change or loss of taste and/or color under the circumstances of the formulation.

The compounds of formula (I) may be formulated for parenteral administration by injection, conveniently intravenous, intra-muscular or subcutaneous injection, for example by bolus injection or continuous intravenous infusion. Formulations for injection may be presented in unit dosage form, e.g. in ampoules or multi-dose containers, including an added preservative. They may take such forms as suspensions, solutions or emulsions in oily or aqueous vehicles, and may contain formulating agents such as isotonizing, suspending, stabilizing and/or dispersing agents. Alternatively, the active ingredient may be present in powder form for mixing with a suitable vehicle, e.g. sterile pyrogen free water, before use.

The compounds of formula (I) may also be formulated in rectal compositions such as suppositories or retention enemas, e.g. containing conventional suppository bases such as cocoa butter and/or other glycerides.

In general it is contemplated that an antivirally effective daily amount would be from 0.01 mg/kg to 500 mg/kg body weight, more preferably from 0.1 mg/kg to 50 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention. The effective daily amount ranges mentioned hereinabove are therefore only guidelines.

Also, the combination of another antiviral agent and a compound of formula (I) can be used as a medicine. Thus, the present invention also relates to a product containing (a) a compound of formula (I), and (b) another antiviral compound, as a combined preparation for simultaneous, separate or sequential use in antiviral treatment. The different drugs may be combined in a single preparation together with pharmaceutically acceptable carriers. For instance, the compounds of the present invention may be combined with interferon-beta or tumor necrosis factor-alpha in order to treat or prevent RSV infections. Other antiviral compounds (b) to be combined with a compound of formula (I) for use in the treatment of RSV are RSV fusion inhibitors or RSV polymerase inhibitors. Specific antiviral compounds for combination with any of the compounds of formula (I) that are useful in the treatment of RSV are the RSV inhibiting compounds selected from ribavirin, 4'-chloromethyl-2'-deoxy-3',5'-di-O-isobutyryl-2'-fluorocytidine (ALS-8176), N-(2-((S)-2-(5-((S)-3-aminopyrrolidin-1-yl)-6-methylpyrazolo[1,5-a]pyrimidin-2-yl)piperidine-1-carbonyl)-4-chlorophenyl)methanesulfonamide (GS-5806), MDT-637, BTA-9881, BMS-433771, YM-543403, A-60444, TMC-353121, RFI-641, CL-387626, MBX-300, 3-({5-chloro-1-[3-(methylsulfonyl)propyl]-1H-benzimidazol-2-yl}methyl)-1-cyclopropyl-1,3-dihydro-2H-imidazo[4,5-c]pyridin-2-one, 3-[[7-chloro-3-(2-ethylsulfonyl-ethyl)imidazo[1,2-a]pyridin-2-yl]methyl]-1-cyclopropyl-imidazo[4,5-c]pyridin-2-one, and 3-({5-chloro-1-[3-(methylsulfonyl)propyl]-1H-indol-2-yl}methyl)-1-(2,2,2-trifluoroethyl)-1,3-dihydro-2H-imidazo[4,5-c]pyridin-2-one.

The invention will hereinafter be illustrated with reference to the following, non-limiting examples.

Experimental Part

A. Abbreviations

| | |
|---|---|
| $(CO_2Me)_2$ | dimethyl oxalate |
| $(M + H)^+$ | protonated molecular ion |
| AcCl | acetyl chloride |
| AcOH | acetic acid |
| $Al_2O_3$ | aluminum oxide |
| APTS | p-toluenesulfonic acid monohydrate |
| aq. | aqueous |
| $B_2pin_2$/bispin | bis(pinacolato)diboron |
| Boc | tert-butyloxycarbonyl |
| $Boc_2O$ | di-tert-butyl dicarbonate |
| BOP | (benzotriazol-1-yloxy)tris(dimethylamino)phosphonium hexafluorophosphate - CAS [56602-33-6] |
| br | broad |
| CataCXium PtB ® | 2-(di-tert-butylphosphino)-1-phenylpyrrole, CataCXium Pt ® CAS [672937-61-0] |
| cc | concentrated |
| CDI | carbonyldiimidazole |
| $CH_3CN$ | acetonitrile |
| $CHCl_3$ | chloroform |
| CO | carbon monoxide |
| $CO_2$ | carbon dioxide |
| COMU ® | N-[1-(cyano-2-ethoxy-2-oxoethylideneaminooxy)dimethylamino(morpholino)uronium hexafluorophosphate |
| CPME | cyclopentyl methyl ether (CPME) |
| $CrO_3$ | chromium(VI) oxide CAS [1333-82-0] |
| $Cs_2CO_3$ | cesium carbonate |
| CuBr | copper (I) bromide |
| CuCl | copper(I) chloride |
| CuI | copper(I) iodide |
| $CuSO_4.5H_2O$ | copper(II) sulfate pentahydrate |
| d | doublet |
| DABCO | 1,4-diazabicyclo[2.2.2]octane CAS [280-57-9] |
| DAST | diethylaminosulfur trifluoride |
| DCM | dichloromethane |
| DEAD | 1,2-diazenedicarboxylic acid, 1,2-diethyl ester CAS [1972-28-7] |
| DIEA | diisopropylethylamine |
| DIPE | diisopropyl ether |
| DMA | dimethylacetamide |
| DMAP | 4-dimethylaminopyridine |
| DME | 1,2-dimethoxyethane |
| DMF | dimethylformamide |
| DMSO | dimethyl sulfoxide |
| EDC | 1-ethyl-3-(3-dimethylaminopropyl)carbodiimide - CAS [1892-57-5] |
| eq. | equivalent |
| $Et_2O$ | diethyl ether |
| $Et_3N$ | triethylamine |
| EtOAc | ethyl acetate |
| EtOH | ethanol |
| Grubbs II | benzylidene(1,3-dimesityl-4-imidazolin-2-ylidene)(tricyclohexylphosphine) ruthenium dichloride; Grubbs catalyst 2nd generation CAS [223415-64-3] |
| $H_2O$ | water |

| | |
|---|---|
| H₂SO₄ | sulfuric acid |
| HATU | O-(7-aza-1H-benzotriazol-1-yl)-N,N,N',N'-tetramethyluronium hexafluorophosphate - CAS [148893-10-1] |
| HCl | hydrochloric acid |
| HOAt | 1-hydroxy-7-azabenzotriazole - CAS [39968-33-7] |
| HPLC | high performance liquid chromatography |
| iPrNH₂ | isopropylamine |
| IprOH | 2-propanol |
| K₂CO₃ | potassium carbonate |
| K₃PO₄ | potassium orthophosphate |
| KCN | potassium cyanide |
| KOAc | potassium acetate |
| KOH | potassium hydroxide |
| LiAlH₄ | lithium aluminium hydride |
| LiOH, H₂O | lithium hydroxide monohydrate |
| m/z | mass-to-charge ratio |
| Me | methyl |
| MeLi | methyllithium |
| MeOH | methanol |
| Me—THF | 2-methyl tetrahydrofuran |
| MgSO₄ | magnesium sulfate |
| min | minute(s) |
| N,N'-DMEDA | rac-trans-N,N'-dimethylcyclohexane-1,2-diamine CAS [61798-24-1] |
| N₂ | nitrogen |
| Na₂CO₃ | sodium carbonate |
| Na₂SO₄ | sodium sulfate |
| NaBH₃CN 1M in THF | sodium cyanoborohydride 1M solution in THF |
| NaBH₄ | sodium borohydride |
| NaHCO₃ | sodium bicarbonate |
| NaNO₂ | sodium nitrite |
| NaOH | sodium hydroxide |
| n-BuLi | n-butyllithium |
| NH₄Cl | ammonium chloride |
| NMP | 1-methyl-2-pyrrolidinone |
| PCl₅ | phosphorus pentachloride |
| Pd(OAc)₂ | palladium(II) acetate |
| Pd(PPh₃)₄ | tetrakis triphenylphosphine palladium(0) |
| Pd/C | palladium on carbon (10%) |
| Pd₂(dba)₃ | tris(dibenzylideneacetone)dipalladium CAS [51364-51-3] |
| PdCl₂(dppf) | dichloro [1,1'-bis(diphenylphosphino) ferrocene] palladium(II) CAS [72287-26-4] |
| PdCl₂(dppf)DCM | dichloro[1,1'-bis(diphenylphosphino)ferrocene]palladium(II) dichloromethane adduct CAS [95464-05-4] |
| PdCl₂(dtbpf) | palladium, [1,1'-bis[bis(1,1-dimethylethyl)phosphino]ferrocene-P,P']dichloro CAS [95408-45-0] |
| PdCl₂(PPh₃) | palladium(II)-bis(triphenylphosphine) dichloride CAS [13965-03-2] |
| POCl₃ | phosphoryle chloride |
| PPh₃ | triphenylphosphine |
| PtO₂ | platinum oxide |
| q | quartet |
| Rh/C | rhodium on activated carbon CAS [7440-16-6] |
| rt or RT | room temperature |
| s | singlet |
| SnCl₂•2H₂O | tin(II) chloride dihydrate CAS [10025-69-1] |
| SO₂ | sulfur dioxide |
| t | triplet |
| TBAF | tetrabutylammonium fluoride CAS [429-41-4] |
| TBTU | O-(benzotriazol-1-yl)-N,N,N',N'-tetramethyluronium tetrafluoroborate CAS [125700-67-6] |
| tBuOH | tert-butanol |
| TEA | triethylamine CAS [121-44-8] |
| TES | triethylsilane CAS [617-86-7] |
| TFA | trifluoroacetic acid |
| THF | tetrahydrofuran |
| TMSCl | trimethylsilyl chloride |
| XantPhos | 9,9-dimethyl-4,5-bis(diphenylphosphino)xanthene CAS [161265-03-8] |
| tBuXPhos | bis(1,1-dimethylethyl)[2',4',6'-tris(1-methylethyl)[1,1'-biphenyl]-2-yl]-phosphine CAS [564483-19-8] |
| XPhos | 2,4',6'-diisopropyl-1,1'-biphenyl-2-yldicyclohexylphosphine |
| ZIRAM ® | bis(N,N-dimethylcarbamodithioato-κS,κS')-(T-4)-zinc CAS [137-30-4] |

The stereochemical configuration for some compounds has been designated as R* or S* (or *R or *S) when the absolute stereochemistry is undetermined although the compound itself has been isolated as a single stereoisomer and is enantiomerically pure.

B. Synthesis of the Intermediates

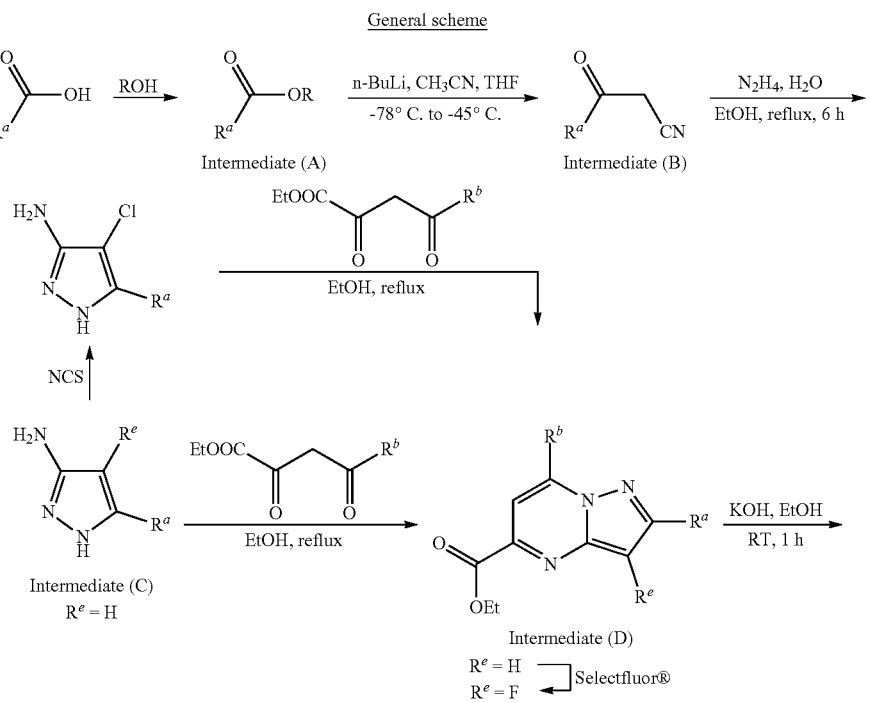

General scheme

Intermediate (A)

Intermediate (B)

Intermediate (C)
R$^e$ = H

Intermediate (D)
R$^e$ = H
R$^e$ = F ⎯⎯ Selectfluor®

-continued

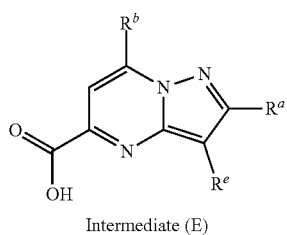 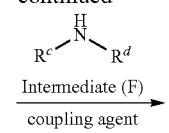 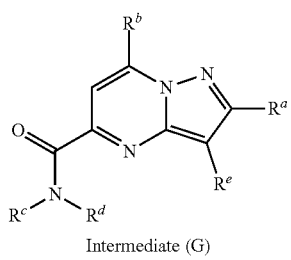

Intermediate (E)     Intermediate (F) coupling agent     Intermediate (G)

Intermediate (A)
Intermediate (A1):

CDI (3.77 g, 23 mmol), then EtOH (2.43 g, 53 mmol) were added to a solution of 5-bromo-3-chloro-2-pyridinecarboxylic acid (5 g, 21 mmol) in THF (100 mL). The reaction mixture was stirred at RT for 24 hours. The solvent was evaporated and the residue was washed with water and extracted with $CHCl_3$. The organic layer was separated, dried over sodium sulfate, filtered and evaporated. The residue was purified by column chromatography (silica gel, $CHCl_3$/ether (1/1)). The pure fractions were collected and the solvent was evaporated to give 5.28 g (100%) of intermediate (A1).

Intermediate (A1)

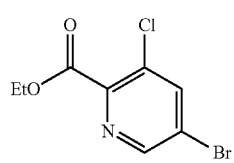

Intermediate (B)
Intermediate (B1):

n-BuLi (1.6M in hexane) (46.13 mL, 73.81 mmol) was added to THF (50 mL) at −78° C. then a solution of $CH_3CN$ (3.86 mL, 73.81 mmol) in THF (40 mL) was added dropwise. The resulting slurry was stirred for 1 h at −78° C. then a solution of methyl-4-bromo-2-fluorobenzoate (8.6 g, 36.90 mmol) in THF (20 mL) was added. The reaction mixture was warmed to −45° C. and allowed to stir for 15 min. The reaction was quenched with HCl 1N and extracted with EtOAc. The organic layer was separated, washed with water then brine, dried over magnesium sulfate and evaporated till dryness to give 8.69 g (97%) of intermediate (B1).

Intermediate (B1)

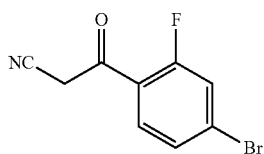

The following compounds were prepared according to the procedure above:

Intermediate (B2)

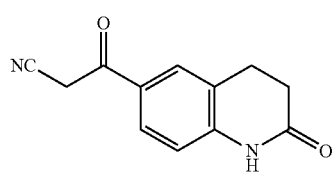

Intermediate (B3)

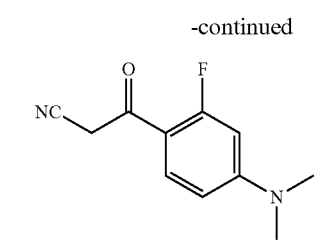

Intermediate (B4)

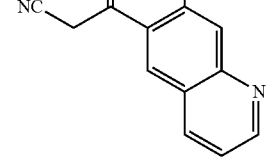

Intermediate (B5)

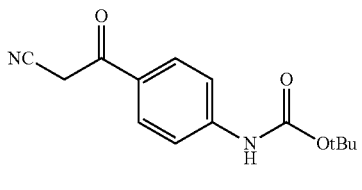

Intermediate (B6)

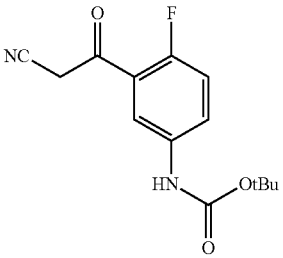

Intermediate (B7)

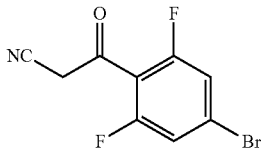

Intermediate (B8)

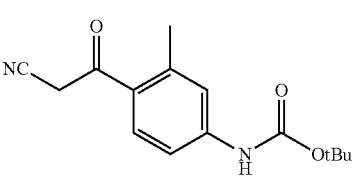

Intermediate (B9)

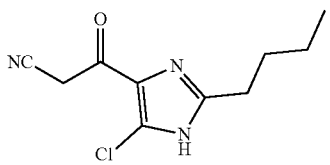

Intermediate (B10)

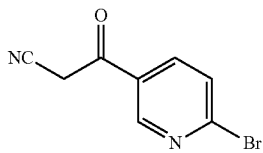

intermediate (B11)

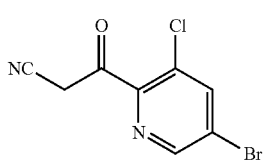

Intermediate (B12):

Prepared according to the above procedure from 2-[bis [(1,1-di-methylethoxy)carbonyl]amino]-4-Thiazolecarboxylic acid ethyl ester CAS [930303-58-5]. The crude product was purified by column chromatography (silica gel, CHCl$_3$). The pure fractions were collected and the solvent was evaporated to give 7.44 g (86%) of intermediate (B12).

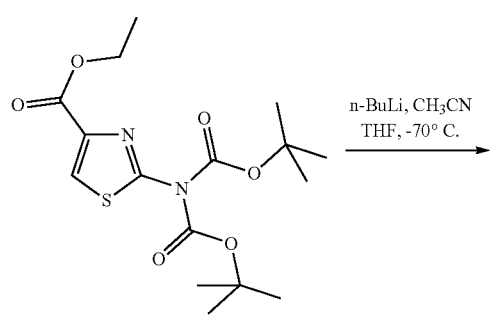

CAS [930303-58-5]

n-BuLi, CH$_3$CN
THF, -70° C.

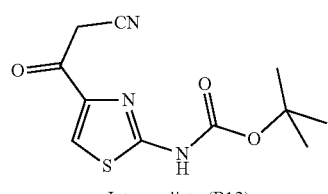

Intermediate (B12)

Intermediate (C)

Intermediate (C1):

A mixture of intermediate (B1) and hydrazine hydrate (6.10 mL, 107.71 mmol) in EtOH (175 mL) was stirred at 85° C. for 8 hours. The mixture was cooled down to RT and evaporated till dryness. The residue was taken up in DCM and stirred at 0° C. for 15 min. The solid was filtered off, washed with DCM and dried (60° C., vacuum) to give 5.61 g (61%) of intermediate (C1).

Intermediate (C1)

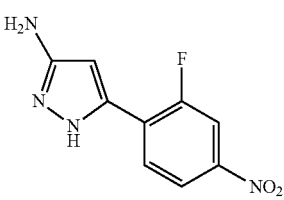

Intermediate (C2):

Hydrazine hydrate (7 mL, 140 mmol) was added to a solution of 2-fluoro-4-nitro-β-oxo-benzenepropanenitrile CAS [276880-94-4] (9.5 g, 45.6 mmol) in EtOH (100 mL) and the resulting mixture was heated at reflux for 5 hours. After completion of the reaction, the solvent was evaporated till dryness. The precipitate was taken up in water, filtered off, washed with water and dried to give 7.15 g (71%) of intermediate (C$_2$).

Intermediate (C2)

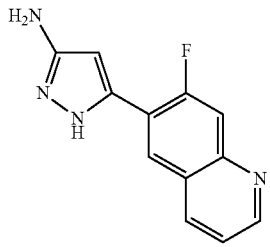

The following compounds were prepared according to the procedure above:

Intermediate (C3)

Intermediate (C4)

Intermediate (C5)

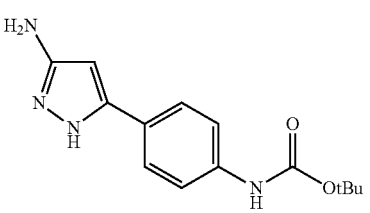

-continued

Intermediate (C6)

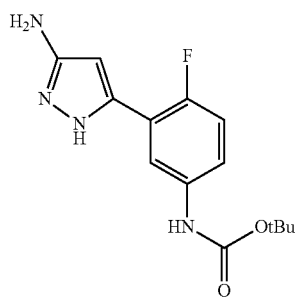

Intermediate (C7)

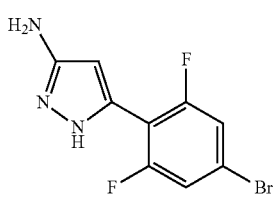

Intermediate (C8)

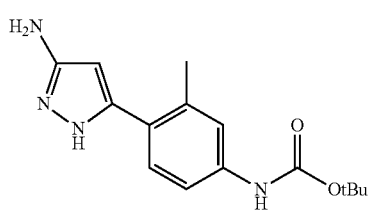

Intermediate (C9)

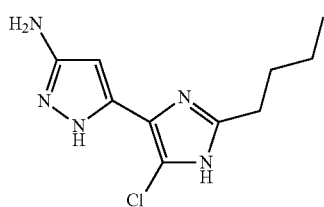

Intermediate (C10)

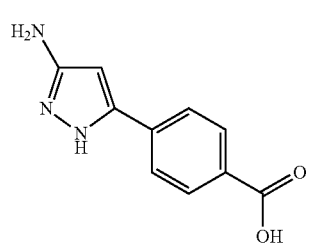

Intermediate (C11)

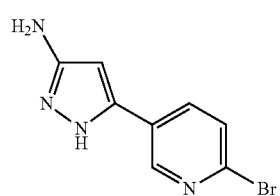

Intermediate (C12):

A mixture of intermediate (B2) (1 g, 47 mmol) and hydrazine hydrate (1 mL) was heated at reflux in AcOH for 1 hour. The solvent was evaporated and the residue was taken up in water. The solid was filtered off and dried to give 1.1 g (87%) of intermediate (C12).

Intermediate (C12)

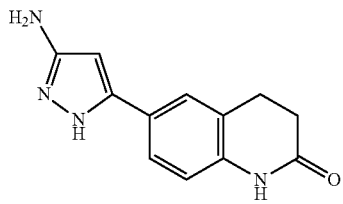

Intermediate (C13):

LiAlH$_4$ (1.0 g, 26.2 mmol) was added portionwise to a solution of methyl-4-(5-amino-1H-pyrazol-3-yl)-benzoate CAS [333337-29-4] (1.9 g, 8.7 mmol) in dry THF (50 mL) at 0° C., after then the reaction mixture was stirred for 6 hours. The reaction mixture was quenched cold by dropwise addition of H$_2$O (2 mL) and NaOH (20%, 3 g). The resulting slurry was filtered, the solid was washed with EtOH and the filtrate was evaporated to dryness to give 1.4 g (85%) of intermediate (C13).

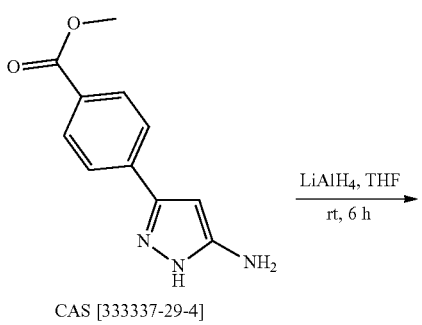

CAS [333337-29-4]

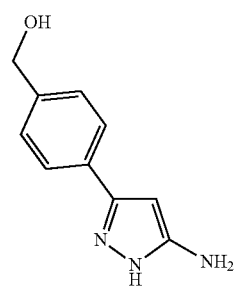

Intermediate (C13)

Intermediate (C14):

N-chlorosuccinimide (300 mg, 2.25 mmol) was added to a mixture of intermediate (C2) (500 mg, 2.25 mmol) in CH$_3$CN (5 mL) and the reaction mixture was stirred at RT overnight. The reaction mixture was poured into water and extracted with EtOAc. The organic layer was dried over sodium sulfate, filtered and the solvent was evaporated to give 570 mg (100%) of intermediate (C14).

Intermediate (C14)

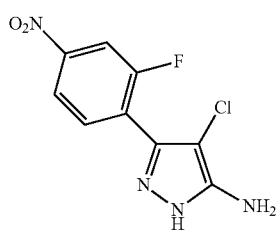

Intermediate (C15):

The mixture of intermediate (B11) (5.33 g, 20 mmol) and hydrazine hydrochloride (1.44 g, 21 mmol) in EtOH (50 mL) was heated at reflux for 12 hours. The solvent was evaporated and the residue was washed with water and extracted with EtOAc. The organic layer was separated, dried over sodium sulfate and evaporated to give 5.25 g (96%) of intermediate (C15).

Intermediate (C15)

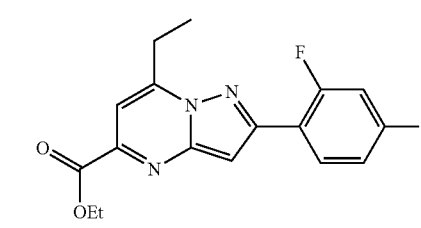

Intermediate (D)

Intermediate (D1):

Intermediate (C1) (1.5 g, 5.86 mmol) and ethyl-2,4-dioxohexanoate CAS [13246-52-1] (1.01 g, 5.86 mmol) in EtOH (15 mL) were heated at reflux overnight. While cooling down to RT, crystallization occurred. The mixture was cooled to 0° C., the solid was filtered off, washed with cold EtOH and dried (vacuum, 60° C.) to give 1.85 g (81%) of intermediate (D1).

Intermediate (D1)

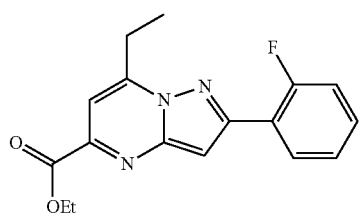

The following compounds were prepared according to the procedure above:

Intermediate (D2)

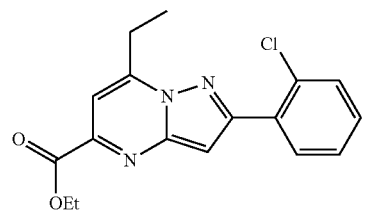

Intermediate (D3)

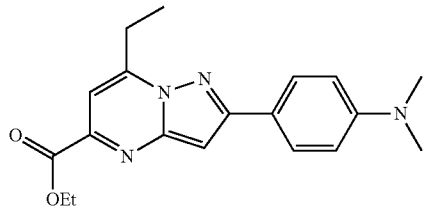

Intermediate (D4)

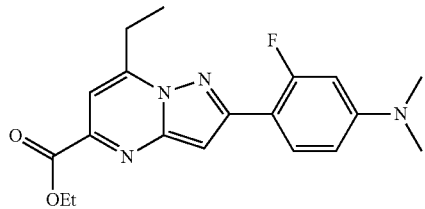

Intermediate (D5)

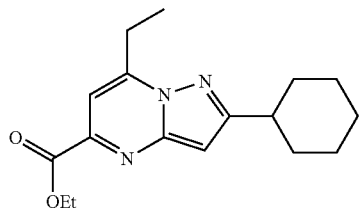

Intermediate (D6)

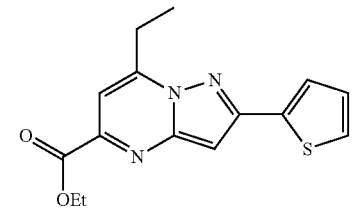

Intermediate (D7)

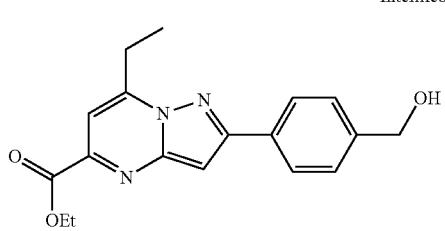

Intermediate (D8)

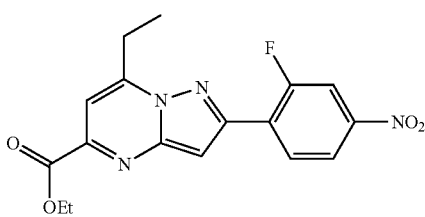

Intermediate (D9)

Intermediate (D10)
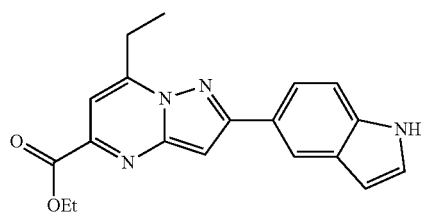
Intermediate (D11)
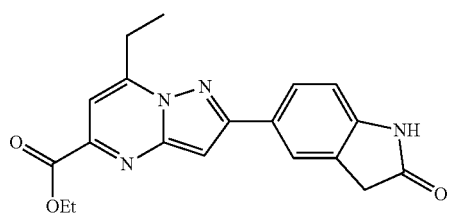
Intermediate (D12)
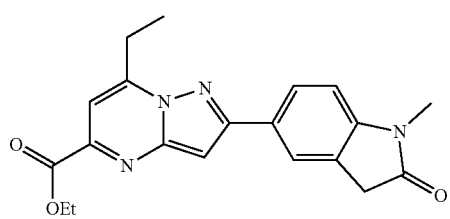
Intermediate (D13)
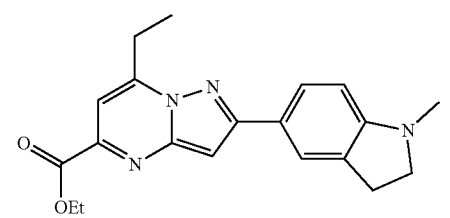
Intermediate (D14)
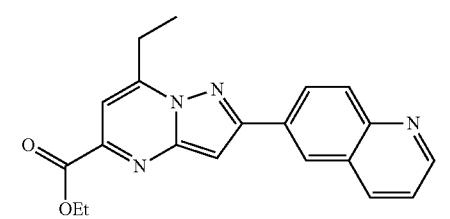
Intermediate (D15)
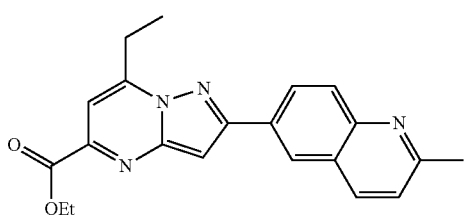
Intermediate (D16)
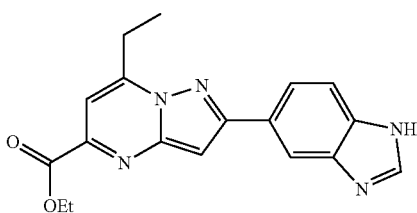
Intermediate (D17)
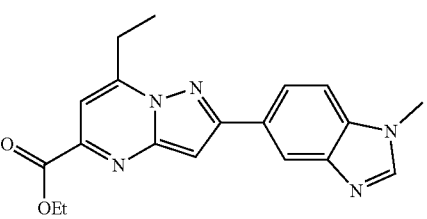
Intermediate (D18)
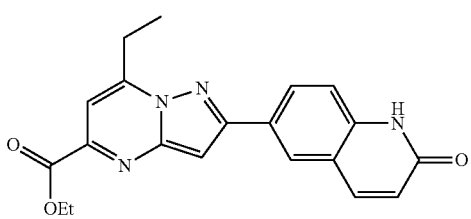
Intermediate (D19)
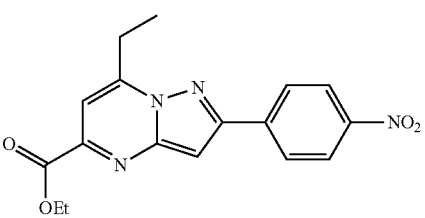
Intermediate (D20)
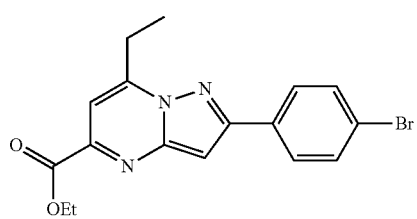
Intermediate (D21)
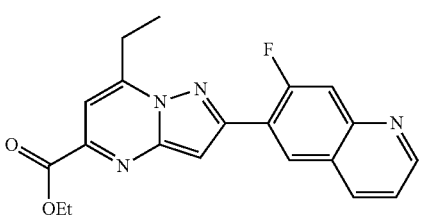

Intermediate (D22)
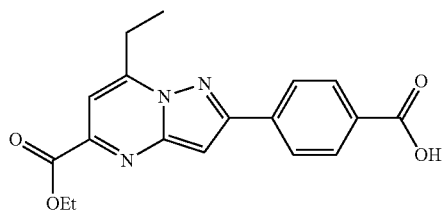
Intermediate (D23)
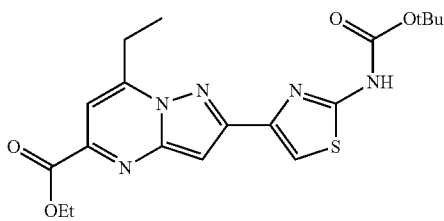
Intermediate (D24)
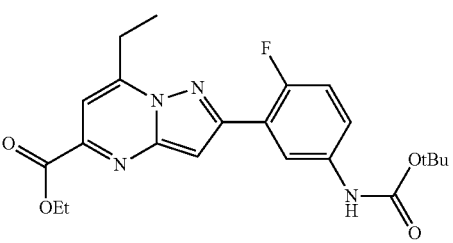
Intermediate (D25)
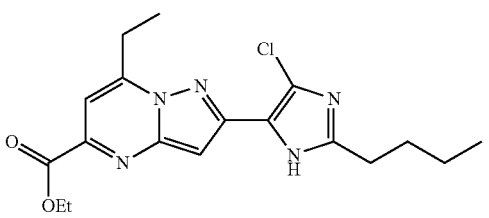
Intermediate (D26)
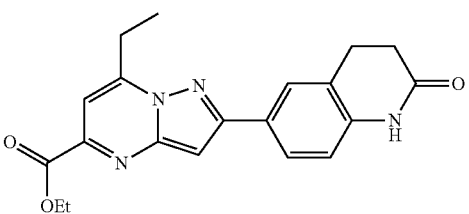
Intermediate (D27)
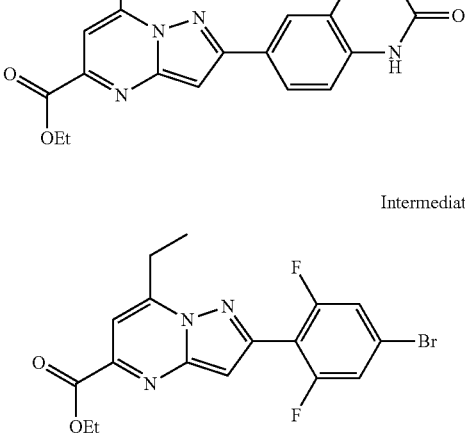
Intermediate (D28)
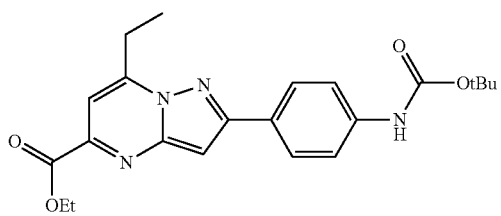
Intermediate (D29)
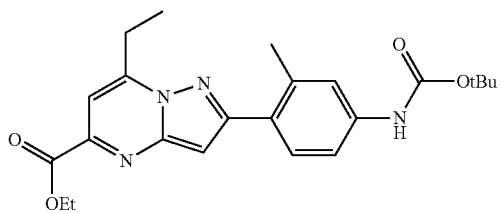
Intermediate (D30)
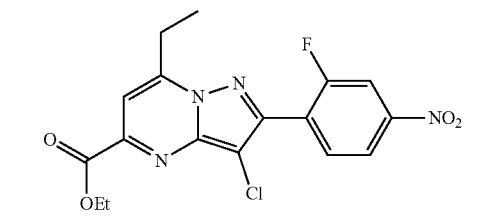
Intermediate (D31)
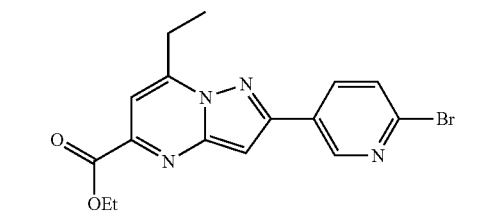
Intermediate (D32)
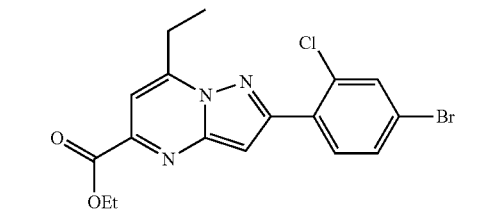
Reaction scheme:
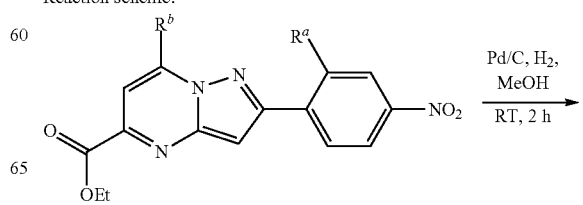

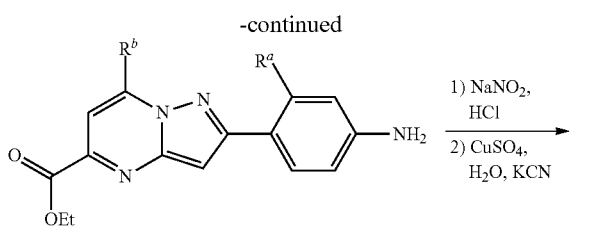

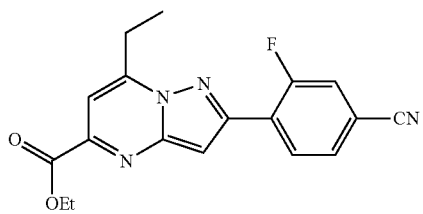

Intermediate (D33):
Intermediate (D9) (22.6 g, 0.06 mol) was dissolved in MeOH (250 mL) and Pd/C (2.0 g) was added. The reaction mixture was shaken for 2 hours at RT under hydrogen (1 bar). Then the solution was filtered through a pad of Celite® to remove the catalyst and the filtrate was evaporated to give 17.8 g (86%) of intermediate (D33).

Intermediate (D33)

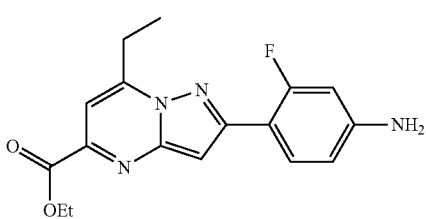

Intermediate (D34):
A solution of sodium nitrite (4.1 g, 0.06 mol) in water (10 mL) was added dropwise to a suspension of intermediate (D33) (17.8 g, 54 mmol) in HCl cc (27 mL) and AcOH (12 mL) at 0° C. The reaction mixture was stirred at 0° C. for 1 hour until the entire solid had dissolved. Then, toluene (100 mL) was added and the reaction mixture was heated at 60° C. for 1 hour. The diazonium salt solution, still at 0° C., was treated cautiously with solid NaHCO$_3$ to achieve pH 6-7. The reaction mixture was then added dropwise over 15 min to a previously prepared solution of copper cyanide (preparation: CuSO$_4$,5H$_2$O (17.5 g) in water (10 mL) was added to a solution of KCN (17.5 g) in water (100 mL) at 0° C.). The reaction mixture was allowed to warm to RT, stirred overnight and then partitioned between EtOAc and water. The aqueous layer was extracted with EtOAc (×3). The combined organic extracts were dried over sodium sulfate, filtered and evaporated. The residue was purified by column chromatography (silica gel, DCM). The pure fractions were collected and the solvent was evaporated to give 6.7 g (37%) of intermediate (D34).

Intermediate (D34)

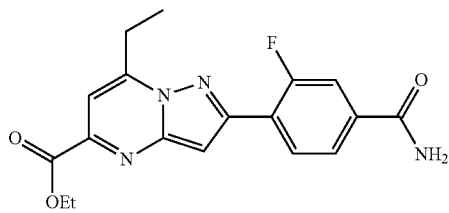

Intermediate (D35):
A mixture of intermediate (D34) (6.7 g, 0.02 mol) in TFA/H$_2$SO$_4$ (70 mL, 4/1) was stirred at RT for 48 hours. Then, the reaction mixture was diluted with water and the precipitate was filtered off, washed with water and dried to give 4.2 g (60%) of intermediate (D35).

Intermediate (D35)

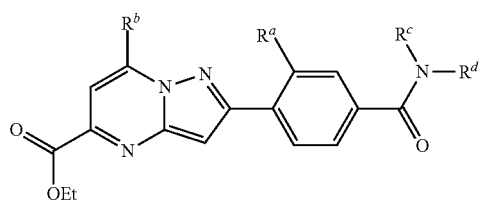

Reaction scheme:

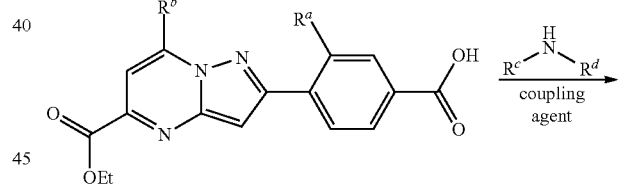

Intermediate (D36):
TBTU (4.0 g, 12.0 mmol) was added to a mixture of intermediate (D22) (3.5 g, 10.3 mmol), NH$_4$Cl (2.7 g, 50.0 mmol) and DIEA (10 mL, 60.0 mmol) in DCM (50 mL). The reaction mixture was stirred at RT overnight then partitioned between DCM and water. The aqueous layer was extracted with DCM. The combined organic extracts were dried over sodium sulfate, filtered and evaporated. The residue was taken up with Et$_2$O and dried to give 3.25 g (94%) of intermediate (D36).

Intermediate (D36)

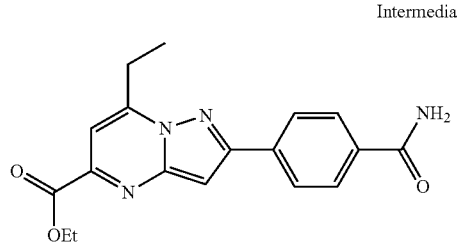

Intermediate (D37):

EDC (0.13 g, 0.65 mmol) was added to a mixture of intermediate (D22) (0.2 g, 0.59 mmol), methylamine hydrochloride (0.65 mmol), HOAt (0.08 g, 0.59 mmol) and DIEA (0.15 mL, 0.88 mmol) in DCM (20 mL). The reaction mixture was stirred at RT overnight. The reaction mixture was poured into water. The organic layer was separated, washed with brine, dried over sodium sulfate, filtered and evaporated. The residue was purified by column chromatography (silica gel, DCM/EtOAc). The pure fractions were collected and the solvent was evaporated to give 220 mg (quant.) of intermediate (D37).

Intermediate (D37)

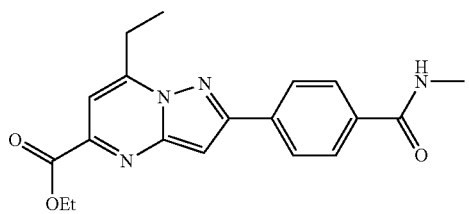

Intermediate (D38):

A mixture of 5-(2-fluorophenyl)-1H-Pyrazol-3-amine CAS [502132-86-7] (0.50 g, 2.8 mmol) and ethyl α,γ-dioxocyclohexanepentanoate CAS [1561966-01-5] (0.746 g, 3.1 mmol) in dry EtOH (50 mL) was heated at reflux for 1 hour. After cooling down to RT, the precipitate was filtered off to give 0.82 g (77%) of intermediate (D38).

Intermediate (D38)

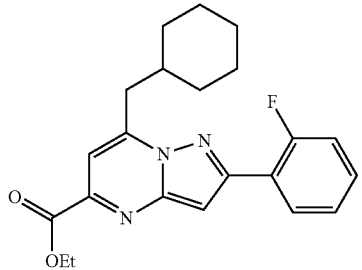

Reaction scheme:

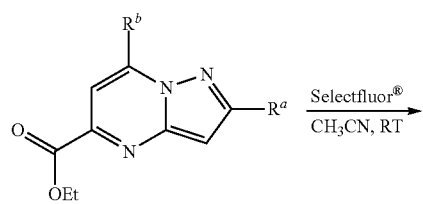

-continued

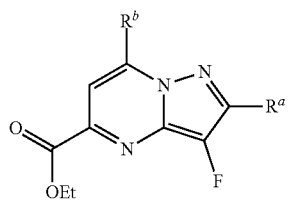

Intermediate (D39):

Selectfluor® (2.0 g, 5.6 mmol) was added to a mixture of intermediate (D9) (1.0 g, 2.8 mmol) and NaHCO$_3$ (0.24 g, 2.8 mmol) in CH$_3$CN (10 mL). The reaction mixture was stirred at RT overnight. Et$_3$N (0.8 mL, 5.6 mmol) was added and the reaction mixture was stirred at RT for 2 hours. The reaction mixture was evaporated, then the residue was dissolved in DCM and washed with water. The organic layer was separated, washed with brine, dried over sodium sulfate, filtered and evaporated. The residue was purified by column chromatography (silica gel, DCM/EtOAc). The pure fractions were collected and the solvent was evaporated to give 0.2 g (19%) of intermediate (D39).

Intermediate (D39)

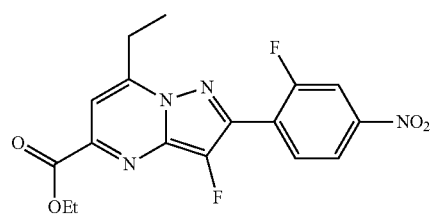

Alternative Way when R$^b$ is an Amino Group:

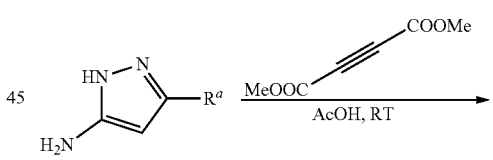

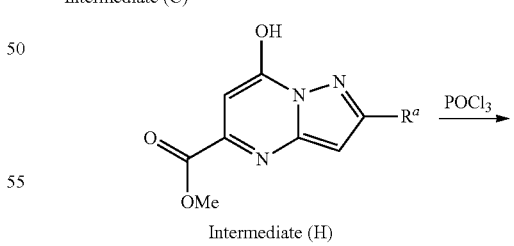

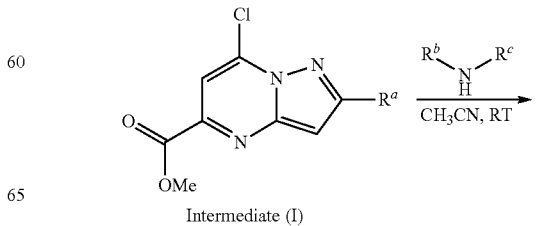

-continued

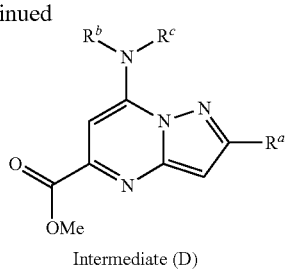
Intermediate (D)

Intermediate (D40):

A mixture of intermediate (I1) (1.5 g, 3.9 mmol), methylamine (2M in THF) (2.93 mL, 5.85 mmol) and Et₃N (1.63 mL, 11.70 mmol) in CH₃CN (30 mL) was heated at reflux for 2 hours. The mixture was cooled down to RT, water was added and the product was extracted with DCM. The organic layer was dried over MgSO₄, filtered and the solvent was evaporated. The residue was taken up in EtOH, stirred on ice-bath, filtered and the precipitate was dried under vacuum (60° C.) to give 1.24 g (83%) of intermediate (D40).

Intermediate (D40)

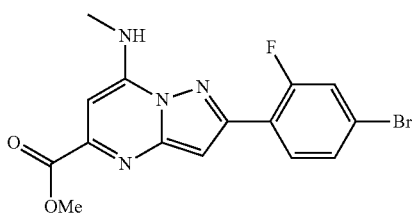

Intermediate (D41):

Pyrrolidine (0.71 g, 10 mmol) was added to a suspension of intermediate (I3) (1.52 g, 4.5 mmol) in CH₃CN (100 mL) at 0° C., then the reaction mixture was stirred at RT for 3 hours. The solvent was evaporated (T<45° C.) and water was added to the residue. The precipitate was filtered off and dried to give 1.67 g (quant.) of intermediate (D41).

Intermediate (D41)

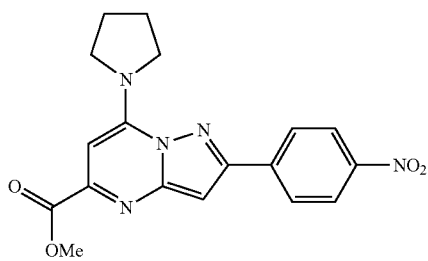

The following compounds were prepared according to the above procedure:

Intermediate (D42)

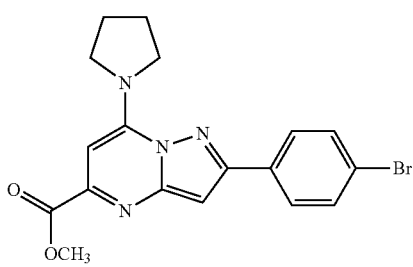

Intermediate (D43)

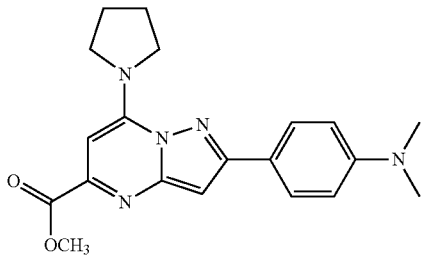

Intermediate (D44)

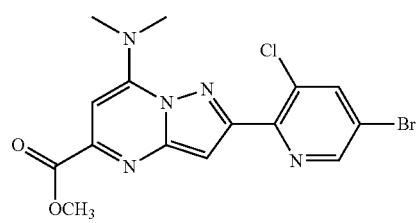

Intermediate (D44):

Dimethylamine (281 mg, 2.1 mmol) was added to a suspension of intermediate (I2) (377 mg, 0.94 mmol) in CH₃CN (50 mL) at 0° C. The reaction mixture was stirred at RT for 3 hours. The solvent was evaporated and water was added. The precipitate was filtered and dried to give 290 mg (75%) of intermediate (D44).

Intermediate (D45):

A mixture of intermediate (I1) (5 g, 13 mmol), pyrrolidine (1.6 mL, 19.5 mmol) and Et₃N (5.42 mL, 39 mmol) in CH₃CN (100 mL) was refluxed for 4 hours. The mixture was cooled down to RT. Water was added, the mixture was stirred 30 min on an ice bath, the precipitate was filtered off and dried under vacuum to afford 4.1 g (75%) of intermediate (D45).

intermediate (D45)

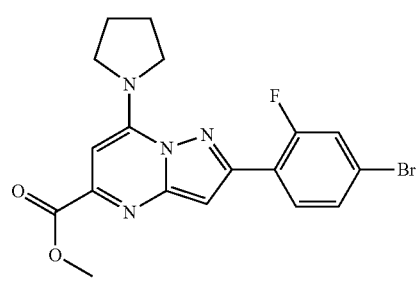

Intermediate (D46):

A mixture of intermediate (C1) (2.67 g, 10.4 mmol) and 4-cyclo-propyl-2-hydroxy-4-oxo 2-butenoic acid ethyl ester CAS [1021017-81-1] (2.5 g, 13.6 mmol) in EtOH (20 mL) was refluxed for 2 hours then cooled to 5° C. and stirred for 1 hour. The precipitate was filtered off, washed with cold EtOH and dried (50° C., vacuum) to afford 4.8 g of a residue. The residue was purified by column chromatography (silica gel, from Heptane/EtOAc 90/10 to 80/20). The pure fractions were collected and evaporated to afford 3.1 g (73%) of intermediate (D46).

intermediate (D46)

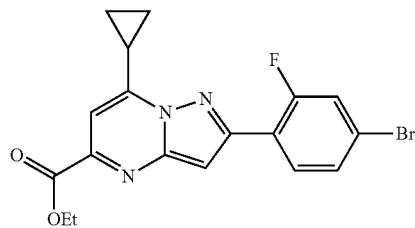

The following intermediates were prepared according to the above procedure.

intermediate (D49)

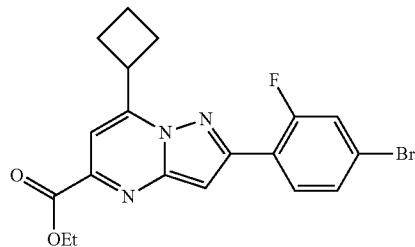

intermediate (D50)

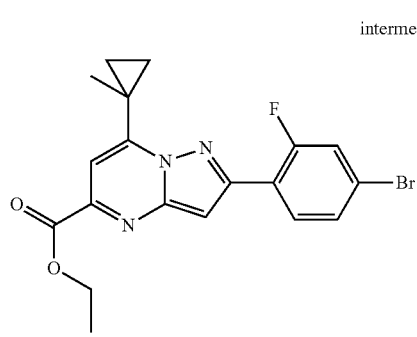

intermediate (D51)

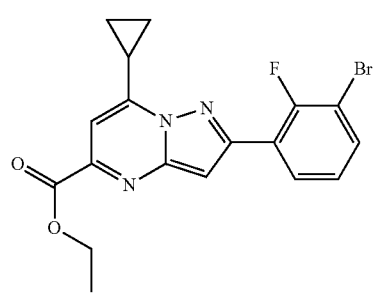

intermediate (D52)

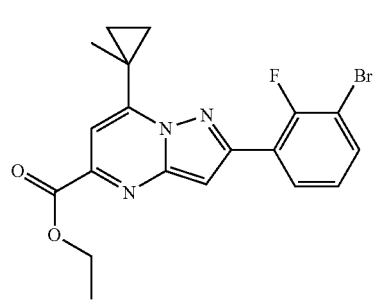

intermediate (D53)

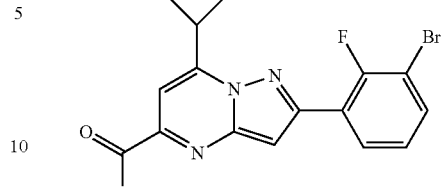

intermediate (D56)

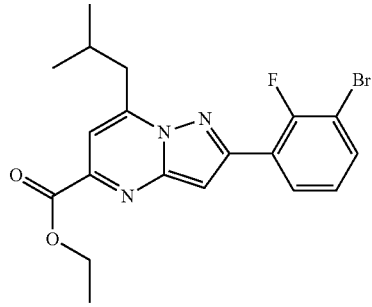

intermediate (D57)

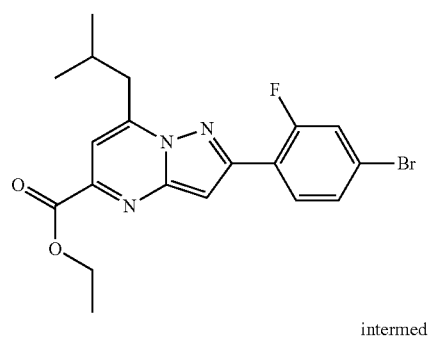

intermediate (D59)

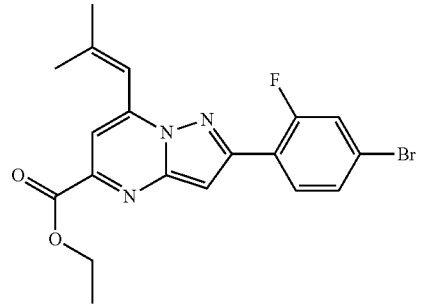

Intermediate (D47):

A mixture of 5-bromo-1H-pyrazol-3-amine CAS [950739-21-6)](65.8 g; 406 mmol) and 2-hydroxy-4-oxo-2-hexenoic acid methyl ester CAS [91029-29-7](74.4 g; 339 mmol) in MeOH (1.2 L) was refluxed for 18 hours. The mixture was cooled to RT and the precipitate was filtered, washed with MeOH and dried to give 80.8 g of intermediate (D47) as a yellow crystals (first batch). The filtrate was evaporated and MeOH (200 mL) was added, the solid was filtered and the solid was washed with MeOH (40 mL) and dried to give 6.1 g of intermediate (D47) as yellow solid (second batch). The filtrate was evaporated and MeOH (100 mL) was added, the solid was filtered, washed with MeOH (20 mL) and dried to give 1.6 g intermediate (D47) (third batch). Global yield: 88.5 g (92%) of intermediate (D47).

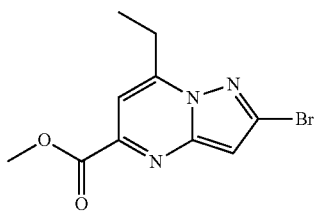

intermediate (D47)

The following intermediates were prepared according to the above procedure.

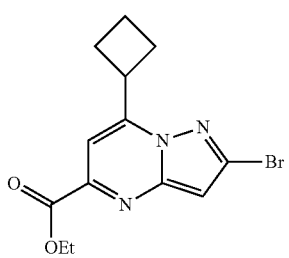

intermediate (D54)

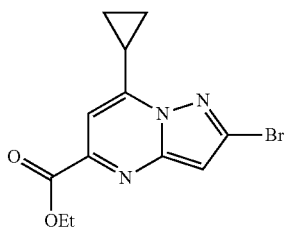

intermediate (D55)

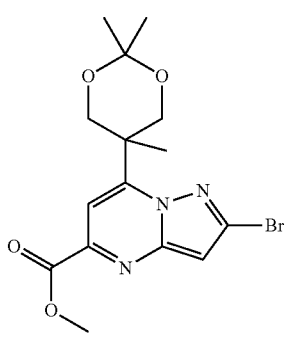

intermediate (D60)

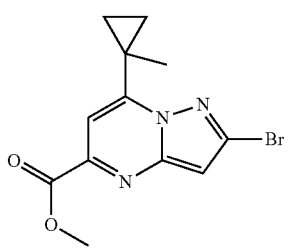

intermediate (D61)

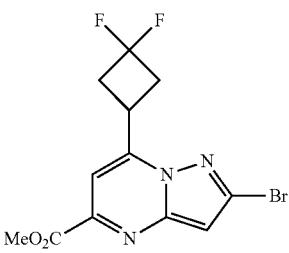

intermediate (D62)

Reaction scheme:

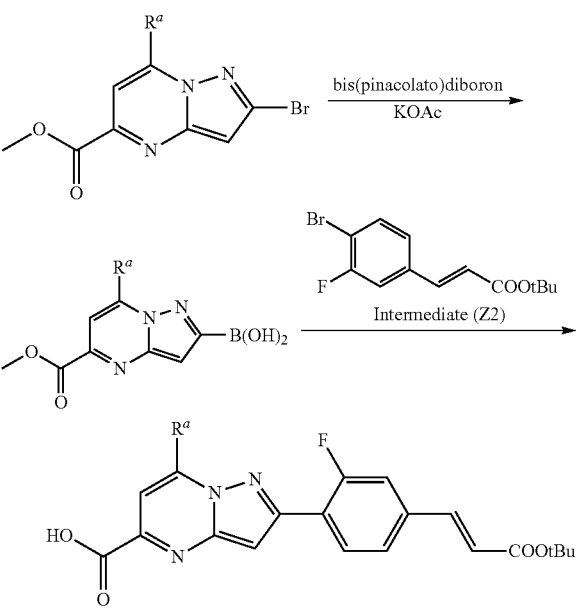

Intermediate (D48):

Under $N_2$, in a Schlenk tube, bis(pinacolato)diboron (1.65 g; 6.50 mmol) and KOAc (1.06 g; 10.8 mmol) were added to a solution of intermediate (D47) (1.54 g; 5.41 mmol) in 1,4-dioxane (20 mL). The solution was purged with nitrogen and charged with $PdCl_2(dppf)$ (443 mg; 542 μmol). The resulting solution was purged again with nitrogen and stirred at 100° C. for 5 hours. The reaction mixture was cooled down to RT overnight. EtOAc and water were added. The two combined layers were filtered on a frit. The precipitate was kept (167 mg). The filtrate was decanted. Then the organic layer was washed with water and brine (twice), dried over $MgSO_4$ and concentrated to give 1.5 g of a brown solid which was triturated in heptane. The precipitate was filtered to give 729 mg (63%) of intermediate (D48).

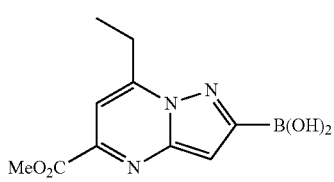

intermediate (D48)

Reaction scheme for intermediate (D58):

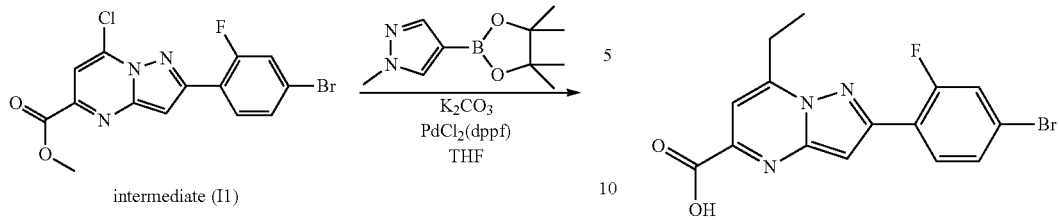

intermediate (I1)

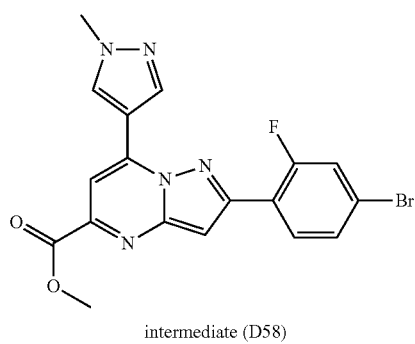

intermediate (D58)

Intermediate (D58):

A solution of intermediate (I1) (1 g, 2.6 mmol) and 1-methyl-4-(4,4,5,5-tetramethyl-1,3,2-dioxaborolan-2-yl)-1H-pyrazole (541.011 mg, 2.6 mmol) in $K_2CO_3$ (3.9 mL, 2 M, 7.8 mmol) and THF (10 mL) was degased with nitrogen for 10 min. $PdCl_2$(dppf)DCM (0.213 g, 0.26 mmol) was added and the resulting mixture was heated at 100° C. using a single mode microwave (Biotage® initiator60) with a power output ranging from 0 to 400 W for 20 min. The mixture was poured out into water, the precipitate was filtered off, dried under vacuum to afford 850 mg of intermediate (D58) as a crude product which was used in the next step without further purification.

intermediate (D58)

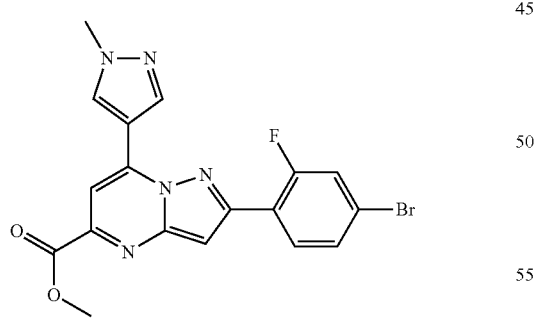

Intermediate (E)

Intermediate (E1):

A mixture of intermediate (D1) (3.7 g, 9.43 mmol) and KOH (2.65 g, 47.17 mmol) in EtOH (70 mL) was stirred at reflux overnight. The reaction mixture was cooled down to 0° C. and stirred for 15 min. The precipitate was filtered off and dried (vacuum, 60° C.) to give 3.86 g (quant.) of intermediate (E1) as carboxylate salt.

Intermediate (E1)

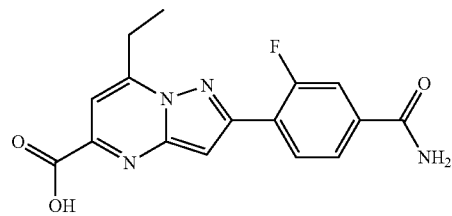

Intermediate (E2):

KOH (1.3 g, 20 mmol) was added to a solution of intermediate (D35) (4.2 g, 10 mmol) in EtOH (50 mL). The reaction mixture was stirred at RT for 1 hour. The solvent was evaporated and the residue was extracted with water and washed with ether. The organic layer was separated and the aqueous one was neutralized with HCl cc to pH 7. The precipitate was filtered off and dried to give 3.8 g (99%) of intermediate (E2).

Intermediate (E2)

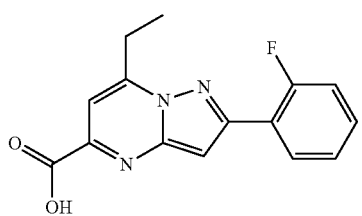

The following intermediates were prepared according to the procedure above:

Intermediate (E3)

Intermediate (E4)

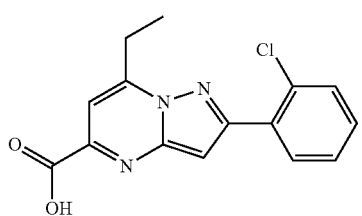

Intermediate (E5)

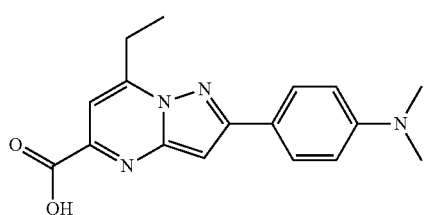

-continued

Intermediate (E6): 7-ethyl-2-(2-fluoro-4-(dimethylamino)phenyl)pyrazolo[1,5-a]pyrimidine-5-carboxylic acid Intermediate (E7): 7-ethyl-2-cyclohexylpyrazolo[1,5-a]pyrimidine-5-carboxylic acid Intermediate (E8): 7-ethyl-2-(thiophen-2-yl)pyrazolo[1,5-a]pyrimidine-5-carboxylic acid Intermediate (E9): 7-ethyl-2-(4-(hydroxymethyl)phenyl)pyrazolo[1,5-a]pyrimidine-5-carboxylic acid Intermediate (E10): 7-ethyl-2-(2-fluoro-4-nitrophenyl)pyrazolo[1,5-a]pyrimidine-5-carboxylic acid Intermediate (E11): 7-ethyl-2-(1H-indol-5-yl)pyrazolo[1,5-a]pyrimidine-5-carboxylic acid Intermediate (E12): 7-ethyl-2-(2-oxoindolin-5-yl)pyrazolo[1,5-a]pyrimidine-5-carboxylic acid Intermediate (E13): 7-ethyl-2-(1-methyl-2-oxoindolin-5-yl)pyrazolo[1,5-a]pyrimidine-5-carboxylic acid Intermediate (E14): 7-ethyl-2-(1-methylindolin-5-yl)pyrazolo[1,5-a]pyrimidine-5-carboxylic acid Intermediate (E15): 7-ethyl-2-(quinolin-6-yl)pyrazolo[1,5-a]pyrimidine-5-carboxylic acid Intermediate (E16): 7-ethyl-2-(2-methylquinolin-6-yl)pyrazolo[1,5-a]pyrimidine-5-carboxylic acid Intermediate (E17): 7-ethyl-2-(1H-benzo[d]imidazol-5-yl)pyrazolo[1,5-a]pyrimidine-5-carboxylic acid Intermediate (E18): 7-ethyl-2-(1-methyl-1H-benzo[d]imidazol-5-yl)pyrazolo[1,5-a]pyrimidine-5-carboxylic acid Intermediate (E19)
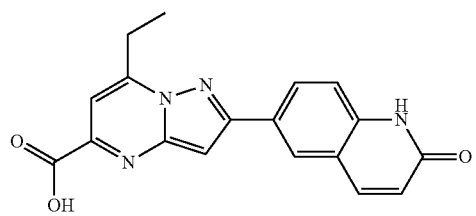
Intermediate (E20)
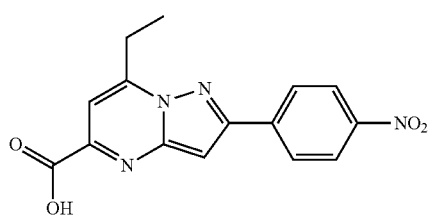
Intermediate (E21)

Intermediate (E22)
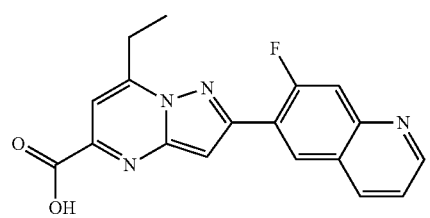
Intermediate (E23)
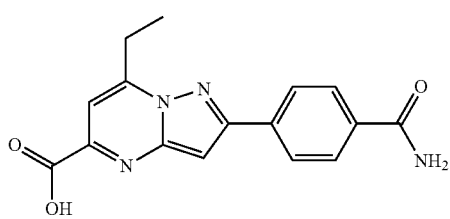
Intermediate (E24)
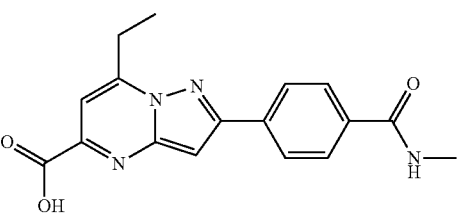
Intermediate (E25)
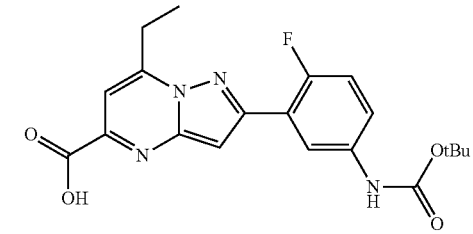
Intermediate (E26)
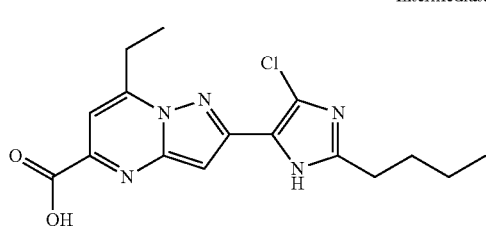
Intermediate (E27)
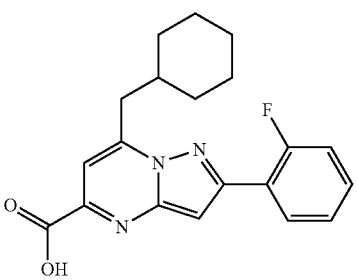
Intermediate (E28)
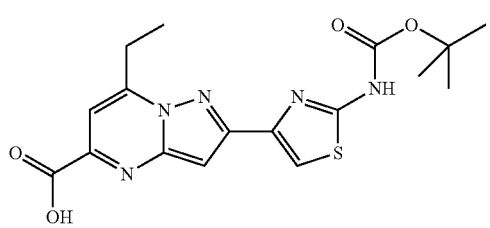
Intermediate (E29)
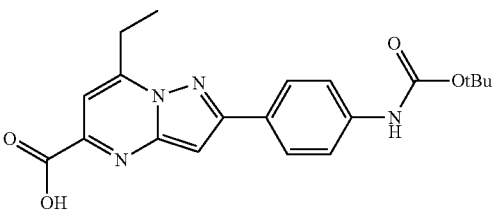
Intermediate (E30)
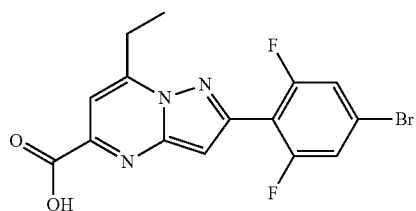

Intermediate (E31)

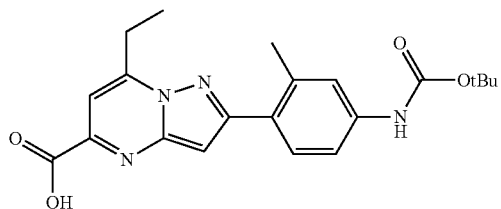

Intermediate (E32)

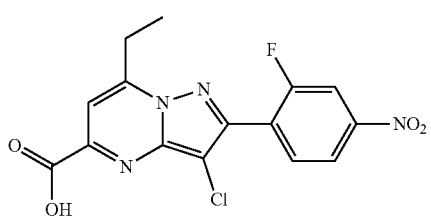

Intermediate (E33)

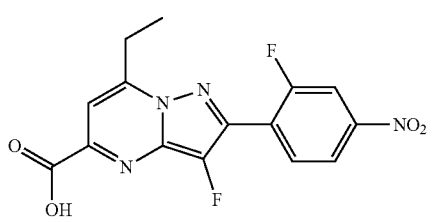

Intermediate (E34)

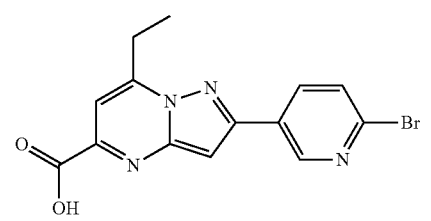

Intermediate (E35)

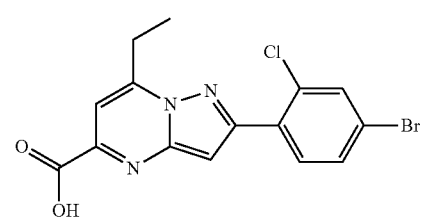

Intermediate (E36):

KOH (291 mg, 5.2 mmol) was added to a solution of intermediate (D40) (985 mg, 2.6 mmol) in MeOH (50 mL). The reaction mixture was stirred at RT for 1 hour. The solvent was evaporated, then the residue was taken up with water and washed with ether. The aqueous layer was neutralized with HCl cc to pH 7 and the precipitate was filtered off to give 0.90 g (95%) of intermediate (E36).

Intermediate (E36)

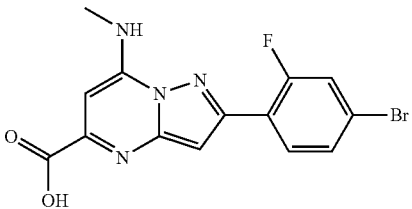

The compounds (E37) to (E41) were prepared according to the procedure above.

Intermediate (E37)

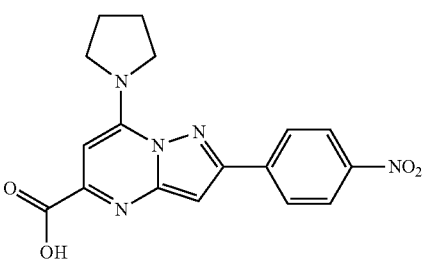

Intermediate (E38)

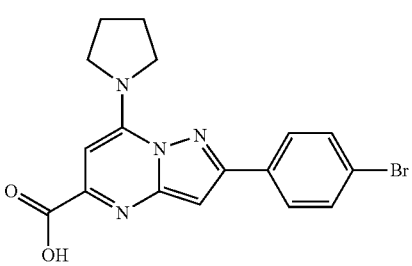

Intermediate (E39)

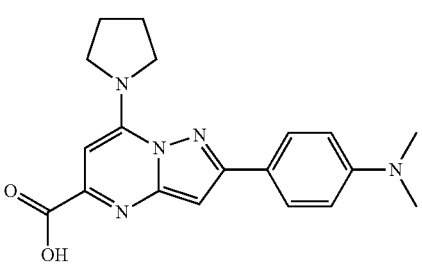

Intermediate (E40)

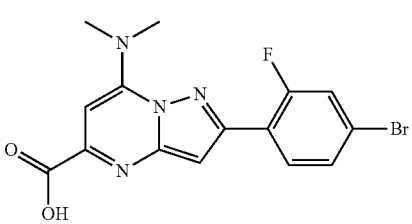

Intermediate (E41)

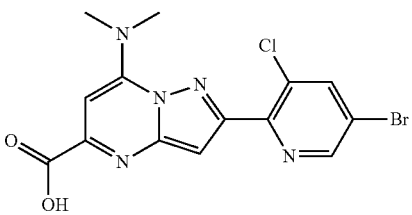

Intermediate (E42):
Intermediate (D26) (0.8 g, 2.21 mmol) was heated at reflux in HCl cc (5 mL) for 5 hours. After cooling down to RT, the reaction mixture was poured into water, then the precipitate was filtered off, washed with water and dried to give 0.6 g (81%) of intermediate (E42).

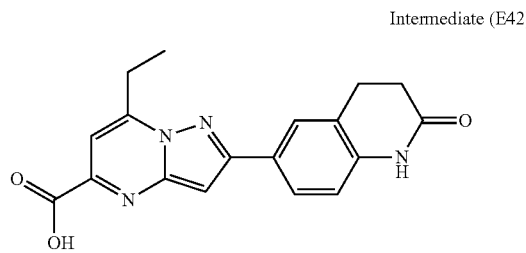

Intermediate (E42)

Reaction scheme:

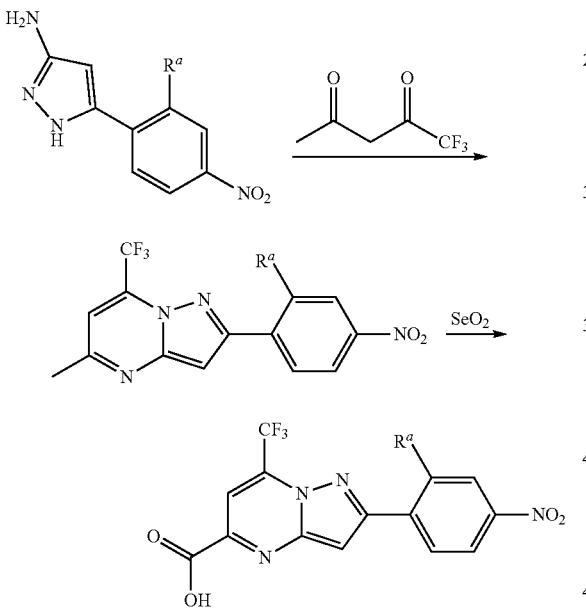

Intermediate (E43):
Intermediate (C₂) (0.75 g, 3.37 mmol) and 1,1,1-trifluoropentane-2,4-dione CAS [367-57-7] (0.57 g, 3.70 mmol) were heated at reflux in AcOH (20 mL) for 1 hour. The solvent was evaporated and the residue was taken up with ether, the resulting precipitate was filtered off and dried to give 0.88 g (70%) of intermediate (E43).

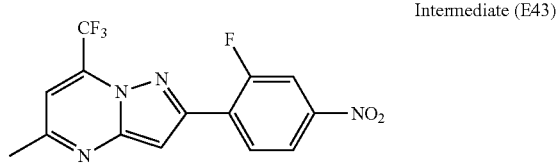 [SMILES: Cc1cc(C(F)(F)F)n2nc(-c3ccc([N+](=O)[O-])cc3F)cc2n1]

Intermediate (E43)

Intermediate (E44):
Intermediate (E43) (0.88 g, 2.58 mmol) and selenium dioxide (1.1 g, 10 mmol) were heated at reflux in pyridine (20 mL) for 24 hours. The reaction mixture was filtered through a short pad of Celite®. The filtrate was evaporated, the residue was taken up in HCl 1N. The solid was filtered off, washed with HCl 1N, then water and dried (on the air) to give 0.95 g (99%) of intermediate (E44).

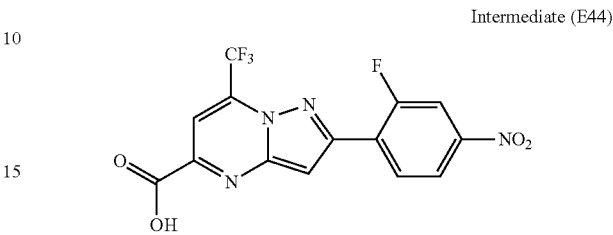

Intermediate (E44)

Intermediate (E45):
A mixture of intermediate (D45) (4.1 g, 9.78 mmol) and KOH (2.74 g, 48.9 mmol) in EtOH (40 mL) was refluxed overnight. The mixture was cooled down to 0° C., stirred for 15 min, the precipitate was filtered off and dried (vacuum, 60° C.) to give 4.5 g (100%) of intermediate (E45).

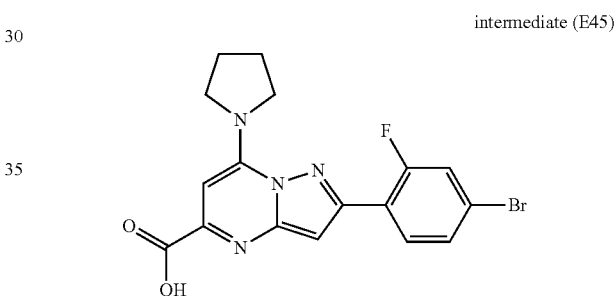

intermediate (E45)

Intermediate (E46):
KOH (0.74 g, 11.1 mmol) was dissolved in EtOH (40 mL) then intermediate (D46) (1.5 g, 3.71 mmol) was added portionwise and the suspension was refluxed for 4 hours then overnight at RT. The mixture was cooled down to 0° C., stirred for 15 min, the precipitate was filtered off, washed twice with DIPE and dried (vacuum, 60° C.) to give 1.52 g (98%) of intermediate (E46).

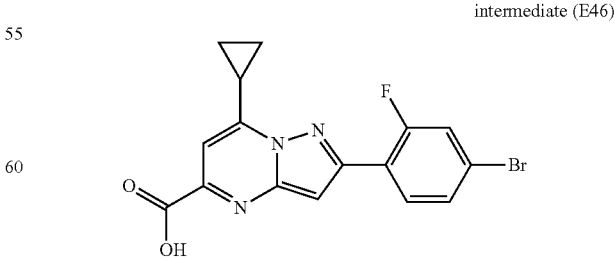

intermediate (E46)

The following intermediates were prepared according to the above procedure.

intermediate (E48)

intermediate (E50)

intermediate (E51)

intermediate (E52)

intermediate (E53)

intermediate (E57)

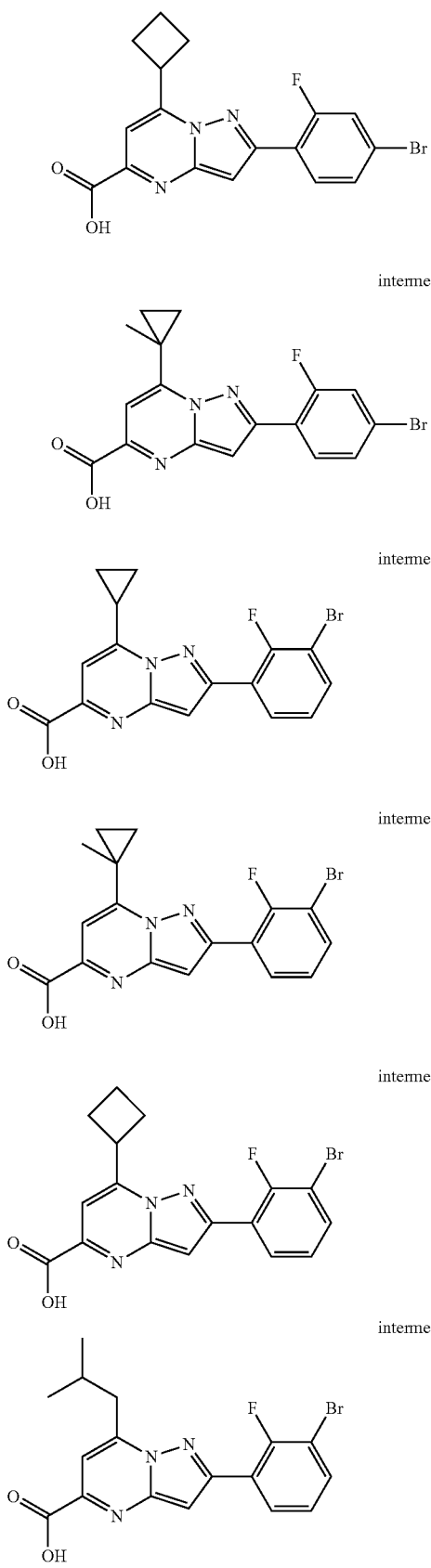

-continued intermediate (E58)

intermediate (E59)

intermediate (E60)

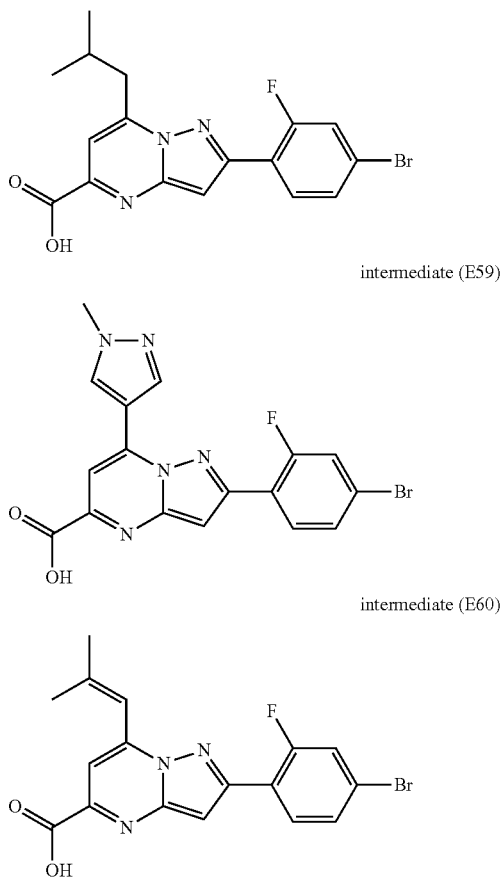

Reaction scheme:

intermediate (D)

intermediate (E)

Intermediate (E47):

Intermediate (D47) (8.07 g; 28.4 mmol) was suspended in EtOH (170 mL) then KOH (5.63 g; 85.2 mmol) was added and the reaction mixture was heated at reflux for 3 hours. The reaction mixture was filtered and the residual sticky solid was washed with $Et_2O$ to give 8.25 g (94%) of intermediate (E47) as a white solid.

intermediate (E47)

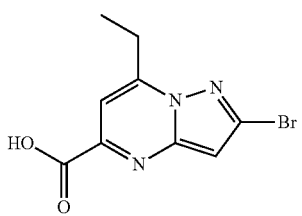

The following intermediates were prepared according to the above procedure.

intermediate (E55)

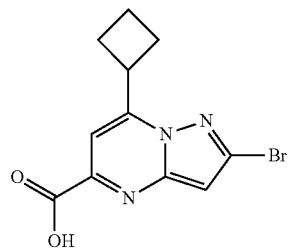

intermediate (E56)

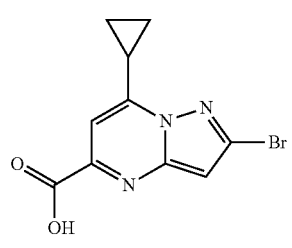

intermediate (E63)

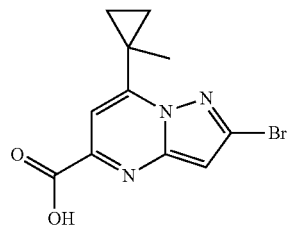

intermediate (E64)

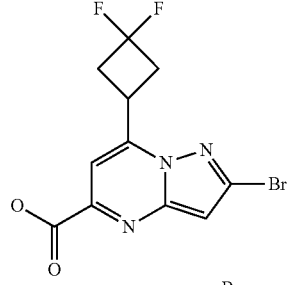

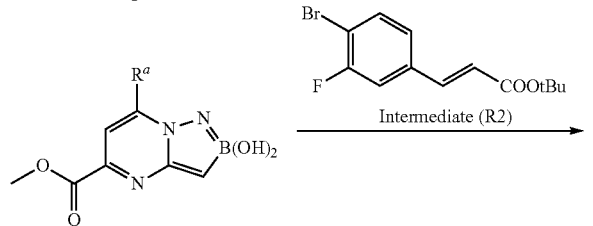

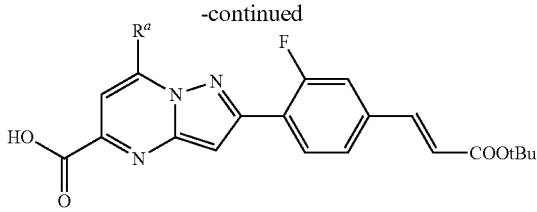

Intermediate (E49): A solution of intermediate (D48) (100 mg; 0.402 mmol), intermediate (R²) (121 mg; 0.402 mmol) and K₃PO₄ (256 mg; 1.21 mmol) in 1,4-dioxane (2.9 mL) and water (878 μL) was purged with N₂. PdCl₂(dtbpf) (28 mg; 43.0 μmol) was added, the mixture was purged again with N₂ and heated at 100° C. using one single mode microwave (Biotage Initiator EXP 60) with a power output ranging from 0 to 400 W for 30 min. The reaction mixture was concentrated to dryness to afford 472 mg (100%) of intermediate (E49) as brown oil. The product was used without further purification for the next step.

intermediate (E49)

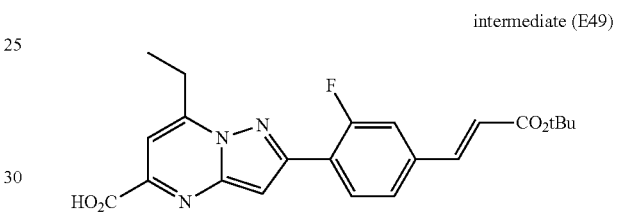

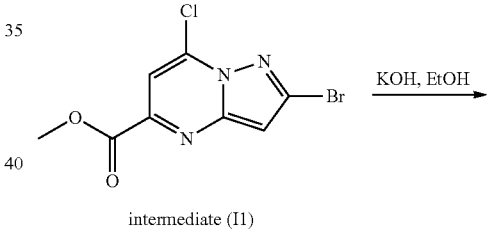

intermediate (I1)

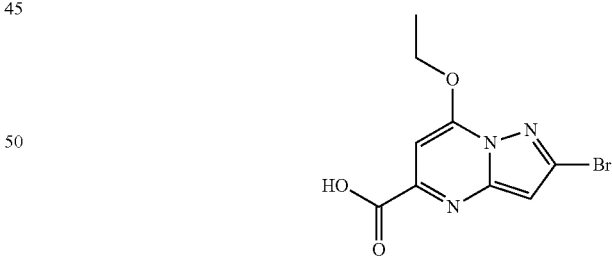

intermdiate (E54)

Intermediate (E54):

Intermediate (I1) (0.5 g, 1.3 mmol) was put in suspension in EtOH (20 mL), then KOH (0.257 g, 3.9 mmol) was added and the reaction mixture was heated to reflux for 2 h. The reaction mixture was filtered and the residual sticky solid was dried under vacuum (60° C.) to afford 0.7 g of intermediate (E54).

The following intermediates were prepared according to intermediate (E54).

intermediate (E61)

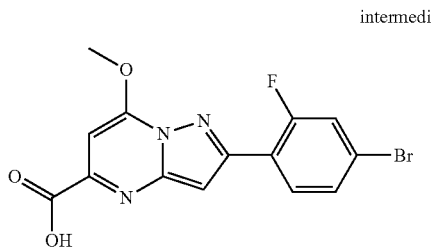

Intermediate (F1)

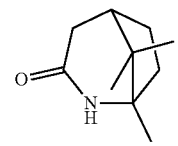

Intermediate (E62):

A solution of LiOH.H₂O (0.327 g, 13.7 mmol) in H₂O (6 ml) was added to a solution of intermediate (D60) (3.50 g, 9.11 mmol) in THF (60 ml) at rt. The reaction mixture was stirred at rt for 16 h. Reaction mixture was concentrated under reduced pressure. EtOH was added and the mixture was concentrated under reduced pressure. EtOH was added and the solid was filtered, washed with Et₂O and dried to yield 2.60 g (77%) of intermediate (E62) as a lithium salt.

Intermediate (F2):

At −35° C., LiAlH₄ (5 g, 135 mmol) was added to a solution of intermediate (F1) in THF (150 mL). The reaction mixture was stirred at −35° C. for 1 h30. Then, the reaction was warmed to RT, allowed stir for 2 h and heated at reflux for 5 hours. The mixture was cooling down to RT, water and 20% aqueous solution of NaOH were added. The mixture was filtered. HCl cc (10 mL) was added to the filtrate and the solvent was evaporated. At 0° C., 30% aqueous solution of NaOH was added to a residue. The mixture was extracted with Et₂O, the organic layer was separated, dried, filtered and evaporated. The residue was purified by vacuum distillation (70° C., 20 torr) to give 1.4 g (14%) of intermediate (F2).

intermediate (E62)

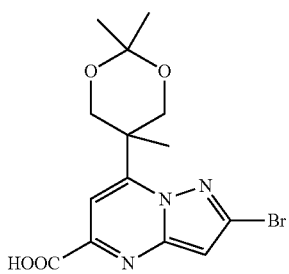

Intermediate (F2)

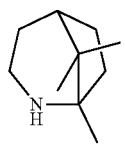

Intermediate (F)

Reaction scheme:

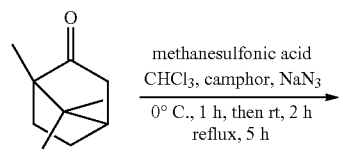

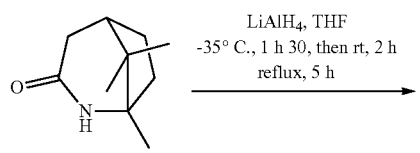

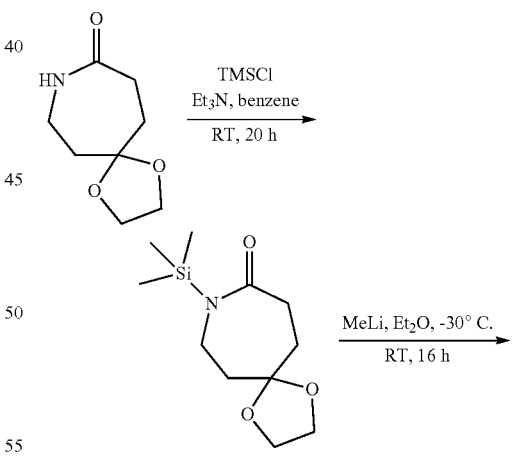

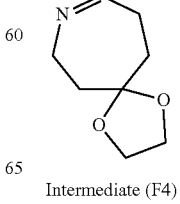

Intermediate (F4)

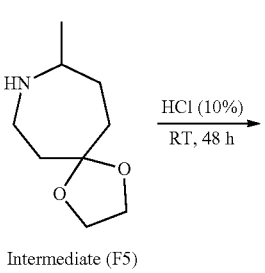

Intermediate (F5)

Intermediate (F1): At 0° C., camphor (10 g, 66 mmol), then sodium azide (8.56 g, 132 mmol) were added small portionwise to a mixture of methanesulfonic acid (75 g) in CHCl₃ (200 mL). The reaction mixture was stirred at 0° C. for 1 hour. Then, the reaction was warmed to RT, allowed stir for 2 h and heated at reflux for 5 hours. The mixture was cooling down to RT, an aqueous solution of Na₂CO₃ was added to pH 8. The mixture was extracted with DCM, the organic layer was dried, filtered and evaporated to give intermediate (F1). The product was used without purification for the next step.

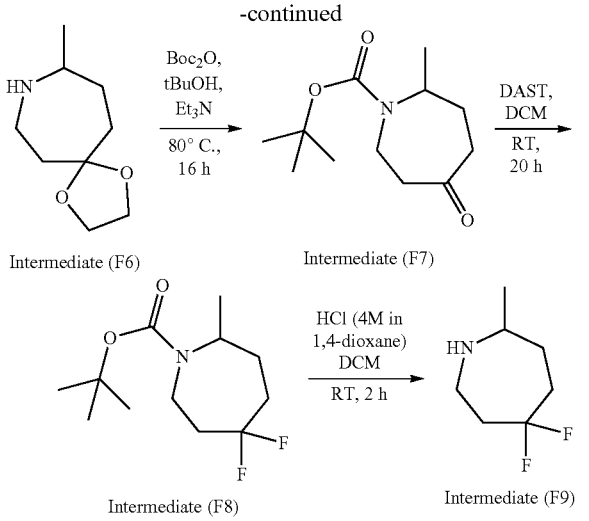

Intermediate (F3):

Et₃N (12.8 g, 0.13 mol) and TMSCl (12.1 g, 0.11 mol) were added to a solution of 1,4-dioxa-8-azaspiro[4.6]undecan-9-one CAS [172090-55-0] (17.3 g, 0.10 mol) in benzene (200 mL). The reaction mixture was stirred at RT for 20 hours. The mixture was filtered and the filtrate was evaporated to give 23 g (90%) of intermediate (F3).

Intermediate (F3)

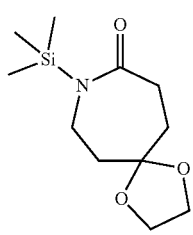

Intermediate (F4): At −30° C., MeLi (25 mmol) was added to a solution of intermediate (F3) (6.1 g, 25 mmol) in Et₂O (100 mL). N The reaction mixture was stirred at RT for 16 hours. Then, the aqueous solution of NH₄Cl (1 g in 40 mL of water) was added and the mixture was extracted with Et₂O. The organic layer was separated, dried over sodium sulfate, filtered and evaporated to give 4 g (94%) of intermediate (F4).

Intermediate (F4)

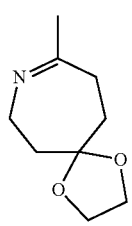

Intermediate (F5): NaBH₄ (1.2 g) was added to a solution of intermediate (F4) in EtOH (30 mL). The reaction mixture was stirred at RT for 20 hours. 10% aqueous solution of K₂CO₃ (50 mL) was added, the mixture was stirred for 30 min and extracted with DCM. The organic layer was separated, dried, filtered and evaporated to dryness. The residue was purified by column Intermediate (F5) chromatography to give 1.73 g (43%) of intermediate (F5).

Intermediate (F5)

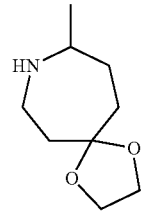

Intermediate (F6):

A solution of intermediate (F5) in HCl (10%) (30 mL) was stirred at RT for 48 hours. The reaction mixture was evaporated to dryness and the residue was washed with Et₂O. The precipitate was filtered and dried to give 1.32 g (64%) of hydrochloride intermediate (F6).

Intermediate (F6)

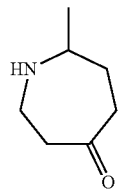

Intermediate (F7):

Boc₂O (1.95 g, 8.3 mmol) and Et₃N (1.62 g, 16 mmol) were added to a solution of hydrochloride intermediate b (F6) (1.32 g, 8.1 mmol) in tBuOH (4 mL). The reaction mixture was stirred at 80° C. for 16 hours. The solvent was evaporated to dryness and the residue was washed with an aqueous solution of citric acid. The mixture was extracted with DCM. The organic Intermediate (F7) layer was separated, dried, filtered and evaporated to give 1.4 g (76%) of intermediate (F7).

Intermediate (F7)

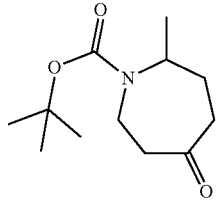

Intermediate (F8):

DAST (2.4 g, 15 mmol) was added to a solution of intermediate (F7) (1.4 g, 6.14 mmol) in DCM (4 mL) at RT. The reaction mixture was stirred at RT for 20 hours. 10% aqueous solution of K₂CO₃ (50 mL) was added, the mixture was stirred for 30 min and extracted with DCM. The organic layer was Intermediate (F8) separated, dried, filtered and evaporated to dryness. The residue was purified by column chromatography to give 1.4 g (86%) of intermediate (F8).

Intermediate (F8)

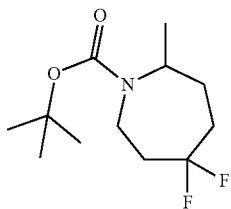

Intermediate (F9):

HCl (4M in 1,4-dioxane) (3 mL) was added to a solution of intermediate (F8) (1.4 g, 5.3 mmol) in DCM (3 mL). The reaction mixture was stirred at RT for 2 hours. The solvent was evaporated to dryness and the residue was washed F with ether. The precipitate was filtered and dried to give 0.6 g of Intermediate (F9) hydrochloride intermediate (F9).

Intermediate (F9)

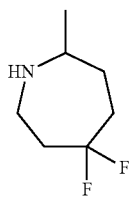

Reaction scheme:

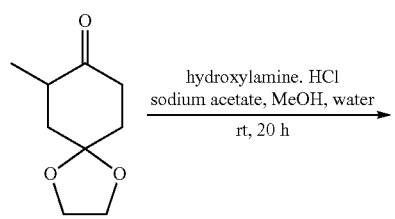

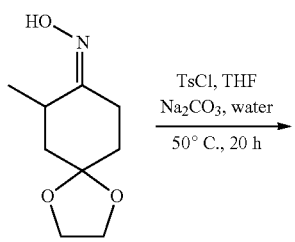

Intermediate (F10)

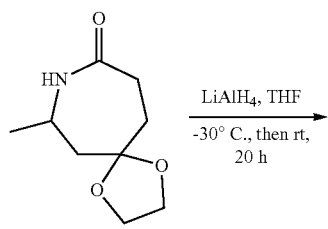

Intermediate (F11)

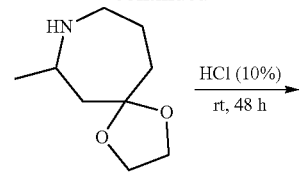

Intermediate (F12)

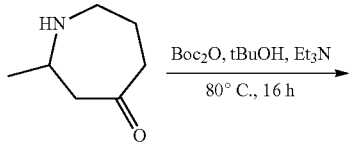

Intermediate (F13)

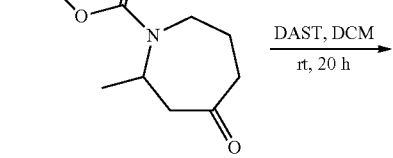

Intermediate (F14)

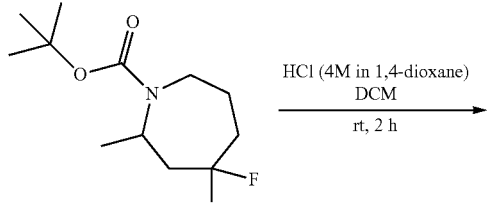

Intermediate (F15)

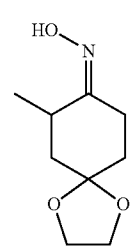

Intermediate (F16)

Intermediate (F10):

Hydroxylamine hydrochloride (6.3 g, 91 mmol) and a solution of sodium acetate (7.5 g, 91 mmol) in water (40 mL) were added to a solution of 7-methyl-1,4-dioxaspiro[4,5]decan-8-one CAS [702-69-2] (7.2 g, 42.30 mmol) in MeOH (100 mL). The reaction mixture was stirred at RT for 20 hours. MeOH was evaporated and the mixture was extracted with DCM. The organic layer was separated, dried, filtered and evaporated to give 7.3 g of intermediate (F10).

Intermediate (F10)

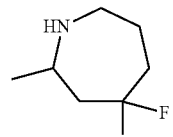

Intermediate (F11):

Tosylchloride (13 g) and a solution of Na$_2$CO$_3$ (14.5 g) in water (140 mL) were added to a solution of intermediate (F10) (7.3 g) in THF (150 mL). The reaction was stirred at 50° C. for 20 hours. A 10% aqueous solution of K$_2$CO$_3$ (50 mL) was added, the mixture was stirred for 30 min and Intermediate (F11) extracted with DCM. The organic layer was separated, dried, filtered and evaporated to dryness. The residue was purified by column chromatography to give 1.7 g (22%) of intermediate (F11).

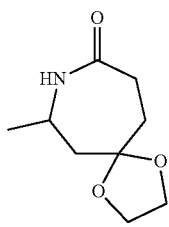

Intermediate (F11)

Intermediate (F12):

At −30° C., LiAlH$_4$ (2 g, 54 mmol) was added to a solution of intermediate (F11) (1.7 g, 8.2 mmol) in THF (50 mL). The reaction mixture was stirred at RT for 20 hours. Then, an aqueous solution of NaOH was added and the mixture was filtered off. The cake was washed with THF and the filtrate was evaporated to give 1.4 g of intermediate (F12).

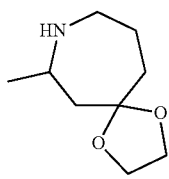

Intermediate (F12)

Intermediate (F13):

A solution of intermediate (F12) in HCl (10%) (30 mL) was stirred at RT for 48 hours. The reaction mixture was evaporated to dryness and the residue was washed with Et$_2$O. The precipitate was filtered and dried to give 1.32 g Intermediate (F13) (64%) of hydrochloride intermediate (F13)

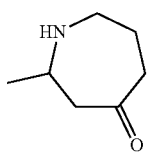

Intermediate (F13)

Intermediate (F14):

Boc$_2$O (1.95 g, 8.3 mmol) and Et$_3$N (1.62 g, 16 mmol) were added to a solution of hydrochloride intermediate (F13) (1.32 g, 8.1 mmol) in tBuOH (4 mL). The reaction mixture was stirred at 80° C. for 16 hours. The solvent was evaporated to dryness and the residue was washed with an aqueous solution of citric acid. The mixture was extracted with DCM. The organic layer was separated, dried, filtered and evaporated to give 1.4 g (76%) of intermediate (F14).

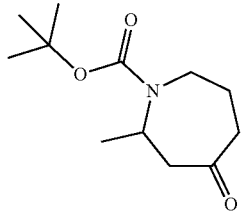

Intermediate (F14)

Intermediate (F15):

DAST (2.4 g, 15 mmol) was added to a solution of intermediate (F14) (1.4 g, 6.14 mmol) in DCM (4 mL) at RT. The reaction mixture was stirred at RT for 20 hours. 10% aqueous solution of K$_2$CO$_3$ (50 mL) was added, the mixture was stirred for 30 min and extracted with DCM. The organic layer was Intermediate (F15) separated, dried, filtered and evaporated to dryness. The residue was purified by column chromatography to give 1.4 g (86%) of intermediate (F15).

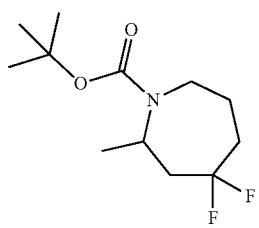

Intermediate (F15)

Intermediate (F16):

HCl (4M in 1,4-dioxane) (3 mL) was added to a solution of intermediate (F15) (1.4 g, 5.3 mmol) in DCM (3 mL). The reaction mixture was stirred at RT for 2 hours. The solvent was evaporated to dryness and the residue was washed Intermediate (F16) with ether. The precipitate was filtered and dried to give 0.6 g of hydrochloride intermediate (F16).

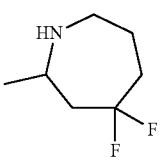

Intermediate (F16)

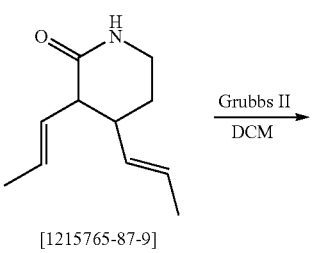

[1215765-87-9]

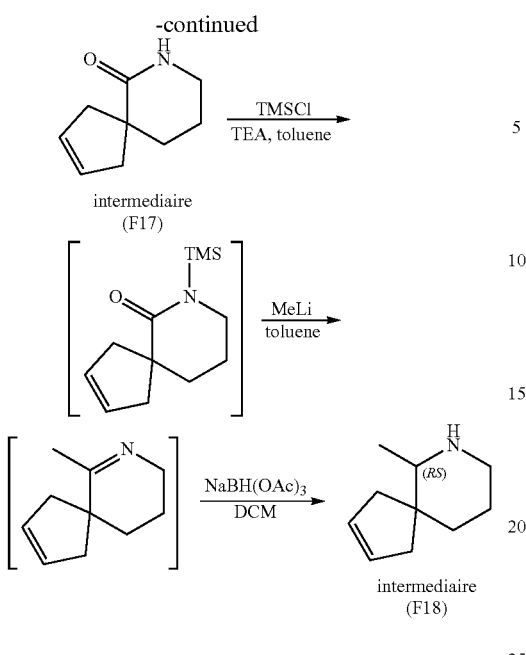

intermediaire (F17)

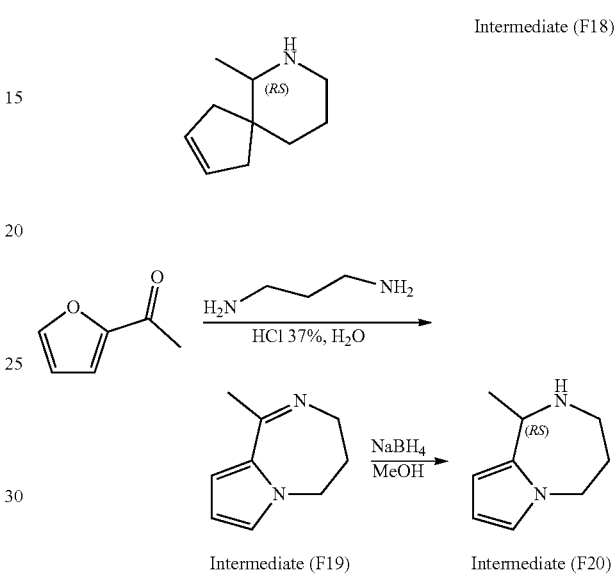

Intermediate (F19)  Intermediate (F20)

Intermediate (F17):

A solution of 3,3-di-2-propen-1-yl-2-piperidinone (9.0 g, 50.2 mmol) in DCM (200 ml) was degassed and Grubbs II (0.013 g, 0.015 mmol) was added and the reaction was stirred at room temperature for 2 days and 40° C. for 10 h. The reaction was concentrated under reduced pressure. The crude oil was purified by preparative LC (irregular SiOH, 40-63 μm, Fluka®, mobile phase gradient: from pentane/Et$_2$O 50/50 to 0/100) to give silver solid. The solid was dissolved in 10 mL of dichloromethane and 5 g of Silica-MetS DMT (Silicycle®, 40-63 μm, ruthenium scavenger) was added and stirred at room temperature for 1 h. The scavenger was filtered off and the filtrate was evaporated to give 6.52 g (86%) of intermediate (F17) as white solid.

Intermediate (F17)

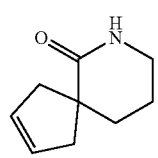

Intermediate (F18):

TMSCl (1.7 mL, 13.4 mmol) was added dropwise to a mixture of intermediate (F17) (2.0 g, 13.2 mmol) and TEA (2.8 mL, 19.8 mmol) in toluene (25 ml) at rt. The resulting suspension was stirred at 60° C. for 5 hours. Anhydrous diethyl ether (20 mL) and pentane (20 mL) were added and the solid was filtered on millipore filter. The filtrate was partially evaporated (pentane and Et$_{2O}$) to afford 15 ml of TMS adduct in residual toluene. This solution was added dropwise to MeLi 1.6M in Et$_2$O (9.6 ml, 14.8 mmol) at −30° C. The resulting mixture was stirred at −30° C. for 20 min and allowed to warm to room temperature over 1 h. The reaction mixture was quenched by the addition of 20 ml of saturated aqueous NH$_4$Cl and extracted with Et$_2$O (2×40 mL). The combined organic layers were dried over Na$_2$SO$_4$, filtered and concentrated under reduced pressure to eliminate the diethyl ether and give a solution of imine in toluene. This solution was diluted with DCM (30 mL) then NaBH(OAc)$_3$ (3.50 g, 16.5 mmol) was added portionwise at 0° C. The mixture was stirred at rt for 16 h and quenched by the addition of 20 ml of saturated aqueous NH$_4$Cl and extracted with DCM (2×40 mL). The combined organic layers were dried over Na$_2$SO$_4$, filtered, treated with HCl 4 M in dioxane (4.6 mL, 18.5 mmol) and concentrated under reduced pressure. The residue was purified by column chromatography (silica gel, mobile phase: DCM/MeOH/$_{aq}$NH$_3$ 90/10/1) to give 1.5 g (60%) of intermediate (F18) as white solid.

Intermediate (F18)

Intermediate (F19):

H$_2$O (2.00 mL) and then HCl 37% (2.20 mL, 26.8 mmol) were added dropwise with caution to stirred 1,3-Diaminopropane (6.17 g, 83.2 mmol) at 0° C. (ice bath) followed by addition of 2-Furyl methyl ketone (4.00 g, 36.3 mmol). The resulting mixture was stirred at reflux (oil bath 120° C.) for 15 min then at rt for 45 min. K$_2$CO$_3$ (4 g) and water (4 mL) were added and the mixture was extracted with DCM (3×25 mL). The combined organic layers were washed with aq. K$_2$CO$_3$ (10 mL, 30 wt %), dried over Na$_2$SO$_4$, filtered and concentrated under reduced pressure and purified by Preparative LC (neutral aluminum oxide (Typ 507C, Brockmann I, ~150 mesh, Sigma-Aldrich® 19,997-4); mobile phase: DCM/MeOH 100/0 to 98/2). The pure fractions were collected and the solvent was evaporated to give 1.70 g of intermediate (F19) as yellow brownish oil (32%).

intermediate (F19)

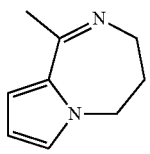

Intermediate (F20):

NaBH$_4$ (0.564 g, 14.9 mmol) was added portionwise within 10 min to a solution of intermediate (F19) (1.70 g, 11.5 mmol) in MeOH (11.5 mL) at 0° C. (ice-water bath). The resulting mixture was stirred at rt for 2 hours and then concentrated under reduced pressure. The residue was taken in H$_2$O (20 mL) and extracted with DCM (3×20 mL). The combined organic layers were dried over Na$_2$SO$_4$, filtered and concentrated under reduced pressure to give 1.51 g (88%) of intermediate (F20) as an oil.

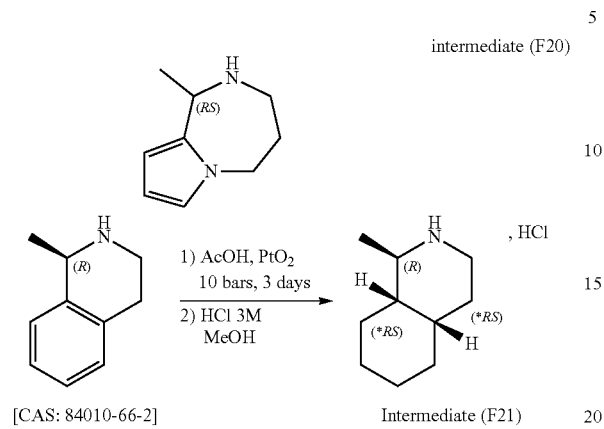

intermediate (F20)

Intermediate (F21):

In a Parr® reactor, (1R)-1,2,3,4-tetrahydro-1-methyl-Isoquinoline (2.00 g, 13.6 mmol) was dissolved in AcOH (32 mL). PtO$_2$ (1.60 g, 7.06 mmol) was added and the reaction was purged 3 times with H$_2$. The reaction mixture was stirred under 10 bar for 3 days. Catalyst was filtered off, the residue was washed with AcOH and EtOAc and evaporated to dryness to give 4.46 g of a crude product as colourless oil. This oil was dissolved in toluene and coevaporated twice to give 3.12 g of an intermediate which was dissolved in MeOH (154 mL) and HCl 3M in CPME (34 mL) was added. The reaction mixture was stirred at 0° C. for 4 h. The reaction mixture was evaporated in vacuo to give 3.90 g of intermediate (F21) as pale yellow solid (quant.).

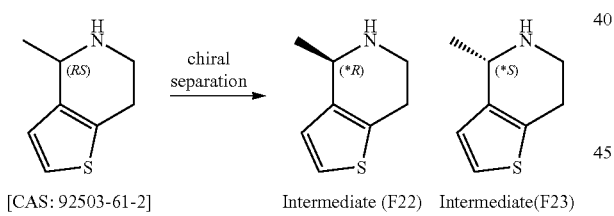

Intermediates (F22) and (F23):
4,5,6,7-tetrahydro-4-methyl-thieno[3,2-c]pyridine was purified by chiral SFC (Stationary phase: Lux Cellulose® 2 5 μm 250*21.2 mm, Mobile phase: 80% CO$_2$, 20% iPOH (0.3% iPrNH2)) to give 2 fractions: 2 g of intermediate (F22) as a colorless oil (*R) and 2.1 g of intermediate (F23) as a colorless oil (*S).

Intermediate (G)

Intermediate (G1):

A mixture of intermediate (E1) (2 g, 4.97 mmol), (R)-2-methylazepane hydrochloride (0.893 g, 5.97 mmol), HATU (2.84 g, 7.46 mmol) and DIEA (2.61 mL, 14.92 mmol) in DMF (20 mL) was stirred overnight at RT. The reaction mixture was poured into water (100 mL), the precipitate was filtered off, washed with water and dried (vacuum, 60° C.). The residue (2.38 g, >100%) was purified by column chromatography over silica gel (80 g, 15-40 μm, eluent: from 80% heptane, 20% EtOAc to 70% heptane, 30% EtOAc). The pure fractions were collected and the solvent was evaporated to give 1.96 g (86%) of intermediate (G1).

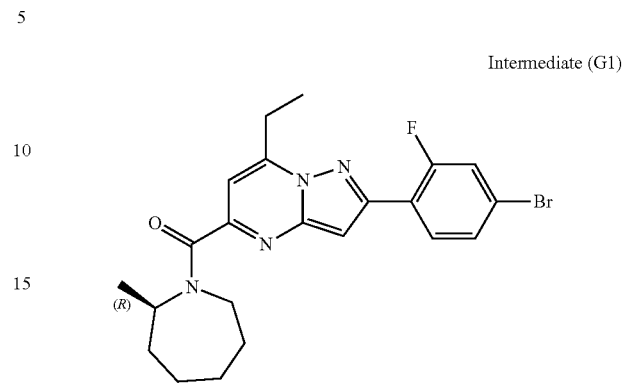

The following intermediates were prepared according to the above procedure:

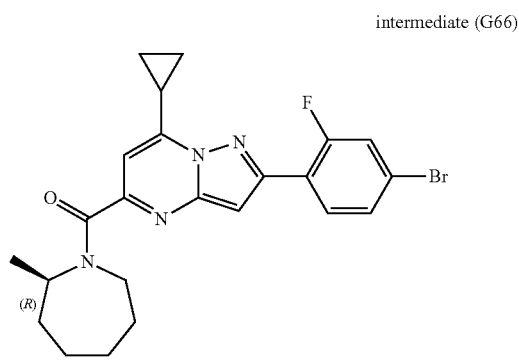

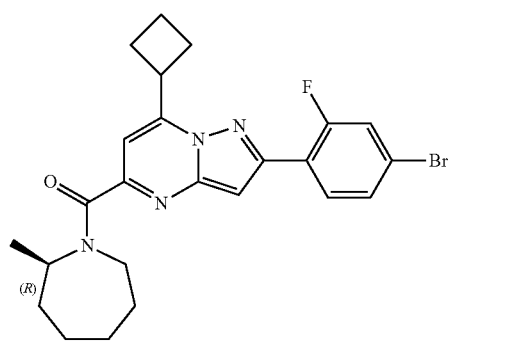

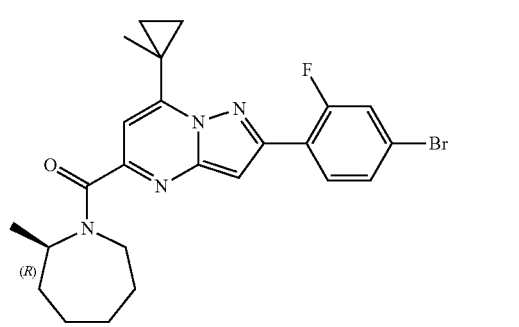

91
-continued
intermediate (G93)
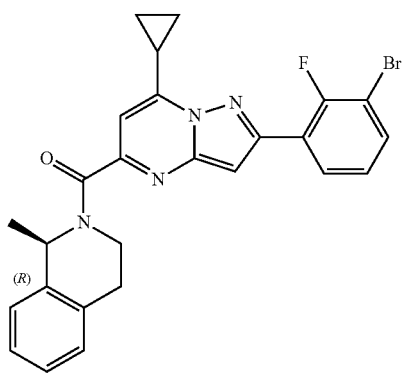
intermediate (G112)
intermediate (G113)
intermediate (G115)
92
-continued
intermediate (G116)
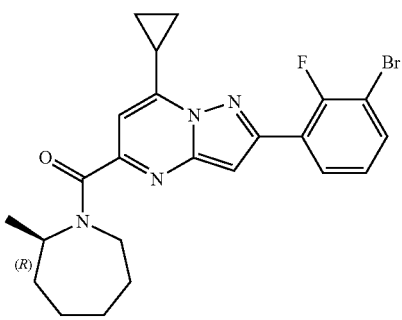
intermediate (G131)
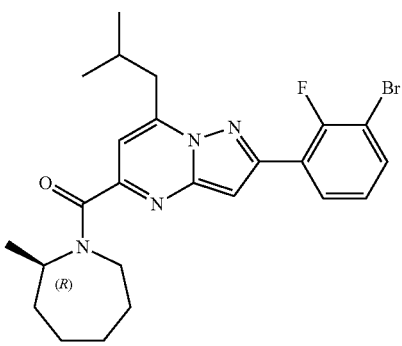
intermediate (G132)
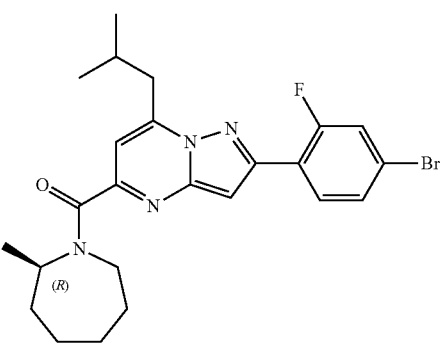
intermdiate (G136)
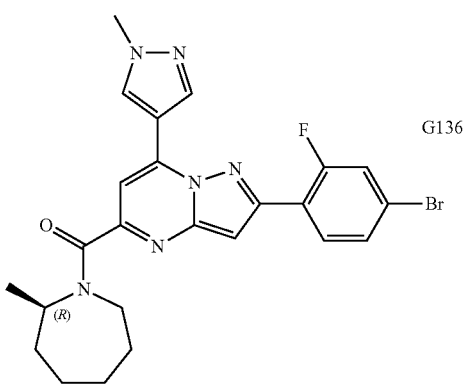

intmerediate (G138)
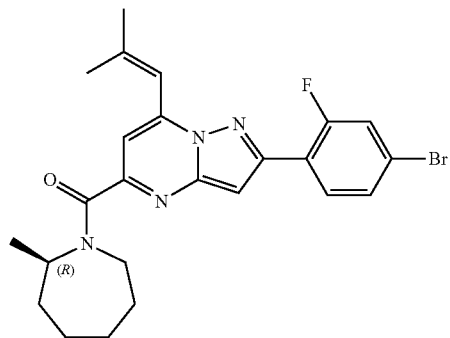
intermediate (G147)
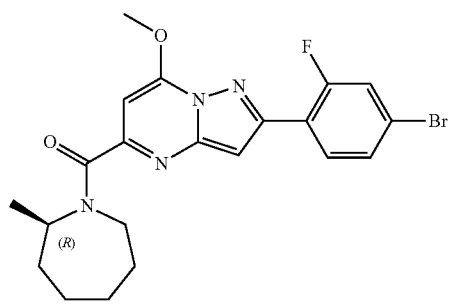
intermeidate (G169)
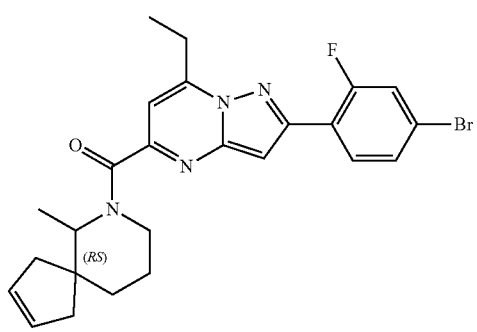
intermeidate (G234)
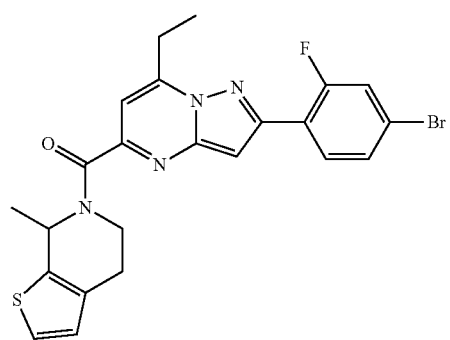
intermediate (G237)
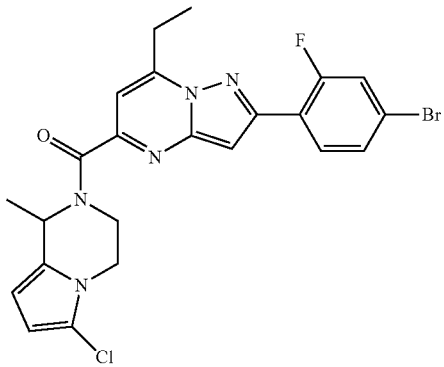
intermediate (G240)
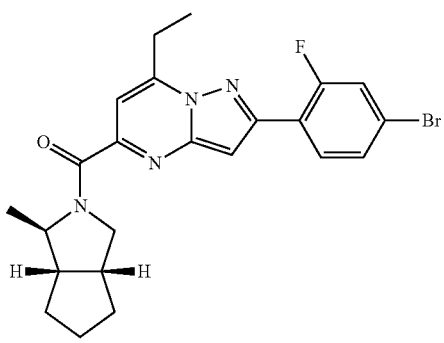
intermeidate (G243)
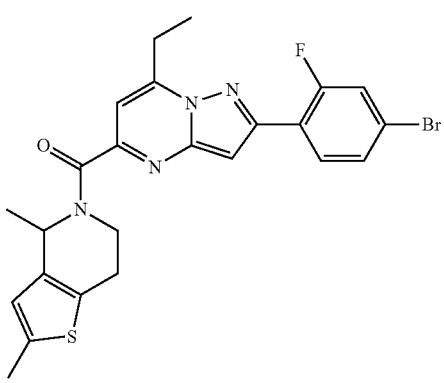
intermediate (G246)
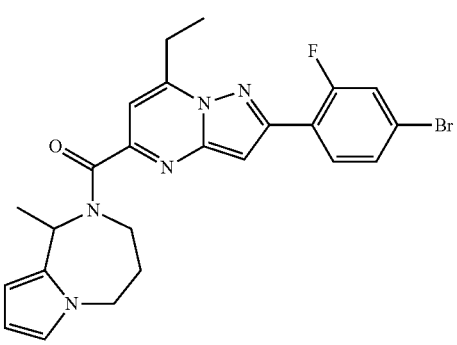

intermediate (G262)

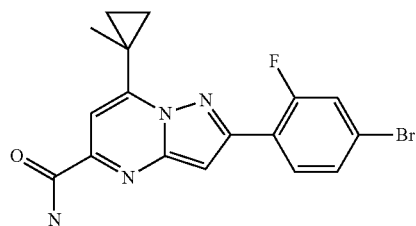

intermediate (G263)

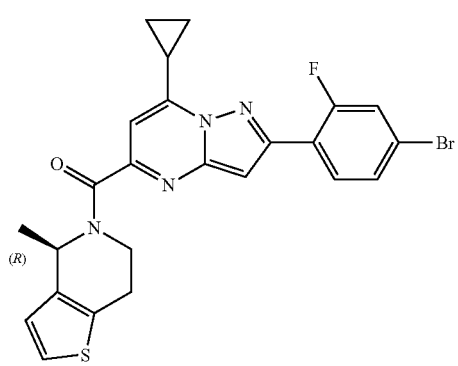

intermediate (G264)

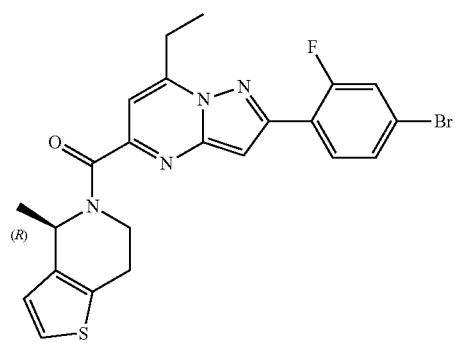

intermediate (G265)

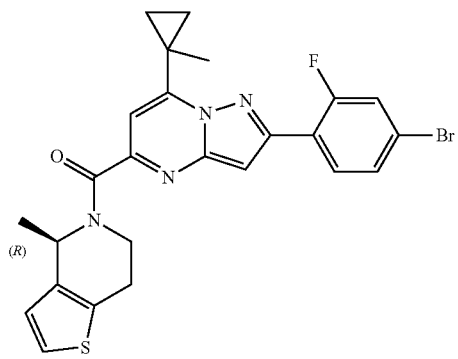

intermediate (G266)

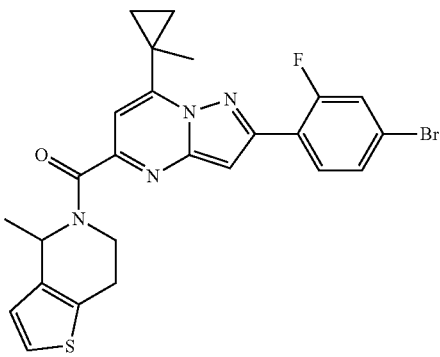

intermediate (G310)

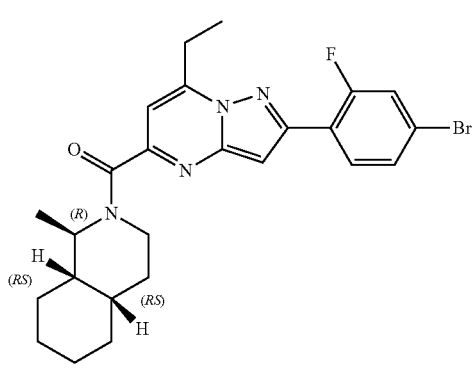

intermediate (G311)

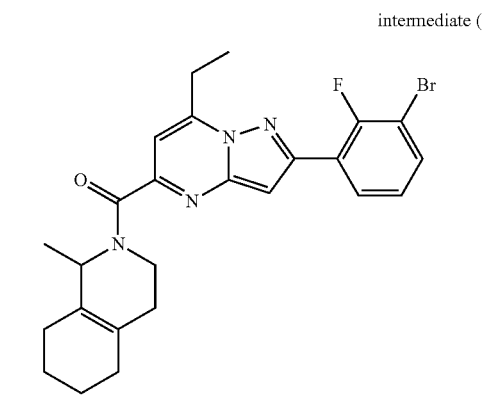

Intermediate (G2):

A mixture of intermediate (E1) (8.19 g, 22.5 mmol), BOP (10.86 g, 25 mmol), DIEA (7.10 g, 56 mmol) and 2-methylazepan hydrochloride (3.46 g, 23.1 mmol) in dry DMF (50 mL) was stirred at RT for 6 hours. The solvent was evaporated, then the residue was taken up with CHCl$_3$ and washed with water. The organic layer was separated and evaporated till dryness. The crude product was purified by column chromatography (silica gel, CHCl$_3$/EtOAc (14/1)). The pure fractions were collected and the solvent was evaporated. The residue was crystallized from hexane/Et$_2$O (1/1) to give 8.62 g (85%) of intermediate (G2).

Intermediate (G2)

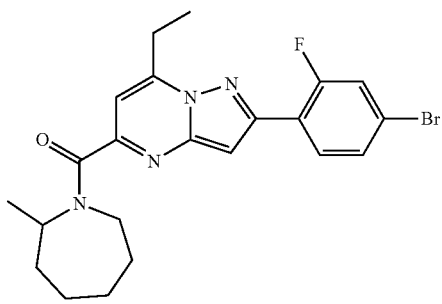

The following intermediates were prepared according to the above procedure:

Intermediate (G3)

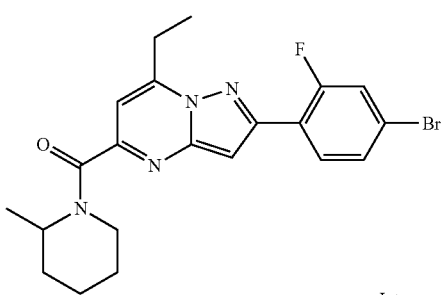

Intermediate (G4)

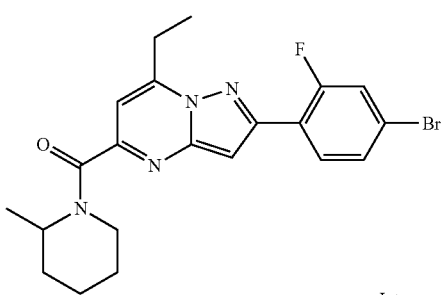

Intermediate (G5)

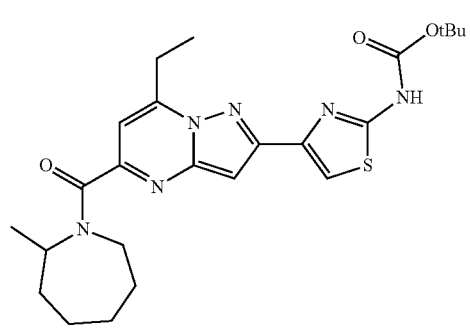

Intermediate (G6)

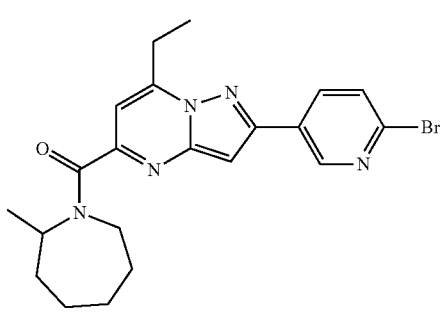

Intermediate (G7)

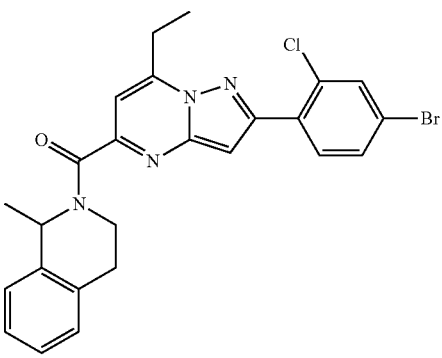

Intermediate (G8):

A mixture of intermediate (E36) (0.90 g, 2.47 mmol), BOP (1.10 g, 2.7 mmol), DIEA (0.797 g, 6.2 mmol) and 2-methylazepane hydrochloride (0.388 g, 2.5 mmol) in dry DMF (25 mL) was stirred at RT for 6 hours. The solvent was evaporated, then the residue was extracted with $CHCl_3$ and washed with water. The organic layer was separated and evaporated till dryness. The residue was purified by column chromatography (silica gel, $CHCl_3/Et_2O$). The pure fractions were collected and the solvent was evaporated. The residue was crystallized from hexane/$Et_2O$ (1/1) to give 0.72 g (64%) of intermediate (G8).

Intermediate (G8)

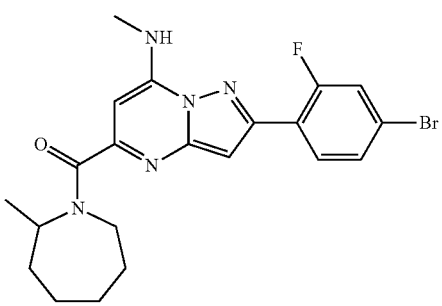

The following intermediates were prepared according to the above procedure:

Intermediate (G9)

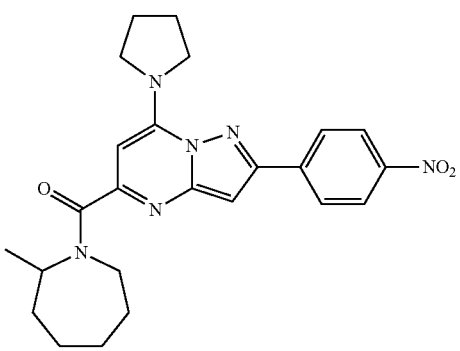

-continued

Intermediate (G10)

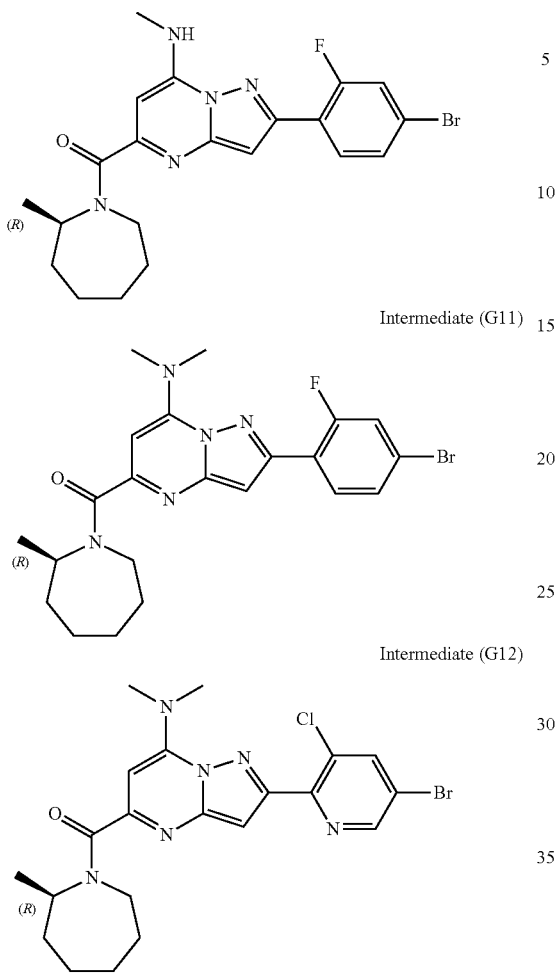

Intermediate (G11)

Intermediate (G12)

Intermediate (G13):

TBTU (1.4 mmol) was added to a mixture of intermediate (E10) (1.3 mmol), 2-methylazepane (1.4 mmol) and DIEA (3.2 mmol) in DCM (50 mL). The reaction mixture was stirred at RT overnight. The mixture was poured into water, then the organic layer was separated, washed with brine, dried over sodium sulfate, filtered and the filtrate was evaporated. The residue was purified by column chromatography (silica gel, DCM). The pure fractions were collected and the solvent was evaporated to give intermediate (G13).

Intermediate (G13)

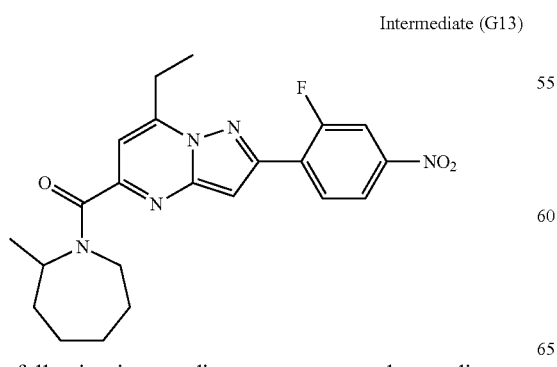

The following intermediates were prepared according to the above procedure:

intermediate (G14)

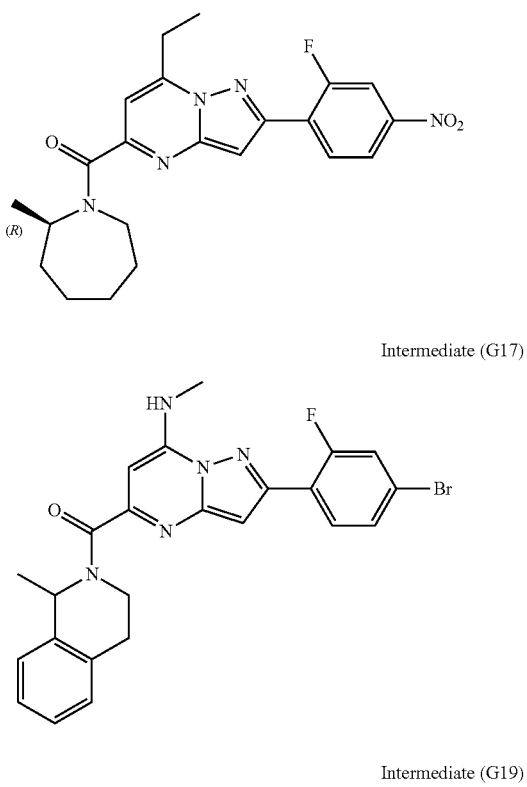

Intermediate (G17)

Intermediate (G19)

Intermediate (G20)

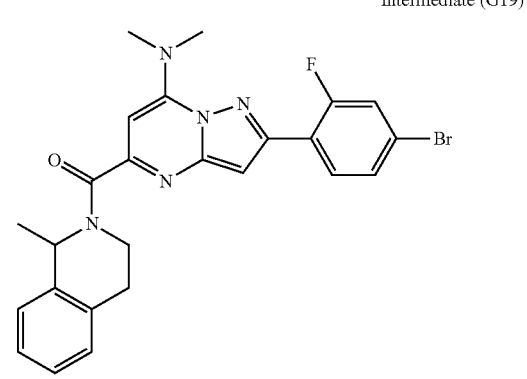

Intermediate (G21):

TBTU (0.18 g, 0.56 mmol) was added to a mixture of intermediate (E33) (0.18 g, 0.5 mmol), 2-methylazepane hydrochloride (0.08 g, 0.56 mmol) and DIEA (0.25 mL, 1.5 mmol) in DCM (5 mL). The reaction mixture was stirred at RT overnight. Water was added, then the organic layer was separated, washed with brine, dried over sodium sulfate, filtered and evaporated. The residue was purified by column chromatography (silica gel, DCM). The pure fractions were collected and the solvent was evaporated to give 0.23 g (99%) of intermediate (G21).

Intermediate (G21)

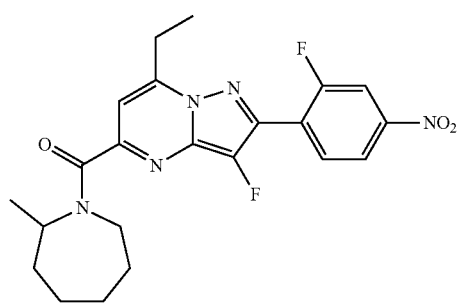

Intermediate (G22): TBTU (0.45 g, 1.4 mmol) was added to a mixture of intermediate (E32) (0.49 g, 1.3 mmol), 2-methylazepane hydrochloride (0.21 g, 1.4 mmol) and DIEA (0.5 mL, 3.2 mmol) in DCM (50 mL). The reaction mixture was stirred at RT overnight. Water was added, then the organic layer was separated, washed with brine, dried over sodium sulfate, filtered and evaporated. The residue was purified by column chromatography (silica gel, DCM). The pure fractions were collected and the solvent was evaporated to give 0.54 g (80%) of intermediate (G22).

Intermediate (G22)

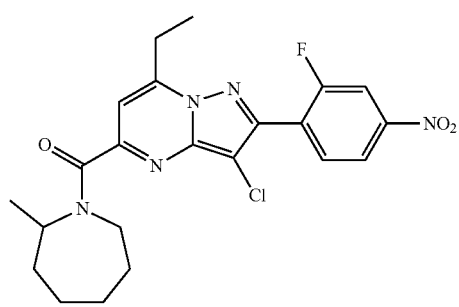

Intermediate (G23):

DIEA (0.48 g, 3.72 mmol) was added to a mixture of intermediate (E44) (0.46 g, 1.24 mmol), 2-methylazepane hydrochloride (140 mg, 1.24 mmol), HOAt (0.243 g, 1.24 mmol) and EDC (0.356 g, 1.86 mmol) in DCM. The reaction mixture was stirred at RT for 12 hours. The reaction mixture was poured into water, extracted with DCM, dried over sodium sulfate, filtered and evaporated to dryness. The residue was purified by column chromatography (silica gel, DCM/EtOAc (1/1)). The pure fractions were collected and the solvent was evaporated to give 0.4 g (88%) of intermediate (G23).

Intermediate (G23)

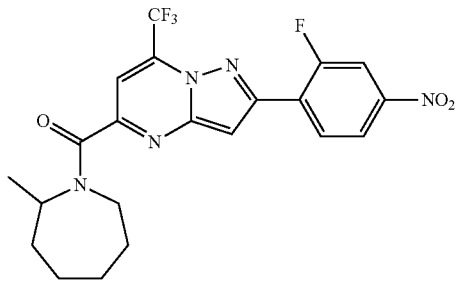

The following intermediates were prepared according to the above procedure:

Intermediate (G24)

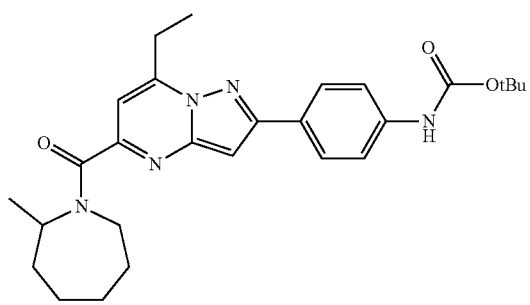

Intermediate (G25)

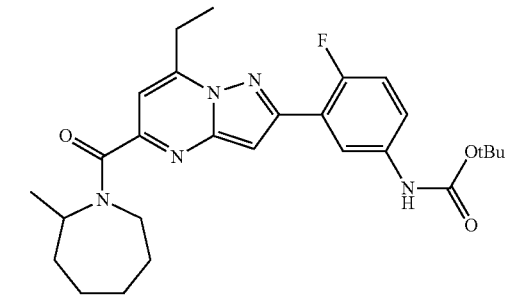

Intermediate (G26)

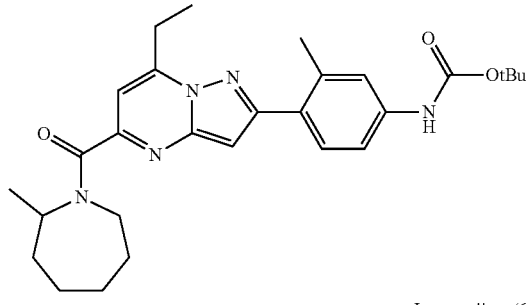

Intermediate (G27)

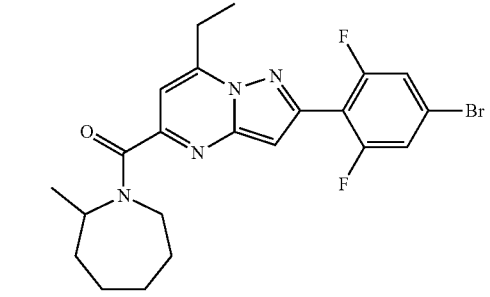

Intermediate (G28)

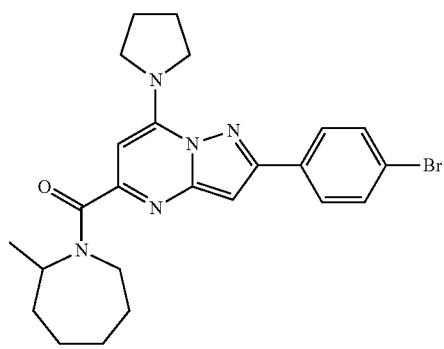

Reaction scheme:

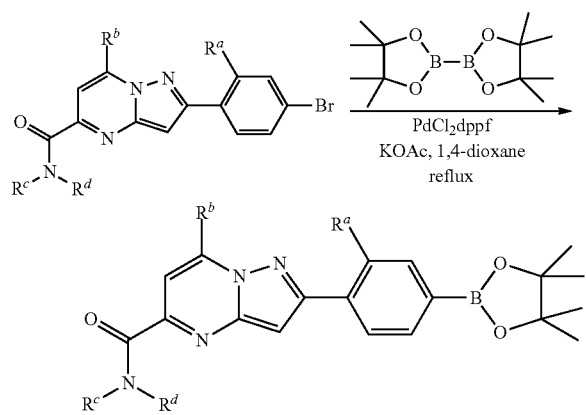

Intermediate (G29):

A mixture of intermediate (G2) (6.60 g, 14.4 mmol), KOAc (4.23 g, 43.2 mmol), bis(pinacolato)diboron (5.12 g, 20.1 mmol) and PdCl₂dppf (0.527 g, 7.2 mmol) in dry 1,4-dioxane was heated at reflux for 48 hours. The reaction mixture was filtered through a pad of Celite® and the filtrate was evaporated under vacuum. The residue was purified by column chromatography (silica gel, CHCl₃). The pure fractions were collected and the solvent was evaporated. The residue was crystallized in hexane to give 5.15 g (71%) of intermediate (G29).

Reaction scheme:

Intermediate (G29)

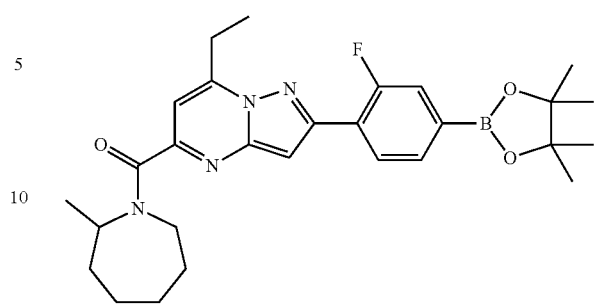

Intermediate (G30):

A mixture of intermediate (G1) (8 g, 17.41 mmol), bispin (6.63 g, 26.12 mmol) and KOAc (5.13 g, 52.25 mmol) in Me-THF (60 mL) was purged with N₂ flow for 10 min then PdCl₂(dppf)DCM (1.42 g, 1.74 mmol) was added. The resulting mixture was heated at 120° C. using a singlemode microwave (Biotage® initiator60) with a power output ranging from 0 to 400 W for 40 min. The mixture was poured out into water and EtOAc, the mixture was filtered through a short pad of Celite®, the organic layer was separated, washed with brine, dried (MgSO₄) and evaporated till dryness. Purification of the crude product was carried out by flash chromatography over silica gel (cartridge 120 g, 15-40 μm, Heptane/EtOAc 80/20). The pure fractions were collected and evaporated to dryness to afford 7.5 g (85%) of intermediate (G30). The product was used as such for the next step.

Intermediate (G30)

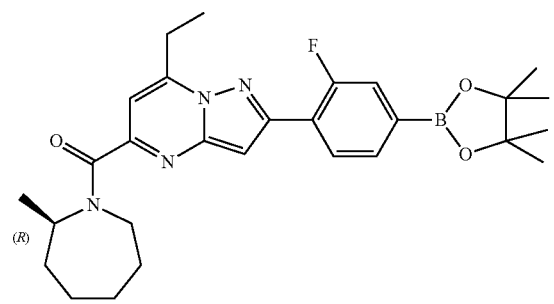

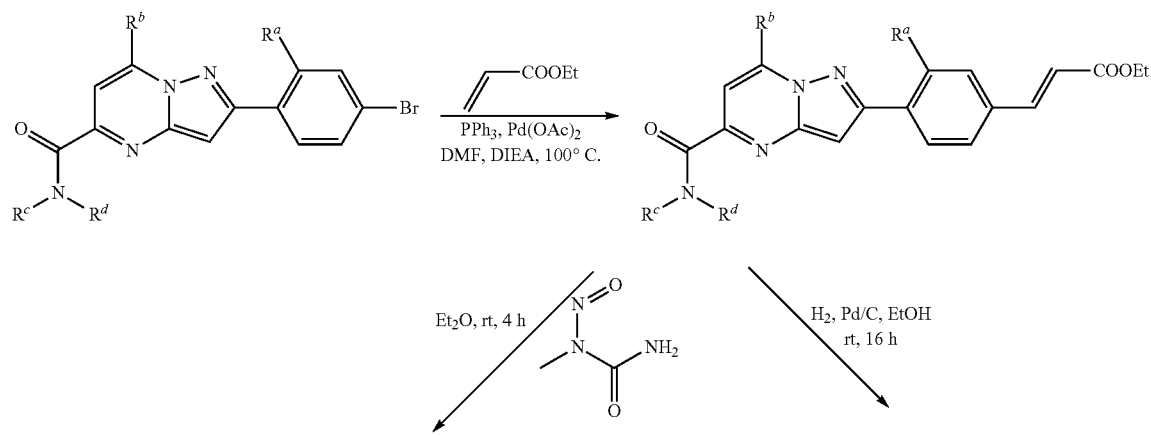

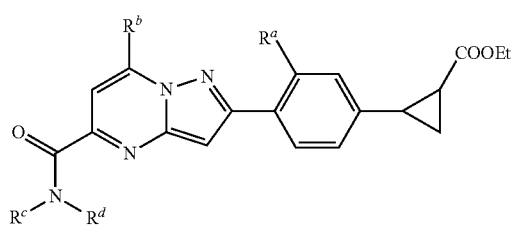 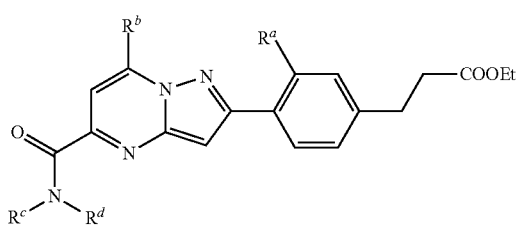

Intermediate (G31):

Ethyl acrylate (330 mg, 3.3 mmol) was added to a mixture of intermediate (G2) (300 mg, 0.65 mmol), PPh$_3$ (100 mg, 0.33 mmol), Pd(OAc)$_2$ (10 mg) and DIEA (0.4 mL, 6.5 mmol) in DMF (5 mL). The reaction mixture was stirred at 100° C. for 5 hours. Then, the solution was poured into water and EtOAc was added. The organic layer was separated, washed with brine, dried over sodium sulfate, filtered and evaporated. The residue was purified by column chromatography (silica gel, DCM/EtOAc). The pure fractions were collected and the solvent was evaporated to give 170 mg (55%) of intermediate (G31).

Intermediate (G31)

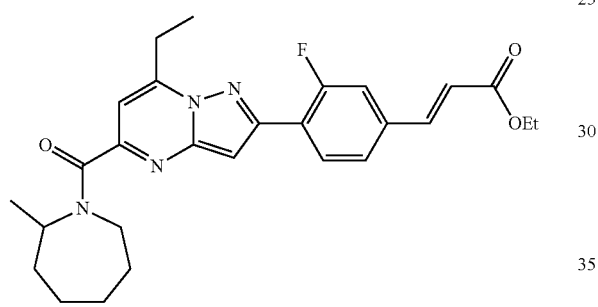

The following intermediates were prepared according to the above procedure:

Intermediate (G33)

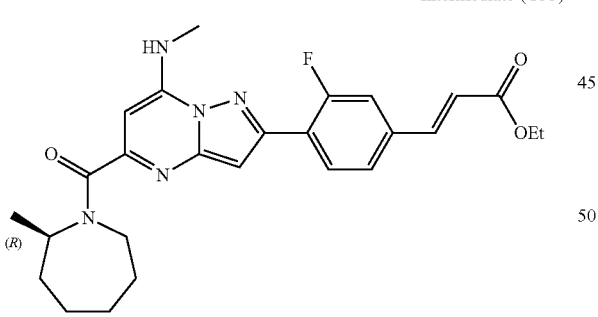

Intermediate (G34)

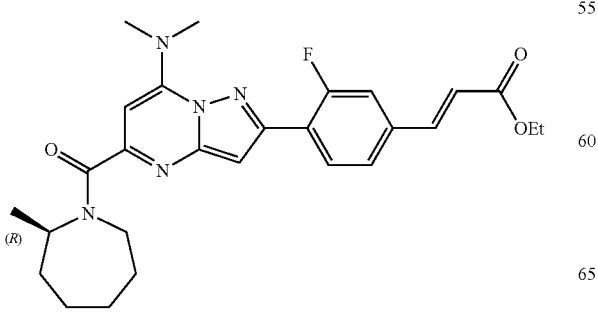

Intermediate (G36)

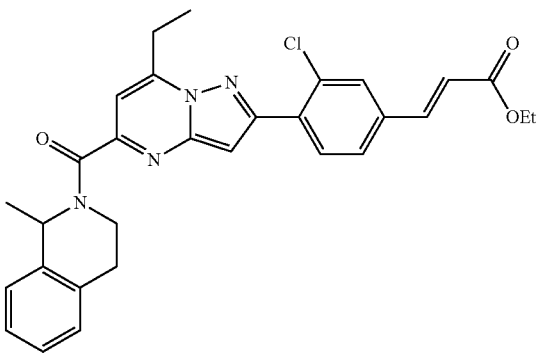

Intermediate (G37)

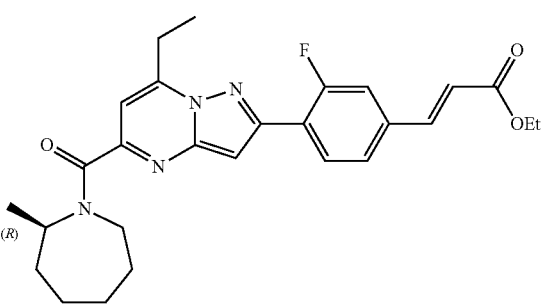

Intermediate (G38)

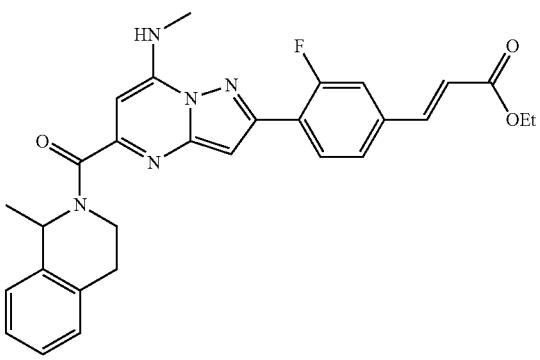

Intermediate (G40)
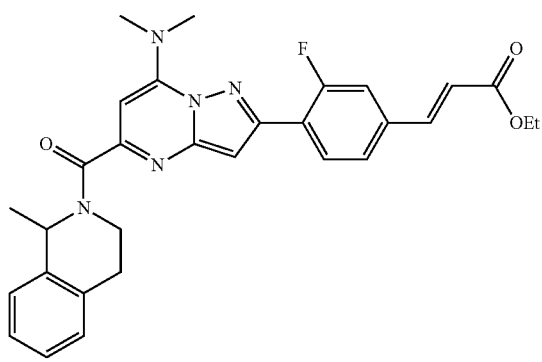

Intermediate (G41)
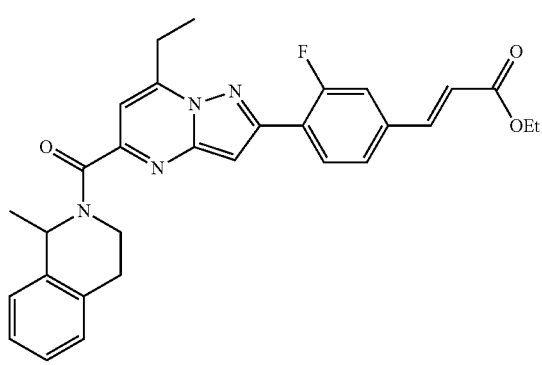

Intermediate (G42)
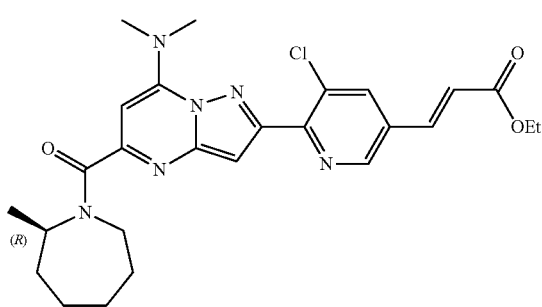

intermediate (G231)
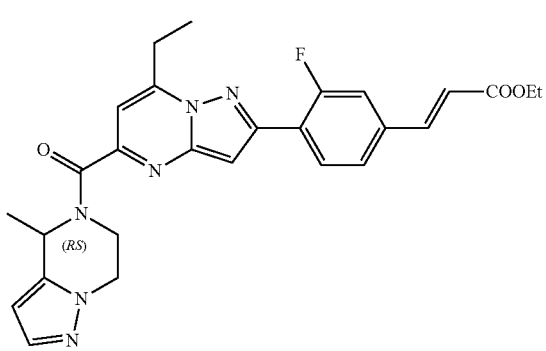

intermediate (G232)
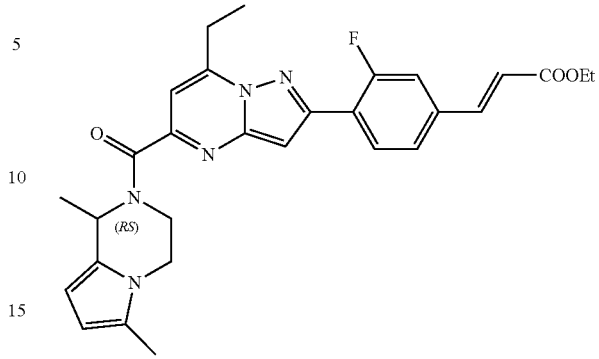

intermediate (G233)
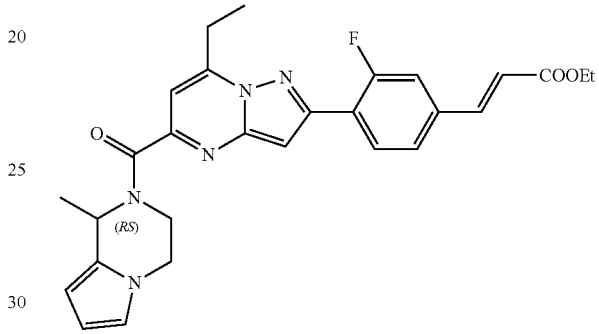

Intermediate (G43):

Intermediate (G31) (514 mg, 1.1 mmol) was dissolved in EtOH (10 mL) and Pd/C (0.1 g) was added. The mixture was shaken for 16 h at RT under hydrogen (1 bar). Then the solution was filtered through a pad of Celite® to remove the catalyst and the filtrate was evaporated. The residue was purified by column chromatography (silica gel, DCM/EtOAc). The pure fractions were collected and the solvent was evaporated to give 0.16 g (31%) of intermediate (G43).

Intermediate (G43)
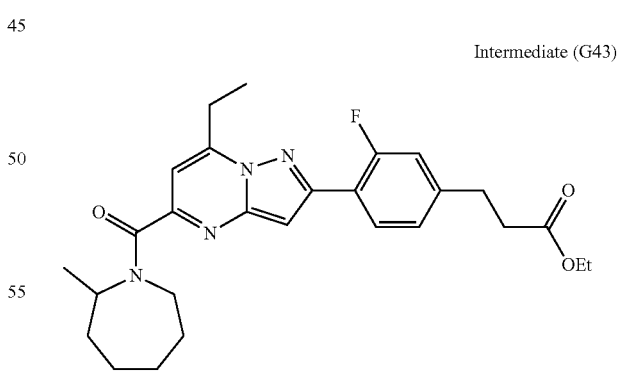

Intermediate (G44):

A solution of diazomethane in $Et_2O$ (prepared from 0.5 g of N-nitrosomethylurea) was added to a solution of intermediate (G31) (0.11 g, 0.23 mmol) in $Et_2O$ (10 mL). The reaction mixture was stirred at RT for 4 hours. The mixture was evaporated and the residue was purified by column chromatography to give 80 mg of intermediate (G44).

Intermediate (G44)

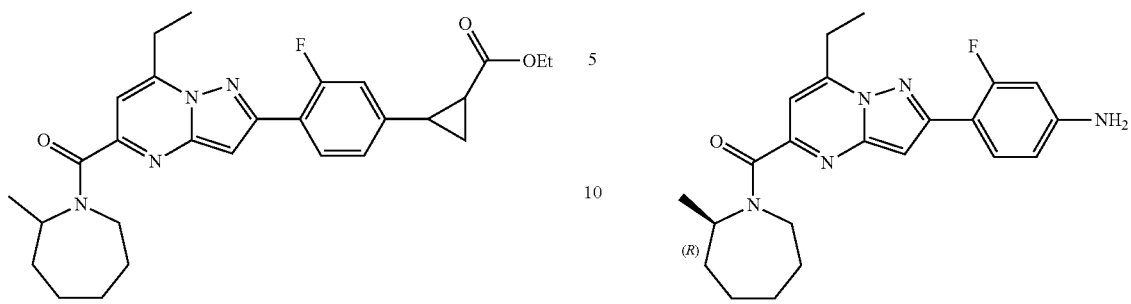

Reaction scheme:

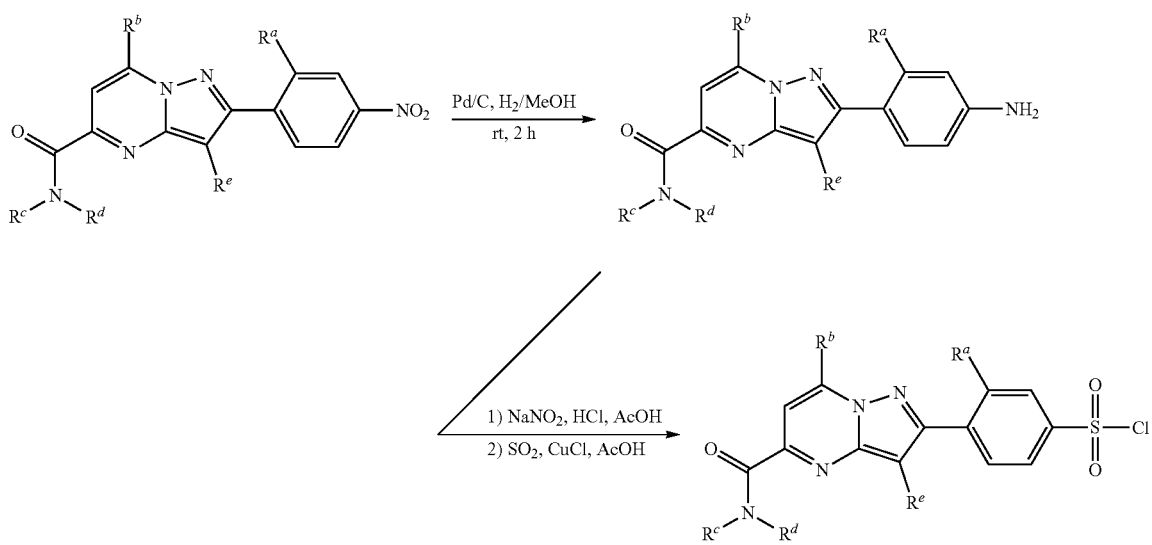

Intermediate (G45):

Intermediate (G13) (0.4 g, 0.9 mmol) was dissolved in MeOH (50 mL) and Pd/C (0.1 g) was added. The mixture was shaken for 2 hours at RT under hydrogen (1 bar). Then the solution was filtered through a pad of Celite® to remove the catalyst and the filtrate was evaporated to give 0.35 g (99%) of intermediate (G45).

Intermediate (G45)

The following intermediates were prepared according to the above procedure:

intermediate (G46)

-continued

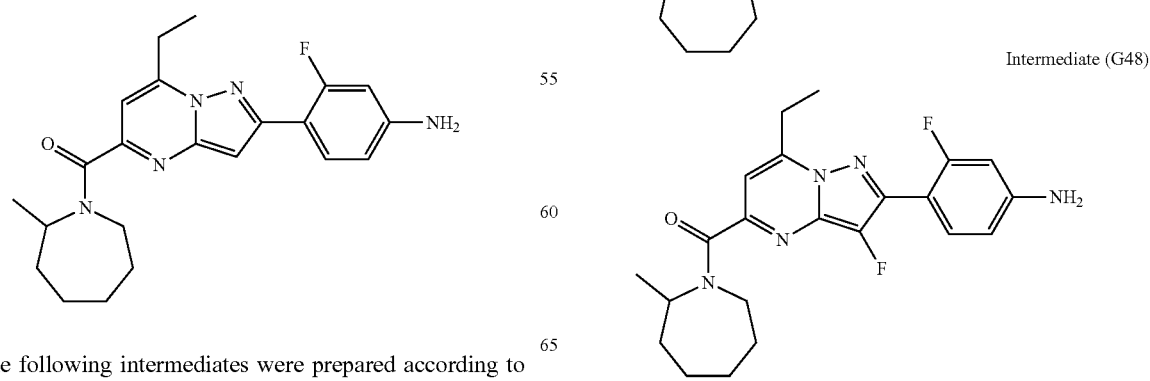

intermediate (G47)

Intermediate (G48)

Intermediate (G49):

Intermediate (G45) (0.6 g, 1.52 mmol) was dissolved in a mixture of HCl cc (0.77 mL) and AcOH (0.39 mL). The solution was cooled to 0° C. and a solution of sodium nitrite (0.13 g, 1.9 mmol) in water (2 mL) was added dropwise with stirring. After 30 min, the reaction mixture was added dropwise to a suspension of CuCl (77 mg, 0.77 mmol) in saturated solution of $SO_2$ in AcOH (0.43 mL) at 5° C. The reaction mixture was stirred for 30 min at 10° C. then poured into water. The reaction mixture was extracted with EtOAc. The organic layer was washed with saturated aqueous solution of $NaHCO_3$, then brine, dried over sodium sulfate, filtered and evaporated to give 0.25 g of intermediate (G49).

Intermediate (G50)

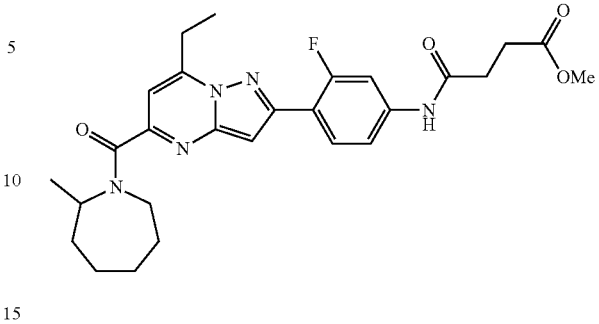

intermediate (G49)

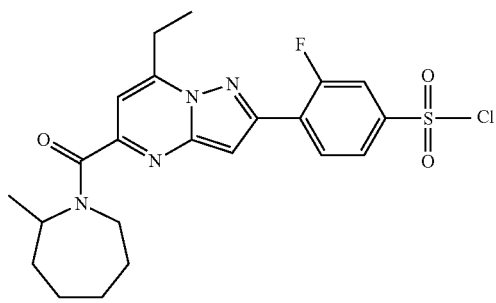

Reaction scheme:

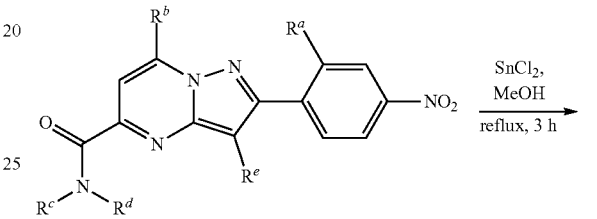

Reaction scheme:

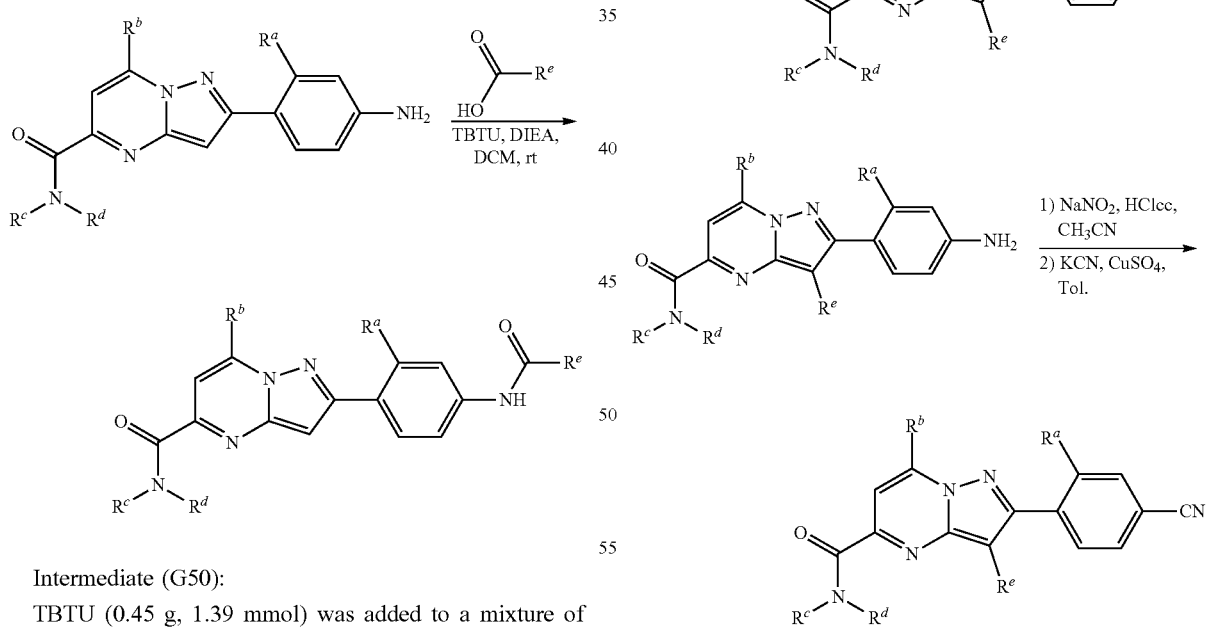

Intermediate (G50):

TBTU (0.45 g, 1.39 mmol) was added to a mixture of intermediate (G45) (0.5 g, 1.26 mmol), butanedioic acid 1-methyl ester (0.19 g, 1.39 mmol) and DIEA (0.3 mL, 1.9 mmol) in DCM (10 mL). The reaction mixture was stirred at RT overnight. The reaction mixture was poured into water. The organic layer was separated, washed with brine, dried over sodium sulfate, filtered and evaporated till dryness. The residue was purified by column chromatography (silica gel, DCM). The pure fractions were collected and the solvent was evaporated to give 500 mg (78%) of intermediate (G50).

Intermediate (G51):

Intermediate (G23) (0.35 g, 0.75 mmol) and $SnCl_2.2H_2O$ (3 eq.) in MeOH in presence of 1 drop of HCl cc were heated at reflux for 3 hours. The solvent was evaporated, water was added and the mixture was extracted with DCM. The organic layer was dried over sodium sulfate, filtered and evaporated under reduced pressure to give 0.3 g of intermediate (G51).

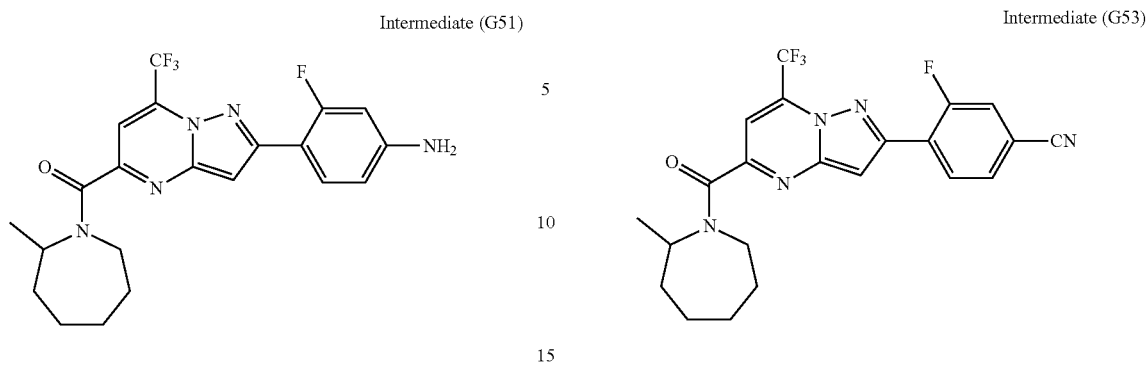

Intermediate (G51)

Intermediate (G52):

SnCl$_2$,2H$_2$O (710 mg, 3.1 mmol) was added to a solution of intermediate (G22) (0.47 g, 1.0 mmol) in MeOH (50 mL). The reaction mixture was heated at reflux for 2 h, then cooled and evaporated. A saturated aqueous solution of NaHCO$_3$ was added to the residue and the mixture was extracted. The organic layer was separated, washed with brine, dried over sodium sulfate, filtered and evaporated to give 0.5 g (99%) of intermediate (G52).

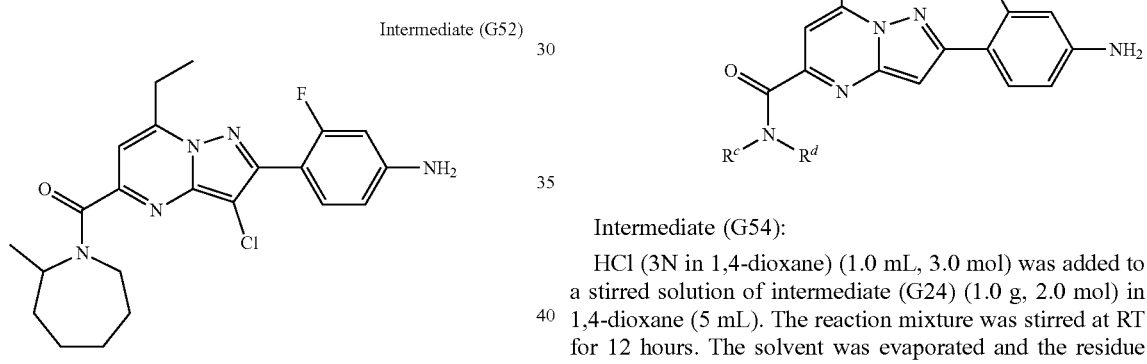

Intermediate (G52)

Intermediate (G53):

Sodium nitrite (55 mg, 0.80 mol) in water (3.5 mL) was added dropwise to a suspension of intermediate (G51) (0.3 g, 0.80 mol) and HCl cc (1 mL) in water (1 mL) and CH$_3$CN (17 mL) at 0° C. The reaction mixture was stirred at 0° C. for 1 h until the solid was dissolved. Then, an aqueous solution of Na$_2$CO$_3$ was added till pH 6-7. Simultaneously, a solution of CuSO$_4$,5H$_2$O (0.3 g, 1.2 mol) in water (3 mL) was added dropwise to a solution of KCN (0.3 g, 4.6 mol) in water (3 mL) at 0° C. Toluene (12 mL) was then added and the reaction mixture was heated at 60° C. for 1 hour. The diazonium salt solution was added dropwise over 15 min to this copper cyanide mixture at 60° C. The reaction mixture was heated at 70° C. for 1.5 h, allowed to cool down to RT, partitioned between EtOAc and water. The aqueous layer was extracted with EtOAc (×3). The combined organic extracts were dried over sodium sulfate, filtered and evaporated. The resulting solid was purified by column chromatography (silica gel, DCM/EtOAc (5/1)). The pure fractions were collected and the solvent was evaporated to give 0.05 g (14%) of intermediate (G53).

Intermediate (G53)

Reaction scheme:

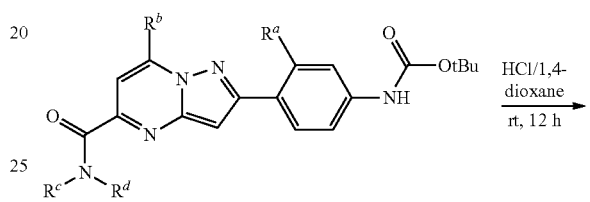

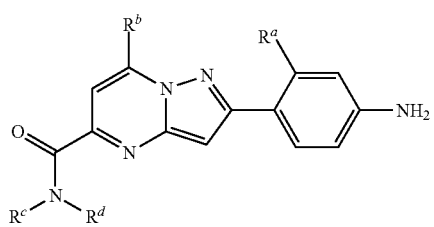

Intermediate (G54):

HCl (3N in 1,4-dioxane) (1.0 mL, 3.0 mol) was added to a stirred solution of intermediate (G24) (1.0 g, 2.0 mol) in 1,4-dioxane (5 mL). The reaction mixture was stirred at RT for 12 hours. The solvent was evaporated and the residue was taken up with DCM and a saturated aqueous solution of Na$_2$CO$_3$ (pH 7). The organic layer was separated, dried over sodium sulfate, filtered and evaporated under reduced pressure. The residue was purified by column chromatography (silica gel, DCM/EtOAc). The pure fractions were collected and the solvent was evaporated to give 0.8 g of intermediate (G54).

Intermediate (G54)

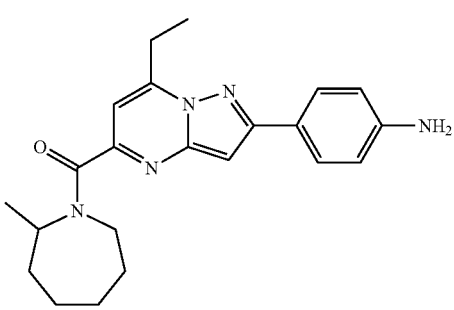

The following intermediates were prepared according to the above procedure:

Intermediate (G55)

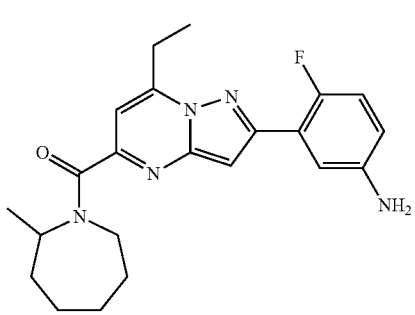

Intermediate (G56)

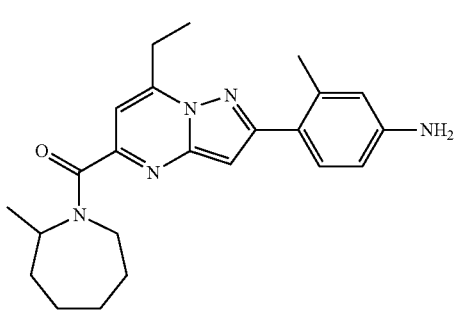

Reaction scheme:

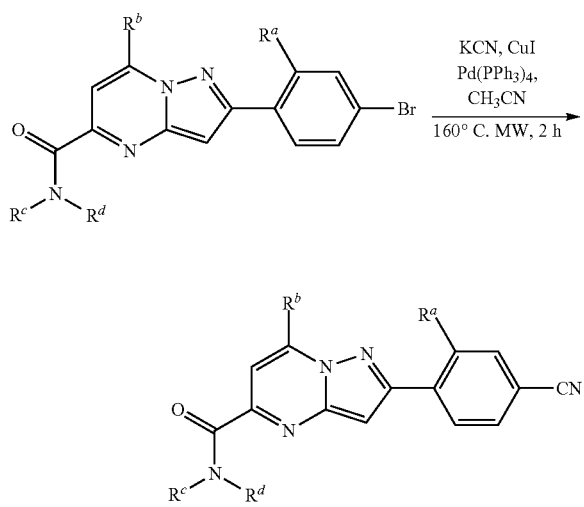

Intermediate (G57):

Pd(PPh$_3$)$_4$ (77 mg, 0.07 mmol) was added to a stirred solution of intermediate (G27) (160 mg, 0.33 mmol), KCN (87 mg, 1.34 mmol) and CuI (5 mg) in anhydrous CH$_3$CN (5 mL). The reaction mixture was heated at 160° C. for 2 h using one single mode microwave (Biotage initiator60) with a power output ranging from 0 to 400 W. The solvent was evaporated. The residue was purified by column chromatography (silica gel, DCM/EtOAc). The pure fractions were collected and the solvent was evaporated to give 120 mg (86%) of intermediate (G57).

Intermediate (G57)

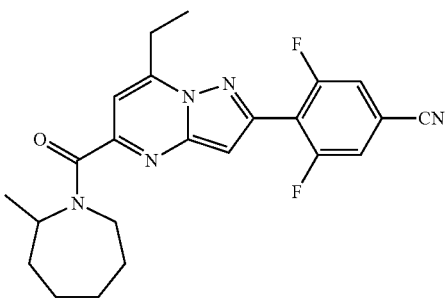

The following intermediate was prepared according to the above procedure

Intermediate (G58)

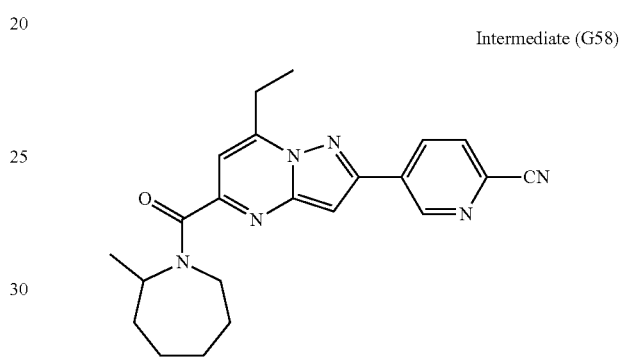

Reaction scheme:

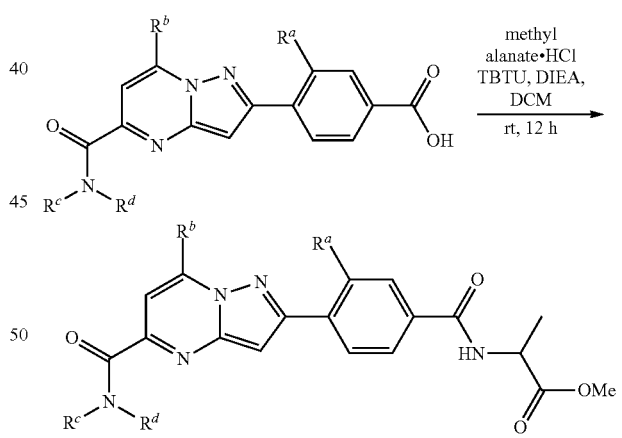

Intermediate (G59):

TBTU (110 mg, 0.36 mmol) was added to a solution of compound (K1) (0.15 g, 0.33 mmol), methyl alanate hydrochloride (55 mg, 0.39 mmol) and DIEA (0.13 g, 0.1 mmol) in DCM. The reaction mixture was stirred at RT for 12 hours. The mixture was poured into water and extracted with DCM. The organic layer was separated, dried over sodium sulfate, filtered and evaporated. The residue was purified by column chromatography (silica gel, DCM/EtOAc (10/1)). The pure fractions were collected and the solvent was evaporated to give 100 mg (32%) of intermediate (G59).

Intermediate (G59)

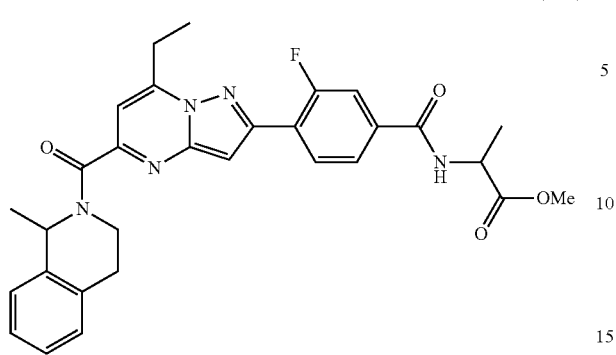

intermediate (G61)

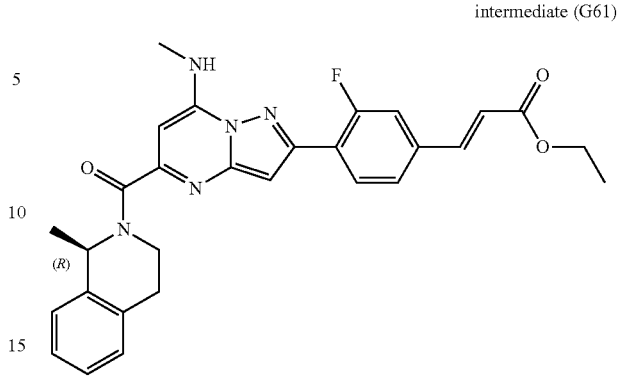

Intermediate (G60):

A mixture of intermediate (E36) (0.75 g, 1.86 mmol), (R)-1,2,3,4-tetrahydro-1-methylisoquinoline (0.33 g, 2.23 mmol), HATU (1.06 g, 2.79 mmol) and DIEA (0.9 mL, 5.58 mmol) in DMF (10 mL) was stirred overnight at RT. The mixture was poured out into water, extracted twice with EtOAc. The organic layers were washed with water then brine, dried over MgSO₄ and evaporated till dryness. The residue was purified by column chromatography (silica gel, Heptane/AcOEt 70/30). The pure fractions were collected and evaporated to dryness to afford 455 mg (49%) of intermediate (G60).

Intermediate (G62):

HATU (2.66 g, 7.01 mmol) was added portionwise to a mixture of intermediate (E1) (1.88 g, 4.67 mmol), (R)-1,2,3,4-tetrahydro-1-methylisoquinoline (0.82 g, 5.6 mmol) and DIEA (2.45 mL, 14 mmol) in DMF (20 mL) at RT then the mixture was stirred overnight. The mixture was poured out into water, the precipitate was filtered off, washed with water and dried (vacuum, 50° C.) to give 2.15 g (93%) of intermediate (G62).

intermediate (G60)

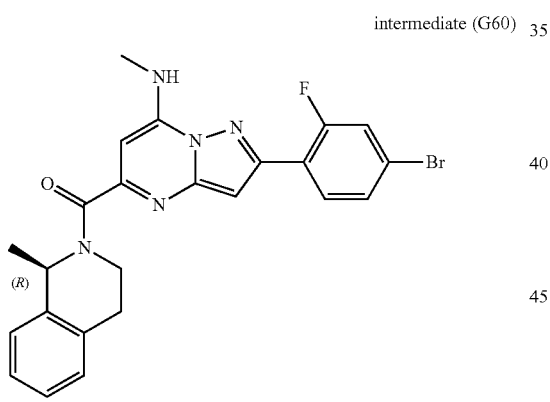

intermediate (G62)

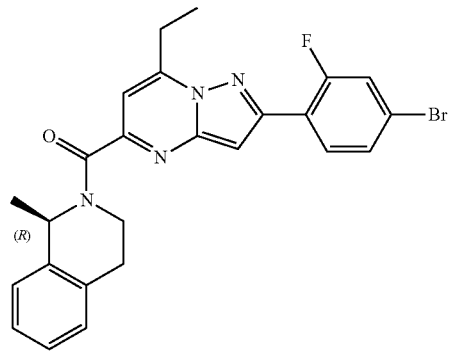

Intermediate (G61):

A mixture of intermediate (G60) (0.45 g, 0.91 mmol), ethyl acrylate (0.6 mL, 0.59 mmol), Pd(OAc)₂ (20 mg, 0.091 mmol) and tri-o-tolylphosphine (55 mg, 0.18 mmol) in Et₃N (0.77 mL, 5.46 mmol) and CH₃CN (11 mL) was heated at 120° C. using a single mode microwave (Biotage® initiator60) with a power output ranging from 0 to 400 W for 25 min. water and DCM were added and the product was separated on a hydrophobic frit, the solvent was evaporated till dryness. Purification was carried out by column chromatography (silica gel, DCM/MeOH: 99/1). The pure fractions were collected and evaporated to dryness. The crude compound was crystallized from Et₂O, filtered and dried under vacuum to afford 350 mg (75%) of intermediate (G61)

Intermediate (G63):

HATU (2.32 g, 6.09 mmol) was added portionwise to a mixture (thick) of intermediate (E45) (1.8 g, 4.06 mmol), (R)-1,2,3,4-tetrahydro-1-methyl-isoquinoline (0.72 g, 4.87 mmol) and DIEA (2.12 mL, 0.74 g/mL, 12.18 mmol) in DMF (20 mL) at RT then the mixture was stirred overnight. The mixture was poured slowly out into water dropwise with stirring (20 min), the precipitate was filtered off and washed with water. The solid was dissolved in DCM, washed with HCl 1N and water, dried (MgSO₄) and evaporated till dryness. Purification of the residue was carried out by flash chromatography over silica gel (Grace Resolve® 40 g, 15-40 μm, DCM/MeOH 97/3). The pure fractions were collected and evaporated to dryness to afford 1.37 g of intermediate (G63).

intermediate (G63)

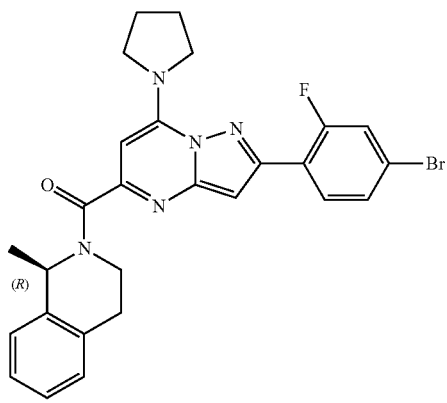

Intermediate (G64):
A solution of intermediate (G30) (0.32 g, 0.63 mmol) and methyl 5-bromo-3-fluoropicolinate CAS[1211538-72-5] (222 mg, 0.9 mmol) in a solution of $K_2CO_3$ 2M (0.63 mL, 1.264 mmol) and Me-THF (4 mL) was degassed with nitrogen for 10 min. $PdCl_2$(dppf) DCM (52 mg, 0.06 mmol) was added and the resulting mixture was heated at 100° C. using a singlemode microwave (Biotage initiator60) with a power output ranging from 0 to 400 W for 20 min. The mixture was poured out into water and EtOAc, the mixture was filtered through a short pad of Celite®, the organic layer was separated, washed with brine, dried over $MgSO_4$ and evaporated till dryness. The residue was purified by column chromatography (silica gel, Heptane/EtOAc 60/40). The pure fractions were collected and evaporated to dryness to afford 180 mg (53%) of intermediate (G64).

intermediate (G64)

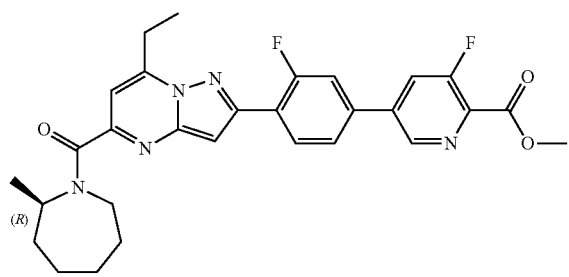

The following intermediates were prepared according to the above procedure intermediate (G65)

intermediate (G74)

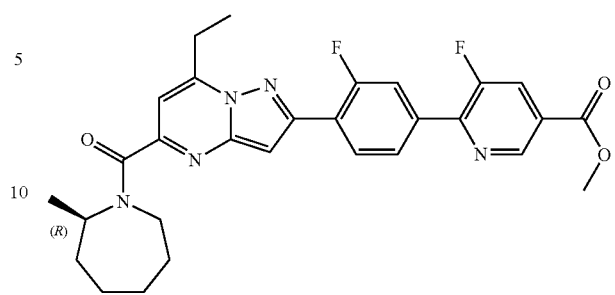

intermediate (G75)

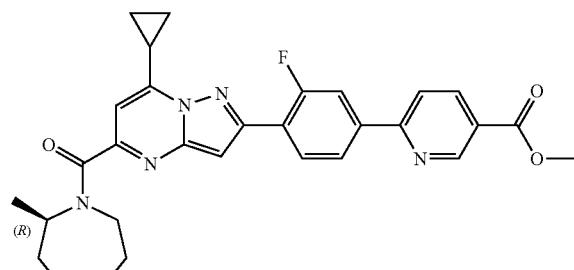

intermediate (G68)

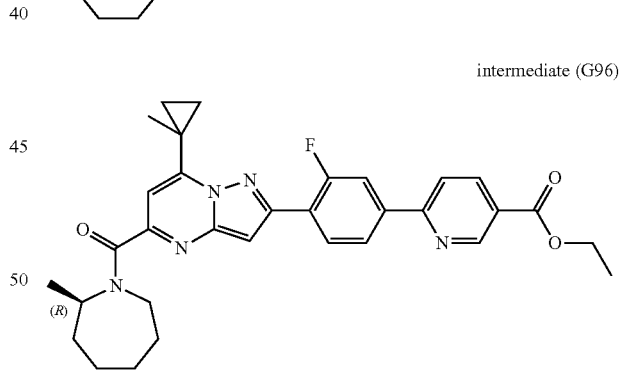

intermediate (G96)

intermediate (G97)

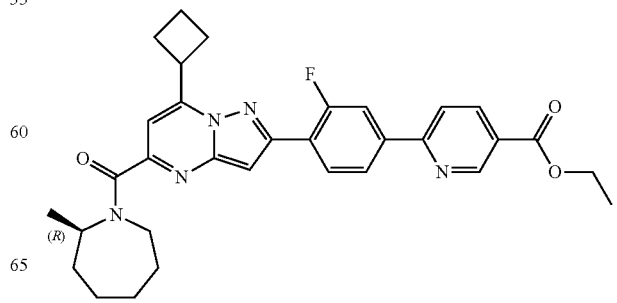

-continued
intermediate (G135)
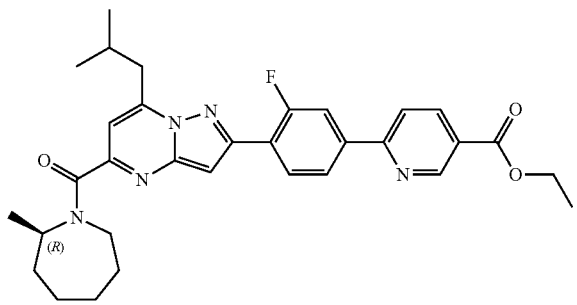
intermediate (G172)
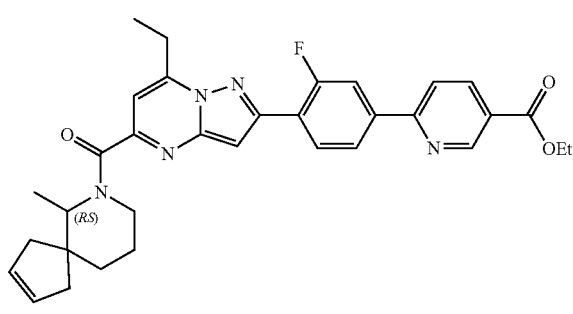
intermediate (G236)
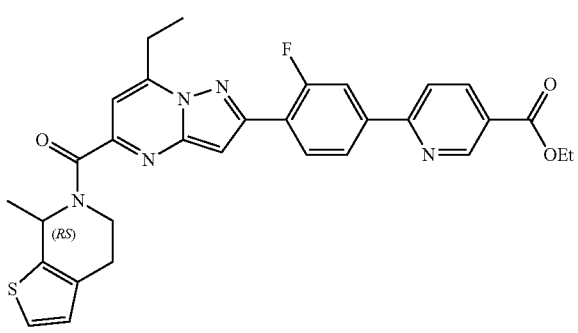
intermediate (G239)
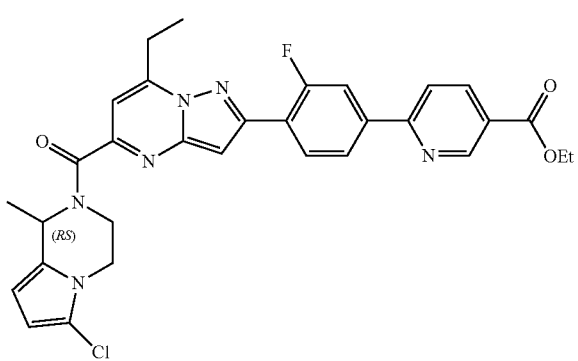
-continued
intermediate (G242)
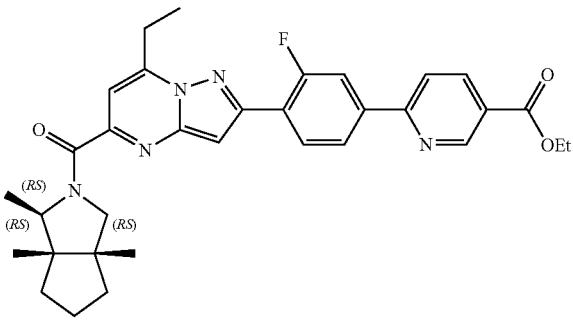
intermediate (G245)
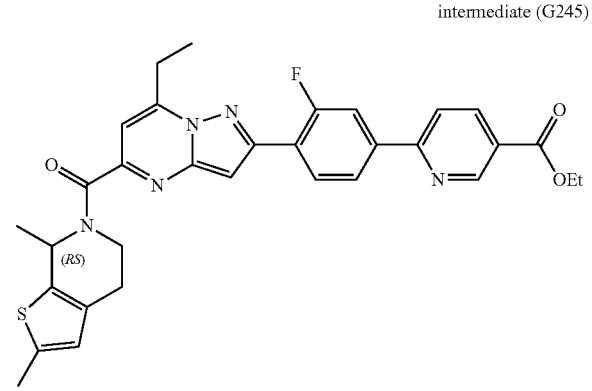
intermediate (G248)
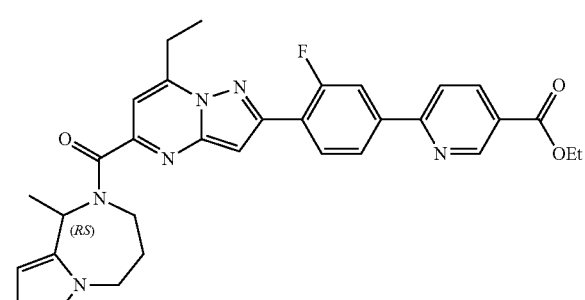
intermediate (G249)
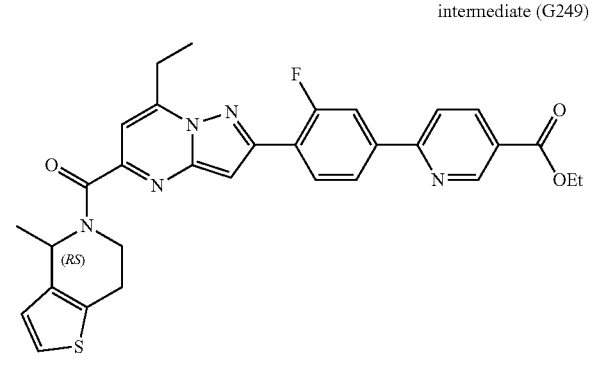

Reaction scheme:

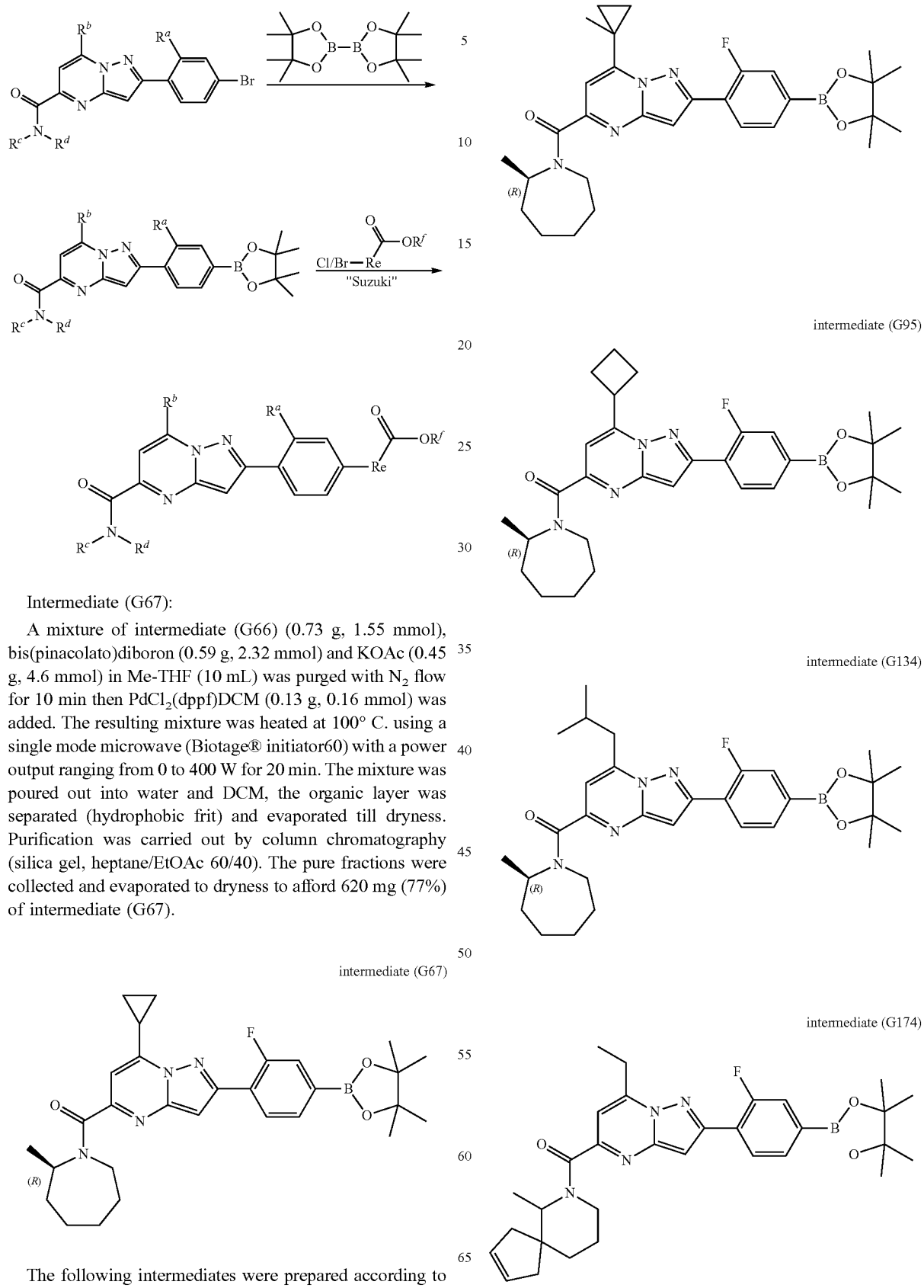

Intermediate (G67):

A mixture of intermediate (G66) (0.73 g, 1.55 mmol), bis(pinacolato)diboron (0.59 g, 2.32 mmol) and KOAc (0.45 g, 4.6 mmol) in Me-THF (10 mL) was purged with $N_2$ flow for 10 min then $PdCl_2$(dppf)DCM (0.13 g, 0.16 mmol) was added. The resulting mixture was heated at 100° C. using a single mode microwave (Biotage® initiator60) with a power output ranging from 0 to 400 W for 20 min. The mixture was poured out into water and DCM, the organic layer was separated (hydrophobic frit) and evaporated till dryness. Purification was carried out by column chromatography (silica gel, heptane/EtOAc 60/40). The pure fractions were collected and evaporated to dryness to afford 620 mg (77%) of intermediate (G67).

The following intermediates were prepared according to the procedure described for intermediate (G67).

intermediate (G235)

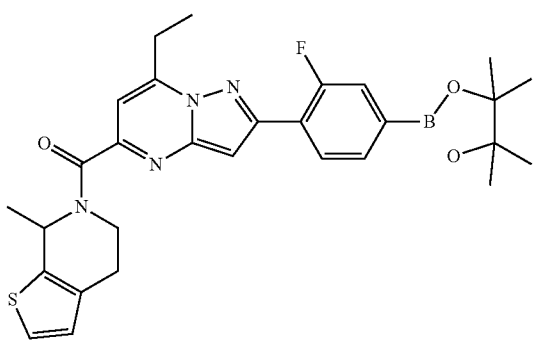

intermediate (G238)

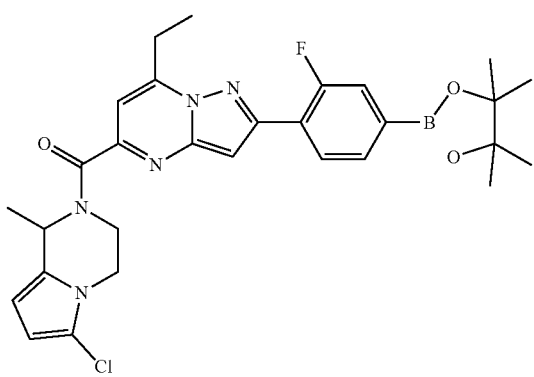

intermediate (G241)

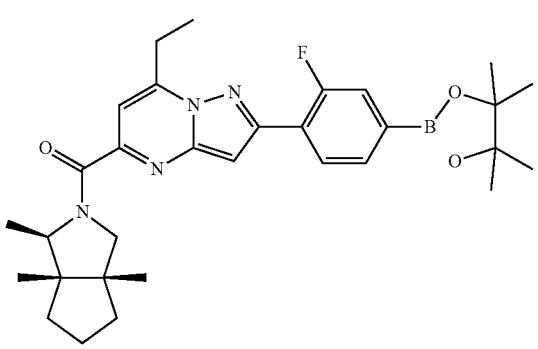

intermediate (G244)

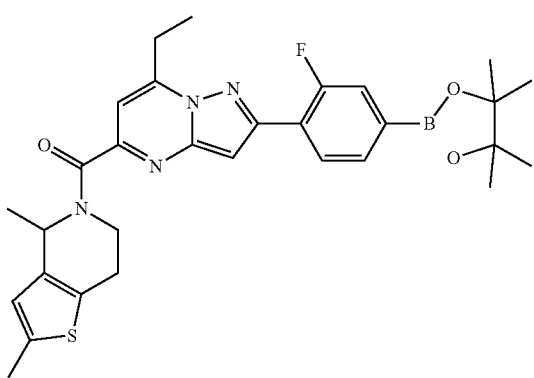

intermediate (G247)

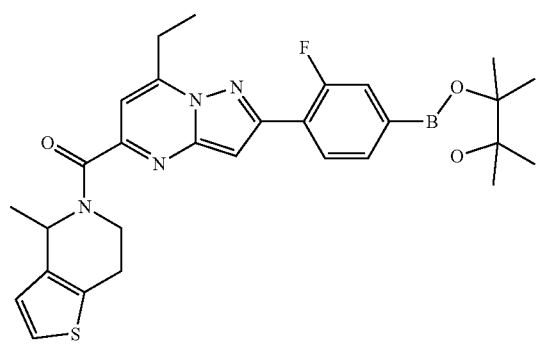

intermediate (G250)

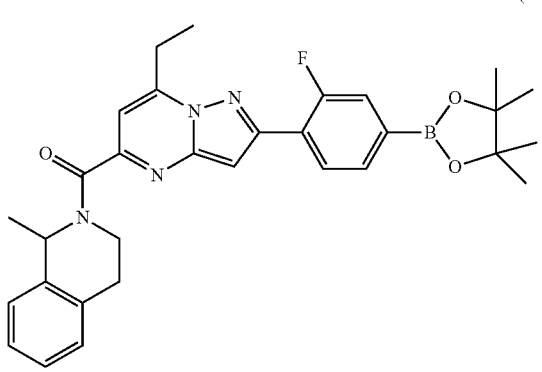

Intermediate (G69):

A mixture of intermediate (G20) (1 g, 2 mmol), bis(pinacolato)diboron (0.77 g, 3.04 mmol) and KOAc (0.60 g, 6.08 mmol) in DME (10 mL) was purged with $N_2$ flow for 10 min then $PdCl_2$(dppf)DCM (0.166 g, 0.2 mmol) was added. The resulting mixture was heated at 100° C. using a singlemode microwave (Biotage® initiator60) with a power output ranging from 0 to 400 W for 20 min. The mixture was poured out into water and DCM, the organic layer was separated (hydrophobic frit) and evaporated till dryness. The residue was crystallized from EtOH, filtered off, washed with EtOH and dried (vacuum, 60° C.) to give 1.08 g (99%) of intermediate (G69).

intermediate (G69)

The following intermediate was prepared according to the above procedure.

intermediate (G70)

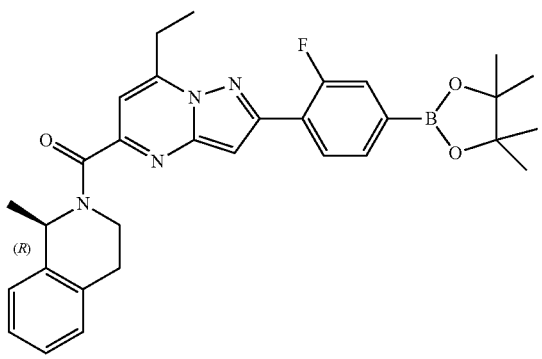

Reaction scheme:

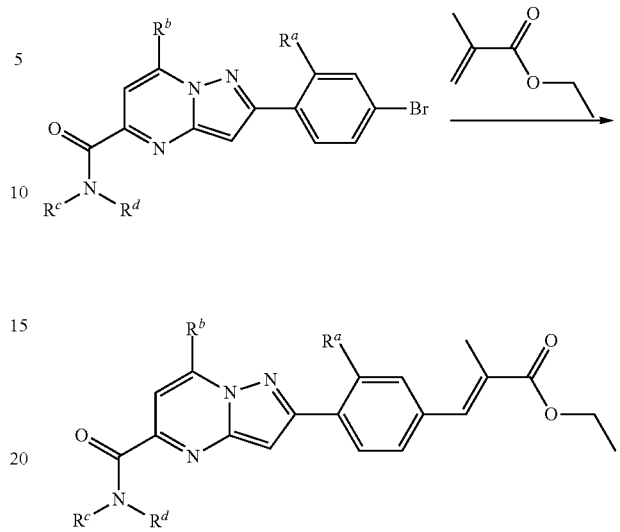

Intermediate (G71):

A solution of intermediate (G69) (0.2 g, 0.37 mmol) and 5-bromo-, 2-pyridinecarboxylic acid, methyl ester CAS [29682-15-3] (0.12 g, 0.55 mmol) in K₂CO₃ aq. (0.56 mL, 2 M, 1.11 mmol) and DME (2 mL) was degassed with nitrogen for 10 min. PdCl₂(dppf)DCM (0.030 g, 0.037 mmol) was added and the mixture was heated at 120° C. using a single mode microwave (Biotage® initiator60) with a power output ranging from 0 to 400 W for 20 min. The mixture was poured out into water and DCM/MeOH (9/1), the organic layer was separated (hydrophobic frit) and evaporated till dryness. Purification of the residue was carried out by flash chromatography (silica gel, from Heptane/EtOAc 80/20 to Heptane/EtOAc 60/40). The pure fractions were collected and evaporated to dryness to afford 0.085 g (42%) of intermediate (G71)

Intermediate (G73):

A solution of intermediate (G20) (0.35 g, 0.71 mmol) and tetrabutylammonium bromide (0.023 g, 0.071 mmol) in DMA (3.5 mL) was purged with N₂ for 10 min, then N-cyclohexyl-N-methyl-cyclohexanamine (0.226 mL, 1.06 mmol), 2-methyl-2-propenoic acid methyl ester (0.429 mL, 3.55 mmol) and dichlorobis[tris(o-tolyl)phosphine]-palladium CAS [40691-33-6] (0.028 g, 0.036 mmol) were added. The mixture was heated at 120° C. using a single mode microwave (Biotage initiator60) with a power output ranging from 0 to 400 W for 20 min. The mixture was poured out into water, extracted with EtOAc, the organic layer was separated, washed with water then brine, dried over MgSO₄ and evaporated till dryness (0.74 g). Purification of the residue was carried out by column chromatography (silica gel, from Heptane/EtOAc 80/20 to Heptane/EtOAc 70/30). The pure fractions were collected and evaporated to dryness to afford a mixture of 2 isomers. A purification of this residue was performed via achiral SFC (Stationary phase: Lux Cellulose® 4 5 μm 250*21.2 mm, Mobile phase: 60% CO2, 40% EtOH) to afford 0.19 g (51%) of the intermediate (G73).

intermediate (G71)

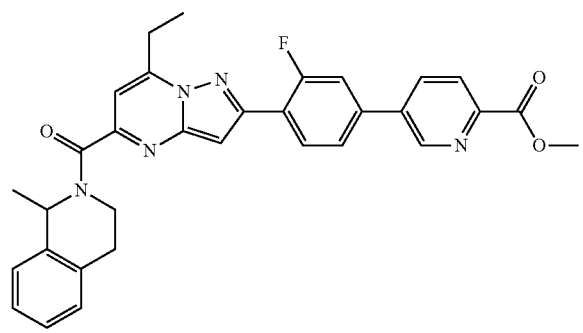

The following intermediate was prepared according to the above procedure.

intermediate (G72)

intermediate (G73)

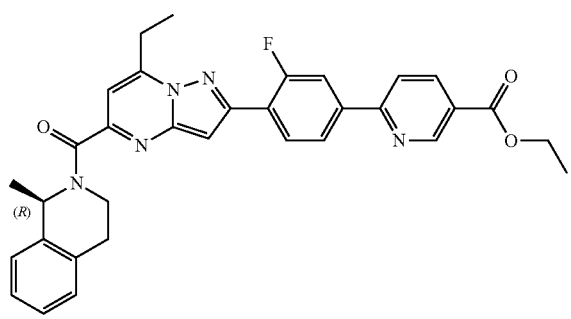

Intermediate (G76):

A mixture of intermediate (E47) (18.7 g, 60.7 mmol), 1H-Azepine, hexahydro-2-methyl-, hydrochloride, (2R)

CAS [331994-00-4] (10.0 g; 66.8 mmol), HATU (30.0 g; 78.9 mmol) and DIEA (32 mL; 186 mmol) in DMF (350 mL) was stirred at RT for 20 hours. The reaction mixture was diluted in AcOEt, washed with an aqueous solution of NaHCO₃ saturated (twice), brine (3 times), dried over MgSO₄ and evaporated in vacuo to give brownish oil. The brownish oil was purified by column chromatography (silica gel from heptane/EtOAc 90/10 to 50/50). The pure fractions were collected and evaporated to give 21.9 g (99%) of intermediate (G76) as a yellow gum.

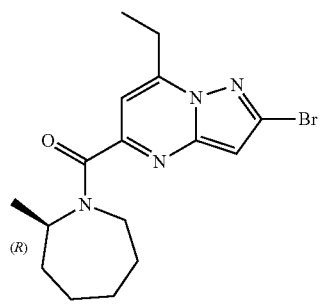

intermediate (G76)

The following intermediates were prepared according to the above procedure.

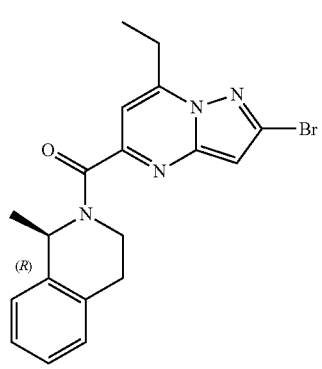

intermediate (G83)

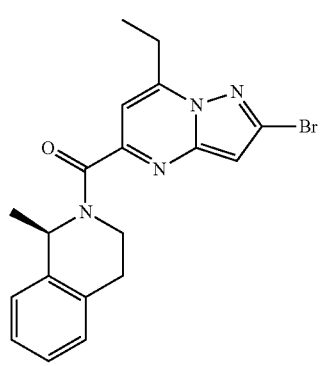

intermediate (G86)

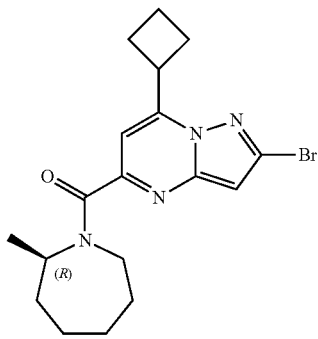

intermediate (G120)

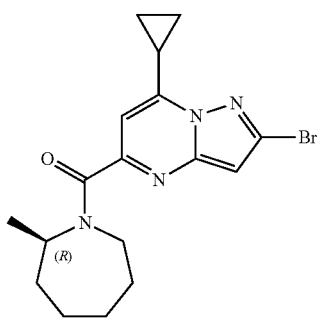

intermediate (G121)

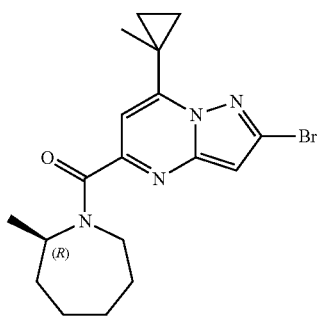

intermediate (G158)

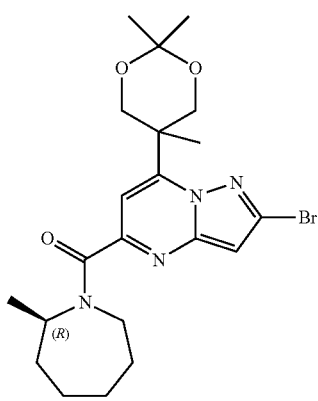

intermediate (G161)

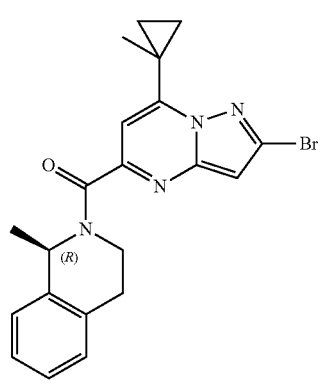
intermediate (G176)
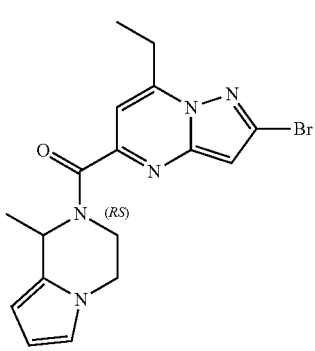
intermediate (G252)
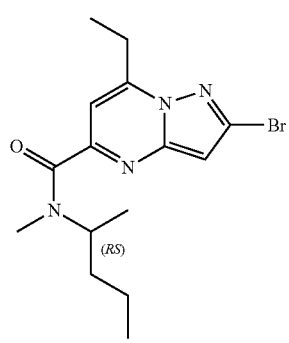
intermediate (G198)
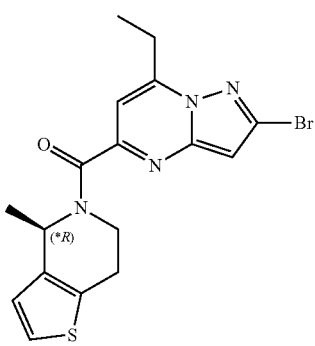
intermediate (G257)
intermediate (G203)
intermediate (G258)
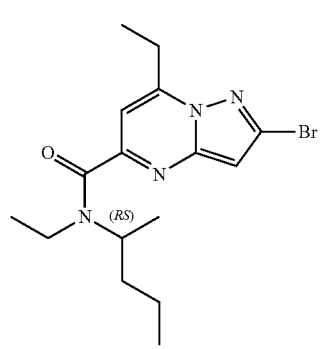
intermediate (G215)
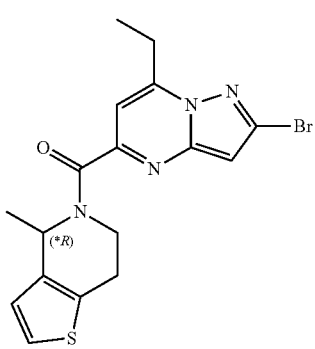
intermediate (G259)

intermediate (G260)

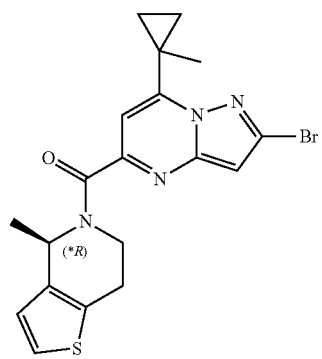

intermediate (G77)

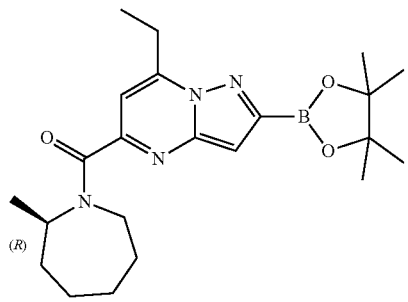

The following intermediates were prepared according to the above procedure.

intermediate (G261)

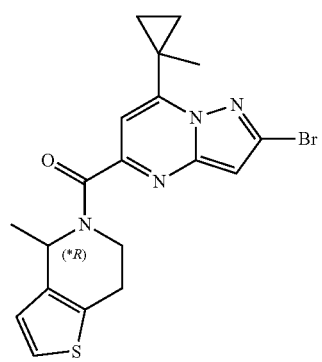

intermediate (G84)

intermediate (G301)

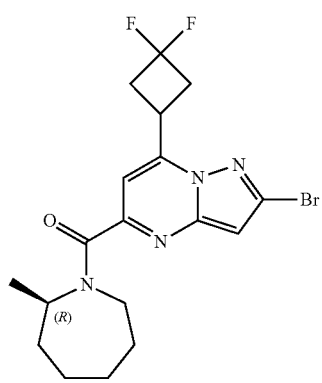

intermediate (G122)

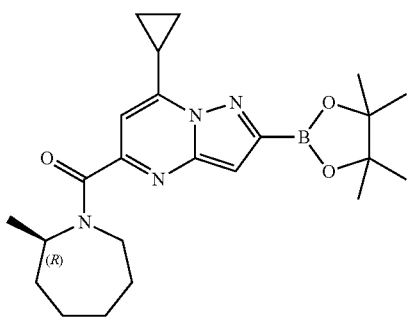

Intermediate (G77):

Under N$_2$, in a Schlenk tube, bis(pinacolato)diboron (4.12 g, 16.2 mmol) and KOAc (2.66 g, 27.0 mmol) were added to a solution of intermediate (G76) (4.94 g, 13.5 mmol) in 1,4-dioxane (56 mL). The solution was purged with nitrogen and charged with PdCl$_2$(dppf) (1.11 g, 1.35 mmol). The resulting solution was purged again with N$_2$ and stirred at 100° C. for 4 hours then cooled down. EtOAc was added. The organic layer was washed with water and brine (twice), dried over MgSO$_4$ and concentrated to give 8.14 g (quant.) of intermediate (G77) as a brown oil. The product was used in the next step without further purification.

intermediate (G123)

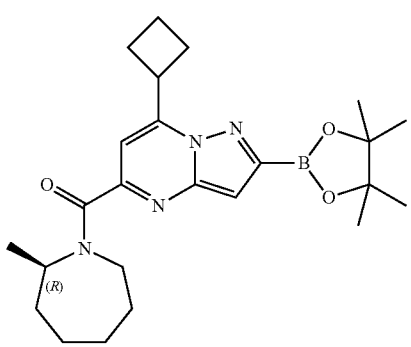

intermediate (G159)
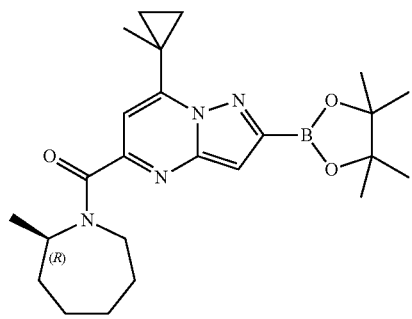
intermediate (G175)
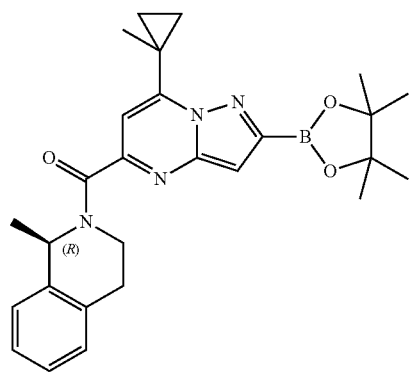
intermediate (199)
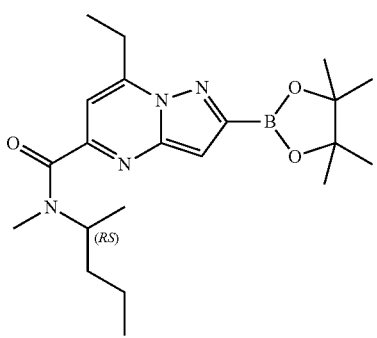
intermediate (G202)
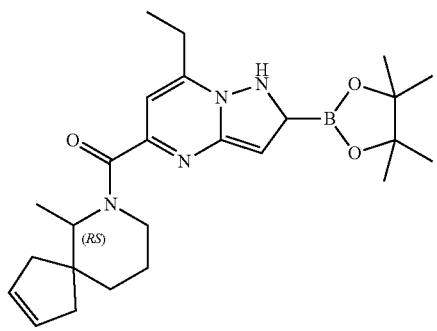
intermediate (G216)
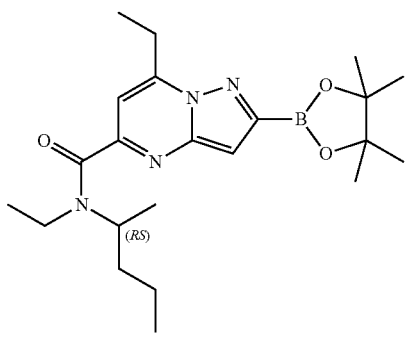
intermediate (G253)
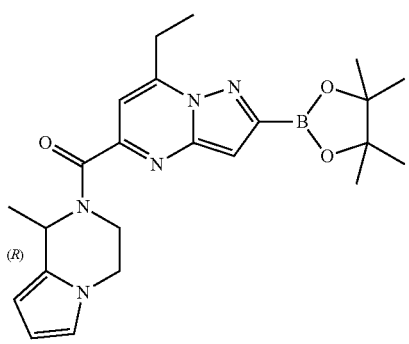
intermediate (G267)
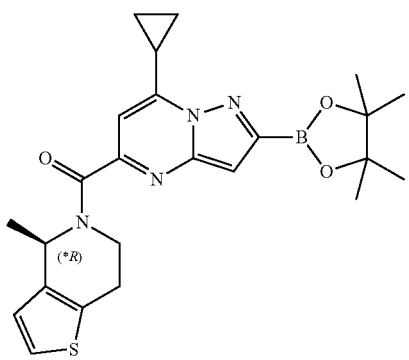
intermediate (G268)
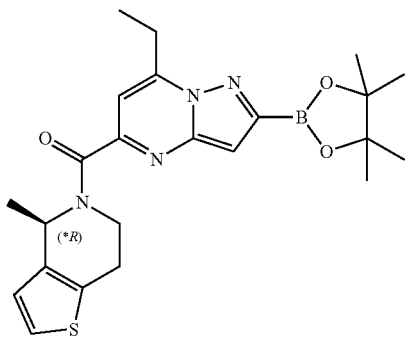

intermediate (G269)

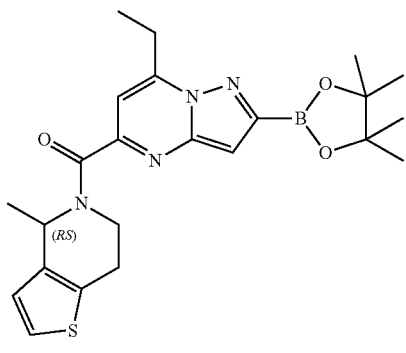

intermediate (G270)

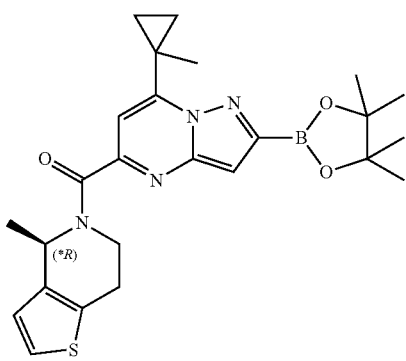

intermediate (G271)

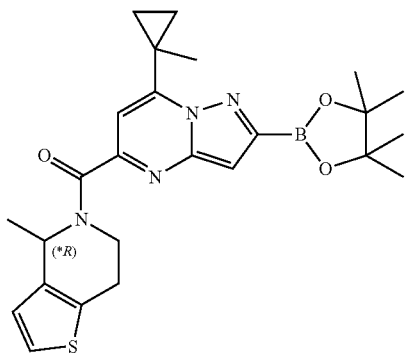

intermediate (G302)

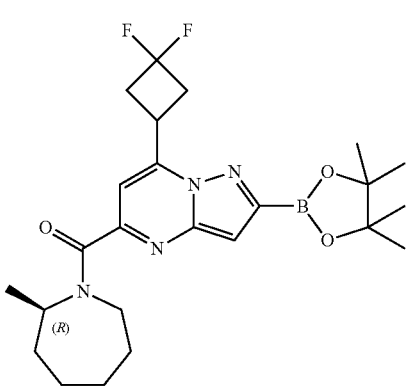

Reaction scheme:

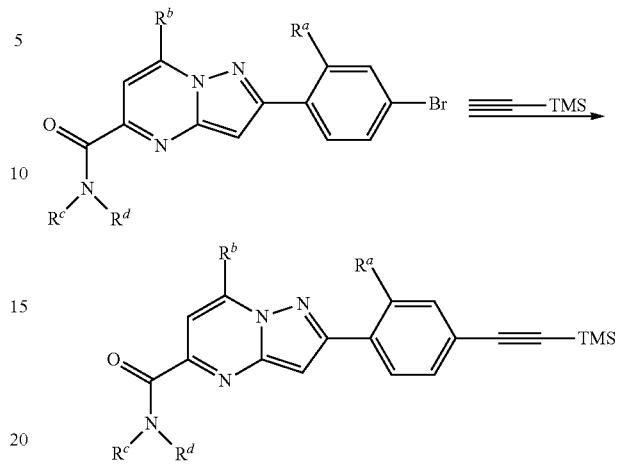

Intermediate (G78):

In a Schlenk tube, to a degassed mixture of intermediate (G1) (1.0 g; 2.2 mmol), CuI (41 mg; 0.22 mmol) and $Et_3N$ (1.2 mL; 8.8 mmol) in Me-THF (20 mL) was added trimethylsilylacetylene CAS [1066-54-2] (1.2 mL; 8.7 mmol) then $PdCl_2(PPh_3)_2$ (76 mg; 0.11 mmol) at RT. The resulting mixture was stirred at 100° C. for 16 hours then cooled down. The mixture was filtered over Celite®. Water and EtOAc were added to the filtrate. The layers were separated and the aqueous layer was extracted with EtOAc (once). The combined organic layers were washed with brine, dried over $MgSO_4$, filtered and the solvent was removed in vacuo. The residue was purified by column chromatography (silica gel from heptane/EtOAc 100/0 to 40/60). The pure fractions were collected and evaporated to give 791 mg (76%) of intermediate (G78).

intermediate (G78)

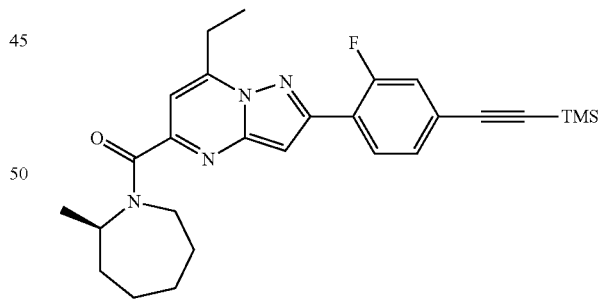

Reaction scheme:

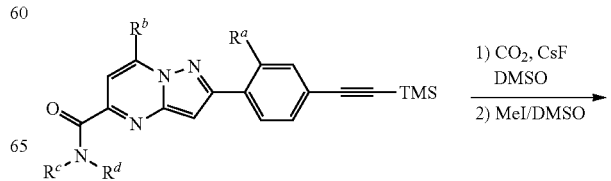

1) $CO_2$, CsF
DMSO
2) MeI/DMSO

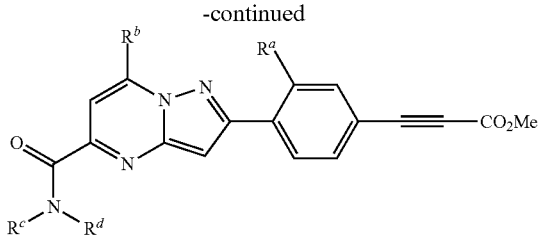

Intermediate (G79):

CO$_2$ was bubbled in a mixture of cesium fluoride (472 mg; 3.11 mmol) in DMSO (20 mL) for 5 min then intermediate (G78) (741 mg; 1.55 mmol) in DMSO (20 mL) was added. The bubbling of CO$_2$ was continued for 2 hours. CO$_2$ bubbling was stopped then methyl iodide (145 µL; 2.33 mmol) was added and the mixture was stirred at RT for 4 hours. The mixture was poured into water and the product was extracted with EtOAc (twice). The combined organic layers were washed with brine, dried over MgSO$_4$, filtered and the solvent was removed in vacuum. The residue was purified by column chromatography (silica gel, from heptane/EtOAc 100/0 to 60/40). The good fractions were collected and evaporated to give 449 mg (62%) of intermediate (G79).

intermediate (G79)

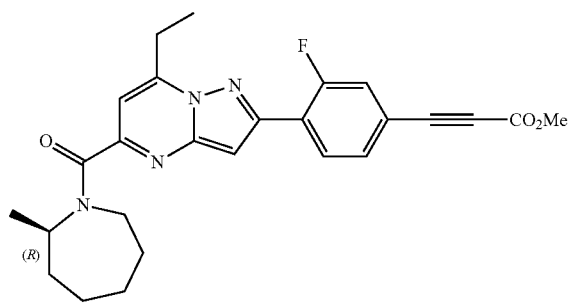

Reaction scheme:

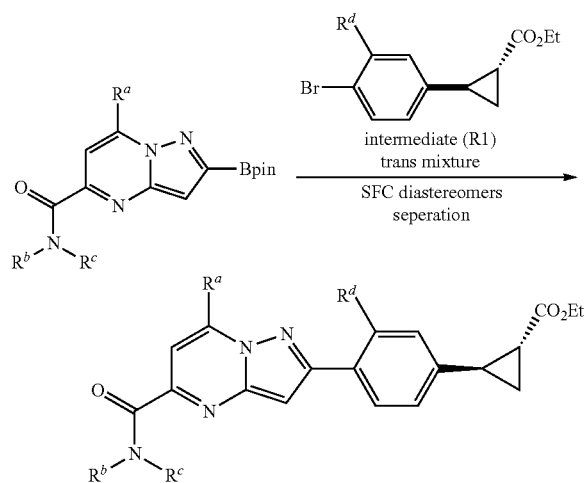

Intermediate (G80):
In a sealed tube, a solution of intermediate (G77) (490 mg; 0.81 mmol; 68%), intermediate (R1) (232 mg; 0.808 mmol) and K$_3$PO$_4$ (515 mg; 2.42 mmol) in dioxane (9.1 mL) and H$_2$O (1.4 mL) was purged with N$_2$. PdCl$_2$(dtbpf) (53 mg; 81 µmol) was added, the mixture was purged again with N$_2$ and heated at 80° C. using one single mode microwave (Biotage® Initiator EXP 60) with a power output ranging from 0 to 400 W for 30 min. The mixture was poured into DCM, washed with water (twice), brine, dried over MgSO$_4$, filtered and evaporated in vacuum. The residue was purified by column chromatography (silica gel, from heptane/EtOAc 100/0 to 60/40). The pure fractions were collected and evaporated to give 0.21 g of a mixture of 2 diastereomers.

The mixture of 2 diastereomers was purified by chiral SFC (Stationary phase: Chiralcel® OJ-H 5 µm 250×20 mm, Mobile phase: 90% CO$_2$, 10% MeOH). The pure fractions were collected to give 79 mg of intermediate (G80) (R*, R*) (first diastereomer) and 87 mg of intermediate (G80') (S*, S*) (second diastereomer).

intermediate (G80)

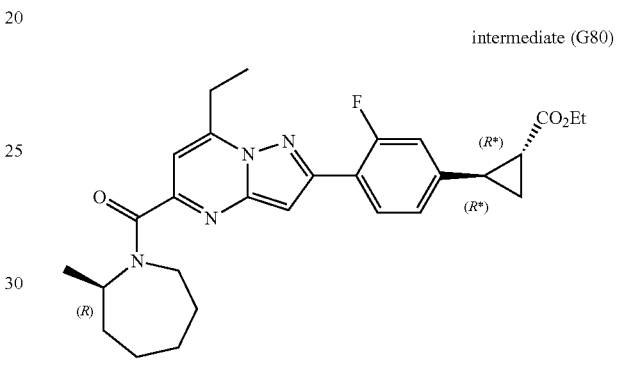

The following intermediates were prepared according to the above procedure:

intermediate (G128)

intermediate (G130)

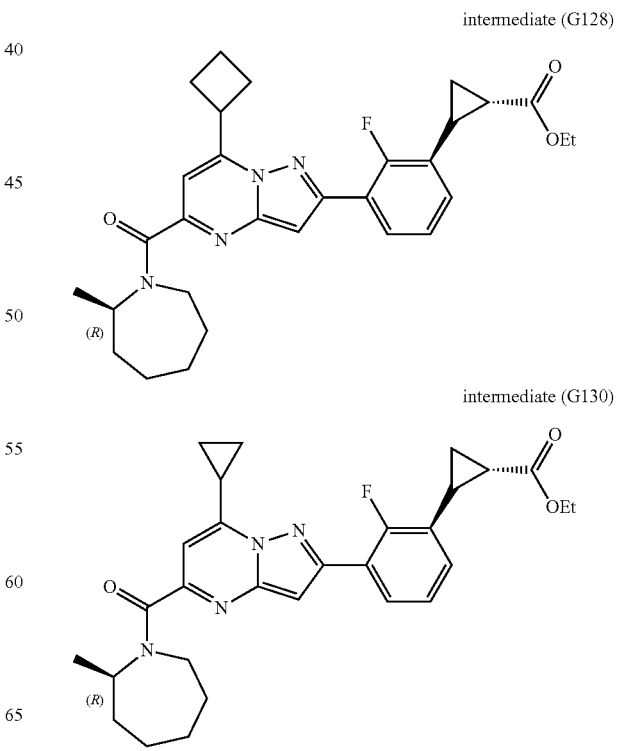

intermediate (G171)

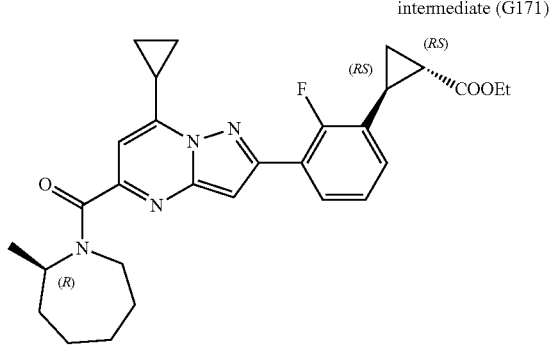

intermediate (G194)

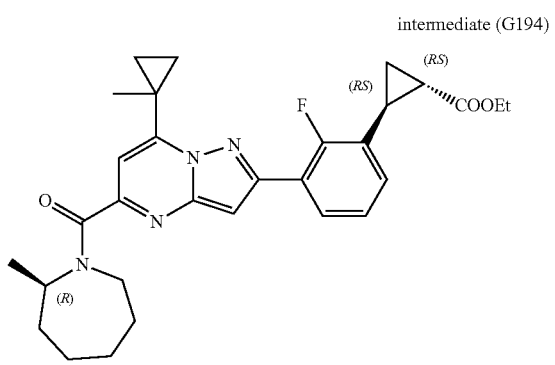

Intermediate (G81):

In a sealed tube, a solution of intermediate (G77) (444 mg; 1.08 mmol), ethyl(E)-3-(3-bromo-2-fluoro-phenyl)prop-2-enoate (245 mg; 0.897 mmol) and K$_3$PO$_4$ (571 mg; 2.69 mmol) in 1,4-dioxane (8.9 mL) and H$_2$O (1.3 mL) was purged with N$_2$. PdCl$_2$(dtbpf) (58 mg; 90 μmol) was added, the mixture was purged again with N$_2$ and heated at 80° C. using one single mode microwave (Biotage® Initiator EXP 60) with a power output ranging from 0 to 400 W for 30 min. The mixture was poured into DCM, washed with water (twice), brine, dried over MgSO$_4$, filtered and evaporated in vacuum to give a brown solid which was purified by column chromatography (silica gel, from DCM/EtOAc 100/0 to 95/5). The pure fractions were collected and evaporated to give 223 mg (52%) of intermediate (G81).

intermediate (G81)

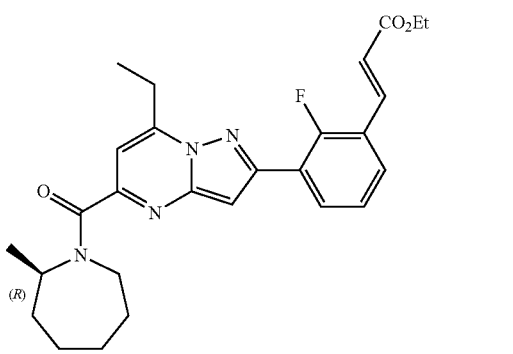

The following intermediates were prepared according to the above procedure:

intermediate (G85)

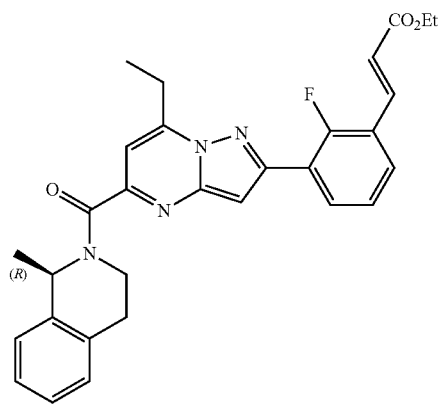

intermediate (G151)

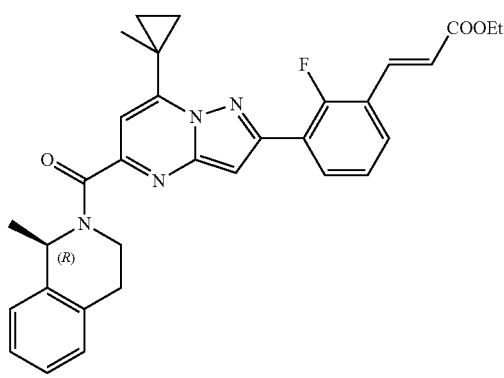

intermediate (G154)

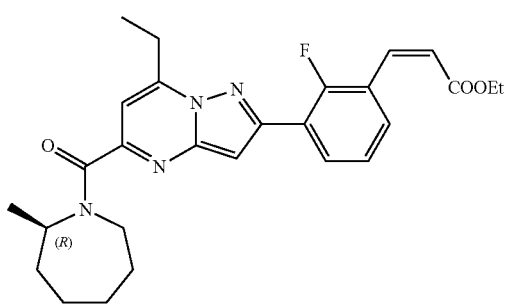

intermediate (G157)

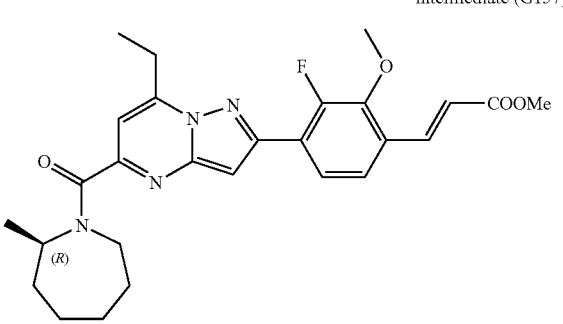

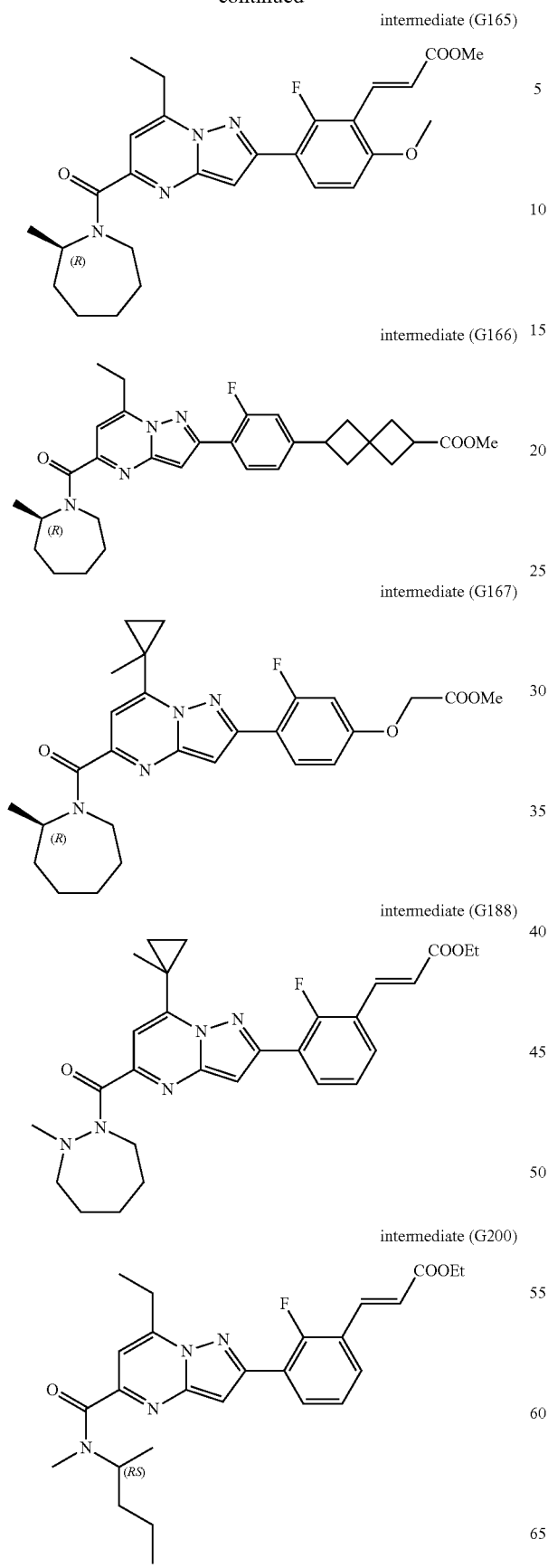

145
-continued
intermediate (G275)
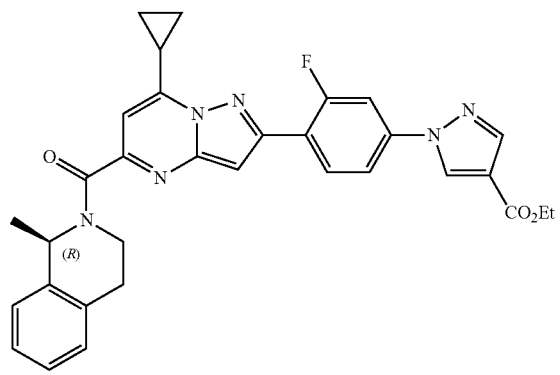
intermediate (G276)
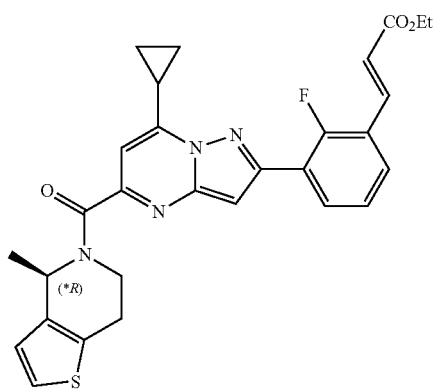
intermediate (G277)
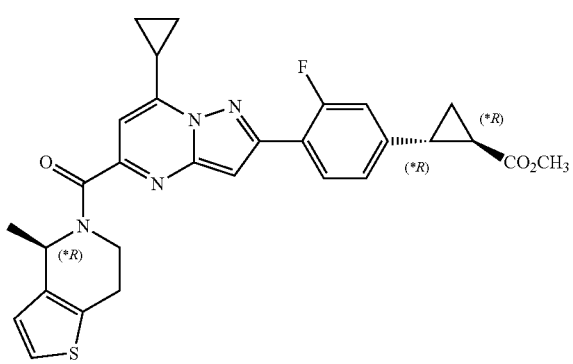
intermediate (G278)
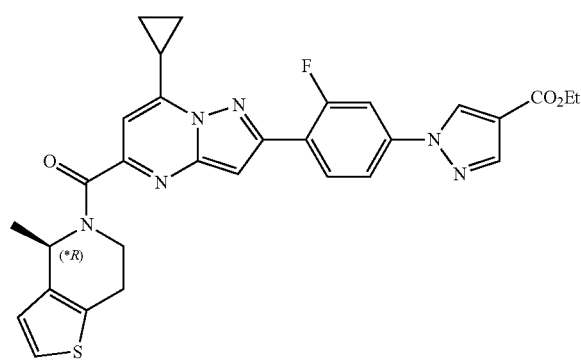
146
-continued
intermediate (G279)
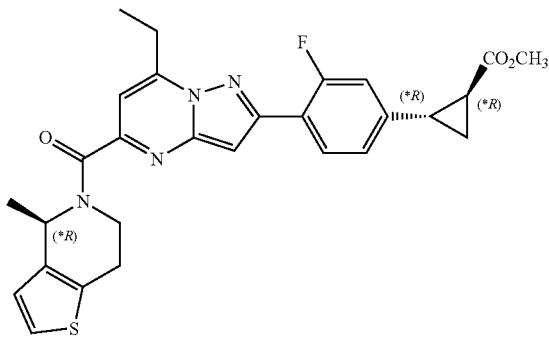
intermediate (G280)
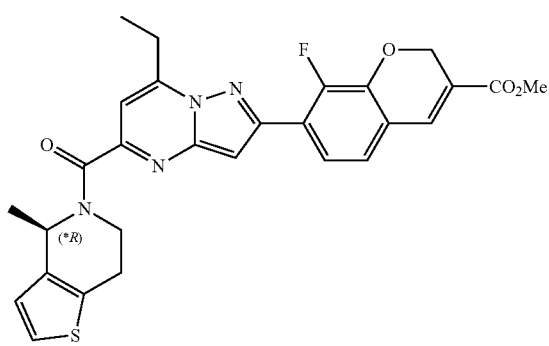
intermediate (G281)
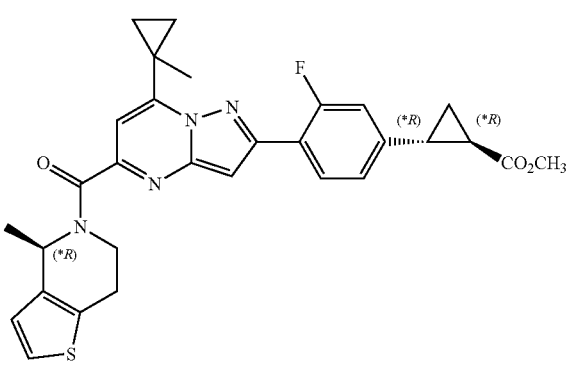
intermediate (G282)
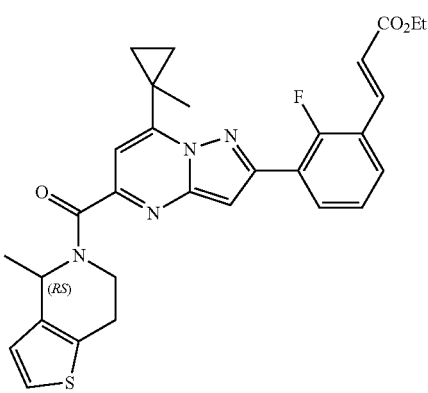

-continued intermediate (G283)

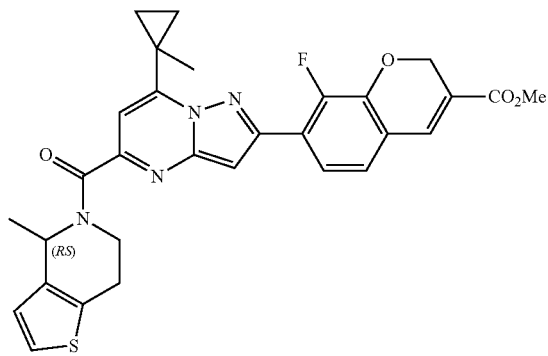

intermediate (G284)

intermediate (G285)

intermediate (G304)

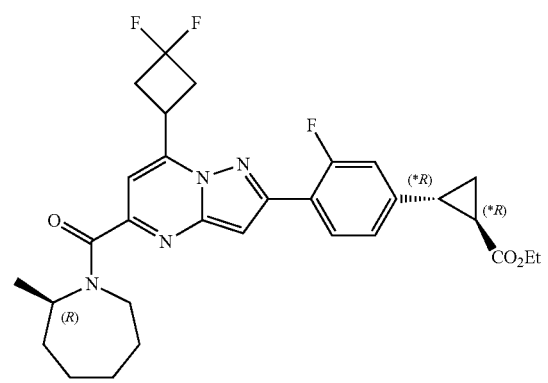

-continued intermediate (G305)

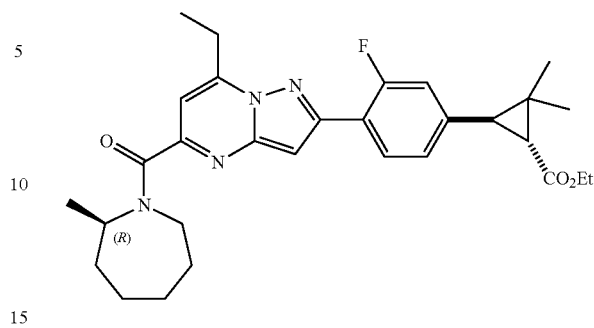

Reaction scheme:

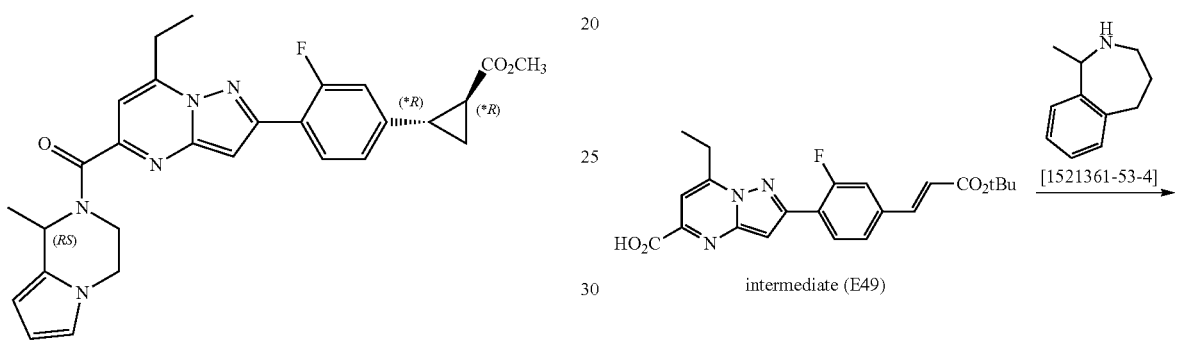

intermediate (E49)

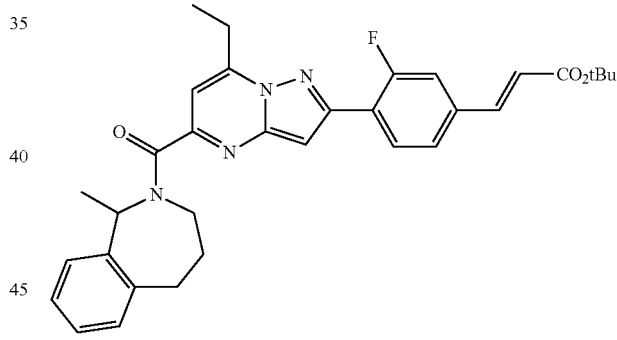

intermediate (G82)

Intermediate (G82):

DIEA (0.250 mL; 1.44 mmol) then HATU (0.328 g; 0.863 mmol) were added to a mixture of intermediate E49 (0.300 g; 0.719 mmol) and, 2,3,4,5-tetrahydro-1-methyl-1H-2-benzazepine CAS [1521361-53-4] (0.139 g, 0.863 mmol) in DMF (3 mL) and the resulting mixture was stirred at RT for 15 hours, then added dropwise to stirred water (20 mL). The resulting precipitate was collected by filtration on a glass frit, then taken in DCM (50 mL), washed with HCl 1M (2×10 mL) and brine (10 mL), dried over $Na_2SO_4$, filtered and concentrated under reduced pressure. The crude brownish solid was purified by column chromatography (silica gel: from DCM/EtOAc 100/0 to 99/1 to 98/2). The pure fractions were collected and evaporated to give 250 mg (63%) of intermediate (G82) as a yellowish solid.

intermediate (G82)

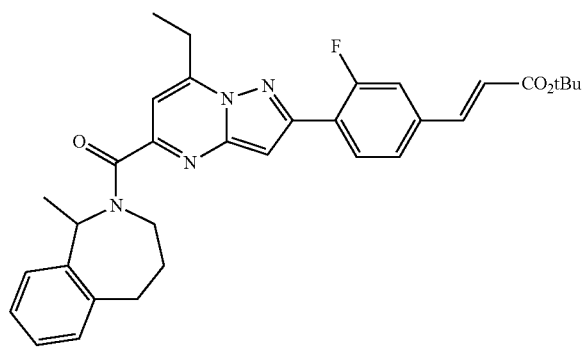

The following intermediates were prepared according to the above procedure.

intermediate (G108)

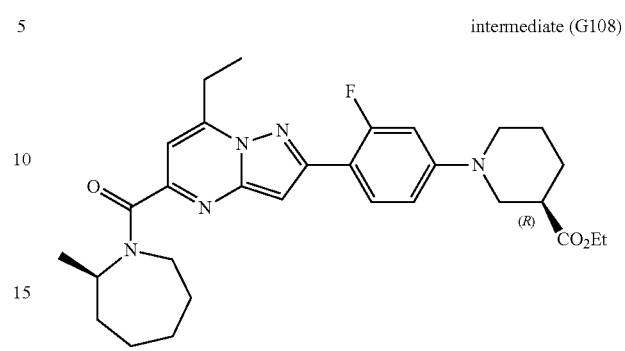

Reaction scheme:

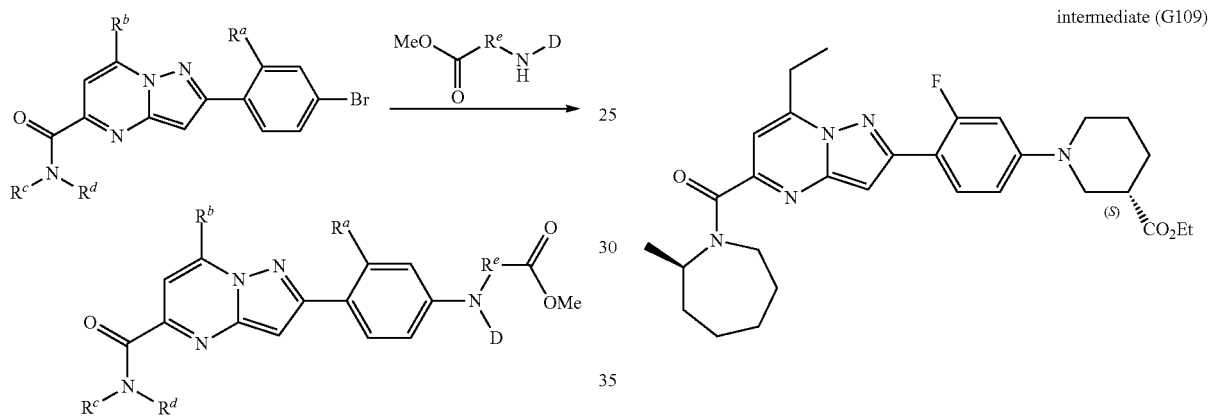

Intermediate (G89):

To a degassed mixture of intermediate (G1) (473 mg, 1.03 mmol), methyl azetidine-3-carboxylate, hydrochloride (188 mg, 1.24 mmol) and $Cs_2CO_3$ (1.0 g, 3.1 mmol) in 1,4-dioxane (19 mL) was added successively X-Phos (44 mg; 93 μmol) then $Pd_2(dba)_3$ (38 mg; 41 μmol) at RT. The resulting mixture was stirred at 100° C. for 4 hours then cooled down. Water was added and the mixture was extracted with EtOAc (twice). The combined organic layers were washed with brine, dried over $MgSO_4$, filtered and the solvent was removed in vacuum to give 0.51 g of crude product which was purified by column chromatography (silica gel, from heptane/EtOAc 80/20 to 40/60). The pure fractions were collected and evaporated to give 0.407 g (80%) of intermediate (Q1).

intermediate (G109)

intermediate (G110)

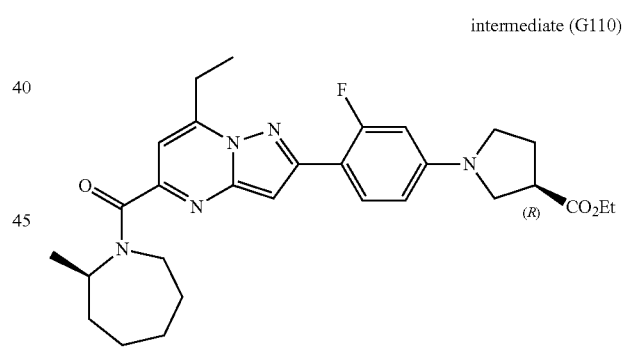

intermediate G89 intermediate (G111)

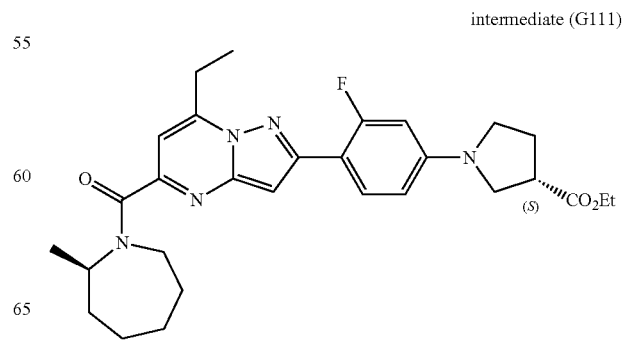

151
-continued
intermediate (G124)
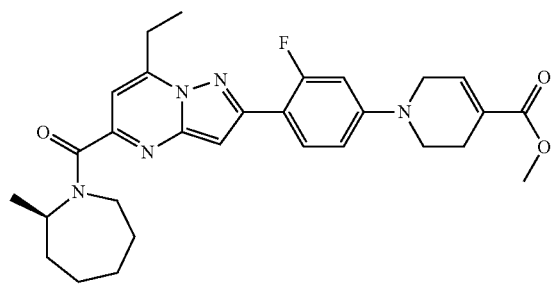
intermediate (G137)
152
-continued
intermediate (G197)
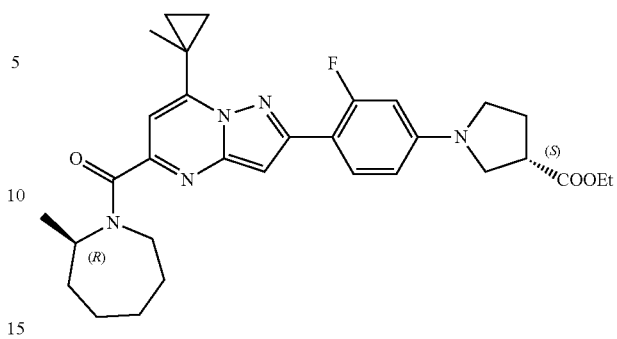
intermediate (G214)
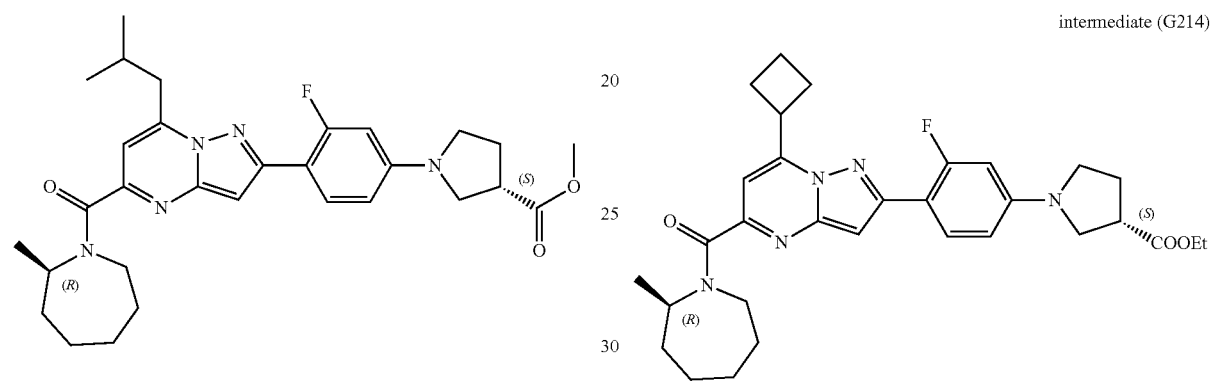
intermediate (G139)
intermediate (G226)
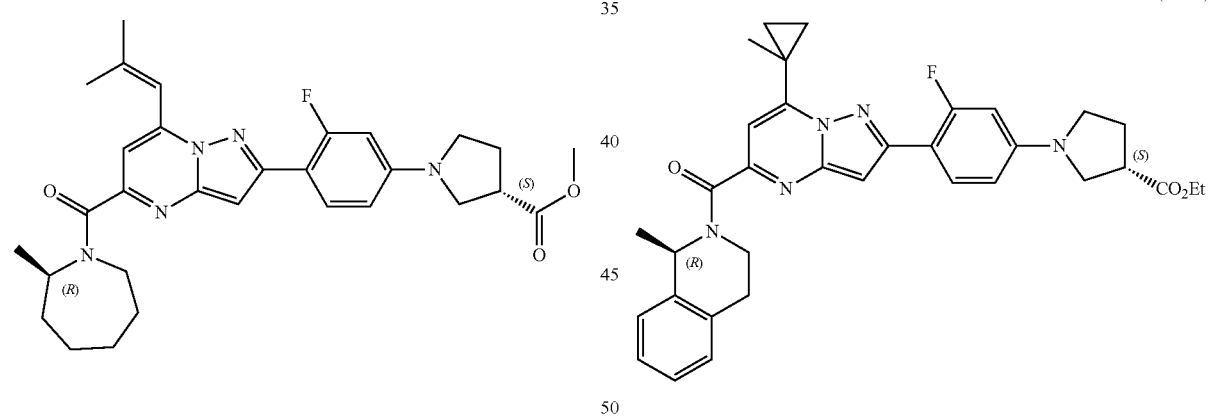
intermediate (G190)
intermediate (G289)
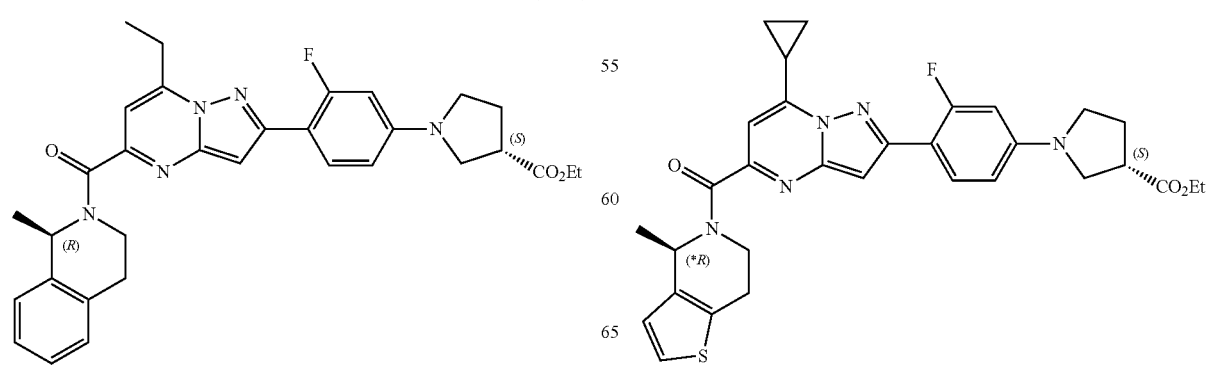

-continued intermediate (G290)

intermediate (G291)

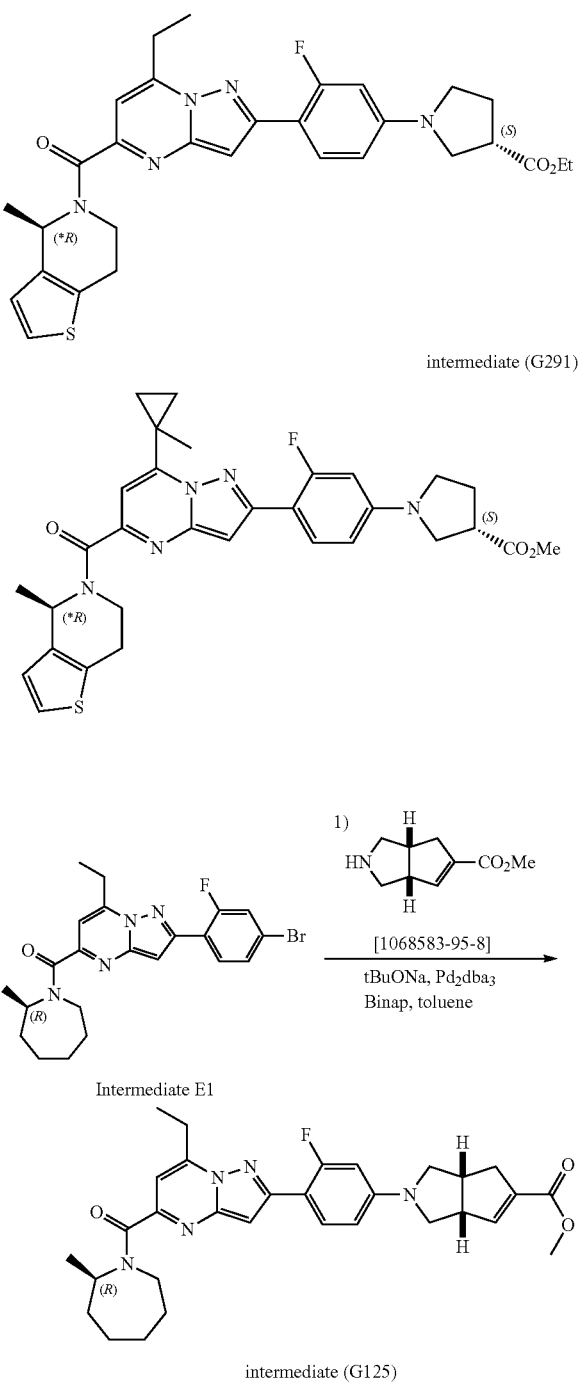

intermediate (G125)

A mixture of intermediate E1 (0.500 g, 1.09 mmol), [1068583-95-8] (0.266 g, 1.31 mmol), ᵗBuONa (0.314 g, 3.27 mmol), Pd₂dba₃ (0.0498 g, 0.0544 mmol) and Binap (0.0678 g, 0.109 mmol) in toluene (10 mL) was stirred under μW irradiation (Biotage) at 90° C. for 0.5 h. The reaction mixture was diluted with EtOAc (100 mL), washed with water (100 mL) and brine (100 mL), dried over Na$_2$SO$_4$, filtered and concentrated under reduced pressure. The residue was purified by preparative LC over silica gel (irregular SiOH, 40-63 m, Fluka®, mobile phase gradient: from DCM/EtOAc 100/0 to 95/5). The product fractions were collected and the solvent was evaporated. The solid was purified again by preparative LC (irregular SiOH, 40-63 μm, Fluka®, mobile phase gradient: from cyclohexane/EtOAc 80/20 to 70/30). The product fractions were collected and the solvent was evaporated to give 0.245 g (21%) of ester intermediate as a yellowish solid.

intermediate (G125)

Reaction scheme:

intermediate (G77)

intermediate (G90)

Intermediate (G90):

In a sealed tube, a solution of intermediate (G77) (738 mg; 1.09 mmol), intermediate (S4) (388 mg; 1.22 mmol) and K$_3$PO$_4$ (775 mg; 3.65 mmol) in 1,4-dioxane (13 mL) and water (2 mL) was purged with N$_2$. PdCl$_2$(dtbpf) (80 mg; 123 μmol) was added, the mixture was purged again with N$_2$ and heated at 80° C. using one single mode microwave (Biotage® Initiator EXP 60) with a power output ranging from 0 to 400 W for 30 minutes. EtOAc and water were added. The layers were separated and the organic layer was washed with brine, dried on MgSO$_4$, filtered and concentrated to give crude product which was purified by column chromatography (silica gel, from heptane/EtOAc 80/20 to 40/60). The pure fractions were collected and evaporated to give 412 mg (74%) of intermediate (G90) as a beige solid.

intermediate-(G90)
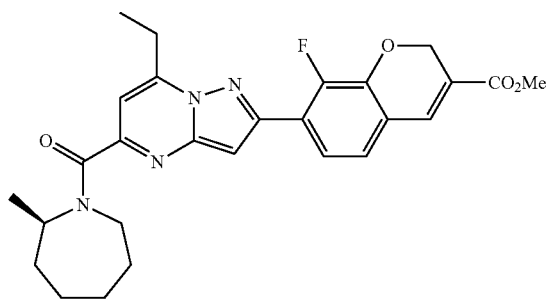
The following intermediates were prepared according to the above procedure:
intermediate (G98)
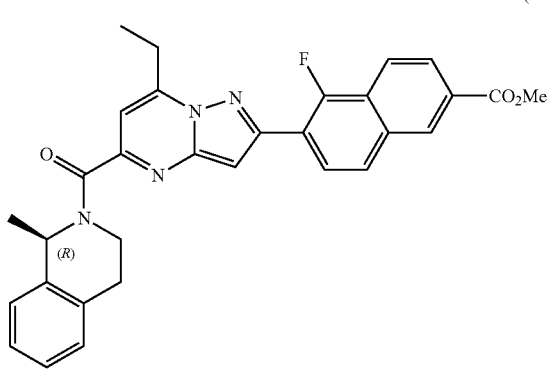
intermediate (G105)
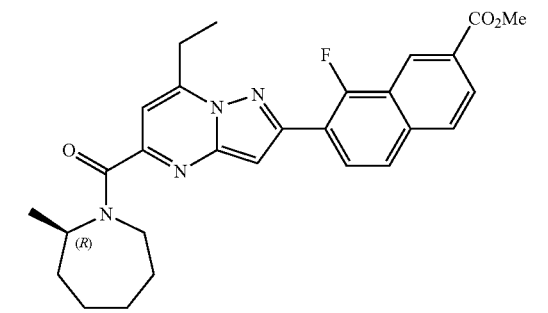
intermediate (G126)
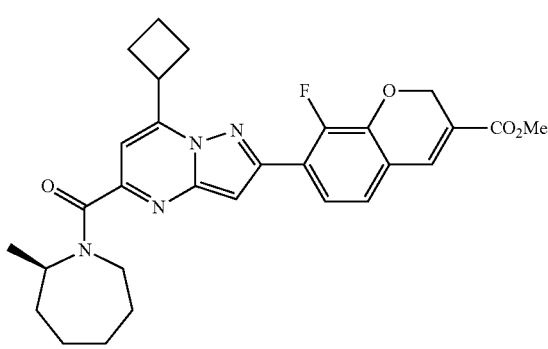
intermediate (G127)
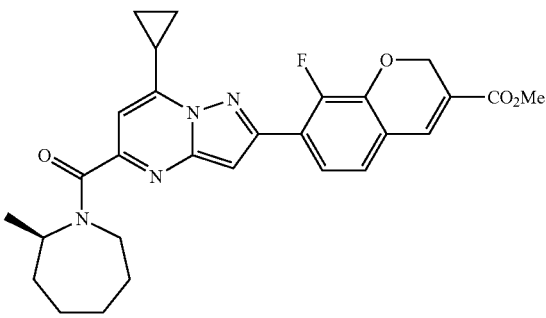
intermediate (G129)
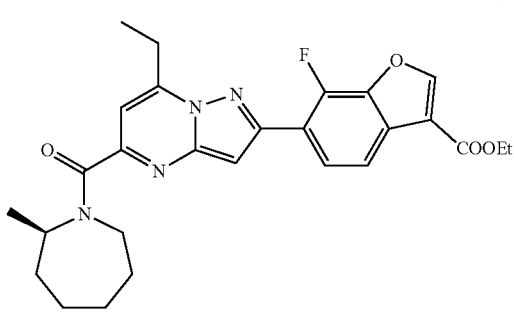
intermediate (G143)
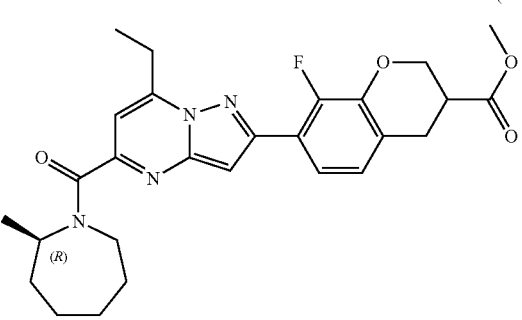
intermediate (G150)
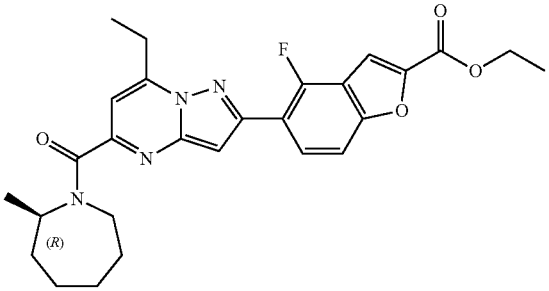
intermediate (G158)

-continued intermediate (G193)

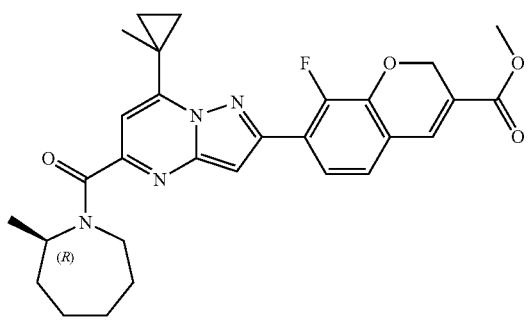

intermediate (G225)

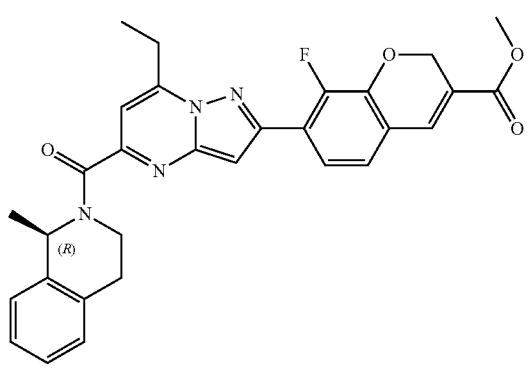

intermediate (G254)

Reaction scheme:

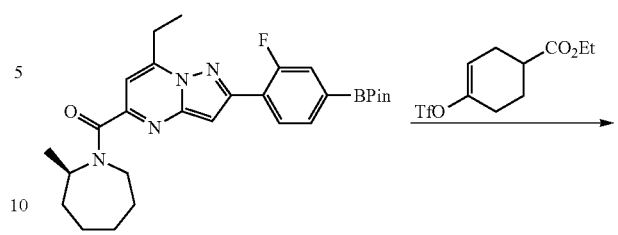

intermediate (G30)

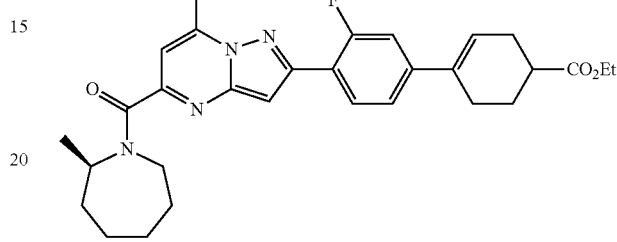

intermediate (G91)

Intermediate (G91):
A solution of intermediate (G30) (400 mg; 0.79 mmol), 4-((trifluoro-methanesulfonyl)oxy)-3-cyclohexene-1-carboxylic acid ethyl ester (239 mg; 0.79 mmol) and $K_3PO_4$ (503 mg; 2.37 mmol) in 1,4-dioxane (11 mL) and $H_2O$ (3.3 mL) was purged by $N_2$ bubbling for 10 minutes before the addition of $PdCl_2(dtbpf)$ (51 mg; 78.9 μmol). The resulting mixture was purged by $N_2$ bubbling, then heated at 80° C. using one single mode microwave (Biotage® Initiator EXP 60) with a power output ranging from 0 to 400 W for 30 minutes. The crude was poured into DCM, washed with water (twice), brine, dried over $MgSO_4$, filtered and evaporated in vacuum. The residue was purified by column chromatography (silica gel, from DCM/EtOAc 100:0 to 90:10). The fractions containing product were combined and the solvent was removed to give 252 mg (60%) of intermediate (G91) as a brown oil and as a mixture of 2 diastereomers.

intermediate (G91)

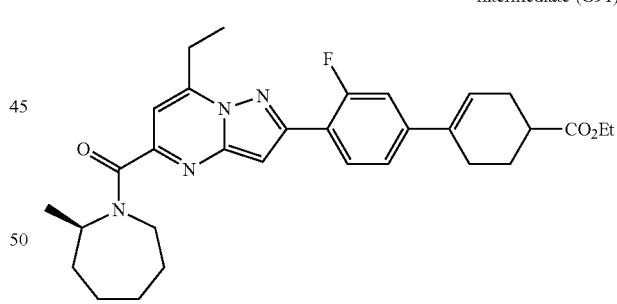

Reaction scheme:

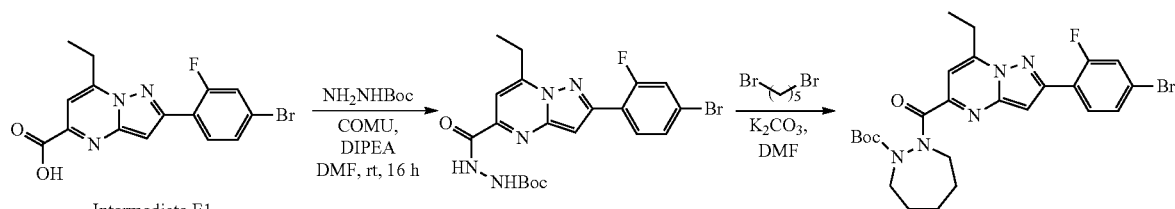

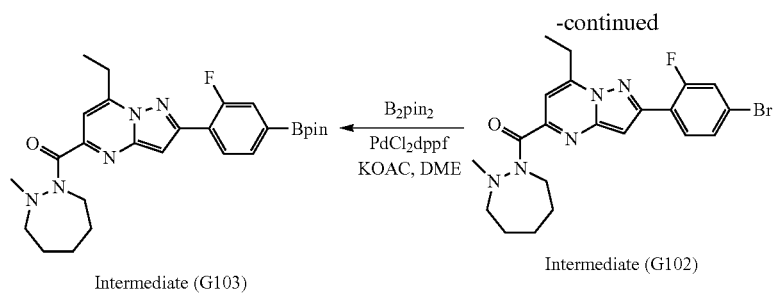

Intermediate (G103)

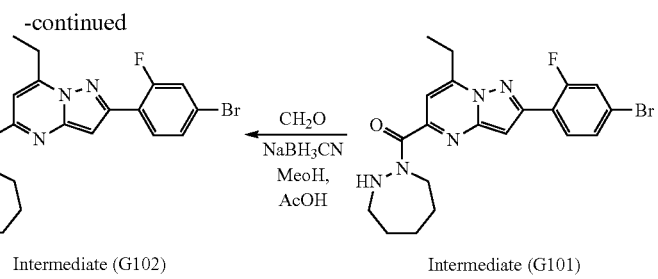

Intermediate (G102)    Intermediate (G101)

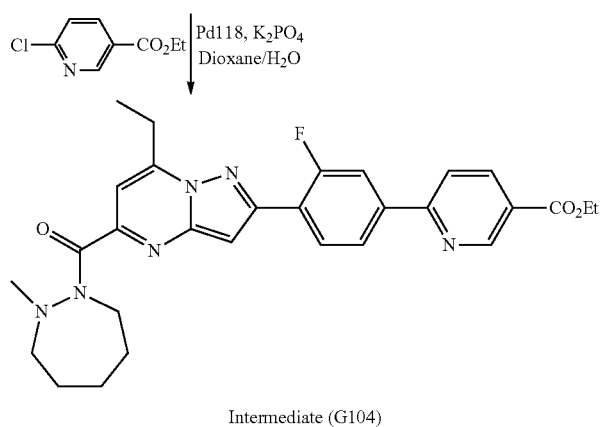

Intermediate (G104)

Intermediate (G99):

To a mixture of intermediate E1 (500 mg; 1.24 mmol), t-butyl carbazate (328 mg; 2.49 mmol) and DIEA (0.64 mL; 3.7 mmol) in DMF (20 mL) was added COMU (798 mg; 1.86 mmol) and the resulting mixture was stirred at rt with mechanical stirring for 16 h. Water was added and the product was extracted with EtOAc (twice). The combined organic layers were washed with brine, dried over MgSO$_4$, filtered and the solvent was removed in vacuo. The residue was purified by preparative LC (regular SiOH, 30 μm, 40 g Interchim®, liquid loading (DCM/heptane), mobile phase gradient: from heptane/EtOAc 100/0 to 40/60) to give 339 mg (57%) of intermediate (G99).

intermediate (G99)

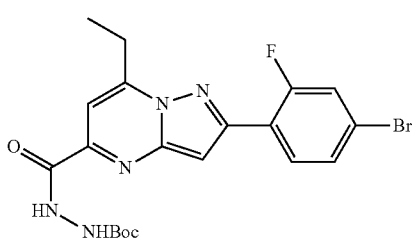

The following intermediates were prepared using analogous procedures:

intermediate (G183)

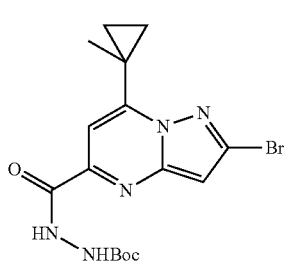

intermediate (G205)

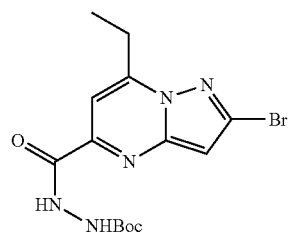

Intermediate (G100):

A mixture of intermediate (G99) (0.72 g; 1.51 mmol), 1,5-dibromopentane (0.22 mL; 1.58 mmol) and Cs$_2$CO$_3$ (490 mg; 1.51 mmol) in MeCN (36 mL) was stirred at 70° C. for 16 h. An extra amount of Cs$_2$CO$_3$ (200 mg; 0.614 mmol) and 1,5-dibromopentane (50 μL; 0.37 mmol) were added and the mixture was stirred at 90° C. for 2 h. Water was added and the mixture was extracted with DCM (twice). The combined organic layers were washed with brine, dried over MgSO$_4$, filtered and the solvent was removed in vacuo. The residue was purified by preparative LC (regular SiOH, 30 μm, 120 g Interchim®, liquid loading (DCM), mobile phase gradient: from heptane/EtOAc 100/0 to 40/60) to give 0.44 g (53%) of intermediate (G100).

intermediate (G100)

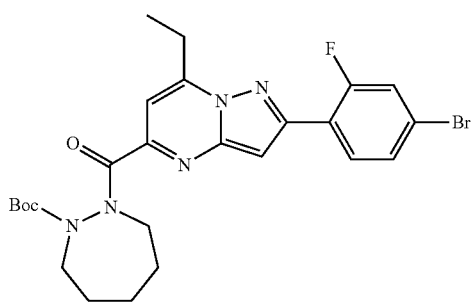

The following intermediates were prepared using analogous procedures:

intermediate (G184)

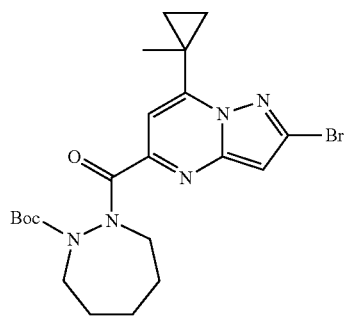

intermediate (G206)

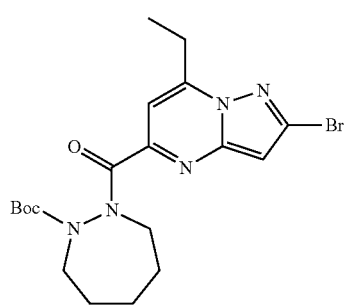

Intermediate (G101):

A mixture of intermediate (G100) (0.71 g; 1.3 mmol) and TFA (3.0 mL; 39 mmol) in DCM (15 mL) was stirred at rt for 16 h. An aqueous solution of NaHCO₃ (sat) and DCM were carefully added and the layers were separated. The aqueous layer was extracted with DCM (once). The combined organic layers were washed with brine, dried over MgSO₄, filtered and the solvent was removed in vacuo to give 0.52 g (90%) of intermediate (G101).

intermediate (G101)

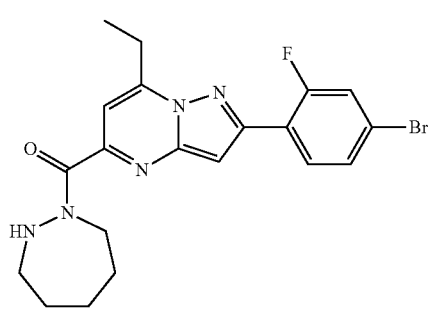

The following intermediates were prepared using analogous procedures:

intermediate (G185)

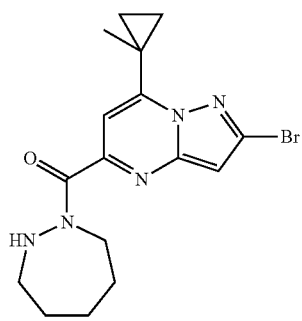

intermediate (G207)

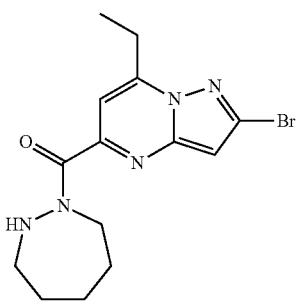

Intermediate (G102):

To a mixture of intermediate (G101) (638 mg; 1.43 mmol) and formaldehyde 37% in water (0.215 mL; 2.86 mmol) in MeOH (14 mL) and AcOH (1.4 mL) was added NaBH₃CN 1M in THF (1.7 mL; 1.7 mmol) at rt. The resulting mixture was stirred at 40° C. for 2 h. DCM and water were added and the layers were separated. The aqueous layer was extracted with DCM (once). The organic layers were washed with an aqueous solution of HCl (1N), then brine, dried over MgSO₄, filtered and the solvent was removed in vacuo. The residue was taken-up with MeCN, the precipitate was filtered off and dried over glass frit to give 280 mg of intermediate (G102). The filtrate was evaporated and purified by preparative LC (regular SiOH, 30 μm, 25 g Intechim®, liquid loading (DCM), mobile phase gradient: from heptane/EtOAc 100/0 to 40/60) to give 99 mg (57%) of intermediate (G102).

intermediate (G102)

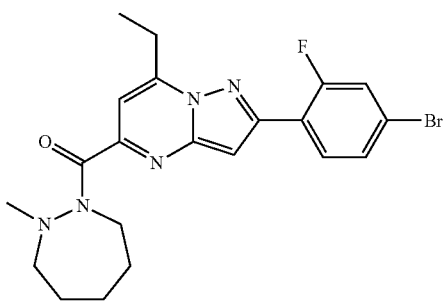

The following intermediates were prepared using analogous procedures:

intermediate (G186)

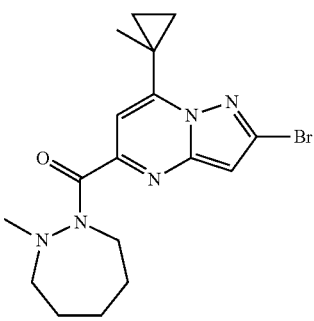

intermediate (G208)

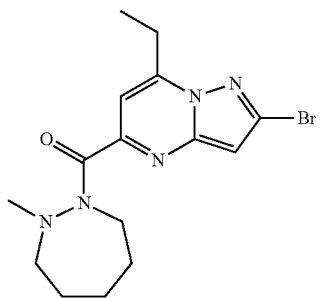

intermediate (G209)

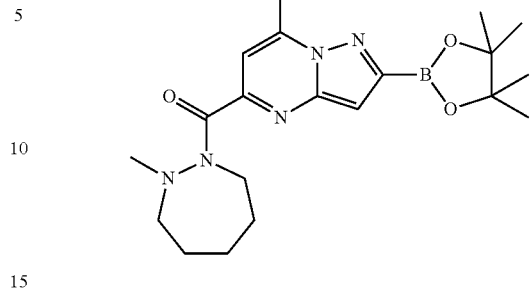

Intermediate (G103):

In a Schlenk, a mixture of intermediate (G102) (0.380 g; 0.825 mmol), B$_2$pin$_2$ (0.314 g; 1.24 mmol) and KOAc (243 mg; 2.48 mmol) in dioxane (10 mL) was purged by N$_2$ bubbling for 10 min before the addition of PdCl$_2$dppf (68 mg; 83 μmol). The resulting mixture was heated at 100° C. for 2 h then at rt for 18 h. The reaction mixture was filtered over celite, the celite was rinsed with EtOAc. Water was added to the filtrate, the aqueous layer was extracted with EtOAc (twice). The combined organic layers were dried over MgSO$_4$, filtered and concentrated in vacuo to give 610 mg (quant, purity 69%) of intermediate (G103).

Intermediate (G104)

In a sealed tube, a solution of intermediate (G103) (765 mg; 1.04 mmol, purity 69%), ethyl 6-chloronicotinate (232 mg; 1.25 mmol) and K$_3$PO$_4$ (662 mg; 3.12 mmol) in dioxane (10 mL) and H$_2$O (2 mL) was purged with N$_2$. Pd118 (54 mg; 83 μmol) was added, the mixture was purged again with N$_2$ and heated at 100° C. for 18 hours. The reaction mixture were filtered over celite, celite was rinsed with EtOAc and water. Brine was added to the filtrate. The aqueous layer was extracted with EtOAc, the combined organic layers were dried over MgSO$_4$, filtered and evaporated in vacuo. The residue was purified by preparative LC (irregular SiOH, 15-40 μm, 40 g Grace Resolve®, liquid loading (DCM), mobile phase: heptane/EtOAc 80/20) give 267 mg (48%) of intermediate (G104) as a solid.

intermediate (G103)

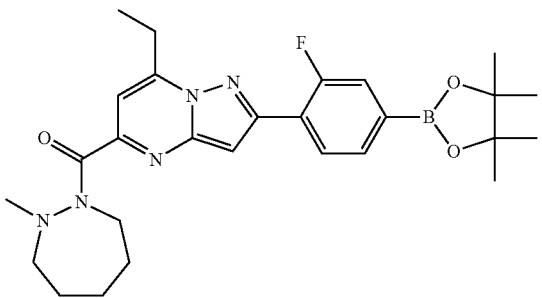

intermediate (G104)

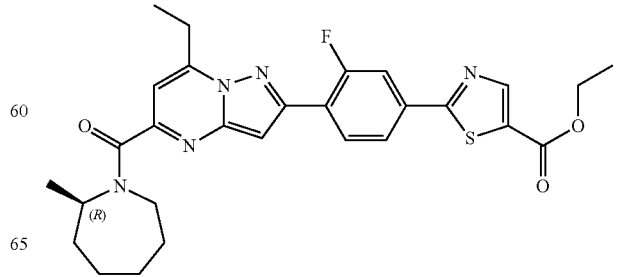

The following intermediates were prepared using analogous procedures:

The following intermediates was prepared according to intermediate (G104):

intermediate (G187)

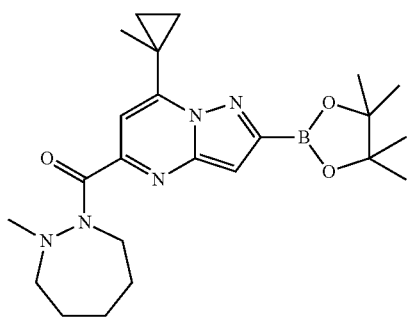

intermediate (G149)

Reaction scheme:

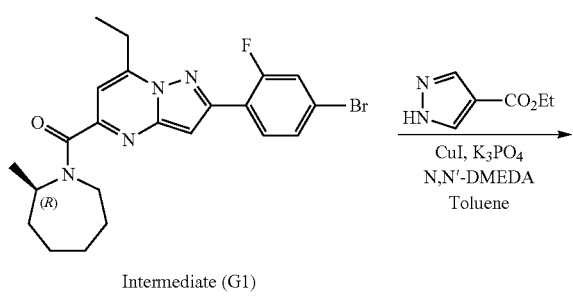
Intermediate (G1)

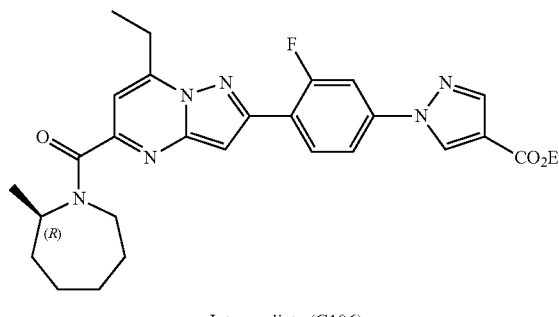
Intermediate (G106)

Intermediate (G106): A screw-cap tube was charged with intermediate (G1) (0.300 g, 0.653 mmol), Ethyl 4-pyrazole-carboxylate (0.100 g, 0.718 mmol), K₃PO₄ (0.291 g, 1.371 mmol) and CuI (0.006 g, 0.033 mmol). The tube was capped with a septum and purged with argon. N,N'dimethylethyl-enediamine (0.014 mL, 0.131 mmol) and toluene (1 ml) were added via a syringe through the septum. The reaction flask was sealed and placed in a pre-heated oil bath at 90° C. and stirred for 24 h. The reaction mixture was cooled to rt and 10 mL of EtOAc were added. The organic layer was washed successively with 5 mL of water and 5 mL of brine, dried with Na₂SO₄, filtered, concentrated in vacuo and purified by Preparative LC (irregular SiOH, 40-63 μm, liquid loading (DCM), mobile phase: DCM/EtOAc, 90/10) to give 317 mg (94%) of intermediate (G106).

The following compounds were prepared according to the above procedure.

intermediate (G107)

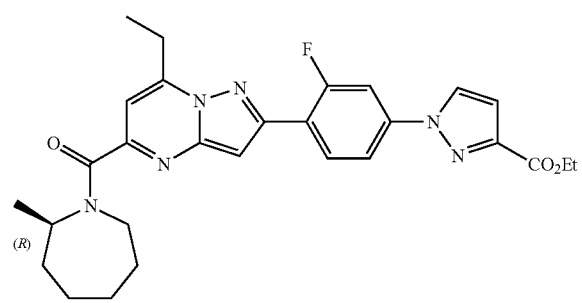

intermediate (G114)

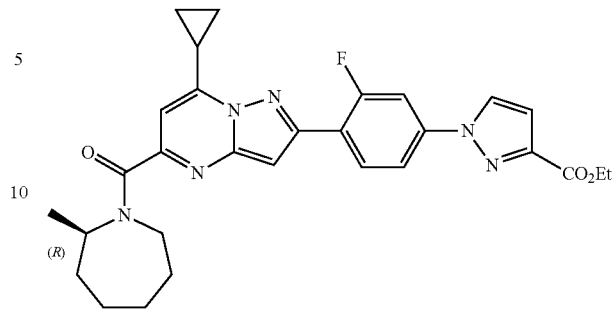

Intermediate (G117): A screw cap tube was charged with intermediate (G88) (0.32 g, 0.659 mmol), ethyl 1H-pyrazole-4-carboxylate (0.277 g, 1.978 mmol), K₂CO₃ (0.273 g, 1.978 mmol), CuI (0.0505 g, 0.264 mmol) and N,N-dimethyl-1,2-cyclohexanediamine (0.0421 mL, 0.264 mmol) and purge with N₂. The tube was capped with a septum then purged again with nitrogen. DMF was added and the mixture was heated at 110° C. for 18 h. The reaction mixture was poured out into water, extracted with EtOAc, the organic layer was washed with water then brine, dried (MgSO₄) and evaporated till dryness. Purification of the residue was carried out by flash chromatography over silica gel (cartridge 24 g, 15-40 μm, Heptane/EtOAc 80/20 to Heptane/EtOAc 70/30). The pure fractions were collected and evaporated to dryness to give 0.22 g (61%) of intermediate (G117).

intermediate (G117)

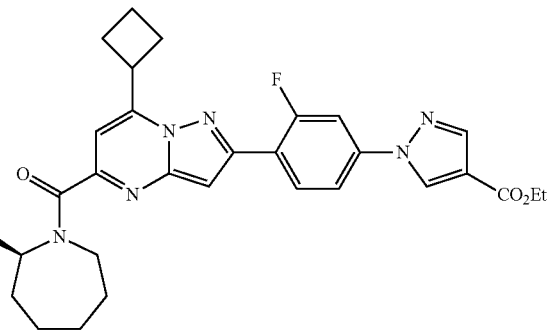

The following intermediates were prepared according to the above procedure:

intermediate (G118)

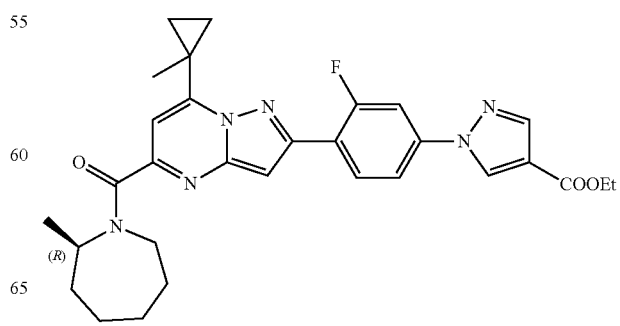

intermediate (G133)
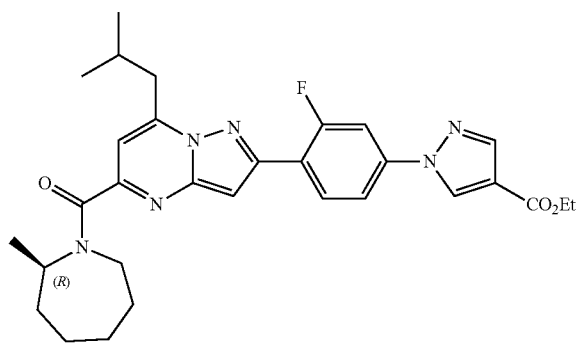
intermediate (G191)
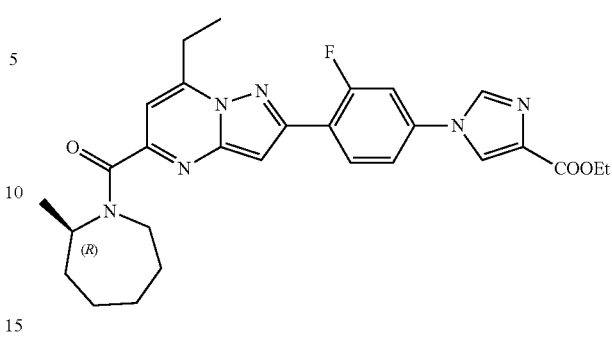
intermediate (G170)
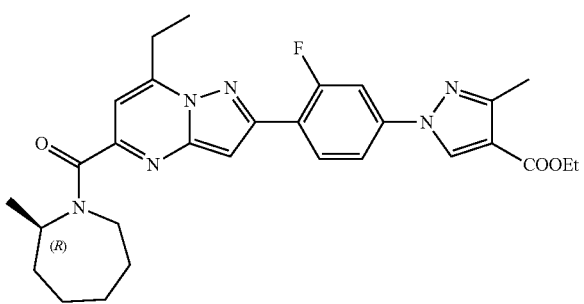
intermediate (G219)
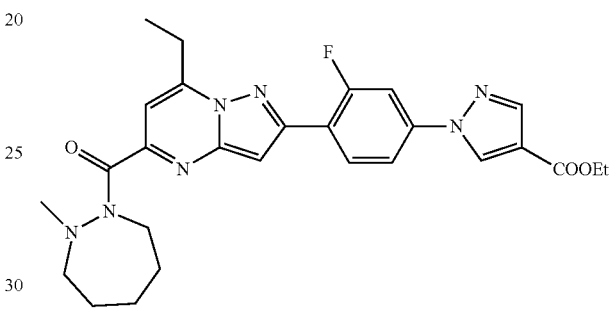
intermediate (G180)
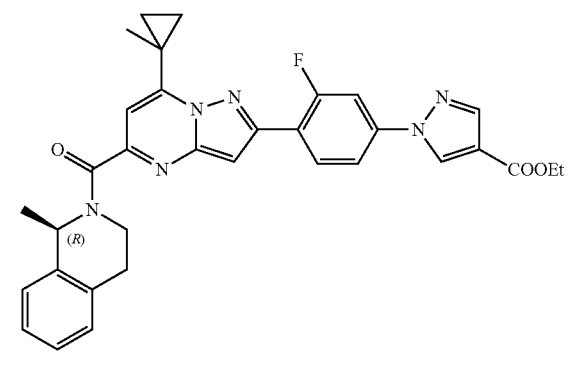
intermediate (G222)
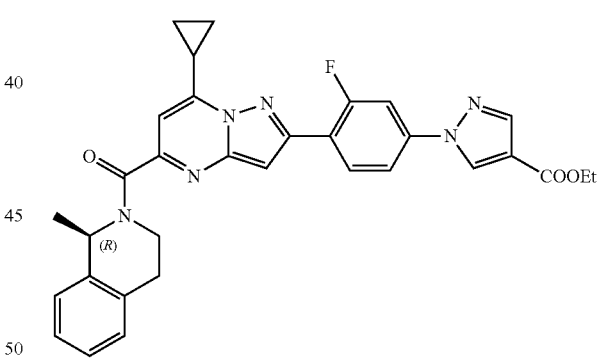
intermediate (G189)
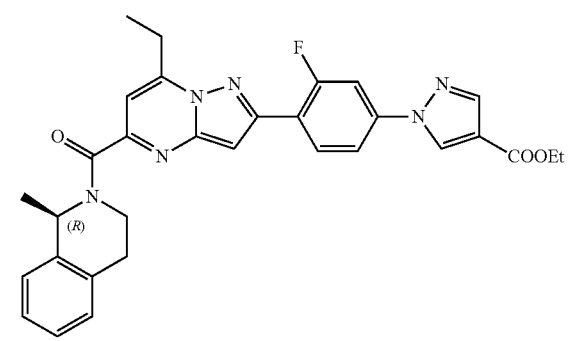
intermediate (G227)
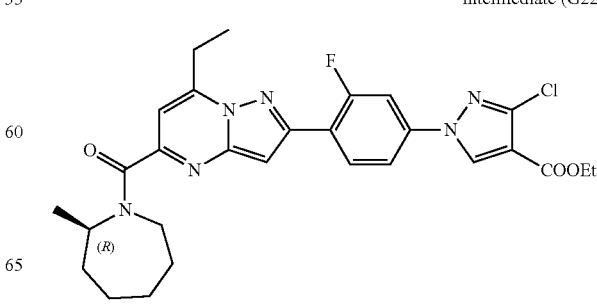

intermediate (G292)

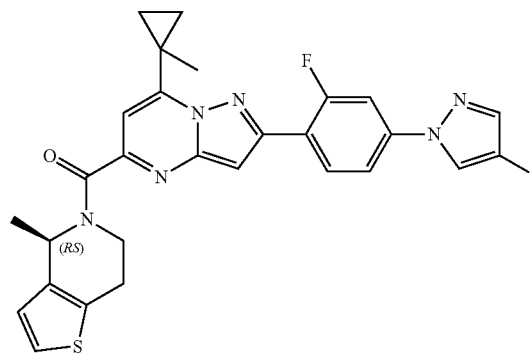

intermediate (G293)

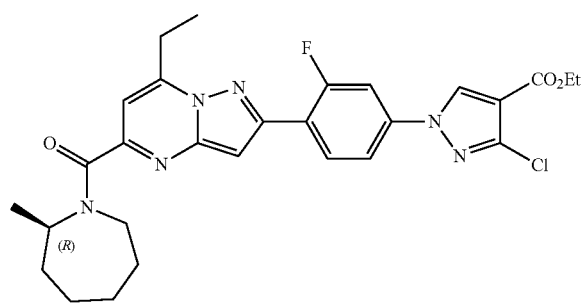

intermediate (G294)

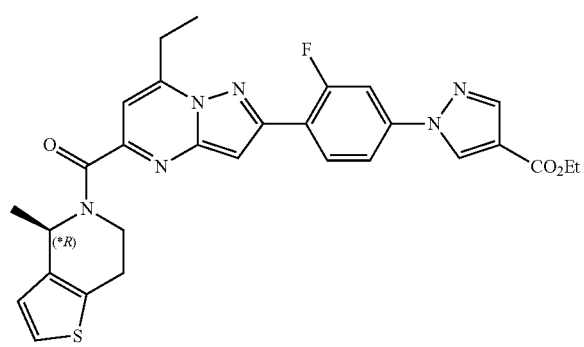

Reaction scheme:

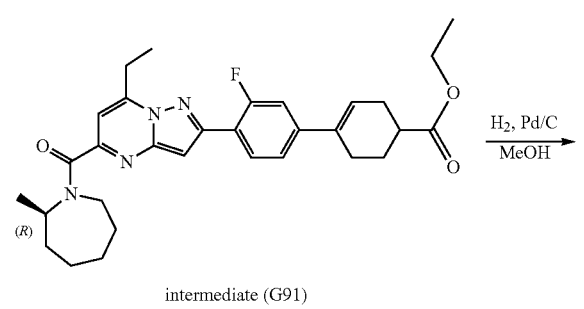

intermediate (G91)

-continued

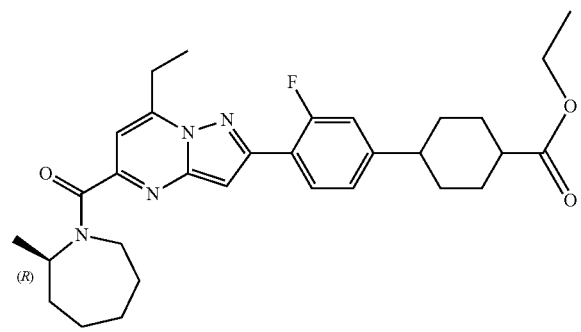

intermediate (G119)

Pd/C (10%) (40 mg; 37.5 µmol) was added to a degassed solution of intermediate (G91) (200 mg; 0.375 mmol) in MeOH (3 mL). The resulting mixture was hydrogenated at rt under 1 bar overnight. The mixture was filtered through a pad of Celite®, the filtrate was concentrated until dryness to give 199 mg of intermediate (G119) (99%) as a colorless oil.

Intermediate (G140):

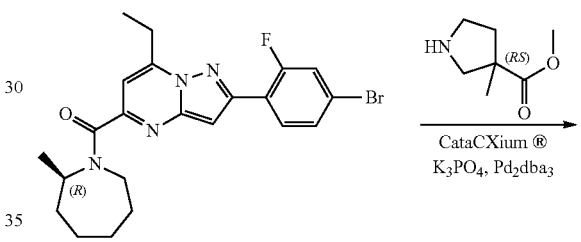

Intermediate (G1)

intermediate (G140)

A solution of CataCXium PtB® (19.9 mg, 0.026 mmol) and $Pd_2dba_3$ (7.5 mg, 0.022 mmol) in 1,4-dioxane was degassed under $N_2$ for 20 min. A solution of intermediate (G1) (200 mg, 0.435), 3-methyl-pyrrolidine-3-methylcarboxylate (67.5 mg, 0.471 mmol) and $K_3PO_4$ (277.2 mg, 1.306 mmol) in 1,4-dioxane (9.2 mL) and water (0.15 mL) was degassed under $N_2$ and added to the previous premix. The mixture was degassed for 5 additional minutes and then heated at 110° C. for 16 h. The mixture was partitioned between water and DCM and the organic layer was separated through a hydrophobic frit and concentrated under reduced pressure. Purification was carried out by flash chromatography over silica gel (15-40 µm, Grace® 12 g, Hept/EtOAc, 70/30) yielding 0.141 g (56%) of intermediate (G140) as a yellow oil.

intermediate (G140)

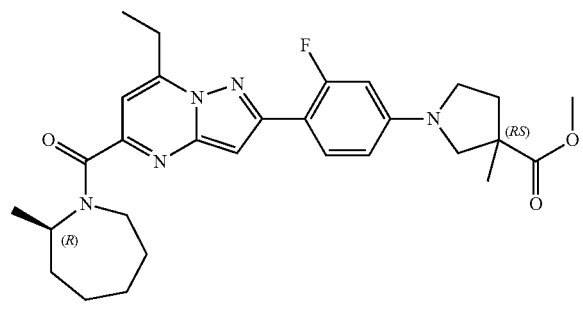

The following intermediates were prepared according to the above procedure:

intermediate (G141)

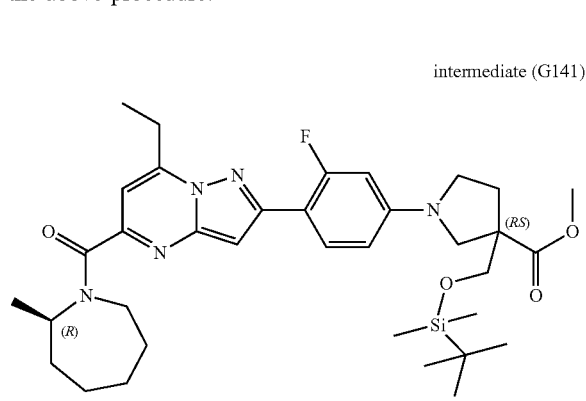

intermediate (G306)

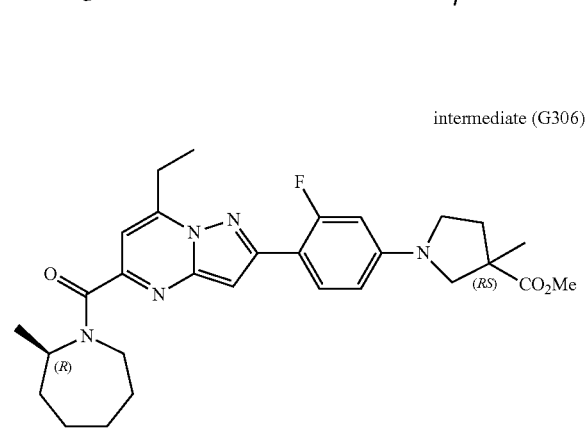

intermediate (G307)

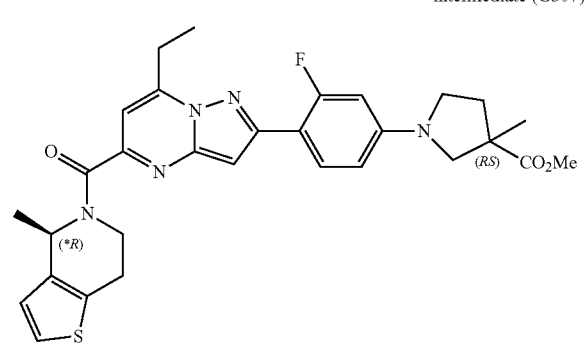

intermediate (G308)

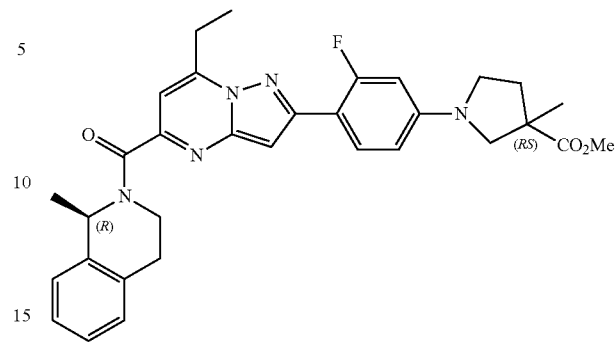

intermediate (G119)

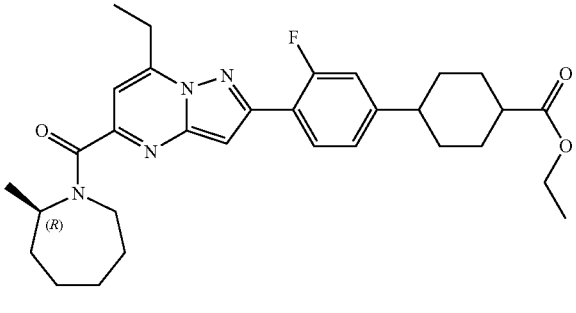

Intermediate (G142):

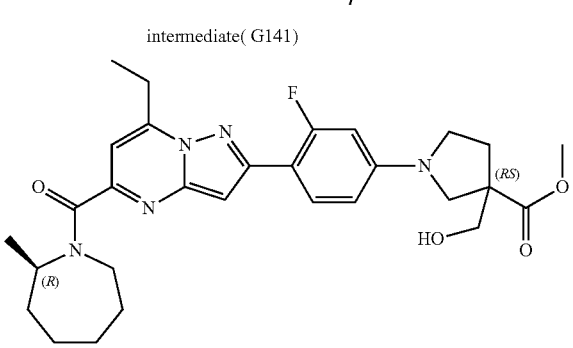

intermediate( G142)

A solution of intermediate (G141) (700 mg, 0.526 mmol), APTS (905.1 mg, 5.26 mmol), pyridine (415.7 µL, 5.26 mmol) and TBAF (1M in THF) (5.25 mL, 5.26 mmol) in THF (5.05 mL) was stirred at room temperature for 63 h then quenched with $NaHCO_3$ 10% and diluted with DCM. The layers were separated and the organic layer was concentrated under reduced pressure. Purification was carried out by flash chromatography (silica gel, Heptane/EtOAc, 70/30)

yielding 0.182 g (63%) of intermediate (I42) as a yellow oil. Heptane/EtOAc, 70/30) yielding 0.182 g (63%) of intermediate (G142) as a yellow oil.

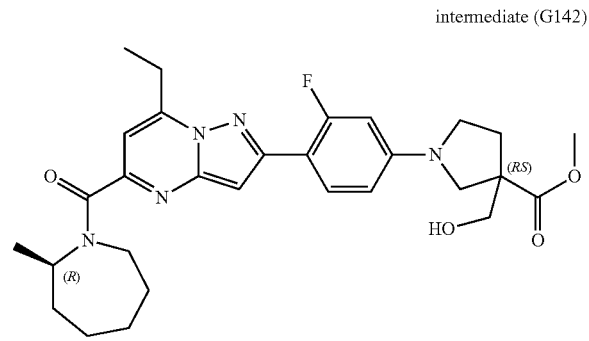

intermediate (G142)

Intermediate (G144):

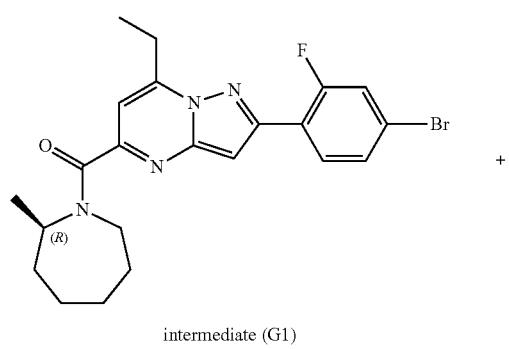

intermediate (G1)

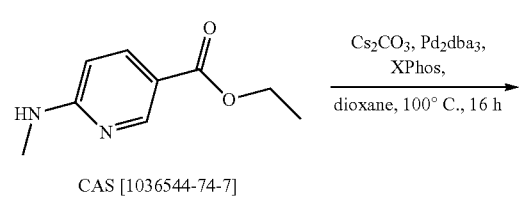

CAS [1036544-74-7]

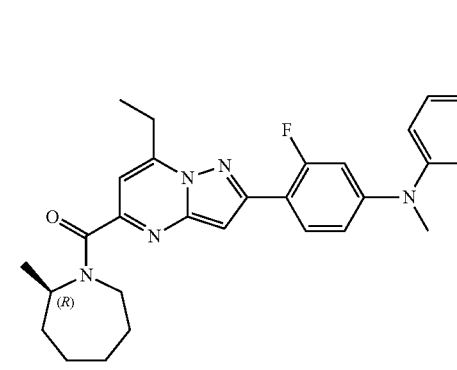

intermediate (G144)

To a degassed mixture of intermediate (G1) (0.35 g, 0.76 mmol), ethyl 6-(methylamino)-pyridine-3-carboxylate (0.16 g, 0.91 mmol) and Cs$_2$CO$_3$ (0.74 g, 2.29 mmol) in 1,4-dioxane (14 mL) was added successively XPhos (0.028 g, 0.03 mmol) then Pd$_2$dba$_3$ (0.033 g, 0.069 mmol) at room temperature. The resulting mixture was stirred at 100° C. for 16 h. The solution was cooled down to room temperature and water was added. The mixture was extracted with EtOAc (twice). The combined organic layers were washed with brine, dried over MgSO$_4$, filtered and the solvent was removed in vacuo to give yellow oil. Purification was carried out by flash chromatography over silica gel (GraceResolv®, 40 g, 15-35 M, Heptane/EtOAc 90/10 to 70/30). Pure fractions were collected and evaporated to afford 0.483 g, as pale yellow oil. A second purification was carried out by flash chromatography over silica gel (GraceResolv®, 40 g, 15-35 M, Heptane/EtOAc 80/20 to 70/30). Pure fractions were collected and evaporated to afford 0.372 g (87%) of intermediate (G144) as a colorless oil. Used as such for next step.

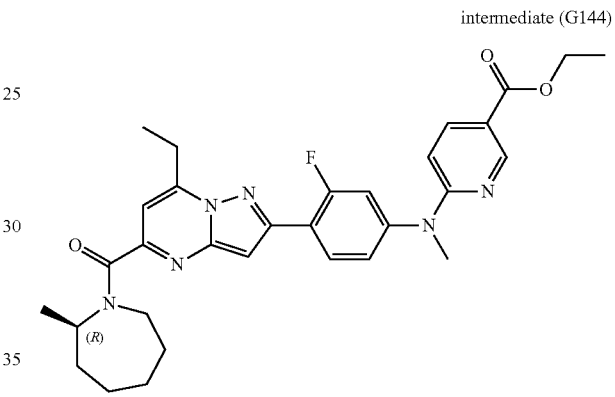

intermediate (G144)

Intermediates (G145) and (G146):

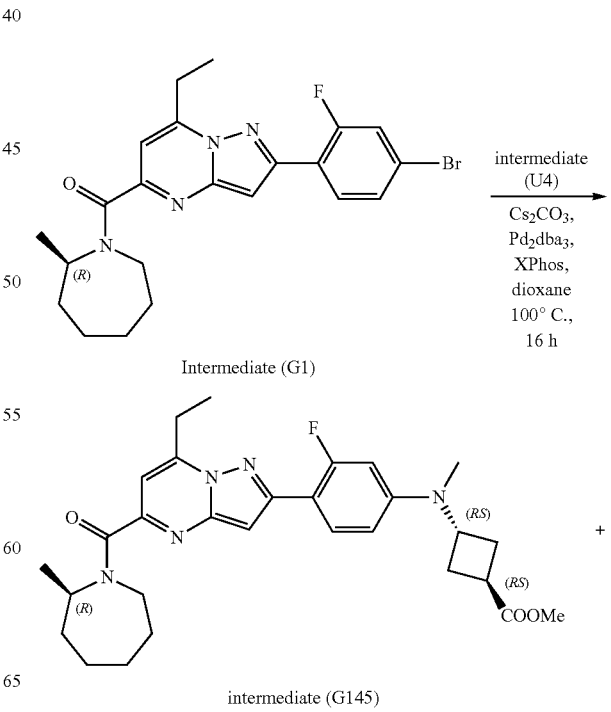

Intermediate (G1)

intermediate (G145)

-continued

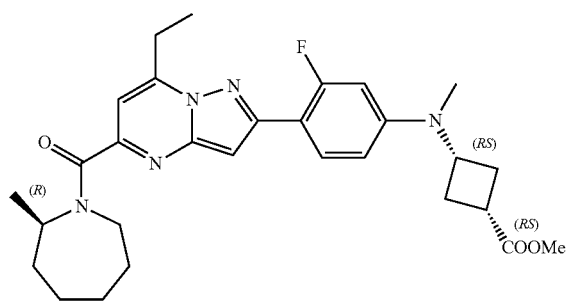

intermediate (G146)

To a degassed mixture of intermediate (G1) (0.38 g, 0.82 mmol), intermediate (U4) (0.22 g, 0.98 mmol) and Cs₂CO₃ (0.8 g, 2.45 mmol) in 1,4-dioxane (15 mL) was added successively XPhos (0.03 g, 0.033 mmol) then Pd₂dba₃ (0.035 g, 0.073 mmol) at room temperature. The resulting mixture was stirred at 100° C. for 16 h. The solution was cooled down to room temperature and water was added. The mixture was extracted with EtOAc (twice). The combined organic layers were washed with brine, dried over MgSO₄, filtered and the solvent was removed in vacuum to give 0.445 g of a crude mixture. Purification was carried out by flash chromatography over silica gel (GraceResolv®, 15-35 μM, 40 g, Heptane/EtOAc from 85/15 to 70/30). Pure fractions were collected and evaporated to give 0.163 g of a pale yellow foam. A second purification was performed via achiral SFC (Stationary phase: CHIRALCEL® OJ-H 5 μm 250×20 mm, Mobile phase: 75% CO₂, 25% MeOH). Pure fractions were collected and evaporated to give 0.126 g of intermediate (G145) and 0.270 g of intermediate (G146).

intermediate (G145)

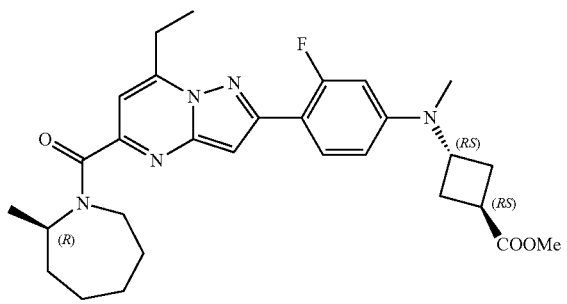

intermediate (G146)

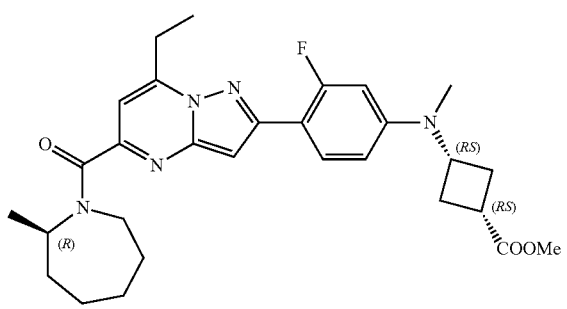

Intermediate (G148):

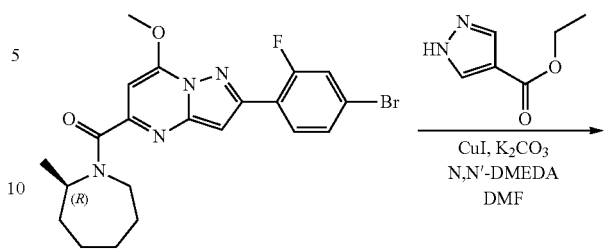

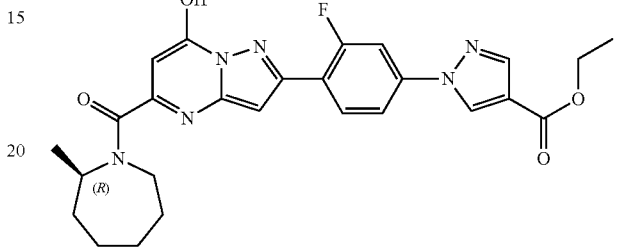

Intermediate (G148)

A mixture of intermediate (G147) (2.3 g, 5.1 mmol), ethyl 1H-pyrazole-4-carboxylate CAS [37622-90-5] (2.1 g, 15.4 mmol), K₂CO₃ (2.1 g, 15.4 mmol), CuI (0.98 g, 5.1 mmol) and N,N'-DMEDA (0.8 mL, 5.1 mmol) was purged with N₂. DMF (20 mL) was added and the mixture was heated at 100° C. overnight. The reaction mixture was poured out into water, extracted with EtOAc, the mixture was filtered through a short pad of Celite® and the organic layer was separated, washed with water then brine, dried (MgSO₄) and evaporated till dryness. Purification was carried out by flash chromatography over silica gel (cartridge 120 g, 15-40 μm, DCM to DCM/MeOH 95/5). The pure fractions were collected and evaporated to dryness to afford 1 g (38%) of intermediate (G148).

intermediate (G148)

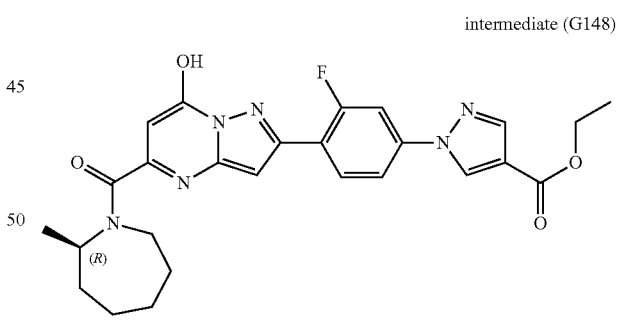

Intermediate (G151):
A mixture of intermediate (E55) (1.58 g; 4.94 mmol), (1R)-1,2,3,4-tetrahydro-1-methyl-isoquinoline (872 mg; 5.92 mmol), HATU (2.44 g; 6.41 mmol) and DIEA (2.6 mL; 15.1 mmol) in DMF (29 mL) was stirred at rt for 20 hours. The reaction mixture was diluted with ethyl acetate, washed with a sat. aq. solution of NaHCO₃ (twice), brine (3 times), dried over MgSO₄ and evaporated till dryness under vacuum. The compound was purified by preparative LC (irregular SiOH 15-40 μm, 80 g Grace® Resolv, liquid loading (DCM), mobile phase gradient: from heptane 90%, EtOAc 10% to Heptane 50%, EtOAc 50%) to give 1.84 g of intermediate (G151) as a white foam (91%).

intermediate (G151)

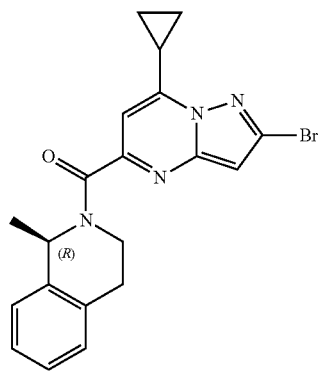

Intermediate (G152):

Under N₂, in a schlenk tube, B₂pin₂ (904 mg; 3.56 mmol) and KOAc (582 mg; 5.93 mmol) were added to a solution of intermediate (G151) (1.22 g; 2.97 mmol) in 1,4-dioxane (20 mL). The solution was purged with nitrogen and charged with PdCl₂(dppf) (243 mg; 0.297 mmol). The resulting solution was purged again with nitrogen and stirred to 100° C. for 4 hours. EtOAc was added. The organic layer was washed with water and brine (twice), dried over MgSO₄ and concentrated till dryness to give 2.2 g of intermediate (G152) as brown oil (the product was engaged without further purification in the following step).

intermediate (G152)

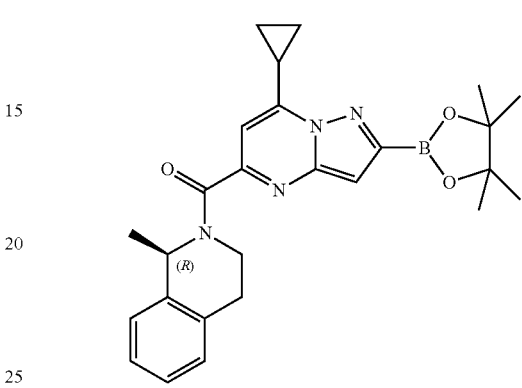

Intermediate (G153):

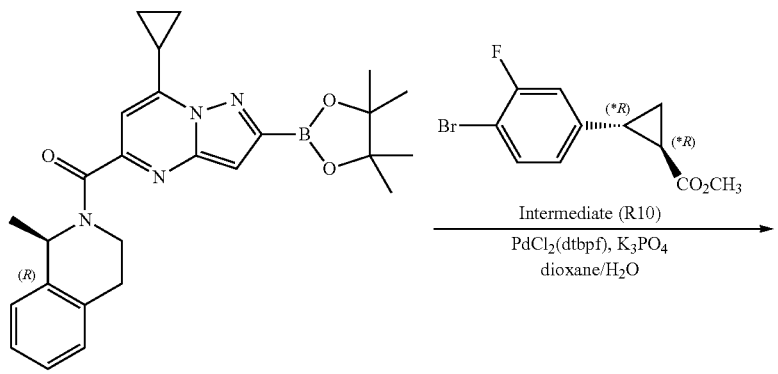

intermediate (G152)

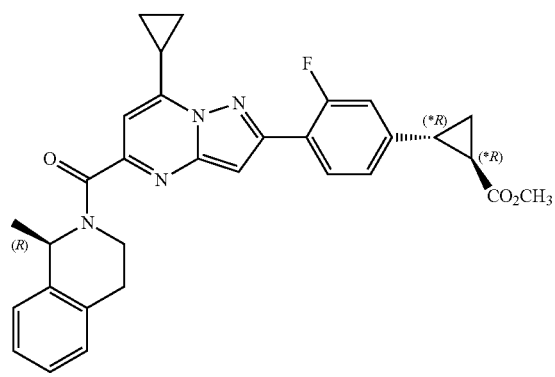

intermediate (G153)

In a sealed tube, a solution of intermediate (G152) (0.75 g; 0.982 mmol; 60% purity), intermediate (R10) (468 mg; 1.18 mmol) and K$_3$PO$_4$ (625 mg; 2.95 mmol) in dioxane (13.9 mL) and H$_2$O (2.1 mL) was purged with N$_2$. PdCl$_2$(dtbpf) (64 mg; 0.098 mmol) was added, the mixture was purged again with N$_2$ and heated at 80° C. using a single mode microwave (Biotage® Initiator EXP 60) with a power output ranging from 0 to 400 W for 30 min [fixed hold time]. EtOAc and water were added. The layers were separated and the organic layer was washed with brine (twice), dried on MgSO$_4$, filtered, concentrated and purified by preparative LC (irregular SiOH, 15-40 μm, 50 g Grace® Resolv, liquid loading (DCM), mobile phase gradient: from Heptane/EtOAc 90/10 to 70/30) to give 1.02 g (80%) of intermediate (G153) as a pale yellowish solid.

intermediate (G153)

The following intermediates were prepared using analogous procedures:

intermediate (G178)

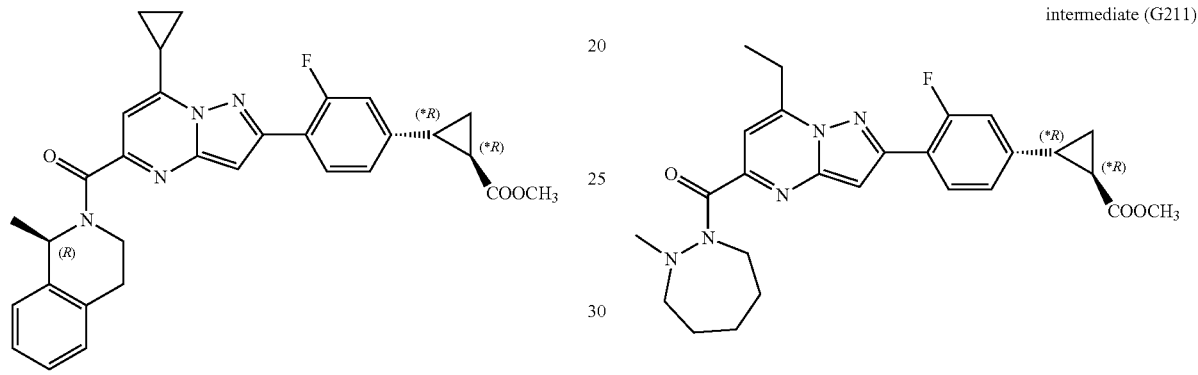

intermediate (G196)

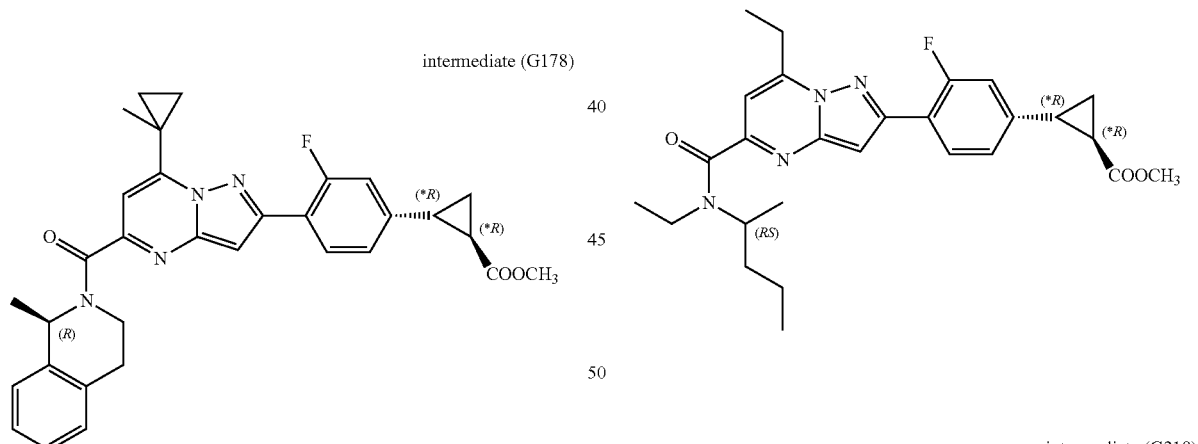

intermediate (G204)

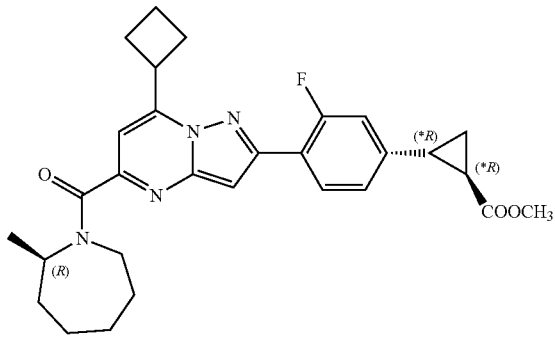

intermediate (G211)

intermediate (G217)

intermediate (G218)

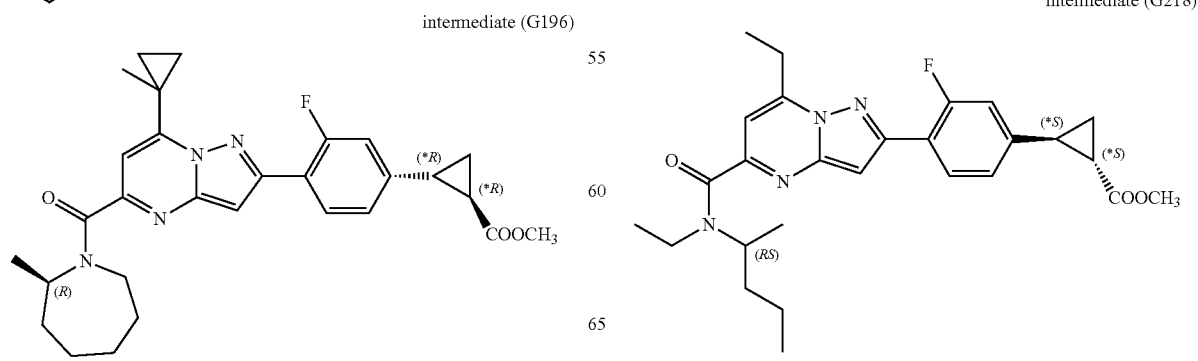

-continued

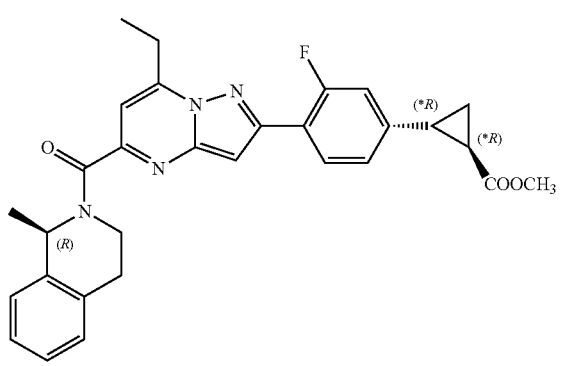

intermediate (G220)

Intermediate (G155):

A solution of intermediate G77 (570 mg; 1.38 mmol), 7-bromo-8-fluoro-2(1H)-Quinolinone (335 mg; 1.38 mmol) and K$_3$PO$_4$ (880 mg; 4.15 mmol) in dioxane (15 mL) and H$_2$O (3 mL) was purged by N$_2$ bubbling for 10 min before the addition of PdCl$_2$dtbpf (270 mg; 0.415 mmol). The resulting mixture was purged by N$_2$ bubbling then heated at 80° C. using a single mode microwave (Biotage Initiator EXP 60) with a power output ranging from 0 to 400 W for 30 min [fixed hold time]. An additional amount of intermediate G77 (200 mg; 0.485 mmol) was added and the mixture was degassed by N$_2$ bubbling for 10 min before the addition of additional PdCl$_2$dtbpf (100 mg; 0.153 mmol). The mixture was degassed again by N$_2$ bubbling for 5 min then heated at 80° C. using a single mode microwave (Biotage® Initiator EXP 60) with a power output ranging from 0 to 400 W for 30 min [fixed hold time]. The crude was poured into DCM, washed with water (twice), brine, dried over MgSO$_4$, filtered and evaporated in vacuum. The crude was taken-up in MeCN, the solid was filtered off and dried under vacuum to give 387 mg (46%) of intermediate (G155) as an off-white solid.

intermediate (G155)

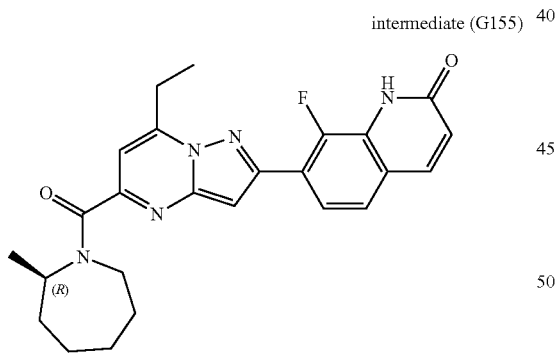

Intermediate (G156):

NaH 60% dispersion in mineral oil (23 mg; 0.908 mmol) was added to a solution of intermediate (G155) (387 mg; 0.865 mmol) in dry DMF (7 mL) at 0° C. The resulting mixture was stirred at 0° C. for 30 min before the addition of PhNTf$_2$ (324 mg; 0.908 mmol). The mixture was allowed to warm to rt then stirred at rt overnight. Water was added and the mixture was extracted with DCM (twice). The combined organic layers were washed with brine (twice), dried over MgSO$_4$, filtered and concentrated in vacuum to give yellow oil which was dissolved in dry DMF (7 mL). The mixture was cooled to 0° C. before the addition of additional NaH (23 mg; 0.908 mmol). The resulting mixture was stirred at 0° C. for 30 min then additional PhNTf$_2$ (324 mg; 0.908 mmol) was added and the mixture was allowed to warm to rt and stirred at rt for 4 h. Water was added and the mixture was extracted with EtOAc (twice). The combined organic layers were washed with brine (3 times), dried over MgSO$_4$, filtered and concentrated in vacuum to give 662 mg (Quant, purity 75%) of intermediate (G156) as a brown solid.

intermediate (G156)

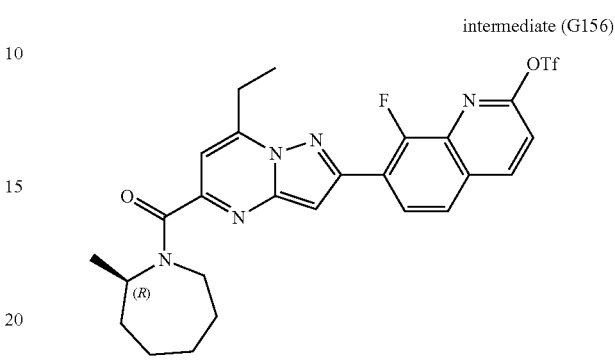

Intermediate (G160):

A mixture of crude intermediate (G159) (0.881 g, 1.50 mmol), 4-bromo-3-fluoro-2-hydroxybenzaldehyde (0.493 g, 2.25 mmol), K$_3$PO$_4$ (0.955 g, 4.50 mmol) and PdCl$_2$(dtbpf) (0.0489 g, 0.0750 mmol) in a mixture of dioxane/H$_2$O (8:2) (10 ml) was stirred at 100° C. for 1 h, then allowed to cool down to rt, diluted with ethyl acetate (50 ml), washed with brine (2×50 mL), dried over Na$_2$SO$_4$, filtered and concentrated under reduced pressure. The crude brown gum was purified by column chromatography (silica gel, mobile phase DCM/EtOAc 100/0 to 95/5). The pure fractions were collected and the solvent was evaporated to yield 0.210 g of intermediate (G160) as a beige sticky solid.

intermediate (G160)

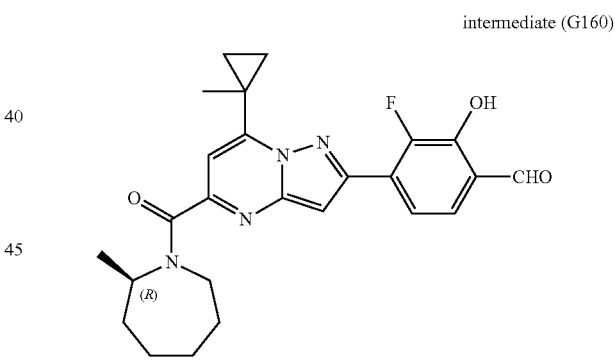

The following intermediates were prepared using analogous procedures:

intermediate (G195)

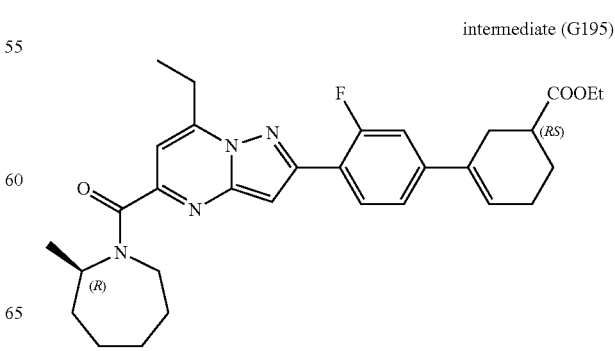

-continued intermediate (G212)

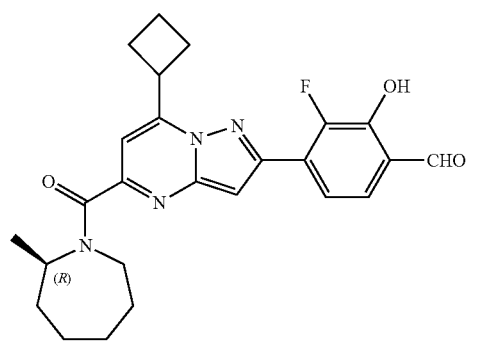

Intermediate (G168):

A mixture of intermediate (G160) (0.210 g, 0.466 mmol), diethylmalonate (0.106 ml, 0.699 mmol), piperidine (0.0046 mL, 0.0466 mmol) and AcOH (0.0027 mL, 0.0466 mmol) in EtOH (3 mL) was stirred at reflux for 16 h, allowed to cool down to rt and diluted with water (15 mL). The precipitate was collected by filtration on a glass frit, washed with water (2×10 mL), taken up in DCM (25 mL), dried over $Na_2SO_4$, filtered and concentrated under reduced pressure. The crude material was purified by column chromatography (silica gel, mobile phase DCM/EtOAc 100/0 to 95/5). The pure fractions were collected and the solvent was evaporated under reduced pressure to yield 0.176 g (69%) of intermediate (G168) as a yellowish solid.

intermediate (G168)

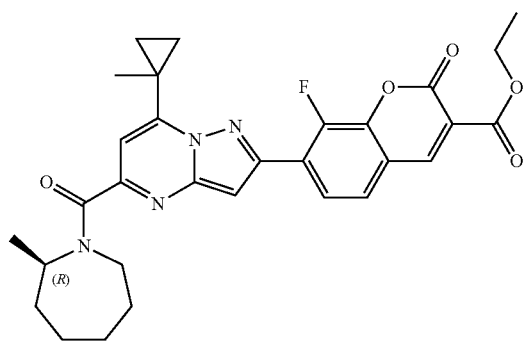

The following intermediate was prepared using analogous procedures:

intermediate (G213)

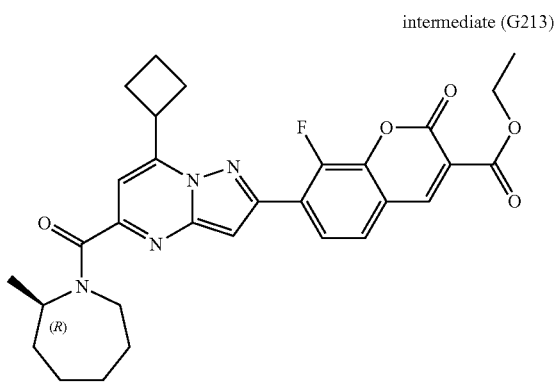

Intermediate (G162):

HCl 4M in dioxane (40.0 mL, 159 mmol) was added to a solution of intermediate (G161) (3.70 g, 7.95 mmol) in dioxane (40.0 ml) and $H_2O$ (0.3 mL, 15.9 mmol) at rt. The reaction mixture was stirred at rt overnight. Reaction mixture was concentrated to dryness and purified by preparative LC (Regular $SiO_2$, 50 µm, Interchim®120 g, mobile phase gradient: from DCM/MeOH 98/2 to 50/50) to give 2.80 g (82%) of intermediate (G162) as a yellow powder.

intermediate (G162)

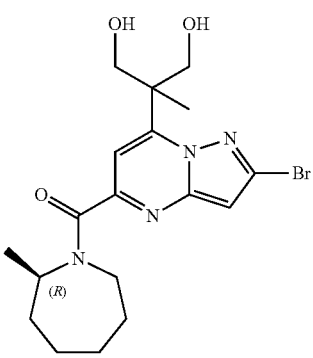

Intermediate (G163):

DEAD 40% in toluene (2.30 mL, 5.08 mmol) was added to a solution of intermediate (G162) (1.80 g, 4.23 mmol), $PPh_3$ (1.33 g, 5.08 mmol) and Ziram® (1.55 g, 5.08 mmol) in toluene (21 mL) at rt. The reaction mixture was stirred at rt for 16 h and filtered. The cake was washed with DCM and the filtrate was concentrated under reduce pressure. The residue was purified by preparative LC (Regular C18, 50 µm, Interchim® 175 g, mobile phase gradient: from MeCN/$H_2O$ 02/98 to 100/0). The desired fraction was collected and evaporated in vacuum to yield 0.690 g (41%) of intermediate (G163) as a beige powder.

intermediate (G163)

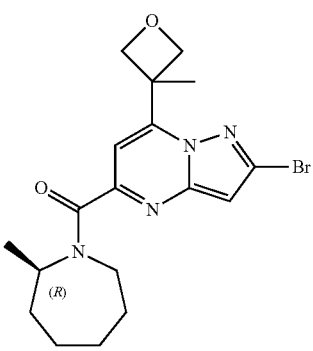

Intermediate (G164):

Intermediate (G163) (0.240 g, 0.590 mmol) and $K_3PO_4$ (0.375 g, 1.780 mmol) were added to a solution of intermediate (R19) (0.570 g, 1.78 mmol) in dioxane (3 ml) and $H_2O$ (0.4 mL) at rt. The mixture was purged (twice) with argon and $PdCl_2dtbpf$ (0.038 g, 0.059 mmol) was added. The mixture was purged again (twice) with argon and stirred at 100° C. for 2 h. The mixture was purged (twice) with argon and an additional amount of $PdCl_2dtbpf$ (0.038 g, 0.059 mmol) was added. The mixture was purged again (twice) with argon and stirred at 100° C. for 2 h. The mixture was purged (twice) with argon and an additional amount of $PdCl_2dtbpf$ (0.038 g, 0.059 mmol) was added. The mixture was purged again (twice) with argon and stirred at 100° C. for 2 h. The reaction mixture was quenched with water and extracted with DCM (50 mL). The organic layer was dried ($Na_2SO_4$), filtered and concentrated under reduced pressure.

The residue was purified by preparative LC (Regular SiOH, 50 μm, Interchim® 40 g, mobile phase gradient: from EtOAc/cyclohexane 10/90 to 50/50). The desired fraction was collected and evaporated in vacuo to give an orange oil which was triturated in pentane several times to yield 0.112 g (36%) of intermediate (G164) as a beige powder.

intermediate (G164)

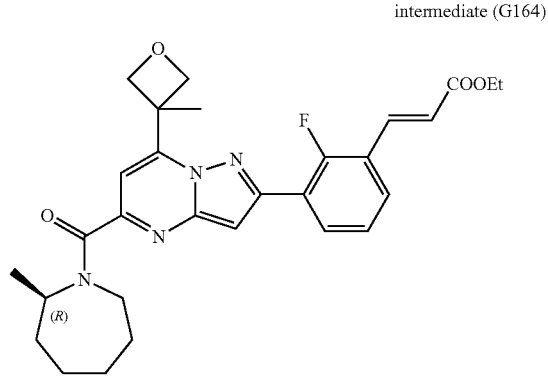

The following intermediates were prepared according to intermediate (G164)

intermediate (G295)

intermediate (G296)

intermediate (G297)

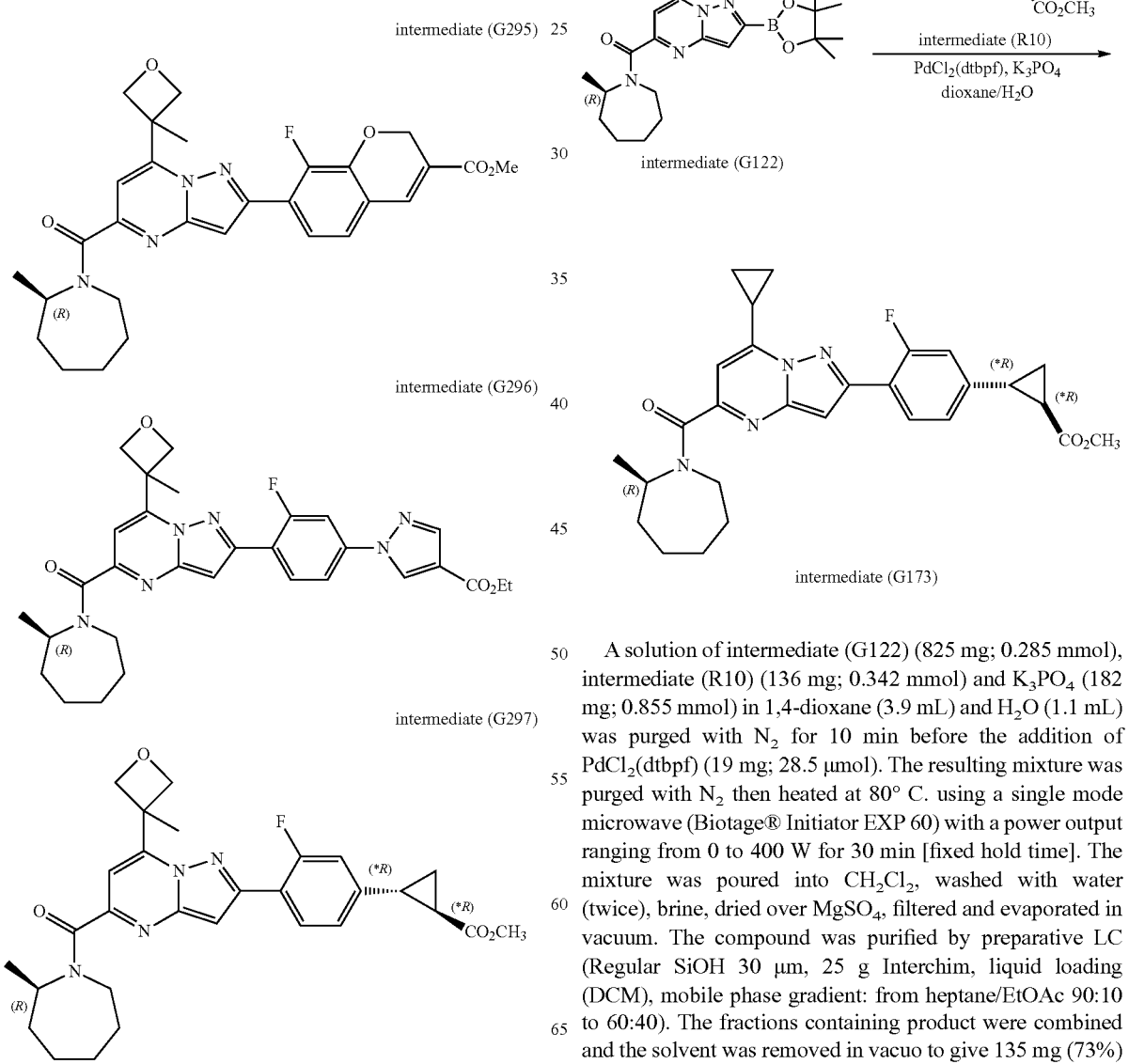

intermediate (G303)

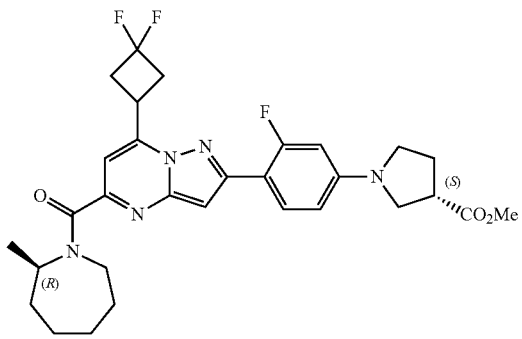

Intermediate (G173):

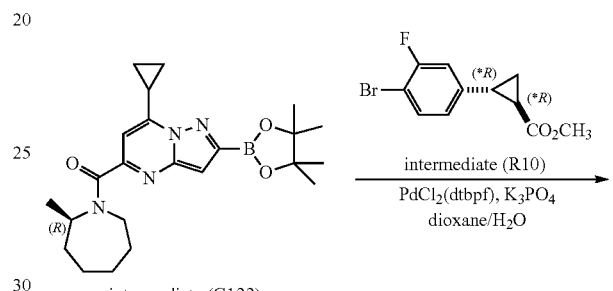

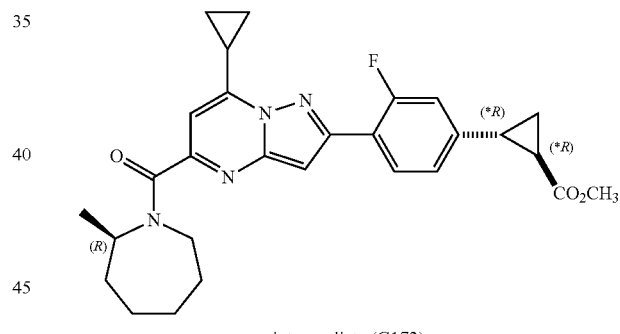

intermediate (G173)

A solution of intermediate (G122) (825 mg; 0.285 mmol), intermediate (R10) (136 mg; 0.342 mmol) and K$_3$PO$_4$ (182 mg; 0.855 mmol) in 1,4-dioxane (3.9 mL) and H$_2$O (1.1 mL) was purged with N$_2$ for 10 min before the addition of PdCl$_2$(dtbpf) (19 mg; 28.5 μmol). The resulting mixture was purged with N$_2$ then heated at 80° C. using a single mode microwave (Biotage® Initiator EXP 60) with a power output ranging from 0 to 400 W for 30 min [fixed hold time]. The mixture was poured into CH$_2$Cl$_2$, washed with water (twice), brine, dried over MgSO$_4$, filtered and evaporated in vacuum. The compound was purified by preparative LC (Regular SiOH 30 μm, 25 g Interchim, liquid loading (DCM), mobile phase gradient: from heptane/EtOAc 90:10 to 60:40). The fractions containing product were combined and the solvent was removed in vacuo to give 135 mg (73%) of intermediate (G173).

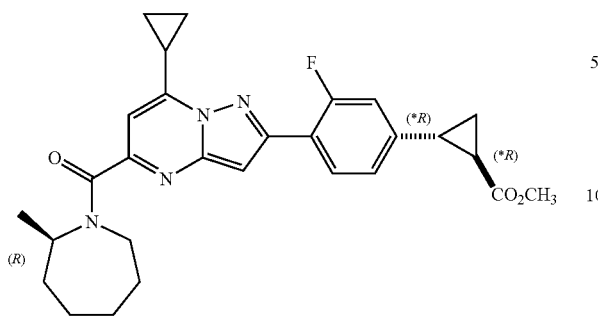

intermediate (G173)

Intermediate (G220):

DIEA (0.65 mL, 3.62 mmol) and HATU (0.55 g, 1.45 mmol) were added to a mixture of intermediate (E46) (0.50 g, 1.21 mmol) and (1R)-1,2,3,4-tetrahydro-1-methyl-isoquinoline (0.20 g, 1.33 mmol) in DMF (8 mL). The resulting mixture was stirred at rt for 16 hours. The reaction mixture was poured into water (80 mL) dropwise with stirring (20 min). The precipitate was centrifuged. The solid was dissolved in DCM (10 mL), washed with 10 mL of 1N aqueous HCl and 10 mL of $H_2O$. The organic layer was dried over $Na_2SO_4$, filtered and concentrated in vacuo to afford 0.720 g (quant.) of intermediate (G220) as a brownish gum.

Intermediate (G223):

$PdCl_2$(15 mg; 4.48 mmol) was added to a degassed solution of intermediate (G1) (1.2 g; 2.61 mmol), potassium vinyltrifluoroborate (600 mg; 4.48 mmol), $Cs_2CO_3$ (3.72 g; 11.4 mmol) and $PPh_3$(60 mg; 0.229 mmol) in THF (30 mL) and $H_2O$ (3 mL). The mixture was stirred at reflux for 7 hours. The mixture was extracted with DCM and water. The organic layer was washed with brine, dried over $MgSO_4$, filtered, evaporated and purified by preparative LC (irregular SiOH 15-40 μm, 120 g Grace® Resolv, mobile phase gradient: from heptane/EtOAc 100/0 to 50/50 to give 858 mg (72%) of intermediate (G223).

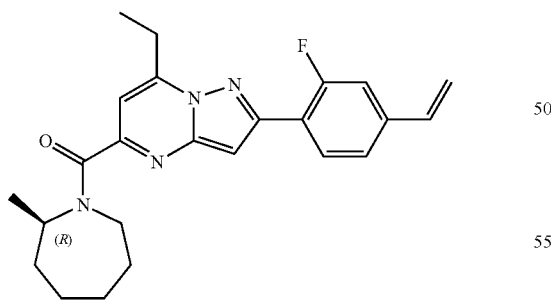

intermediate (G223)

Intermediate (G224):

Under $N_2$, a solution of ethyl diazoacetate (411 μL, 3.32 mmol) in DCM (20 mL) was added slowly over 40 min to a solution of intermediate (G223) (500 mg; 1.11 mmol) and $Rh(OAc)_2$ (15 mg; 67.9 μmol) in DCM (10 mL). The mixture was stirred at rt for 3 hours. An additional amount of ethyl diazoacetate (411 μL, 3.32 mmol) in DCM (20 mL) was added slowly over 40 min and the mixture was stirred at rt for 18 hours. The mixture was evaporated and purified by preparative LC (irregular SiOH 15-40 m, 120 g Grace® Resolv, liquid loading (DCM), mobile phase gradient: from heptane/EtOAc from 100:0 to 70:30 in 10 CV) to give 85 mg (15%) of intermediate (G224) as a yellow solid.

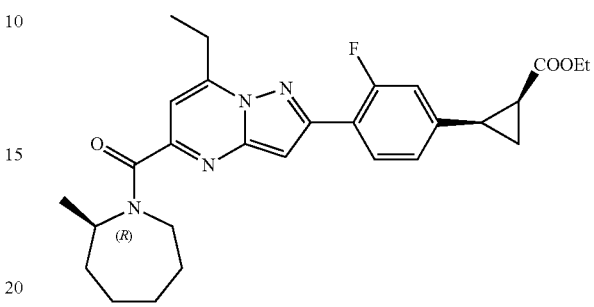

intermediate (G224)

Intermediate (G258):

HATU (1.6 g; 4.21 mmol) was added to a suspension of intermediate (E47) (1 g; 3.24 mmol), intermediate (F22) (0.68 g; 3.57 mmol) and DIEA (1.7 mL; 9.95 mmol) in DMF (20 mL) (the reaction mixture turn on yellow and clearless after a few minutes). The reaction mixture was stirred at rt for 16 h. The reaction mixture was diluted in ethyl acetate, washed with water, brine (3 times), dried over $MgSO_4$ and evaporated in vacuum. The crude mixture was purified by preparative LC (Regular SiOH 15-30 μm, 40 g Interchim®, dry loading (on SiOH), mobile phase gradient: from heptane/EtOAc; 90/10 to 50/50) to give 1.31 g (Quantitative yield) of intermediate (G258) as a white foam.

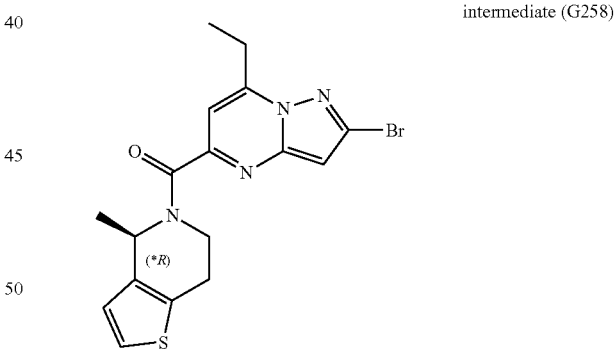

intermediate (G258)

Intermediate (G268):

Under $N_2$, in a sealed tube, Bispin (985 mg; 3.88 mmol) and KOAc (634 mg; 6.46 mmol) were added to a solution of intermediate (G258) (1.31 g; 3.23 mmol) in 1,4-dioxane (15 mL). The solution was purged with nitrogen and charged with $PdCl_2$(dppf)DCM (265 mg; 323 μmol). The resulting solution was purged again with nitrogen and stirred at 100° C. for 4 h. EtOAc was added. The organic layer was washed with water and brine (twice), dried over $MgSO_4$ and concentrated to give 2.37 g (Quant.) of intermediate (G268). The compound was engaged without further purification in the following step.

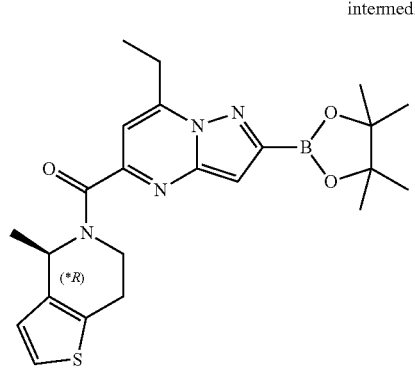

intermediate (G268)

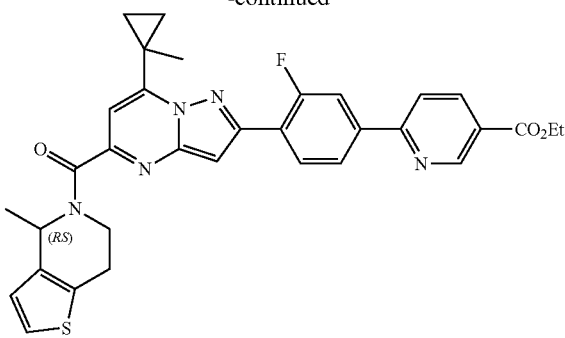

Intermediate (G286)

Intermediate (G279):

In a sealed tube, a solution of intermediate (G268) (500 mg; 0.68 mmol; 62%), intermediate (R10) (286 mg; 0.72 mmol) and K₃PO₄ (436 mg; 2.06 mmol) in 1,4-dioxane (10.5 mL) and H₂O (2.5 mL) was purged with N₂. PdCl₂(dtbpf) (45 mg; 69 mol) was added, the mixture was purged again with N₂ and heated at 80° C. using one single mode microwave (Biotage® Initiator EXP 60) with a power output ranging from 0 to 400 W for 30 min [fixed hold time]. EtOAc and water were added. The layers were separated and the organic layer was washed with brine, dried on MgSO₄, filtered and evaporated till dryness. The crude mixture was purified by preparative LC (Regular SiOH, 15-30 µm, 25 g Interchim®, dry loading (on SiOH), mobile phase gradient: from heptane/EtOAc 100/0 to 50/50) to give 293 mg (67%) of intermediate (G279) as a white foam.

Intermediate (G286):

In a Schlenk tube, a solution of intermediate (G272) (1.79 g; 2.35 mmol; 75% purity), ethyl-6-chloronicotinate (522 mg; 2.81 mmol) and K₃PO₄ (1.49 g; 7.04 mmol) in dioxane (32 mL) and H₂O (6 mL) was purged with N₂. PdCl₂dtbpf (153 mg; 0.234 mmol) was added, the mixture was purged again with N₂ and heated at 80° C. for 4 h. EtOAc and water were added. The layers were separated and the organic layer was washed with brine (3 times), dried on MgSO₄, filtered, concentrated and purified by preparative LC (Regular SiOH, 30 µm, 80 g Grace® Resolv, liquid loading (DCM), mobile phase gradient: from Heptane/EtOAc 90/10 to 60/40) to give 913 mg (65%) of intermediate (G286) as a yellowish solid.

intermediate (G279)

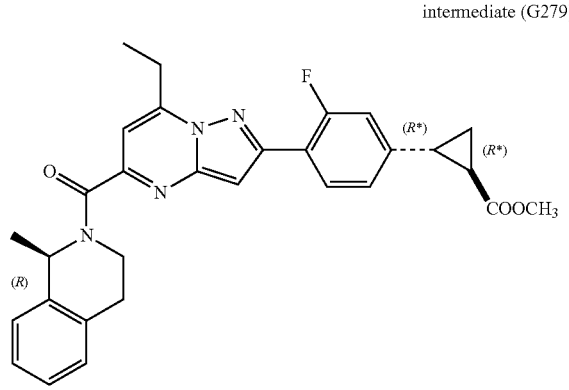

intermediate (G286)

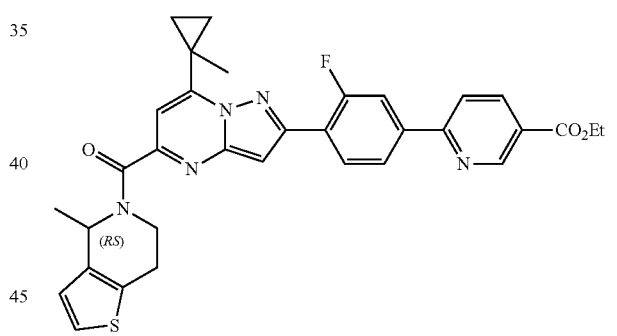

The following intermediate was prepared according to the above procedure.

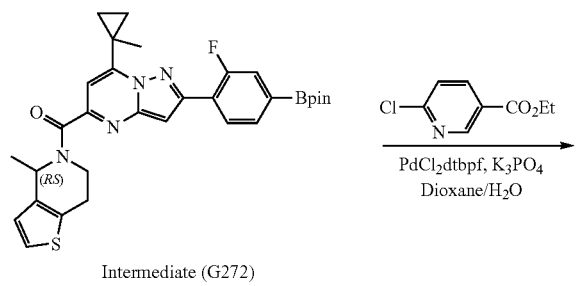

Intermediate (G272)

intermediate (G287)

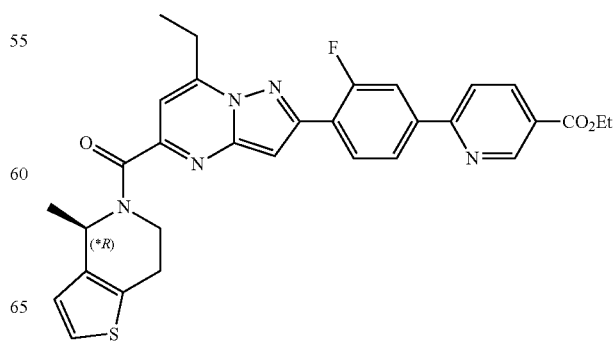

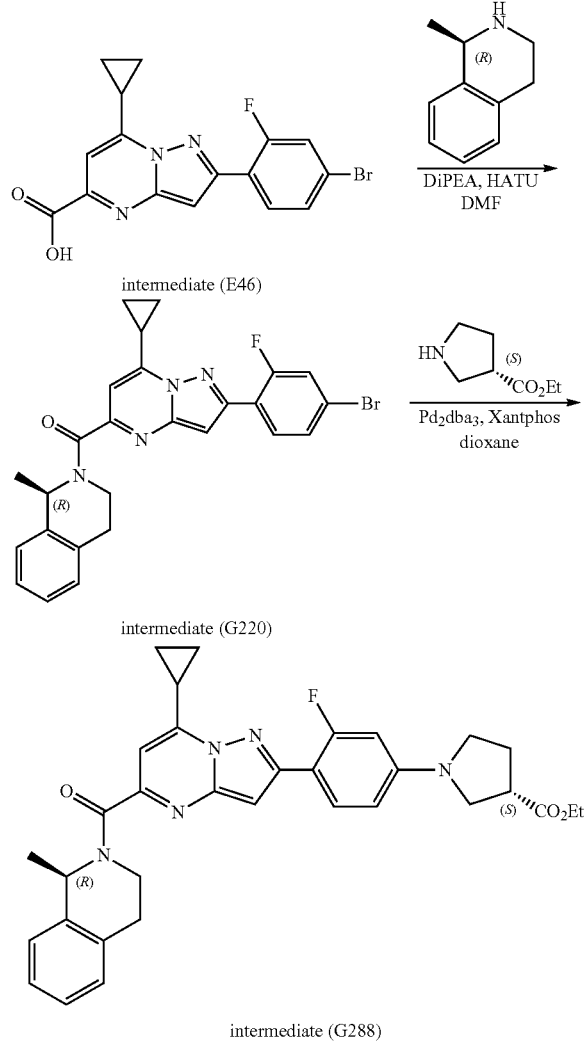

intermediate (E46)

intermediate (G220)

intermediate (G288)

Intermediate (G220):

DIEA (0.65 mL, 3.62 mmol) and HATU (0.55 g, 1.45 mmol) were added to a mixture of intermediate (E46) (0.50 g, 1.21 mmol) and (1R)-1,2,3,4-tetrahydro-1-methyl-isoquinoline (0.20 g, 1.33 mmol) in DMF (8 mL). The resulting mixture was stirred at rt for 16 hours. The reaction mixture was poured into water (80 mL) dropwise with stirring (20 min). The precipitate was centrifuged. The solid was dissolved in DCM (10 mL), washed with 10 mL of 1N aqueous HCl and 10 mL of $H_2O$. The organic layer was dried over $Na_2SO_4$, filtered and concentrated in vacuo to afford 0.720 g (quant.) of intermediate (G220) as a brownish gum.

Intermediate (G288):

A screw-cap tube was charged with intermediate (G220) (0.720 g, 1.207 mmol maximal), Ethyl (3S)-pyrrolidine-3-carboxylate hydrochloride (0.260 g, 1.448 mmol), cesium carbonate (0.590 g, 1.810 mmol), $Pd_2dba_3$ (0.030 g, 0.030 mmol) and Xantphos (0.035 g, 0.060 mmol). The tube was capped with a septum and purged with argon. Dioxane (5 mL) was added via a syringe through the septum. The reaction flask was sealed and placed in a pre-heated oil bath at 100° C. and stirred for 24 h. The reaction mixture was cooled to rt and 10 mL of AcOEt were added. The organic layer was washed successively with 5 mL of water and 5 mL of brine, dried with $Na_2SO_4$, filtered and concentrated in vacuo to give yellowish oil. The crude was purified by preparative LC (silica gel, mobile phase: gradient from DCM/EtOAc 100/00 to 90/10) to give 0.189 g (28%) of intermediate (G288) as yellow solid.

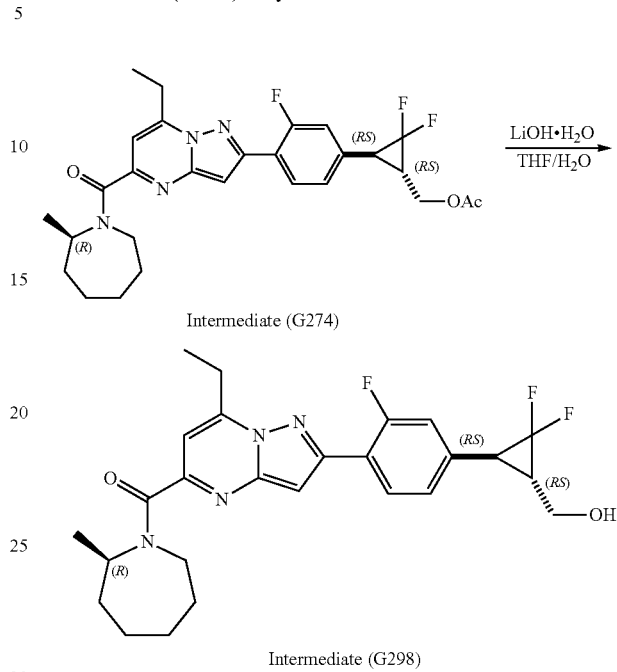

Intermediate (G274)

Intermediate (G298)

Intermediate (G298):

A mixture of intermediate (G274) (370 mg; 0.700 mmol) and $LiOH \cdot H_2O$ (25 mg; 1.1 mmol) in THF (7 mL) and $H_2O$ (3 mL) was stirred at rt for 1 h. Water and EtOAc were added and the layers were separated. The aqueous layer was extracted with EtOAc (once). The combined organic layers were washed with brine, dried over $MgSO_4$, filtered and the solvent was removed in vacuo to give 345 mg of intermediate (G298).

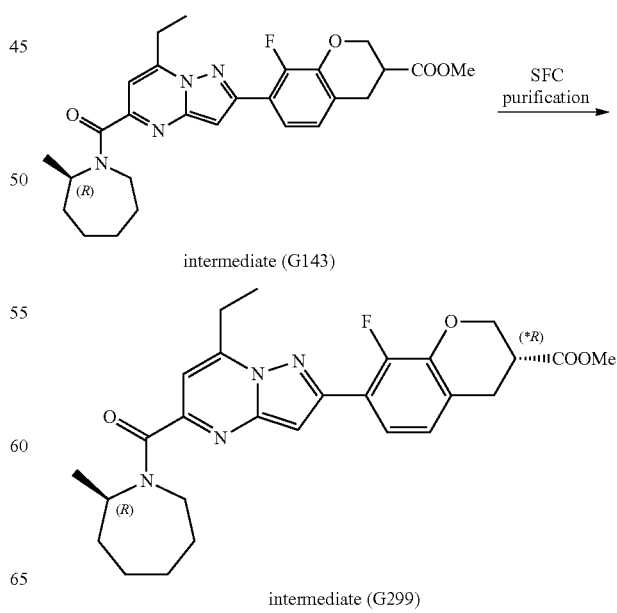

intermediate (G143)

intermediate (G299)

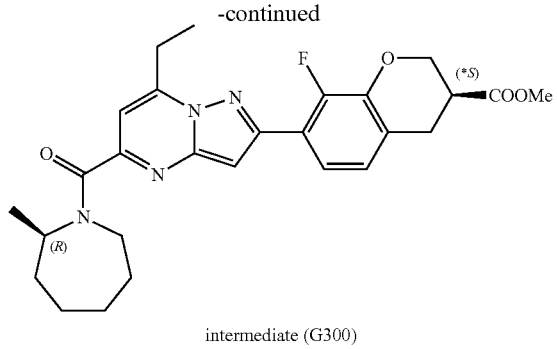

intermediate (G300)

Intermediates (G299) and (G300):

A purification of 0.682 g of intermediate (G143) was performed via chiral SFC (Stationary phase: Whelk® O1 (S,S) 5 μm 250*21.1 mm, Mobile phase: 45% CO₂, 55% MeOH). Pure fractions were collected and evaporated to give 0.26 g of intermediate (G299) as a white powder and 0.237 g of intermediate (G300) as a white powder.

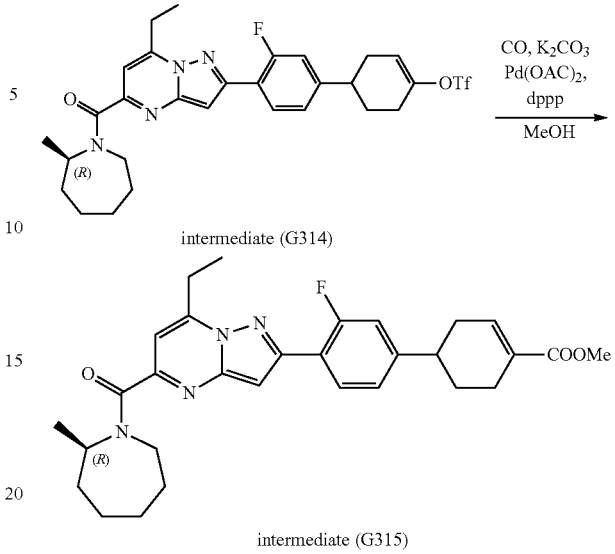

intermediate (G314)

intermediate (G315)

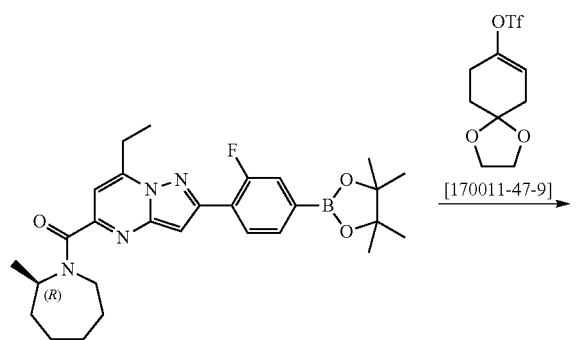

intermediate (G30)

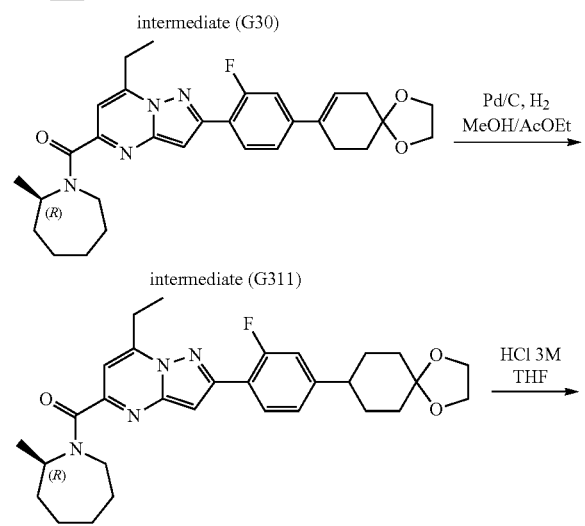

intermediate (G311)

intermediate (G312)

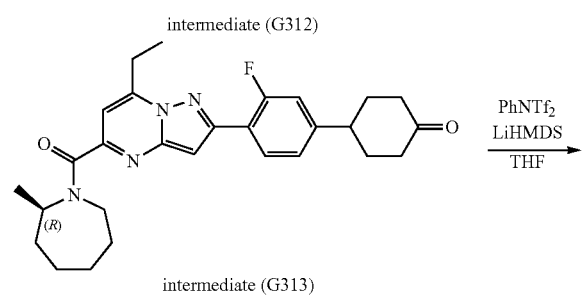

intermediate (G313)

Intermediate (G311):

A solution of intermediate (D30) (500 mg; 0.721 mmol), 1,4-dioxaspiro[4.5]dec-7-en-8-yl trifluoromethanesulfonate (249 mg; 0.865 mmol) and K₃PO₄ (459 mg; 2.16 mmol) in 1,4-dioxane (10 mL) and water (3 mL) was purged by N₂ bubbling for 10 min before the addition of PdCl₂dtbpf (47 mg; 72.1 μmol). The resulting mixture was purged by N₂ bubbling, then heated at 80° C. using a single mode microwave (Biotage® Initiator EXP 60) with a power output ranging from 0 to 400 W for 30 minutes. The mixture was poured into DCM, washed with water (twice), brine, dried over MgSO₄, filtered and evaporated in vacuum. The compound was purified by preparative LC (Irregular SiOH 15-40 μm, 25 g Grace®, liquid loading (DCM), mobile phase gradient: from Heptane/EtOAc 100:0 to 60:40. The fractions containing product were combined and the solvent was removed in vacuum to give 385 mg (44%) of intermediate (G311).

Intermediate (G312):

Pd/C 10% (80 mg; 75.2 μmol) was added to a degassed solution of intermediate (G311) (383 mg; 0.738 mmol) in MeOH (6 mL) and AcOEt (6 mL). The resulting mixture was hydrogenated at rt under 1 bar overnight. EtOAC was added and the mixture was filtered through a pad of Celite®, the filtrate was concentrated until dryness to give 385 mg (quant.) of intermediate (G312) as a off-white foam.

Intermediate (G313):

A mixture of intermediate (G312) (363 mg; 0.697 mmol) in HCl 3M (2 mL) and THF (2 mL) was stirred at 50° C. for 2 days. HCl 3M (2 mL) and THF (2 mL) were added and the mixture was stirred at 50° C. for 4 days. Water was added and the mixture was extracted with Et₂O (twice). The combined organic layers were washed with an aqueous solution of NaHCO₃ (once) and water (twice), then dried over MgSO₄, filtered, concentrated and purified by preparative LC (Irregular SiOH 30 μm, 40 g Grace®, liquid loading (DCM), mobile phase gradient: from Heptane/EtOAc 100:0 to 50:50). The fractions containing product were combined and the solvent was removed in vacuum to give 220 mg (66%) of intermediate (G313) as a white solid.

Intermediate (G314):

LiHMDS 1.5 M in THF (0.8 mL; 1.2 mmol) was added to a stirred solution of intermediate (G313) (220 mg; 0.462 mmol) and PhNTf$_2$ (430 mg; 1.2 mmol) in THF (10 mL) at −78° C. and under N$_2$. The resulting mixture was stirred at −78° C. for 4 h. The mixture was quenched by addition of water and extracted with EtOAc (twice). The combined organic layers were dried over MgSO$_4$, filtered and evaporated in vacuum to give 470 mg (quant.; purity 60%) of intermediate (G314) as a yellow solid. The product was used as such in the next step.

Intermediate (G315):

A suspension of intermediate (G314) (470 mg; 0.463 mmol; purity 60%) and K$_2$CO$_3$ (77 mg; 0.556 mmol) in MeOH (4 mL) was degassed by N$_2$ bubbling for 15 min before the addition of Pd(OAc)$_2$ (10 mg; 44.5 μmol) and dppp (20 mg; 48.5 μmol). The resulting mixture was purged with CO (3×) then pressurised with CO (10 bar) and heated at 120° C. overnight. The mixture was filtered through a pad of Celite® and the celite was washed with EtOAc. Water was added and the organic layer was separated, washed with brine, dried over MgSO$_4$, filtered, concentrated and purified by preparative LC (Irregular SiOH 30 μm, 40 g Grace®, liquid loading (DCM), mobile phase gradient: heptane/AcOEt from 90:10 to 40:60) to give 134 mg (56%) of intermediate (G315) as white foam.

Intermediate (H)

Intermediate (H1)

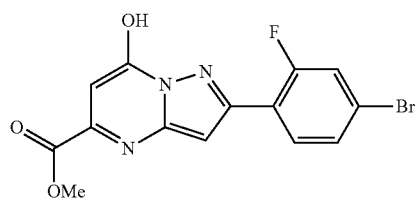

Intermediate (H1):

A mixture of 5-(4-bromo-2-fluorophenyl)-1H-pyrazol-3-amine, (10 g, 39 mmol) and dimethylacetylendicarboxylate (5.54 g, 39 mmol) in AcOH (250 mL) was stirred at RT for 6 hours. The solvent was evaporated and water was added to the residue. The precipitate was filtered off and dried to give 7.75 g (54%) of intermediate (H1).

The following intermediates were prepared according to the above procedure:

Intermediate (H2)

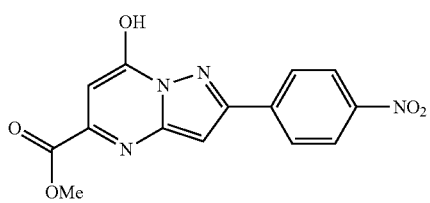

Intermediate (H3)

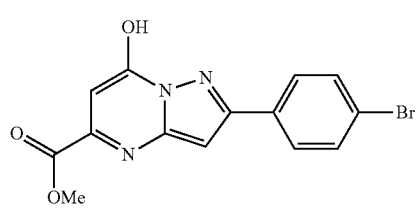

Intermediate (H4)

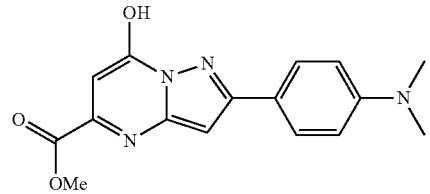

Intermediate (H5)

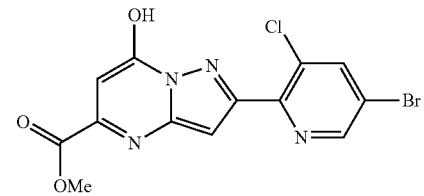

Intermediate (I)

Intermediate (I1)

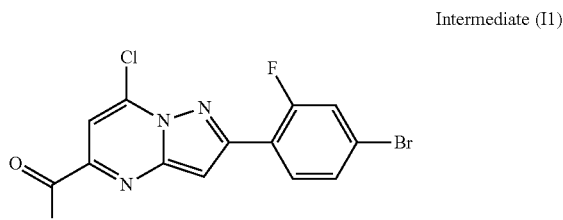

Intermediate (I1):

A suspension of intermediate (H1) (7.75 g, 21.1 mmol) in POCl$_3$ (100 mL) was heated at reflux for 12 hours. POCl$_3$ was evaporated and the residue was taken up in aqueous solution of Na$_2$CO$_3$. The solid was filtered off to give 8.23 g (quant.) of intermediate (I1).

The following intermediates were was prepared according to the above procedure:

Intermediate (I2)

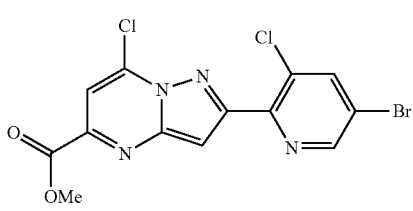

Intermediate (I3)

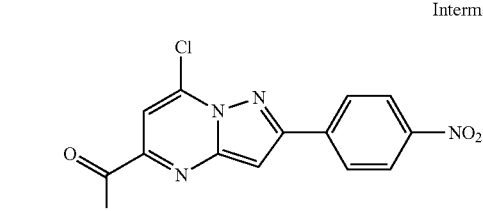

Intermediate (I3):

N,N-dimethylaniline (4.2 g, 34.7 mmol) was added to a suspension of intermediate (H2) (3.5 g, 11 mmol) in POCl$_3$ (90 mL) and the reaction mixture was heated at reflux for 12 hours. POCl$_3$ was evaporated and the residue was taken up in aqueous solution of Na$_2$CO$_3$. The solid was filtered off to give 1.52 g (41%) of intermediate (I3).

Intermediate (14)

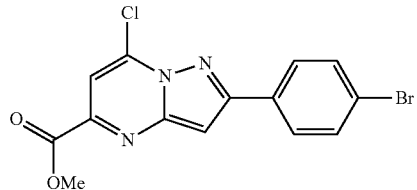

Intermediate (I4):
Intermediate (H$_3$) (1 g, 2.87 mmol) was heated at reflux in POCl$_3$ (10 mL) until it dissolved. After cooling down to RT, the reaction mixture was diluted with ether, then the precipitate was filtered off and washed with ether to give 0.45 g (40%) of intermediate (I4).

The following intermediate was prepared according to the above procedure:

Intermediate (15)

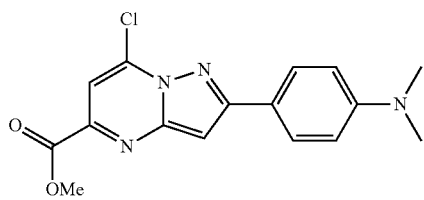

Intermediates (J), (K), (L), (M), (N), (O), (P), 0
First Approach

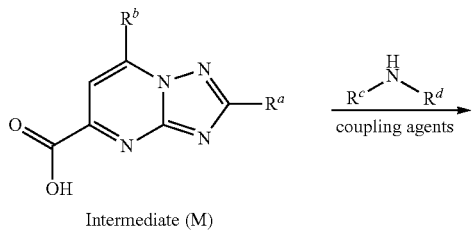

Intermediate (M)

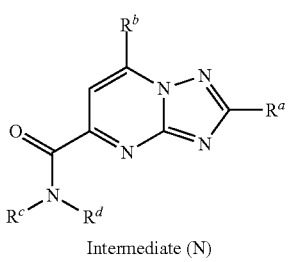

Intermediate (N)

Second Approach

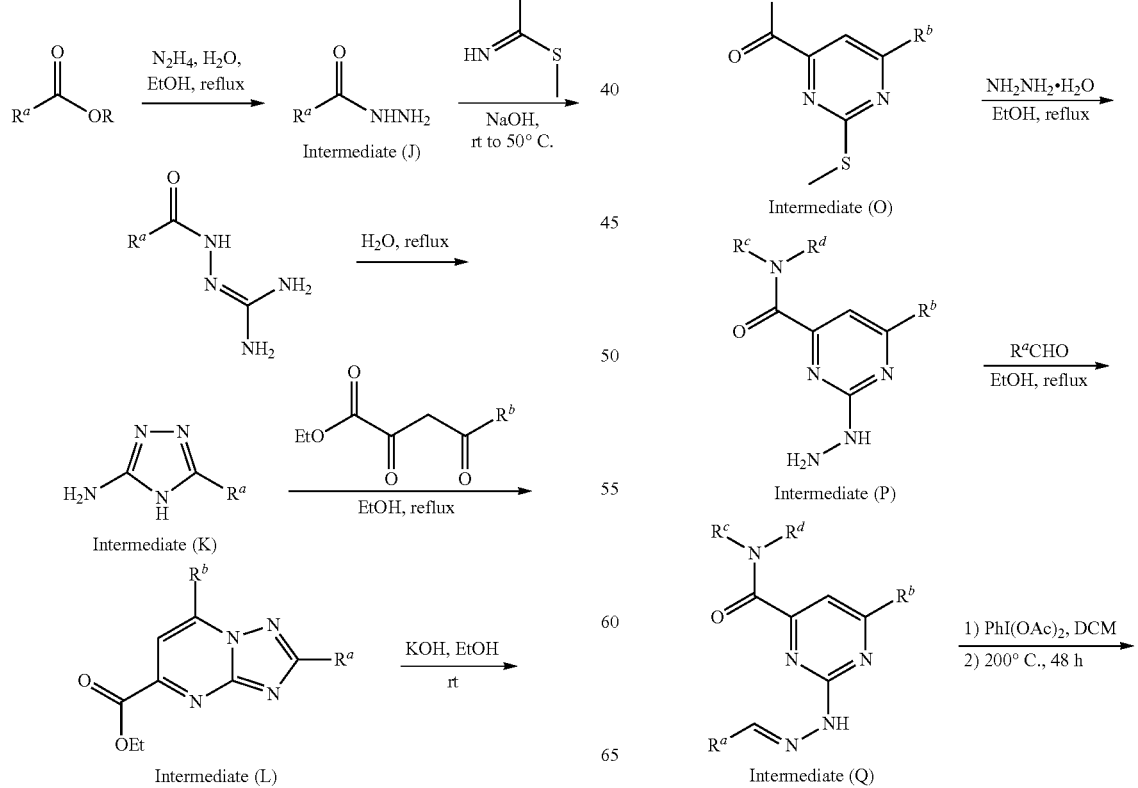

-continued

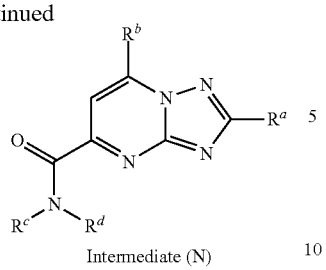

Intermediate (N)

Intermediate (J)

Intermediate (J1):

Hydrazine hydrate (5 mL, 0.12 mol) was added to a solution of 2-fluoro-4-nitro-benzoic acid methyl ester (10.5 g, 0.05 mol) in anhydrous EtOH (100 mL). The reaction mixture was heated at reflux for 4 hours. Then, the solvent was evaporated under reduced pressure and the crude intermediate (J1) was used without purification for the next step.

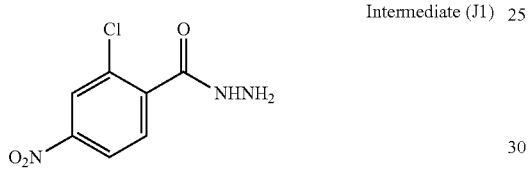

Intermediate (J1)

Intermediate (K)

Intermediate (K1): S-methylisothiouronium sulfate (7.0 g, 0.05 mol) was added to a solution of intermediate (J1) (0.05 mol) in NaOH (1% aqueous solution) (250 mL). The resulting mixture was stirred for 12 hours. The precipitate was filtered off, washed with ice-water and dried. The residue was dissolved in water and the reaction mixture was heated at reflux for 26 hours. The precipitate was filtered off, washed with ice-water and dried to give 2.5 g (21% by 2 steps) of intermediate (K1).

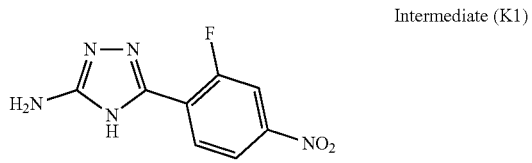 [SMILES: Nc1nnc(-c2ccc([N+](=O)[O-])cc2F)[nH]1]

Intermediate (K1)

Intermediate (L)

Intermediate (L1):

Ethyl 2,4-dioxohexanoate (1.9 g, 11.0 mmol) was added to a stirred solution of intermediate (K1) (2.5 g, 11.0 mmol) in anhydrous EtOH (50 mL). The reaction mixture was heated at reflux for 1 hour. The solvent was evaporated. The residue was purified by column chromatography (silica gel, DCM/EtOAc). The pure fractions were collected and the solvent was evaporated. The residue was purified by re-crystallization from EtOH to give 0.7 g (18%) of intermediate (L1).

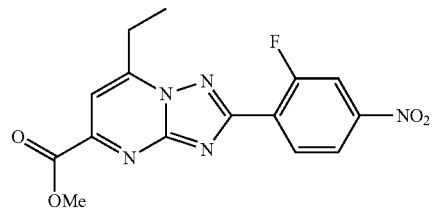

Intermediate (L1)

Intermediate (L2):

A mixture of 3-(2-thienyl)-1H-1,2,4-Triazol-5-amine (1.00 g, 6 mmol) and ethyl 2,4-dioxohexanoate (1.03 g, 6 mmol) in dry EtOH (50 mL) was heated at reflux for 2 hours. After cooling down to RT, the precipitate was filtered off and dried to give 0.7 g (39%) of intermediate (L2).

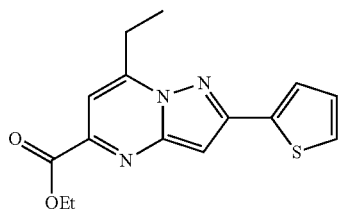

Intermediate (L2)

Intermediate (M)

Intermediate (M1):

KOH (0.22 g, 3.9 mmol) was added to a stirred solution of intermediate (L1) (0.7 g, 1.9 mmol) in EtOH (10 mL). The reaction mixture was stirred at RT for 1 hour. The solvent was evaporated and the residue was taken up with water and washed with ether. The aqueous layer was neutralized with HCl cc (0.35 mL) to pH 7. The precipitate was filtered off and dried to give 0.6 g (99%) of the intermediate (M1).

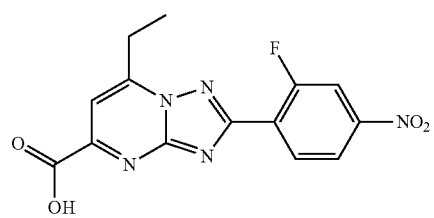

Intermediate (M1)

Intermediate (M2):

KOH (0.259 g, 4.6 mmol) was added to a solution of intermediate (L2) (0.70 g, 2.3 mmol) in EtOH (25 mL). The reaction mixture was stirred at RT for 1 hour. The solvent was evaporated, then the residue was taken up with water and washed with ether. The aqueous layer was neutralized with HCl cc to pH 7. The precipitate was filtered off and dried to give 0.56 g (88%) of intermediate (M2).

Intermediate (M2)

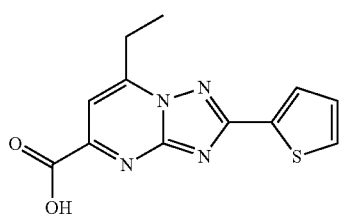

Reaction scheme:

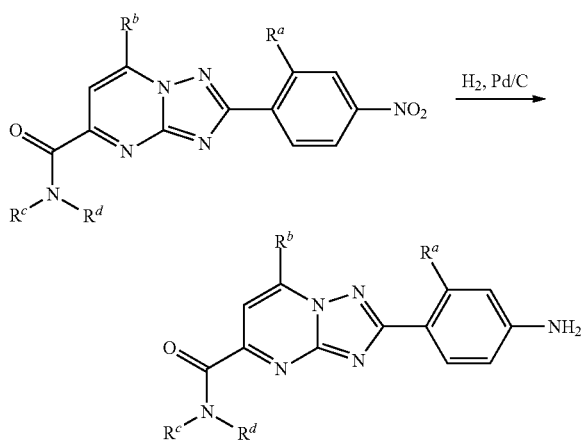

Intermediate (N)

Intermediate (N1): TBTU (0.68 g, 2.1 mmol) was added to a mixture of intermediate (M1) (0.6 g, 1.8 mmol), 2-methylazepane (0.24 g, 2.1 mmol) and DIEA (0.5 mL, 2.9 mmol) in DCM (50 mL). The reaction mixture was stirred at RT overnight. The reaction mixture was poured into water. The organic layer was separated, washed with brine, dried over sodium sulfate, filtered and evaporated. The residue was purified by column chromatography (silica gel, DCM). The pure fractions were collected and the solvent was evaporated to give 0.7 g (90%) of intermediate (N1).

Intermediate (N1)

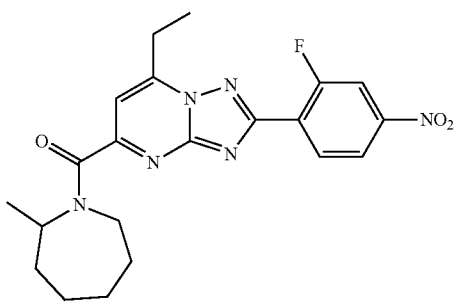

Intermediate (N2):
Intermediate (N1) (0.7 g, 1.6 mmol) was dissolved in MeOH (10 mL) and Pd/C (0.1 g) was added. The reaction mixture was shaken for 2 h at RT under hydrogen (1 bar). Then, the solution was filtered through a pad of Celite® to remove the catalyst and the filtrate was evaporated. The residue was purified by re-crystallization from EtOAc/ether to give 0.63 g (99%) of intermediate (N2).

Intermediate (N2)

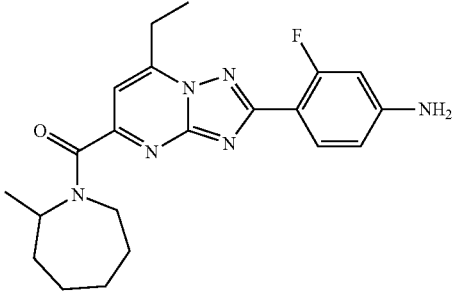

Intermediate (N3):
(diacetoxyiodo)benzene (7.27 g, 22.6 mmol) was added to a solution of intermediate (Q1) (8.70 g, 22.6 mmol) in dry DCM (100 mL) at 0° C. The reaction mixture was stirred at RT for 12 hours. The solvent was evaporated and the residue was purified by column chromatography (silica gel, EtOAc). The pure fractions were collected and the solvent was evaporated. The residue was heated at 200° C. for 48 hours. The crude product was purified by HPLC. The pure fractions were collected and the solvent was evaporated to give 1.2 g of intermediate (N3).

Intermediate (N3)

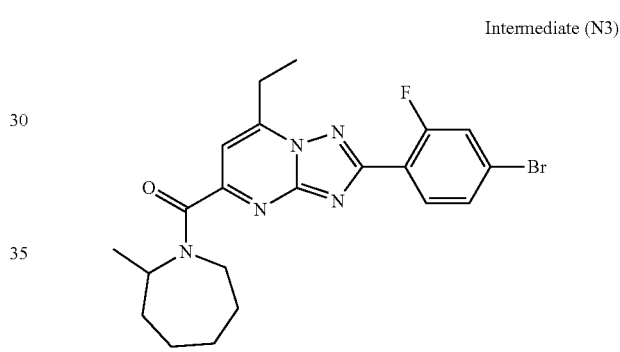

Intermediate (N4):
Pd(PPh$_3$)$_4$ (150 mg, 0.13 mmol) was added to a solution of intermediate (N3) (300 mg, 0.65 mmol), KCN (170 mg, 2.6 mmol) and CuI (10 mg) in anhydrous CH$_3$CN (5 mL). The reaction mixture was heated at 160° C. for 2 hours using one single mode microwave with a power output ranging from 0 to 400 W. The solvent was evaporated. The residue was purified by column chromatography (silica gel, DCM/EtOAc). The pure fractions were collected and the solvent was evaporated to give 170 mg (64%) of intermediate (N4).

Intermediate (N4)

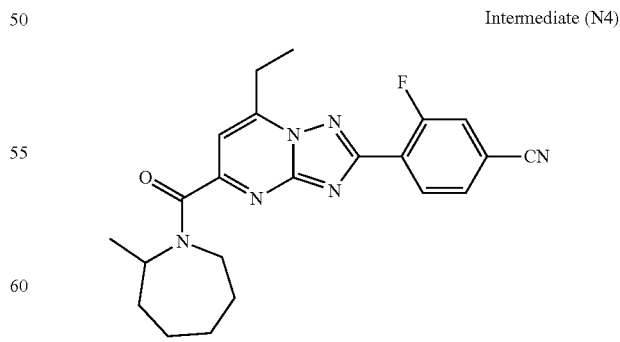

Intermediate (O)
Intermediate (O1):
The mixture of 6-ethyl-2-(methylthio)-4-pyrimidinecarboxylic acid (4.73 g, 23.9 mmol), BOP (11.79 g, 26 mmol) and DIEA (4.61 g, 36 mmol) and 2-methylazepane (2.97 g, 26 mmol) in dry DMF (25 mL) was stirred at RT for 6 hours. The solvent was evaporated, then the mixture was washed with water and extracted with CHCl₃. The residue was purified by column chromatography (silica gel, hexane/EtOAc (2/1)). The pure fractions were collected and the solvent was evaporated to give 5.55 g (79%) of intermediate (O1).

Intermediate (O1)

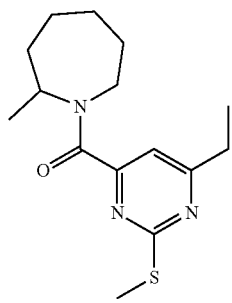

Intermediate (P)
Intermediate (P1):

The mixture of intermediate (O1) (5.55 g, 18.9 mmol) and hydrazine hydrate (50 mL) in EtOH (50 mL) was heated at reflux for 48 hours. The solvent was evaporated and the residue was purified by column chromatography (silica gel, THF). The pure fractions were collected and the solvent was evaporated to give 5.25 g (100%) of intermediate (P1).

Intermediate (P1)

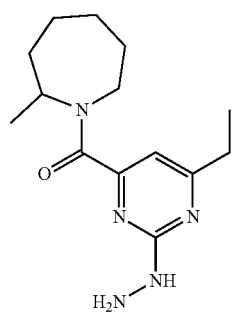

Intermediate (O)
Intermediate (Q1):

The mixture of intermediate (P1) (5.25 g, 19 mmol) and 2-fluoro-4-bromobenzaldehyde (3.84 g, 19 mmol) was heated at reflux for 12 hours. The solvent was evaporated to give 8.70 g (100%) of intermediate (Q1). The product was used without purification for the next step.

Intermediate (Q1)

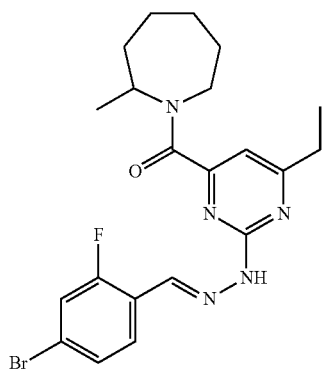

Intermediate (R):

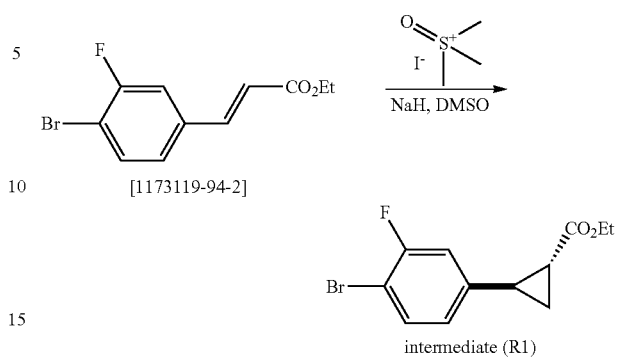

[1173119-94-2]

intermediate (R1)

Intermediate (R1):

Trimethylsulfoxonium iodide CAS [1774-47-6] (10.6 g; 48.3 mmol) was added to a mixture of NaH (60% dispersion in mineral oil) (1.9 g; 48 mmol) in DMSO (330 mL) at RT. The resulting mixture was stirred at RT for 20 min then (2E)-3-(4-bromo-3-fluorophenyl)-ethyl ester CAS [1173119-94-2] (11 g; 40 mmol) was added. The resulting mixture was stirred at RT for 24 hours then 60° C. for 24 hours. Water and EtOAc were added and the layers were separated. The aqueous layer was extracted with EtOAc (once). The combined organic layers were washed with brine, dried over MgSO₄, filtered and the solvent was removed in vacuum. The residue was triturated in EtOAc, filtered (the solid was discarded). The mother liquor was evaporated and purified by column chromatography (silica gel, from heptane/EtOAc 100/0 to 90/10). The pure fractions were collected and evaporated to give 3.45 g (30%) of intermediate (R1) as a mixture of trans isomers.

intermediate (R1)

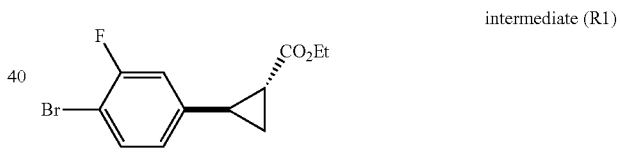

The following intermediate was prepared according to the above procedure:

intermediate (R3)

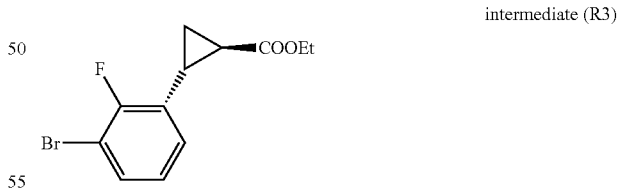

Reaction scheme:

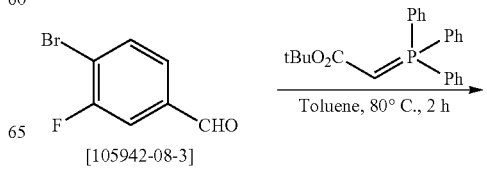

[105942-08-3]

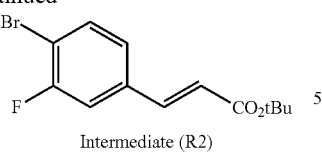

Intermediate (R2)

Intermediate (R2):

A mixture of 4-bromo-3-fluorobenzaldehyde CAS [105942-08-3](11.4 g; 56.2 mmol) and (tert-butoxycarbonylmethylene)triphenylphosphorane (25.4 g; 67.5 mmol) in dry toluene (100 mL) was stirred at 80° C. for 2 hours. Water was added and the layers were separated. The aqueous layer was extracted with EtOAc (twice). The combined organic layers were dried over MgSO$_4$, filtered and the solvent was removed in vacuum to give a white solid which was triturated in heptane and filtered (twice). The precipitate (PPh$_3$O) was discarded and the filtrate was evaporated to dryness to give crude compound. The solid was recrystallized in heptane, filtered and washed with heptane to give 5.4 g (32%) of intermediate (R2) as a white solid.

The following intermediates were prepared according to the above procedure:

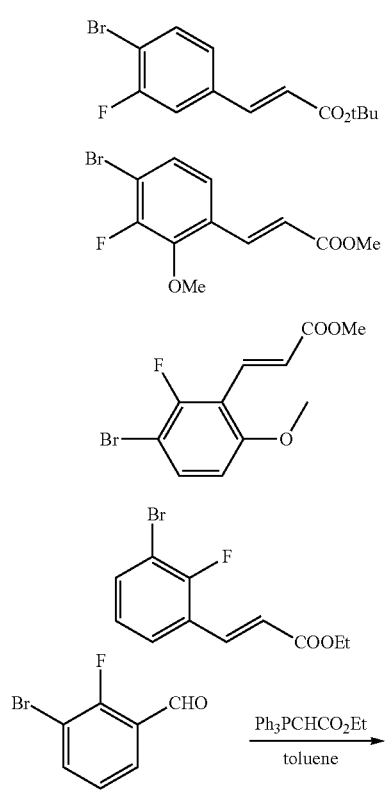

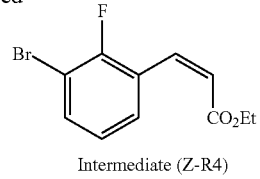

Intermediate (Z-R4)

Intermediate (E-R4)-(Z-R4):

(Carbethoxymethylene)-triphenylphosphorane (144 g; 414 mmol) was added portionwise to a mixture of 3-bromo-2-fluoro-benzaldehyde (70 g; 345 mmol) in toluene (700 mL) with temperature control (ice bath). Then the reaction mixture was stirred at 80° C. for 18 h. Water was added and the layers were separated. The aqueous layer was extracted with EtOAc (twice). The combined organic layers were dried over MgSO$_4$, filtered and the solvent was removed in vacuum to give a white solid. The solid was triturated in Et$_2$O and filtered. The solid was discarded (PPh$_3$O) and the filtrate was evaporated to dryness. The residue was purified by preparative LC (irregular SiOH, 15-40 μm, 1080 g (330 g+750 g), Grace Resolv®, liquid loading (Heptane), mobile phase gradient: from heptane/DCM 80/20 to 50/50) to give 93.5 g of a solid. The solid was purified again by preparative LC (irregular SiOH, 15-40 μm, 1500 g, Grace Resolv®, liquid loading (Heptane), mobile phase gradient: from heptane/DCM 80/20 to 50/50) 42.5 g of a mixture of intermediate (E)-R4 and (Z)-R4 and 53.2 g (55%) of pure intermediate (E)-R4. 28.8 g of mixture of intermediates (E)-R4 and (Z)-R4 were purified via achiral SFC (Stationary phase: Chiralcel® OD-H 5 μm 250*30 mm, Mobile phase: 90% CO$_2$, 10% iPrOH) to give 4.37 g (5%) of pure intermediate (Z)-R4 and 22.0 g (23%) of intermediate (E)-R4 as a colorless oil.

Intermediate (R9):

A mixture of intermediate R$^1$ (6.60 g; 21.8 mmol) and LiOH.H$_2$O (2.75 g; 65.5 mmol) in THF (100 mL) and H$_2$O (50 mL) was stirred at rt for 18 h. An aqueous solution of KHSO$_4$ (10%) and EtOAc were added to the reaction mixture and the organic layer was separated. The aqueous layer was extracted with EtOAc (twice). The combined organic layers were dried over MgSO$_4$, filtered and evaporated in vacuum. The residue was purified by preparative LC (irregular SiOH 15-40 μm, 120 g GraceResolv®, dry loading (SiOH), mobile phase gradient: from heptane/EtOAc/AcOH 90/10/0.25 to 60/40/1) to give 4.00 g (71%) of intermediate (R9) as a white solid.

intermediate (R9)

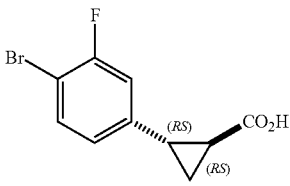

Intermediate (R10):

A mixture of intermediate (R9) (4.0 g; 15.4 mmol), L-menthol (2.90 g; 18.5 mmol), COMU® (9.92 g; 23.2 mmol) and DIEA (corrected) (8.0 mL; 46 mmol) in DMF (150 mL) was stirred at rt overnight. H$_2$O and 50 mL of HCl 1M were added and the mixture was extracted with EtOAc (3 times). The combined organic layers were dried over MgSO$_4$, filtered and evaporated in vacuum. The residue was dissolved in DMF (100 mL) and L-menthol (2.90 g; 18.5 mmol), COMU® (9.92 g; 23.2 mmol) and DIEA (8.0 mL; 46 mmol) were added and stirred at rt overnight. Brine was added and the mixture was extracted with EtOAc (3 times). The combined organic layers were dried over MgSO$_4$, filtered and evaporated in vacuum. The residue was purified by preparative LC (irregular SiOH 15-40 µm, 220 g Graceresolv®, liquid loading (DCM), mobile phase gradient: from Heptane/EtOAc/AcOH 98/2/0.625 to 60/40/1). The fractions containing product were combined and the solvent was removed in vacuo to give 4.2 g of a mixture of 2 diastereomers as colorless oil. The mixture was purified via chiral SFC (Stationary phase: CHIRALPAK® IC 5 µm 250×30 mm, Mobile phase: 93% CO$_2$, 7% iPrOH) to give 2.23 g of first diastereomer intermediate (R10') (*S,*S) as a white solid and 1.98 g of a second diastereoisomer intermediate (R10) (*R,*R) as white solid.

Intermediate (R7):
19.9 g of intermediate (R9) were purified via chiral SFC (Stationary phase: Lux Cellulose® 2 5 µm 250*21.2 mm, Mobile phase: 80% CO$_2$, 20% iPrOH (1.0% iPrNH$_2$)) to give 10.9 g of the first diastereomer (*S,*S) and 12.7 g of the second diastereomer (*R,*R) intermediate (R7).

Intermediate (R8):
H$_2$SO$_4$ 98% (9.80 mL; 184 mmol) was added to a solution of intermediate (R7) (12.7 g; 36.8 mmol) in EtOH (170 mL) at rt. The reaction mixture was stirred at rt for 18 h. Then an aqueous solution of NaHCO$_3$, brine and EtOAc were added to the reaction mixture. The layers were separated. The aqueous layer was extracted with EtOAc (twice). The organic layer was dried over MgSO$_4$, filtered and dried to give 11.5 g (quant) of intermediate (R8).

Reaction scheme:

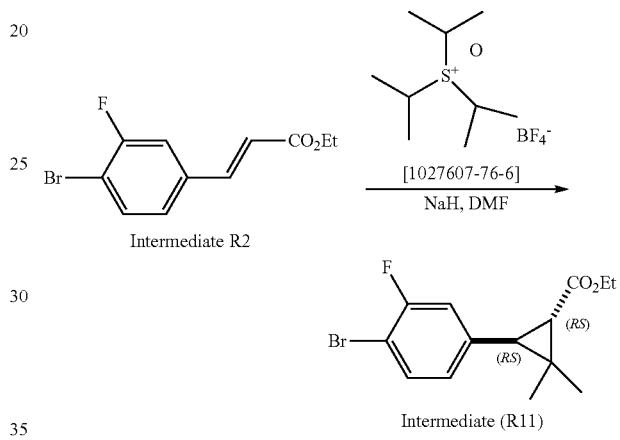

Intermediate (R11):
At 0° C., under N$_2$, NaH 60% (310 mg; 7.75 mmol) was added to a solution of tris-(1-methylethyl)-sulfoxonium (2.5 g; 7.57 mmol) in DMF (60 mL). The mixture was stirred for 15 min before the slow addition of intermediate R$^2$ (1.7 g; 6.23 mmol) in DMF (40 mL). The reaction mixture was stirred at rt for 42 h. Water was added dropwise. Then HCl 1M, brine and EtOAc were added. The layers were separated. The aqueous layer was extracted with EtOAc (twice). The combined organic layers were washed with brine, dried over MgSO$_4$, filtered, evaporated and purified by preparative LC (irregular SiOH 15-40 µm, 120 g Grace®, loading (DCM), mobile phase gradient: from Heptane/EtOAc 100/0 to 90/10 in 10 CV) to give 60 mg of intermediate (R11).

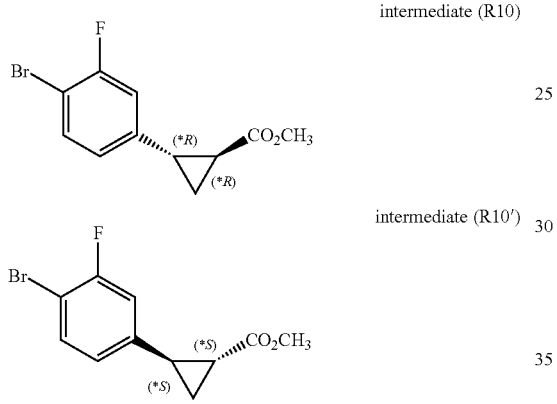

Reaction scheme:

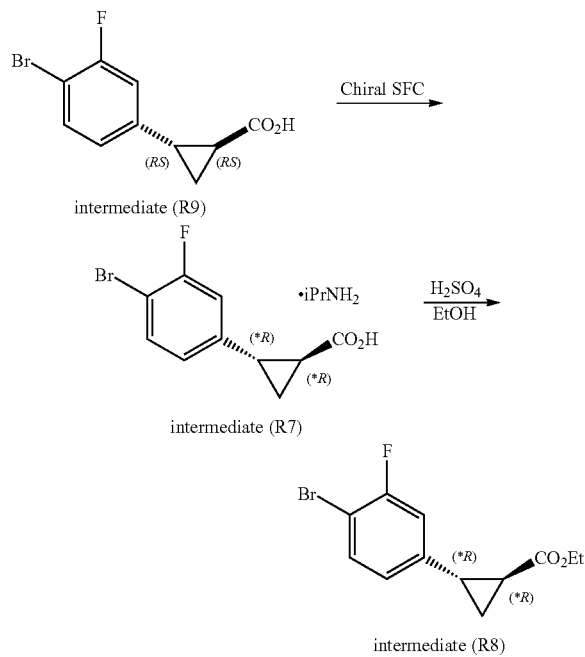

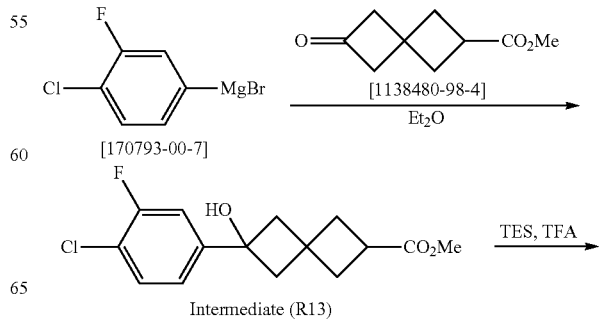

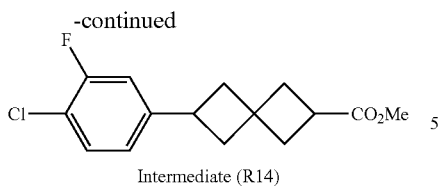

Intermediate (R14)

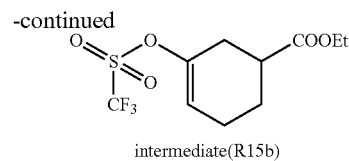

intermediate(R15b)

Intermediate (R13):
Under N$_2$ at 0° C., 4-chloro-3-fluorophenylmagnesium bromide 0.5M in THF (2 mL; 1 mmol) was added slowly (over about 7 min) to a solution of methyl 6-oxo-spiro[3.3]heptane-2-carboxylate (168 mg; 1 mmol) in dry Et$_2$O (10 mL). The mixture was stirred at 0° C. for 3 h. 10% aq. NH$_4$Cl was added and an extraction was performed with EtOAc. The organic layer was washed with brine, dried (MgSO$_4$), evaporated and purified by preparative LC (irregular SiOH 15-40 µm, 40 g Grace® Resolv, liquid loading (DCM), mobile phase gradient: from heptane/EtOAc from 100:0 to 0:100) to give 152 mg (50%) of intermediate (R13) as a colorless gum.

Intermediates (R15a/R15b):
LiHMDS 1.5 M in THF (0.41 mL, 617 µmol) was added to a solution of ethyl-3-oxocyclohexanecarboxylate (100 mg, 588 µmol) in THF (1.3 mL) at −78° C. The resulting mixture was stirred at −78° C. for 1 h before the addition of PhNTf$_2$ (220 mg, 617 µmol) in THF (1.3 mL). The mixture was stirred at −78° C. for 30 min and then allowed to warm to rt overnight. The mixture was quenched by addition of NH$_4$Cl sat. (0.86 mL) and the solvent was removed under vacuum. Et$_2$O and an aqueous solution of NaOH (0.3 M) were added and the layers were separated. The organic layer was washed with an aqueous solution of NaOH (0.3 M) (once), a saturated aqueous solution of NH$_4$Cl (once) and brine (once), dried over MgSO$_4$, filtered and concentrated in vacuum to give 143 mg of a mixture of intermediate (R15a) and intermediate (R15b) as yellow oil. The crude product was used without further purification in the next step.

intermediate (R13)

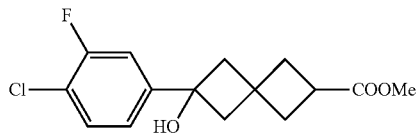

Intermediate (R14):
TFA (5 mL; 65.3 mmol) was added slowly at 0° C. to a mixture of Intermediate (R13) (2 g; 6.70 mmol) and TES (1.2 mL; 7.51 mmol) in DCM (40 mL). The mixture was stirred at 0° C. for 1 h and at rt for 3 h. NaOH 1N was added (until basic pH). The mixture was extracted with DCM. The organic layer was separated, washed with brine, dried (MgSO$_4$), evaporated and purified by preparative LC (irregular SiOH 15-40 µm, 120 g Grace® Resolv, liquid loading (DCM), mobile phase gradient: from heptane/EtOAc from 100:0 to 80:20) to give 1.01 g (53%) of intermediate (R14) as a colorless oil.

Reaction scheme:

intermediate (R14)

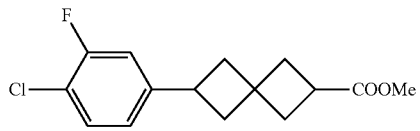

Reaction scheme:

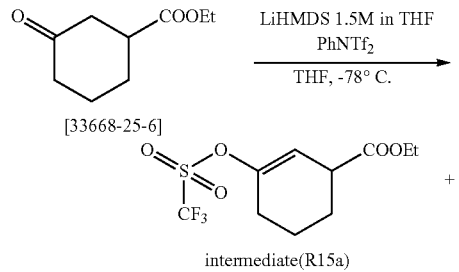

intermediate(R15a)

Intermediate (R17)

Intermediate (R18)

Intermediate (R17):
AcCl (0.28 mL; 4.0 mmol) was added dropwise to a mixture of 3-(4-bromo-3-fluorophenyl)-2-Propen-1-ol (0.84 g; 3.64 mmol) and TEA (1.0 mL; 7.3 mmol) in DCM (36 mL) and the mixture was stirred at rt for 4 h. An extra amount of AcCl (52 µL; 0.73 mmol) and DMAP (22 mg; 0.182 mmol) were added and the mixture was stirred at rt for 16 h. An extra amount of AcCl (0.13 mL; 1.8 mmol) was added and the mixture was stirred at rt for 48 h. The reaction was diluted with DCM and an aqueous solution of NaHCO$_3$ (10%). The aqueous layer was extracted with DCM (once). The combined organic layers were dried over MgSO$_4$, filtered and the solvent was removed in vacuo to give 983 mg of intermediate (R17).

Intermediate (R18):
Trimethylsilyl-(fluorosulfonyl)-difluoroacetate (2.2 mL; 11 mmol) in toluene (9 mL) was added dropwise over 6 h (with a syringe pump) to a mixture of intermediate (R17) (1.2 g; 4.4 mmol) and NaF (18 mg; 0.43 mmol) in toluene (8 mL) at 105° C. The resulting mixture was stirred at 105° C. for 16 h. An extra amount of Trimethylsilyl-(fluorosulfonyl)-difluoroacetate (2.2 mL; 11 mmol) in toluene (2 mL) was added dropwise over 4 h (with a syringe pump). The mixture was evaporated and purified by preparative LC (regular SiOH, 30 μm, 80 g Interchim®, liquid loading (DCM), mobile phase gradient: from heptane/toluene 50/50 to 0/100) to give 0.63 g (44%) of intermediate (R18).

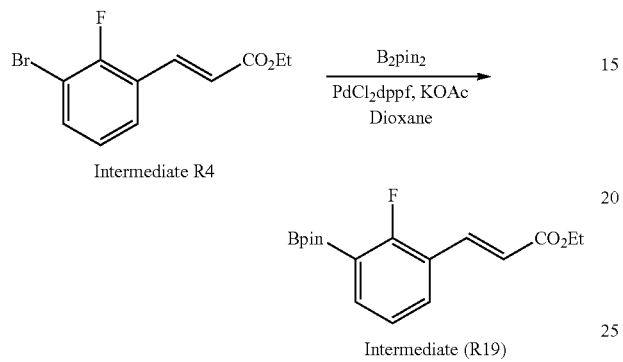

Intermediate (R19):

B₂pin₂ (0.560 g, 2.20 mmol) and KOAc (0.360 g, 3.66 mmol) were added to a solution of intermediate (R4) (0.500 g, 1.83 mmol) in dioxane (6 mL) at rt. The mixture was purged (twice) with argon and PdCl₂dppf (0.134 g, 0.183 mmol) was added. The mixture was purged again (twice) with argon and stirred at 100° C. for 16 h. The reaction mixture was quenched with H₂O and extracted with DCM (50 mL). The organic layer was dried (Na₂SO₄), filtered and concentrated under reduced pressure. The residue was purified by flash column chromatography (Regular SiOH; 50 μm, Interchim® 40 g, mobile phase gradient: from cyclohexane/EtOAc 98/02 to 50/50). The desired fraction was collected and evaporated in vacuo to give 0.850 g (100%) of intermediate (R19) as brown oil.

The following intermediate was prepared according to intermediate (R19):

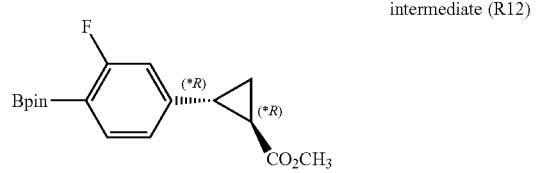

Intermediate (S):

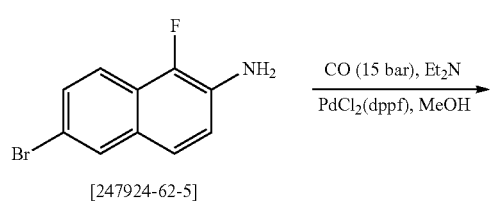

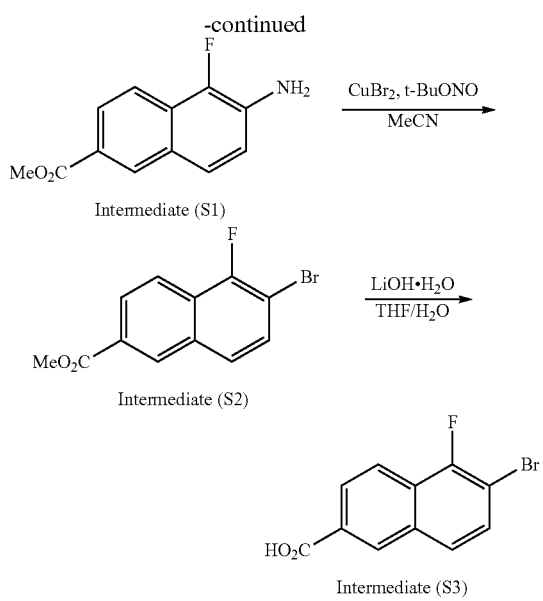

Intermediate (S1):

In a stainless-steel bomb, to a degassed mixture of 2-amino-6-bromo-1-fluoronaphtalene CAS [247924-62-5] (988 mg; 4.12 mmol) and Et₃N (1.4 mL; 10.1 mmol) in MeOH (28 mL) was added PdCl₂(dppf) (212 mg; 0.289 mmol). The resulting mixture was carbonylated under 15 bar of CO for 24 hours at 130° C. The mixture was cooled to RT and evaporated to dryness to give 1.91 g of crude product which was purified by column chromatography (silica gel, from heptane/EtOAc 80/20 to 50/50). The pure fractions were collected and evaporated to give 801 mg (89%) of intermediate (S1).

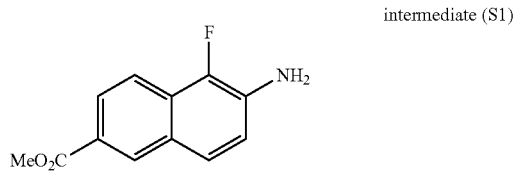 [SMILES: COC(=O)c1ccc2c(F)c(N)ccc2c1]

Intermediate (S2):

To a mixture of CuBr (1.15 g; 5.15 mmol) and t-butyl nitrite CAS [540-80-7] (613 μL; 5.15 mmol) in CH₃CN (45 mL) was added intermediate (S1) (753 mg; 3.44 mmol). The resulting mixture was stirred at 65° C. for 2 hours. Water was added and the mixture was extracted with EtOAc (twice). The combined organic layers were washed with brine, dried over MgSO₄, filtered and the solvent was removed in vacuum to give 870 mg of crude product which was purified by column chromatography (silica gel, from heptane/EtOAc 100/0 to 70/30). The pure fractions were collected and evaporated to give 350 mg (36%) of intermediate (S2).

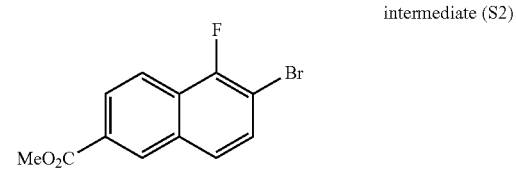 [SMILES: COC(=O)c1ccc2c(F)c(Br)ccc2c1]

Intermediate (S3):

A mixture of intermediate (S2) (350 mg; 1.24 mmol) and LiOH.H₂O (78 mg; 1.85 mmol) in THF (7 mL) and H₂O (3.5 mL) was stirred at RT for 64 hours. Water was added and the mixture was washed (twice) with DCM. The aqueous layer was acidified with 3N HCl and extracted with DCM (3 times). The combined organic layers were dried over MgSO$_4$, filtered and evaporated to dryness to give 337 mg (100%) of intermediate (S3).

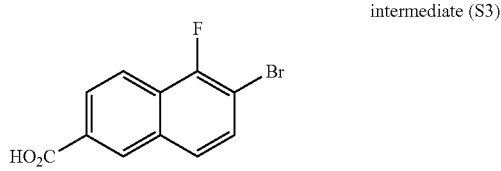 [SMILES: O=C(O)c1ccc2c(F)c(Br)ccc2c1]

intermediate (S3)

Reaction scheme:

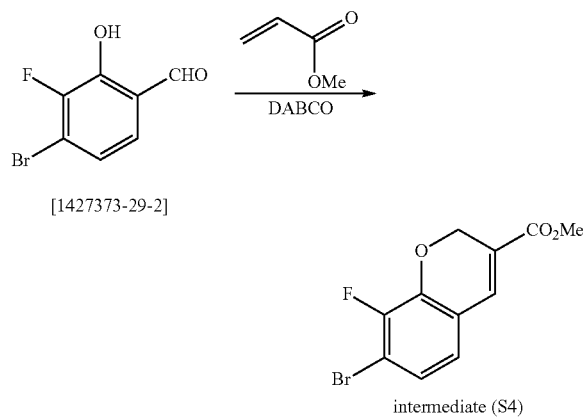

intermediate (S4)

Intermediate (S4):

A mixture of 4-bromo-3-fluoro-2-hydroxybenzaldehyde (2.8 g; 12.8 mmol), methyl acrylate ester (6.9 mL; 76.7 mmol) and 1,4-diazabicyclo[2.2.2]octane (287 mg; 2.56 mmol) was heated at 150° C. using a singlemode microwave (Biotage® initiator60) with a power output ranging from 0 to 400 W for 45 minutes. The reaction mixture was concentrated to dryness. Water and brine were added and the aqueous layer was extracted with DCM (twice). The organic layer was dried over MgSO$_4$, filtered and concentrated to give crude product which was purified by column chromatography (silica gel, from heptane/EtOAc: 95/5 to 50/50) to give 1.23 g (30%) of intermediate (S4) as a white solid.

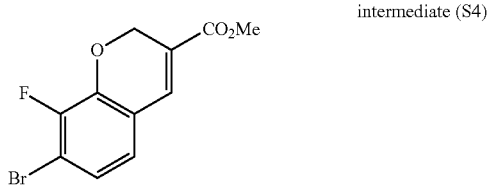 [SMILES: COC(=O)C1=Cc2ccc(Br)c(F)c2OC1]

intermediate (S4)

Reaction scheme:

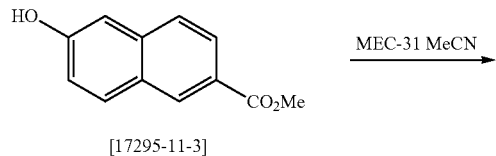

MEC-31 MeCN

[17295-11-3]

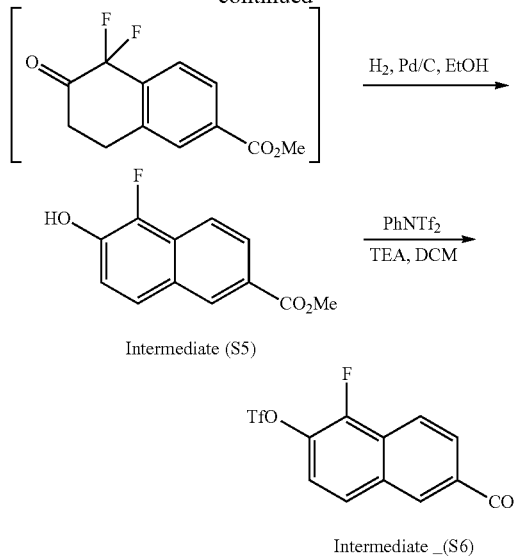

Intermediate (S5):

1,1'-Difluoro-2,2'-bipyridinium bis(tetrafluoroborate) (MEC-31) CAS[178439-26-4] (6.5 g; 18 mmol) was added to a solution of 6-methoxy carbonyl-2-naphthol [17295-11-3] (3.0 g; 15 mmol) in CH$_3$CN (75 mL). The reaction mixture was stirred at 70° C. for 5 h. An aqueous solution of HCl (1N) and DCM were added and the precipitate was filtered off. The filtrate was decanted and the aqueous layer was extracted with DCM (once). The combined organic layers were washed with brine, dried over MgSO$_4$, filtered and the solvent was removed in vacuo to give 3.7 g of difluoro intermediate as an orange solid. Difluoro intermediate was hydrogenated in EtOH (147 mL) with Pd/C (10%) (971 mg) as catalyst at rt under 1 bar of hydrogen for 16 h. The mixture was filtered over celite and the cake was rinsed with EtOH. The filtrate was evaporated to dryness and was purified by preparative LC (regular SiOH, 30 μm, 80 g Interchim®, dry loading, mobile phase gradient: from heptane/EtOAc 100/0 to 60/40) to give 328 mg of intermediate (S5) and 2.2 g of a mixture of CAS [17295-11-3] and intermediate (S5) (25:75).

Intermediate (S6):

N-phenyltrifluoromethanesulfonimide (672 mg; 1.88 mmol) and Et$_3$N (328 μL; 2.37 mmol) were added to a solution of intermediate (S5) (345 mg; 1.57 mmol) in DCM (4.5 mL) at rt and the reaction mixture was stirred at rt for 16 h. Then an aqueous solution of HCl (1M) was added. The aqueous layer was extracted with DCM (once). The organic layer was washed with an aqueous saturated solution of NaHCO$_3$, then with brine, dried over MgSO$_4$, concentrated and purified by preparative LC (irregular SiOH, 15-40 μm, 12 g Grace Resolve®, dry loading (on Celite®), mobile phase gradient: from Heptane/EtOAc 90/10 to 40/60) to give 590 mg (87%) of intermediate (S6) as a colorless oil which crystallized on standing.

Reaction scheme:

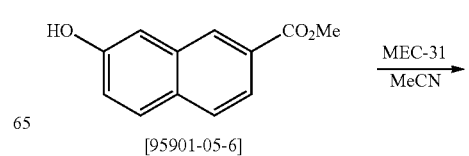

MEC-31 MeCN

[95901-05-6]

-continued

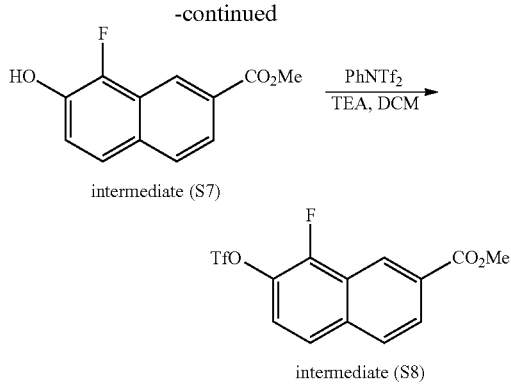

intermediate (S7)

intermediate (S8)

Intermediate (S7)

In a Schlenck tube, MEC-31 CAS [178439-26-4] (2 g; 5.52 mmol) was added to a solution of 7-hydroxy-2-naphthalenecarboxylic acid methyl ester (1 g; 4.60 mmol) in CH$_3$CN (23 mL). The reaction mixture was stirred at 70° C. for 16 hours. The reaction mixture was concentrated, water and an aqueous saturated solution of NaHCO$_3$ were added, and the aqueous layer was extracted with DCM (3 times). The organic layer was dried over MgSO$_4$ and concentrated. The residue was purified by preparative LC (irregular SiOH, 15-40 μm, 10 g Merck®, dry loading (on SiOH), mobile phase gradient: from Heptane/EtOAc 90/10 to 40/60) to give 175 mg of pure intermediate (S7) (17%) as a white solid and 748 mg of impure intermediate (S7) as a yellow oil (purity 55%).

intermediate (S7)

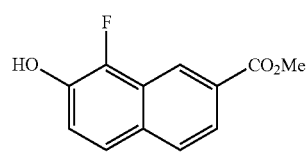

Intermediate (S8):
The formation of intermediate (S8) followed the same procedure than intermediate (S6).

intermediate (S8)

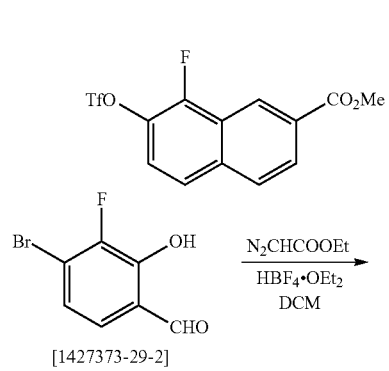

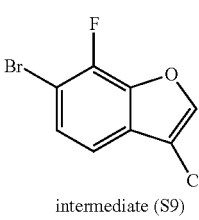

intermediate (S9)

Intermediate (S9):

Ethyl diazoacetate (1.15 mL, 11.0 mmol) was added dropwise to a solution of 4-bromo-3-fluorosalicylaldehyde (0.400 g, 1.83 mmol) and tetrafluoroboric acid diethyl ether complex (0.050 mL, 0.37 mmol) in DCM (4 ml) at rt. After 2 h, the solvent was evaporated and concentrated H$_2$SO$_4$ (0.6 ml) was added. After 10 min, the reaction mixture was diluted with 10 mL of DCM and neutralized with saturated aqueous NaHCO$_3$ (10 ml). The solution was extracted with DCM (2×20 mL). The combined organic layers were dried over Na$_2$SO$_4$, filtered and concentrated under reduced pressure to give a yellow oil. The crude was purified by preparative LC (irregular SiOH, 40-63 μm, Fluka® mobile phase gradient: from pentane/EtOAc 100/00 to 90/10) to give 0.190 g (38%) of intermediate (S9) as white solid.

Intermediate (S)

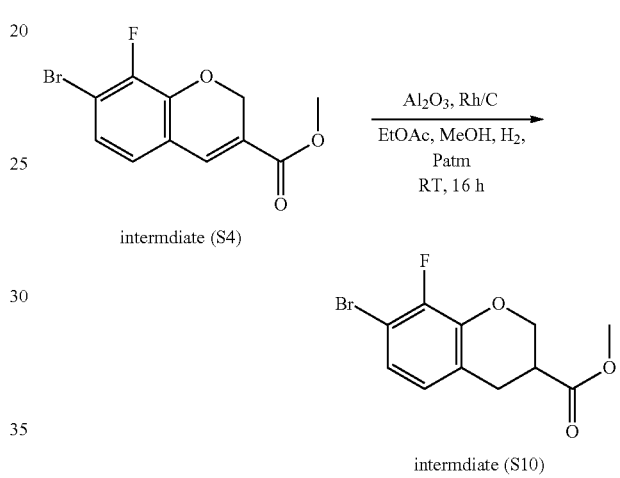

intermdiate (S4)

intermdiate (S10)

Intermediate (S10):

To a solution of intermediate (S4) (0.237 g; 0.83 mmol) in EtOAc (9.5 mL) and MeOH (1.6 mL) degassed with N$_2$, were added Al$_2$O$_3$ (0.0051 g; 0.05 mmol) and Rhodium on activate charcoal (0.085 g, 0.041 mmol) and the mixture was hydrogenated under an atmospheric pressure of H$_2$ at room temperature for 16 h. The solution was filtered off on a pad of Celite® and the solvent was removed under reduced pressure to give 0.219 g (92%) of intermediate (S10) as colorless oil which crystallized on standing.

intermediate (S10)

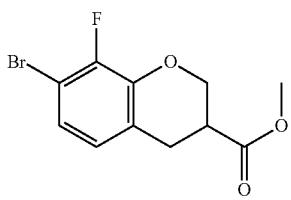

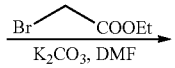

217

-continued

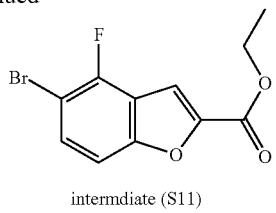

intermdiate (S11)

Intermediate (S11):

Ethyl bromoacetate (0.33 ml, 2.97 mmol) was added to a solution of 3-bromo-2-fluoro-6-hydroxy-benzaldehyde (0.5 g, 2.28 mmol) and $K_2CO_3$ (0.63 g, 4.57 mmol) in DMF (5 ml) at room temperature. The reaction mixture was heated at 120° C. for 1.5 h, cooled to room temperature and filtered through a short pad of Celite®. The filtrate was acidified to pH 2 with HCl 3N and the solution was extracted with DCM (2×25 ml). The combined organic layers were dried over $Na_2SO_4$, filtered and concentrated under reduced pressure. The crude was purified by column chromatography (silica gel, mobile phase pentane/EtOAc 100/00 to 90/10) to give after evaporation 0.252 g (38%) of intermediate (S11) as white solid.

intermediate (S11)

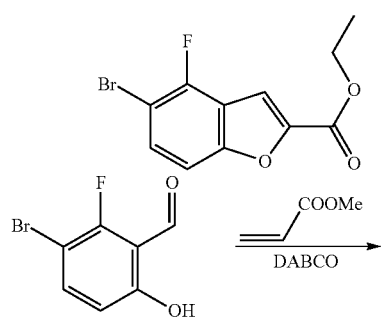

Intermediate (S12):

Methyl acrylate (1.96 ml, 21.9 mmol) and DABCO (0.082 g, 0.730 mmol) were added to 3-bromo-2-fluoro-6-hydroxy-benzaldehyde (0.850 g, 3.65 mmol) at rt. The reaction mixture was stirred at 150° C. for 45 minutes using a singlemode microwave (Biotage initiator60) with a power output ranging from 0 to 400 W. The reaction mixture was concentrated to dryness. The residue was purified by column chromatography (silica gel, mobile phase cyclohexane/EtOAc 98/02 to 50/50). The desired fraction was collected and evaporated in vacuo to give 0.230 g (22%) of intermediate (S12) as a white powder.

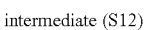
intermediate (S12)

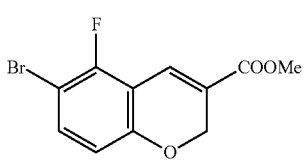

218

Intermediates (T):

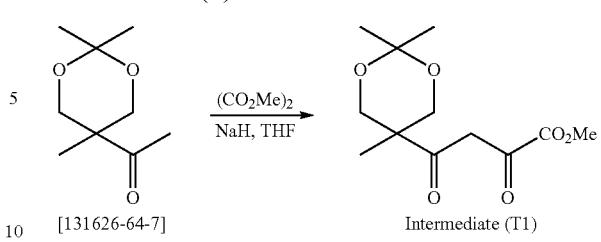

Intermediate (T1):

To a solution of 1-(2,2,5-trimethyl-1,3-dioxan-5-yl)-ethanone (8.4 g, 48.8 mmol) in THF (84 ml) was added NaH 60% in mineral oil (2.9 g, 73.2 mmol) and the resulting mixture was stirred at rt for 30 min. To the resulting reaction mixture was added dimethyl oxalate (8.6 g, 73.2 mmol) and the mixture was heated at reflux for 2 h. After cooling to rt the mixture was quenched with saturated aqueous $NH_4Cl$ (50 ml), extracted with EtOAc (3 times), dried over $Na_2SO_4$, filtered and concentrated under reduced pressure. The crude was purified by column chromatography (silica gel, mobile phase: pentane/EtOAc 90/10) to give 4 g (32%) of intermediate (T1) as an orange oil.

The following intermediate was prepared according to intermediate (T1):

intermediate (T2)

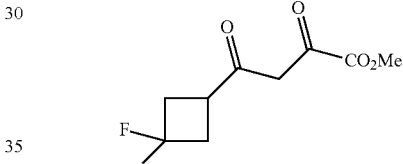

Intermediates (U):

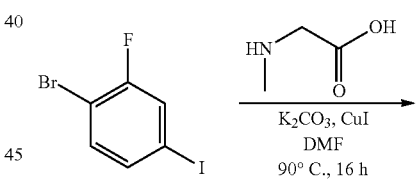

Intermediate (U1):

A solution of 1-Bromo-2-fluoro-4-iodobenzene (0.5 g, 1.66 mmol), Sarcosine (0.37 g, 4.15 mmol), $K_2CO_3$ (0.23 g, 1.66 mmol) and CuI (0.063 g, 0.33 mmol) in DMF (13 mL) was purged with $N_2$ flow for 5 min and then stirred and heated at 90° C. overnight. The solution was cooled down to room temperature. Water was added and the aqueous layer was acidified with HCl 3N. The organic layer was extracted with EtOAc, washed with water, dried over $MgSO_4$, filtered and evaporated to give 0.41 g (94%) of intermediate (R5) as an orange oil.

intermediate (U1)

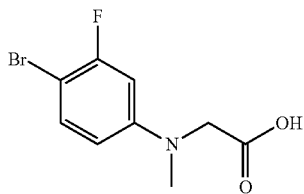

Reaction scheme:

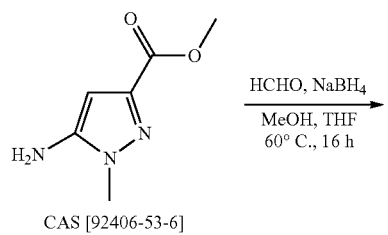

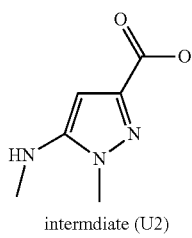

intermdiate (U2)

Intermediate (U2):

Formaldehyde (1.51 mL, 20.11 mmol) was added to a solution of Methyl 5-amino-1-methyl-1H-pyrazole-3-carboxylate (0.78 g, 5.03 mmol) in MeOH (8 mL) and THF (8 mL) at room temperature and the solution was stirred 1 hour at room temperature. Then sodium borohydride (0.95 g, 25.14 mmol) was added and the mixture was stirred at 60° C. overnight. The mixture was poured out into ice, the organic layer was extracted with CH$_2$Cl$_2$, dried over MgSO$_4$, filtered off and evaporated till dryness to give 0.218 g (22%) of intermediate (U2).

intermediate (U2)

Reaction scheme:

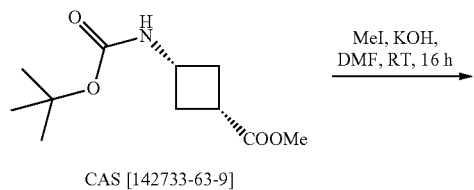

CAS [142733-63-9]

intermediate (U3)

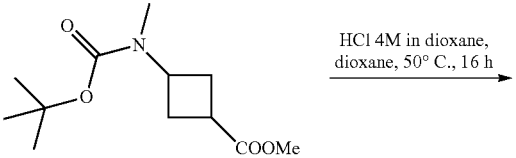

intermediate (U3)

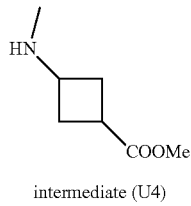

intermediate (U4)

Intermediate (U3):

A solution of methyl cis-3-(Boc-amino)-cyclobutanecarboxylate (0.95 g, 4.14 mmol), MeI (0.28 mL, 4.56 mmol) and KOH (0.26 g, 4.56 mmol) in DMF (32 mL) was stirred at room temperature overnight. Then the solution was diluted with EtOAc. The organic layer was washed with water (4×) then brine, dried over MgSO$_4$ and concentrated under reduced pressure. DMF (32 mL) was added to the residue and then iodomethane (0.28 mL, 4.56 mmol) and KOH (0.26 g, 4.56 mmol) were added, the resulting solution was stirred at room temperature overnight. Then the solution was diluted with EtOAc. The organic layer was washed with water (4×) then brine, dried over MgSO$_4$ and concentrated under reduced pressure to give 0.636 g (54%) of intermediate (U3) as colorless oil.

intermediate (U3)

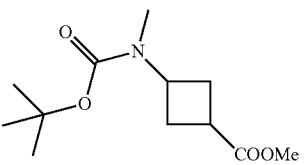

Intermediate (U4):

HCl 4M in dioxane (10.29 mL, 41.15 mmol) was added to a solution of intermediate (U3) (0.589 g, 2.06 mmol) in 1,4-dioxane (35.2 mL) at room temperature and the solution was stirred overnight at 50° C. The solution was concentrated under reduce pressure affording 0.436 g (94%) of intermediate (U4) as a colorless oil.

intermediate (U4)

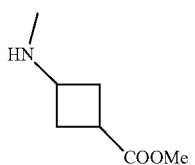

Reaction scheme:

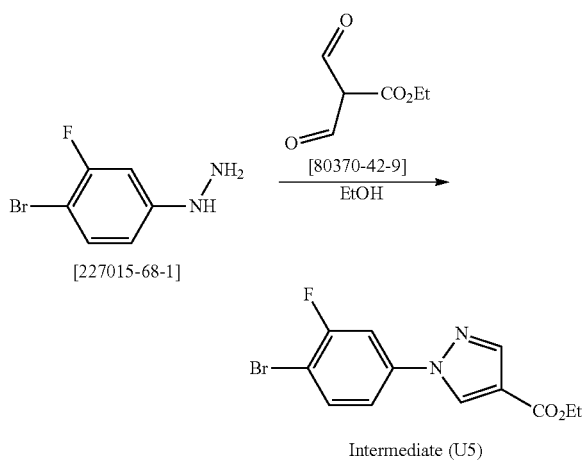

Intermediate (U5)

Intermediate (U5):

In a sealed tube, (4-bromo-3-fluorophenyl)-hydrazine (931 mg; 4.54 mmol) was added at 0° C. to a solution of ethyl 2-formyl-3-oxopropanoate (654 mg; 4.54 mmol) in EtOH (3.8 mL). The reaction mixture was stirred at rt for 18 hours. The solid was filtered off, washed with EtOH and dried on frit to give 1.21 g (85%) of intermediate (U5) as a pale orange solid.

Reaction scheme:

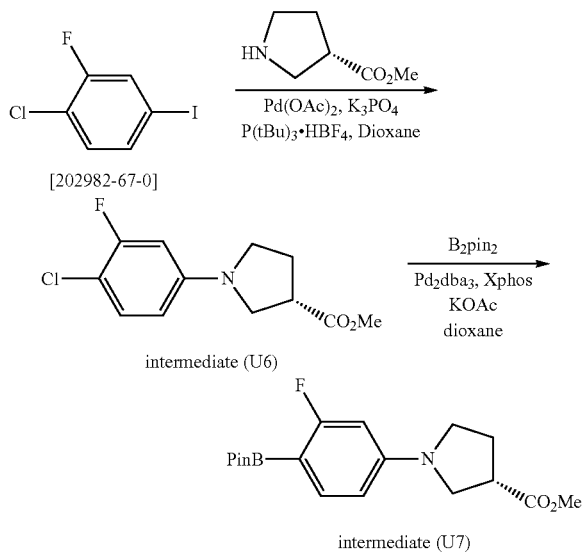

intermediate (U6)

intermediate (U7)

Intermediate (U6):

In a Schlenk tube, a solution of 4-Chloro-3-fluoroiodobenzene (7.3 g, 28.4 mmol), $K_3PO_4$ (16.1 g, 75.9 mmol), (S)-methylpyrrolidine-3-carboxylate hydrochloride (3.1 g, 19.0 mmol) and $P(tBu)_3 \cdot HBF_4$ (551 mg, 1.90 mmol) in dioxane (150 mL) was purged with $N_2$ (3×). $Pd(OAc)_2$ (213 mg; 0.95 mmol) was added and the reaction mixture was stirred at 100° C. for 16 h, then cooled down to rt. The mixture was diluted with EtOAc and water. The layers were separated. The aqueous layer was extracted with EtOAc (twice). The combined organic layers were washed with brine, dried over $MgSO_4$, filtered and the solvent was removed under reduced pressure. The residue was purified by preparative LC (irregular SiOH, 15-40 μm, 220 g Grace®, liquid injection (Heptane), mobile phase gradient: from Heptane 100%, to heptane 70%, EtOAc 30%) to give 1.91 g (37%) of intermediate (U6) as an orange oil.

Intermediate (U7):

A mixture of intermediate (U6) (3.88 g; 8.28 mmol; 55%), $B_2pin_2$ (3.15 g; 12.4 mmol) and KOAc (1.6 g; 16.6 mmol) in dioxane (70 mL) was purged with nitrogen. $Pd_2dba_3$ (758 mg; 0.828 mmol) and XPhos (395 mg; 0.828 mmol) were added and the mixture was purged with nitrogen then stirred for 18 hours at 110° C. EtOAc and water were added. The mixture was filtered over a pad of Celite® and the filtrate was decanted. The organic layer was washed with brine (once), dried over $MgSO_4$, concentrated and purified by preparative LC (Irregular SiOH, 15-40 μm, 220 g Grace®, dry loading (on SiOH), mobile phase gradient: from heptane/EtOAc 90/10 to 50/50) to give 1.85 g (64%) of intermediate (U7) as a beige solid.

The following intermediate was prepared according to intermediate (U7):

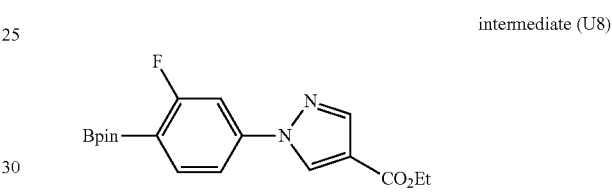

intermediate (U8)

C. Synthesis of the Final Compounds

General scheme

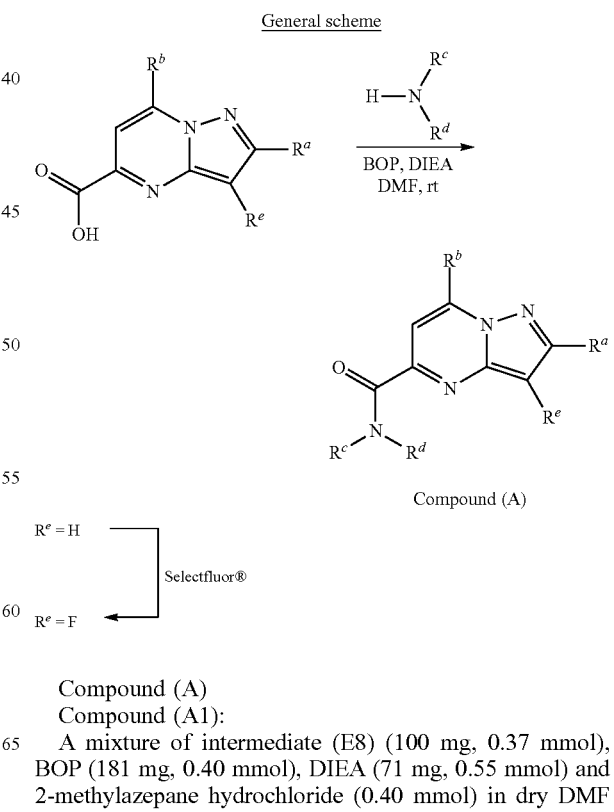

Compound (A)

Compound (A)
Compound (A1):

A mixture of intermediate (E8) (100 mg, 0.37 mmol), BOP (181 mg, 0.40 mmol), DIEA (71 mg, 0.55 mmol) and 2-methylazepane hydrochloride (0.40 mmol) in dry DMF (25 mL) was stirred at RT for 6 hours. The solvent was evaporated, then the residue was taken up in CHCl₃ and washed with water. The organic layer was separated, dried over sodium sulfate and evaporated till dryness. The residue was purified by column chromatography (silica gel, CHCl₃/Et₂O). The pure fractions were collected and the solvent was evaporated. The residue was crystallized from hexane/Et₂O (1/1) to give (100%) compound (A1).

compound (A1)

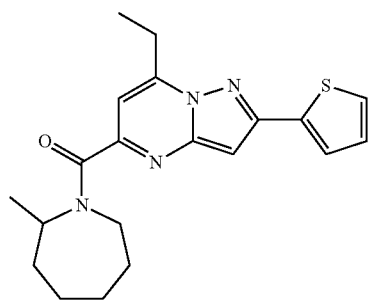

The following compounds were prepared according to the procedure above:

compound (A2)

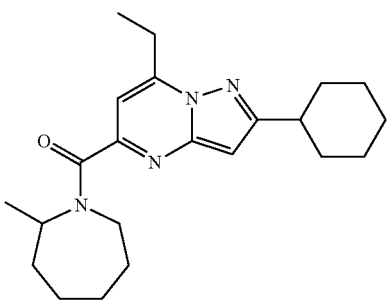

compound (A3)

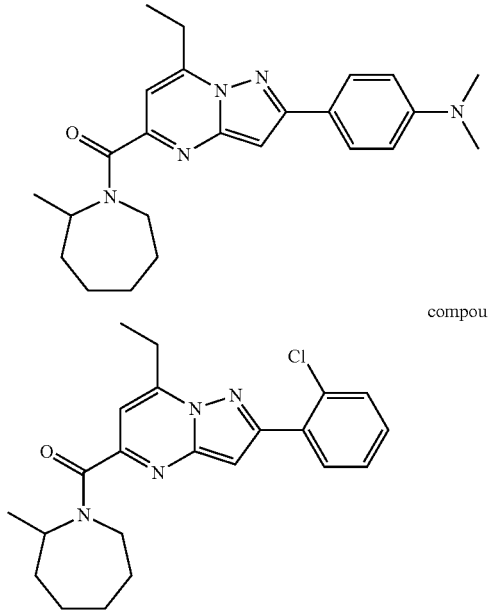

Compound (A4)

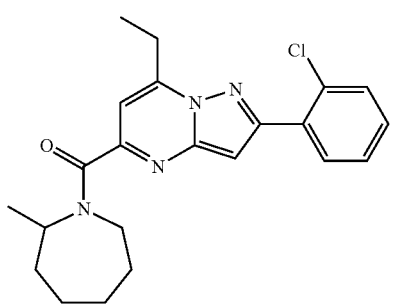

-continued compound (A5)

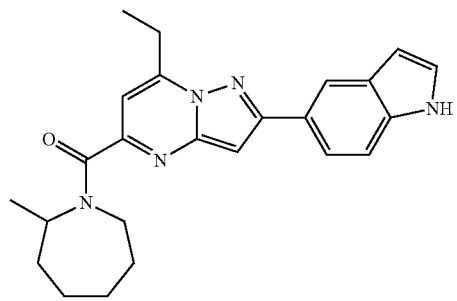

compound (A6)

compound (A7)

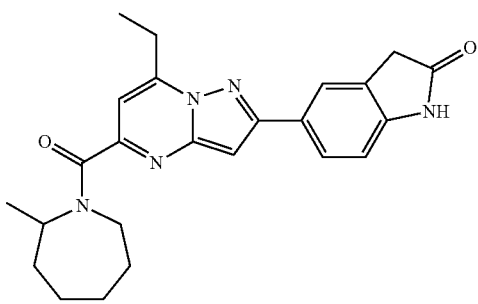

compound (A8)

compound (A9)

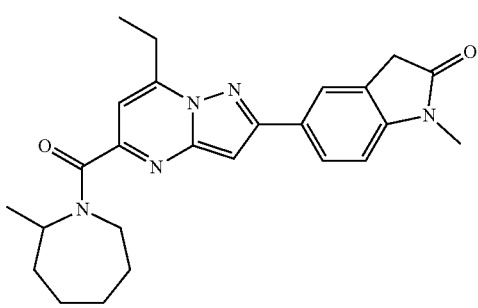

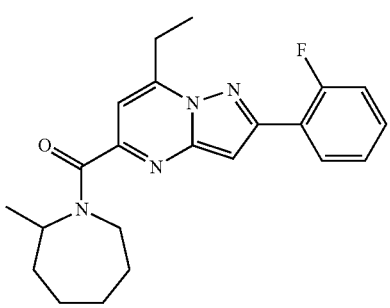

compound (A10)
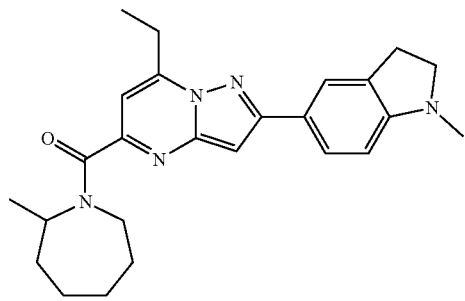
compound (A11)
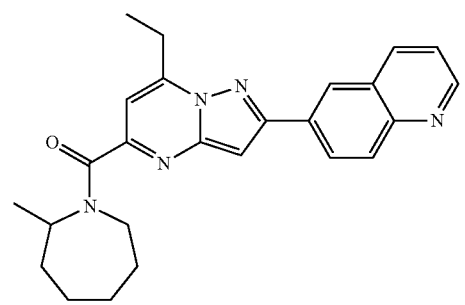
compound (A12)
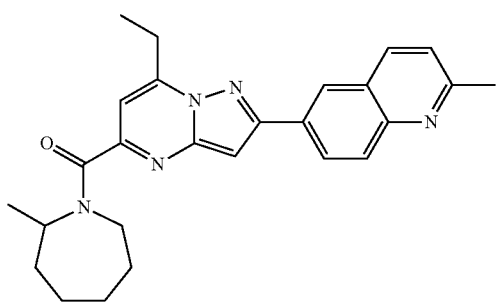
compound (A13)
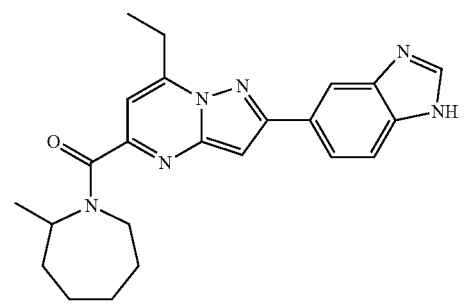
compound (A14)
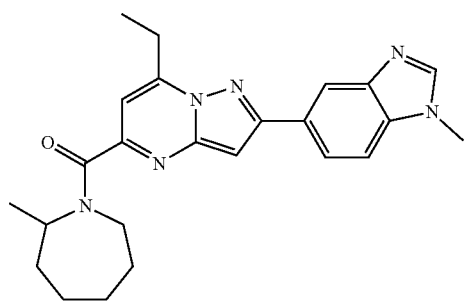
compound (A15)
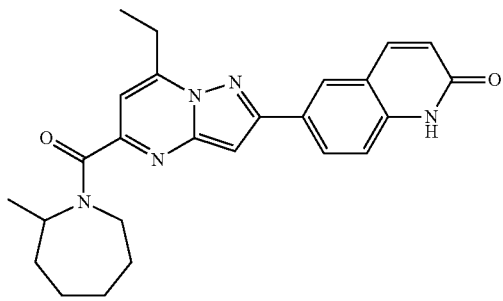
compound (A16)
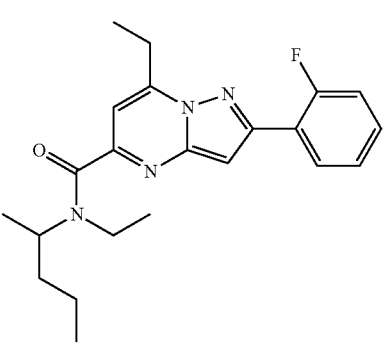
compound (A17)
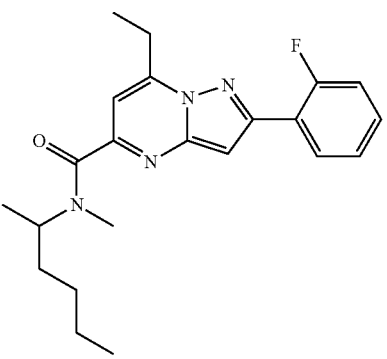
compound (A18)
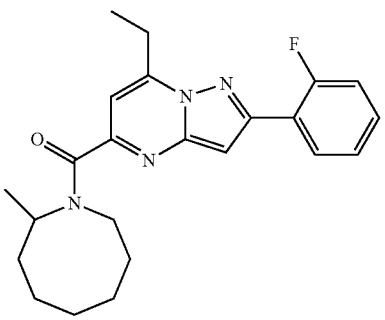

compound (A19)

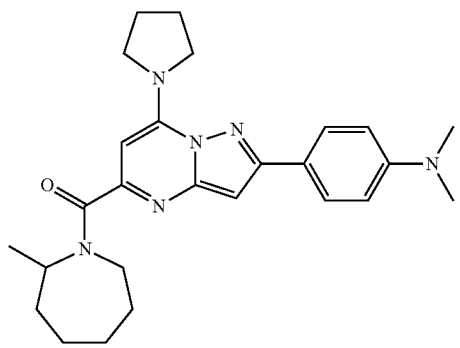

compound (A20)

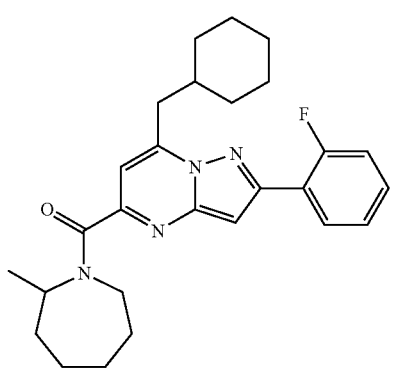

compound (A21)

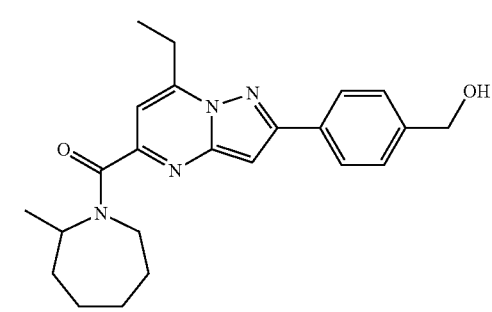

Compound (A22)

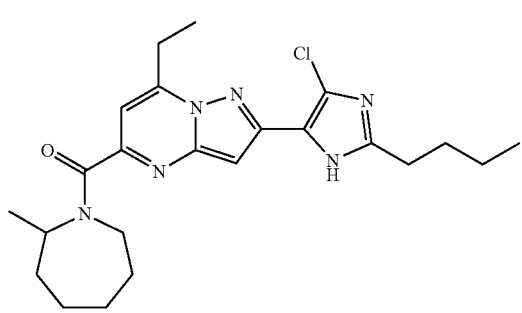

Compound (A23):

TFA (1 g, 8.8 mmol) was added to a solution of intermediate (G5) (0.50 g, 1.0 mmol) in dry DCM (50 mL). The reaction mixture was stirred at RT for 6 hours. The mixture was neutralized with Na₂CO₃ and washed with water. The organic layer was separated, dried over sodium sulfate, filtered and evaporated till dryness. The residue was taken up in hexane, the solid was filtered off and dried to give 0.38 g (96%) of compound (A23).

Compound (A23)

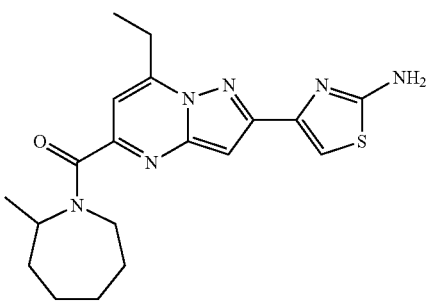

Compound (A24):

TBTU (100 mg, 0.3 mmol) was added to a mixture of intermediate (E22) (110 mg, 0.3 mmol), 2-methylazepane hydrochloride (44 mg, 0.3 mmol) and DIEA (0.15 mL, 0.9 mmol) in DCM (2 mL). The reaction mixture was stirred at RT overnight. The reaction mixture was poured into water. The organic layer was separated, washed with brine, dried over sodium sulfate, filtered and evaporated. The residue was purified by column chromatography (silica gel, DCM). The pure fractions were collected and the solvent was evaporated to give 23 mg (18%) of compound (A24).

compound (A24)

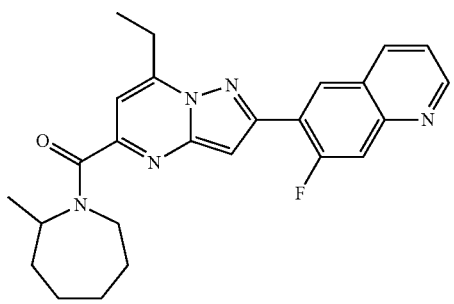

The following compounds were prepared according to the above procedure:

compound (A25)

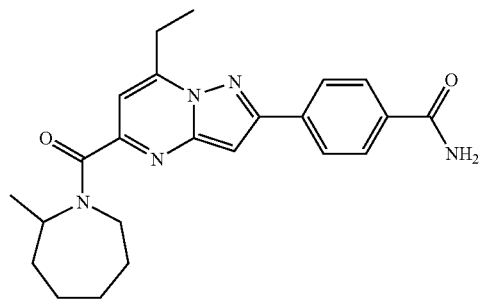

compound (A26)

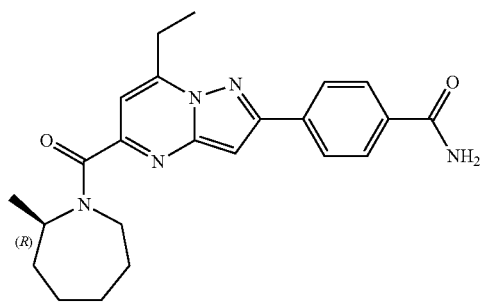

compound (A27)

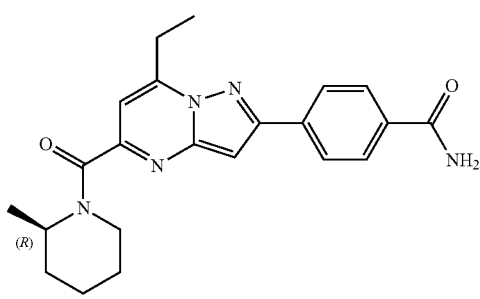

compound (A31)

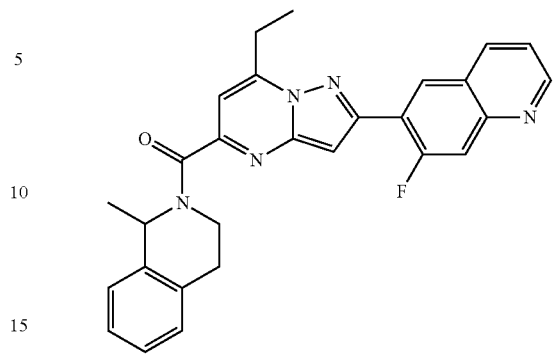

compound (A28)

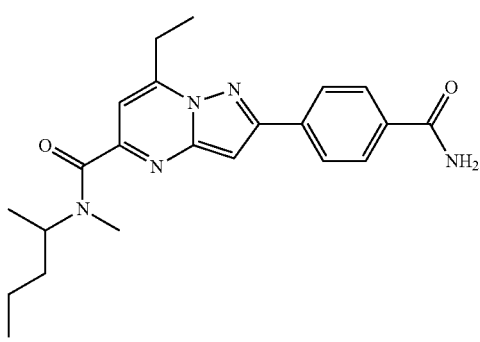

compound (A32)

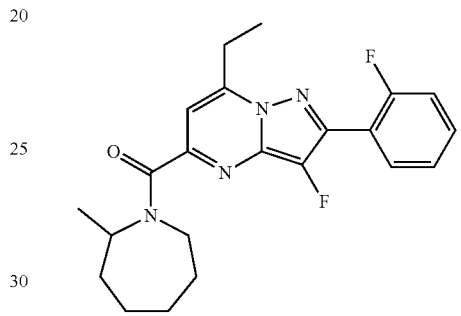

Compound (A32):
Selectfluor® (0.5 g, 1.4 mmol) was added to a solution of compound (A4) (0.265 g, 0.7 mmol) in CH$_3$CN (20 mL). The reaction mixture was stirred at RT for 24 h, then aqueous solution of NaHCO$_3$ (90 mg) was added and the reaction mixture was stirred for 1 hour. The reaction mixture was extracted with DCM (2×50 mL). The combined organic layers were washed with water, dried over sodium sulfate and evaporated till dryness. The residue was purified by HPLC to give 23 mg (9%) of compound (A32).

Compound (B)

compound (A29)

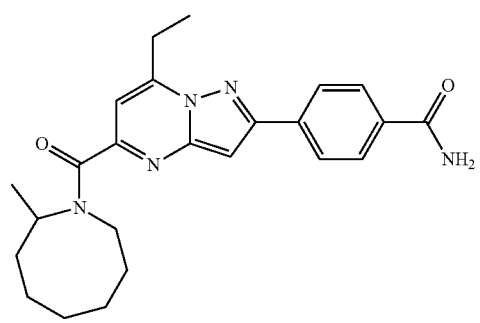

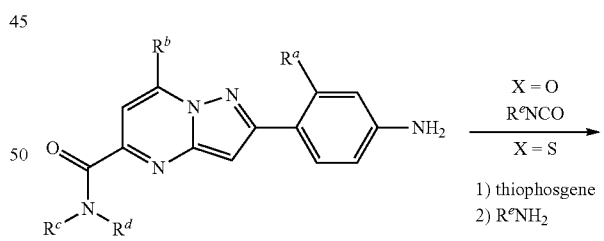

Intermediate (G)

compound (A30)

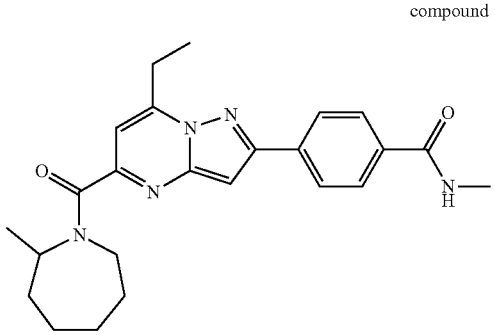

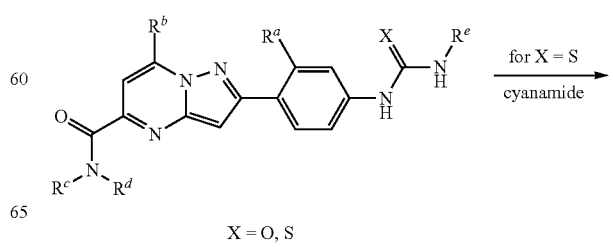

X = O, S

-continued

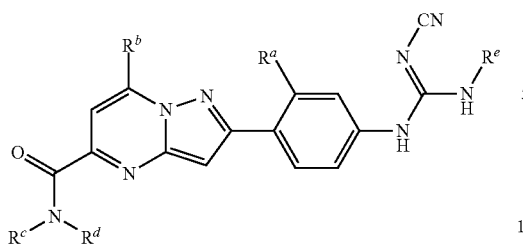

Compound (B1):

2-(isocyanatomethyl)tetrahydrofuran (120 mg, 0.95 mmol) was added to a solution of intermediate (G45) (250 mg, 0.6 mmol) in CH₃CN (5 mL). The reaction mixture was stirred at RT overnight. The reaction mixture was evaporated and the residue was purified by re-crystallization from EtOAc/hexane to give 270 mg (87%) of compound (B1).

compound (B1)

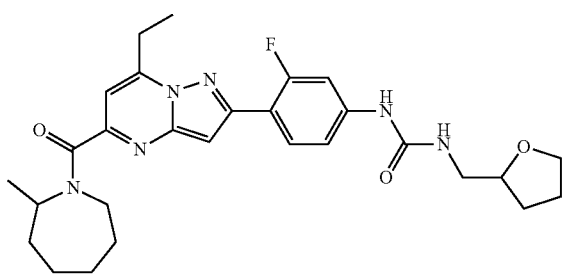

The following compounds were prepared according to the above procedure:

compound (B2)

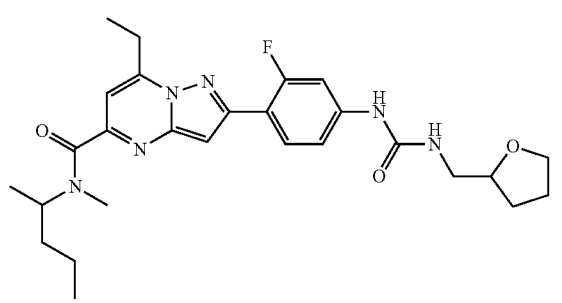

compound (B3)

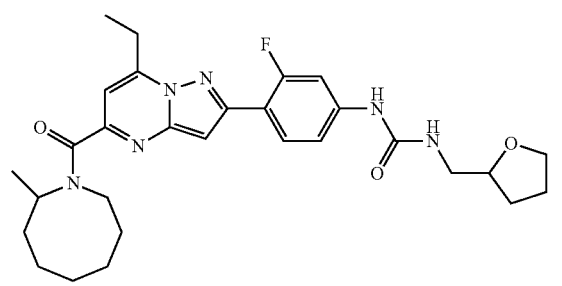

-continued compound (B4)

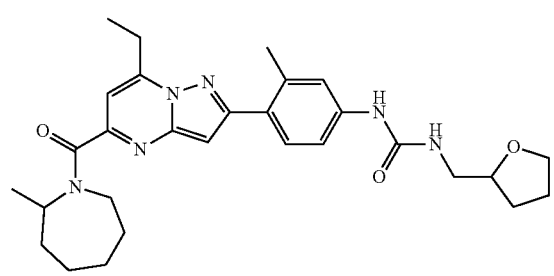

compound (B5)

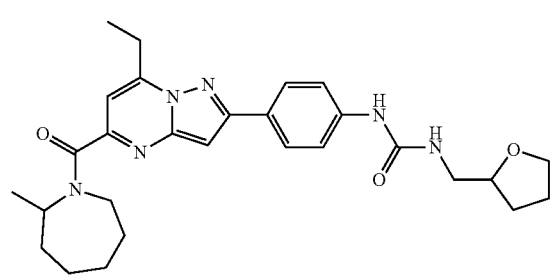

Compound (B5):

2-(isocyanatomethyl)tetrahydrofuran (52 mg, 0.41 mmol) was added to a mixture of intermediate (G54) (150 mg, 0.41 mmol) in CH₃CN (1 mL). The reaction mixture was stirred at RT overnight. The reaction mixture was evaporated and the residue was purified by column chromatography (silica gel, DCM/EtOAc (8/1)). The pure fractions were collected and the solvent was evaporated to give 43 mg (32%) of compound (B5).

The following compounds were prepared according to the above procedure:

compound (B6)

compound (B7)

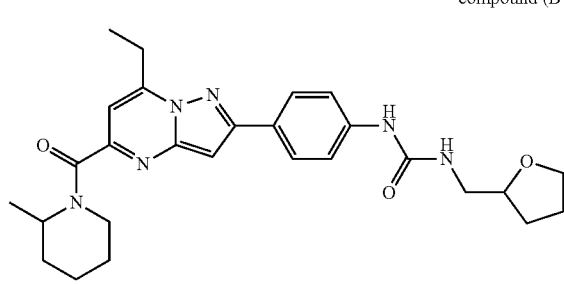

compound (B8)

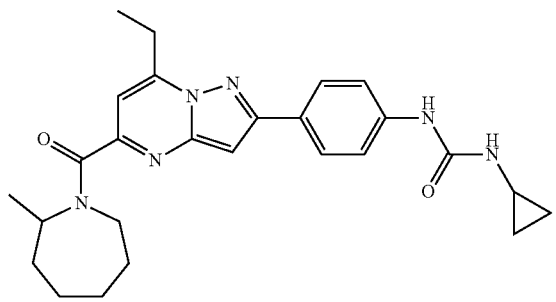

compound (B9)

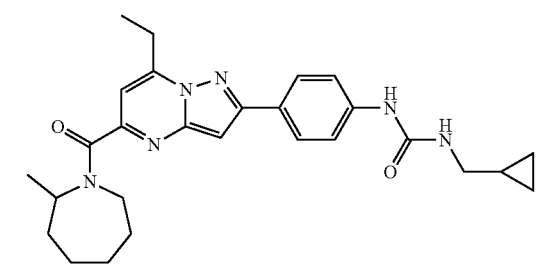

Compound (B10):
2-(isocyanatomethyl)tetrahydrofuran (84 mg, 0.66 mmol) was added to a solution of intermediate (G47) (0.250 g, 0.60 mmol) in dry THF (25 mL). The reaction mixture was stirred at RT for 6 hours. The mixture was poured into water and extracted with EtOAc. The organic layer was separated, washed with water, dried over sodium sulfate and evaporated till dryness. The residue was purified by HPLC to give (22%) compound (B10).

(Compound B10)

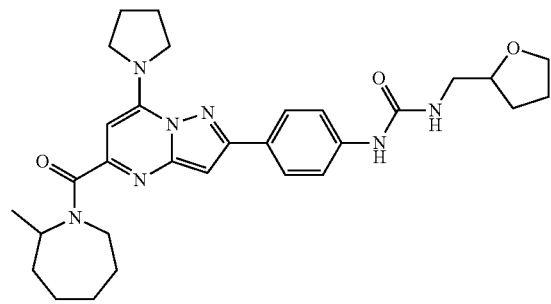

The following compounds were prepared according to the above procedure:

(Compound B11)

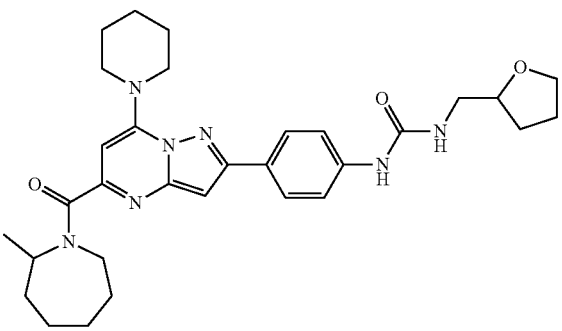

(Compound B12)

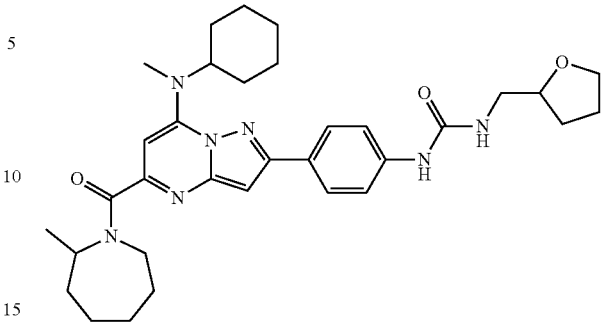

Compound (B13): Thiophosgene (58 mg, 0.5 mmol) was added at 0° C. to a mixture of intermediate (G45) (0.2 g, 0.5 mmol) and DIEA (0.25 mL, 1.5 mmol) in DCM (5 mL). The reaction mixture was stirred for 15 min. Then (tetrahydrofuran-2-ylmethyl)amine (60 mg, 0.6 mmol) was added and the reaction mixture was stirred at RT overnight. A saturated aqueous solution of NaHCO₃ was added and the organic layer was separated, washed with brine, dried over sodium sulfate, filtered and evaporated till dryness. The residue was purified by column chromatography (silica gel, DCM/EtOAc). The pure fractions were collected and the solvent was evaporated to give 250 mg (92%) of compound (B13).

compound (B13)

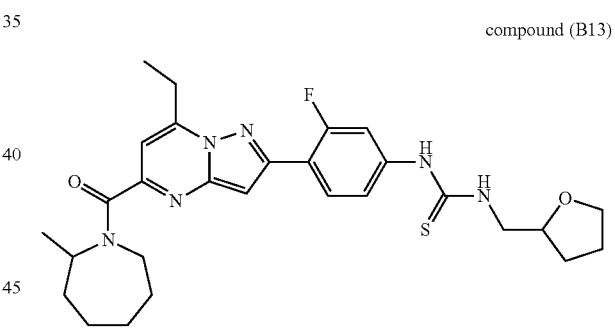

The following compounds were prepared according to the above procedure compound (B14)

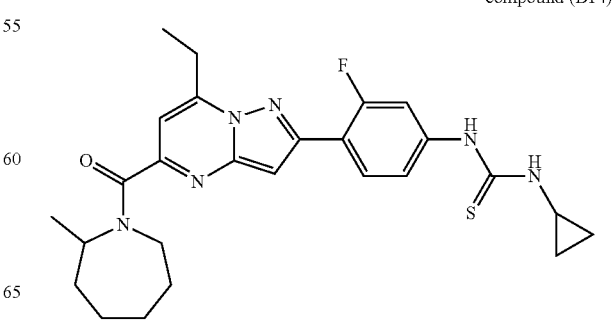

compound (B15)

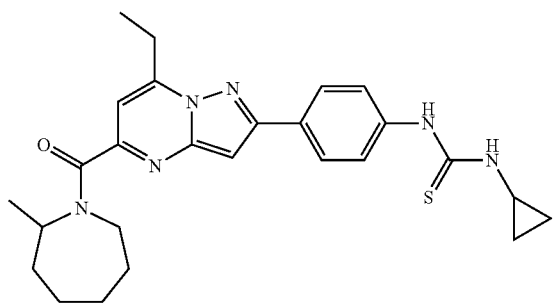

Compound (B16):

Cyanamide (10 mg, 0.2 mmol) was added to a mixture of compound (B13) (100 mg, 0.2 mmol), EDC (53 mg, 0.3 mmol) and Et₃N (0.1 mL, 0.74 mmol) in CH₃CN (5 mL). The reaction mixture was stirred at 80° C. overnight. The solvent was evaporated, then the residue was taken up in EtOAc and washed with water. The organic layer was separated, washed with brine, dried over sodium sulfate, filtered and evaporated till dryness. The residue was purified by column chromatography (silica gel, DCM/EtOAc). The pure fractions were collected and the solvent was evaporated to give 40 mg (43%) of compound (B16).

compound (B16)

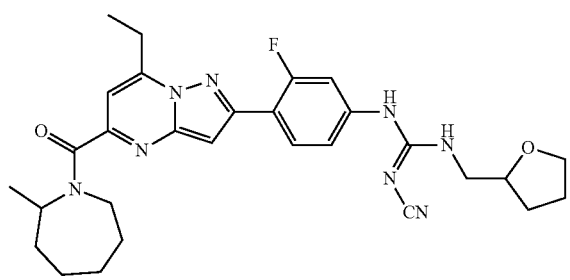

The following compounds were prepared according to the above procedure compound (B17)

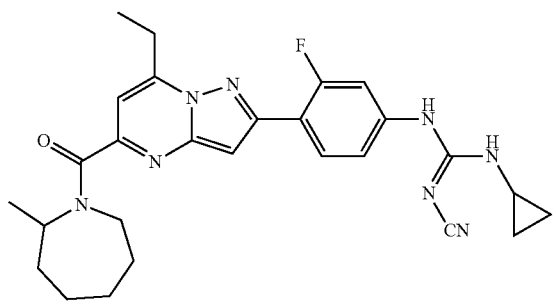

compound (B18)

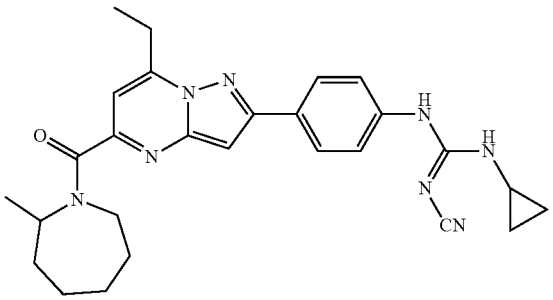

Compound (C)

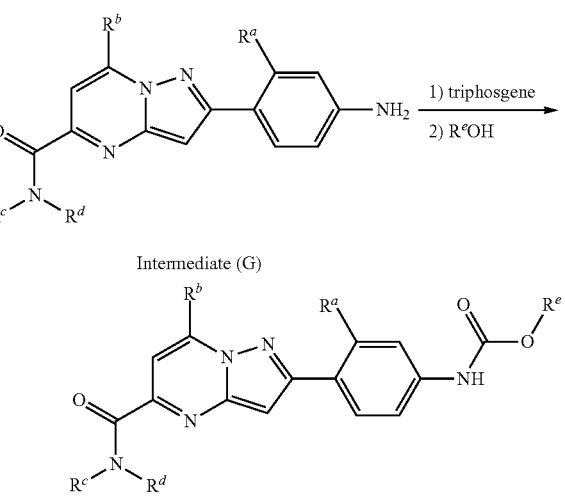

Compound (C1):

Triphosgene (23 mg, 0.03 mmol) was added at 0° C. to a mixture of intermediate (G45) (120 mg, 0.3 mmol) and DIEA (0.15 mL, 0.9 mmol) in DCM (1 mL). The reaction mixture was stirred for 15 min. Then tetrahydrofuran-2-ylmethanol (35 mg, 0.33 mmol) was added and the reaction mixture was stirred at RT overnight. A saturated aqueous solution of NaHCO₃ was added and the organic layer was separated, washed with brine, dried over sodium sulfate, filtered and evaporated till dryness. The residue was purified by column chromatography (silica gel, DCM/EtOAc). The pure fractions were collected and the solvent was evaporated to give 0.94 g (60%) of compound (C1).

compound (C1)

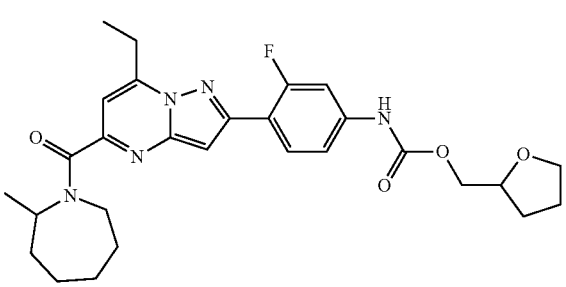

The following compounds were prepared according to the above procedure:

compound (C2)

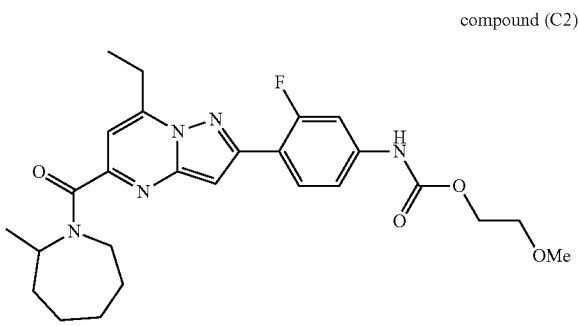 [SMILES: CCc1cc(C(=O)N2CCCCCC2C)nc2cc(-c3ccc(NC(=O)OCCO)cc3)nn12]

compound (C6)

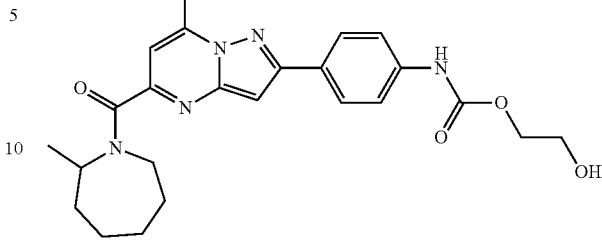

compound (C3)

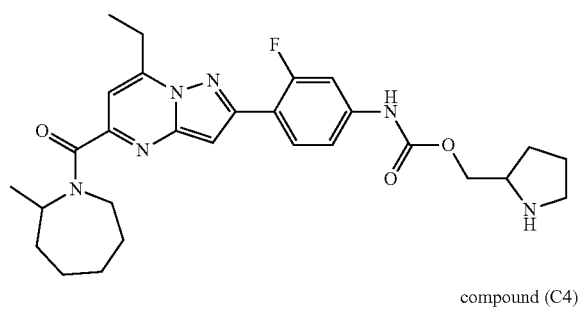

The following compound was prepared according to the above procedure:

compound (C7)

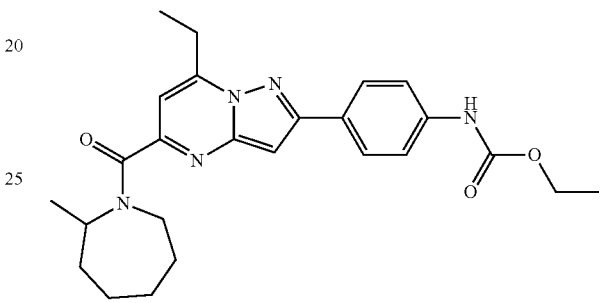

compound (C4)

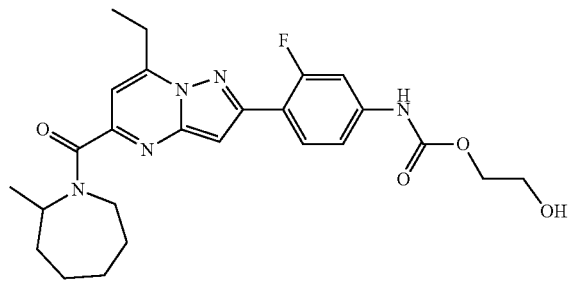

Compound (D)

compound (C5)

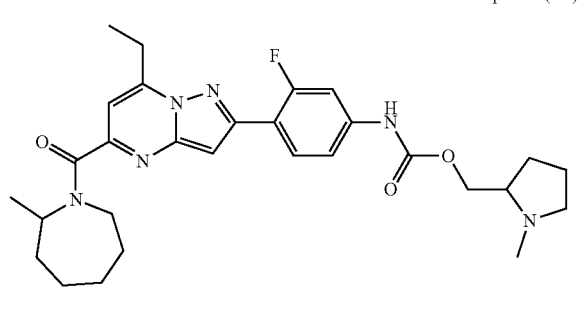

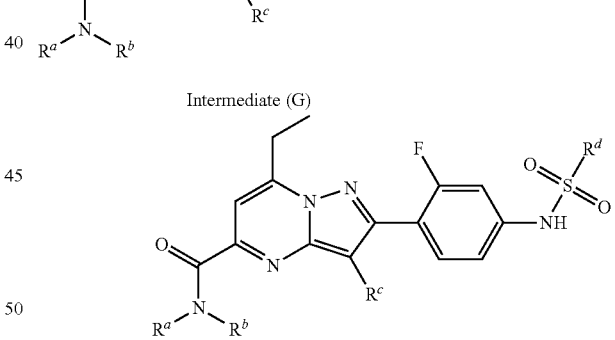

Compound (C6):

Triphosgene (47 mg, 0.16 mmol) was added at 0° C. to a mixture of intermediate (G54) (0.2 g, 0.53 mmol) and DIEA (0.205 g, 1.59 mmol) in DCM (20 mL). The reaction mixture was stirred for 15 min. Then ethylene glycol (36 mg, 0.58 mmol) was added and the reaction mixture was stirred at RT for 6 hours. A saturated aqueous solution of NaHCO$_3$ was added and the organic layer was separated, washed with brine, dried over sodium sulfate, filtered and evaporated till dryness. The residue was purified by column chromatography (silica gel, DCM/EtOAc). The pure fractions were collected and the solvent was evaporated to give (41%) compound (C6).

Compound (D1) and (D'1):

Methanesulfonyl chloride (22 mg, 0.27 mmol) was added to a mixture of intermediate (G45) (100 mg, 0.27 mmol) and Et₃N (0.04 mL, 0.27 mmol) in DCM (1 mL). The reaction mixture was stirred at RT overnight. A saturated aqueous solution of NaHCO₃ was added and the organic layer was separated, washed with brine, dried over sodium sulfate, filtered and evaporated till dryness. The residue was purified by column chromatography (silica gel, DCM/EtOAc). The pure fractions were collected and the solvent was evaporated to give (34%) compound (D'1) and (24%) compound (D1).

compound (D'1)

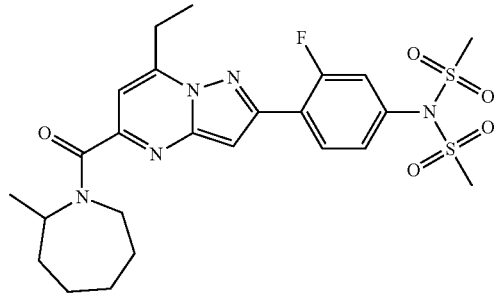

and
compound (D1)

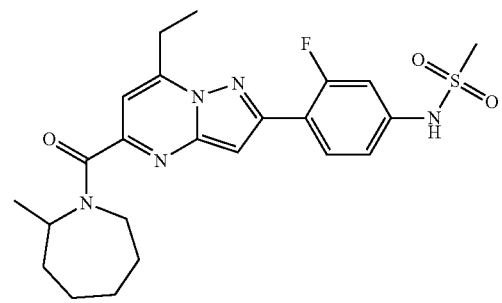

The following compounds were prepared according to the above procedure:

compound (D2)

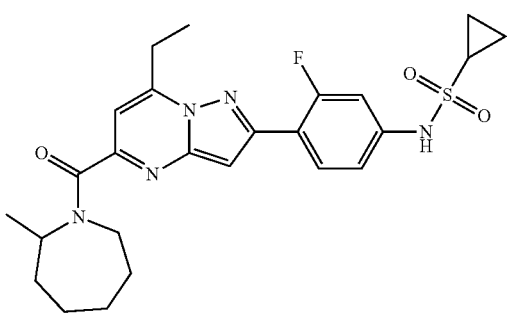

compound (D3)

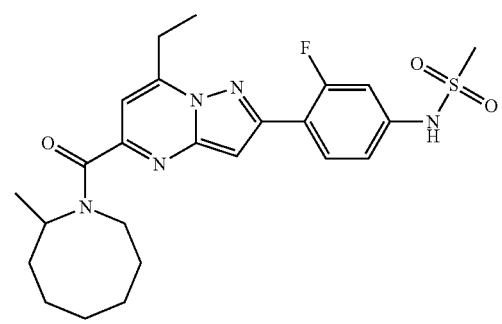

compound (D4)

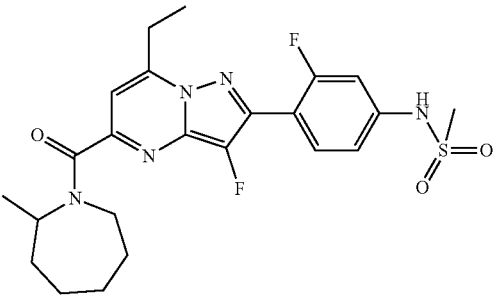

Compound (E)

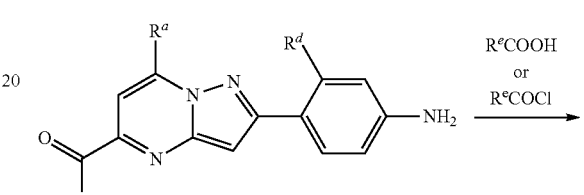

Intermediate (G)

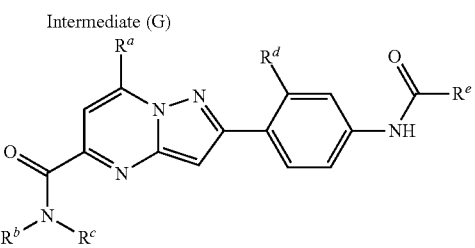

compound (E)

Compound (E1):

TBTU (0.90 g, 0.27 mmol) was added to a mixture of intermediate (G45) (0.1 g, 0.25 mmol) with 1-methyl-1H-imidazole-2-carboxylic acid (0.40 g, 0.27 mmol) and DIEA (0.65 mL, 0.39 mmol) in DCM (5 mL). The reaction mixture was stirred at RT overnight. The reaction mixture was poured into water. The organic layer was separated, washed with brine, dried over sodium sulfate, filtered and evaporated till dryness. The residue was purified by column chromatography (silica gel, DCM). The pure fractions were collected and the solvent was evaporated to give 97 mg (76%) of compound (E1).

compound (E1)

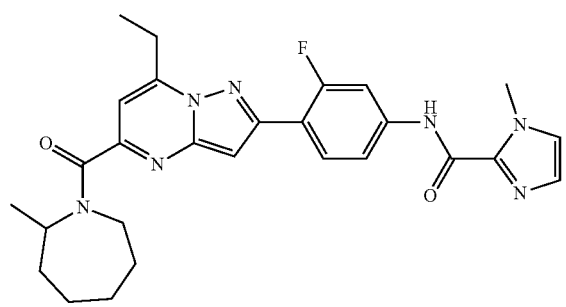

The following compounds were prepared according to the above procedure:

compound (E2)

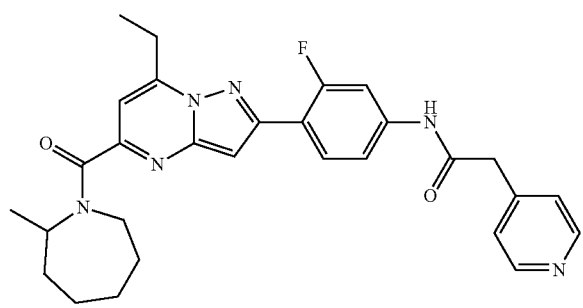

compound (E7)

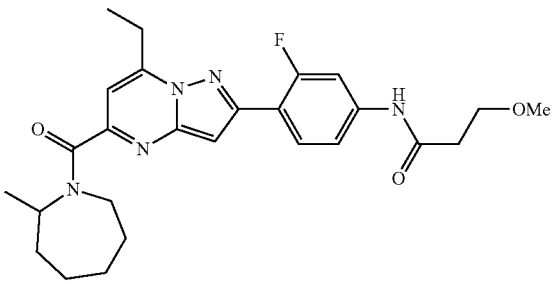

compound (E3)

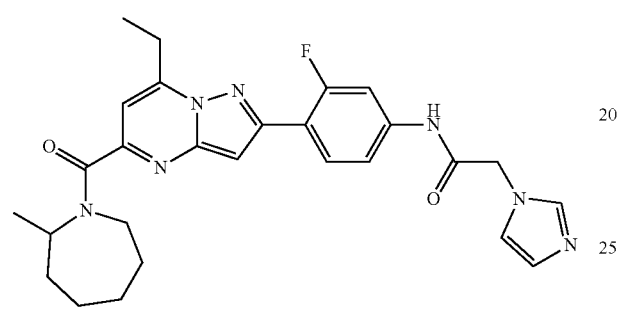

compound (E8)

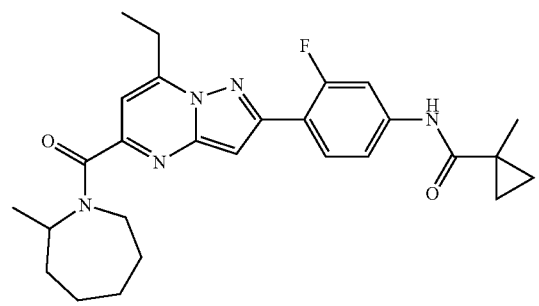

compound (E4)

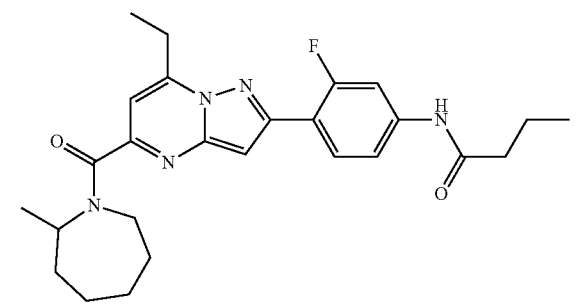

compound (E9)

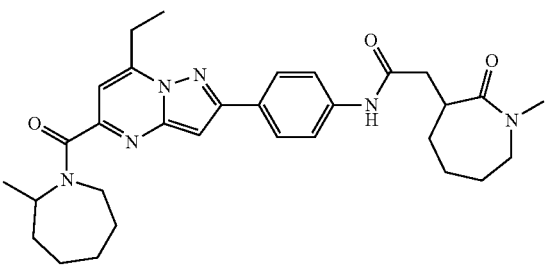

compound (E5)

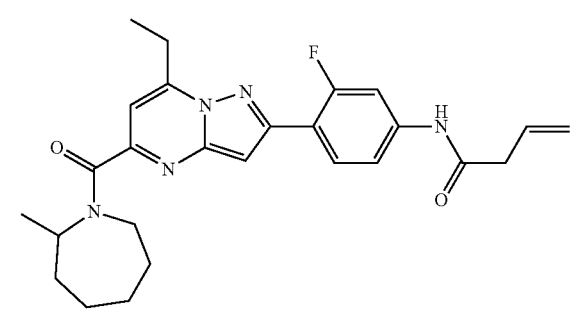

Compound (E10):

Cyclopropanecarbonyl chloride (110 mg, 0.55 mmol) was added to a mixture of intermediate (G46) (200 mg, 0.5 mmol) and Et$_3$N (0.1 mL, 0.55 mmol) in DCM (5 mL). The reaction mixture was stirred at RT overnight. A saturated aqueous solution of NaHCO$_3$ was added and the organic layer was separated, washed with brine, dried over sodium sulfate, filtered and evaporated till dryness. The residue was purified by re-crystallization from EtOAc/ether to give 145 mg (63%) of compound (E10).

compound (E6)

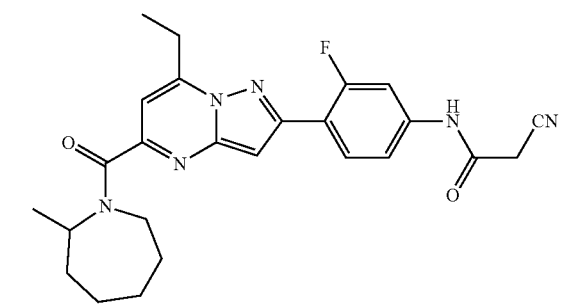

compound (E10)

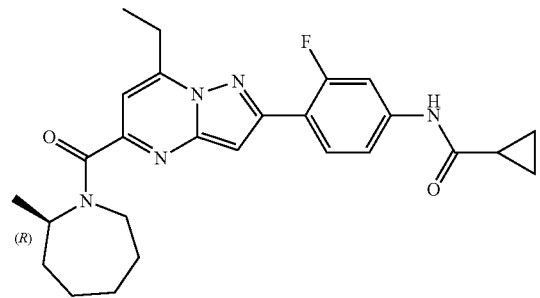

The following compounds were prepared according to the above procedure:

compound (E11)

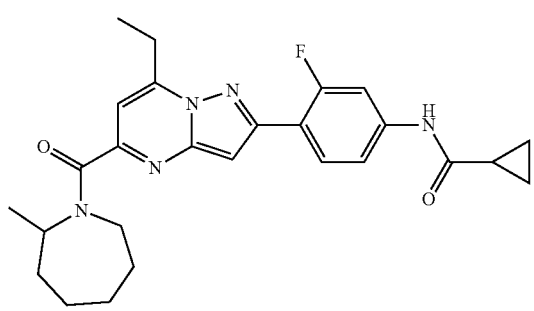

compound (E15)

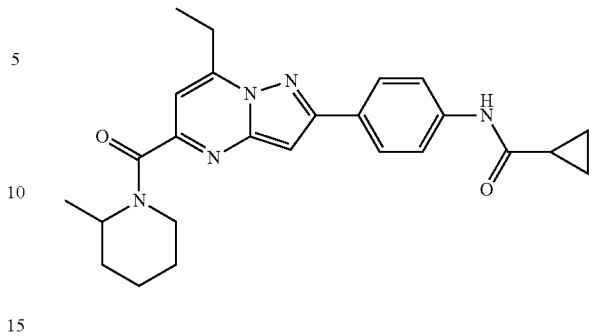

compound (E12)

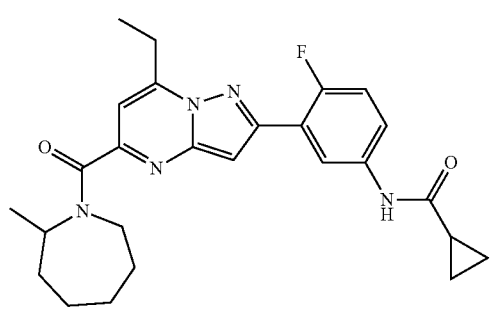

compound (E16)

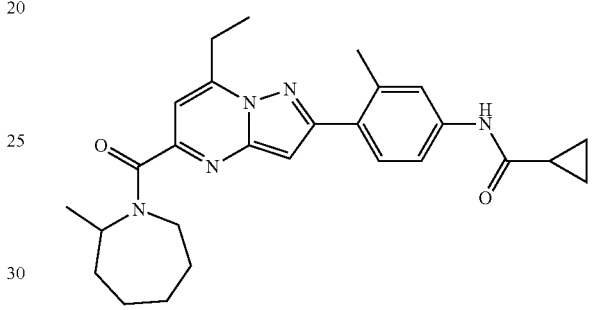

compound (E13)

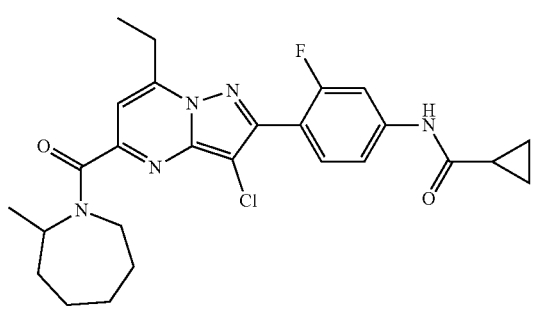

Compound (E17):

Cyclopropylcarbonyl chloride (70 mg, 0.66 mmol) was added to a solution of intermediate (G47) (0.250 g, 0.60 mmol) in dry THF (25 mL) and DIEA (0.114 mL, 0.66 mmol). The reaction mixture was stirred at RT for 6 hours. The mixture was poured into water and extracted with EtOAc. The organic layer was separated, washed with water, dried over sodium sulfate, filtered and evaporated till dryness. The residue was purified by HPLC to give (45%) compound (E17).

compound (E17)

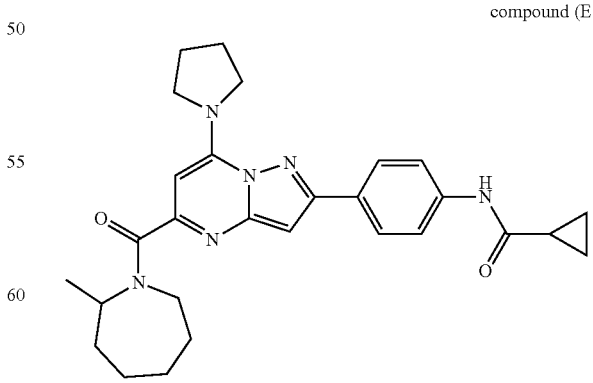

compound (E14)

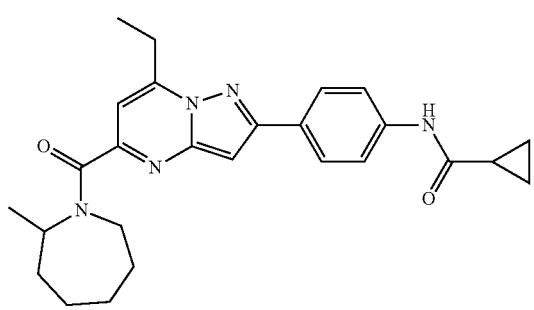

The following compounds were prepared according to the above procedure:

compound (E18)

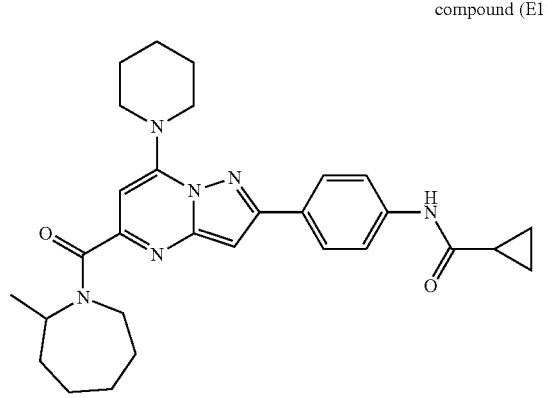

compound (E19)

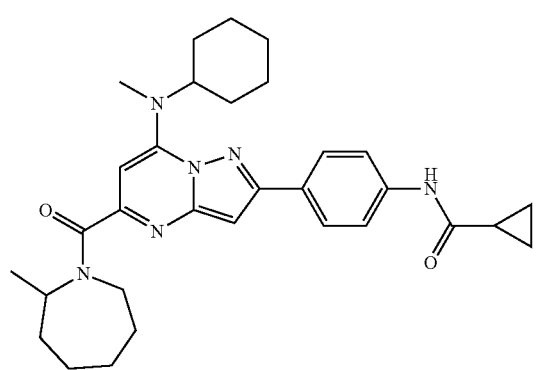

Compound (E20):

Propylcarbonyl chloride (57 mg, 0.53 mmol) was added to a solution of intermediate (G54) (0.200 g, 0.53 mmol) and DIEA (0.091 mL, 0.53 mmol) in dry THF (25 mL). The mixture was stirred at RT for 6 hours. The mixture was poured into water and extracted with EtOAc. The organic layer was washed with water, dried over sodium sulfate, filtered and evaporated till dryness. The residue was purified by column chromatography then crystallized from Et$_2$O to give (56%) compound (E20).

compound (E20)

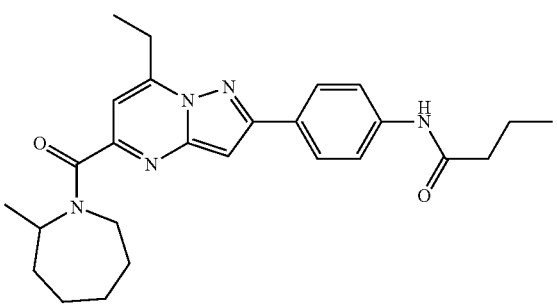

Compound (E21):

Prepared according to the above procedure from intermediate (G54) and propen-2-carbonyl chloride.

compound (E21)

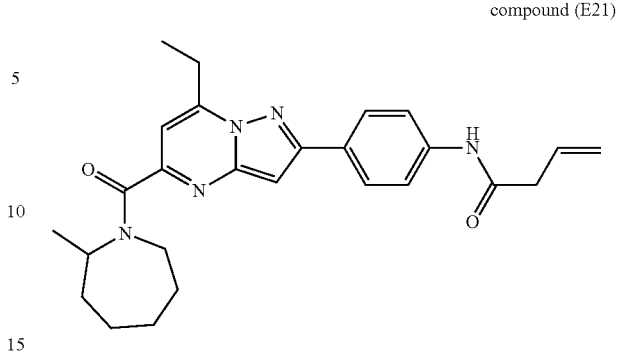

Compound (E22):

1-methyl-1H-imidazole-2-carboxylic acid (67 mg, 0.53 mmol) was added to a solution of intermediate (G54) (0.200 g, 0.53 mmol), DIEA (0.40 mL, 2.3 mmol) and BOP (0.786 g, 1.7 mmol) in dry DMF (15 mL). The reaction mixture was stirred at RT for 6 hours. The mixture was poured into water and extracted with EtOAc. The organic layer was washed with water, dried over sodium sulfate, filtered and evaporated till dryness. The residue was purified by column chromatography then crystallized from Et$_2$O to give (24%) compound (E22).

compound (E22)

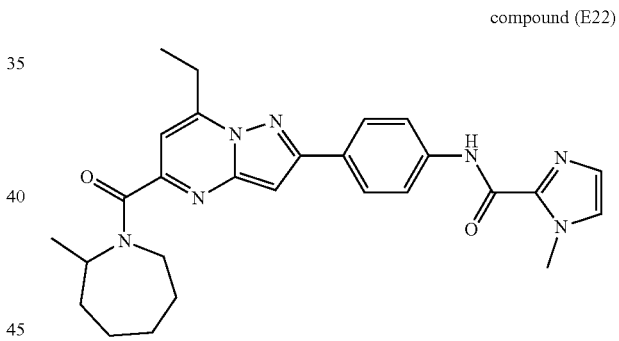

Compound (E23):

Prepared according to the above procedure from intermediate (G54) and pyridin-4-ylacetic acid.

compound (E23)

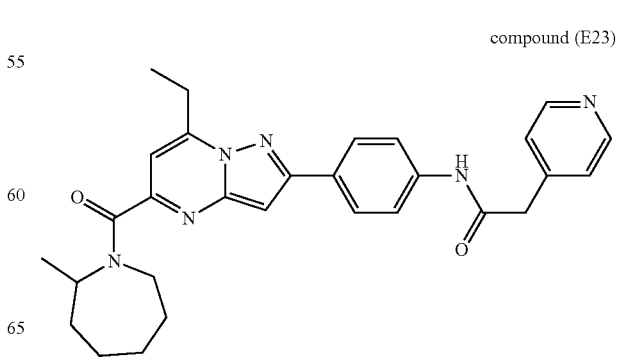

Reaction scheme :

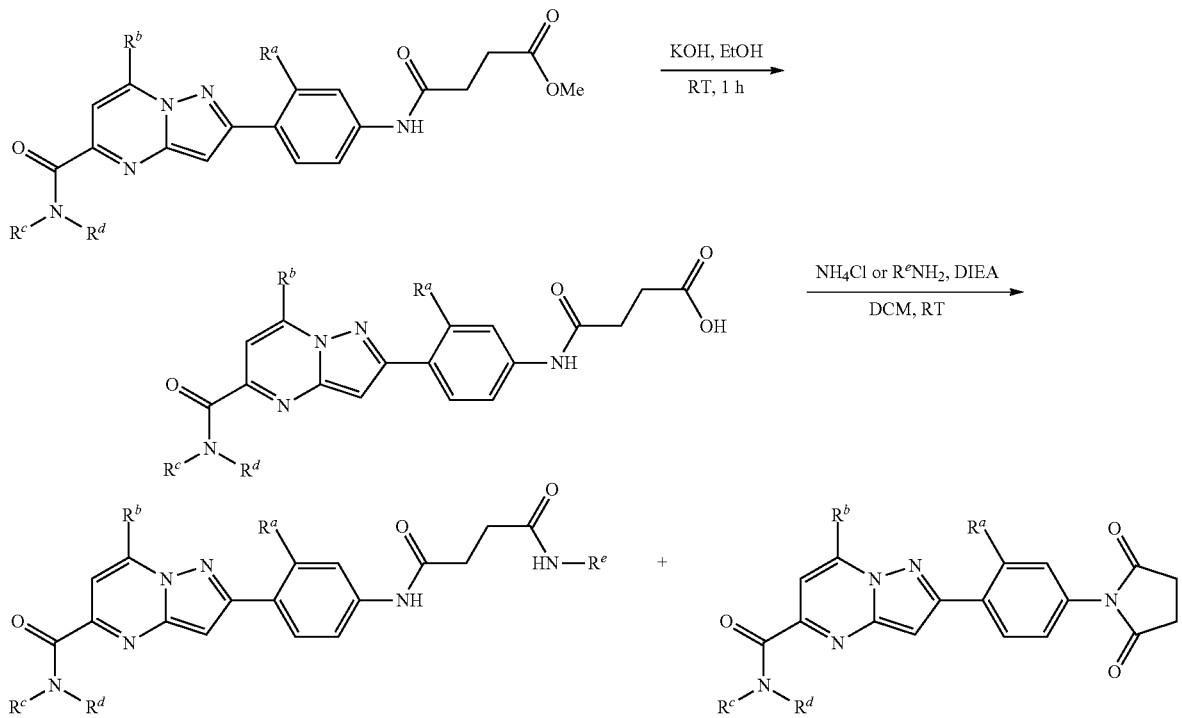

Compound (E24):

KOH (100 mg, 1.96 mmol) was added to a stirred solution of intermediate (G50) (500 mg, 0.98 mmol) in EtOH (5 mL). The reaction mixture was stirred at RT for 1 hour. The solvent was evaporated, then the residue was taken up in water and washed with ether. The aqueous layer was neutralized with HCl cc (0.2 mL) to pH 7. The precipitate was filtered off and dried to give 480 mg (100%) of compound (E24).

compound (E24)

Compound (E25) and (E26):

TBTU (90 mg, 0.28 mmol) was added to a mixture of compound (E24) (150 mg, 0.3 mmol), NH₄Cl (100 mg, 1.3 mmol) and DIEA (0.25 mL, 1.3 mmol) in DCM (5 mL). The reaction mixture was stirred at RT overnight. The reaction mixture was poured into water. The organic layer was separated, washed with brine, dried over sodium sulfate, filtered and evaporated till dryness. The residue was purified by column chromatography (silica gel, DCM/EtOAc). The pure fractions were collected and the solvent was evaporated to give 32 mg (21%) of compound (E25) and 66 mg (46%) of compound (E26).

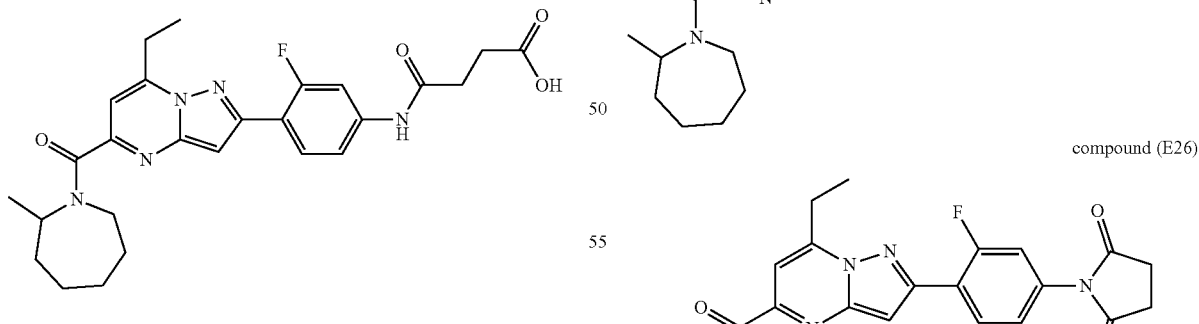

compound (E25)

compound (E26)

The following compounds were prepared according to the above procedure:

249 250

Compound (F) and (G)

compound (E27)

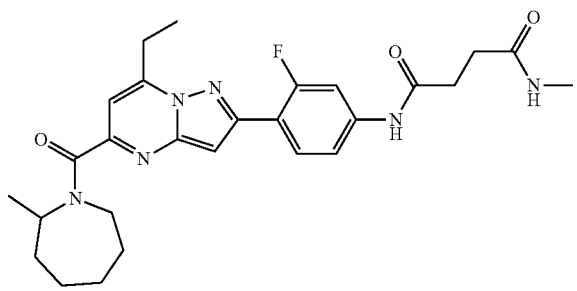

Intermediate (G)

compound (E28)

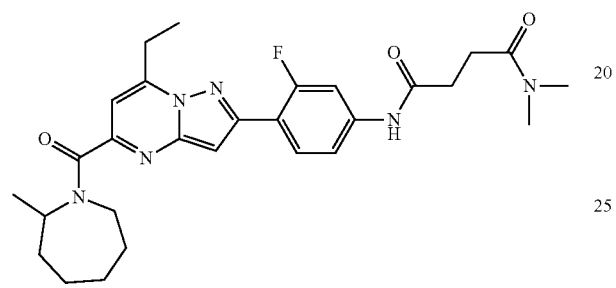

compound (F)

compound (E29)

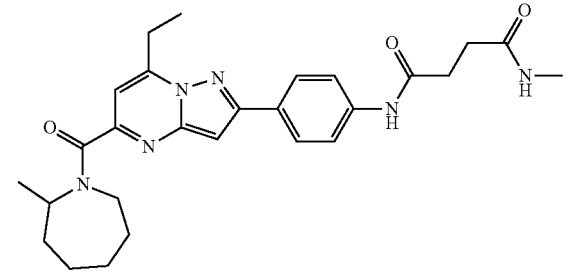

Intermediate (G')

compound (E30)

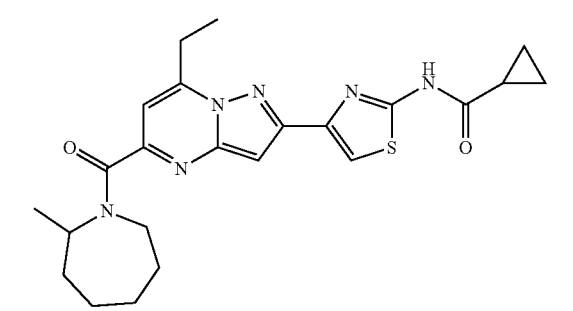

compound (G)

Compound (F1):

A mixture of intermediate (G3) (0.47 mmol), 4-pyridine boronic acid (0.51 mmol), Cs$_2$CO$_3$ (0.107 g, 10 mmol) and Pd(PPh$_3$)$_4$ (0.012 g, 0.01 mmol) in 1,4-dioxane (19 mL) and water (1 mL) under argon was heated at 130° C. for 4 h using one single mode microwave (Biotage®) with a power output ranging from 0 to 400 W. The solvent was evaporated and the mixture was taken up in CHCl$_3$ and water. The organic layer was separated, washed with water, dried over sodium sulfate, filtered and evaporated till dryness. The residue was purified by column chromatography (silica gel, CHCl$_3$/Et$_2$O (1/1)). The pure fractions were collected and the solvent was evaporated to give (41%) compound (F1).

Compound (E30):

Cyclopropylcarbonyl chloride (50 mg, 0.47 mmol) was added to a solution of compound (A23) (0.150 g, 0.43 mmol) and DIEA (0.081 mL, 0.47 mmol) in dry THF (25 mL). The reaction mixture was poured into water. The organic layer was separated, washed with brine, dried over sodium sulfate, filtered and evaporated till dryness. The residue was purified by HPLC to give (64%) compound (E30).

compound (F1)

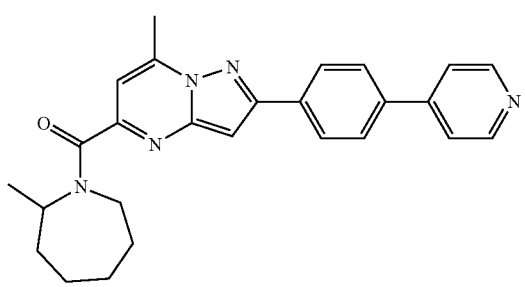

The following compounds were prepared according to the above procedure:

compound (F2)

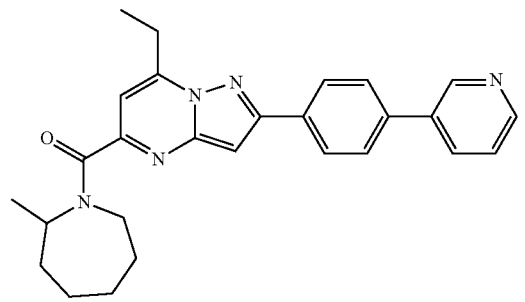

compound (F3)

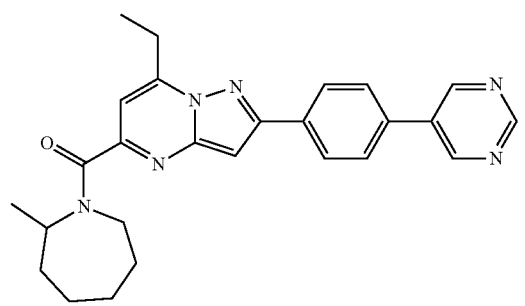

compound (F4)

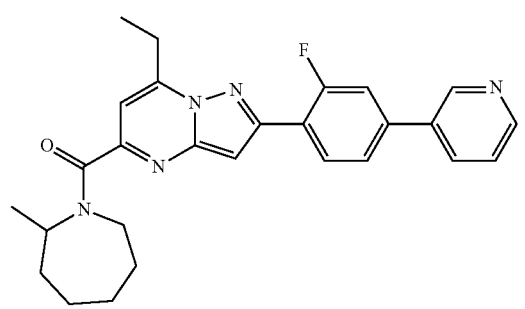

Compound (F4):

A mixture of intermediate (G2) (0.100 g, 0.22 mmol), $Cs_2CO_3$ (0.156 g, 4.36 mmol), $Pd(PPh_3)_4$ (23 mg, 0.02 mmol) and 3-pyridine boronic acid (32 mg, 0.26 mmol) in 1,4-dioxane (20 mL) and water (1 mL) was heated at 150° C. for 2 hours using one single mode microwave (Biotage®) with a power output ranging from 0 to 400 W. The solvent was evaporated and the mixture was taken up in $CHCl_3$ and water. The organic layer was separated, washed with water, dried over sodium sulfate, filtered and evaporated till dryness. The residue was purified by column chromatography to give (28%) the compound (F4).

Compound (F5):

A mixture of intermediate (G2) (0.100 g, 0.22 mmol), $Cs_2CO_3$ (0.156 g, 4.36 mmol), $Pd(PPh_3)_4$ (23 mg, 0.02 mmol) and 1-(tetrahydro-2H-pyran-2-yl)-5-(4,4,5,5-tetramethyl-1,3,2-dioxaborolan-2-yl)-1H-pyrazole (73 mg, 0.26 mmol) in 1,4-dioxane (20 mL) and water (1 mL) was heated at 150° C. for 2 h using one single mode microwave (Biotage®) with a power output ranging from 0 to 400 W. The solvent was evaporated and the mixture was taken up in $CHCl_3$ and water. The organic layer was separated, washed with water, dried over sodium sulfate, filtered and evaporated till dryness. The residue was purified by column chromatography and after then the product was stirred in a mixture of THF and HCl cc (1/1) at RT for 4 hours. The reaction mixture was evaporated till dryness and the residue was purified by HPLC to give (86%) compound (F5).

compound (F5)

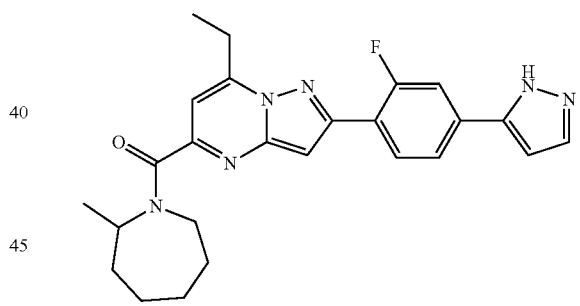

The following compound was prepared according to the above procedure:

compound (F6)

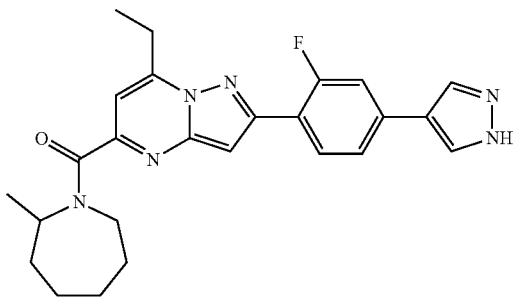

-continued

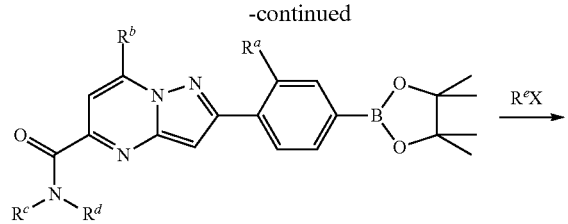

Intermediate (G')

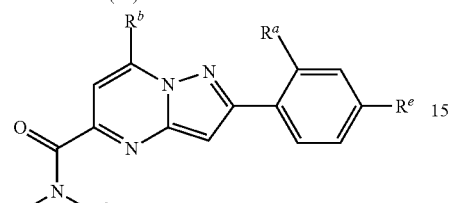

compound (F)

Typical Procedure for the Synthesis of Compounds (F) Via Intermediate (G29):

Intermediate (G29) (0.250 g, 0.49 mmol), $Na_2CO_3$ (0.115 g, 1.08 mmol), $Pd(PPh_3)_4$ (56 mg, 0.05 mmol) and the corresponding halide (0.54 mmol) was dissolved in 1,4-dioxane (20 mL) and water (1 mL). The reaction mixture was heated at 150° C. for 2 h using one single mode microwave (Biotage®) with a power output ranging from 0 to 400 W. The crude product was purified by column chromatography or HPLC.

The following compounds were prepared according to the above procedure:

compound (F7)

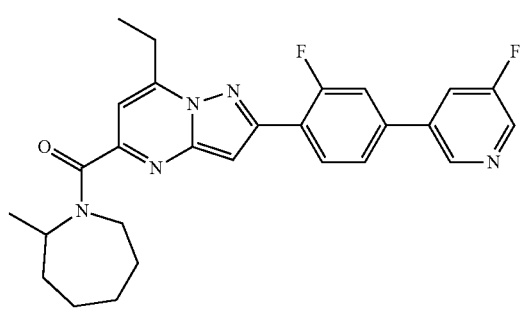

compound (F8)

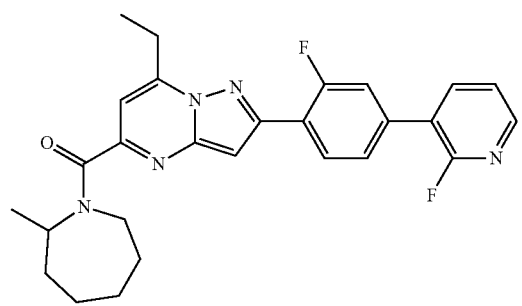

-continued compound (F9)

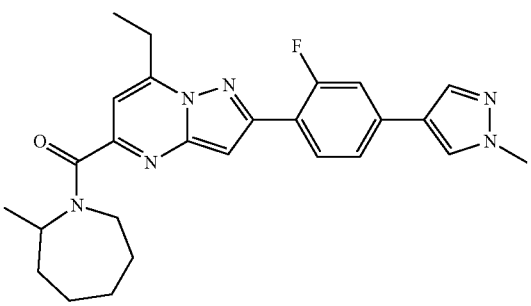

compound (F10)

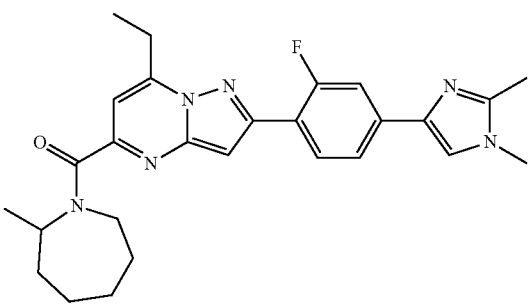

compound (F11)

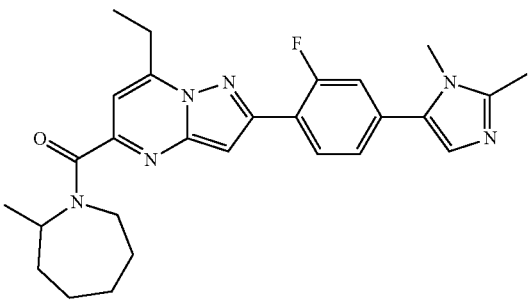

compound (F12)

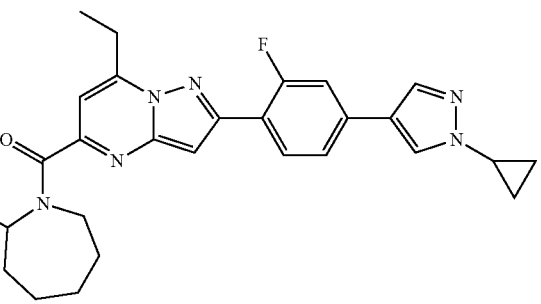

compound (F13)

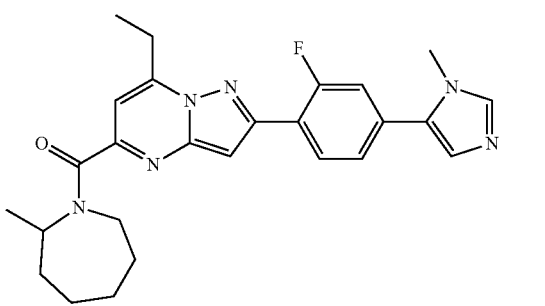

compound (F14)
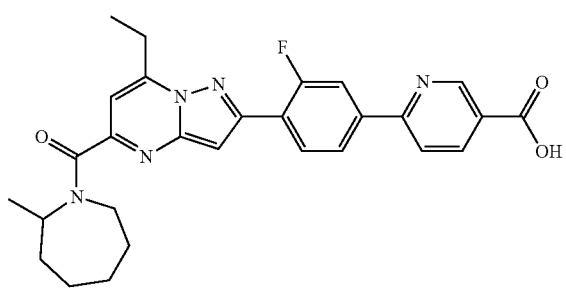
Compound (F16)
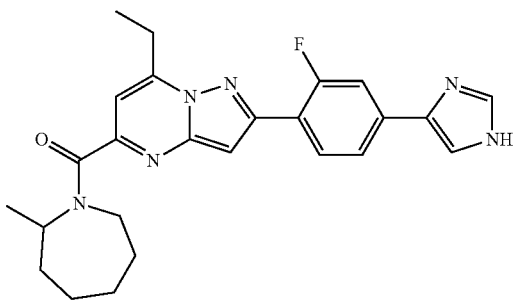
compound (F15)
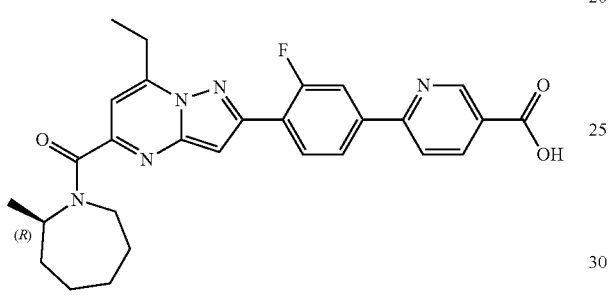
Compound (F17)
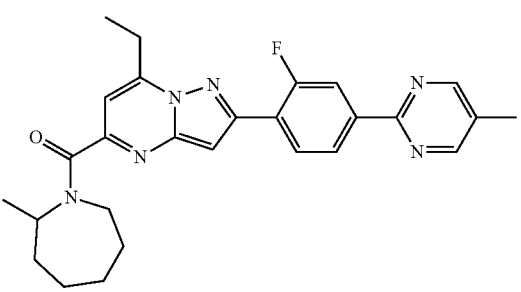
Compound (F15)
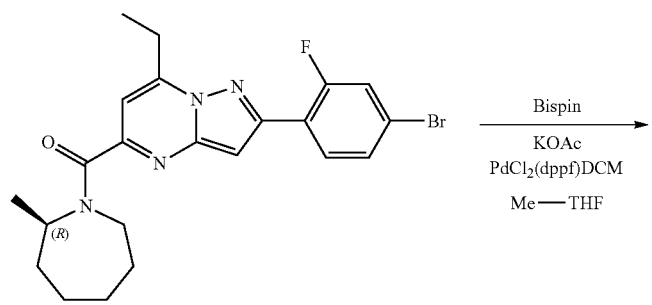
intermediate (G1)
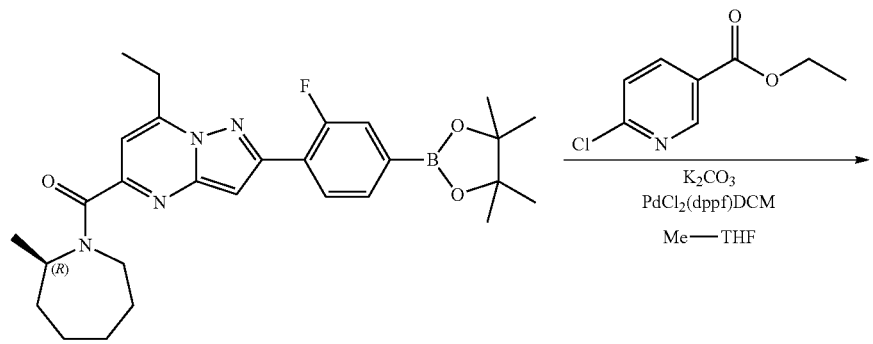
intermediate (G30)

intermediate (G316)

Intermediate (G316):

A solution of intermediate (G30) (7.5 g, 14.81 mmol) and ethyl 6-chloronicotinate (5.50 g, 29.62 mmol) in K$_2$CO$_3$ (9.48 mL, 2 M, 18.96 mmol) and Me-THF (36 mL) was degased with nitrogen for 10 min. PdCl$_2$(dppf)DCM (1.21 g, 1.48 mmol) was added and the mixture was heated at 120° C. using a singlemode microwave (Anton Paar® Monowave 300) with a power output ranging from 0 to 850 W for 30 min. The reaction mixture was filtered through a short pad of Celite®, the cake was washed with EtOAc, the organic layer was separated, washed with brine, dried (MgSO$_4$) and evaporated till dryness. Purification of the residue was carried out by flash chromatography over silica gel (cartridge 180 g, 15-40 µm, Heptane/EtOAc 80/20). The pure fractions were collected and evaporated to dryness to afford 4.3 g (55%) of intermediate (G316).

A mixture of intermediate (G312) (4.3 g, 8.12 mmol) and KOH (0.68 g, 12.18 mmol) in EtOH (45 mL) was stirred at reflux for 1 h30. The mixture was cool down to RT and evaporated till dryness. The residue was taken up in water (75 mL), HCl 3M (4.06 mL, 3 M, 12.18 mmol) was added, the gel-like mixture was filtered, taken up in CH$_3$CN, stirred 1 hour, filtered and dried under vacuum to afford 3.1 g of compound (F15).

compound (F15)

Compound (F18):

Intermediate (G29) (0.2 g, 0.4 mmol), Na$_2$CO$_3$ (0.130 g, 1.2 mmol), PdCl$_2$(PPh$_3$)$_2$ (5% mol) and 2-bromo-4-methyl-1,3-thiazole-5-carboxylic acid (90 mg, 0.4 mmol) was dissolved in 1,4-dioxane (1 mL) and water (1 mL). The reaction mixture was heated at reflux for 5 hours. Then, the solution was filtered to remove the precipitate and the filtrate was evaporated. DCM and water were added to the residue and the organic layer was separated. The aqueous layer was acidified HCl cc to pH 3. The mixture was extracted with DCM. The organic layers were combined, dried over sodium sulfate, filtered and the solvent was evaporated. The residue was recrystallized with EtOAc to give 30 mg (15%) of compound (F18).

compound (F18)

Compound (F26):

In a sealed tube, a solution of intermediate (G77) (421 mg; 0.613 mmol), intermediate (S3) (165 mg; 0.613 mmol) and K$_3$PO$_4$ (391 mg; 1.84 mmol) in 1.4dioxane (8 mL) and H$_2$O (1.2 mL) was purged with N$_2$. PdCl$_2$(dtbpf) (40 mg; 61 µmol) was added, the mixture was purged again with N$_2$ and heated at 80° C. using one single mode microwave (Biotage® Initiator EXP 60) with a power output ranging from 0 to 400 W for 30 min. The mixture was evaporated in vacuum to give a brown solid which was purified by column chromatography (silica gel, from DCM/MeOH/AcOH 100/0/0 to 95/5/0.5), the pure fractions were collected and evaporated to give a solid. The solid was triturated in MeOH, filtered, washed with MeOH and dried under high vacuum (50° C., 2 hours) to afford 202 mg (69%) of compound (F26).

compound (F26)

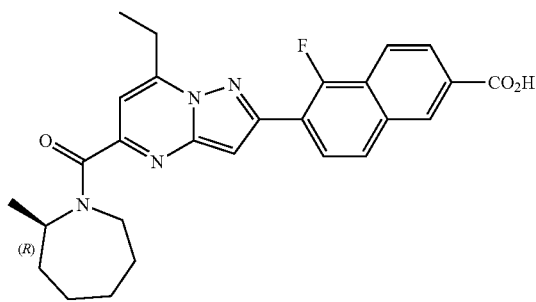

The following compounds were prepared according to the above procedure.

compound (F27)

compound (F28)

Compound (F33):

A solution of intermediate (G77) (492 mg; 0.716 mmol, 60% purity), 6-bromo-7-fluoro-2-Quinolinecarboxylic acid CAS [1598112-25-4] (193 mg; 0.716 mmol) and K₃PO₄ (456 mg; 2.15 mmol) in dioxane (9.7 mL) and H₂O (3.0 mL) was purged by N₂ bubbling for 10 min before the addition of Pd118 (47 mg; 71 µmol). The resulting mixture was purged by N₂ bubbling, then heated at 80° C. using one single mode microwave (Biotage® Initiator EXP 60) with a power output ranging from 0 to 400 W for 30 min [fixed hold time]. The crude was evaporated until dryness and purified by preparative LC (Regular SiOH 30 µm, 25 g Interchim®, dry loading (Celite®), mobile phase gradient: from CH₂Cl₂/MeOH/AcOH 100:0:0 to 90:10:1) to give 147 mg of impure compound which was purified again by preparative LC (Regular SiOH 30 µm, 4 g Interchim®, dry loading (Celite®), mobile phase gradient: from CH₂Cl₂/MeOH 100:0 to 95:5) to give 90 mg (26%) of compound (F33) as an off-white solid.

compound (F33)

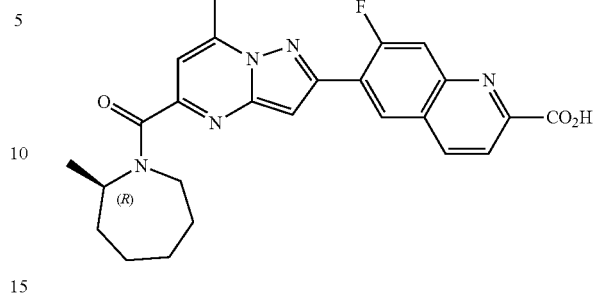

Reaction scheme:

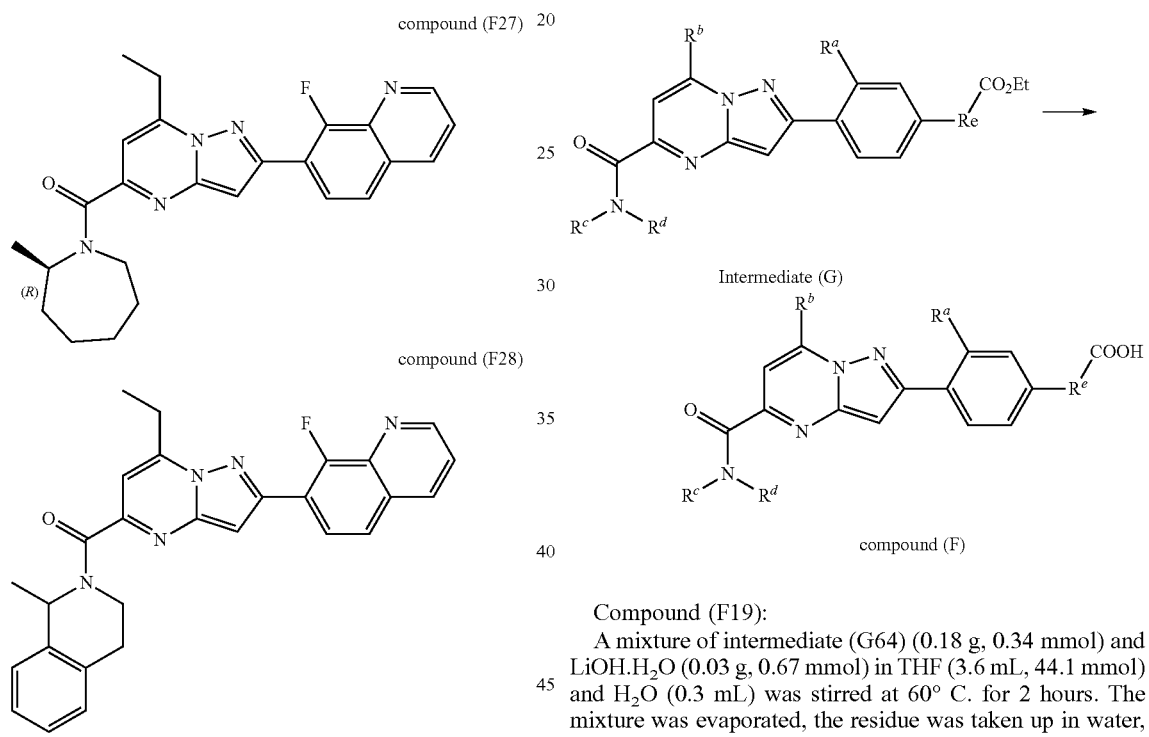

Compound (F19):

A mixture of intermediate (G64) (0.18 g, 0.34 mmol) and LiOH.H₂O (0.03 g, 0.67 mmol) in THF (3.6 mL, 44.1 mmol) and H₂O (0.3 mL) was stirred at 60° C. for 2 hours. The mixture was evaporated, the residue was taken up in water, acidified with HCl 3M (0.56 mL, 1.68 mmol), filtered and dried till dryness under vacuum (60° C.) to give 152 mg (87%) of compound (F19).

compound (F19)

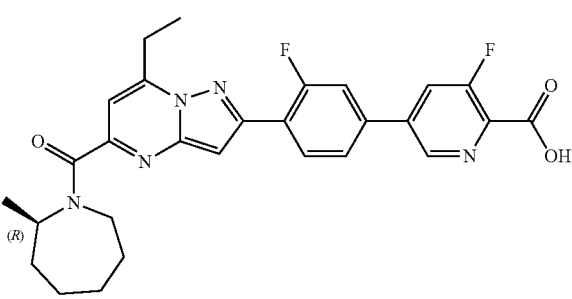

The following compounds were prepared according to the above procedure:

compound (F20)
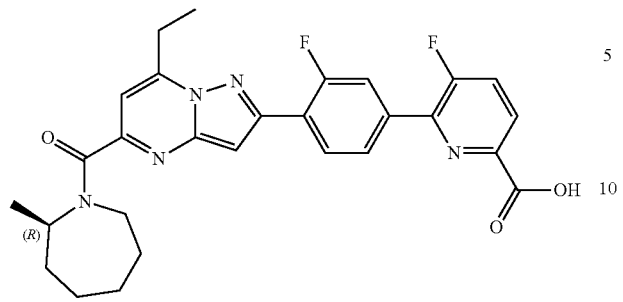
compound (F21)
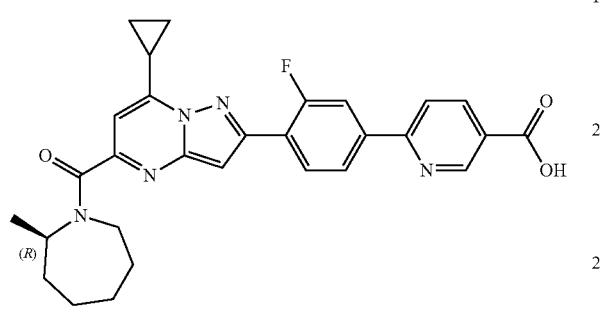
compound (F31)
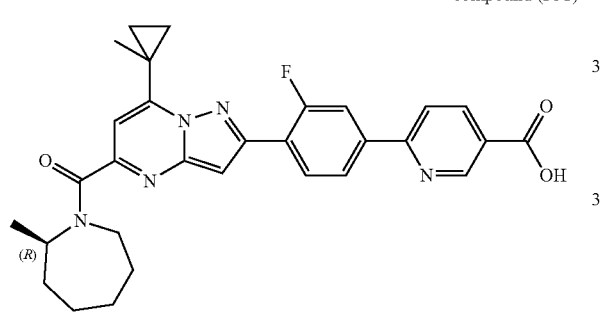
compound (F41)
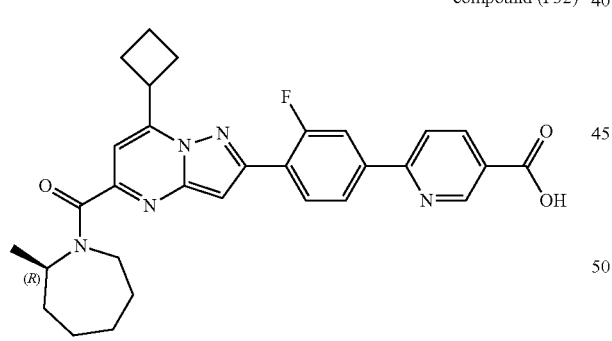
compound (F43)
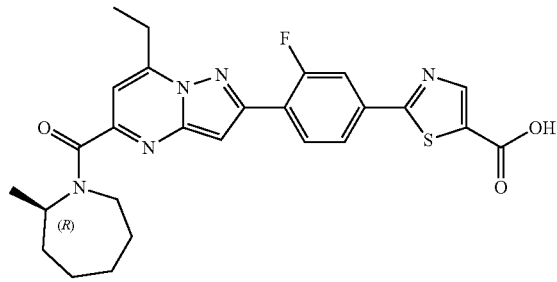
compound (F49)
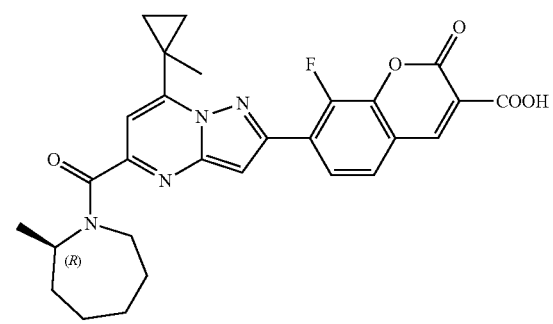
compound (F50)
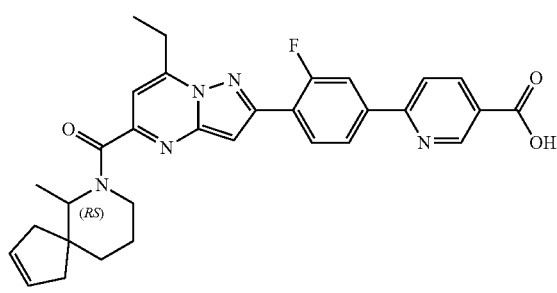
compound (F53)
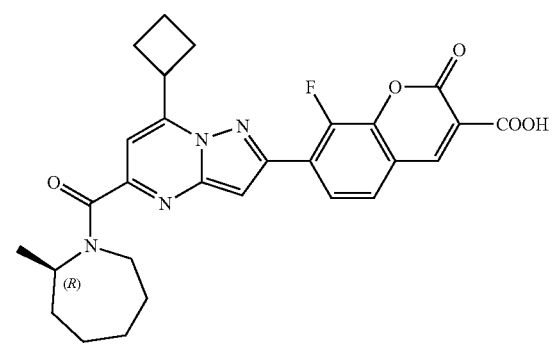
compound (F55)
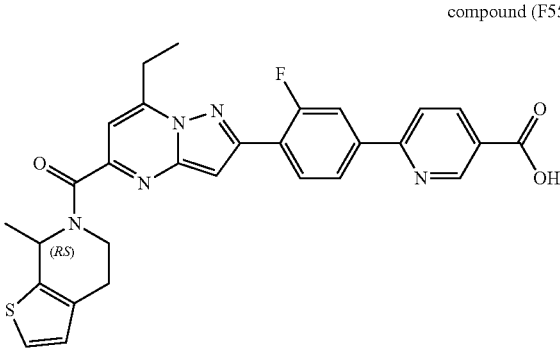
compound (F32)
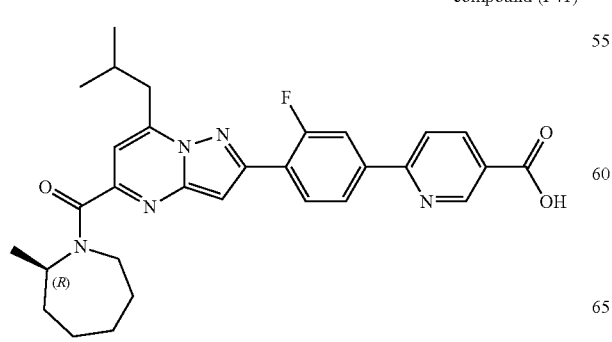
-continued compound (F56)

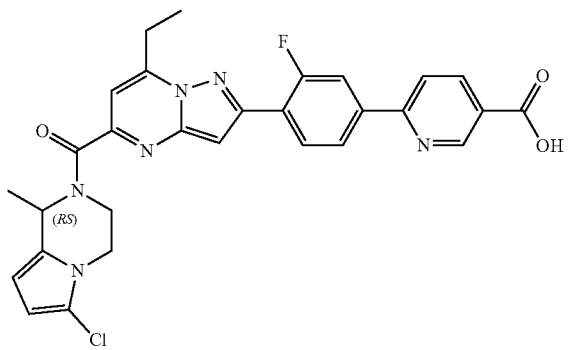

compound (F57)

compound (F58)

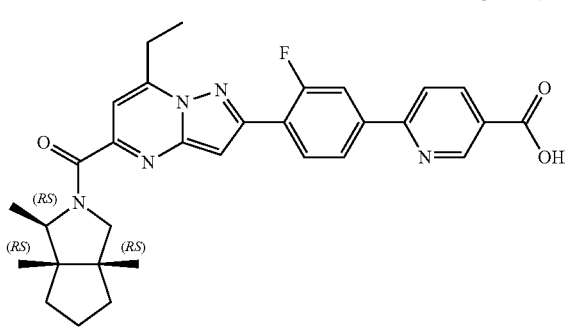

compound (F59)

compound (F60)

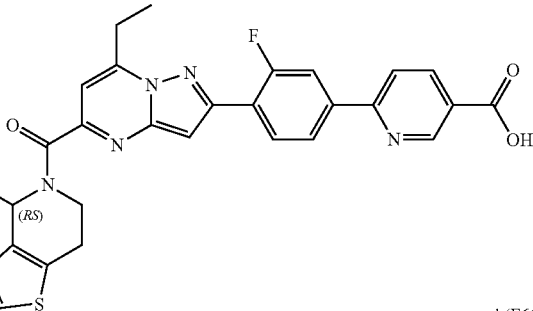

compound (F61)

Compound (F22):
A mixture of intermediate (G71) (0.085 g, 0.155 mmol) and KOH (0.043 g, 0.77 mmol) in EtOH (5 mL) was stirred at reflux for 1 hour The mixture was cooled down to RT and evaporated till dryness. The residue was taken up in water, HCl (3M in $H_2O$) (0.26 mL, 0.77 mmol) was added, the gel-like mixture was filtered, the solid was washed with water and dried (vacuum, 60° C.) to give 0.053 g, (64%) of compound (F22).

compound (F22)

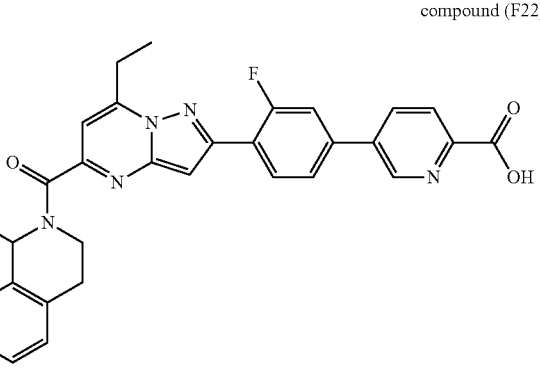

The following compound was prepared according to the above procedure:

compound (F23)

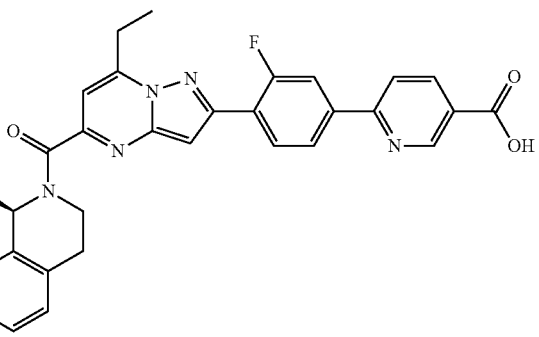

compound (F24)

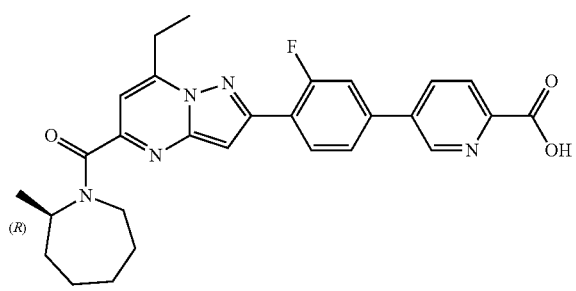

compound (F30)

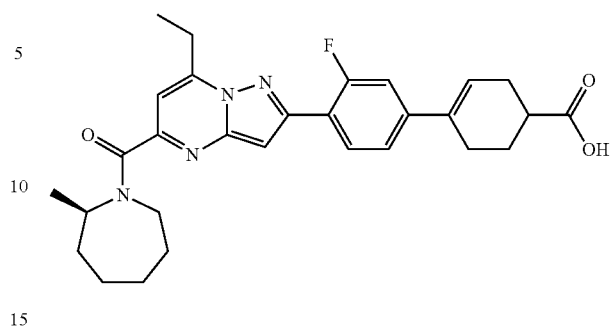

compound (F25)

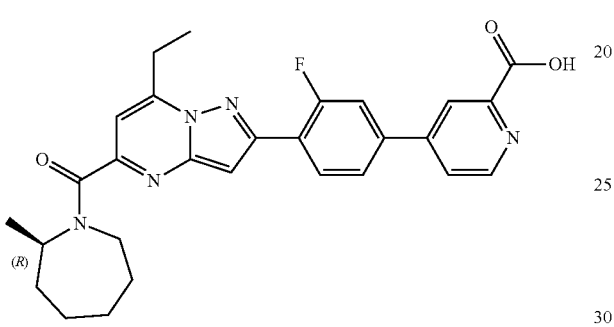

compound (F34)

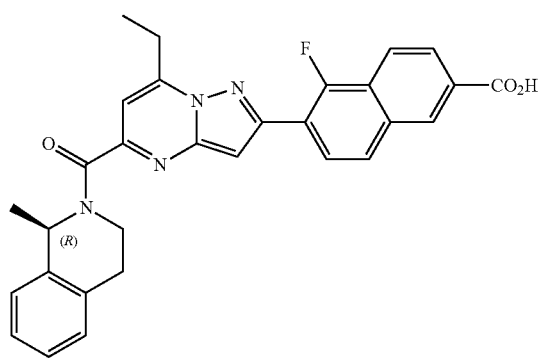

Compound (F29):

LiOH.H$_2$O (131 mg; 3.12 mmol) was added to a solution of intermediate (G90) (317 mg; 0.624 mmol) in THF (4.5 mL) and water (1.5 mL). The reaction mixture was stirred at RT for 16 hours. Then a solution of HCl 3M in CPME (1 mL; 3.12 mmol) was added and the reaction mixture was concentrated to give crude product which was purified by column chromatography (silica gel, from DCM/MeOH 100/0 to 80/20). The pure fractions were collected and evaporated to give a yellow solid. The solid was triturated in hot acetonitrile, filtered and dried under high vacuum (50° C., 18 hours) to give 143 mg (48%) of compound (F29) as a yellow solid.

compound (F36)

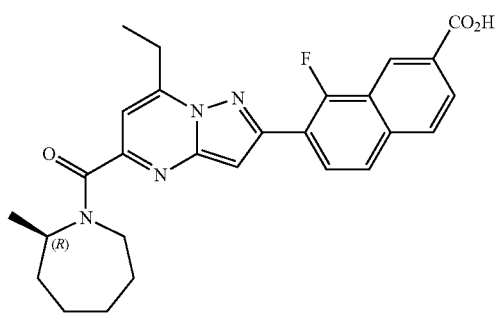

compound (F29)

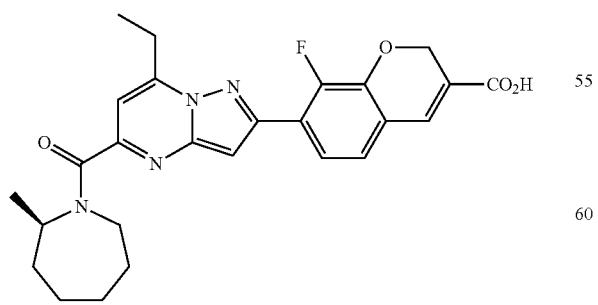

compound (F38)

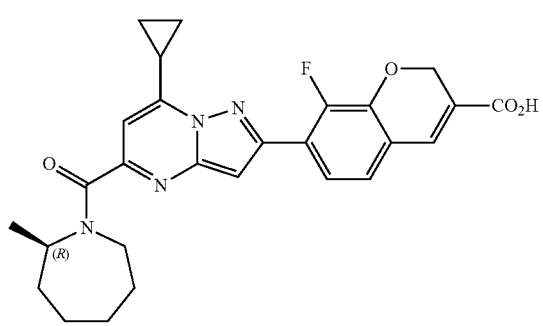

The following compound was prepared according to the above procedure:

compound (F39)
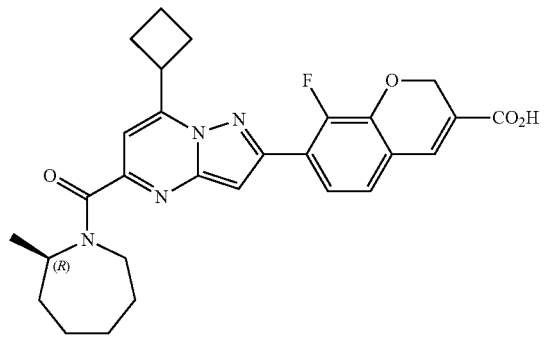
compound (F40)
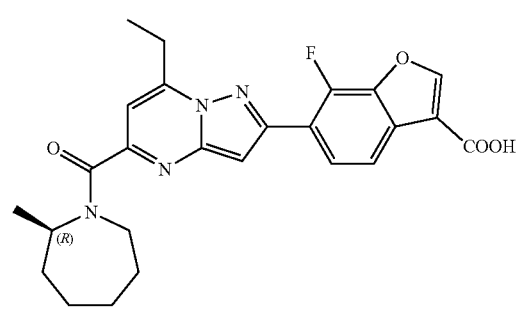
compound (F42)
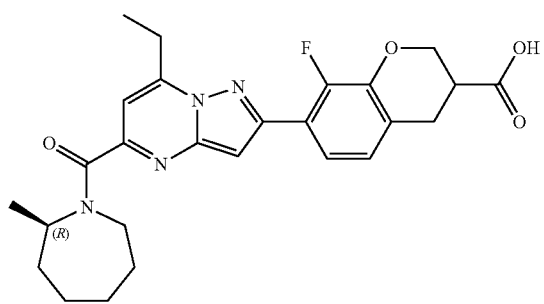
compound (F44)
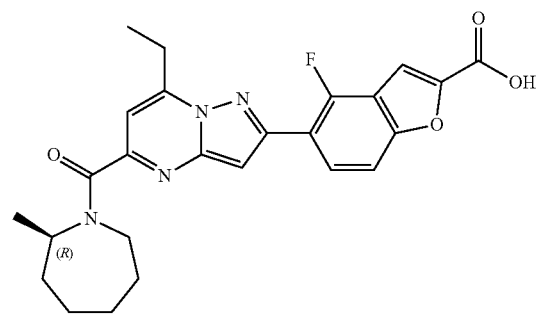
compound (F46)
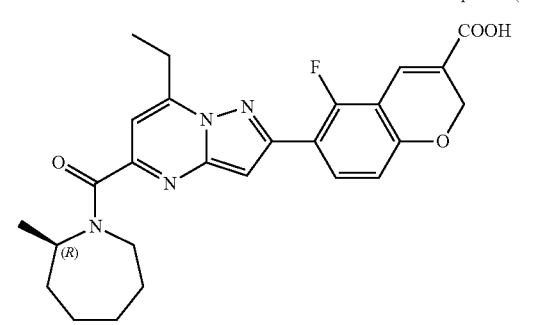
compound (F47)
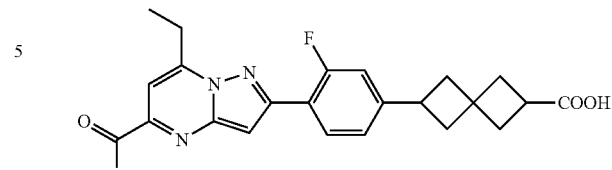
compound (F48)
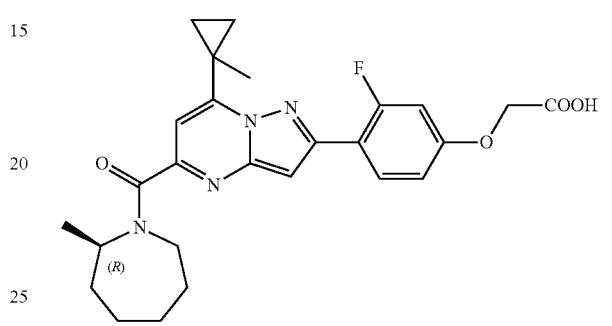
compound (F51)
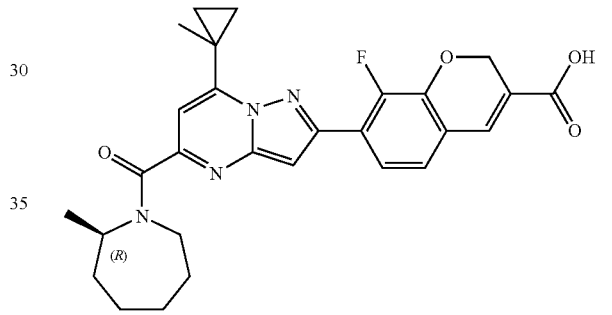
compound (F52)
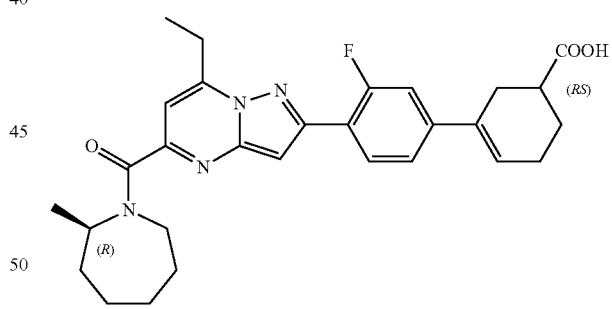
compound (F54)
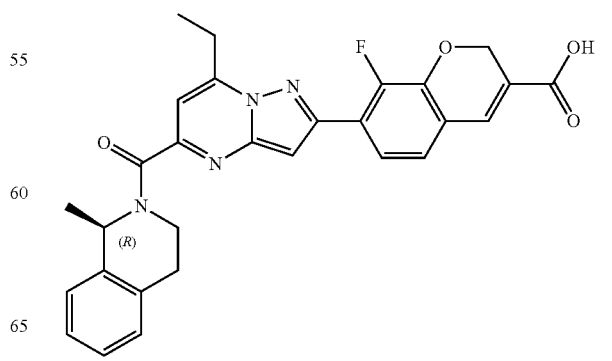

compound (F62)

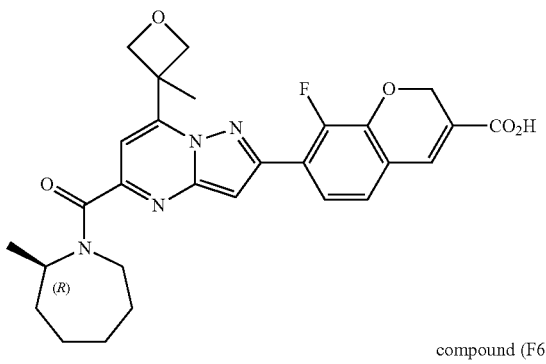

compound (F63)

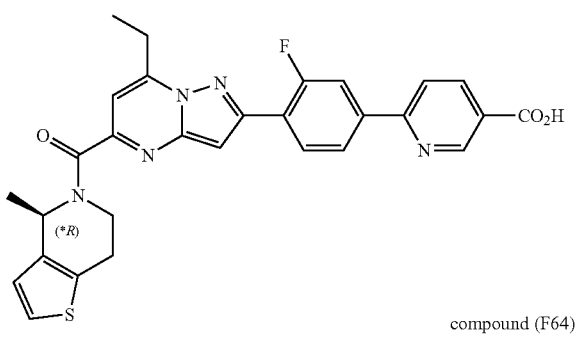

compound (F64)

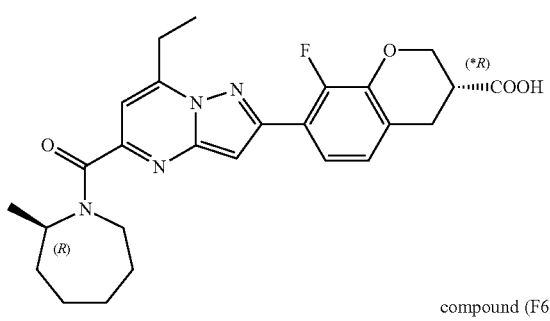

compound (F65)

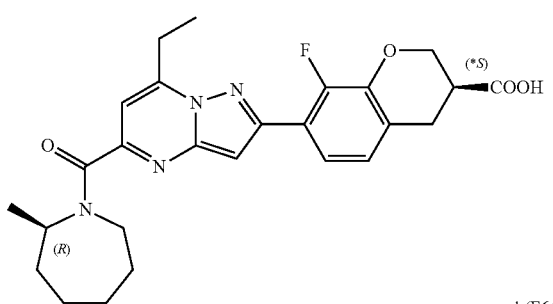

compound (F66)

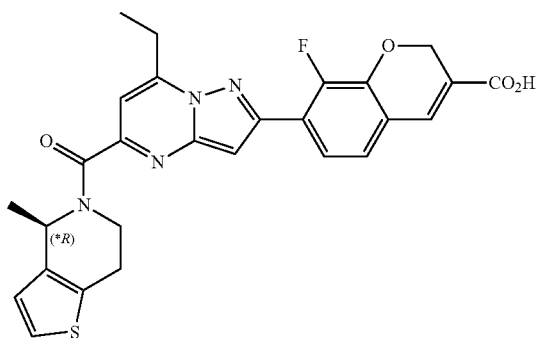

compound (F67)

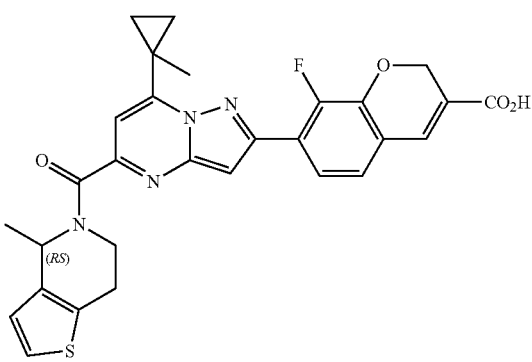

compound (F68)

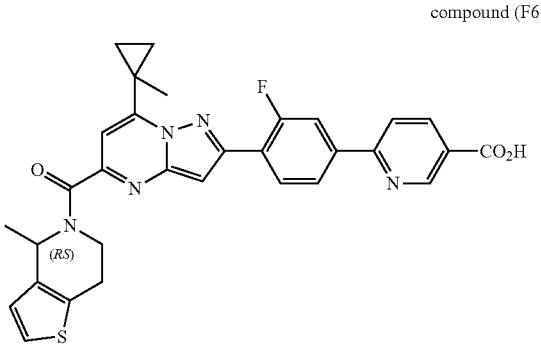

compound (F69)

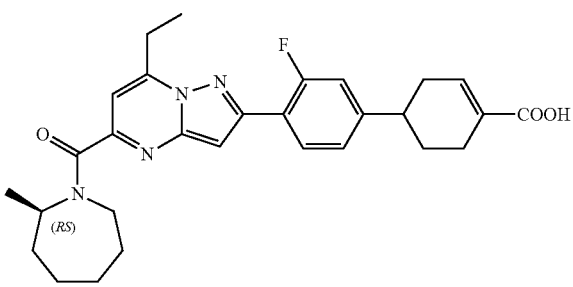

Compound (F36)

Intermediate (G105):

In a sealed tube, a solution of intermediate (G77) (500 mg; 0.84 mmol), intermediate (S8) (305 mg; 0.87 mmol) and K$_3$PO$_4$ (594 mg; 2.8 mmol) in 4-dioxane (10 mL) and H$_2$O (1.6 mL) was purged with N$_2$. PdCl$_2$(dtbpf) (55 mg; 84 µmol) was added, the mixture was purged again with N$_2$ and heated at 80° C. using a single mode microwave (Biotage® Initiator EXP 60) with a power output ranging from 0 to 400 W for 30 min [fixed hold time]. Water and EtOAc were added. The layers were separated. The organic layer was dried over MgSO$_4$, filtered and concentrated. This mixture was purified by preparative LC (Regular SiOH, 30 µm, 12 g Interchim®, dry loading (on SiOH), mobile phase gradient: from heptane/EtOAc 90/10 to 30/70) to give 374 mg (86%) of intermediate (G105) as a white solid.

intermediate (G105)

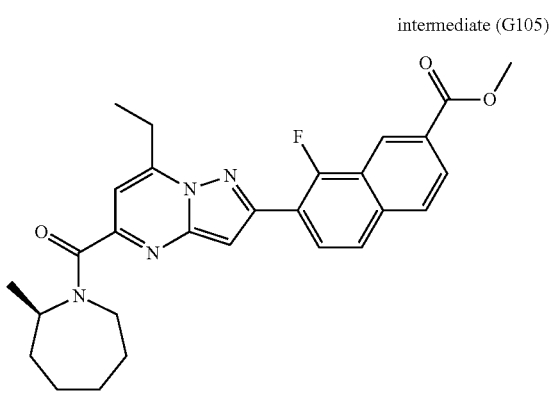

b) Compound (F36):

LiOH—H₂O (123 mg; 2.93 mmol) was added to a solution of intermediate (G105) (286 mg; 0.58 mmol) in H₂O (1.4 mL) and THF (4.3 mL) at rt and the reaction mixture was stirred at rt for 16 h. Then HCl 3 M (975 μL; 2.92 mmol) was added dropwise at rt and the reaction mixture was concentrated. It was purified by preparative LC (Regular SiOH, 30 μm, 12 g Interchim®, dry loading (on SiOH), mobile phase gradient: from DCM/EtOH 95/5 to DCM/(EtOH/AcOH 10%) 90/10) to give a beige residue which was taken up in EtOH. The precipitate was filtered and dried under high vacuum at 50° C. for 16 hours to give 187 mg (67%) of compound (F36) as a white solid.

compound (F36)

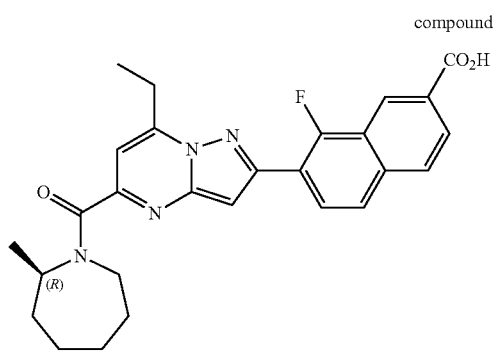

Compound (F37):

LiOH.H₂O (23 mg; 0.56 mmol) was added to a solution of intermediate (G91)(199 mg; 0.372 mmol) in THF (5 mL) and H₂O (2 mL). The mixture was stirred at rt overnight then heated at 50° C. for 3 days. HCl 3M in CMPE (100 μL; 0.3 mmol) was added (until pH=7) and the resulting mixture was stirred at rt overnight. The mixture was concentrated until dryness and purified by preparative LC (Irregular SiOH 15-40 μm, 10 g Merck®, dry loading (Celite®), mobile phase gradient: from DCM/MeOH/AcOH 100:0:0 to 95:5:0.5). The fractions containing product were combined and the solvent was removed in vacuo to give a yellow oil which was azeotroped with toluene (twice) to give 130 mg of a mixture of 2 diastereomers. The mixture was purified via Reverse phase (Stationary phase: X-Bridge-C18® 10 μm 30*150 mm, mobile phase: gradient from aq HCOONH₄ (0.6 g/L pH=3.5)/MeCN 60:40 to 0:100) to give 24 mg of compound (F37) (13%) as a yellow solid and 56 mg of cis isomer (30%) as a yellow solid.

compound (F37)

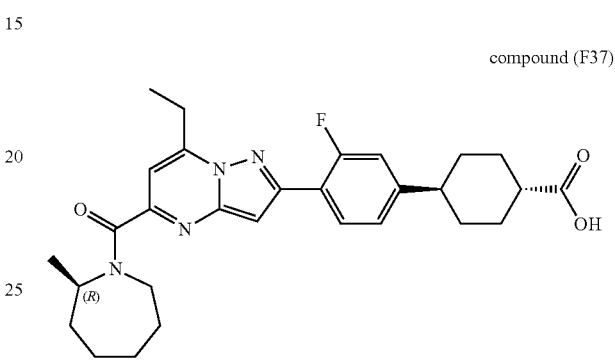

Compound (F35): In a sealed tube, a mixture of intermediate (G104) (267 mg; 0.503 mmol) and LiOH monohydrate (42 mg; 1.0 mmol) in THF (3 mL) and H2O (1.5 mL) was stirred at rt for 2 days. Brine, an aqueous solution of KHSO₄ (10%) and EtOAc were added to the reaction mixture, aqueous layer was extracted with EtOAc (twice). The combined organic layers were dried over MgSO₄, filtered and evaporated in vacuo.

The residue was triturated in DCM and the solid was filtered and dried to give 173 mg (68%) of compound (F35) as a white solid.

Compound (F35)

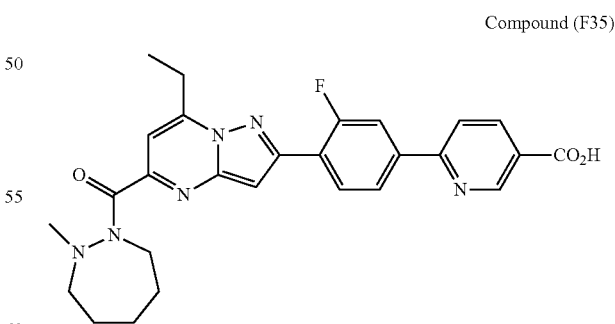

Compound (F45):

A suspension of intermediate (G156) (662 mg; 0.857 mmol) and K₂CO₃ (142 mg; 1.03 mmol) in H₂O (619 μL)

and NMP (15 mL) was degassed by N₂ bubbling for 15 min before the addition of Pd(OAc)₂ (19 mg; 85.7 µmol) and dppp (35 mg; 85.7 µmol). The resulting mixture was purged with CO (twice) then pressurised with CO (10 bar) and heated at 120° C. overnight. Water and EtOAc were added and the mixture was filtered through a pad of Celite® and the Celite® was rinsed with a mix of water and EtOAc. The layers were separated and the aqueous layer was extracted with EtOAc (twice). The aqueous layer was acidified by addition of aq HCl (3 N) then extracted with EtOAc (twice). The combined organic layers were washed with brine (3 times), dried over MgSO₄, filtered and concentrated in vacuo. The residue was purified by preparative LC (Regular SiOH 30 µm, 25 g Interchim®, dry loading (Celite®), mobile phase gradient: from DCM/MeOH 100:0 to 90:10). The fractions containing product were combined and the solvent was removed in vacuum. Water was added to the residue leading to precipitation, the solid was filtered off and dried under high vacuum. The solid was solubilized in a mixture of MeOH/THF (50:50) and then water was added. The mixture was partially evaporated leading to precipitation, the precipitate was filtered off and dried under high vacuum to give 27 mg (7%) of compound (F45) as an off-white solid.

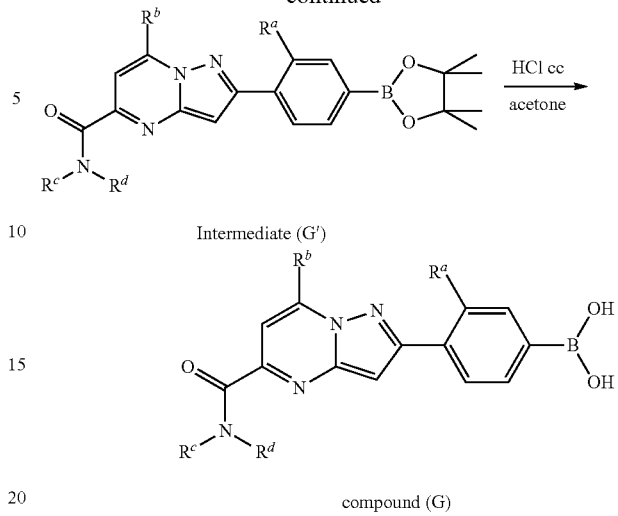

Compound (G1):

HCl cc (0.1 mL) was added to a mixture of intermediate (G29) (0.1 g, 0.2 mmol) in acetone (1 mL). The reaction mixture was stirred at RT overnight. The precipitate was filtered off, washed with hexane and dried to give 75 mg (90%) of compound (G1).

Compound (H), (I), (J), (K) and (L)

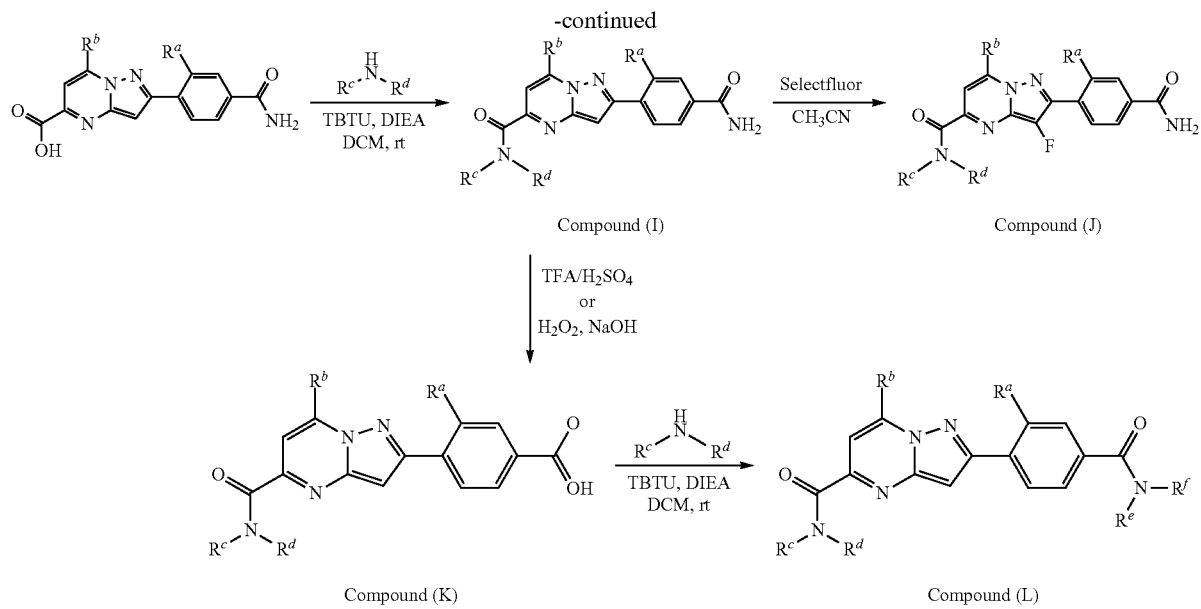

Compound (H) from Bromo by Cyanation:

Compound (H1):

Intermediate (G8) (0.72 g, 1.56 mmol), KCN (0.407 g, 6.3 mmol), CuI (50 mg) and Pd(PPh$_3$)$_4$ (0.360 g, 0.31 mmol) was dissolved in dry CH$_3$CN (25 mL). The reaction mixture was heated at 150° C. for 2 h using one single mode microwave (Biotage) with a power output from 0 to 400 W. The crude product was purified by HPLC to give 325 mg (51%) of compound (H1).

Compound (H1)

The following compound was prepared according to the above procedure:

compound (H2)

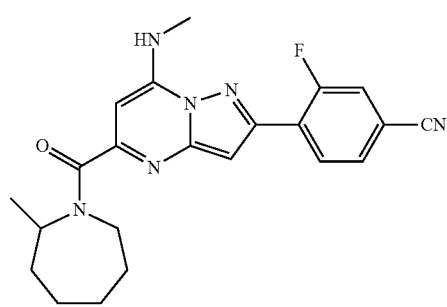

compound (H3)

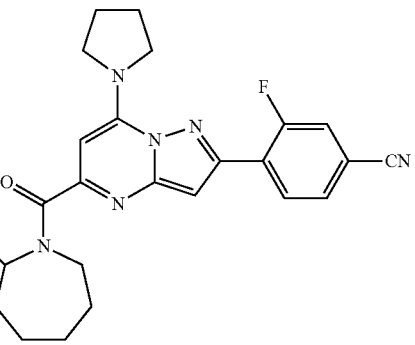

compound (H4)

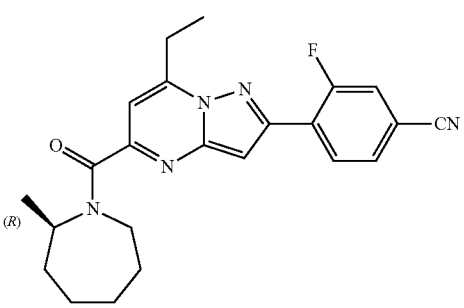

Compound (H) from amino via diazonium:

Compound (H5):

Sodium nitrite (0.12 g, 1.74 mmol) in water (4 mL) was added dropwise to a suspension of intermediate (G45) (0.54 g, 1.4 mmol), HCl cc (1.7 mL) in water (3.4 mL) and CH$_3$CN (6.5 mL) at 0° C. The reaction mixture was stirred at 0° C. for 1 h until the solid dissolution then an aqueous solution of Na$_2$CO$_3$ was added till pH 6-7. Simultaneously, a solution of CuSO$_4$,5H$_2$O (0.45 g, 1.8 mmol) in water (2 mL) was added dropwise to a solution of KCN (0.45 g, 6.9 mmol) in water (3 mL) at 0° C. Toluene (6 mL) was then added and the reaction mixture was heated at 60° C. for 1 hour. The diazonium salt solution was added dropwise over 15 min to this copper cyanide mixture at 60° C. The reaction

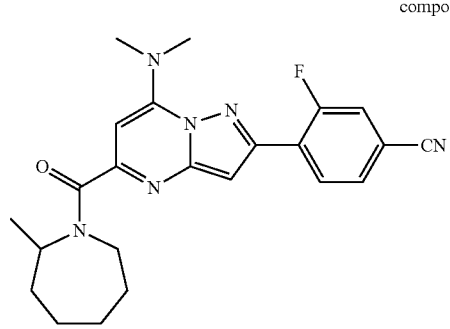

mixture was heated at 70° C. for 1.5 h, allowed to cool down to RT, partitioned between EtOAc and water and the aqueous layer was extracted with EtOAc (×3). The combined organic extracts were dried with sodium sulfate, filtered and evaporated. The solid was purified by column chromatography (silica gel, DCM/EtOAc (5/1)). The pure fractions were collected and the solvent was evaporated to give 0.28 g of compound (H5).

Compound (H5)

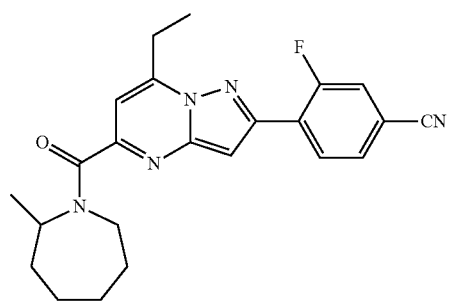

Compound (I1):

TBTU (0.05 g, 0.33 mmol) was added to a mixture of intermediate (E2) (0.1 g, 0.3 mmol), (2R)-2-methylazepane hydrochloride CAS ([331994-00-4], 0.045 g, 0.3 mmol) and DIEA (0.15 mL, 0.9 mmol) in DCM (1 mL). The reaction mixture was stirred at RT overnight. The reaction mixture was poured into water. The organic layer was separated, washed with brine, dried over sodium sulfate, filtered and evaporated till dryness. The residue was purified by column chromatography (silica gel, DCM). The pure fractions were collected and the solvent was evaporated to give 76 mg (61%) of compound (I1).

Compound (I1)

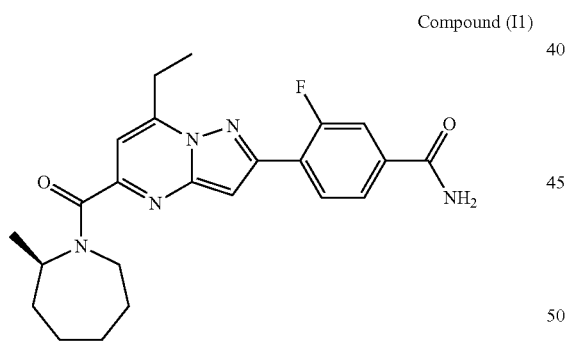

The following compounds were prepared according to the above procedure:

Compound (1)

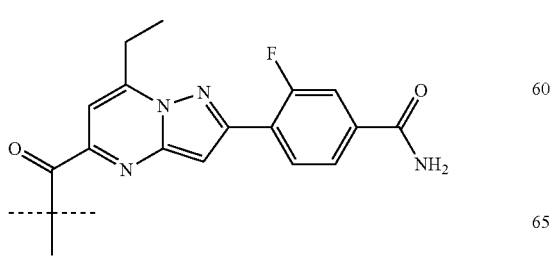

-continued (I2)

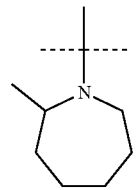

(I3)

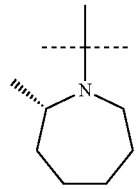

(I4)

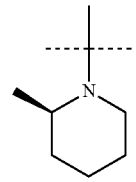

(I5)

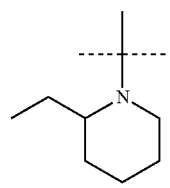

(I6)

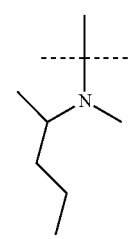

(I7)

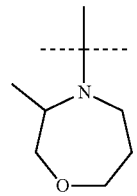

(I9)

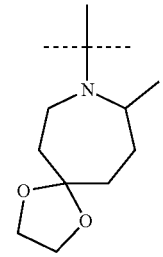

(I10)
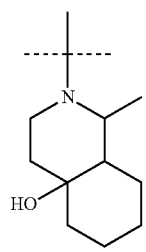
(I11)
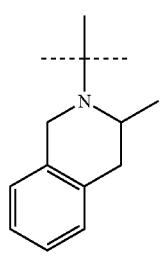
(I12)
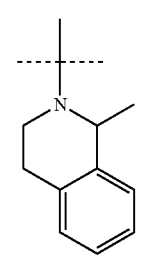
(I13)
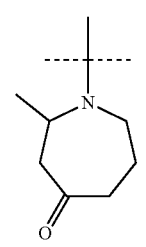
(I14)
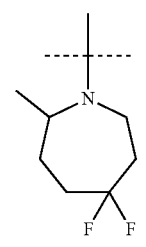
(I16)
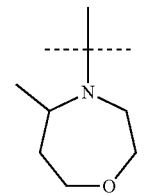
(I17)
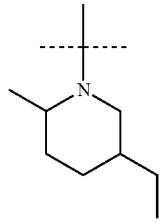
(I19)
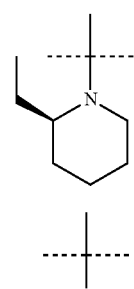
(I20)
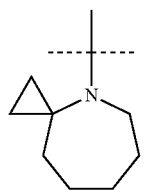
(I21)
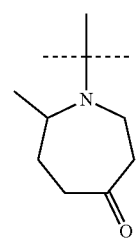
(I22)
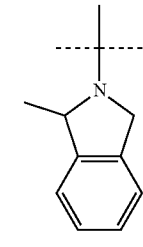
(I23)
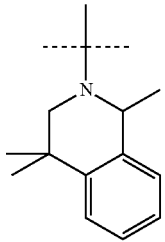
(I23)

-continued compound (I26)
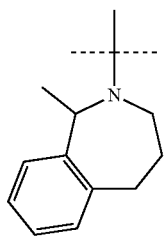

compound (I33)
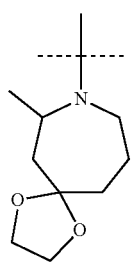

compound (I34)
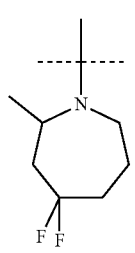

The following compounds were prepared according to compounds (I1):

compound (I35)
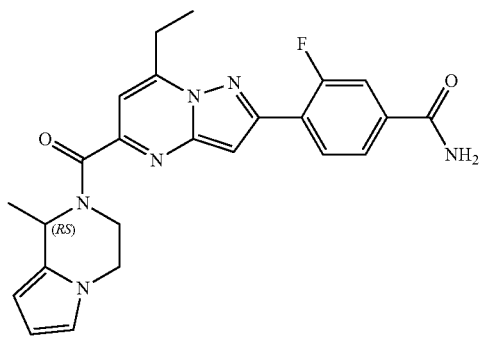

compound (I36)
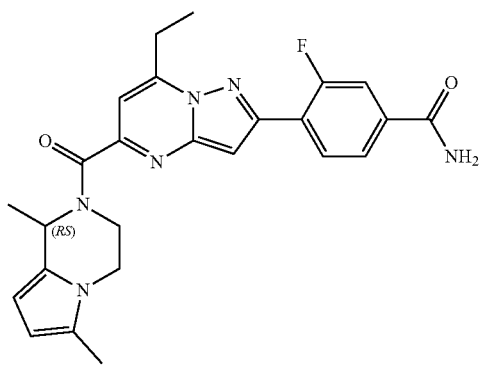

-continued compound (I37)
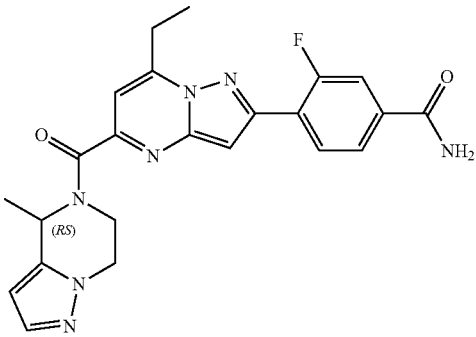

compound (I38)
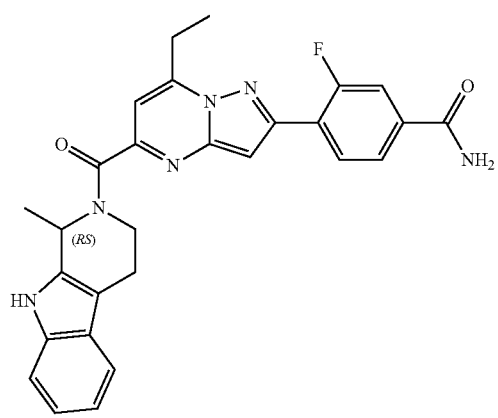

Compound (127):

A mixture of intermediate (G57) (120 mg, 0.28 mmol) in TFA/H$_2$SO$_4$ (2.5 mL, 4/1) was stirred at RT for 48 hours. The reaction mixture was diluted with water and a precipitate was filtered off, washed with water and dried to give 116 mg (93%) of compound (127).

Compound (I27)
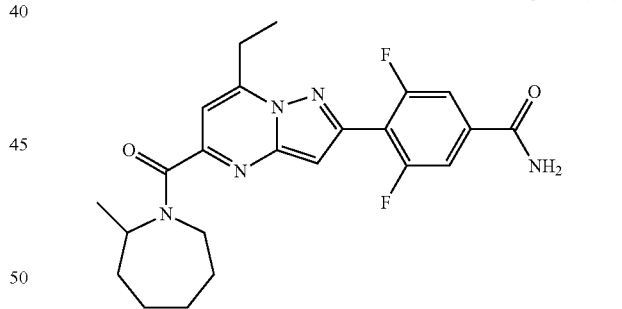

The compound (128) was also prepared according to the above procedure.

Compound (I28)
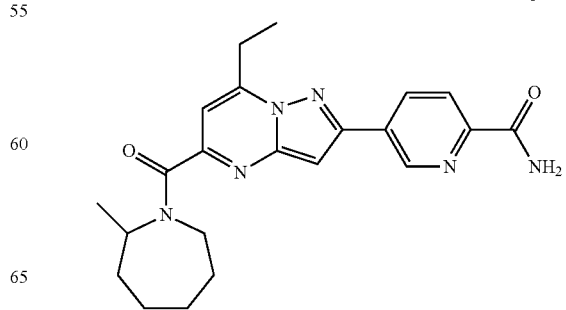

Compound (J1):

Compound (I) (0.2 g, 0.47 mmol) and NaHCO$_3$ (0.04 g, 4.8 mmol) were suspended in CH$_3$CN (5 mL) and heated at 60° C. A solution of Selectfluor® reagent (0.334 g, 0.94 mmol) in CH$_3$CN (3 mL) was added dropwise during 1.5 h to the previous mixture. The reaction mixture was stirred at that temperature for another hour and cooled to RT. The solution was diluted with EtOAc and washed with water. The organic layer was separated, dried over sodium sulfate, filtered and evaporated till dryness. The residue was purified by column chromatography to give 29 mg of compound (J1).

Compound (J1)

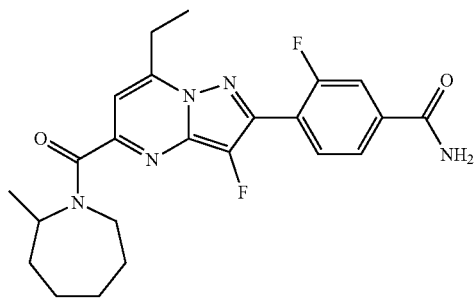

The compound (J2) was also prepared according to the above procedure.

Compound (J2)

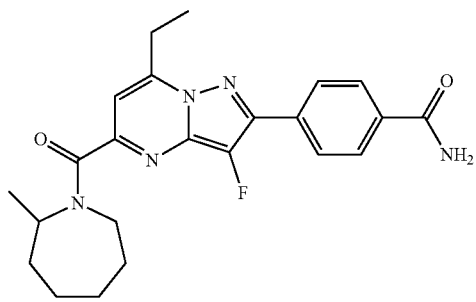

Compound (K1):

A mixture of compound (I) (100 mg, 0.22 mmol) in HCl cc (1 mL) was heated at reflux for 2 hours. The reaction mixture was poured into water and the resulting suspension was filtered. The precipitate was washed with water and dried to give 40 mg (40%) of compound (K1).

Compound (K1)

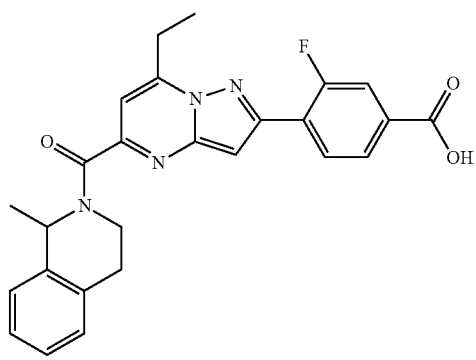

Compound (K2):

A mixture of compound (I) (200 mg, 0.47 mmol) in HCl cc (2 mL) was heated at reflux for 2 hours. The reaction mixture was poured into water and the resulting suspension was filtered. The precipitate was washed with water and dried to give 160 mg (80%) of compound (K2).

Compound (K2)

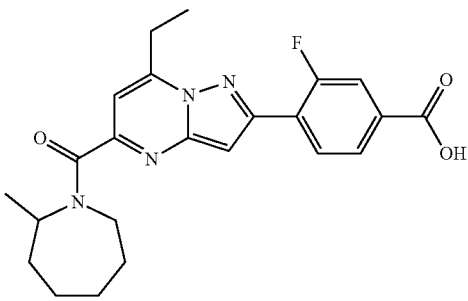

The compounds (K3) to (K9) were prepared according to the above procedure:

Compound (K3)

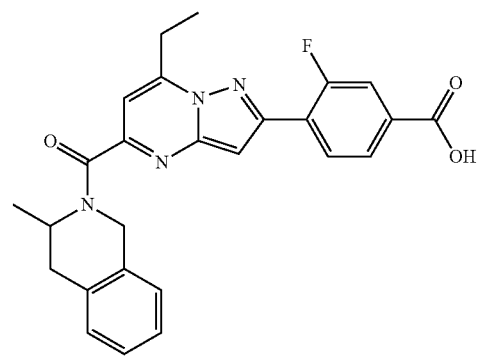

Compound (K4)

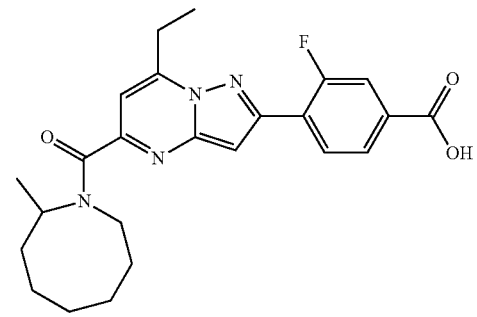

Compound (K5)

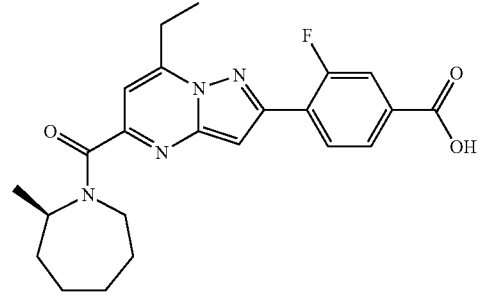

Compound (K6)

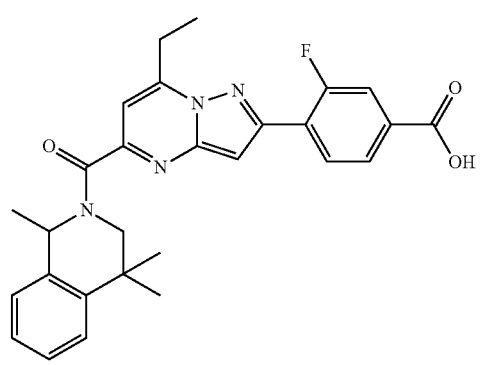

Compound (K8)

Compound (K9)

Compound (L1):
Compound (K2) (90 mg, 0.21 mmol), TBTU (0.31 mmol), DIEA (0.1 mL) and cyclopropylamine (0.26 mmol) were dissolved in DCM. The reaction was stirred at RT for 2 hours. The reaction mixture was poured into water and the organic layer was separated, washed with water, dried over sodium sulfate, filtered and evaporated till dryness. The residue was purified by column chromatography to give (78%) compound (L1).

Compound (L1)

The compounds (L2) to (L9) were prepared according to the above procedure.

Compound (L2)

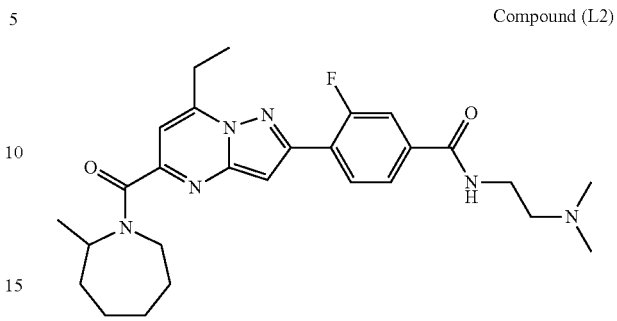

Compound (L3)

Compound (L4)

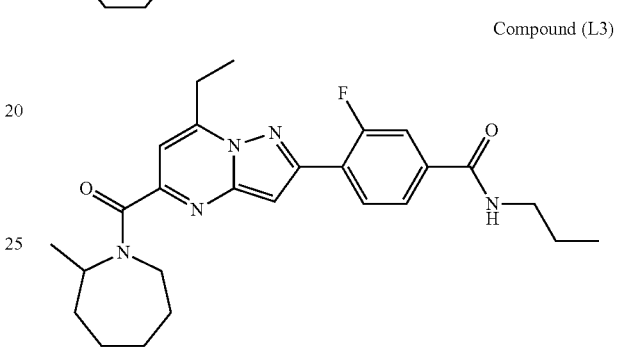

Compound (L5)

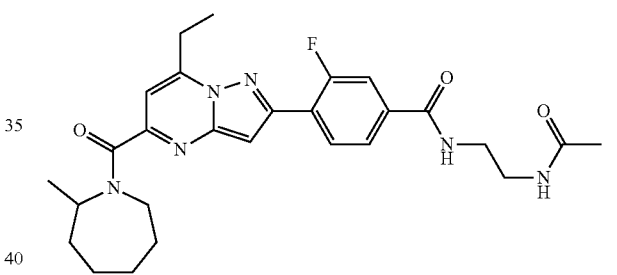

Compound (L6)

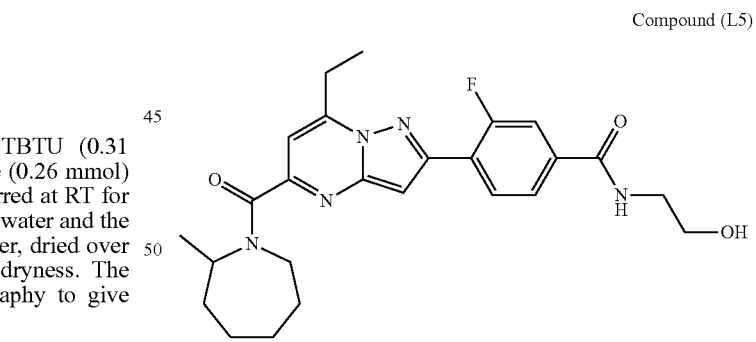

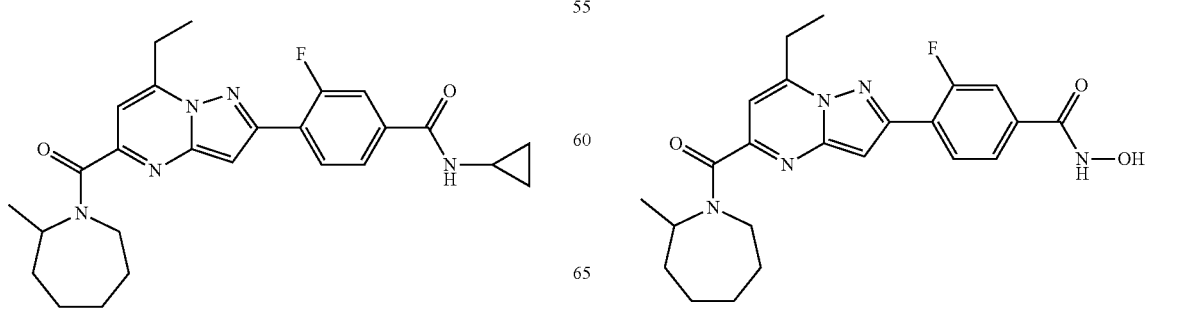

-continued

Compound (L7)

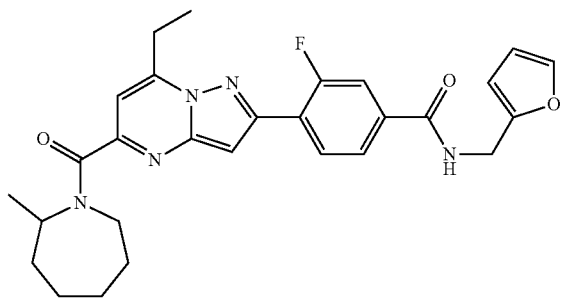

Compound (L8)

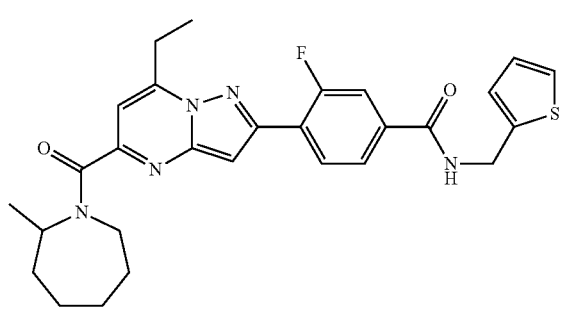

Compound (L9)

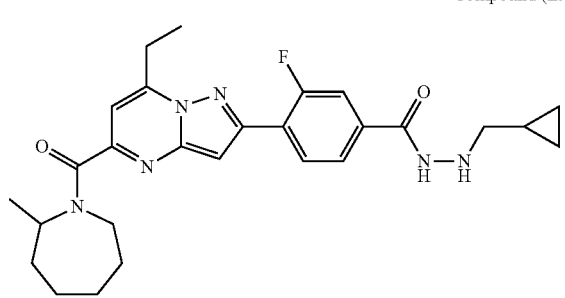

Compound (L10):

Compound (K2) (0.1 g, 0.24 mmol), TBTU (0.1 g, 0.31 mmol), DIEA (0.12 mL), methanesulfonamide (0.03 g, 0.32 mmol) and DMAP (0.1 g, 0.82 mmol) were dissolved in DCM. The reaction mixture was stirred at RT overnight. The reaction mixture was poured into water and the organic layer was separated, washed with water, dried over sodium sulfate, filtered and evaporated till dryness. The residue was purified by column chromatography to give 0.65 g of compound (L10).

Compound (L10)

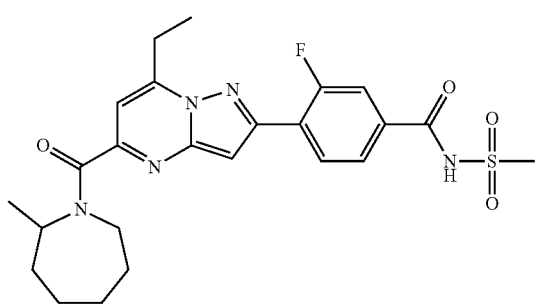

Reaction scheme:

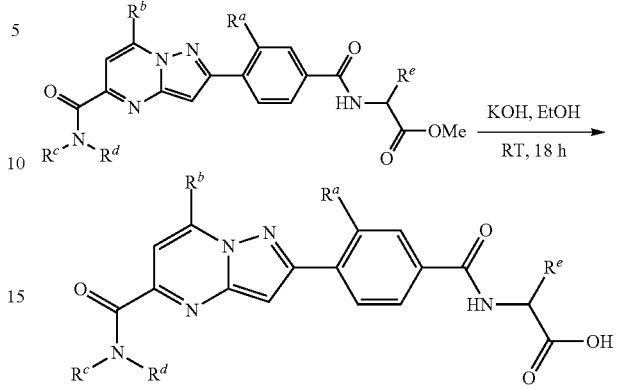

Compound (L11):

KOH (26 mg, 0.4 mmol) was added to a solution of intermediate (G59) (100 mg, 0.19 mmol) in EtOH. The reaction mixture was stirred at RT overnight. The mixture was poured into water and acidified with HCl to pH 3. The precipitate was filtered off, washed with water and dried to give 56 mg (56%) of compound (L11).

Compound (L11)

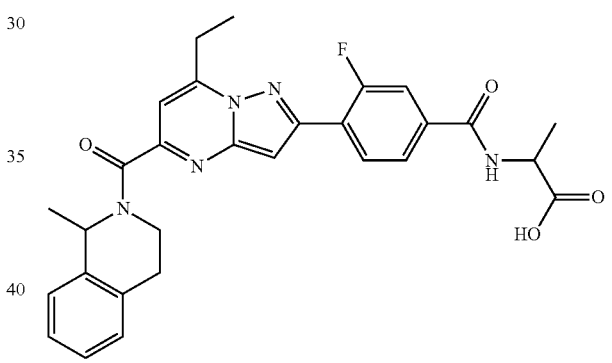

Compound (I) from Cyano (H) by Acidic Hydrolysis Compound (129):

A solution of compound (H1) (0.150 g, 0.37 mmol) in a mixture of TFA/H$_2$SO$_4$ (4/1) (15 mL) was stirred at RT for 24 hours. The mixture was poured into water and the precipitate was filtered off and dried to give 80 mg (51%) of compound (129).

Compound (I29)

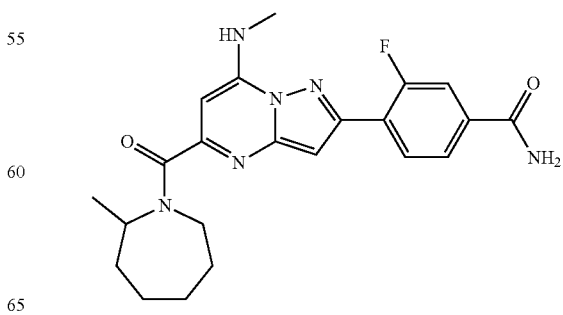

The following compounds were prepared according to the above procedure:

Compound (I30)

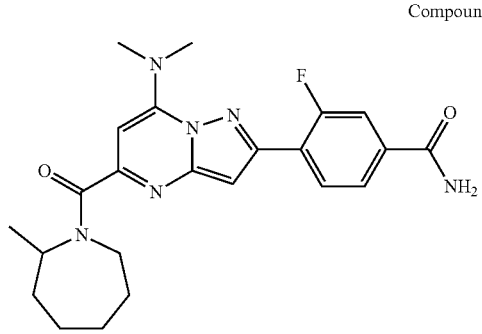

Compound (I31)

Compound (I) from Cyano (H) by Basic Hydrolysis
Compound (I32):

Compound (H3) (0.1 g, 0.23 mmol) was dissolved in MeOH, hydrogen peroxide 35% (0.025 mL, 0.025 mmol) and NaOH (5%, 0.1 mL) were added and the reaction mixture was stirred at 40° C. for 4 hours. Water was added and the precipitate was filtered off to give 55 mg (50%) of compound (I32).

Compound (I32)

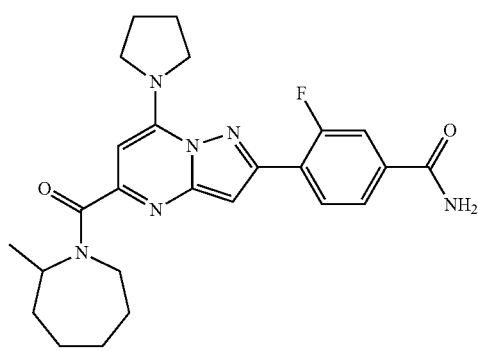

Compound (M) and (N)

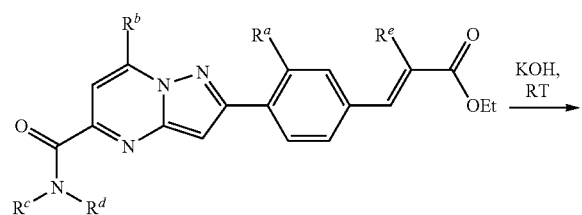

Compound (M)

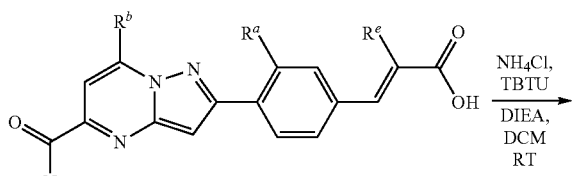

Compound (N)

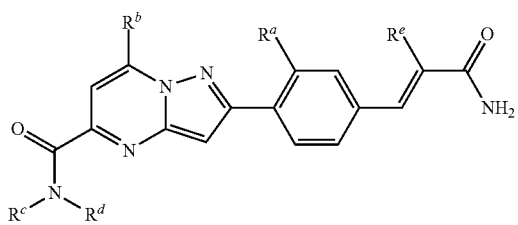

Compound (M1):

KOH (40 mg, 7.1 mmol) was added to a stirred solution of intermediate (G31) (170 mg, 3.6 mmol) in EtOH (5 mL). The reaction mixture was stirred at RT for 1 hour. The solvent was evaporated and the residue was poured into water and extracted with ether. The organic layer was separated and the aqueous one was acidified with HCl cc (0.1 mL) to pH 3. The precipitate was filtered off and dried to give 150 mg (94%) of compound (M1).

Compound (M1)

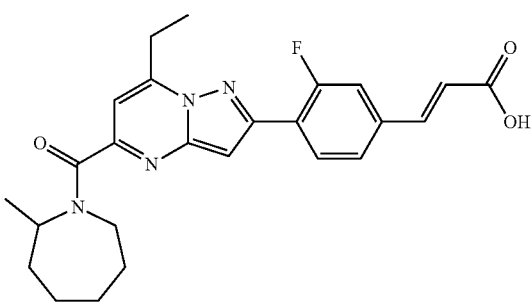

The compounds (M2) to (M13) were prepared according to the above procedure.

Compound (M3)

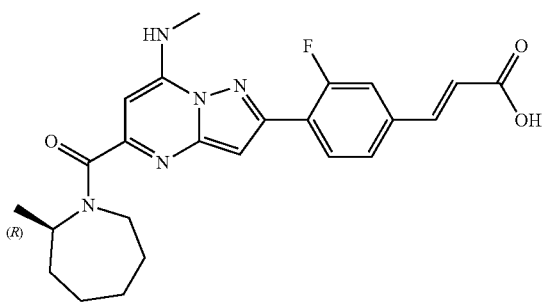

Compound (M4)
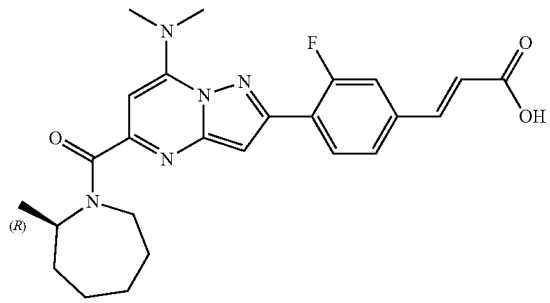
Compound (M10)
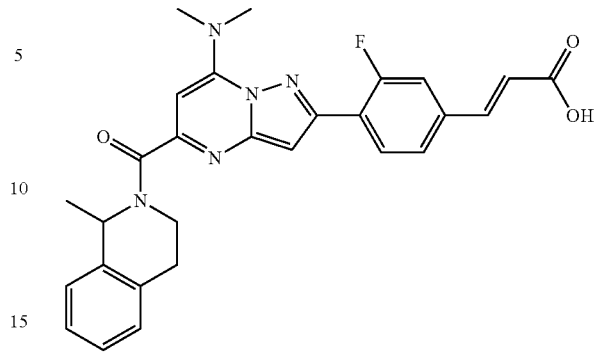
Compound (M6)
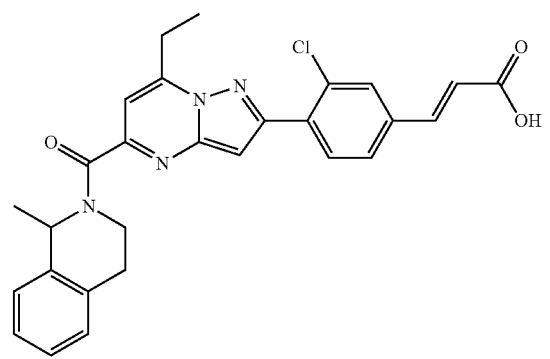
Compound (M11)
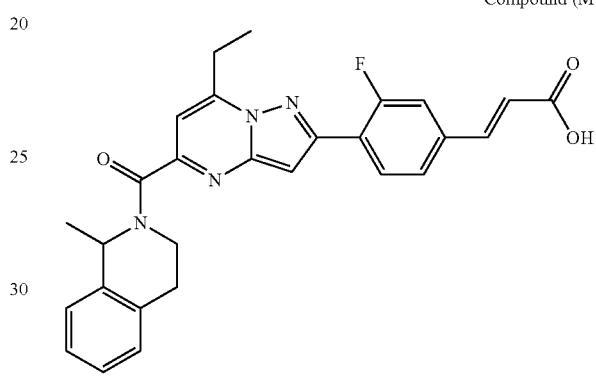
Compound (M7)
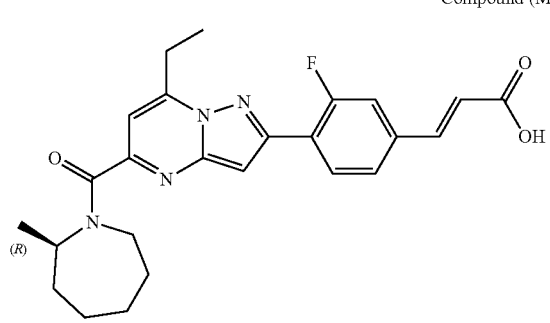
Compound (M12)
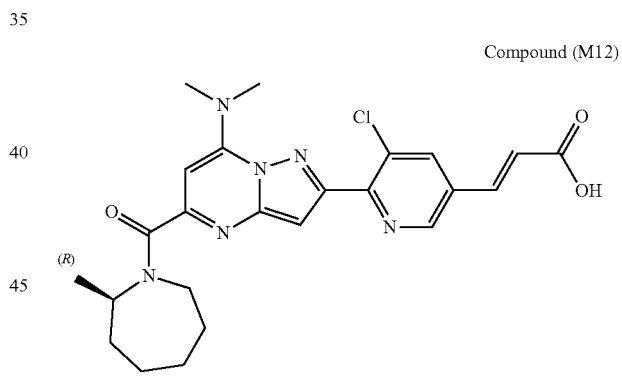
Compound (M8)
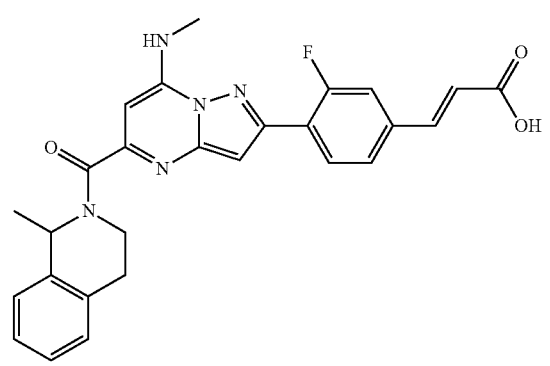
Compound (M13)
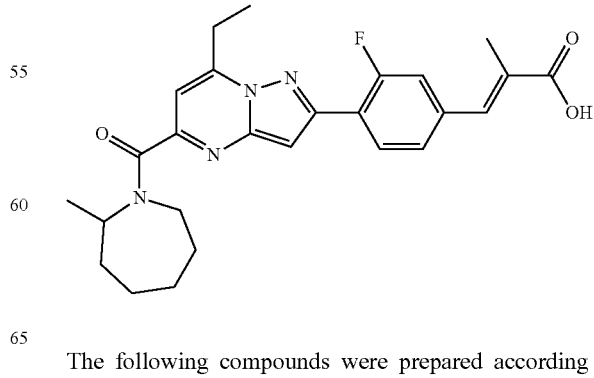
The following compounds were prepared according to compounds (M1):

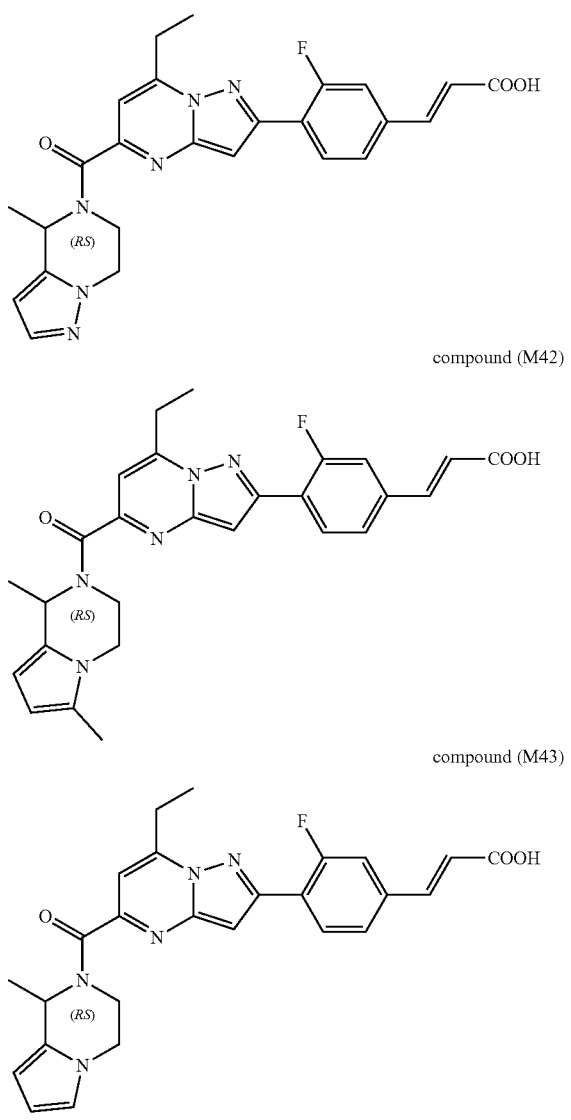

compound (M41)

compound (M42)

compound (M43)

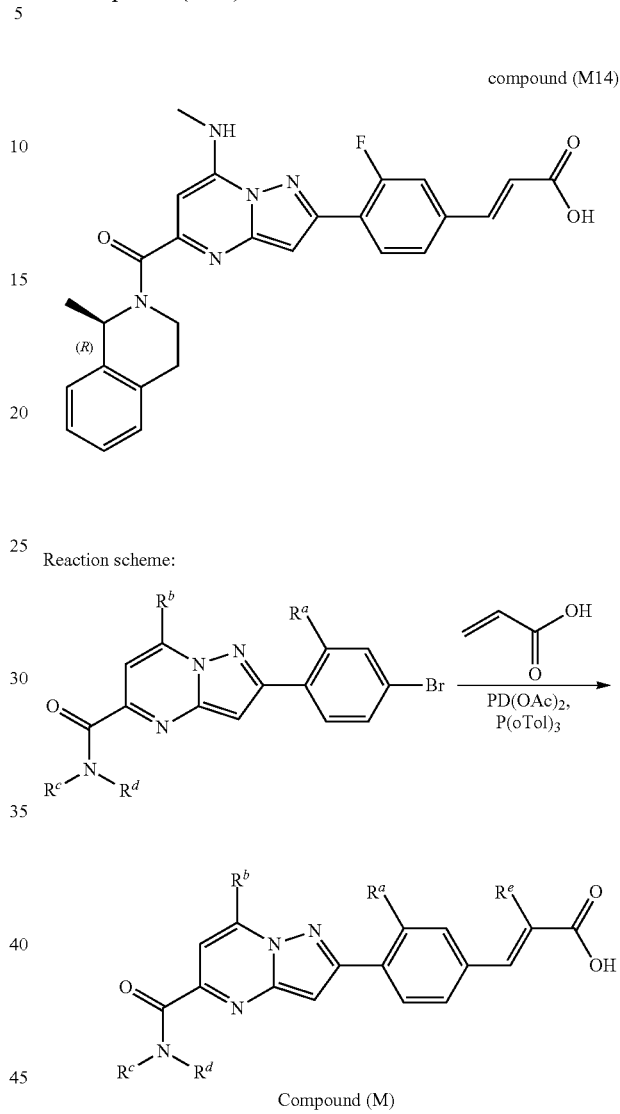

that was washed with DCM and 1 ml of HCl 1N, filtered on an hydrophobic frit, evaporated till dryness, taken up in Et$_2$O, filtered and dried under vacuum to afford 78 mg (24%) of compound (M14).

compound (M14)

Reaction scheme:

Compound (M)

Compound (M14):

A mixture of intermediate (G61) (0.35 g, 0.68 mmol) and LiOH.H$_2$O (57.2 mg, 1.36 mmol) in THF (2 mL), MeOH (2 mL) and H$_2$O (0.1 mL) was stirred at 60° C. for 1 hour. The mixture was cooled down to RT, the solvents were evaporated, the residue was taken up in few H$_2$O and HCl (3M in H$_2$O)(0.45 mL, 1.36 mmol) was added. The aqueous layer was separated extracted with CH$_2$Cl$_2$ and MeOH (50/50), dried over MgSO$_4$ and evaporated till dryness, crystallized from EtOH, filtered and dried to afford 220 mg of a residue which was purified by column chromatography (silica gel, from 98/2 to 95/5 CH$_2$Cl$_2$/MeOH). The pure fractions were collected and evaporated to dryness to afford 170 mg of an intermediate which was crystallized in EtOH, filtered and dried under vacuum (50° C.). This compound and the mother layer were purified via achiral SFC (Stationary phase: CYANO® 6 μm 150×21.2 mm, Mobile phase: 70% CO$_2$, 30% EtOH (0.3% iPrNH$_2$). The good fractions were collected and the solvent was evaporated to afford 150 mg of a crude product which was crystallized in Et$_2$O, filtered and dried under vacuum (50° C.) to afford of an intermediate Compound (M15):

A solution of intermediate (G62) (0.73 g, 1.48 mmol) in CH$_3$CN (8 mL) was degassed with nitrogen for 10 min. Acrylic acid (0.2 mL, 2.96 mmol), Pd(OAc)$_2$ (0.033 g, 0.15 mmol), tri-o-tolylphosphine (0.067 g, 0.22 mmol) and Et$_3$N (0.42 mL, 2.96 mmol) were added and the mixture was heated at 120° C. using a singlemode microwave (Biotage®initiator60) with a power output ranging from 0 to 400 W for 20 min. The reaction mixture was filtered through a short pad of Celite®, washed with DCM, water and HCl (3M in H$_2$O) was added to the filtrate, the organic layer was separated (hydrophobic frit) and evaporated to afford 980 mg of a residue. Purification of the residue was carried out by flash chromatography (silica gel, DCM/MeOH 97/3). The pure fractions were collected and evaporated to dryness to afford 610 mg of the good compound. This compound was crystallized in CH$_3$CN, filtered and dried under vacuum (50° C.) to afford 352 mg (49%) of (M15).

compound (M15)

The following compounds were prepared according to the above procedure.

compound (M19)

compound (M20)

compound (M21)

compound (M22)

compound (M24)

compound (M23)

compound (M28)

compound (M29)

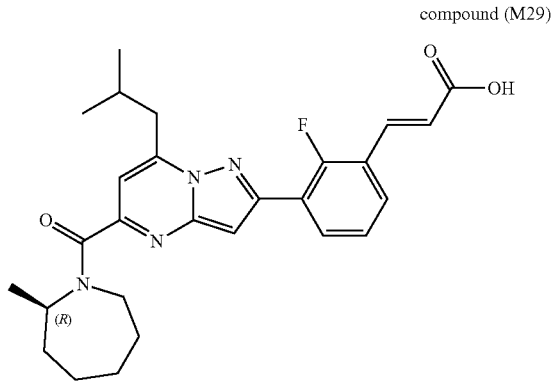

compound (M30)

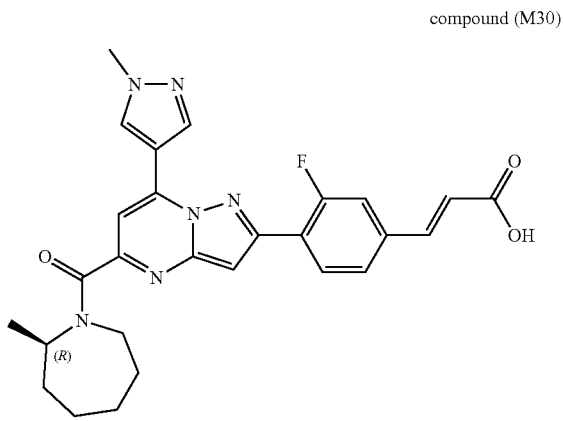

compound (M35)

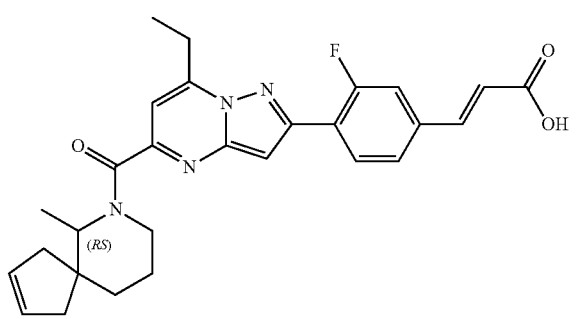

compound (M50)

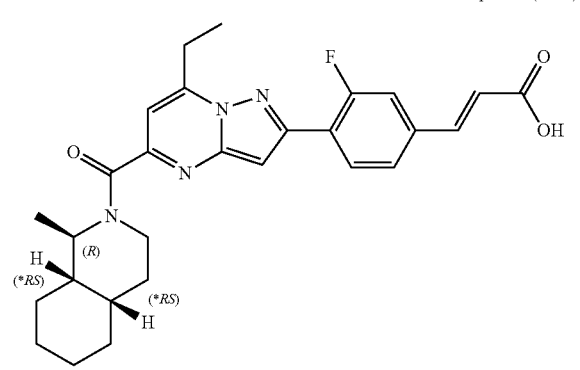

compound (M51)

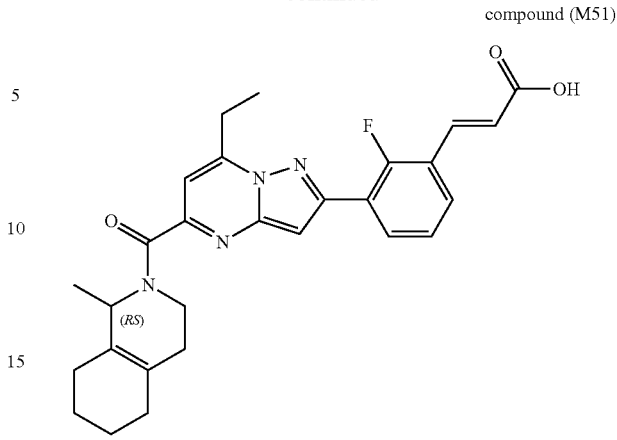

Compound (M16):

A solution of intermediate (G63) (0.3 g, 0.56 mmol) in CH$_3$CN (8 mL) was degased with nitrogen for 10 min. Acrylic acid (0.08 mL, 1.12 mmol), Pd(OAc)$_2$ (12.60 mg, 0.056 mmol), tri-o-tolylphosphine (25.63 mg, 0.084 mmol) and Et$_3$N (0.16 mL, 0.72 g/mL, 1.12 mmol) were added and the mixture was heated at 120° C. using a singlemode microwave (Biotag® initiator60) with a power output ranging from 0 to 400 W for 60 min. The reaction mixture was filtered through a short pad of Celite®, washed with DCM, water and HCl 3N was added to the filtrate, the organic layer was separated (hydrophobic frit) and evaporated. Purification of the residue was carried out by flash chromatography over silica gel (Grace Resolve® 24 g, 15-40 µm, DCM/MeOH 97/3). The pure fractions were collected and evaporated to dryness. The crude compound was taken up in DIPE, filtered and dried under vacuum (50° C.) to afford 46 mg (16%) of compound (M16).

compound (M16)

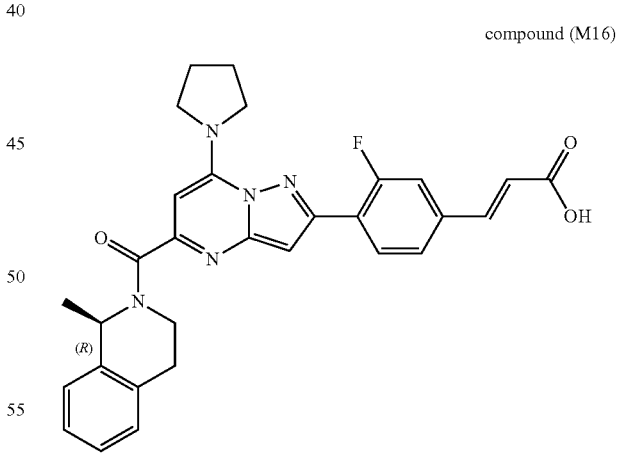

Compound (M17):

A solution of intermediate (G73) (0.19 g, 0.36 mmol) and LiOH—H$_2$O (0.030 g, 0.722 mmol) in THF (4 mL) and water (0.4 mL) was heated at 60° C. for 8 hours. The mixture was cooled down to RT, the precipitate (lithium carboxylate) was filtered off, washed with THF, taken up in water, HCl (3M in H$_2$O) (0.241 mL, 0.722 mmol) was added and the precipitate was filtered off, washed with water and dried (60° C., vacuum) to give 0.066 g (37%) of compound (M17).

compound (M17)
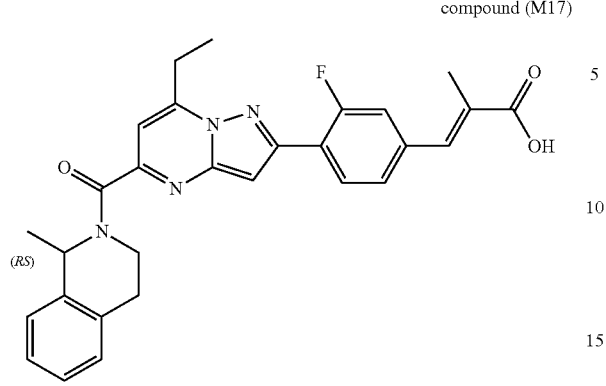
compound (M34)
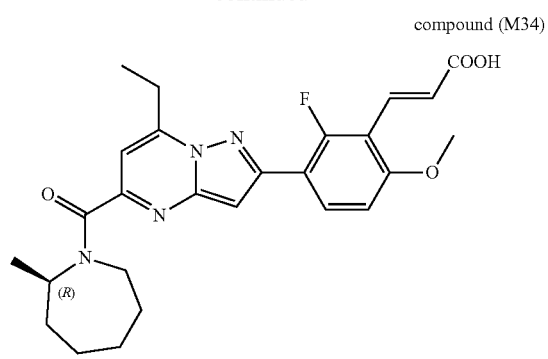
compound (M31)
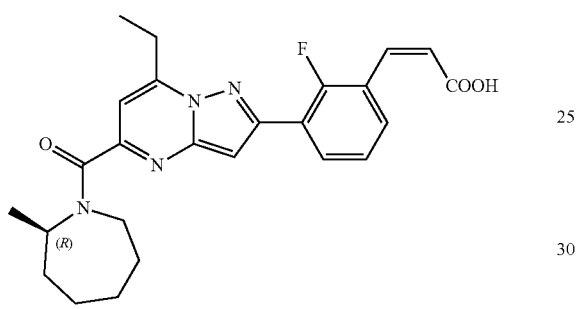
compound (M36)
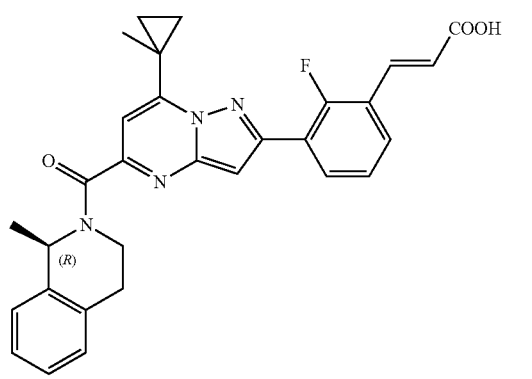
compound (M32)
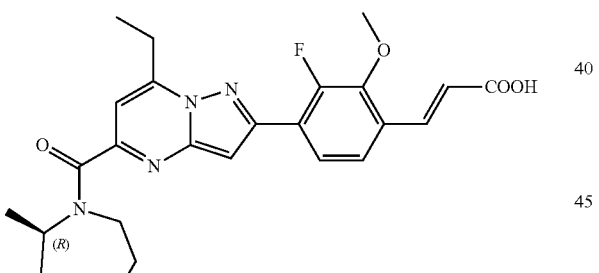
compound (M37)
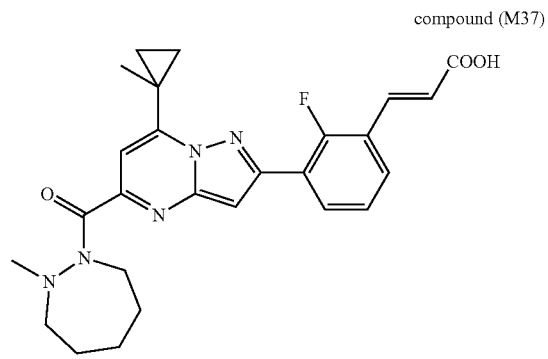
compound (M33)
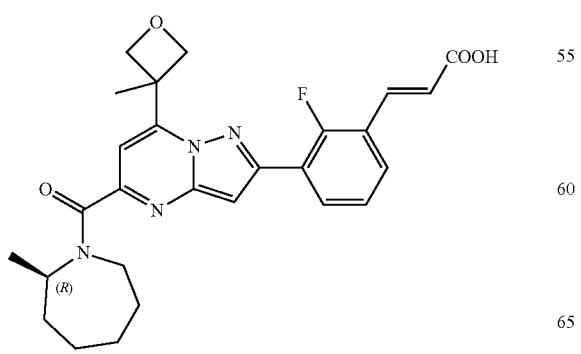
compound (M38)
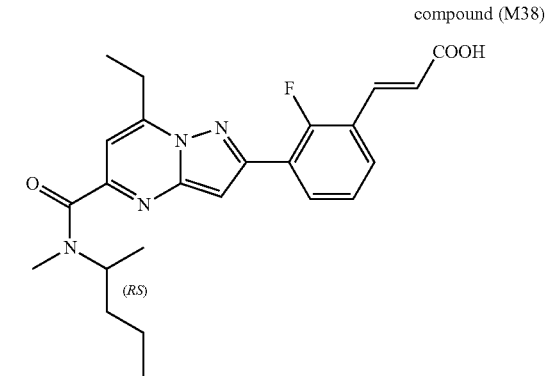

-continued compound (M39)

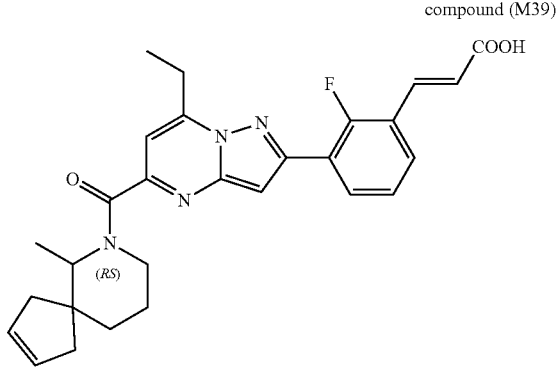

compound (M40)

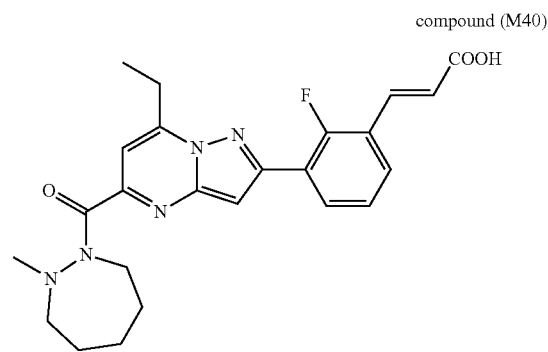

compound (M45)

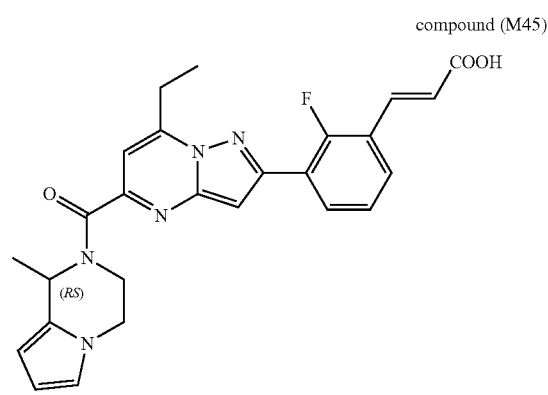

compound (M46)

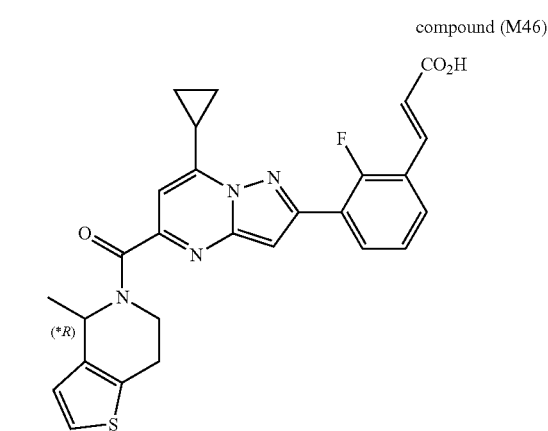

-continued compound (M47)

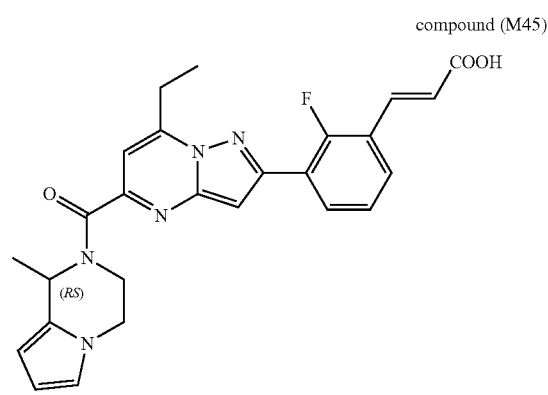

compound (M48)

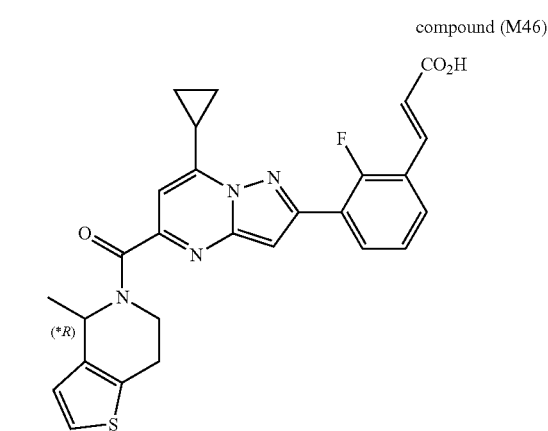

Compound (M18):

H$_2$SO$_4$ (0.060 mL; 1.12 mmol) was added to a solution of intermediate (G82) (220 mg; 0.397 mmol) in DCM (4 mL). The reaction mixture was stirred at RT overnight (precipitation occurred). The suspension was partitioned between DCM and water. Layers were separated and the aqueous layer was extracted with DCM (once). The organic layer was filtered to give a yellow solid and the filtrate was dried over MgSO$_4$, filtered and concentrated in vacuum. The solid and the residue were purified by column chromatography (silica gel, from DCM/MeOH/AcOH 100:0:0 to 90:10:1). The pure fractions were collected and the solvent was removed to give a colorless oil, which was azeotroped with toluene (twice). The residue was taken-up in CH$_3$CN, the solid was filtered and dried in vacuum to give 52 mg (26%) of compound (M18) as a white solid.

compound (M18)

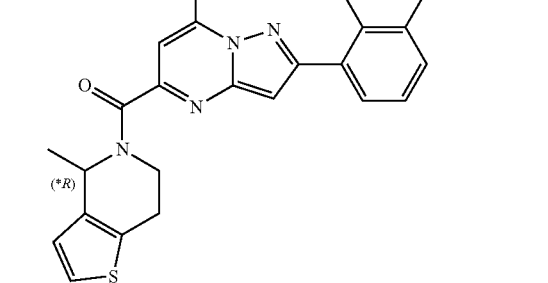

Compound (M25):

A mixture of intermediate (G81) (223 mg; 0.466 mmol) and LiOH.H₂O (29 mg; 0.70 mmol) in THF (2.5 mL) and H₂O (1.3 mL) was stirred at RT for 64 hours. HCl 3M in CPME (0.1 mL; 0.3 mmol) was added. The mixture was evaporated to dryness and the residue was purified by column chromatography (silica gel, from DCM/MeOH/AcOH 100/0/0.1 to 95/5/0.5) to give a gum which was taken-up with CH₃CN. The mixture was evaporated to dryness to afford 148 mg (71%) of compound (M25) as an off-white solid.

compound (M25)

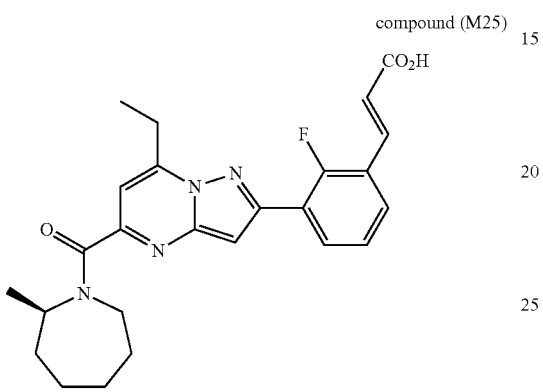

The following compound was prepared according to the above procedure:

compound (M26)

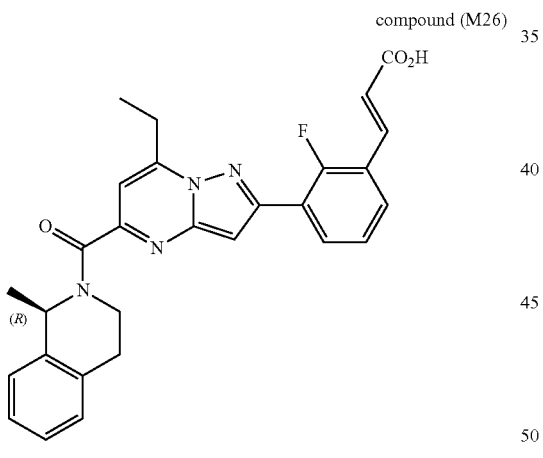

Compound (M27)
a) Intermediate (G318):

In a Schlenk tube, a solution of intermediate (G152) (1.46 g; 1.98 mmol; 62%), intermediate (R4) (0.65 g; 2.37 mmol) and K₃PO₄ (1.26 g; 5.93 mmol) in 1,4-dioxane (30 mL) and water (5 mL) was purged with N₂. PdCl₂(dtbpf) (0.13 g; 0.2 mmol) was added, the mixture was purged again with N₂ and heated at 80° C. for 2 h. EtOAc and water were added. The layers were separated and the organic layer was washed with brine (twice), dried over MgSO₄, filtered and concentrated to give brown oil. This oil was purified by preparative LC (irregular SiOH 15-40 μm, 50 g Grace Resolv®, liquid loading (DCM), mobile phase gradient: from heptane 90%/EtOAc 10% to heptane 50%/EtOAc 50%) to give 943 mg (86%) of intermediate (G318) as a pale brownish gum.

intermediate (G318)

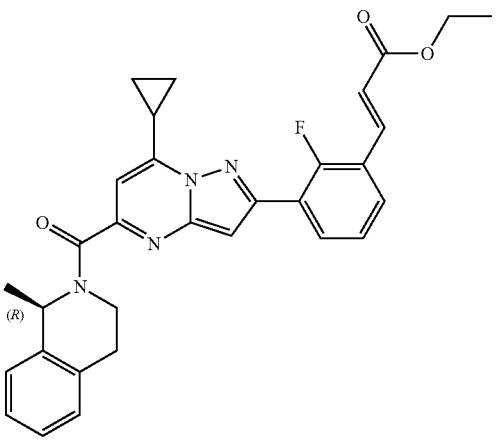

b) Compound (M27):

LiOH.H₂O (0.22 g; 5.14 mmol) was added to a solution of intermediate (G314) (0.94 g; 1.71 mmol) in water (7 mL) and THF (19 mL). The reaction mixture was stirred at rt for 18 h. Brine, aqueous solution of KHSO₄ (10%) and EtOAc were added to the reaction mixture, aqueous layer was extracted with EtOAc (twice). The combined organic layers were washed with water/brine 1/1, dried over MgSO₄, filtered and evaporated in vacuum to give a yellowish gum which was triturated in CH₃CN, filtered and dried on frit to give 0.77 g (90%) of compound (M27) as an off-white solid.

compound (M27)

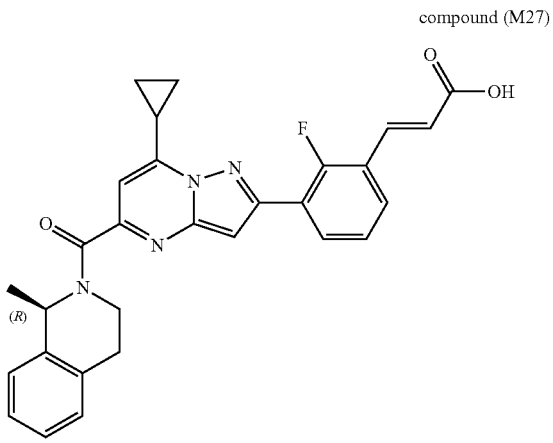

Compound (M44):

Separation of compound (M43) (1.755 g) was performed via chiral SFC (Stationary phase: Chiralpak AD-H® 5 μm 250*30 mm, Mobile phase: 45% CO₂, 55% MeOH). The pure fractions were collected and the solvent was evaporated to afford 0.88 g of the first enantiomer (*R) as iPrNH₂ salt and 0.948 g of the second enantiomer (*S) as iPrNH₂ salt. A purification of the first fraction was performed via preparative LC (Stationary phase: irregular 15-40 μm 50 g Merck®, Mobile phase: Gradient from 95% DCM, 5% MeOH to 0.1% H₂O, 90% DCM, 10% MeOH) to give 0.73 g (42%). The residue was dissolved in hot EtOH, crystallization occurred on standing at rt, the solid was filtered off and dried (60° C., vacuum) to give 0.558 g (32%) of compound (M44).

compound (M44)

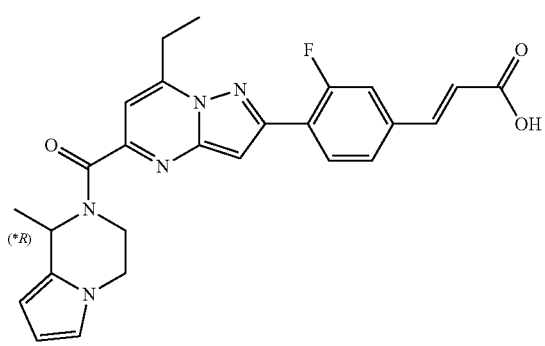

Compound (M46)
a) Intermediate (D55):

A mixture of 2-Butenoic acid, 4-cyclopropyl-2-hydroxy-4-oxo-, ethyl ester (11.4 g, 61.89 mmol) and 5-bromo-1H-pyrazol-3-amine (12.19 g, 47.61 mmol) in EtOH (90 mL) was stirred at reflux for 2 h. The mixture was cooled to 5° C. and the precipitate was filtered off, washed with cold EtOH and dried. Purification was performed via preparative LC (Stationary phase: irregular SiOH 40 μm 200 g, Mobile phase: 100% DCM). The good fractions were collected and the solvent was evaporated to afford 9.4 g (49%) of intermediate (D55).

intermediate (D55)

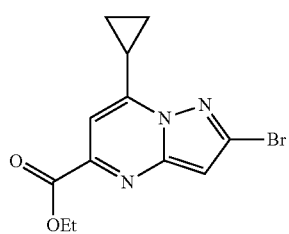

b) Intermediate (E56):

KOH (10.4 g; 16 mmol) was dissolved in EtOH (340 mL) then intermediate (E56) (15.5 g; 52.3 mmol) was added portionwise and the suspension was stirred at reflux for 4 h. The mixture was cool down, the precipitate was filtered off, washed with cold EtOH then Et₂O and dried under vacuum to give 16.5 g (98%) of intermediate (E56) as a white solid.

intermediate (E56)

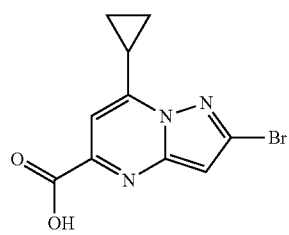

c) Intermediate (G257):

A mixture of intermediate (E56) (2 g; 6.25 mmol), intermediate (F22) (1.15 g; 7.50 mmol), HATU (4.6 g; 12.1 mmol) and DIEA (4.3 mL; 25.0 mmol) in DMF (36 mL) was stirred at rt for 20 h. A sat. aq. solution of NaHCO₃, brine and EtOAc were added to the reaction mixture. The layers were separated. The aqueous layer was extracted twice with EtOAc. The combined organic layers were washed with brine (4 times), dried over MgSO₄ and evaporated in vacuum. The crude compound was purified by preparative LC (irregular SiOH 15-40 μm, 50 g Grace Resolv®, liquid loading (DCM), mobile phase gradient: from heptane 90%, EtOAc 10% to Heptane 50%, EtOAc 50%) to give 2.9 g of intermediate (G257) as a yellowish gum.

intermediate (G257)

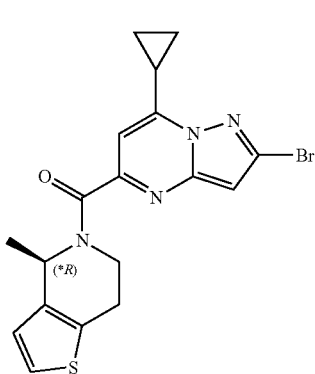

d) Intermediate (G267):

Under N₂, in sealed tube, bispin (2.2 g; 8.66 mmol) and KOAc (1.13 g; 11.6 mmol) were added to a solution of intermediate (G 257) (2.41 g; 5.78 mmol) in 1, 4-dioxane (27 mL). The solution was purged with nitrogen and charged with PdCl₂(dppf) (473 mg; 0.58 mmol). The resulting solution was purged again with nitrogen and stirred at 100° C. for 5 h. EtOAc was added. The organic layer was washed with water and brine (twice), dried over MgSO₄ and concentrated to give 5.14 g of intermediate (G267).

intermediate (G267)

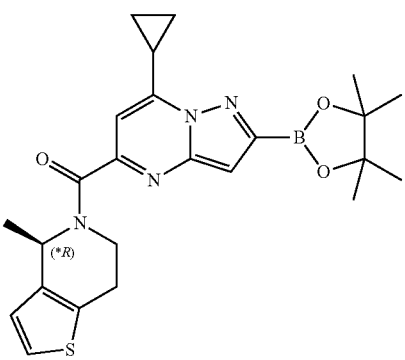

e) Intermediate (G276):

A mixture of intermediate (R4) (0.200 g, 0.72 mmol), intermediate (G267) (0.52 g, 0.80 mmol at 72 wt % purity), K₃PO₄ (0.47 g, 2.2 mmol) and PdCl₂(dtbpf) (0.048 g, 0.07 mmol) in 1,4-dioxane (15 mL) and H₂O (1 mL) was stirred at 90° C. for 1.5 h. The reaction mixture was poured into 30 mL of DCM, washed successively with 15 mL of water and 15 mL of brine, dried with Na₂SO₄, filtered and concentrated in vacuum. The crude was purified by column chromatography over silica gel (eluent: DCM/EtOAc 100/0 to 90/10) to give 0.36 g (91%) of intermediate (G276) as a brownish solid.

intermediate (G276)

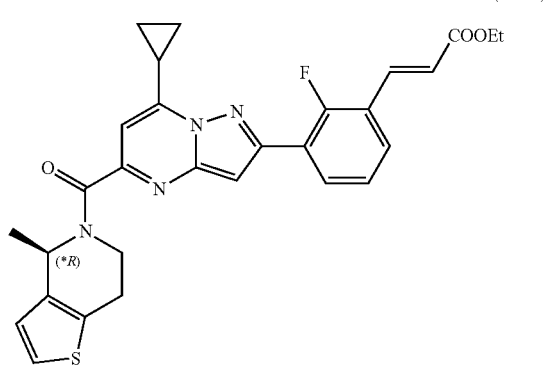

f) Compound (M46):

LiOH.H$_2$O (80 mg; 1.90 mmol) was added to a solution of intermediate (G276) (337 mg; 0.64 mmol) in H$_2$O (1.9 mL) and THF (5.7 mL) and the reaction mixture was stirred at rt for 16 h. Then HCl 3M (0.8 mL; 2.4 mmol) was added and the reaction mixture was concentrated to give a beige residue taken up in water and EtOAc. An aqueous solution of KHSO$_4$ 10% was added and the layers were separated. The organic layer was washed with water, dried over MgSO$_4$, filtered and concentrated to give a beige solid. This solid was triturated in MeOH, filtered and dried over glass frit to give 168 mg (53%) of compound (M46) as a white solid.

compound (M46)

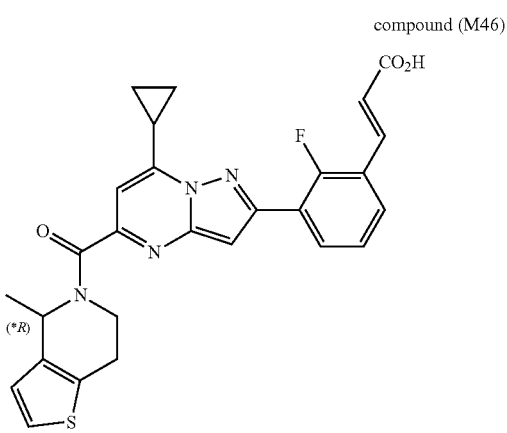 [SMILES: CC1c2ccsc2CCN1C(=O)c1cc(C2CC2)n2nc(-c3cccc(/C=C/C(=O)O)c3F)cc2n1]

Compound (M49):

compound (M48) was purified by chiral SFC (Stationary phase: Chiralpak AS-H® 5 µm 250*20 mm, Mobile phase: 60% CO$_2$, 40% MeOH) to give 101 mg of 1$^{st}$ diastereomer (Compound (M49)) as a white solid and 103 mg of 2$^{nd}$ diastereomer as a white solid.

Compound (M49)

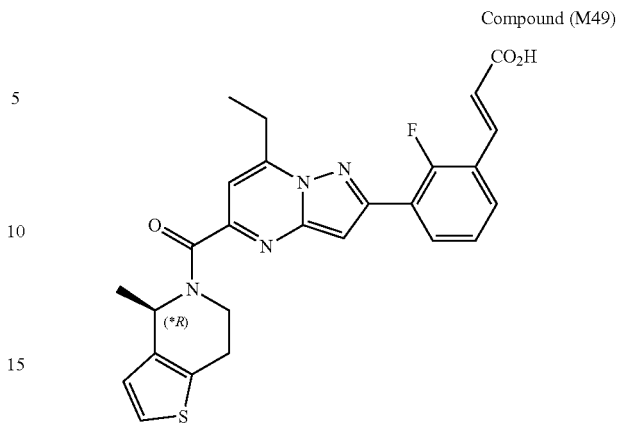

Compound (N1):

TBTU (75 mg, 1.0 mmol) was added to a mixture of compound (M1) (100 mg, 0.2 mmol), NH$_4$Cl (50 mg, 1.0 mmol) and DIEA (0.2 mL, 1.0 mmol) in DCM (1 mL). The reaction mixture was stirred at RT overnight. The reaction mixture was poured into water, then the organic layer was separated, washed with brine, dried over sodium sulfate, filtered and evaporated till dryness. The residue was purified by re-crystallization from EtOAc, washed with hexane and dried to give 22 mg (22%) of compound (N1).

Compound (N1)

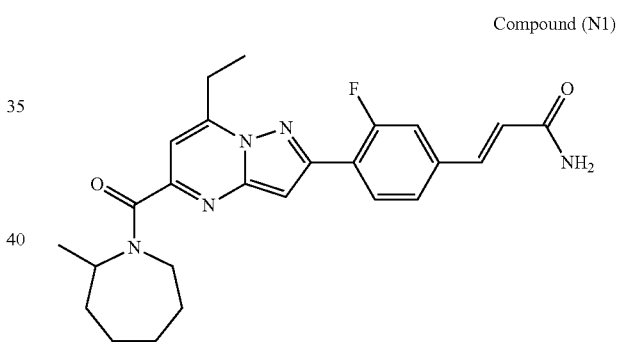

Compound (O)

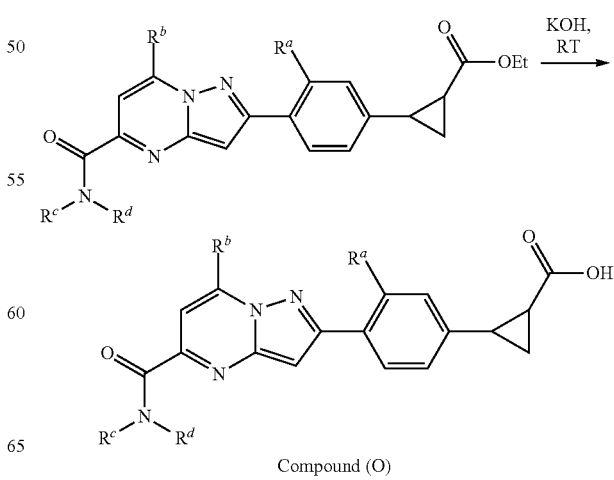

Compound (O)

The following compound was prepared according to the previously described procedure.

Compound (O1)

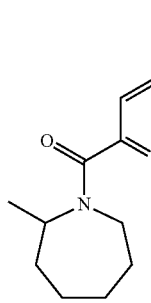

Compound (O2):

LiOH.H$_2$O (21 mg; 0.498 mmol) was added to a solution of intermediate (G80) (72 mg; 0.146 mmol) in THF (1 mL) and water (360 µL). The reaction mixture was stirred at 60° C. for 4 h 30 then cooled down. Then HCl 3M in CPME (195 µL; 0.585 mmol) was added and the reaction mixture was concentrated. The residue was purified by column chromatogarphy (silca gel, from DCM/(EtOH/AcOH 10%) 100/0 to 90/10) to give 50 mg of a solid which was co-evaporated (3×) with a mixture of DCM/EtOH/CH$_3$CN then was dried under high vacuum at 50° C. for 16 hours to give 42 mg (62%) of compound (O2) as a beige solid.

Compound (O2)

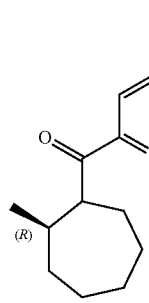

The following compound were prepared according to the above procedure:

compound (O3)

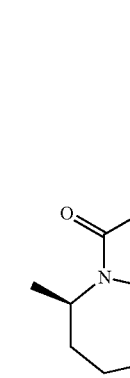

compound (O4)

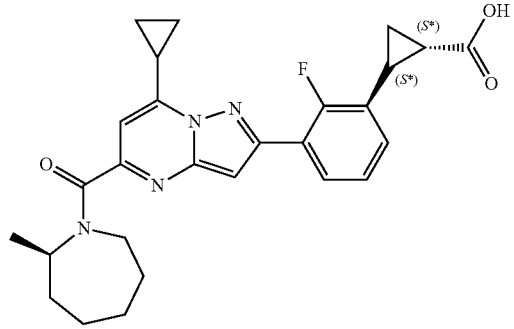

Compound (O5):

In a schlenk tube, NaOH (104 mg; 2.60 mmol) was added to a solution of intermediate (G153) (842 mg; 1.30 mmol) in EtOH (18 mL) and the reaction mixture was stirred at 85° C. for 3 h. A solution of KHSO$_4$ 10% was added and the mixture was diluted with EtOAc and water. The layers were separated and the organic layer was washed with brine, dried over MgSO$_4$, filtered, concentrated and purified by preparative LC (irregular SiOH 15-40 µm, 30 g Grace® Resolv, liquid loading (DCM), mobile phase gradient: from DCM 100%, to DCM 95%, MeOH 5%, then DCM 90%, MeOH/AcOH (90:10) 10%) to give 650 mg of a solid. The solid was triturated in MeOH, filtered off and dried on frit to give 322 mg of a first batch of compound (O5) as a beige solid. The mother liquor was evaporated in vacuum and the residue was triturated in MeOH, filtered and dried on frit to give 120 mg of compound (O5) (second batch) as a beige solid. (Global yield 67%).

compound (O5)

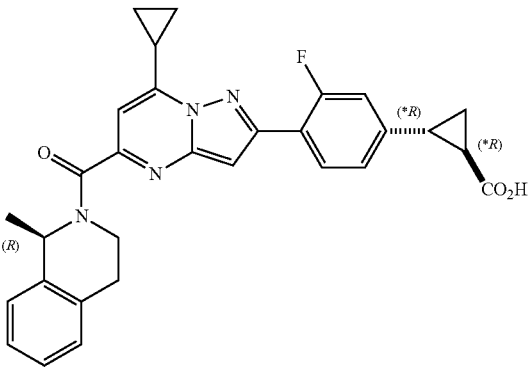

The following compounds were prepared according to compound (O5):

compound (O8)

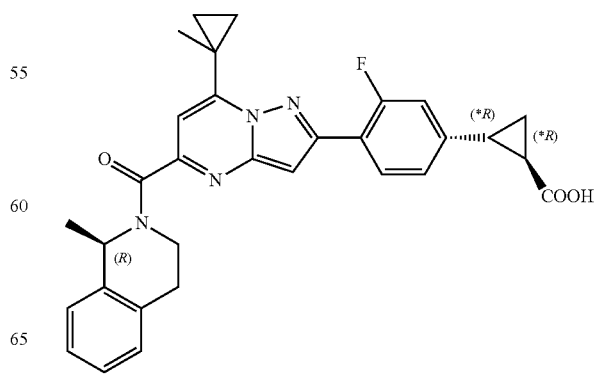

compound (O10)
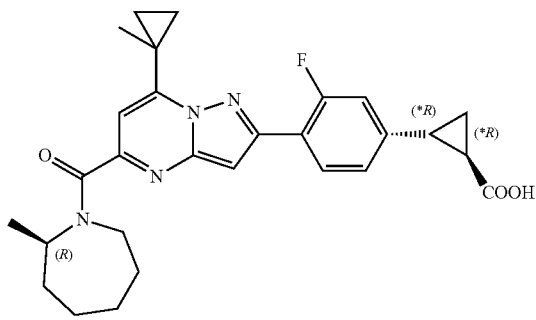
compound (O14)
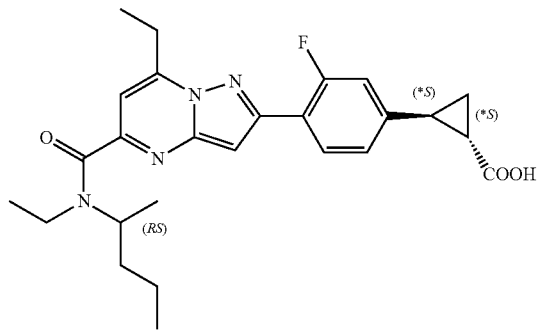
compound (O11)
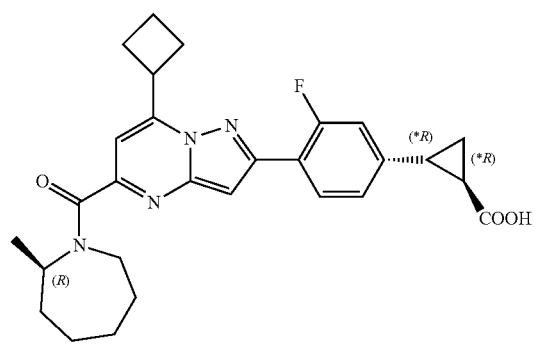
compound (O15)
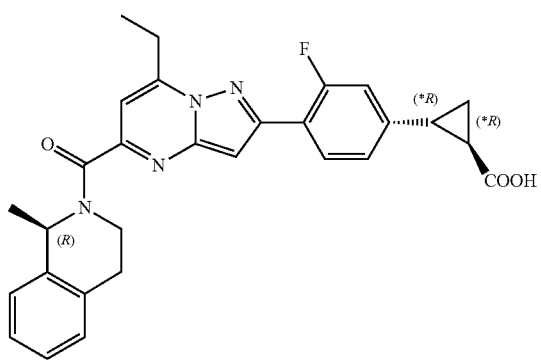
compound (O12)
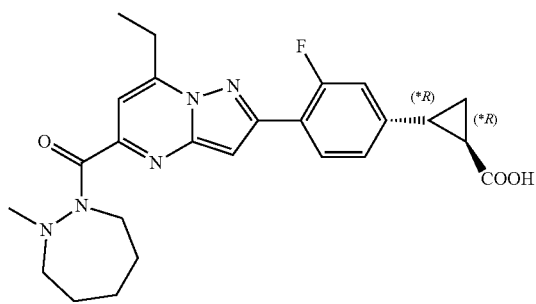
compound (O17)
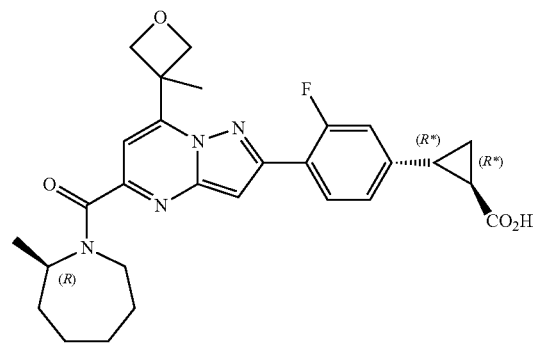
compound (O13)
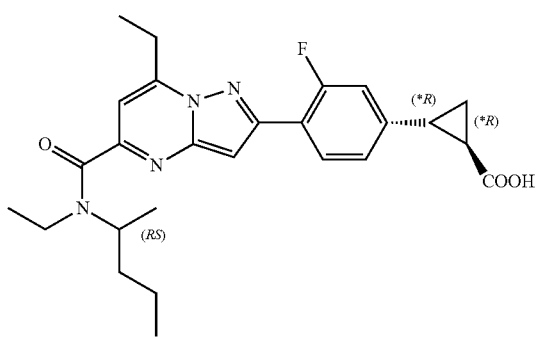
compound (O20)
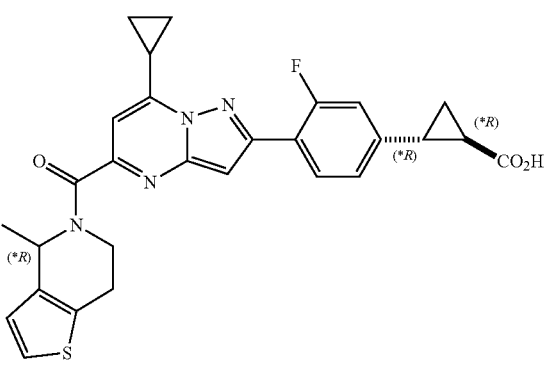

313
-continued

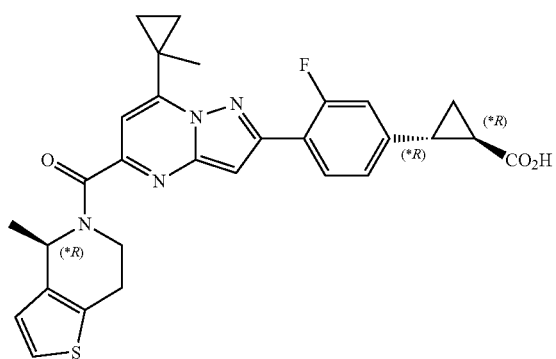
compound (O21)

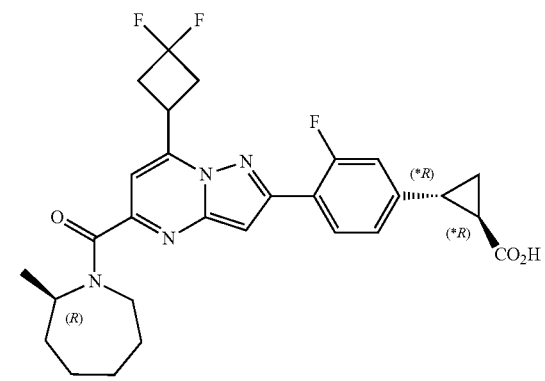
compound (O23)

Reaction scheme for compound (O6):

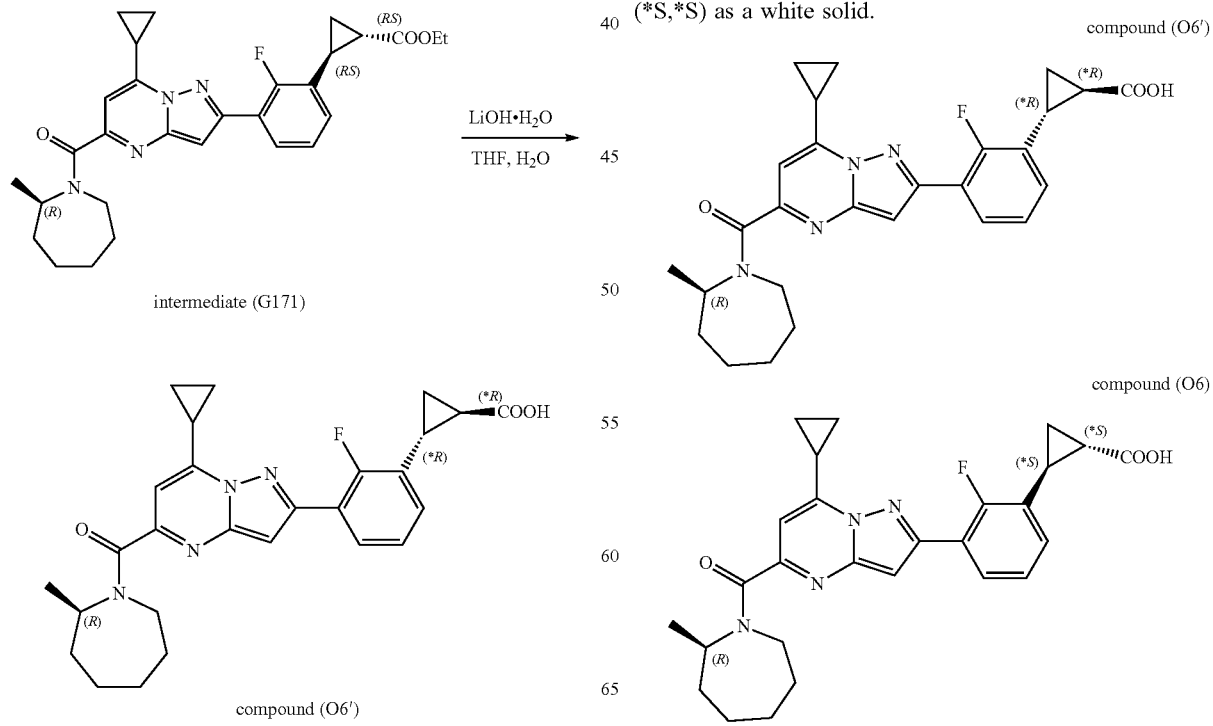

314
-continued

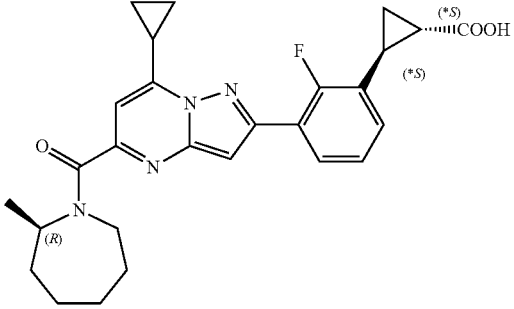
compound (O6)

Compound (O6):

LiOH.H$_2$O (46 mg; 1.09 mmol) was added to a solution of intermediate (G171) (367 mg; 0.727 mmol) in THF (7.3 mL) and H$_2$O (4 mL). The mixture was stirred at rt overnight. Brine and an aqueous solution of KHSO$_4$ (10%) were added and the mixture was extracted with EtOAc (twice). The combined organic layers were dried over MgSO$_4$, filtered and evaporated in vacuum to give 388 mg of a crude mixture. This mixture was purified by preparative LC (Regular SiOH 30 µm, 25 g Interchim®, liquid loading (CH$_2$Cl$_2$), mobile phase gradient: from CH$_2$Cl$_2$/MeOH/ AcOH 100:0:0 to 95:5:0.5). The fractions containing product were combined and the solvent was removed in vacuum to give colorless oil which was azeotroped with toluene (twice) then with MeCN (once) to give 254 mg of colorless oil. This oil was purified via achiral SFC (Stationary phase: Chiralpak® AD-H 5 µm 250*30 mm, mobile phase: CO$_2$/ EtOH 65:35) to give 144 mg of a white foam (*R,*R) (first diastereomer) and 149 mg of a white foam (*S,*S) (second diastereomer). The first diastereomer was dissolved in MeCN and the solution was extended with distilled water. The resulting mixture was freeze-dried to yield 118 mg (34%) of compound (O6') (*R,*R) as a white solid. The second diastereomer was dissolved in MeCN and the solution was extended with distilled water. The resulting mixture was freeze-dried to yield 136 mg (39%) of compound (O6) (*S,*S) as a white solid.

The following intermediates were prepared according to the above procedure:

compound (O9)

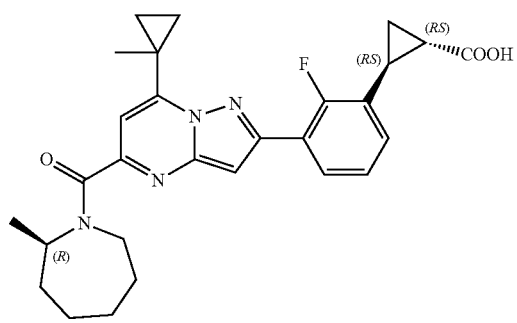

compound (O16)

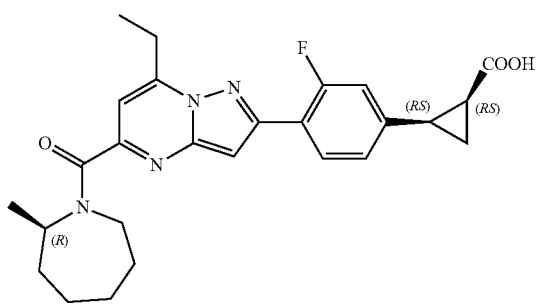

Compound (O7):

In a sealed tube, NaOH (17.9 mg; 0.446 mmol) was added to a solution of intermediate (G173) (183 mg; 0.298 mmol) in iPrOH (8.6 mL) and H$_2$O (100 µL). The mixture was stirred at 85° C. for 4 hours. Brine and an aqueous solution of KHSO$_4$ (10%) were added and the mixture was extracted with EtOAc (twice). The combined organic layers were dried over MgSO$_4$, filtered and evaporated in vacuo to give 281 mg of a crude compound. This compound was purified by preparative LC (Regular SiOH 30 µm, 12 g Interchim®, dry loading (Celite®), mobile phase gradient: from CH$_2$Cl$_2$/MeOH 100:0 to 98:2). The fractions containing product were combined and the solvent was removed in vacuum to give 143 mg of a yellow solid which was taken-up in MeCN, the solid was filtered off and dried under high vacuum to give 101 mg (71%) of compound (O7) as a white solid.

compound (O7)

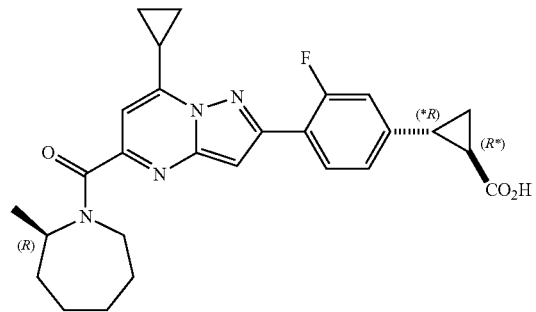

Reaction scheme for compound (O18):

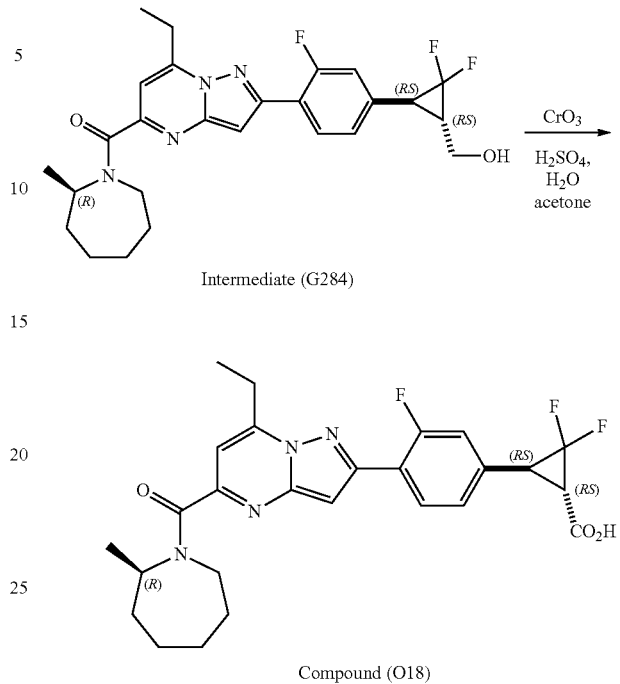

Intermediate (G284)

Compound (O18)

Compound (O18):

H$_2$SO$_4$ (96%) (0.28 mL; 5.3 mmol) was added to CrO$_3$ (318 mg; 3.18 mmol) then H$_2$O (0.31 mL) and acetone (2 mL) were added successively at 0° C. The resulting mixture was stirred at 0° C. for 5 min and this mixture was added to a mixture of Intermediate (G284) (313 mg; 0.643 mmol) and acetone (10 mL). iPrOH was added and the mixture was stirred at rt for 15 min. The resulting mixture was filtered over Celite® and washed with DCM. The filtrate was evaporated to dryness and taken-up with EtOAc and water. The layers were separated and the aqueous layer was extracted with EtOAc (once). The combined organic layers were washed with brine, dried over MgSO$_4$, filtered and the solvent was removed in vacuo. The crude was purified by preparative LC (regular SiOH, µm, 40 g Interchim®, liquid loading (DCM), mobile phase gradient: DCM/MeOH/aqNH$_3$ 98/2/0.2 to 95/5/0.5) to give a solid which was taken-up with EtOH and water and evaporated to dryness. The solid was dried under high vacuum at 50° C. for 16 h to give 75 mg of Compound (O18).

compound (O18)

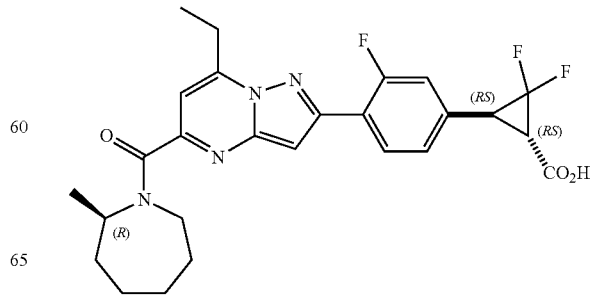

Reaction scheme for compound (O19):

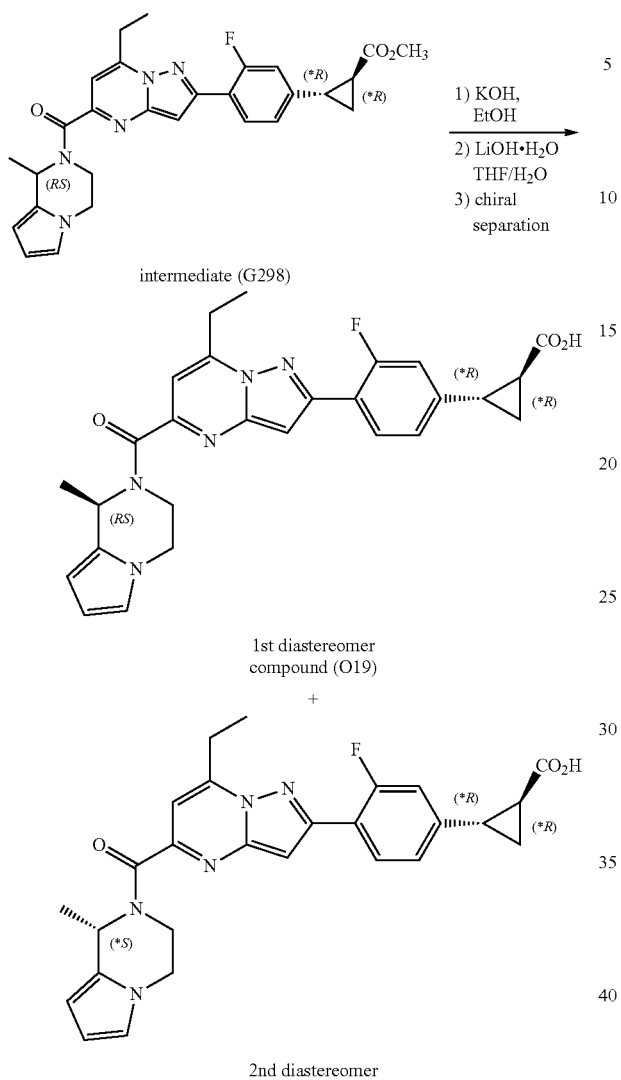

Compound (O19):
KOH (55 mg; 0.827 mmol) was added to a solution of intermediate (G298) (345 mg; 0.551 mmol) in EtOH (5 mL). The reaction mixture was heated at 50° C. for 16 h. The reaction mixture was cooled down to rt and HCl 3M in CPME (150 μL; 0.45 mmol) was added (pH=6). The reaction mixture was concentrated. The residue was diluted in a mixture of THF (4 mL) and H$_2$O (1 mL) and LiOH.H$_2$O (13 mg; 0.55 mmol) was added. The reaction mixture was stirred at rt for 56 h. An aqueous solution of KHSO$_4$ 10% was added until pH=6. The mixture was diluted with EtOAc and water. The layers were separated and the organic layer was washed with water, dried over MgSO$_4$, filtered, concentrated and purified by preparative LC (Irregular SiOH, 15-40 μm, 12 g Interchim®, dry loading (on SiOH), mobile phase gradient: from DCM/EtOH 100/0 to 90/10) to give a yellow solid. The solid was purified again by preparative LC (Irregular SiOH, 15-40 μm, 10 g Merck®, dry loading (on SiOH), mobile phase gradient: from DCM/MeOH 100/0 to 80/20) to give 112 mg of a mixture of diastereomers after drying under high vacuum at 50° C. as a yellow solid (42%). This mixture was purified via chiral SFC (Stationary phase: Chiralpak® AS-H 5 μm 250*20 mm, Mobile phase: 60% CO$_2$, 40% iPrOH) to give 222 mg of 1$^{st}$ diastereomer as salt form as a white foam and 215 mg of 2$^{nd}$ diastereomer as salt form as a yellow foam (discarded).

1$^{st}$ diastereomer was taken up with an aqueous solution of KHSO$_4$ 10% and EtOAc. Layers were separated and the organic layers were washed with water (twice), dried over MgSO$_4$, concentrated and dried under high vacuum at 60° C. for 48 h to give 148 mg (27%) of Compound (O19) as a white solid.

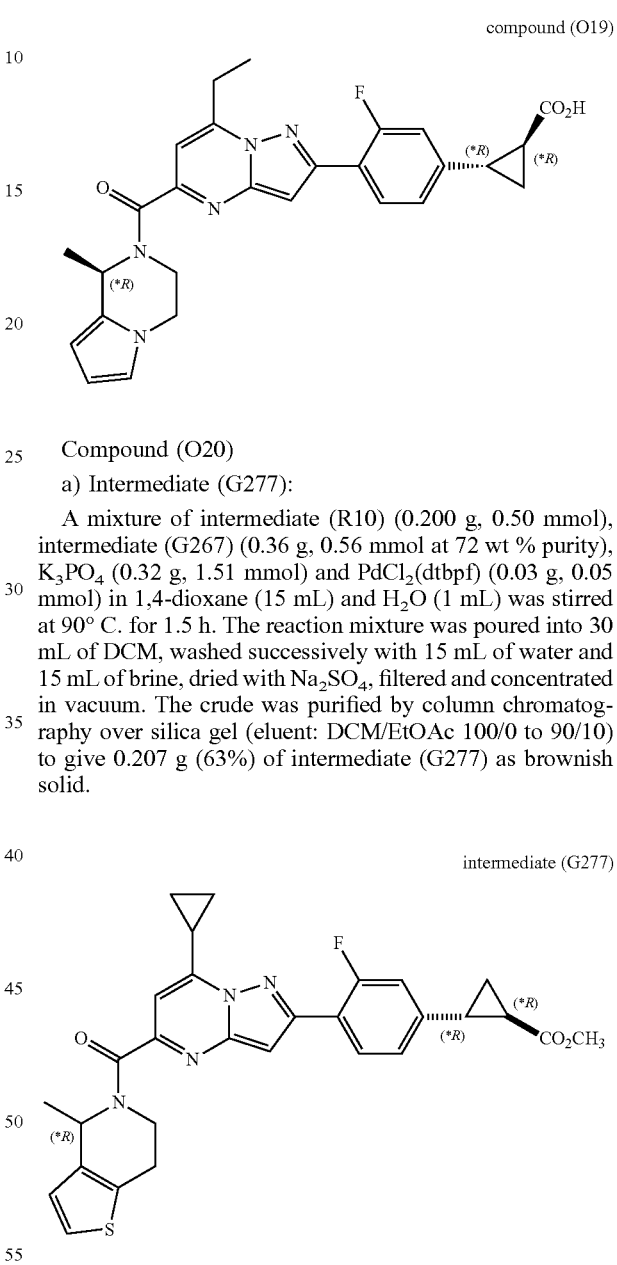

Compound (O20)
a) Intermediate (G277):

A mixture of intermediate (R10) (0.200 g, 0.50 mmol), intermediate (G267) (0.36 g, 0.56 mmol at 72 wt % purity), K$_3$PO$_4$ (0.32 g, 1.51 mmol) and PdCl$_2$(dtbpf) (0.03 g, 0.05 mmol) in 1,4-dioxane (15 mL) and H$_2$O (1 mL) was stirred at 90° C. for 1.5 h. The reaction mixture was poured into 30 mL of DCM, washed successively with 15 mL of water and 15 mL of brine, dried with Na$_2$SO$_4$, filtered and concentrated in vacuum. The crude was purified by column chromatography over silica gel (eluent: DCM/EtOAc 100/0 to 90/10) to give 0.207 g (63%) of intermediate (G277) as brownish solid.

b) Compound (O20):

In a sealed tube, NaOH (21 mg; 0.52 mmol) was added to a solution of intermediate (G277) (167 mg; 0.26 mmol) in EtOH (3.5 mL) and the reaction mixture was stirred at 85° C. for 1 h and at rt for 17 h. Brine and a solution of HCl 1N were added and the mixture was diluted with EtOAc and water. The layers were separated and the organic layer was washed with brine, dried over MgSO$_4$, filtered and concentrated to give 114 mg of an orange solid. This solid was triturated in MeCN, filtered and dried on frit to give 97 mg (74%) of compound (O20) as a pale orange solid.

compound (O20)

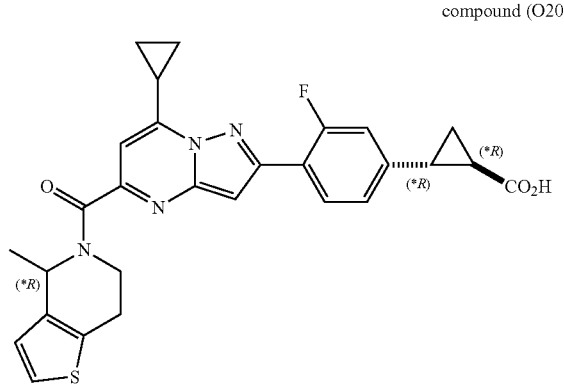

Compound (O22):

In a screw cap vial, NaOH (36 mg; 0.912 mmol) was added to a solution of intermediate (G279) (293 mg; 456 µmol) in iPrOH (3.8 mL) and H₂O (0.8 mL) at rt. The reaction mixture was stirred at 80° C. for 16 h. The reaction mixture was cooled down to rt and concentrated. An aqueous solution of KHSO₄ 10% was added until pH=6. The mixture was diluted with EtOAc and water. The layers were separated and the organic layer was washed with brine, dried over MgSO₄, filtered, concentrated and purified by preparative LC (irregular SiOH, 15-40 µm, 12 g Grace® Resolv, dry loading (on SiOH), mobile phase gradient: from DCM/(EtOH-AcOH 10%) 100/0 to 90/10) to give a solid which was dried under high vacuum at 50° C. for 24 h to give 147 mg (64%) of compound (O22) as a yellow solid.

compound (O22)

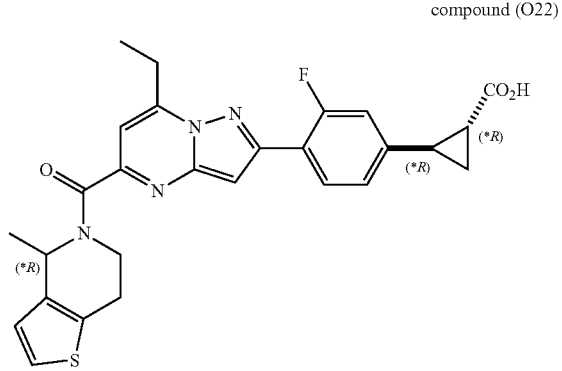

Reaction scheme for compound (O24):

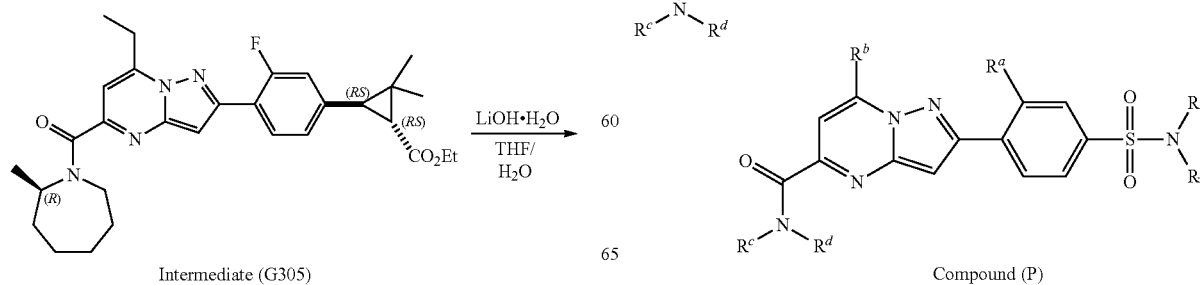

Intermediate (G305)

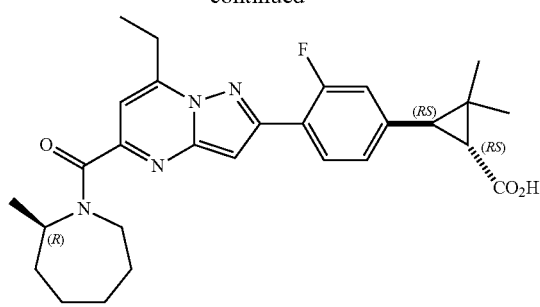

Compound (O24)

Compound (O24):

LiOH.H₂O (8 mg; 0.19 mmol) was added to a solution of intermediate (G305) (18 mg; 35 µmol) in THF (0.3 mL) and H₂O (0.1 mL). The reaction mixture was stirred at rt for 18 h then at 40° C. for 3 days. LiOH.H₂O (8 mg; 0.19 mmol) was added and the mixture was stirred at 50° C. for 2 days. HCl 3M in CPME was added until pH 7. A dry loading with Celite® was performed and was purified by preparative LC (spherical C18 25 µm, 40 g YMC-ODS-25®, dry loading (Celite®), mobile phase gradient: 0.2% aq. NH₄HCO₃/MeCN from 70:30 to 30:70). The fraction containing product was freeze-dried to give 15 mg (88%) of compound (O24) as a white solid.

Compound (O24)

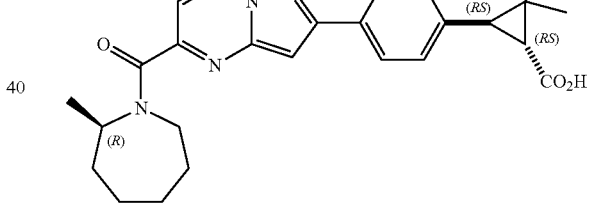

Compound (P):

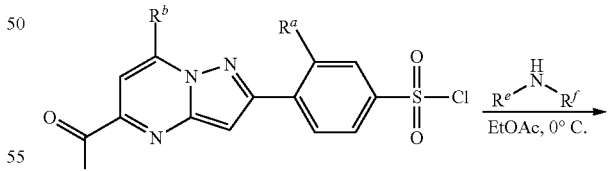

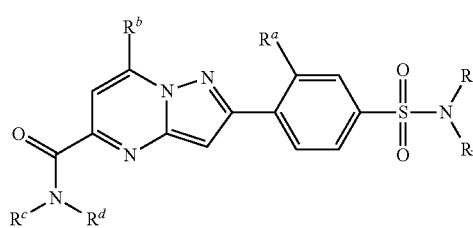

Compound (P)

Compound (P1):

Intermediate (G49) (0.17 mmol) was dissolved in EtOAc (1 mL) and the solution was cooled to 0° C. Then a large excess of dimethylamine in THF was added and the reaction mixture was stirred at 0° C. for 2 hours. The reaction mixture was poured into water, the organic layer was separated, washed with brine, dried over sodium sulfate, filtered and evaporated to give (84%) compound (P1).

Compound (P1)

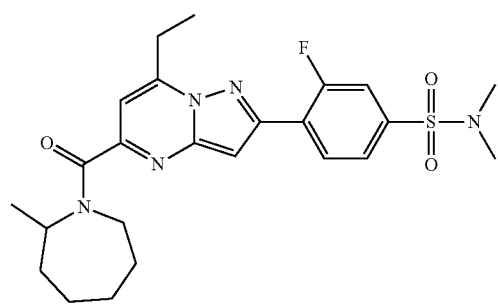

The following compounds were prepared according to the above procedure:

Compound (P2)

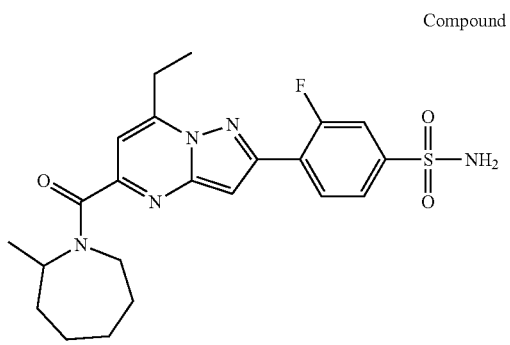

Compound (P3)

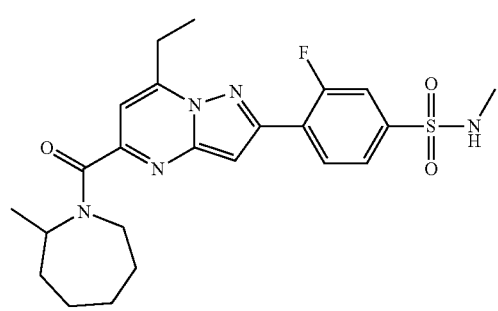

Compound (Q) and (R)

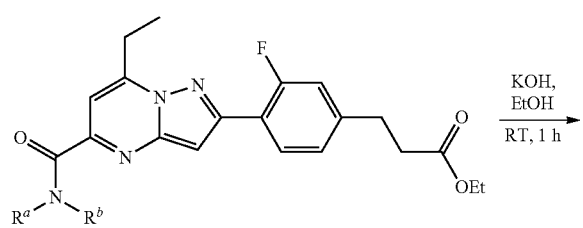

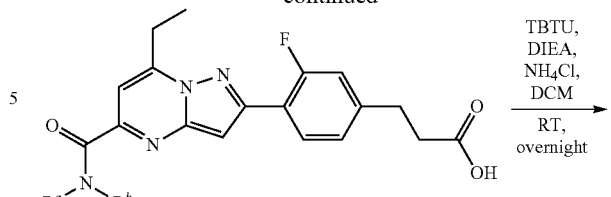

Compound (Q)

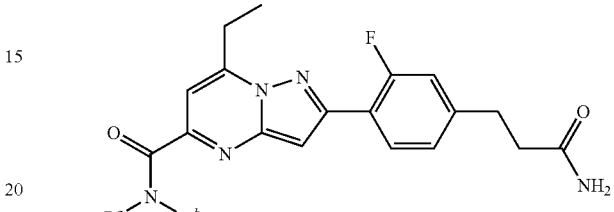

Compound (R)

Compound (Q1):

KOH (40 mg, 7.1 mmol) was added to a solution of intermediate (G43) (160 mg, 0.33 mmol) in EtOH (5 mL). The reaction mixture was stirred at RT for 1 hour. The solvent was evaporated and water was added. The mixture was extracted with ether, the organic layer was separated and the aqueous layer was acidified with HCl cc (0.05 mL) to pH 3. The precipitate was filtered off and dried to give 120 mg (79%) of compound (Q1).

compound (Q1)

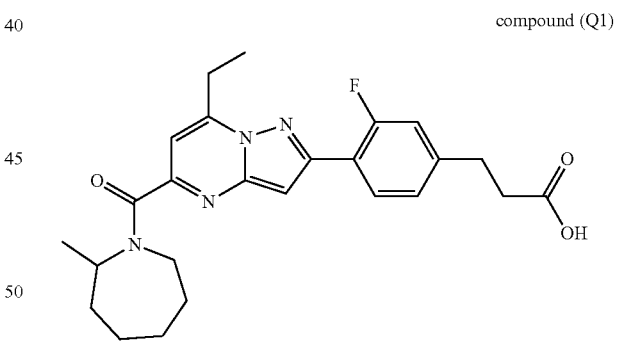

Compound (R1):

TBTU (55 mg, 0.17 mmol) was added to a mixture of compound (Q1) (70 mg, 0.15 mmol), NH$_4$Cl (42 mg, 0.8 mmol) and DIEA (0.13 mL, 0.8 mmol) in DCM (1 mL). The reaction mixture was stirred at RT overnight. The mixture was poured into water. The organic layer was separated, washed with brine, dried over sodium sulfate, filtered and evaporated. The residue was recrystallized with EtOAc, washed with hexane and dried to give 46 mg (66%) of compound (R1).

323

Intermediate (R1)

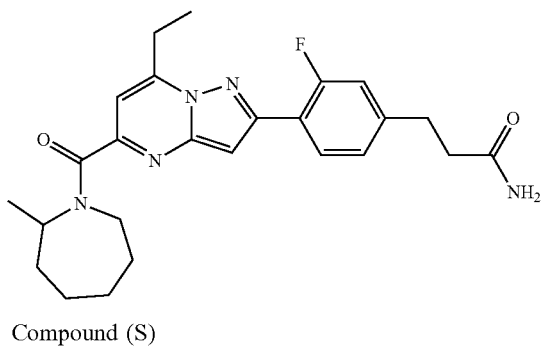

Compound (S)

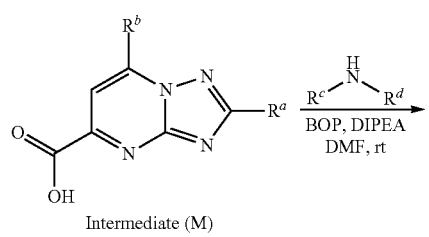

Intermediate (M)

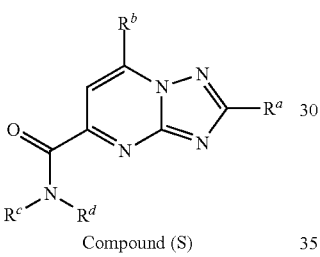

Compound (S)

Compound (S1):
A mixture of intermediate (M2) (0.100 g, 0.36 mmol), BOP (0.181 g, 0.40 mmol), DIEA (71 mg, 0.55 mmol) and 2-methylazepane (45 mg, 0.40 mmol) in dry DMF (25 mL) was stirred at RT for 6 hours. The reaction mixture was poured into water and extracted with CHCl$_3$. The organic layer was separated, washed with brine, dried over sodium sulfate, filtered and evaporated. The residue was purified by column chromatography (silica gel, CHCl$_3$/Et$_2$O). The pure fractions were collected and the solvent was evaporated. The residue was crystallized from hexane/Et$_2$O (1/1) to give the racemate compound.

The racemate mixture was separated by chiral column chromatography (Phenomenex Lux®3 µm 4.5×0.5 Cellulose-1, eluent: heptane/iPrNH$_2$ 95/5, 22° C.). The pure fractions were collected and the solvent was evaporated to give compound (S1) (35%, ee 86%).

Compound (S1)

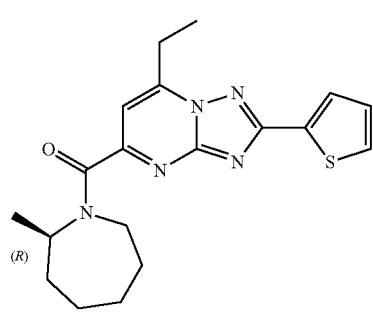

324

Compound (T) and (U)

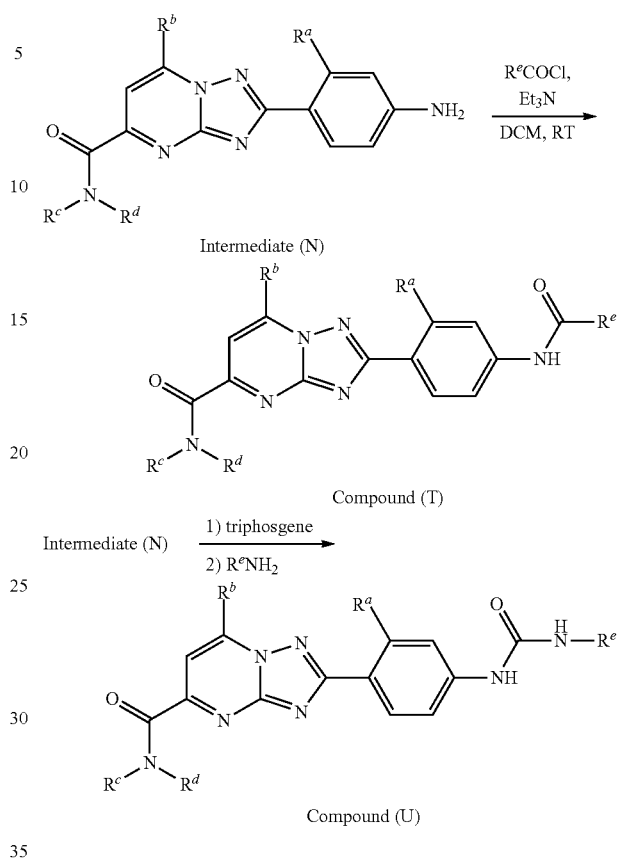

Compound (U1):
Triphosgene (23 mg, 0.08 mmol) was added at 0° C. to a mixture of intermediate (N2) (100 mg, 0.25 mmol) and DIEA (0.125 mL, 0.75 mmol) in DCM (1 mL). The reaction mixture was stirred for 15 min. Then (tetrahydrofuran-2-ylmethyl)-amine (28 mg, 0.27 mmol) was added and the reaction mixture was stirred at RT overnight. A saturated aqueous solution of NaHCO$_3$ was added and the organic layer was separated, washed with brine, dried over sodium sulfate, filtered and evaporated till dryness. The residue purified by column chromatography (silica gel, DCM/EtOAc). The pure fractions were collected and the solvent was evaporated to give 42 mg (36%) of compound (U1).

compound (U1)

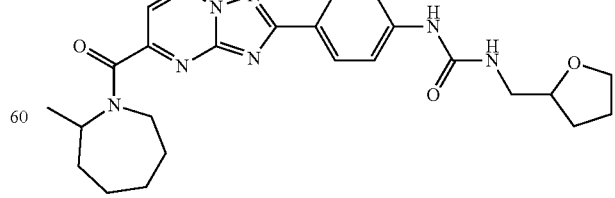

Compound (T1):
Cyclopropanecarbonyl chloride (30 mg, 0.28 mmol) was added to a mixture of intermediate (N2) (80 mg, 0.2 mmol)

and Et₃N (0.04 mL, 0.28 mmol) in DCM (1 mL). The reaction mixture was stirred at RT overnight. A saturated aqueous solution of NaHCO₃ was added and the organic layer was separated, washed with brine, dried over sodium sulfate, filtered and evaporated till dryness. The residue was purified by re-crystallization from EtOAc/ether to give 65 mg (70%) of compound (T1).

compound (T1)

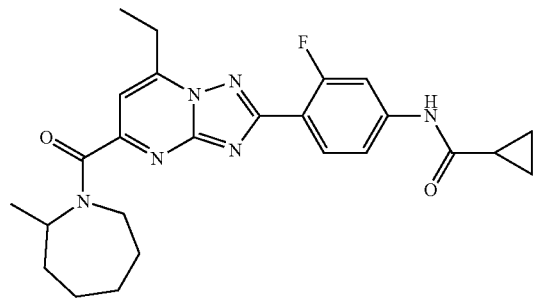

Compound (V)

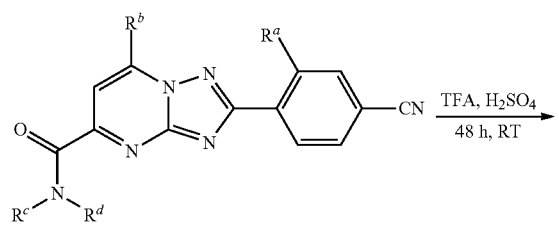

Compound (V1):
A mixture of intermediate (N4) (170 mg, 0.42 mmol) in TFA/H₂SO₄ (2.5 mL, 4/1) was stirred at RT for 48 hours. The reaction mixture was diluted with water and the precipitate was filtered off, washed with water and dried to give 100 mg (57%) of compound (V1).

compound (V1)

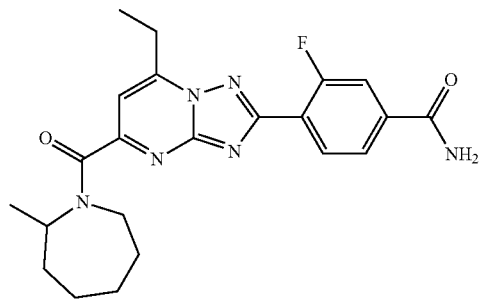

Compound (W):

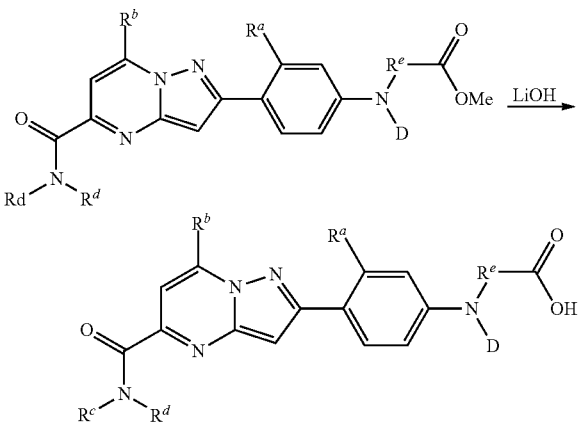

Compound (W1):
A mixture of intermediate (G89) (407 mg, 0.825 mmol) and LiOH.H₂O (52 mg, 1.2 mmol) in THF (17 mL) and H₂O (17 mL) was stirred at RT for 3 hours. HCl 3M in CPME (0.246 mL; 0.739 mmol) was added. The mixture was evaporated to dryness and the residue was purified by column chromatography (silica gel, from DCM/MeOH/AcOH 99/1/0.1 to 95/5/0.5). The pure fractions were collected and evaporated to give 0.5 g of a gum which was taken-up with heptane and DCM. The mixture was evaporated to dryness and the solid was dried under high vacuum at 60° C. for 24 hours to give 240 mg (61%) of compound (W1) as an off-white solid.

compound (W1)

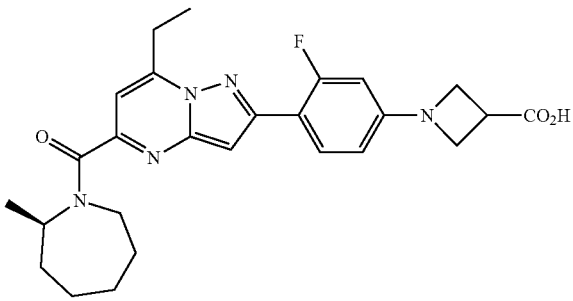

The following compounds were prepared according to the above procedure:

Compound (W3)

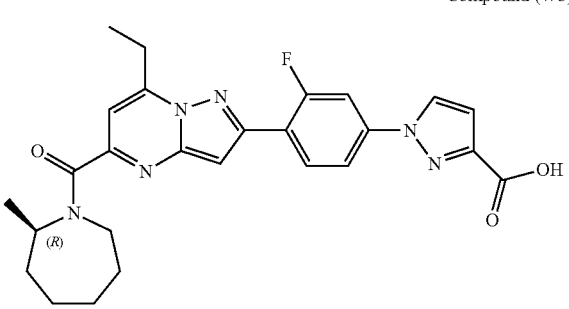

compound (W4)
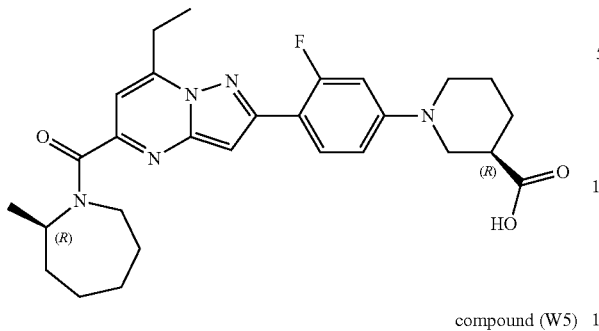
compound (W5)
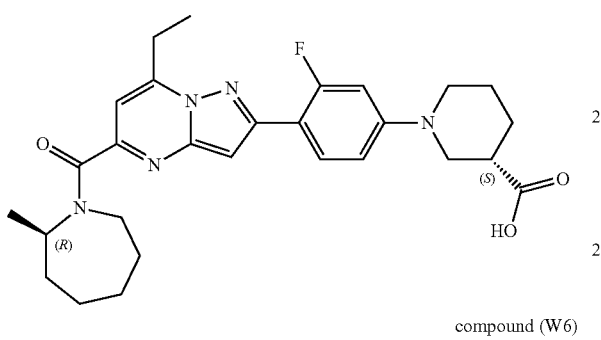
compound (W6)
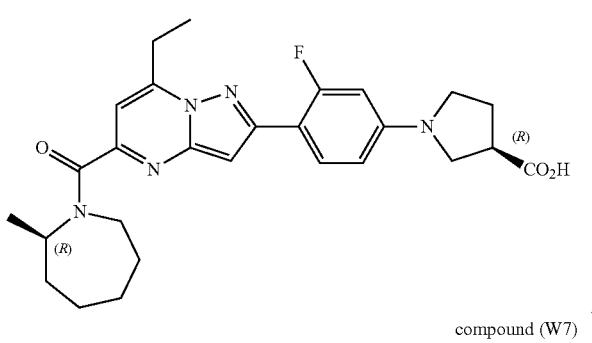
compound (W7)
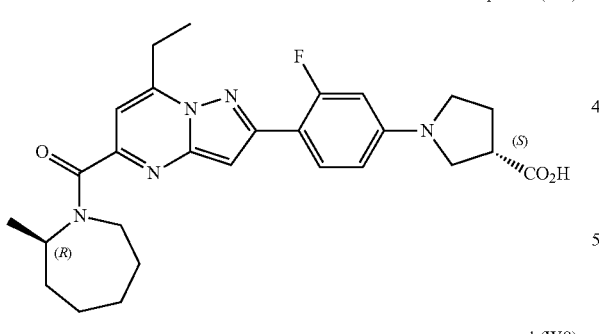
compound (W8)
compound (W9)
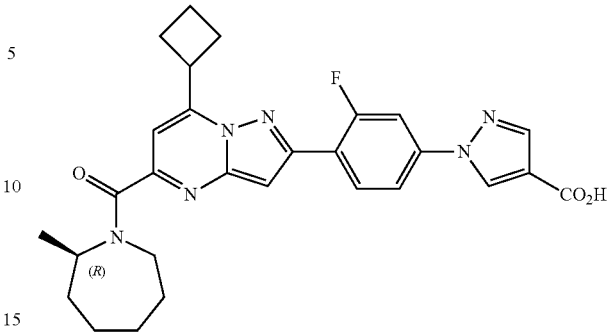
compound (W10)
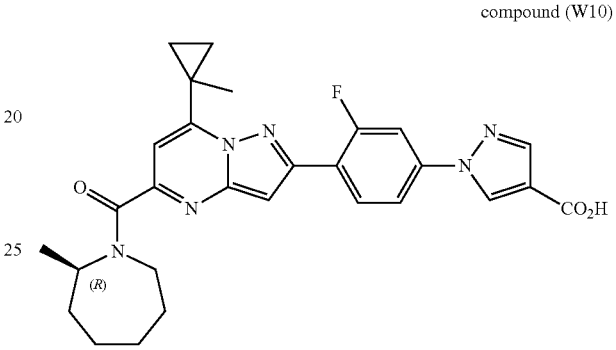
Compound (W11)
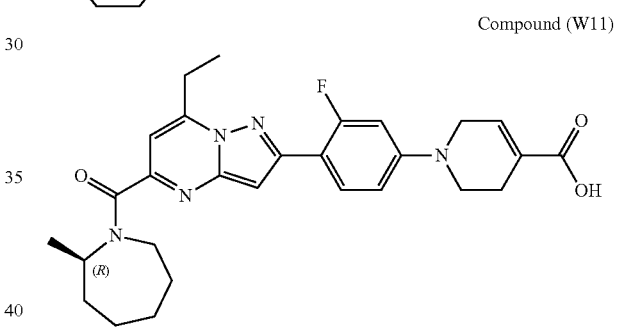
compound (W12)
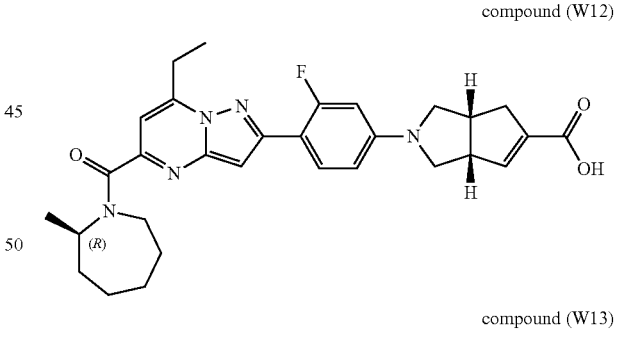
compound (W13)

compound (W14)
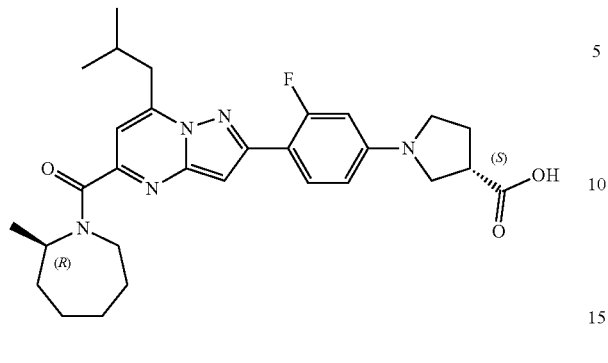
compound (W20)
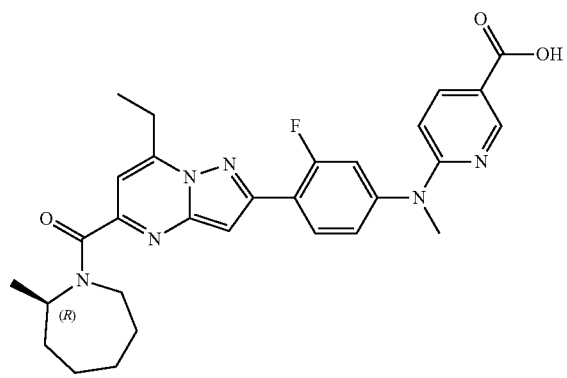
compound (W15)
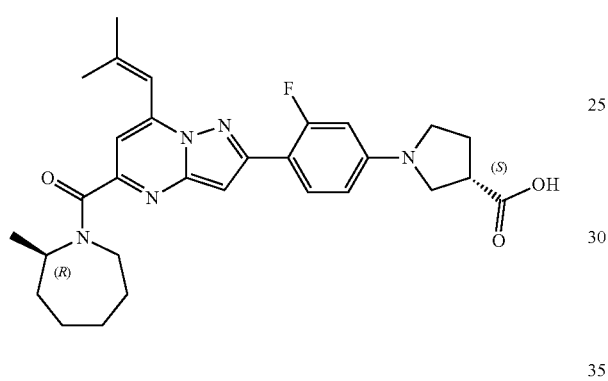
compound (W22)
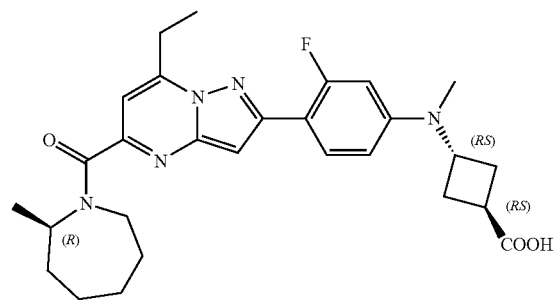
compound (W17)
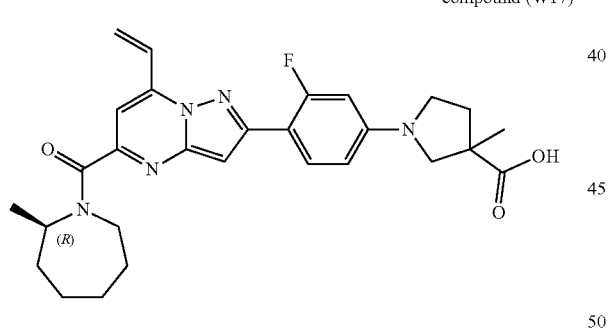
compound (W23)
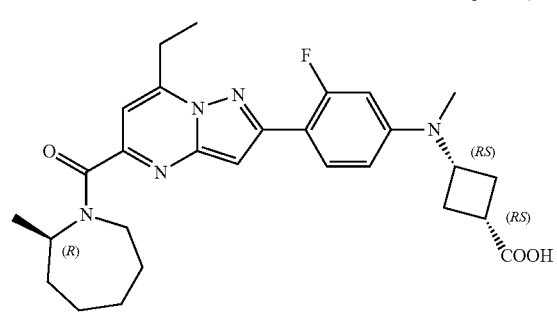
compound (W18)
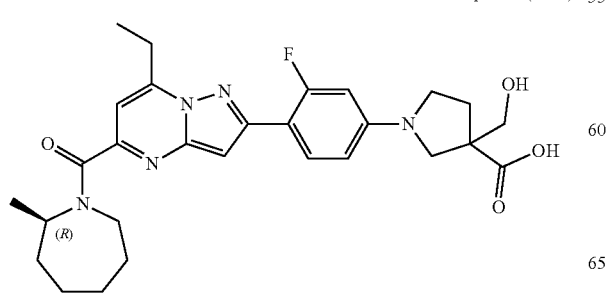
compound (W24)
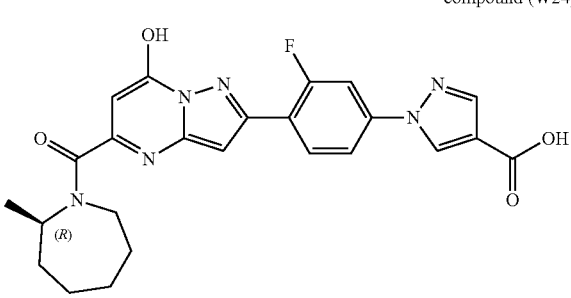

compound (W25)
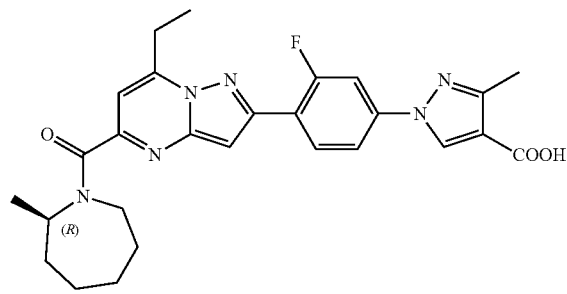
compound (W26)
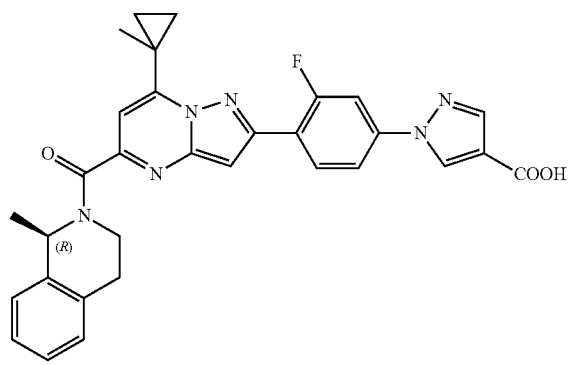
compound (W27)
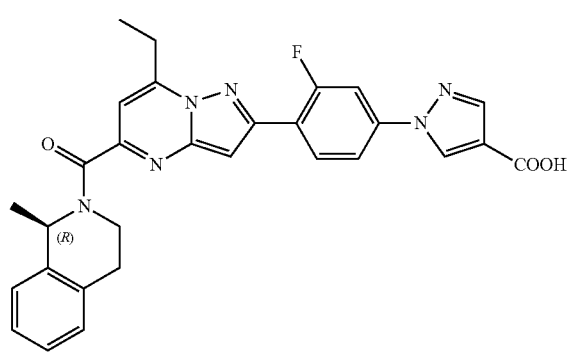
compound (W28)
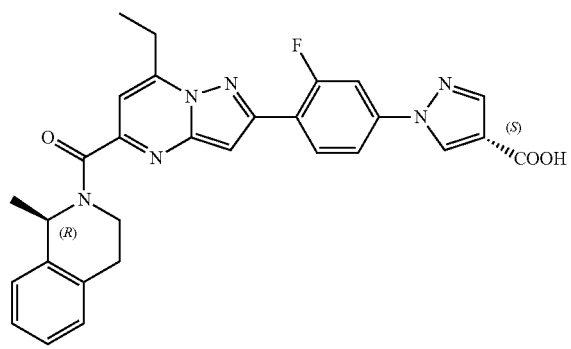
compound (W29)
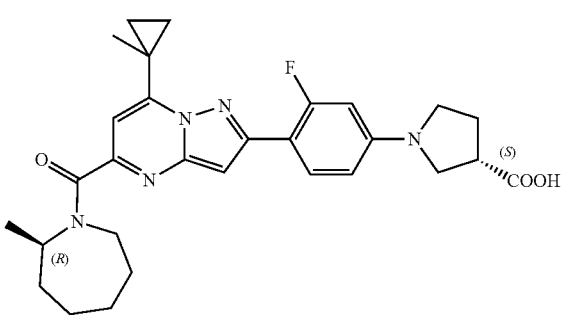
compound (W30)
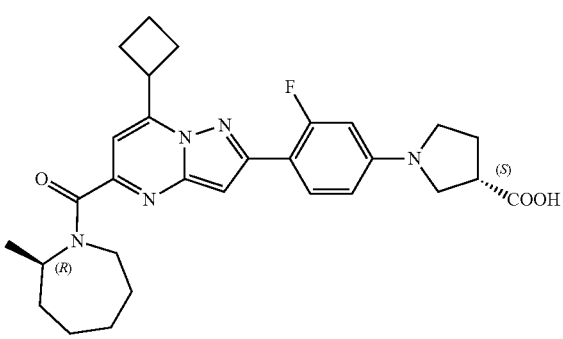
compound (W31)
compound (W32)
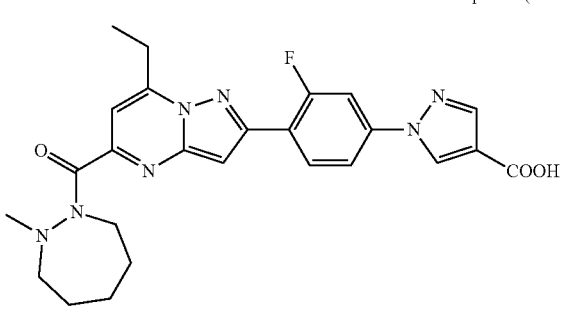

compound (W33)
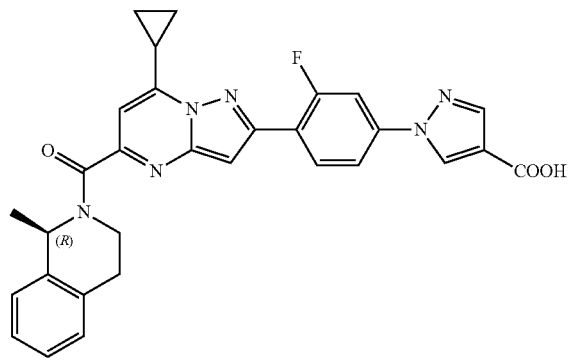
compound (W37)
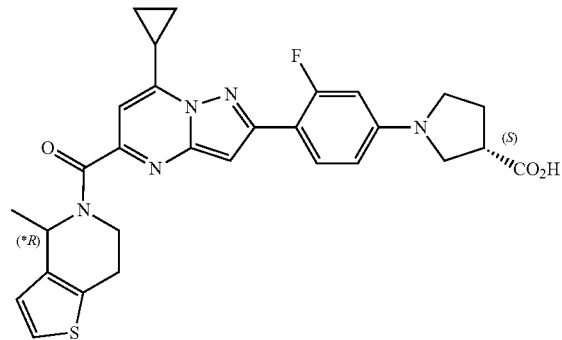
compound (W34)
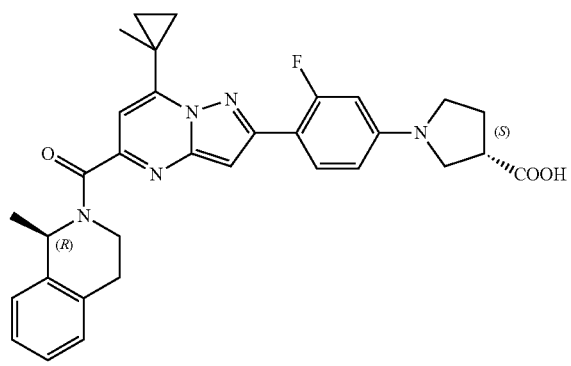
compound (W39)
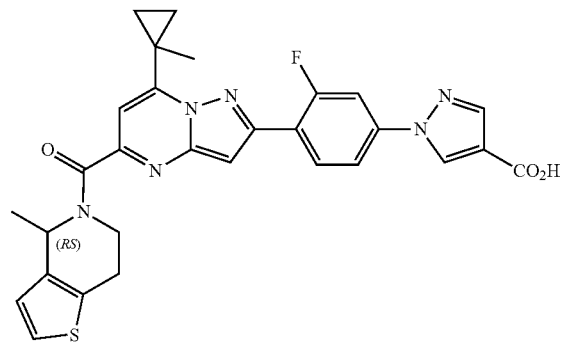
compound (W35)
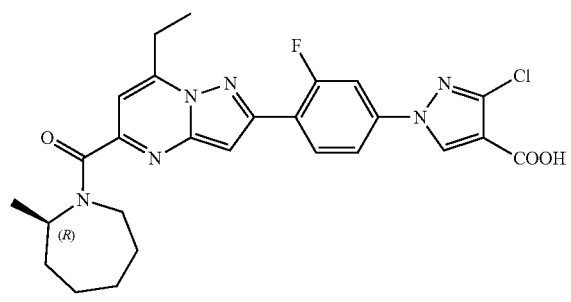
compound (W40)
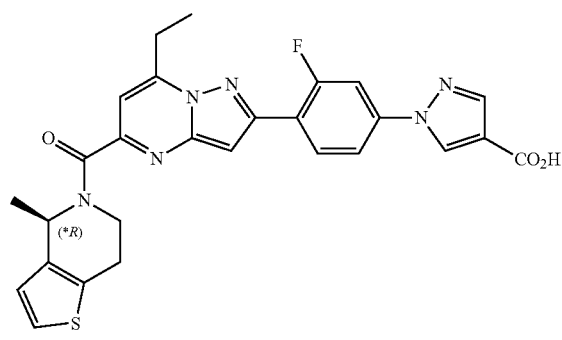
compound (W36)
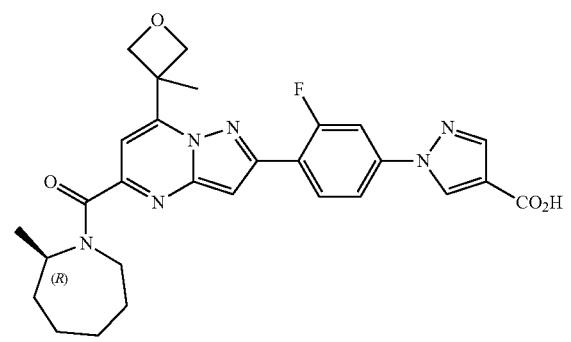
compound (W41)
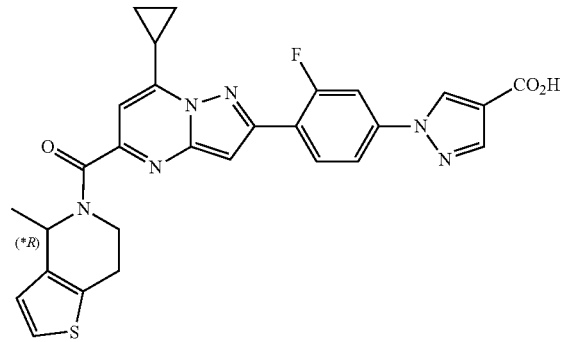

compound (W43)

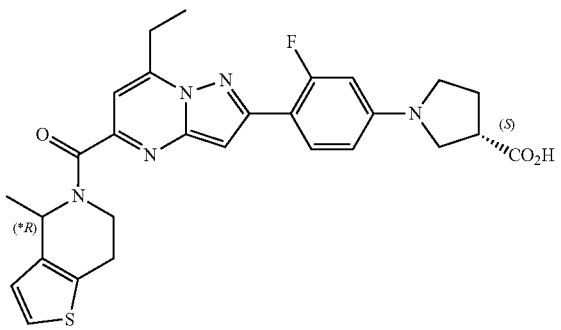

compound (W44)

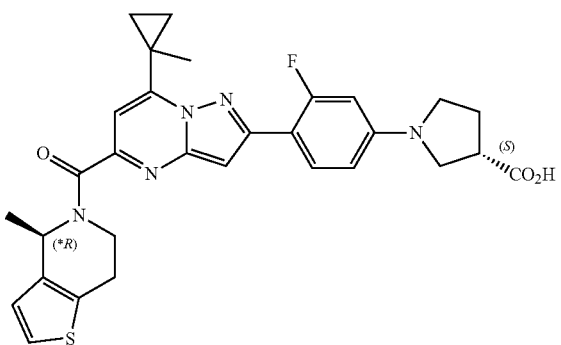

compound (W46)

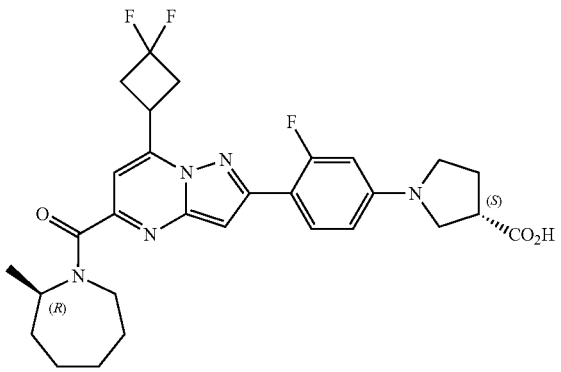

compound (W47)

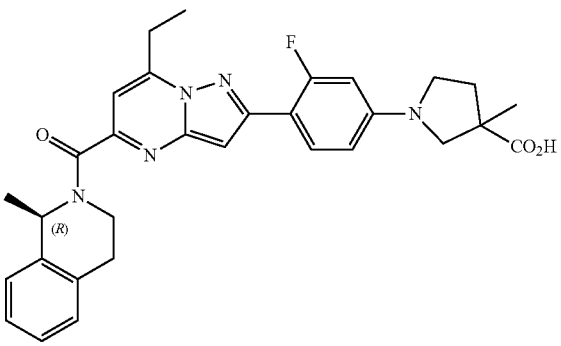

compound (W48)

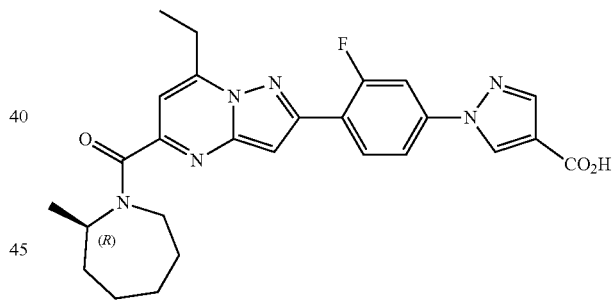

Compound (W2)

LiOH.H$_2$O (210 mg; 5.01 mmol) was added to a solution of intermediate (G106) (87 mg; 1.67 mmol) in H$_2$O (5 mL) and THF (15 mL). The reaction mixture was stirred at 50° C. for 16 h, cooled down to rt. Then HCl 3M (1.7 mL; 5 mmol) was added and the reaction mixture was concentrated. The compound was purified by preparative LC (Regular SiOH, 30 μm, 25 g Interchim®, dry loading (on SiOH), mobile phase gradient:

from DCM/(MeOH/AcOH 10%) 100/0 to 80/20) to give a pale yellow solid. This compound was recrystallized in hot EtOH (20 mL) and the mixture was concentrated to dryness to give 783 mg of a pale yellow solid which was dried under high vacuum to give 586 mg (66%) of compound (W2) as a white solid.

Compound (W2)

Compound (W7)

a) Intermediate (G111):

A schlenk tube was charged with intermediate (G1) (1 g; 2.18 mmol), (S)-methyl pyrrolidine-3-carboxylate hydrochloride (433 mg; 2.61 mmol), Cs$_2$CO$_3$ (2.13 g; 6.53 mmol) and XantPhos (126 mg; 0.22 mmol) and purged with N$_2$. 1,4-dioxane (30 mL) was added and the mixture was purged again with N$_2$, then Pd(OAc)$_2$ (49 mg; 0.22 mmol) was added. The reaction mixture was purged with N$_2$ and heated at 100° C. for 17 h. The mixture was diluted with EtOAc and water. The layers were separated. The aqueous layer was extracted with EtOAc (twice). The combined organic layers were washed with brine, dried with MgSO$_4$, filtered and the solvent was removed under reduced pressure. The crude mixture was purified by prepartive LC (irregular SiOH, 15-40 μm, 50 g Grace®, liquid injection (DCM), mobile phase gradient: from Heptane 90%, EtOAc 10% to heptane 50%, EtOAc 50%) to give 887 mg (80%) of intermediate (G111) as a yellow foam.

intermediate (G111)

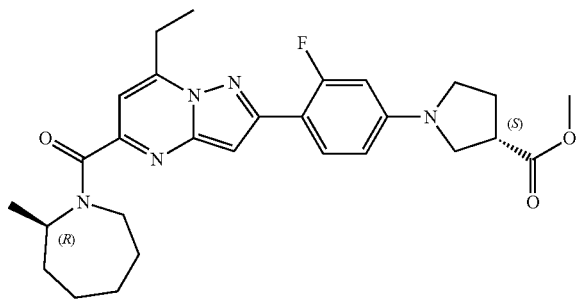

b) Compound (W7):

LiOH.H$_2$O (213 mg; 5.08 mmol) was added to a solution of intermediate (G110) (857 mg; 1.69 mmol) in H$_2$O (7.8 mL) and THF (19 mL). The reaction mixture was stirred at rt for 18 h. Brine, an aqueous solution of KHSO$_4$ (10%) and EtOAc were added to the reaction mixture, aqueous layer was extracted with EtOAc (twice). The combined organic layers were washed with water/brine 1/1, dried over MgSO$_4$, filtered and evaporated in vacuum to give a yellowish gum which was taken up in MeCN and evaporated to give 761 mg (91%) of compound (W7) as a yellow solid.

compound (W7)

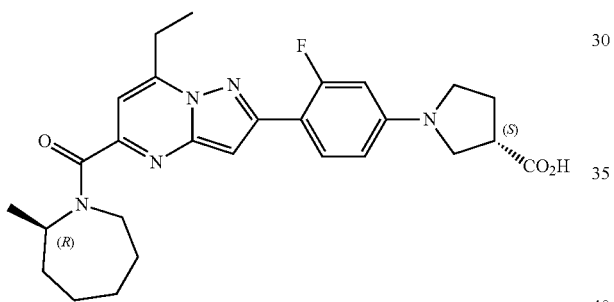

Compound (W16):

To a degassed mixture of intermediate (G1) (300 mg, 0.653 mmol), 1-aminocyclopropane-1-carboxylic acid (198.1 mg, 1.95 mmol) and K$_2$CO$_3$ (180.5 mg, 1.31 mmol) in DMSO (10 mL) was added successively CuI (37.3 mg, 0.196 mmol) at room temperature and the mixture was degassed for 5 min with N$_2$. The resulting mixture was heated at 110° C. for 16 h. Water and DCM were added. The organic layer was separated through a hydrophobic frit and concentrated. Purification was carried out by flash chromatography (silica gel, Heptane/EtOAc, 90/10) to give 168 mg (54%) of compound (W16) as a yellow solid.

Compound (W16)

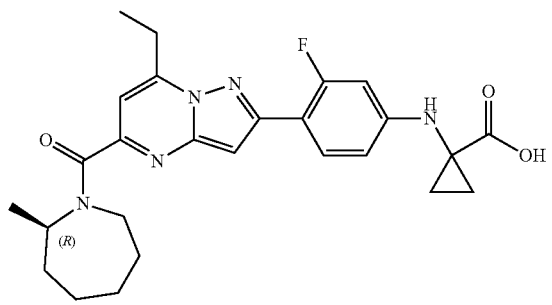

Reaction scheme for compound (W19):

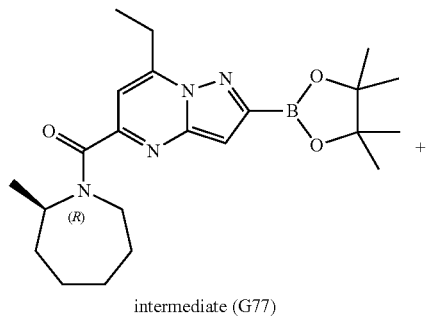

intermediate (G77)

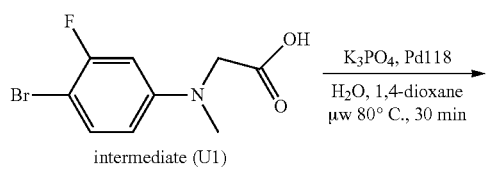

intermediate (U1)

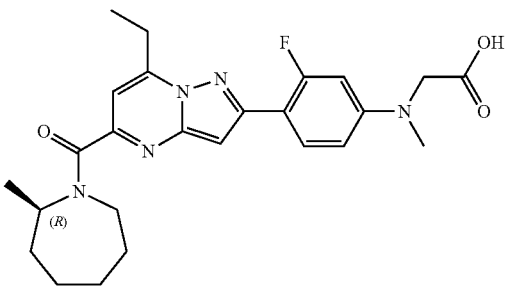

compound (W19)

Compound (W19):

In a sealed tube, a solution of intermediate (G77) (0.05 g, 0.079 mmol), intermediate (U1) (0.021 g; 0.079 mmol) and K$_3$PO$_4$ (0.05 g; 0.24 mmol) in 1,4-dioxane (1 mL) and water (0.14 mL) was purged with N$_2$. PdCl$_2$(dtbpf) (0.005 g; 0.0079 mmol) was added, the mixture was purged again with N$_2$ and heated at 80° C. using a single mode microwave (Biotage® Initiator EXP 60) with a power output ranging from 0 to 400 W for 30 min [fixed hold time]. Water was added and the aqueous layer was acidified with HCl 1N. The organic layer was extracted with DCM, dried over MgSO$_4$, filtered and evaporated to give crude compound. Purification was carried out by flash chromatography over silica gel (Grace® Resolv, 15-35 M, 40 g, DCM/MeOH from 100/0 to 95/5). Pure fractions were collected and evaporated to give oil, 0.189 g. A purification was performed via Reverse phase (Stationary phase: YMC-Actus® Triart-C18 10 μm 30*150 mm, Mobile phase: Gradient from 85% NH$_4$HCO$_3$ 0.2%, 15% ACN to 45% NH$_4$HCO$_3$ 0.2%, 55% ACN). Pure fractions were collected and evaporated to give 0.066 g. This fraction was crystallized from DIPE, filtered off and dried under vacuum at 60° C. affording 0.053 g (20%) of compound (W19) as a white powder.

Compound (W19)

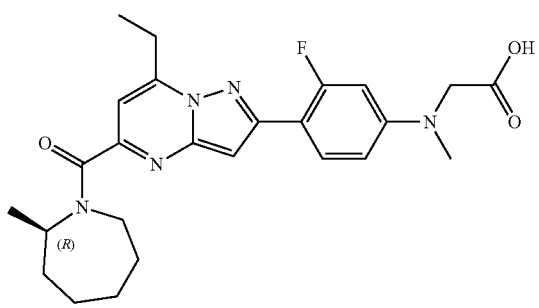

Compound (W21):

To a degassed mixture of intermediate (G1) (0.42 g, 0.91 mmol), intermediate (U2) (0.22 g, 1.1 mmol) and $Cs_2CO_3$ (0.89 g, 2.74 mmol) in 1,4-dioxane (16.8 mL) was added successively XPhos (0.033 g, 0.037 mmol) then $Pd_2dba_3$ (0.039 g, 0.082 mmol) at room temperature. The resulting mixture was stirred at 100° C. for 16 h. The solution was cooled down to room temperature and water was added. The mixture was extracted with EtOAc (twice). The combined organic layers were washed with brine, dried over $MgSO_4$, filtered and the solvent was removed in vacuum to give yellow oil. Purification was carried out by flash chromatography over silica gel (GraceResolv®, 15-35 µM, 40 g, DCM/MeOH from 100/0 to 98/2). Pure fractions were collected and evaporated to give 0.366 g. A purification of the residue was performed via preparative LC (Stationary phase: irregular bare silica 40 g, Mobile phase: 61% Heptane, 4% MeOH, 35% AcOEt). Pure fractions were collected and evaporated to give 0.08 g. A purification was performed via Reverse phase (Stationary phase: X-Bridge-C18® 10 µm 30*150 mm, Mobile phase: Gradient from 60% $H_2O$, 40% ACN to 0% $H_2O$, 100% ACN). Pure fractions were collected and evaporated to give 0.032 g (7%) of Compound (W21) as a white solid.

Compound (W21)

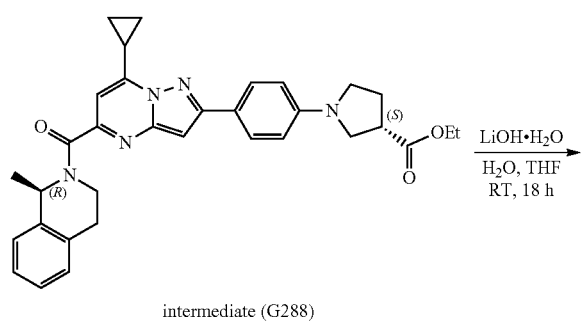

Reaction scheme for compound (W38):

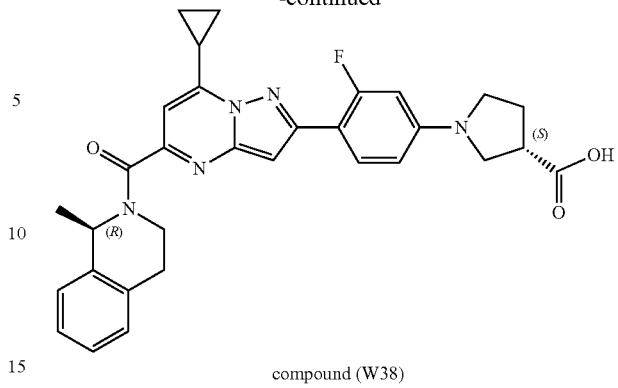

compound (W38)

Compound (W33)

a) Intermediate (G222):

A mixture of intermediate (U5) (0.20 g, 0.64 mmol), intermediate (G152) (0.57 g, 0.78 mmol at 63 wt % purity), $K_3PO_4$ (0.41 g, 1.92 mmol) and $PdCl_2(dtbpf)$ (0.04 g, 0.06 mmol) in 1,4-dioxane (15 ml) and water (1 ml) was stirred at 90° C. for 1.5 h under Ar. The reaction mixture was poured into dichloromethane, washed successively with water and brine, dried over $Na_2SO_4$, filtered and concentrated in vacuum.

The crude was purified by column chromatography over silica gel (eluent: dichloromethane/EtOAc 100/0 to 90/10) to give 0.27 g (75%) of intermediate (G222) as yellowish solid.

intermediate (G222)

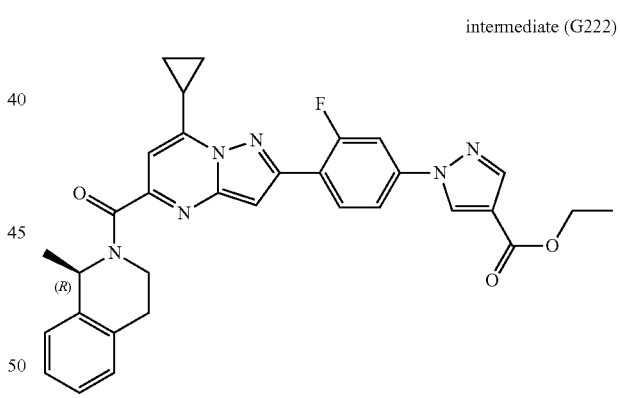

b) Compound (W33):

$LiOH \cdot H_2O$ (0.059 g; 1.40 mmol) was added to a solution of intermediate (G222) (0.26 g; 0.76 mmol) in water (1.4 mL) and THF (4.2 mL) and the reaction mixture was stirred at rt for 16 h then at 50° C. for 4 h. Then HCl (3M in CPME) (0.6 mL; 1.8 mmol) was added and the mixture was concentrated to give a yellow solid. This solid was purified by preparative LC (Regular SiOH, 15-30 µm, 12 g Interchim®, dry loading (on SiOH), mobile phase gradient: from heptane/(EtOAc/AcOH 2.5%) 80/20 to 20/80) to give a white residue which was taken up in MeOH and concentrated to give 0.18 g (71%) of compound (W33) as a white solid.

compound (W33)

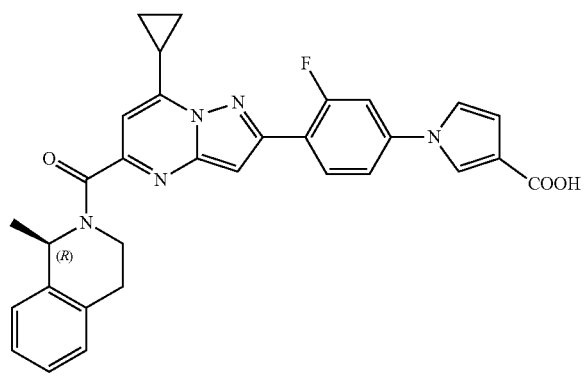

Compound (W37)
a) Intermediate (G289):
A screw-cap tube was charged with intermediate (G263) (0.69 g, 1.207 mmol), (S)-methyl pyrrolidine-3-carboxylate hydrochloride CAS [81049-27-6] (0.26 g, 1.45 mmol), Cs₂CO₃ (0.59 g, 1.810 mmol), Pd₂dba₃ (0.03 g, 0.03 mmol) and Xantphos (0.04 g, 0.06 mmol). The tube was capped with a septum and purged with argon. 1,4-dioxane (5 mL) was added via a syringe through the septum. The reaction flask was sealed and placed in a pre-heated oil bath at 100° C. and stirred for 24 h. The reaction mixture was cooled to room temperature and 10 mL of EtOAc were added. The organic layer was washed successively with 5 mL of water and 5 mL of brine, dried with Na₂SO₄, filtered and concentrated in vacuo to give yellow oil. The crude was purified by column chromatography over silica gel (eluent: DCM/EtOAc, gradient: 100/00 to 90/10) to give 0.15 g (22%) of intermediate (G289) as yellow solid.

intermediate (G289)

b) Compound (W37):
LiOH.H₂O (31 mg; 0.73 mmol) was added to a solution of intermediate (G289) (140 mg; 0.24 mmol) in H₂O (0.7 mL) and THF (2.2 mL) and the reaction mixture was stirred at rt for 16 h. An aqueous solution of KHSO₄ 10% was added and the layers were separated. The organic layer was washed with water, dried over MgSO₄, filtered and concentrated to give yellow oil. This oil was purified by preparative LC (Irregular SiOH, 15-40 µm, 12 g Grace Resolv®, dry loading (on SiOH), mobile phase gradient: from heptane/(EtOAc/AcOH 2.5%) 80/20 to 20/80) to give 95 mg of a yellow sticky oil. It was taken-up in acetonitrile and sonicated (precipitation occurred). The mixture was concentrated to give 88 mg (66%) of compound (W37) as a yellow solid.

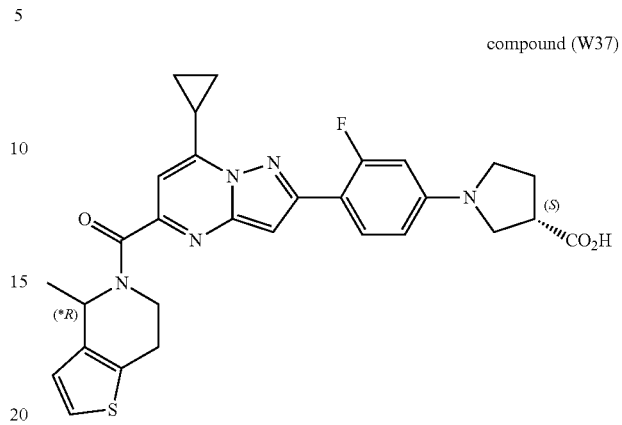

compound (W37)

Compound (W38):
LiOH—H₂O (38 mg; 0.897 mmol) was added to a solution of intermediate (G288) (166 mg; 0.292 mmol) in water (1.5 mL) and THF (3.7 mL). The reaction mixture was stirred at rt for 18 h. Brine, an aqueous solution of KHSO₄ (10%) and EtOAc were added to the reaction mixture, aqueous layer was extracted with EtOAc (twice). The combined organic layers were washed with water/brine 1/1, dried over MgSO₄, filtered and evaporated in vacuo to give a yellowish gum which was taken up in MeCN and evaporated under reduced pressure to give 145 mg of a yellow solid. The compound was triturated in MeCN, filtered off and dried on frit to give 115 mg (73%) of compound (W38) as a yellow solid.

Compound (W38)

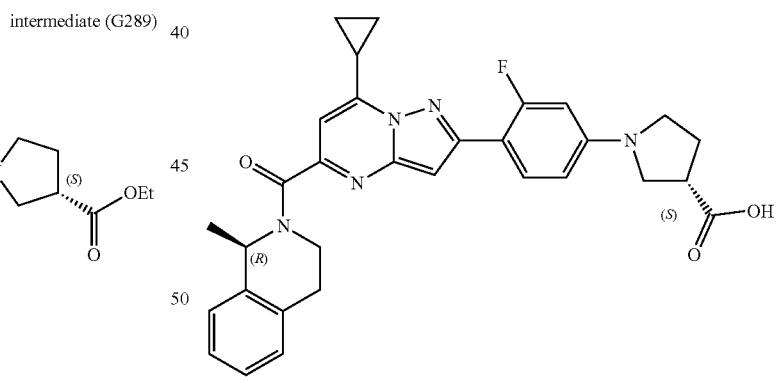

Compound (W41)
a) Intermediate (G278):
A mixture of intermediate (U5) (0.22 g, 0.70 mmol), intermediate (G267) (0.51 g, 0.8 mmol at 72 wt % purity), K₃PO₄ (0.45 g, 2.11 mmol) and PdCl₂(dtbpf) (0.05 g, 0.07 mmol) in 1,4-dioxane (15 mL) and H₂O (1 mL) was stirred at 90° C. for 1.5 h. The reaction mixture was poured into 30 mL of DCM, washed successively with 15 mL of water and 15 mL of brine, dried with Na₂SO₄, filtered and concentrated in vacuum. The crude was purified by column chromatography over silica gel (eluent: DCM/EtOAc 100/0 to 90/10) to give 0.398 g (99%) of intermediate (G278) as brown solid.

intermediate (G278)

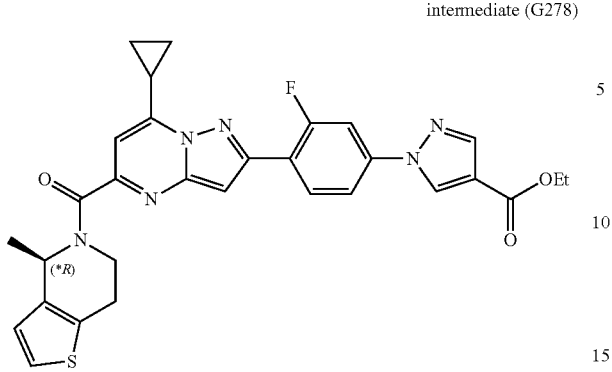

b) Compound (W41):

LiOH.H$_2$O (138 mg; 3.29 mmol) was added to a solution of intermediate (G278) (35 mg; 0.61 mmol) in H$_2$O (1.5 mL) and THF (5 mL). The reaction mixture was stirred at rt for 24 h. Then HCl 3M (1.1 mL; 3.3 mmol) was added and the reaction mixture was evaporated and purified by preparative LC (spherical C18 25 µm, 120 g YMC-ODS-25®, dry loading (celite), mobile phase gradient: 0.2% aq. NH$_4$+ HCO$_3$−/MeOH from 80:20 to 30:70 in 15 CV). The pure fractions were collected and concentrated and extracted with AcOEt and 10% aq. KHSO$_4$. The organic layer was washed with brine, dried (MgSO$_4$) and evaporated to give 215 mg (65%) of compound (W41) as a yellow solid.

compound (W41)

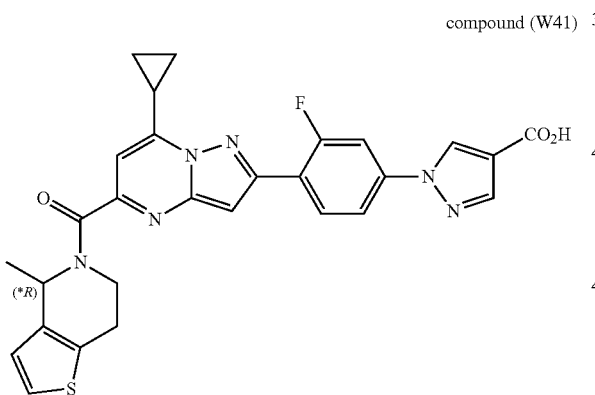

Compound (W43):

a) Intermediate (G264):

A mixture of intermediate (E1) (1.04 g; 2.58 mmol), intermediate (F22) (538 mg; 2.84 mmol), COMU® (1.66 g; 3.87 mmol; 1.5 eq) and DIEA (1.3 mL; 7.54 mmol) in DMF (15 mL) was stirred at rt for 18 h. The reaction mixture was diluted in ethyl acetate, washed with a sat. aq. solution of NaHCO$_3$ (twice), brine (3 times), dried over MgSO$_4$ and evaporated in vacuum. The crude compound was purified by preparative LC (irregular SiOH 15-40 µm, 40 g Grace Resolv®, liquid loading (DCM), mobile phase gradient: from heptane 90%, EtOAc 10% to Heptane 70%, EtOAc 30%) to give 1.04 g (81%) of intermediate (G264) as a pink solid.

intermediate (G264)

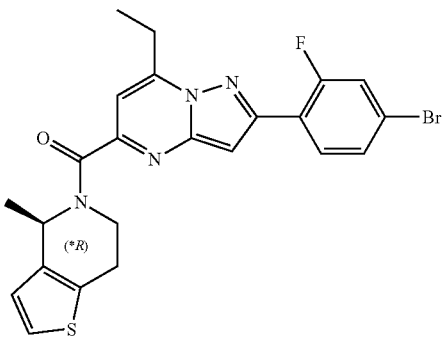

b) Intermediate (G290):

A sealed tube was charged with intermediate (G264) (478 mg; 0.96 mmol), (S)-methyl pyrrolidine-3-carboxylate hydrochloride (169 mg; 1.18 mmol), Cs$_2$CO$_3$ (624 mg; 1.91 mmol) and XantPhos (55 mg; 0.1 mmol) and purged with N$_2$. 1,4-dioxane (13 mL) was added and the mixture was purged again with N$_2$, then Pd(OAc)$_2$ (21 mg; 0.1 mmol) was added. The reaction mixture was purged with N$_2$ and heated at 100° C. for 17 h. The mixture was diluted with EtOAc and water. The layers were separated. The aqueous layer was extracted with EtOAc (twice). The combined organic layers were washed with brine, dried with MgSO$_4$, filtered and the solvent was removed under reduced pressure. The crude compound was purified by prepartive LC (irregular SiOH, 15-40 µm, 24 g Grace®, liquid injection (DCM), mobile phase gradient: from Heptane 90%, EtOAc 10% to heptane 70%, EtOAc 30%) to give 273 mg (51%) of intermediate (G290) as a yellow foam.

intermediate (G290)

c) Compound (W43):

LiOH—H$_2$O (61 mg; 1.46 mmol) was added to a solution of intermediate (G290) (273 mg; 0.49 mmol) in H$_2$O (2.1 mL) and THF (5.5 mL). The reaction mixture was stirred at rt for 18 h. Brine, an aqueous solution of KHSO$_4$ (10%) and EtOAc were added to the reaction mixture, aqueous layer was extracted with EtOAc (twice). The combined organic layers were washed with water/brine 1/1, dried over MgSO$_4$, filtered and evaporated in vacuum to give a yellowish gum which was taken up in MeCN and evaporated to give 237 mg (91%) of compound (W43) as a yellow solid.

compound (W43)

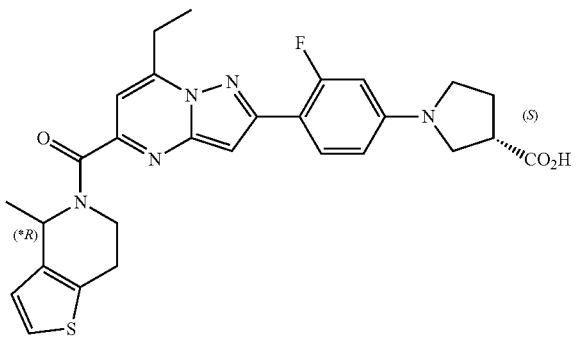

Reaction scheme for compounds (W49) and (W50):

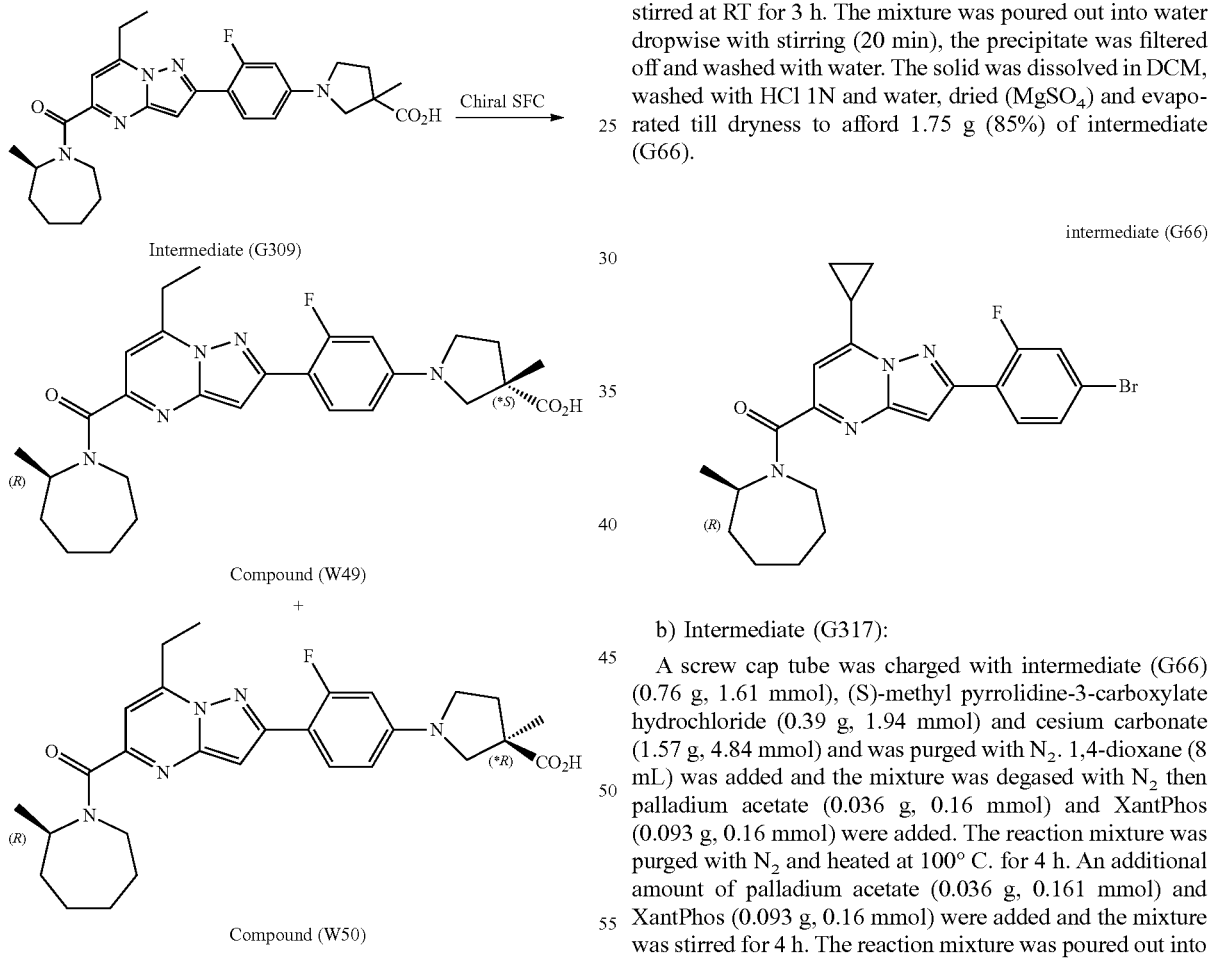

Compounds (W49) and (W50):

Intermediate (G309) was purified via chiral SFC (Stationary phase: Chiralpak® AD-H 5 μm 250*30 mm, Mobile phase: 55% CO$_2$, 45% mixture of EtOH/iPrOH 50/50 v/v (+0.3% iPrNH$_2$)) to give 256 mg of 1st diastereomer as iPrNH$_2$ salt and 245 mg of 2$^{nd}$ diastereomer as iPrNH$_2$ salt. 1$^{st}$ diastereomer was taken-up with EtOAc and an aqueous solution of KHSO$_4$ (10%). The layers were separated and the aqueous layer was extracted with EtOAc (once). The combined organic layers were dried over MgSO$_4$, filtered and the solvent was removed in vacuo. The product was crystallized (3 times) from MeOH to give 3 batches of 1$^{st}$ diastereomer. These batches were suspended in water, filtered off and dried over glass frit to give 160 mg of compound (W49). 2$^{nd}$ diastereomer was taken-up with EtOAc and an aqueous solution of KHSO$_4$ (10%). The layers were separated and the aqueous layer was extracted with EtOAc (once). The combined organic layers were dried over MgSO$_4$, filtered and the solvent was removed in vacuo. The product was crystallized (3 times) from MeOH to give 3 batches of 2$^{nd}$ diastereomer. These batches were suspended in water, filtered off and dried over glass frit to give 202 mg of compound (W50).

Compound (W51)

a) Intermediate (G66):

DIEA (2.28 mL, 13.035 mmol) then HATU (2.15 g, 5.65 mmol) were added to a mixture of (R)-2-methylazepane hydrochloride (0.78 g, 5.21 mmol) and intermediate (E46) (1.8 g, 4.35 mmol) in DMF (50 mL) then the mixture was stirred at RT for 3 h. The mixture was poured out into water dropwise with stirring (20 min), the precipitate was filtered off and washed with water. The solid was dissolved in DCM, washed with HCl 1N and water, dried (MgSO$_4$) and evaporated till dryness to afford 1.75 g (85%) of intermediate (G66).

intermediate (G66)

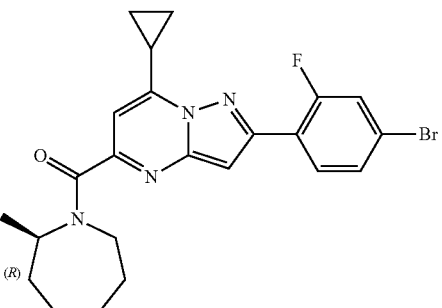

b) Intermediate (G317):

A screw cap tube was charged with intermediate (G66) (0.76 g, 1.61 mmol), (S)-methyl pyrrolidine-3-carboxylate hydrochloride (0.39 g, 1.94 mmol) and cesium carbonate (1.57 g, 4.84 mmol) and was purged with N$_2$. 1,4-dioxane (8 mL) was added and the mixture was degased with N$_2$ then palladium acetate (0.036 g, 0.16 mmol) and XantPhos (0.093 g, 0.16 mmol) were added. The reaction mixture was purged with N$_2$ and heated at 100° C. for 4 h. An additional amount of palladium acetate (0.036 g, 0.161 mmol) and XantPhos (0.093 g, 0.16 mmol) were added and the mixture was stirred for 4 h. The reaction mixture was poured out into water and extracted with EtOAc. The mixture was filtered through a pad of Celite®, the Celite® was rinsed with EtOAc and the organic layer was separated. The aqueous layer was extracted with EtOAc. The combined organic layers were washed with brine, dried with MgSO$_4$, filtered and the solvent was removed under reduced pressure to give a residue (1.1 g). Purification of the residue was carried out by flash chromatography over silica gel (cartridge 40 g, 15-40 μm, from Heptane/EtOAc 70/30 to 50/50). The pure fractions were collected and evaporated to dryness to give 0.44 g (52%) of intermediate (G317).

intermediate (G317)

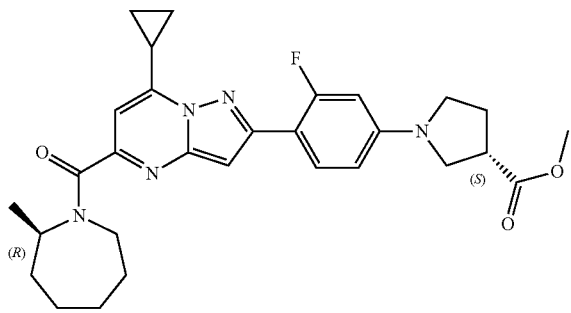

Compound (W51):

LiOH monohydrate (0.107 g, 2.54 mmol) was added to a solution of intermediate (G313) (0.44 g, 0.847 mmol) in water (0.87 mL) and THF (4.4 mL). The reaction mixture was stirred at rt for 2 h. The mixture was poured out into KHSO$_4$ (10% aq.) and extracted with DCM. The organic layer was separated (hydrophobic frit) and evaporated till dryness. The residue was crystallized from iPrOH, the precipitate was filtered off and dried (60° C., vacuum) to give 0.25 g (60%) of compound (W51).

Compound (W51)

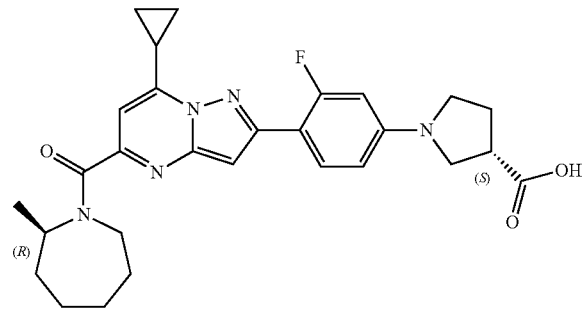

Compound (Y) (X):

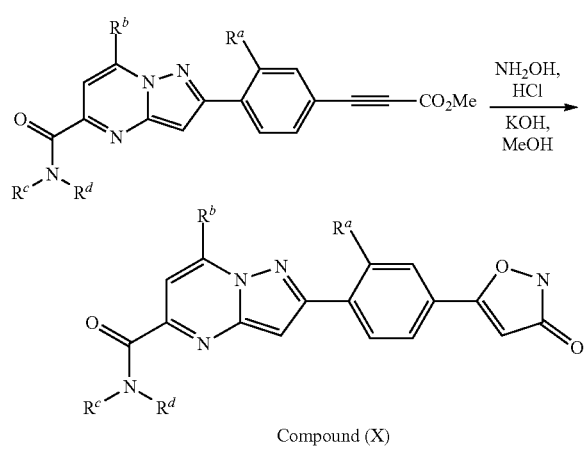

Compound (X)

Compound (X1):

To a mixture of intermediate (G79) (449 mg; 0.971 mmol) and hydroxylamine hydrochloride (236 mg; 3.40 mmol) in MeOH (8 mL) was added KOH (327 mg; 5.83 mmol) and the mixture was stirred at RT for 16 hours. Water was added and the mixture was extracted with DCM (once) (DCM organic layer was discarded). The aqueous layer was acidified with an aqueous solution of HCl (solution of 1N in H$_2$O) and extracted with EtOAc (twice). The combined organic layers (EtOAc) were washed with brine, dried over MgSO$_4$, filtered and the solvent was removed in vacuum. The residue was purified by column chromatography (silica gel, from heptane/EtOAc 80/20 to 0/100). The pure fractions were collected and the solvent was evaporated to give a yellow solid. This solid was triturated in CH$_3$CN, filtered and dried under high vacuum at 50° C. for 16 hours to give 98 mg (22%) of compound (X1) as a yellow solid.

compound (X1)

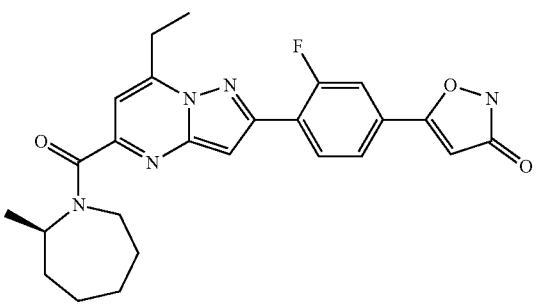

D. Compound Identification

NMR

For a number of compounds, NMR spectra were recorded using a Bruker Avance 500 spectrometer equipped with a reverse triple-resonance ($^1$H, $^{13}$C, $^{15}$N TXI) probe head with z gradients and operating at 500 MHz for the proton and 125 MHz for carbon; a Bruker DPX 400 spectrometer equipped with a 5 mm reverse triple-resonance ($^1$H, $^{13}$C, $^{19}$F BBI) probe head operating at 400 MHz for the proton and 100 MHz for carbon; or a Bruker DPX 300 spectrometer equipped with a 5 mm dual probe ($^1$H, $^{13}$C, QNP) probe head with z gradients and operating at 300 MHz for the proton and 75 MHz for carbon.

Deuterated solvents were chloroform-d (deuterated chloroform, CDCl$_3$) or DMSO-d$_6$ (deuterated DMSO, dimethyl-d6 sulfoxide). Chemical shifts (δ) are reported in parts per million (ppm) relative to tetramethylsilane (TMS), which was used as internal standard.

Compound (B1)

Major Rotamer (60%)

$^1$H NMR (400 MHz, chloroform-d) δ ppm 8.07 (s, 1H) 7.39-7.65 (m, 2H) 6.98-7.11 (m, 1H) 6.72 (s, 1H) 6.18-6.46 (m, 1H) 4.28 (br d, J=12.6 Hz, 1H) 4.06-4.11 (m, 1H) 3.73-3.98 (m, 3H) 3.53-3.65 (m, 1H) 2.86-3.32 (m, 4H) 1.57-2.23 (m, 10H) 1.17-1.51 (m, 9H)

Minor Rotamer (40%)

$^1$H NMR (400 MHz, chloroform-d) δ ppm 8.07 (s, 1H) 7.39-7.65 (m, 2H) 6.98-7.11 (m, 1H) 6.76 (s, 1H) 6.18-6.46 (m, 1H) 4.68 (br s, 1H) 4.06-4.11 (m, 1H) 3.73-3.98 (m, 3H) 3.53-3.65 (m, 1H) 2.86-3.32 (m, 4H) 1.57-2.23 (m, 10H) 1.17-1.51 (m, 9H)

Compound (B3)

Major Rotamer (80%)

$^1$H NMR (400 MHz, DMSO-d$_6$) δ ppm 8.98 (s, 1H) 8.02 (br t, J=8.7 Hz, 1H) 7.64 (br d, J=14.8 Hz, 1H) 6.86-7.27 (m, 3H) 6.34 (br s, 1H) 3.55-4.02 (m, 6H) 2.95-3.27 (m, 3H) 1.75-2.05 (m, 4H) 1.35-1.70 (m, 12H) 0.97-1.29 (m, 5H)

Minor Rotamer (20%)

$^1$H NMR (400 MHz, DMSO-d$_6$) δ ppm 8.98 (s, 1H) 8.02 (br t, J=8.7 Hz, 1H) 7.64 (br d, J=14.8 Hz, 1H) 6.86-7.27 (m, 3H) 6.34 (br s, 1H) 4.43-4.56 (m, 1H) 3.55-4.02 (m, 5H) 2.95-3.27 (m, 3H) 1.75-2.05 (m, 4H) 1.35-1.70 (m, 12H) 0.97-1.29 (m, 5H)

Compound (C4)

Major Rotamer (60%)

$^1$H NMR (400 MHz, DMSO-d$_6$) δ ppm 10.15 (br s, 1H) 8.06 (br t, J=8.3 Hz, 1H) 7.56 (br d, J=13.6 Hz, 1H) 7.39 (br d, J=8.8 Hz, 1H) 7.01-7.08 (m, 2H) 4.78-4.93 (m, 1H) 4.15 (br s, 2H) 3.99 (br d, J=12.5 Hz, 1H) 3.36-3.78 (m, 3H) 3.01-3.29 (m, 2H) 2.92 (br t, J=12.5 Hz, 1H) 1.86-2.11 (m, 1H) 1.51-1.82 (m, 4H) 1.08-1.43 (m, 9H)

Minor Rotamer (40%)

$^1$H NMR (400 MHz, DMSO-d$_6$) δ ppm 10.15 (br s, 1H) 8.06 (br t, J=8.3 Hz, 1H) 7.56 (br d, J=13.6 Hz, 1H) 7.39 (br d, J=8.8 Hz, 1H) 7.01-7.08 (m, 2H) 4.78-4.93 (m, 1H) 4.35-4.52 (m, 1H) 4.15 (br s, 2H) 3.36-3.78 (m, 3H) 3.01-3.29 (m, 3H) 1.86-2.11 (m, 1H) 1.51-1.82 (m, 4H) 1.08-1.43 (m, 9H)

Compound (D3)

Major Rotamer (70%)

$^1$H NMR (400 MHz, DMSO-d$_6$) δ ppm 10.25 (s, 1H) 8.11 (br t, J=8.7 Hz, 1H) 6.86-7.24 (m, 4H) 3.37-3.84 (m, 3H) 3.24 (q, J=7.7 Hz, 2H) 3.13 (s, 3H) 0.99-2.06 (m, 16H)

Minor Rotamer (30%)

$^1$H NMR (400 MHz, DMSO-d$_6$) δ ppm 10.25 (s, 1H) 8.11 (br t, J=8.7 Hz, 1H) 6.86-7.24 (m, 4H) 4.44-4.58 (m, 1H) 3.37-3.84 (m, 2H) 3.24 (q, J=7.7 Hz, 2H) 3.13 (s, 3H) 0.99-2.06 (m, 16H)

Compound (E2)

Major Rotamer (60%)

$^1$H NMR (500 MHz, DMSO-d$_6$) δ ppm 10.64 (s, 1H), 8.52 (d, J=4.8 Hz, 2H) 8.12 (t, J=7.9 Hz, 1H) 7.75-7.85 (m, 1H) 7.40-7.50 (m, 1H) 7.35 (d, J=4.6 Hz, 2H), 6.98-7.15 (m, 2H) 4.00 (br d, J=13.2 Hz, 1H) 3.77 (s, 2H) 3.46-3.73 (m, 1H) 3.30-3.50 (m, 2H) 2.91 (br t, J=12.7 Hz, 1H) 0.97-2.12 (m, 14H)

Minor Rotamer (40%)

$^1$H NMR (500 MHz, DMSO-d$_6$) δ ppm 10.64 (s, 1H), 8.52 (d, J=4.8 Hz, 2H) 8.12 (t, J=7.9 Hz, 1H) 7.75-7.85 (m, 1H) 7.40-7.50 (m, 1H) 7.35 (d, J=4.6 Hz, 2H), 6.98-7.15 (m, 2H) 4.5-4.60 (m, 1H) 3.77 (s, 2H) 3.52 (br d, J=13.2 Hz, 1H) 3.20-3.50 (m, 3H) 0.97-2.12 (m, 14H)

Compound (E3)

Major Rotamer (60%)

$^1$H NMR (500 MHz, DMSO-d$_6$) δ ppm 10.70 (s, 1H), 8.14 (t, J=8.8 Hz, 1H) 7.70-7.80 (m, 1H) 7.67 (s, 1H) 7.40-7.50 (m, 1H) 7.19 (s, 1H), 6.99-7.12 (m, 2H) 6.92 (s, 1H), 4.96 (s, 2H) 3.95 (br d, J=13.1 Hz, 1H) 3.60-3.75 (m, 1H) 2.85-3.27 (m, 3H) 1.03-2.12 (m, 14H)

Minor Rotamer (40%)

$^1$H NMR (500 MHz, DMSO-d$_6$) δ ppm 10.70 (s, 1H), 8.14 (t, J=8.8 Hz, 1H) 7.70-7.80 (m, 1H) 7.67 (s, 1H) 7.40-7.50 (m, 1H) 7.19 (s, 1H), 6.99-7.12 (m, 2H) 6.92 (s, 1H), 4.96 (s, 2H) 4.35-4.70 (m, 1H) 3.52 (br d, J=13.1 Hz, 1H) 2.85-3.27 (m, 3H) 1.03-2.12 (m, 14H)

Compound (E5)

Major Rotamer (65%)

$^1$H NMR (400 MHz, DMSO-d$_6$) δ ppm 10.36 (br s, 1H) 8.10 (br s, 1H) 7.67-7.95 (m, 1H) 7.44 (br s, 1H) 6.70-7.17 (m, 2H) 5.83-6.25 (m, 1H) 5.06-5.34 (m, 1H) 3.99 (br d, J=9.4 Hz, 1H) 3.45-3.81 (m, 1H) 3.09-3.25 (m, 6H) 1.53-2.19 (m, 6H) 1.41 (br s, 3H) 1.22-1.34 (m, 2H) 1.13 (br s, 3H)

Minor Rotamer (35%)

$^1$H NMR (400 MHz, DMSO-d$_6$) δ ppm 10.36 (br s, 1H) 8.10 (br s, 1H) 7.67-7.95 (m, 1H) 7.44 (br s, 1H) 6.70-7.17 (m, 2H) 5.83-6.25 (m, 1H) 5.06-5.34 (m, 1H) 4.33-4.54 (m, 1H) 3.45-3.81 (m, 1H) 3.09-3.25 (m, 6H) 1.53-2.19 (m, 6H) 1.41 (br s, 3H) 1.22-1.34 (m, 2H) 1.13 (br s, 3H)

Compound (E7)

Major Rotamer (60%)

$^1$H NMR (400 MHz, DMSO-d$_6$) δ ppm 10.34 (s, 1H) 8.10 (t, J=8.5 Hz, 1H) 7.81 (br d, J=13.4 Hz, 1H) 7.43 (br d, J=8.6 Hz, 1H) 7.03-7.10 (m, 2H) 3.99 (br d, J=12.7 Hz, 1H) 3.49-3.76 (m, 3H) 2.73-3.26 (m, 6H) 2.59 (t, J=6.1 Hz, 2H) 1.88-2.13 (m, 1H) 1.53-1.85 (m, 4H) 1.41 (t, J=7.5 Hz, 3H) 1.22-1.36 (m, 3H) 1.10-1.20 (m, 3H)

Minor Rotamer (40%)

$^1$H NMR (400 MHz, DMSO-d$_6$) δ ppm 10.34 (s, 1H) 8.10 (t, J=8.5 Hz, 1H) 7.81 (br d, J=13.4 Hz, 1H) 7.43 (br d, J=8.6 Hz, 1H) 7.03-7.10 (m, 2H) 4.39-4.49 (m, 1H) 3.49-3.76 (m, 3H) 2.73-3.26 (m, 6H) 2.59 (t, J=6.1 Hz, 2H) 1.88-2.13 (m, 1H) 1.53-1.85 (m, 4H) 1.41 (t, J=7.5 Hz, 3H) 1.22-1.36 (m, 3H) 1.10-1.20 (m, 3H)

Compound (E10)

Major Rotamer (60%)

$^1$H NMR (500 MHz, DMSO-d$_6$) δ ppm 10.58 (s, 1H) 8.10 (t, J=8.6 Hz, 1H) 7.72-7.82 (m, 1H) 7.35-7.50 (m, 1H) 6.97-7.11 (m, 2H) 4.00 (br d, J=12.9 Hz, 1H) 3.70-3.78 (m, 1H) 3.20-3.27 (m, 2H) 2.90 (t, J=12.2 Hz, 1H) 1.06-2.16 (m, 15H) 0.76-0.91 (m, 4H)

Minor Rotamer (40%)

$^1$H NMR (500 MHz, DMSO-d$_6$) δ ppm 10.58 (s, 1H) 8.10 (t, J=8.6 Hz, 1H) 7.72-7.82 (m, 1H) 7.35-7.50 (m, 1H) 6.97-7.11 (m, 2H) 4.38-4.49 (m, 1H) 3.55 (br d, J=12.9 Hz, 1H) 3.07-3.20 (m, 3H) 1.06-2.16 (m, 15H) 0.76-0.91 (m, 4H)

Compound (E25)

Major Rotamer (60%)

$^1$H NMR (400 MHz, DMSO-d$_6$) δ ppm 10.34 (br s, 1H) 8.09 (br t, J=7.9 Hz, 1H) 7.79 (br d, J=13.6 Hz, 1H) 7.29-7.44 (m, 2H) 7.01-7.10 (m, 2H) 6.77 (br s, 1H) 3.94-4.04 (m, 1H) 3.62-3.77 (m, 1H) 3.44-3.57 (m, 1H) 3.05-3.27 (m, 3H) 2.85-3.00 (m, 1H) 2.53-2.61 (m, 1H) 1.49-2.12 (m, 5H) 1.03-1.45 (m, 10H)

Minor Rotamer (40%)

$^1$H NMR (400 MHz, DMSO-d$_6$) δ ppm 10.34 (br s, 1H) 8.09 (br t, J=7.9 Hz, 1H) 7.79 (br d, J=13.6 Hz, 1H) 7.29-7.44 (m, 2H) 7.01-7.10 (m, 2H) 6.77 (br s, 1H) 4.38-4.49 (m, 1H) 3.62-3.77 (m, 1H) 3.44-3.57 (m, 1H) 3.05-3.27 (m, 3H) 2.85-3.00 (m, 1H) 2.53-2.61 (m, 1H) 1.49-2.12 (m, 5H) 1.03-1.45 (m, 10H)

Compound (E27)

Major Rotamer (60%)

$^1$H NMR (500 MHz, DMSO-d$_6$) δ ppm 10.34 (s, 1H), 8.05 (t, J=7.8 Hz, 1H) 7.75-7.90 (m, 2H) 7.41 (d, J=7.9 Hz, 1H), 6.95-7.12 (m, 2H), 3.90-4.05 (m, 1H), 3.62-3.75 (m, 1H) 3.25-3.30 (m, 2H) 2.91 (br d, J=12.9 Hz, 1H) 2.35-2.70 (m, 6H) 1.06-2.15 (m, 15H)

Minor Rotamer (40%)

$^1$H NMR (500 MHz, DMSO-d$_6$) δ ppm 10.34 (s, 1H), 8.05 (t, J=7.8 Hz, 1H) 7.75-7.90 (m, 2H) 7.41 (d, J=7.9 Hz, 1H), 6.95-7.12 (m, 2H) 4.38-4.53 (m, 1H) 3.52-3.61 (m, 1H) 3.25-3.30 (m, 2H) 3.05-3.20 (m, 1H) 2.35-2.70 (m, 6H) 1.06-2.15 (m, 15H)

Compound (E28)
Major Rotamer (60%)
¹H NMR (400 MHz, DMSO-d₆) δ ppm 10.34 (br s, 1H) 8.09 (t, J=8.7 Hz, 1H) 7.79 (br d, J=13.2 Hz, 1H) 7.43 (br d, J=7.2 Hz, 1H) 7.01-7.09 (m, 2H) 3.93-4.06 (m, 1H) 3.61-3.77 (m, 1H) 3.24 (q, J=7.0 Hz, 2H) 2.88-3.18 (m, 4H) 2.82 (s, 3H) 2.56-2.66 (m, 4H) 1.86-2.13 (m, 1H) 1.51-1.85 (m, 4H) 1.41 (brt, J=7.3 Hz, 3H) 1.21-1.36 (m, 3H) 1.07-1.19 (m, 3H)
Minor Rotamer (40%)
¹H NMR (400 MHz, DMSO-d₆) δ ppm 10.34 (br s, 1H) 8.09 (t, J=8.7 Hz, 1H) 7.79 (br d, J=13.2 Hz, 1H) 7.43 (br d, J=7.2 Hz, 1H) 7.05 (br t, J=7.2 Hz, 2H) 4.38-4.50 (m, 1H) 3.54 (br d, J=14.9 Hz, 1H) 3.24 (q, J=7.0 Hz, 2H) 2.88-3.18 (m, 4H) 2.82 (s, 3H) 2.56-2.66 (m, 4H) 1.86-2.13 (m, 1H) 1.51-1.85 (m, 4H) 1.41 (br t, J=7.3 Hz, 3H) 1.21-1.36 (m, 3H) 1.07-1.19 (m, 3H)

Compound (F15)
Major Rotamer (60%)
¹H NMR (500 MHz, DMSO-d₆) δ ppm 13.5 (br s, 1H) 9.18-9.20 (m, 1H) 8.38 (dd, J=8.2, 2.2 Hz, 1H) 8.34 (t, J=7.9 Hz, 1H) 8.17-8.28 (m, 3H) 7.21 (d, J=3.8 Hz, 1H) 7.13 (br s, 1H) 4.00 (br d, J=13.2 Hz, 1H) 3.68-3.75 (m, 1H) 3.22-3.31 (m, 2H) 2.94 (t, J=12.5 Hz, 1H) 1.91-1.98 (m, 1H) 1.55-1.86 (m, 5H) 1.44 (t, J=7.4 Hz, 3H) 1.23-1.39 (m, 2H) 1.16 (d, J=6.6 Hz, 3H)
Minor Rotamer (40%)
¹H NMR (500 MHz, DMSO-d₆) δ ppm 13.5 (br s, 1H) 9.18-9.20 (m, 1H) 8.38 (dd, J=8.2, 2.2 Hz, 1H) 8.34 (t, J=7.9 Hz, 1H) 8.17-8.28 (m, 3H) 7.23 (d, J=3.8 Hz, 1H) 7.14 (br s, 1H) 4.41-4.49 (m, 1H) 3.55 (br d, J=13.2 Hz, 1H) 3.22-3.31 (m, 2H) 3.11-3.18 (m, 1H) 2.03-2.10 (m, 1H) 1.55-1.86 (m, 5H) 1.44 (t, J=7.4 Hz, 3H) 1.23-1.39 (m, 2H) 1.14 (d, J=6.6 Hz, 3H)

Compound (F16)
Major Rotamer (60%)
¹H NMR (400 MHz, chloroform-d) δ ppm 8.05-8.16 (m, 1H) 7.78 (br s, 1H) 7.37-7.53 (m, 2H) 7.32 (br d, J=5.6 Hz, 1H) 7.15 (t, J=4.3 Hz, 1H) 6.58-6.96 (m, 2H) 4.26 (br d, J=13.2 Hz, 1H) 3.92-4.02 (m, 1H) 2.87-3.26 (m, 3H) 1.93-2.21 (m, 1H) 1.64-1.75 (m, 1H) 1.21-1.49 (m, 12H)
Minor Rotamer (40%)
¹H NMR (400 MHz, chloroform-d) δ ppm 8.05-8.16 (m, 1H) 7.78 (br s, 1H) 7.37-7.53 (m, 2H) 7.32 (br d, J=5.6 Hz, 1H) 7.15 (t, J=4.3 Hz, 1H) 6.58-6.96 (m, 2H) 4.61-4.74 (m, 1H) 3.85 (br d, J=15.3 Hz, 1H) 2.87-3.26 (m, 3H) 1.93-2.21 (m, 1H) 1.64-1.75 (m, 1H) 1.21-1.49 (m, 12H)

Compound (F19):
Major Rotamer (65%)
¹H NMR (500 MHz, DMSO-d₆) δ ppm 13.69 (br s, 1H) 9.01 (s, 1H) 8.38 (dd, J=11.7, 1.3 Hz, 1H) 8.32 (t, J=8.0 Hz, 1H) 8.03 (dd, J=12.3, 1.3 Hz, 1H) 7.93 (dd, J=8.2, 1.6 Hz, 1H) 7.20-7.24 (m, 1H) 7.13 (s, 1H) 4.00 (br d, J=12.6 Hz, 1H) 3.65-3.77 (m, 1H) 3.28 (q, J=7.4 Hz, 2H) 2.94 (br t, J=12.6 Hz, 1H) 1.89-1.99 (m, 1H) 1.55-1.86 (m, 4H) 1.44 (t, J=7.6 Hz, 3H) 1.20-1.40 (m, 3H) 1.10-1.19 (m, 3H)
Minor Rotamer (35%)
¹H NMR (500 MHz, DMSO-d₆) δ ppm 13.69 (br s, 1H) 9.01 (s, 1H) 8.38 (dd, J=11.7, 1.3 Hz, 1H) 8.32 (t, J=8.0 Hz, 1H) 8.03 (dd, J=12.3, 1.3 Hz, 1H) 7.93 (dd, J=8.2, 1.6 Hz, 1H) 7.20-7.24 (m, 1H) 7.14 (s, 1H) 4.39-4.49 (m, 1H) 3.55 (br d, J=15.4 Hz, 1H) 3.28 (q, J=7.4 Hz, 2H) 3.10-3.18 (m, 1H) 2.01-2.12 (m, 1H) 1.55-1.86 (m, 4H) 1.44 (t, J=7.6 Hz, 3H) 1.20-1.40 (m, 3H) 1.10-1.19 (m, 3H)

Compound (F20):
Major Rotamer (65%)
¹H NMR (500 MHz, DMSO-d₆) δ ppm 13.50 (br s, 1H) 8.23-8.38 (m, 1H) 8.12-8.17 (m, 1H) 7.94-8.07 (m, 3H) 7.21-7.25 (m, 1H) 7.10-7.17 (m, 1H) 3.97-4.04 (m, 1H) 3.67-3.76 (m, 1H) 3.28 (q, J=7.6 Hz, 2H) 2.94 (br t, J=12.5 Hz, 1H) 1.92-1.97 (m, 1H) 1.54-1.87 (m, 4H) 1.44 (t, J=7.4 Hz, 3H) 1.22-1.38 (m, 3H) 1.12-118 (m, 3H)
Minor Rotamer (35%)
¹H NMR (500 MHz, DMSO-d₆) δ ppm 13.50 (br s, 1H) 8.23-8.38 (m, 1H) 8.12-8.17 (m, 1H) 7.94-8.07 (m, 3H) 7.21-7.25 (m, 1H) 7.10-7.17 (m, 1H) 4.40-4.50 (m, 1H) 3.55 (br d, J=15.4 Hz, 1H) 3.28 (q, J=7.6 Hz, 2H) 3.10-3.18 (m, 1H) 2.03-2.10 (m, 1H) 1.54-1.87 (m, 4H) 1.44 (t, J=7.4 Hz, 3H) 1.22-1.38 (m, 3H) 1.12-118 (m, 3H)

Compound (F21):
Major Rotamer (65%)
¹H NMR (500 MHz, DMSO-d₆) δ ppm 13.52 (br s, 1H) 9.19 (d, J=1.6 Hz, 1H) 8.34-8.41 (m, 2H) 8.27 (d, J=8.2 Hz, 1H) 8.17-8.25 (m, 2H) 7.17-7.22 (m, 1H) 6.85-6.89 (m, 1H) 3.98 (br d, J=13.2 Hz, 1H) 3.58-3.69 (m, 1H) 2.85-3.05 (m, 2H) 1.87-1.99 (m, 1H) 1.19-1.87 (m, 11H) 1.07-1.19 (m, 3H)
Minor Rotamer (35%)
¹H NMR (500 MHz, DMSO-d₆) δ ppm 13.52 (br s, 1H) 9.19 (d, J=1.6 Hz, 1H) 8.34-8.41 (m, 2H) 8.27 (d, J=8.2 Hz, 1H) 8.17-8.25 (m, 2H) 7.17-7.22 (m, 1H) 6.85-6.89 (m, 1H) 4.39-4.49 (m, 1H) 3.48 (br d, J=15.1 Hz, 1H) 3.04-3.17 (m, 1H) 2.95-3.05 (m, 1H) 2.01-2.10 (m, 1H) 1.19-1.87 (m, 11H) 1.07-1.19 (m, 3H)

Compound (F22):
Major Rotamer (65%)
¹H NMR (500 MHz, DMSO-d₆) δ ppm 13.31 (br s, 1H) 9.17 (d, J=1.9 Hz, 1H) 8.41 (dd, J=8.2, 2.2 Hz, 1H) 8.35 (t, J=7.9 Hz, 1H) 8.16 (d, J=8.2 Hz, 1H) 7.98 (dd, J=12.5, 1.4 Hz, 1H) 7.88 (dd, J=8.2, 1.3 Hz, 1H) 7.34 (d, J=7.6 Hz, 1H) 7.06-7.29 (m, 5H) 5.63 (q, J=6.5 Hz, 1H) 3.92 (br dd, J=13.7, 3.9 Hz, 1H) 3.48-3.56 (m, 1H) 2.89-3.31 (m, 3H) 2.75 (br d, J=16.4 Hz, 1H) 1.55 (d, J=6.9 Hz, 3H) 1.40-1.48 (m, 3H)
Minor Rotamer (35%)
¹H NMR (500 MHz, DMSO-d₆) δ ppm 13.31 (br s, 1H) 9.17 (d, J=1.9 Hz, 1H) 8.41 (dd, J=8.2, 2.2 Hz, 1H) 8.35 (t, J=7.9 Hz, 1H) 8.16 (d, J=8.2 Hz, 1H) 7.98 (dd, J=12.5, 1.4 Hz, 1H) 7.88 (dd, J=8.2, 1.3 Hz, 1H) 7.06-7.29 (m, 6H) 5.06 (q, J=6.8 Hz, 1H) 4.59 (br dd, J=12.8, 3.3 Hz, 1H) 2.84-3.31 (m, 5H) 1.59 (d, J=6.6 Hz, 3H) 1.40-1.48 (m, 3H)

Compound (F23):
Major Rotamer (65%)
¹H NMR (400 MHz, DMSO-d₆) δ ppm 13.48 (br s, 1H) 9.19 (s, 1H) 7.96-8.54 (m, 5H) 6.99-7.45 (m, 6H) 5.62 (q, J=6.6 Hz, 1H) 3.92 (br d, J=9.6 Hz, 1H) 3.52 (br t, J=10.9 Hz, 1H) 2.89-3.32 (m, 3H) 2.75 (br d, J=16.2 Hz, 1H) 1.55 (br d, J=6.6 Hz, 3H) 1.36-1.50 (m, 3H)
Minor Rotamer (35%)
¹H NMR (400 MHz, DMSO-d₆) δ ppm 13.48 (br s, 1H) 9.19 (s, 1H) 7.96-8.54 (m, 5H) 6.99-7.45 (m, 6H) 4.97-5.19 (m, 1H) 4.58 (br d, J=10.1 Hz, 1H) 2.82-3.32 (m, 5H) 1.59 (br d, J=6.6 Hz, 3H) 1.36-1.50 (m, 3H)

Compound (F24):
Major Rotamer (60%)
¹H NMR (500 MHz, DMSO-d₆) δ ppm 13.32 (br s, 1H) 9.16 (d, J=1.9 Hz, 1H) 8.41 (dd, J=8.2, 2.5 Hz, 1H) 8.33 (t, J=8.0 Hz, 1H) 8.15 (d, J=8.2 Hz, 1H) 7.97 (dd, J=12.6, 1.6 Hz, 1H) 7.87 (dd, J=8.2, 1.6 Hz, 1H) 7.19-7.24 (m, 1H) 7.11-7.15 (m, 1H) 4.00 (br d, J=13.6 Hz, 1H) 3.65-3.76 (m, 1H) 3.25-3.31 (m, 2H) 2.94 (t, J=12.6 Hz, 1H) 1.89-2.00 (m, 1H) 1.54-1.86 (m, 4H) 1.44 (t, J=7.6 Hz, 3H) 1.20-1.39 (m, 3H) 1.12-1.18 (m, 3H)

Minor Rotamer (40%)

$^1$H NMR (500 MHz, DMSO-d$_6$) δ ppm 13.32 (br s, 1H) 9.16 (d, J=1.9 Hz, 1H) 8.41 (dd, J=8.2, 2.5 Hz, 1H) 8.33 (t, J=8.0 Hz, 1H) 8.15 (d, J=8.2 Hz, 1H) 7.97 (dd, J=12.6, 1.6 Hz, 1H) 7.87 (dd, J=8.2, 1.6 Hz, 1H) 7.19-7.24 (m, 1H) 7.11-7.15 (m, 1H) 4.40-4.50 (m, 1H) 3.55 (br d, J=15.1 Hz, 1H) 3.25-3.31 (m, 2H) 3.10-3.18 (m, 1H) 2.02-2.12 (m, 1H) 1.54-1.86 (m, 4H) 1.44 (t, J=7.6 Hz, 3H) 1.20-1.39 (m, 3H) 1.12-1.18 (m, 3H)

Compound (F25):

Major Rotamer (60%)

$^1$H NMR (500 MHz, DMSO-d$_6$) δ ppm 13.37 (br s, 1H) 8.82 (d, J=5.0 Hz, 1H) 8.40 (d, J=1.3 Hz, 1H) 8.34 (t, J=8.0 Hz, 1H) 8.08 (dd, J=5.0, 1.9 Hz, 1H) 8.01 (dd, J=12.3, 1.6 Hz, 1H) 7.92 (dd, J=8.2, 1.9 Hz, 1H) 7.20-7.25 (m, 1H) 7.11-7.16 (m, 1H) 4.00 (br d, J=13.6 Hz, 1H) 3.66-3.76 (m, 1H) 3.26-3.31 (m, 2H) 2.94 (t, J=12.5 Hz, 1H) 1.91-2.01 (m, 1H) 1.54-1.85 (m, 4H) 1.44 (t, J=7.4 Hz, 3H) 1.21-1.39 (m, 3H) 1.12-1.18 (m, 3H)

Minor Rotamer (40%)

$^1$H NMR (500 MHz, DMSO-d$_6$) δ ppm 13.37 (br s, 1H) 8.82 (d, J=5.0 Hz, 1H) 8.40 (d, J=1.3 Hz, 1H) 8.34 (t, J=8.0 Hz, 1H) 8.08 (dd, J=5.0, 1.9 Hz, 1H) 8.01 (dd, J=12.3, 1.6 Hz, 1H) 7.92 (dd, J=8.2, 1.9 Hz, 1H) 7.20-7.25 (m, 1H) 7.11-7.16 (m, 1H) 4.38-4.50 (m, 1H) 3.55 (br d, J=15.1 Hz, 1H) 3.26-3.31 (m, 2H) 3.10-3.20 (m, 1H) 2.03-2.11 (m, 1H) 1.54-1.85 (m, 4H) 1.44 (t, J=7.4 Hz, 3H) 1.21-1.39 (m, 3H) 1.12-1.18 (m, 3H)

Compound (F26)

Major rotamer: 60%

$^1$H NMR (400 MHz, DMSO-d$_6$) δ ppm 1.12-1.19 (m, 3H) 1.24-1.37 (m, 3H) 1.45 (t, J=7.6 Hz, 3H) 1.59 (br s, 1H) 1.75-1.81 (m, 3H) 2.04-2.10 (m, 1H) 2.94 (br t, J=12.4 Hz, 1H) 3.25-3.29 (m, 2H) 3.57 (br d, J=15.2 Hz, 1H) 4.01 (br d, J=13.6 Hz, 1H) 7.14 (d, J=6.6 Hz, 1H) 7.36 (dd, J=7.1, 3.5 Hz, 1H) 7.69 (dd, J=8.6, 4.0 Hz, 1H) 7.97 (d, J=8.6 Hz, 1H) 8.39 (dd, J=8.3, 6.8 Hz, 1H) 8.50 (d, J=8.1 Hz, 1H) 9.03 (dd, J=4.0, 1.5 Hz, 1H).

Minor rotamer: 40%

$^1$H NMR (400 MHz, DMSO-d$_6$) δ ppm 1.12-1.19 (m, 3H) 1.24-1.37 (m, 3H) 1.45 (t, J=7.6 Hz, 3H) 1.59 (br s, 1H) 1.75-1.81 (m, 3H) 1.92-1.99 (m, 1H) 3.11-3.18 (m, 1H) 3.25-3.29 (m, 2H) 3.71-3.76 (m, 1H) 4.46 (dt, J=11.9, 6.2 Hz, 1H) 7.14 (d, J=6.6 Hz, 1H) 7.36 (dd, J=7.1, 3.5 Hz, 1H) 7.69 (dd, J=8.6, 4.0 Hz, 1H) 7.97 (d, J=8.6 Hz, 1H) 8.39 (dd, J=8.3, 6.8 Hz, 1H) 8.50 (d, J=8.1 Hz, 1H) 9.03 (dd, J=4.0, 1.5 Hz, 1H).

Compound (F27)

Major rotamer: 60%

$^1$H NMR (400 MHz, DMSO-d$_6$) δ ppm 1.12-1.19 (m, 3H) 1.24-1.37 (m, 3H) 1.45 (t, J=7.6 Hz, 3H) 1.59 (br s, 1H) 1.75-1.81 (m, 3H) 2.04-2.10 (m, 1H) 2.94 (br t, J=12.4 Hz, 1H) 3.25-3.29 (m, 2H) 3.57 (br d, J=15.2 Hz, 1H) 4.01 (br d, J=13.6 Hz, 1H) 7.14 (d, J=6.6 Hz, 1H) 7.36 (dd, J=7.1, 3.5 Hz, 1H) 7.69 (dd, J=8.6, 4.0 Hz, 1H) 7.97 (d, J=8.6 Hz, 1H) 8.39 (dd, J=8.3, 6.8 Hz, 1H) 8.50 (d, J=8.1 Hz, 1H) 9.03 (dd, J=4.0, 1.5 Hz, 1H).

Minor rotamer: 40%

$^1$H NMR (400 MHz, DMSO-d$_6$) δ ppm 1.12-1.19 (m, 3H) 1.24-1.37 (m, 3H) 1.45 (t, J=7.6 Hz, 3H) 1.59 (br s, 1H) 1.75-1.81 (m, 3H) 1.92-1.99 (m, 1H) 3.11-3.18 (m, 1H) 3.25-3.29 (m, 2H) 3.71-3.76 (m, 1H) 4.46 (dt, J=11.9, 6.2 Hz, 1H) 7.14 (d, J=6.6 Hz, 1H) 7.36 (dd, J=7.1, 3.5 Hz, 1H) 7.69 (dd, J=8.6, 4.0 Hz, 1H) 7.97 (d, J=8.6 Hz, 1H) 8.39 (dd, J=8.3, 6.8 Hz, 1H) 8.50 (d, J=8.1 Hz, 1H) 9.03 (dd, J=4.0, 1.5 Hz, 1H).

Compound (F28)

$^1$H NMR (400 MHz, DMSO-d$_6$) δ ppm 1.42-1.48 (m, 3H) 1.54-1.61 (m, 3H) 2.76 (br d, J=16.2 Hz, 1H) 2.91-2.96 (m, 1H) 3.29 (s, 1H) 3.35-3.33 (m, 1H) 3.89-3.98 (m, 1H) 5.07 (br d, J=6.6 Hz, 1H) 5.63 (q, J=6.4 Hz, 1H) 7.08-7.27 (m, 4H) 7.34 (br d, J=7.1 Hz, 1H) 7.38-7.44 (m, 1H) 7.70 (dd, J=8.1, 4.0 Hz, 1H) 7.98 (br d, J=8.6 Hz, 1H) 8.41 (br t, J=7.6 Hz, 1H) 8.51 (br d, J=8.1 Hz, 1H) 9.04 (br d, J=3.0 Hz, 1H).

Minor rotamer: 35%

$^1$H NMR (400 MHz, DMSO-d$_6$) δ ppm 1.42-1.48 (m, 3H) 1.54-1.61 (m, 3H) 2.76 (br d, J=16.2 Hz, 1H) 3.02-3.11 (m, 1H) 3.29 (s, 1H) 3.35-3.33 (m, 1H) 3.53 (br t, J=11.1 Hz, 1H) 4.54-4.63 (m, 1H) 7.08-7.27 (m, 4H) 7.34 (br d, J=7.1 Hz, 1H) 7.38-7.44 (m, 1H) 7.70 (dd, J=8.1, 4.0 Hz, 1H) 7.98 (br d, J=8.6 Hz, 1H) 8.41 (br t, J=7.6 Hz, 1H) 8.51 (br d, J=8.1 Hz, 1H) 9.04 (br d, J=3.0 Hz, 1H)

Compound (F29)

Major Rotamer (60%)

$^1$H NMR (400 MHz, DMSO-d$_6$) δ ppm 1.12 (d, J=6.1 Hz, 3H) 1.20-1.46 (m, 6H) 1.54-1.83 (m, 4H) 1.90-2.09 (m, 1H) 2.93 (br t, J=12.9 Hz, 1H) 3.20-3.28 (m, 2H) 3.66-3.76 (m, 1H) 4.00 (br d, J=13.1 Hz, 1H) 5.06 (s, 2H) 7.09-7.12 (m, 1H) 7.14 (d, J=6.4 Hz, 1H) 7.31 (d, J=8.1 Hz, 1H) 7.50 (s, 1H) 7.70 (t, J=6.8 Hz, 1H) 12.95-13.18 (m, 1H)

Minor Rotamer (40%)

$^1$H NMR (400 MHz, DMSO-d$_6$) δ ppm 1.14 (d, J=6.1 Hz, 3H) 1.20-1.46 (m, 6H) 1.54-1.83 (m, 4H) 1.90-2.09 (m, 1H) 3.06-3.19 (m, 1H) 3.20-3.28 (m, 2H) 3.54 (br d, J=14.1 Hz, 1H) 4.39-4.48 (m, 1H) 5.1 (s, 2H) 7.09-7.12 (m, 1H) 7.14 (d, J=6.4 Hz, 1H) 7.31 (d, J=8.1 Hz, 1H) 7.50 (s, 1H) 7.70 (t, J=6.8 Hz, 1H) 12.95-13.18 (m, 1H)

Compound (F30)

Major rotamers (60%)

$^1$H NMR (400 MHz, DMSO-d$_6$) δ ppm 1.12 (d, J=6.6 Hz, 3H) 1.21-1.36 (m, 3H) 1.42 (t, J=7.3 Hz, 3H) 1.57-1.80 (m, 5H) 1.92-2.12 (m, 2H) 2.37-2.44 (m, 2H) 2.93 (t, J=12.9 Hz, 1H) 3.26 (q, J=7.3 Hz 3H) 3.70 (br s, 1H) 4.00 (br d, J=13.6 Hz, 1H) 6.39 (br s, 1H) 7.07-7.12 (m, 2H) 7.38-7.46 (m, 2H) 8.12 (t, J=8.3 Hz, 1H) 12.26 (br s, 1H)

Minor rotamers (40%)

$^1$H NMR (400 MHz, DMSO-d$_6$) δ ppm 1.14 (d, J=6.6 Hz, 3H) 1.21-1.36 (m, 3H) 1.42 (t, J=7.3 Hz, 3H) 1.57-1.80 (m, 5H) 1.92-2.12 (m, 2H) 2.37-2.44 (m, 2H) 3.09-3.16 (m, 1H) 3.26 (q, J=7.3 Hz 3H) 3.54 (br s, 1H) 4.44 (m, 1H) 6.39 (br s, 1H) 7.07-7.12 (m, 2H) 7.38-7.46 (m, 2H) 8.12 (t, J=8.3 Hz, 1H) 12.26 (br s, 1H)

Compound (F31)

Major Rotamer (60%)

$^1$H NMR (500 MHz, DMSO-d$_6$) δ ppm 9.14 (d, J=1.3 Hz, 1H) 8.26-8.37 (m, 2H) 8.12-8.23 (m, 3H) 7.21 (d, J=3.8 Hz, 1H) 7.08 (s, 1H) 3.99 (br d, J=13.2 Hz, 1H) 3.65-3.76 (m, 1H) 2.93 (brt, J=12.3 Hz, 1H) 1.89-1.99 (m, 1H) 1.54-1.85 (m, 7H) 1.20-1.49 (m, 6H) 1.13 (d, J=6.3 Hz, 3H) 1.01 (br d, J=0.9 Hz, 2H)

Minor Rotamer (40%)

$^1$H NMR (500 MHz, DMSO-d$_6$) δ ppm 9.14 (d, J=1.3 Hz, 1H) 8.26-8.37 (m, 2H) 8.12-8.23 (m, 3H) 7.23 (d, J=3.8 Hz, 1H) 7.09 (s, 1H) 4.38-4.49 (m, 1H) 3.52 (br d, J=15.4 Hz, 1H) 3.08-3.16 (m, 1H) 2.02-2.11 (m, 1H) 1.54-1.85 (m, 7H) 1.20-1.49 (m, 6H) 1.15 (d, J=6.3 Hz, 3H) 1.01 (br d, J=0.9 Hz, 2H)

Compound (F32)
Major Rotamer (60%)
¹H NMR (500 MHz, DMSO-d$_6$) δ ppm 13.53 (br s, 1H) 9.19 (d, J=1.6 Hz, 1H) 8.38 (dd, J=8.2, 2.2 Hz, 1H) 8.31-8.36 (m, 1H) 8.26 (d, J=8.2 Hz, 1H) 8.15-8.23 (m, 2H) 7.20 (d, J=3.5 Hz, 1H) 7.14 (s, 1H) 4.31 (quin, J=8.6 Hz, 1H) 4.01 (br d, J=13.2 Hz, 1H) 3.65-3.81 (m, 1H) 2.94 (br t, J=12.5 Hz, 1H) 2.53-2.61 (m, 2H) 2.33-2.45 (m, 2H) 2.14-2.28 (m, 1H) 1.99-1.88 (m, 2H) 1.87-1.52 (m, 4H) 1.21-1.49 (m, 3H) 1.14 (d, J=6.3 Hz, 3H)

Minor Rotamer (40%)
¹H NMR (500 MHz, DMSO-d$_6$) δ ppm 13.53 (br s, 1H) 9.19 (d, J=1.6 Hz, 1H) 8.38 (dd, J=8.2, 2.2 Hz, 1H) 8.31-8.36 (m, 1H) 8.26 (d, J=8.2 Hz, 1H) 8.15-8.23 (m, 2H) 7.21 (d, J=3.8 Hz, 1H) 7.15 (s, 1H) 4.40-4.49 (m, 1H) 4.31 (quin, J=8.6 Hz, 1H) 3.55 (br d, J=15.4 Hz, 1H) 3.10-3.19 (m, 1H) 2.53-2.61 (m, 2H) 2.33-2.45 (m, 2H) 2.13-2.02 (m, 1H) 1.99-1.88 (m, 2H) 1.87-1.52 (m, 4H) 1.21-1.49 (m, 3H) 1.17 (d, J=6.3 Hz, 3H)

Compound (F33)
Major Rotamer 70%
¹H NMR (500 MHz, DMSO-d$_6$) δ ppm 1.15 (d, J=6.6 Hz, 3H) 1.22-1.39 (m, 3H) 1.47 (t, J=7.4 Hz, 4H) 1.59-1.89 (m, 4H) 1.93-1.99 (m 1H) 2.95 (t, J=12.9 Hz, 1H) 3.28-3.32 (m, 2H) 3.71-3.75 (m, 1H) 4.01 (br d, J=13.2 Hz, 1H) 7.18 (d, J=7.6 Hz, 1H) 7.32 (dd, J=7.8, 3.8 Hz, 1H) 8.09-8.16 (m, 2H) 8.78 (d, J=8.5 Hz, 1H) 8.90 (dd, J=8.2, 1.6 Hz, 1H) 13.61 (br s, 1H)

Minor rotamer 30%
¹H NMR (500 MHz, DMSO-d$_6$) δ ppm 1.16 (d, J=6.6 Hz, 3H) 1.22-1.39 (m, 3H) 1.47 (t, J=7.4 Hz, 4H) 1.59-1.89 (m, 4H) 2.04-2.10 (m 1H) 3.13-3.18 (m, 1H) 3.28-3.32 (m, 2H) 3.55-3.58 (m, 1H) 3.43-3.48 (m, 1H) 7.18 (d, J=7.6 Hz, 1H) 7.32 (dd, J=7.8 Hz, J=3.8 Hz, 1H) 8.09-8.16 (m, 2H) 8.78 (d, J=8.5 Hz, 1H) 8.90 (dd, J=8.2, 1.6 Hz, 1H) 13.61 (br s, 1H)

Compound (F34)
Major Rotamer (60%)
¹H NMR (400 MHz, DMSO-d$_6$) δ ppm 1.41-1.50 (m, 3H) 1.52-1.62 (m, 3H) 2.74-3.11 (m, 2H) 3.24-3.37 (m, 2H) 3.42-3.57 (m, 1H) 3.93 (br dd, J=13.6, 4.6 Hz, 1H) 5.60-5.66 (m, 1H) 7.07-7.26 (m, 4H) 7.32-7.42 (m, 2H) 8.14 (dd, J=8.6, 3.5 Hz, 2H) 8.29 (d, J=8.6 Hz, 1H) 8.38 (t, J=8.1 Hz, 1H) 8.71 (s, 1H) 13.18-13.43 (m, 1H)

Minor Rotamer (40%)
¹H NMR (400 MHz, DMSO-d$_6$) δ ppm 1.41-1.50 (m, 3H) 1.52-1.62 (m, 3H) 2.74-3.11 (m, 2H) 3.24-3.37 (m, 2H) 3.42-3.57 (m, 1H) 4.56-4.62 (m, 1H) 5.06 (br d, J=6.6 Hz, 1H) 7.07-7.26 (m, 4H) 7.32-7.42 (m, 2H) 8.14 (dd, J=8.6, 3.5 Hz, 2H) 8.29 (d, J=8.6 Hz, 1H) 8.38 (t, J=8.1 Hz, 1H) 8.71 (s, 1H) 13.18-13.43 (m, 1H)

Compound (F35)
¹H NMR (400 MHz, DMSO-d$_6$) δ ppm 1.35-1.41 (m, 1H) 1.43 (t, J=7.58 Hz, 3H) 1.45-1.81 (m, 5H) 1.80-1.89 (m, 1H) 2.45 (s, 3H) 3.03-3.11 (m, 1H) 3.15-3.23 (m, 1H) 3.22-3.29 (q, J=7.58, 14.65 Hz, 2H) 3.93 (d, J=13.64 Hz, 1H) 7.06 (s, 1H) 7.15 (d, J=3.54 Hz, 1H) 8.16-8.40 (m, 5H) 9.19 (d, J=2.02 Hz, 1H) 13.48 (m, 1H)

Compound (F36)
Major Rotamer 60%
¹H NMR (500 MHz, DMSO-d$_6$) δ ppm 1.16 (dd, J=8.5, 6.6 Hz, 3H) 1.22-1.40 (m, 3H) 1.46 (t, J=7.4 Hz, 3H) 1.60-1.85 (m, 4H) 1.92-2.02 (m, 1H) 2.95 (br t, J=12.5 Hz, 1H) 3.25-3.30 (m, 2H) 3.70-3.78 (m, 1H) 4.02 (br d, J=13.2 Hz, 1H) 7.14 (d, J=8.2 Hz, 1H) 7.34 (dd, J=8.4, 3.3 Hz, 1H) 8.03 (d, J=8.8 Hz, 1H) 8.11-8.19 (m, 2H) 8.44 (t, J=7.9 Hz, 1H) 8.80 (s, 1H) 13.27-13.48 (m, 1H)

Minor rotamer 40%
¹H NMR (500 MHz, DMSO-d$_6$) δ ppm 1.16 (dd, J=8.5, 6.6 Hz, 3H) 1.22-1.40 (m, 3H) 1.46 (t, J=7.4 Hz, 3H) 1.60-1.85 (m, 4H) 1.92-2.02 (m, 1H) 3.10-3.22 (m, 1H) 3.25-3.30 (m, 2H) 3.57 (br d, J=15.8 Hz, 1H) 4.47 (dt, J=12.0, 6.0 Hz, 1H) 7.14 (d, J=8.20 Hz, 1H) 7.34 (dd, J=8.4, 3.3 Hz, 1H) 8.03 (d, J=8.8 Hz, 1H) 8.11-8.19 (m, 2H) 8.44 (t, J=7.9 Hz, 1H) 8.80 (s, 1H) 13.27-13.48 (m, 1H)

Compound (F37)
Major Rotamer 60%
¹H NMR (500 MHz, DMSO-d$_6$) δ ppm 1.12 (d, J=6.3 Hz, 3H), 1.25-1.29 (m, 3H), 1.40-1.43 (t, J=7.6 Hz, 3H), 1.46-1.62 (m, 5H), 1.67-1.80 (m, 3H), 1.88-2.09 (m, 5H), 2.19-2.23 (t, J=10.7 Hz, 1H), 2.56-2.61 (m, 1H), 3.10-3.15 (m, 1H), 3.21-3.27 (q, J=7.6, 14.8 Hz, 2H), 3.67-3.74 (m, 1H), 3.99 (d, J=13.2 Hz, 1H), 7.06-7.09 (m, 2H) 7.25 (dd, J=7.4, 6.5 Hz, 2H) 8.06 (t, J=7.9 Hz, 1H)

Minor rotamer 40%
¹H NMR (500 MHz, DMSO-d$_6$) δ ppm 1.15 (d, J=6.3 Hz, 3H), 1.25-1.29 (m, 3H), 1.40-1.43 (t, J=7.6 Hz, 3H), 1.46-1.62 (m, 5H), 1.67-1.80 (m, 3H), 1.88-2.09 (m, 5H), 2.19-2.23 (t, J=10.7 Hz, 1H), 2.56-2.61 (m, 1H), 2.90-2.95 (t, J=12 Hz, 1H), 3.21-3.27 (q, J=7.6, 14.8 Hz, 2H), 3.52-3.35 (m, 1H), 4.40-4.47 (m, 1H), 7.06-7.09 (m, 2H) 7.25 (dd, J=7.4, 6.5 Hz, 2H), 8.06 (t, J=7.9 Hz, 1H)

Compound (F38)
Major Rotamer 60%
¹H NMR (500 MHz, DMSO-d$_6$) δ ppm 1.10 (d, J=6.3 Hz, 3H), 1.23-1.36 (m, 6H), 1.39-1.80 (m, 5H), 1.90-1.95 (m, 1H), 2.88-2.96 (m, 2H), 3.62-3.66 (m, 1H), 3.99 (d, J=13.2 Hz, 1H), 5.07 (d, J=1.6 Hz, 2H) 6.85 (d, J=1.6 Hz, 1H) 7.12 (dd, J=8.8, 3.5 Hz, 1H) 7.31 (d, J=8.2 Hz, 1H) 7.50 (s, 1H) 7.71 (t, J=7.2 Hz, 1H), 13.2 (bs, 1H)

Minor rotamer 40%
¹H NMR (500 MHz, DMSO-d$_6$) δ ppm 1.14 (d, J=6.3 Hz, 3H), 1.23-1.36 (m, 6H), 1.39-1.80 (m, 5H), 2.02-2.07 (m, 1H), 2.88-2.96 (m, 1H), 3.06-3.12 (m, 1H), 3.45-3.48 (d, J=15.5 Hz, 1H), 4.39-4.44 (m, 1H), 5.07 (d, J=1.6 Hz, 2H) 6.85 (d, J=1.6 Hz, 1H) 7.12 (dd, J=8.8, 3.5 Hz, 1H) 7.31 (d, J=8.2 Hz, 1H) 7.50 (s, 1H) 7.71 (t, J=7.2 Hz, 1H), 13.2 (bs, 1H)

Compound (F39)
Major Rotamer 60%
¹H NMR (500 MHz, DMSO-d$_6$) δ ppm 1.14 (d, J=6.3 Hz, 3H) 1.20-1.38 (m, 3H) 1.39-1.48 (m, 1H) 1.56-1.66 (m, 2H) 1.68-1.83 (m, 2H) 1.89-2.09 (m, 2H) 2.13-2.24 (m, 1H) 2.32-2.48 (m, 2H) 2.52-2.57 (m, 1H) 2.94 (t, J=12.5 Hz, 1H) 3.72 (dt, J=10.1, 6.3 Hz, 1H) 4.00 (br d, J=13.6 Hz, 1H) 4.23-4.27 (m, 1H) 5.07 (d, J=1.3 Hz, 2H) 7.11-7.15 (m, 2H) 7.32 (d, J=7.9 Hz, 1H) 7.53 (s, 1H) 7.70 (t, J=7.1 Hz, 1H) 12.94-13.17 (br s, 1H)

Minor rotamer 40%
¹H NMR (500 MHz, DMSO-d$_6$) δ ppm 1.16 (dd, J=6.3 Hz, 3H) 1.20-1.38 (m, 3H) 1.39-1.48 (m, 1H) 1.56-1.66 (m, 2H) 1.68-1.83 (m, 2H) 1.89-2.09 (m, 2H) 2.13-2.24 (m, 1H) 2.32-2.48 (m, 2H) 2.52-2.57 (m, 1H) 3.09-3.21 (m, 1H) 3.54 (br d, J=15.1 Hz, 1H) 4.23-4.27 (m, 1H) 4.45 (dt, J=12.1, 6.11 Hz, 1H) 5.07 (d, J=1.3 Hz, 2H) 7.11-7.15 (m, 2H) 7.32 (d, J=7.88 Hz, 1H) 7.53 (s, 1H) 7.70 (t, J=7.1 Hz, 1H) 12.94-13.17 (br s, 1H)

Compound (F40)
Major Rotamer 60%
¹H NMR (500 MHz, DMSO-d$_6$) δ ppm 1.14 (d, J=6.3 Hz, 3H) 1.22-1.39 (m, 3H) 1.44 (t, J=7.6 Hz, 3H) 1.56-1.84 (m, 4H) 1.92-1.98 (m, 1H) 2.94 (t, J=12.5, 1H) 3.25-3.29 (m, 2H) 3.68-3.75 (m, 1H) 4.01 (br d, J=13.6 Hz, 1H) 7.12 (d, J=8.2 Hz, 1H) 7.23 (dd, J=7.6, 3.5 Hz, 1H) 7.92 (d, J=8.2 Hz, 1H) 8.17 (t, J=7.1 Hz, 1H) 8.86 (s, 1H) 13.32 (br s, 1H)

Minor rotamer 40%

$^1$H NMR (500 MHz, DMSO-d$_6$) δ ppm 1.16 (d, J=6.3 Hz, 3H) 1.22-1.39 (m, 3H) 1.44 (t, J=7.6 Hz, 3H) 1.56-1.84 (m, 4H) 2.04-2.08 (m, 1H) 3.11-3.18 (m, 1H) 3.25-3.29 (m, 2H) 3.55 (br d, J=15.5 Hz, 1H) 4.45 (dt, J=12.1, 6.1 Hz, 1H) 7.12 (d, J=8.2 Hz, 1H) 7.23 (dd, J=7.6, 3.5 Hz, 1H) 7.92 (d, J=8.2 Hz, 1H) 8.17 (t, J=7.1 Hz, 1H) 8.86 (s, 1H) 13.32 (br s, 1H)

Compound (I1)

Major Rotamer (60%)

$^1$H NMR (500 MHz, DMSO-d$_6$) δ ppm 8.25 (t, J=7.6 Hz, 1H)) 8.17 (s, 1H) 7.80-7.90 (m, 2H) 7.58 (s, 1H) 7.08-7.22 (m, 2H) 3.99 (br d, J=13.2 Hz, 1H) 3.65-3.75 (m, 1H) 3.18-3.30 (m, 2H) 2.93 (t, J=12.2 Hz, 1H) 1.05-2.15 (m, 14H)

Minor Rotamer (40%)

$^1$H NMR (500 MHz, DMSO-d$_6$) δ ppm 8.25 (t, J=7.6 Hz, 1H)) 8.17 (s, 1H) 7.80-7.90 (m, 2H) 7.58 (s, 1H) 7.08-7.22 (m, 2H) 4.38-4.50 (m, 1H) 3.50 (br d, J=13.2 Hz, 1H) 3.05-3.30 (m, 3H) 1.15-2.15 (m, 14H)

Compound (I2)

Major Rotamer (60%)

$^1$H NMR (400 MHz, chloroform-d) δ ppm 8.24-8.35 (m, 1H) 7.53-7.73 (m, 2H) 7.22 (dd, J=5.1, 4.0 Hz, 1H) 6.90 (s, 1H) 6.54 (br s, 1H) 5.74 (br s, 1H) 4.25 (br d, J=14.8 Hz, 1H) 3.96-4.04 (m, 1H) 3.22-3.35 (m, 2H) 2.84-3.18 (m, 1H) 1.64-2.24 (m, 6H) 1.19-1.56 (m, 8H)

Minor Rotamer (40%)

$^1$H NMR (400 MHz, chloroform-d) δ ppm 8.24-8.35 (m, 1H) 7.53-7.73 (m, 2H) 7.22 (dd, J=5.1, 4.0 Hz, 1H) 6.95 (s, 1H) 6.54 (br s, 1H) 5.74 (br s, 1H) 4.59-4.75 (m, 1H) 3.87 (br d, J=15.3 Hz, 1H) 3.22-3.35 (m, 2H) 2.84-3.18 (m, 1H) 1.64-2.24 (m, 6H) 1.19-1.56 (m, 8H)

Compound (I12)

Major Rotamer (65%)

$^1$H NMR (400 MHz, DMSO-d$_6$) δ ppm 8.27 (br t, J=7.9 Hz, 1H) 8.15 (br s, 1H) 7.79-7.93 (m, 2H) 7.59 (br s, 1H) 7.02-7.37 (m, 6H) 5.62 (br d, J=7.2 Hz, 1H) 3.91 (br d, J=10.4 Hz, 1H) 3.51 (br t, J=10.8 Hz, 1H) 2.68-3.28 (m, 4H) 1.54 (br d, J=6.7 Hz, 3H) 1.37-1.47 (m, 3H)

Minor Rotamer (35%)

$^1$H NMR (400 MHz, DMSO-d$_6$) δ ppm 8.27 (br t, J=7.9 Hz, 1H) 8.15 (br s, 1H) 7.79-7.93 (m, 2H) 7.59 (br s, 1H) 7.02-7.37 (m, 6H) 5.04 (br d, J=6.6 Hz, 1H) 4.57 (br s, 1H) 2.68-3.28 (m, 5H) 1.58 (br d, J=6.7 Hz, 3H) 1.37-1.47 (m, 3H)

Compound (I31)

Major Rotamer (65%)

$^1$H NMR (500 MHz, DMSO-d$_6$) δ ppm 8.14-8.24 (m, 2H) 7.82-7.93 (m, 3H) 7.65 (s, 1H) 7.41-7.50 (m, 1H) 3.75-4.10 (m, 2H) 2.95 (t, J=12.1 Hz, 1H) 1.11-2.11 (m, 11H)

Minor Rotamer (35%)

$^1$H NMR (500 MHz, DMSO-d$_6$) δ ppm 8.14-8.24 (m, 2H) 7.82-7.93 (m, 3H) 7.65 (s, 1H) 7.41-7.50 (m, 1H) 4.35-4.47 (m, 1H) 3.62 (br d, J=13.2 Hz, 1H) 3.10-3.20 (m, 1H) 1.11-2.11 (m, 11H)

Compound (I33)

Major Rotamer (65%)

$^1$H NMR (500 MHz, DMSO-d$_6$) δ ppm 8.25 (t, J=7.6 Hz, 1H) 8.13 (s, 1H) 7.80-7.90 (m, 2H) 7.58 (s, 1H) 7.14-7.23 (m, 1H) 6.91 (s, 1H) 3.00-4.00 (m, 9H) 1.06-2.05 (m, 12H)

Minor Rotamer (35%)

$^1$H NMR (500 MHz, DMSO-d$_6$) δ ppm 8.25 (t, J=7.6 Hz, 1H)) 8.13 (s, 1H) 7.80-7.90 (m, 2H) 7.58 (s, 1H) 7.14-7.23 (m, 1H) 7.05 (s, 1H) 4.35-4.48 (m, 1H) 3.23-4.57 (m, 8H) 1.06-2.05 (m, 12H)

Compound (J1)

Major Rotamer (60%)

$^1$H NMR (500 MHz, DMSO-d$_6$) δ ppm 8.19 (s, 1H), 7.85-7.98 (m, 3H) 7.64 (s, 1H) 7.15-7.20 (m, 1H) 4.03 (br d, J=13.2 Hz, 1H) 3.70-3.90 (m, 1H) 3.18-3.25 (m, 2H) 2.95 (t, J=12.4 Hz, 1H) 1.15-2.15 (m, 14H)

Minor Rotamer (40%)

$^1$H NMR (500 MHz, DMSO-d$_6$) δ ppm 8.19 (s, 1H), 7.85-7.98 (m, 3H) 7.64 (s, 1H) 7.15-7.20 (m, 1H) 4.38-4.50 (m, 1H) 3.55 (br d, J=13.1 Hz, 1H) 3.10-3.25 (m, 3H) 1.15-2.15 (m, 14H)

Compound (L1)

Major Rotamer (60%)

$^1$H NMR (500 MHz, DMSO-d$_6$) δ ppm 8.63 (br s, 1H) 8.25 (t, J=7.9 Hz, 1H) 7.75-7.90 (m, 2H) 7.05-7.25 (m, 2H) 4.00 (br d, J=12.9 Hz, 1H) 3.65-3.75 (m, 1H) 2.70-3.40 (m, 4H) 1.07-2.09 (m, 14H) 0.52-0.80 (m, 4H)

Minor Rotamer (40%)

$^1$H NMR (500 MHz, DMSO-d$_6$) δ ppm 8.63 (br s, 1H) 8.25 (t, J=7.9 Hz, 1H) 7.75-7.90 (m, 2H) 7.05-7.25 (m, 2H) 4.38-4.55 (m, 1H) 3.52 (br d, J=12.9 Hz, 1H) 2.70-3.40 (m, 4H) 1.07-2.09 (m, 14H) 0.52-0.80 (m, 4H)

Compound (L6)

Major Rotamer (60%)

$^1$H NMR (400 MHz, DMSO-d$_6$) δ ppm 11.40 (br s, 1H) 8.25 (t, J=7.7 Hz, 1H) 7.71-7.79 (m, 2H) 7.11-7.21 (m, 3H) 4.00 (br d, J=14.3 Hz, 1H) 3.52-3.78 (m, 2H) 2.92-3.31 (m, 3H) 1.90-2.08 (m, 1H) 1.53-1.82 (m, 4H) 1.43 (br t, J=7.6 Hz, 3H) 1.30 (br d, J=7.0 Hz, 2H) 1.14 (br dd, J=10.6, 6.5 Hz, 3H)

Minor Rotamer (40%)

$^1$H NMR (400 MHz, DMSO-d$_6$) δ ppm 11.40 (br s, 1H) 8.25 (t, J=7.7 Hz, 1H) 7.71-7.79 (m, 2H) 7.11-7.21 (m, 3H) 4.42-4.52 (m, 1H) 3.52-3.78 (m, 2H) 2.92-3.31 (m, 3H) 1.90-2.08 (m, 1H) 1.53-1.82 (m, 4H) 1.43 (br t, J=7.6 Hz, 3H) 1.30 (br d, J=7.0 Hz, 2H) 1.14 (br dd, J=10.6, 6.5 Hz, 3H)

Compound (M6)

Major Rotamer (65%)

$^1$H NMR (500 MHz, DMSO-d$_6$) δ ppm 12.48 (br s, 1H) 7.80-8.08 (m, 3H) 7.69-7.73 (m, 1H) 7.62 (d, J=16.0 Hz, 1H) 7.30 (s, 1H) 7.02-7.27 (m, 5H) 6.70 (d, J=16.0 Hz, 1H) 5.60 (q, J=6.5 Hz, 1H) 3.86-3.98 (m, 1H) 2.70-3.55 (m, 4H) 1.29-1.62 (m, 6H)

Minor Rotamer (35%)

$^1$H NMR (500 MHz, DMSO-d$_6$) δ ppm 12.48 (br s, 1H) 7.80-8.08 (m, 3H) 7.69-7.73 (m, 1H) 7.62 (d, J=16.0 Hz, 1H) 7.30 (s, 1H) 7.02-7.27 (m, 5H) 6.70 (d, J=16.0 Hz, 1H) 5.04 (q, J=6.5 Hz, 1H) 4.50-4.65 (m, 1H) 2.70-3.55 (m, 4H) 1.29-1.62 (m, 6H)

Compound (M7)

Major Rotamer (60%)

$^1$H NMR (500 MHz, DMSO-d$_6$) δ ppm 12.63 (br s, 1H) 8.21 (br t, J=7.7 Hz, 1H) 7.81 (br d, J=12.3 Hz, 1H) 7.71 (br d, J=7.9 Hz, 1H) 7.64 (br d, J=15.8 Hz, 1H) 7.07-7.24 (m, 2H) 6.71 (br d, J=16.1 Hz, 1H) 4.00 (br d, J=12.9 Hz, 1H) 3.64-3.76 (m, 1H) 3.17-3.30 (m, 2H) 2.94 (brt, J=12.6 Hz, 1H) 1.88-2.01 (m, 1H) 1.05-1.86 (m, 13H)

Minor Rotamer (40%)

$^1$H NMR (500 MHz, DMSO-d$_6$) δ ppm 12.63 (br s, 1H) 8.21 (br t, J=7.7 Hz, 1H) 7.81 (br d, J=12.3 Hz, 1H) 7.71 (br d, J=7.9 Hz, 1H) 7.64 (br d, J=15.8 Hz, 1H) 7.07-7.24 (m, 2H) 6.71 (br d, J=16.1 Hz, 1H) 4.37-4.53 (m, 1H) 3.54 (br d, J=14.8 Hz, 1H) 3.07-3.30 (m, 3H) 2.02-2.11 (m, 1H) 1.05-1.86 (m, 13H)

Compound (M8)
Major Rotamer (70%)
$^1$H NMR (300 MHz, DMSO-d$_6$) δ ppm 8.26 (t, J=7.9 Hz, 1H) 7.93 (br s, 1H) 7.51-7.79 (m, 3H) 7.00-7.38 (m, 4H) 6.86 (d, J=3.5 Hz, 1H) 6.63 (d, J=15.9 Hz, 1H) 6.26 (br s, 1H) 5.62 (br s, 1H) 3.94 (s, 1H) 3.23-3.57 (m, 2H) 3.08 (br s, 3H) 2.71-2.94 (m, 2H) 1.56 (br d, J=6.3 Hz, 3H)
Minor Rotamer (30%)
$^1$H NMR (300 MHz, DMSO-d$_6$) δ ppm 8.26 (t, J=7.9 Hz, 1H) 7.93 (br s, 1H) 7.51-7.79 (m, 3H) 7.00-7.38 (m, 4H) 6.86 (d, J=3.5 Hz, 1H) 6.63 (d, J=15.9 Hz, 1H) 6.26 (br s, 1H) 5.09 (s, 1H) 4.55 (s, 1H) 3.23-3.57 (m, 2H) 3.08 (br s, 3H) 2.71-2.94 (m, 2H) 1.56 (br d, J=6.3 Hz, 3H)
Compound (M10)
Major Rotamer (65%)
$^1$H NMR (500 MHz, DMSO-d$_6$) δ ppm 12.55 (br s, 1H) 8.15 (t, J=7.9 Hz, 1H) 7.60-7.82 (m, 3H) 7.02-7.43 (m, 4H) 6.92 (br s, 1H) 6.62 (d, J=15.9 Hz, 1H) 6.35 (s, 1H) 5.60 (q, J=6.6 Hz, 1H) 3.80-3.90 (m, 1H) 3.48 (s, 6H) 2.60-3.41 (m, 3H) 1.50 (d, J=6.4 Hz, 3H)
Minor Rotamer (35%)
$^1$H NMR (500 MHz, DMSO-d$_6$) δ ppm 12.55 (br s, 1H) 8.15 (t, J=7.9 Hz, 1H) 7.60-7.82 (m, 3H) 7.02-7.43 (m, 4H) 6.92 (br s, 1H) 6.62 (d, J=15.9 Hz, 1H) 6.30 (s, 1H) 5.05 (q, J=6.6 Hz, 1H) 4.50-4.55 (m, 1H) 3.45 (s, 6H) 2.60-3.41 (m, 3H) 1.55 (d, J=6.4 Hz, 3H)
Compound (M14):
Major Rotamer (65%)
$^1$H NMR (500 MHz, DMSO-d$_6$) δ ppm 12.56 (br s, 1H) 8.26-8.31 (m, 2H) 7.80 (br d, J=12.0 Hz, 1H) 7.73 (br d, J=8.2 Hz, 1H) 7.64 (d, J=15.8 Hz, 1H) 7.33 (d, J=7.6 Hz, 1H) 7.05-7.29 (m, 2H) 6.85-6.94 (m, 1H) 6.71 (d, J=16.1 Hz, 1H) 6.31 (s, 1H) 5.60 (q, J=6.9 Hz, 1H) 3.84 (br dd, J=13.2, 4.4 Hz, 1H) 3.42-3.53 (m, 1H) 3.19-3.32 (m, 1H) 2.82-3.08 (m, 4H) 2.72 (br d, J=16.7 Hz, 1H) 1.52 (d, J=6.6 Hz, 3H)
Minor Rotamer (35%)
$^1$H NMR (500 MHz, DMSO-d$_6$) δ ppm 12.56 (br s, 1H) 8.26-8.31 (m, 2H) 7.80 (br d, J=12.0 Hz, 1H) 7.73 (br d, J=8.2 Hz, 1H) 7.64 (d, J=15.8 Hz, 1H) 7.05-7.29 (m, 3H) 6.85-6.94 (m, 1H) 6.71 (d, J=16.1 Hz, 1H)) 6.27 (s, 1H) 4.96-5.04 (m, 1H) 4.58 (br d, J=12.6 Hz, 1H) 3.42-3.53 (m, 1H) 3.19-3.32 (m, 1H) 2.82-3.08 (m, 5H) 1.57 (d, J=6.6 Hz, 3H)
Compound (M15):
Major Rotamer (65%)
$^1$H NMR (500 MHz, DMSO-d$_6$) δ ppm 12.59 (br s, 1H) 8.22 (t, J=8.0 Hz, 1H) 7.82 (br d, J=12.3 Hz, 1H) 7.71 (br d, J=8.2 Hz, 1H) 7.64 (d, J=15.8 Hz, 1H) 7.34 (d, J=7.6 Hz, 1H) 7.10-7.27 (m, 5H) 6.71 (d, J=16.1 Hz, 1H) 5.62 (q, J=6.6 Hz, 1H) 3.91 (br dd, J=13.6, 3.5 Hz, 1H) 3.46-3.54 (m, 1H) 3.22-3.30 (m, 2H) 2.91-3.10 (m, 1H) 2.86-2.90 (m, 2H) 2.75 (br d, J=16.1 Hz, 1H) 1.54 (d, J=6.6 Hz, 3H) 1.38-1.48 (m, 3H)
Minor Rotamer (35%)
$^1$H NMR (500 MHz, DMSO-d$_6$) δ ppm 12.59 (br s, 1H) 8.22 (t, J=8.0 Hz, 1H) 7.82 (br d, J=12.3 Hz, 1H) 7.71 (br d, J=8.2 Hz, 1H) 7.64 (d, J=15.8 Hz, 1H) 7.10-7.27 (m, 5H) 7.06-7.10 (m, 1H) 6.71 (d, J=16.1 Hz, 1H) 5.04 (q, J=6.4 Hz, 1H) 4.54-4.62 (m, 1H) 3.46-3.54 (m, 1H) 3.22-3.30 (m, 2H) 2.91-3.10 (m, 2H) 1.58 (d, J=6.6 Hz, 3H) 1.38-1.48 (m, 3H)
Compound (M16):
Major Rotamer (65%)
$^1$H NMR (500 MHz, DMSO-d$_6$) δ ppm 12.58 (br s, 1H) 8.16 (br t, J=7.9 Hz, 1H) 7.79 (br d, J=12.3 Hz, 1H) 7.61-7.74 (m, 2H) 7.32 (br d, J=7.6 Hz, 1H) 7.01-7.27 (m, 3H) 6.80-6.90 (m, 1H) 6.69 (d, J=15.8 Hz, 1H) 6.11 (s, 1H) 5.58 (q, J=6.5 Hz, 1H) 4.28 (br t, J=6.1 Hz, 1H) 3.85 (br dd, J=13.6, 3.8 Hz, 1H) 3.43-3.51 (m, 2H) 3.20-3.27 (m, 2H) 2.81-3.09 (m, 1H) 2.72 (br d, J=16.1 Hz, 1H) 1.95-2.06 (m, 4H) 1.51 (br d, J=6.9 Hz, 3H)
Minor Rotamer (35%)
$^1$H NMR (500 MHz, DMSO-d$_6$) δ ppm 12.58 (br s, 1H) 8.16 (br t, J=7.9 Hz, 1H) 7.79 (br d, J=12.3 Hz, 1H) 7.61-7.74 (m, 2H) 7.01-7.27 (m, 4H) 6.80-6.90 (m, 1H) 6.69 (d, J=15.8 Hz, 1H) 6.07 (s, 1H) 5.02 (q, J=6.5 Hz, 1H) 4.52-4.60 (m, 1H) 4.28 (br t, J=6.1 Hz, 1H) 3.43-3.51 (m, 2H) 3.20-3.27 (m, 2H) 2.81-3.09 (m, 2H) 1.95-2.06 (m, 4H) 1.56 (br d, J=6.6 Hz, 3H)
Compound (M17):
Major Rotamer (65%)
$^1$H NMR (500 MHz, DMSO-d$_6$) δ ppm 12.71 (br s, 1H) 8.24 (t, J=8.0 Hz, 1H) 7.62 (s, 1H) 7.47-7.58 (m, 2H) 7.34 (d, J=7.3 Hz, 1H) 7.11-7.27 (m, 5H) 5.62 (q, J=6.6 Hz, 1H) 3.91 (br dd, J=13.7, 3.6 Hz, 1H) 3.48-3.55 (m, 1H) 3.27 (q, J=7.7 Hz, 2H) 2.91-3.11 (m, 1H) 2.75 (br d, J=16.7 Hz, 1H) 2.10 (d, J=0.9 Hz, 3H) 1.54 (d, J=6.6 Hz, 3H) 1.39-1.47 (m, 3H)
Minor Rotamer (35%)
$^1$H NMR (500 MHz, DMSO-d$_6$) δ ppm 12.71 (br s, 1H) 8.24 (t, J=8.0 Hz, 1H) 7.62 (s, 1H) 7.47-7.58 (m, 2H) 7.11-7.27 (m, 5H) 7.06-7.10 (m, 1H) 5.05 (q, J=6.7 Hz, 1H) 4.58 (br dd, J=13.4, 3.9 Hz, 1H) 3.21-3.31 (m, 3H) 2.91-3.11 (m, 1H) 2.84-2.91 (m, 1H) 2.10 (d, J=0.9 Hz, 3H) 1.59 (d, J=6.6 Hz, 3H) 1.39-1.47 (m, 3H)
Compound (M18):
Major Rotamer (70%):
$^1$H NMR (400 MHz, DMSO-d$_6$) δ ppm 1.40 (t, J=7.1 Hz, 3H) 1.65 (br d, J=7.1 Hz, 3H) 1.73-2.05 (m, 2H) 2.78-2.98 (m, 1H) 3.08-3.18 (m, 1H) 3.24 (q, J=7.1 Hz, 2H) 3.36-3.47 (m, 1H) 3.49-3.65 (m, 1H) 3.65-3.77 (m, 1H) 5.62-5.87 (m, 1H) 6.66-6.78 (m, 2H) 7.07-7.23 (m, 3H) 7.34 (br d, J=4.04 Hz, 1H) 7.63 (d, J=16.2 Hz, 1H) 7.67-7.74 (m, 1H) 7.80 (d, J=11.6 Hz, 1H) 8.20 (t, J=8.1 Hz, 1H) 12.58 (br s, 1H)
Minor Rotamer (30%):
$^1$H NMR (400 MHz, DMSO-d$_6$) δ ppm 1.33 (t, J=7.1 Hz, 3H) 1.57 (d, J=7.1 Hz, 3H)) 1.73-2.05 (m, 2H) 2.78-2.98 (m, 1H) 3.08-3.18 (m, 1H) 3.24 (q, J=7.1 Hz, 2H) 3.36-3.47 (m, 1H) 4.57 (br d, J=13.6 Hz, 1H) 5.08 (d, J=7.1 Hz, 1H) 7.04 (t, J=7.1 Hz, 1H) 7.07-7.23 (m, 6H) 7.64 (d, J=16.2 Hz, 1H) 7.67-7.74 (m, 1H) 7.82 (d, J=11.6 Hz, 1H) 8.23 (t, J=8.1 Hz, 1H) 12.58 (br s, 1H)
Compound (M19):
Major Rotamer (60%)
$^1$H NMR (500 MHz, DMSO-d$_6$) δ ppm 12.58 (br s, 1H) 8.20 (t, J=8.0 Hz, 1H) 7.81 (d, J=12.0 Hz, 1H) 7.67-7.72 (m, 1H) 7.63 (d, J=15.8 Hz, 1H) 7.10-7.19 (m, 2H) 6.70 (d, J=16.1 Hz, 1H) 4.23-4.36 (m, 1H) 4.00 (br d, J=13.2 Hz, 1H) 3.66-3.77 (m, 1H) 2.94 (t, J=12.5 Hz, 1H) 2.53-2.61 (m, 2H) 2.34-2.44 (m, 2H) 2.14-2.25 (m, 1H) 1.88-2.11 (m, 2H) 1.52-1.86 (m, 4H) 1.20-1.50 (m, 3H) 1.13 (d, J=6.3 Hz, 3H)
Minor Rotamer (40%)
$^1$H NMR (500 MHz, DMSO-d$_6$) δ ppm 12.58 (br s, 1H) 8.20 (t, J=8.0 Hz, 1H) 7.81 (d, J=12.0 Hz, 1H) 7.67-7.72 (m, 1H) 7.63 (d, J=15.8 Hz, 1H) 7.10-7.19 (m, 2H) 6.70 (d, J=16.1 Hz, 1H) 4.45 (dt, J=11.9, 6.2 Hz, 1H) 3.66-3.77 (m, 1H) 3.54 (br d, J=15.8 Hz, 1H) 3.13 (br dd, J=14.7, 9.9 Hz, 1H) 2.53-2.61 (m, 2H) 2.34-2.44 (m, 2H) 2.14-2.25 (m, 1H) 1.88-2.11 (m, 2H) 1.52-1.86 (m, 4H) 1.20-1.50 (m, 3H) 1.16 (d, J=6.3 Hz, 3H)
Compound (M20)
Major Rotamer (60%)
$^1$H NMR (500 MHz, DMSO-d$_6$) δ ppm 12.61 (br s, 1H) 8.22 (br t, J=7.9 Hz, 1H) 7.82 (br d, J=12.3 Hz, 1H) 7.72 (br d, J=7.9 Hz, 1H) 7.64 (br d, J=15.8 Hz, 1H) 7.15-7.22 (m, 1H) 7.05-7.12 (m, 1H) 6.70 (br d, J=15.8 Hz, 1H) 3.98 (br d, J=12.9 Hz, 1H) 3.64-3.74 (m, 1H) 2.93 (br t, J=12.5 Hz, 1H) 1.88-1.98 (m, 1H) 1.50-1.84 (m, 7H) 1.07-1.49 (m, 8H) 0.99 (br s, 2H)

Minor Rotamer (40%)

¹H NMR (500 MHz, DMSO-d₆) δ ppm 12.61 (br s, 1H) 8.22 (br t, J=7.9 Hz, 1H) 7.82 (br d, J=12.3 Hz, 1H) 7.72 (br d, J=7.9 Hz, 1H) 7.64 (br d, J=15.8 Hz, 1H) 7.18 (br dd, J=7.3, 3.2 Hz, 1H) 7.08 (d, J=6.9 Hz, 1H) 6.70 (br d, J=15.8 Hz, 1H) 4.37-4.48 (m, 1H) 3.50 (br d, J=15.4 Hz, 1H) 3.07-3.15 (m, 1H) 2.01-2.08 (m, 1H) 1.50-1.84 (m, 7H) 1.07-1.49 (m, 8H) 0.99 (br s, 2H)

Compound (M21):

Major Rotamer (60%)

¹H NMR (500 MHz, DMSO-d₆) δ ppm 12.56 (br s, 1H) 8.22 (br t, J=7.7 Hz, 1H) 7.81 (br d, J=12.3 Hz, 1H) 7.70 (br d, J=8.2 Hz, 1H) 7.63 (br d, J=15.8 Hz, 1H) 7.10-7.21 (m, 1H) 6.86 (s, 1H) 6.70 (br d, J=16.1 Hz, 1H) 3.97 (br d, J=12.9 Hz, 1H) 3.55-3.65 (m, 1H) 2.85-3.14 (m, 2H) 1.86-1.97 (m, 1H) 1.20-1.87 (m, 11H) 1.10 (br d, J=6.0 Hz, 3H)

Minor Rotamer (40%)

¹H NMR (500 MHz, DMSO-d₆) δ ppm 12.56 (br s, 1H) 8.22 (br t, J=7.7 Hz, 1H) 7.81 (br d, J=12.3 Hz, 1H) 7.70 (br d, J=8.2 Hz, 1H) 7.63 (br d, J=15.8 Hz, 1H) 7.10-7.21 (m, 1H) 6.86 (s, 1H) 6.70 (br d, J=16.1 Hz, 1H) 4.32-4.50 (m, 1H) 3.54-3.70 (m, 1H) 2.85-3.14 (m, 2H) 1.99-2.11 (m, 1H) 1.20-1.87 (m, 11H) 1.14 (br d, J=6.0 Hz, 3H)

Compound (M22):

Major Rotamer (60%)

¹H NMR (400 MHz, DMSO-d₆) δ ppm 12.66 (br s, 1H) 8.21 (t, J=6.8 Hz, 1H) 7.96 (br t, J=6.8 Hz, 1H) 7.79 (d, J=16.2 Hz, 1H) 7.44 (t, J=7.8 Hz, 1H) 7.18 (d, J=3.5 Hz, 1H) 7.06 (s, 1H) 6.70 (d, J=16.2 Hz, 1H) 3.98 (br d, J=13.6 Hz, 1H) 3.62-3.81 (m, 1H) 2.92 (br t, J=12.4 Hz, 1H) 1.86-1.99 (m, 1H) 1.52-1.86 (m, 7H) 1.18-1.49 (m, 5H) 1.12 (d, J=6.6 Hz, 3H) 0.98 (s, 2H)

Minor Rotamer (40%)

¹H NMR (400 MHz, DMSO-d₆) δ ppm 12.66 (br s, 1H) 8.21 (t, J=6.8 Hz, 1H) 7.96 (br t, J=6.8 Hz, 1H) 7.79 (d, J=16.2 Hz, 1H) 7.44 (t, J=7.8 Hz, 1H) 7.20 (d, J=3.5 Hz, 1H) 7.08 (s, 1H) 6.70 (d, J=16.2 Hz, 1H) 4.37-4.49 (m, 1H) 3.51 (br d, J=15.7 Hz, 1H) 3.05-3.15 (m, 1H) 1.99-2.11 (m, 1H) 1.52-1.86 (m, 7H) 1.18-1.49 (m, 5H) 1.15 (d, J=6.6 Hz, 3H) 0.98 (s, 2H)

Compound (M23)

Major Rotamer (60%)

¹H NMR (400 MHz, DMSO-d₆) δ ppm 12.64 (br s, 1H) 8.19 (t, J=6.8 Hz, 1H) 7.95 (t, J=6.8 Hz, 1H) 7.78 (d, J=16.2 Hz, 1H) 7.42 (t, J=7.8 Hz, 1H) 7.16 (d, J=3.5 Hz, 1H) 7.11 (s, 1H) 6.69 (d, J=16.2 Hz, 1H) 4.28 (quin, J=8.8 Hz, 1H) 3.95-4.10 (m, 1H) 3.65-3.77 (m, 1H) 2.93 (br t, J=12.1 Hz, 1H) 2.52-2.61 (m, 2H) 2.31-2.45 (m, 2H) 2.13-2.28 (m, 1H) 1.87-1.99 (m, 2H) 1.52-1.87 (m, 4H) 1.20-1.50 (m, 3H) 1.14 (d, J=6.6 Hz, 3H)

Minor Rotamer (40%)

¹H NMR (400 MHz, DMSO-d₆) δ ppm 12.64 (br s, 1H) 8.19 (t, J=6.8 Hz, 1H) 7.95 (t, J=6.8 Hz, 1H) 7.78 (d, J=16.2 Hz, 1H) 7.42 (t, J=7.8 Hz, 1H) 7.18 (d, J=3.5 Hz, 1H) 7.13 (s, 1H) 6.69 (d, J=16.2 Hz, 1H) 4.40-4.52 (m, 1H) 4.28 (quin, J=8.8 Hz, 1H) 3.55 (br d, J=15.2 Hz, 1H) 3.07-3.18 (m, 1H) 2.52-2.61 (m, 2H) 2.31-2.45 (m, 2H) 2.13-2.28 (m, 1H) 2.01-2.12 (m, 1H) 1.87-1.99 (m, 1H) 1.52-1.87 (m, 4H) 1.20-1.50 (m, 3H) 1.16 (d, J=6.6 Hz, 3H)

Compound (M25):

Major Rotamer (60%)

¹H NMR (500 MHz, DMSO-d₆) δ ppm 1.13 (d, J=6.3 Hz, 3H) 1.22-1.39 (m, 3H) 1.43 (t, J=7.4 Hz, 3H) 1.54-1.84 (m, 4H) 1.91-2.01 (m, 1H) 2.94 (br t, J=12.6 Hz, 1H) 3.26 (q, J=7.6 Hz, 2H) 3.67-3.74 (m, 1H) 4.00 (br d, J=13.6 Hz, 1H) 6.71 (d, J=16.1 Hz, 1H) 7.13 (d, J=7.9 Hz, 1H) 7.20 (dd, J=8.0, 3.3 Hz, 1H) 7.43 (t, J=7.7 Hz, 1H) 7.79 (d, J=16.1 Hz, 1H) 7.97 (br t, J=6.8 Hz, 1H) 8.21 (t, J=6.9 Hz, 1H) 12.68 (br s, 1H)

Minor Rotamer (40%)

¹H NMR (500 MHz, DMSO-d₆) δ ppm 1.16 (d, J=6.3 Hz, 3H) 1.22-1.39 (m, 3H) 1.43 (t, J=7.4 Hz, 3H) 1.54-1.84 (m, 4H) 2.01-2.10 (m, 1H) 3.15 (br dd, J=7.1 Hz, 1H) 3.26 (q, J=7.6 Hz, 2H) 3.54 (br d, J=15.5 Hz, 1H) 4.41-4.49 (m, 1H) 6.71 (d, J=16.1 Hz, 1H) 7.13 (d, J=7.9 Hz, 1H) 7.20 (dd, J=8.0, 3.3 Hz, 1H) 7.43 (t, J=7.7 Hz, 1H) 7.79 (d, J=16.1 Hz, 1H) 7.97 (br t, J=6.8 Hz, 1H) 8.21 (t, J=6.9 Hz, 1H) 12.68 (br s, 1H)

Compound (M26):

Major rotamer: 60%

¹H NMR (400 MHz, DMSO-d₆) δ ppm 1.38-1.46 (m, 3H) 1.51-1.60 (m, 3H) 2.71-2.79 (m, 1H) 2.84-3.09 (m, 1H) 3.22-3.29 (m, 2H) 3.48-3.54 (m, 1H) 5.02-5.07 (m, 1H) 5.59-5.64 (m, 1H) 6.70 (d, J=16.2 Hz, 1H) 7.07-7.26 (m, 4H) 7.33 (d, J=7.6 Hz, 1H) 7.43 (t, J=7.6 Hz, 1H) 7.79 (d, J=16.2 Hz, 1H) 7.96 (br t, J=7.3 Hz, 1H) 8.22 (br t, J=7.6 Hz, 1H) 12.65 (br s, 1H) Minor rotamer: 40%

¹H NMR (400 MHz, DMSO-d₆) δ ppm 1.38-1.46 (m, 3H) 1.51-1.60 (m, 3H) 2.71-2.79 (m, 1H) 2.84-3.09 (m, 1H) 3.22-3.29 (m, 2H) 3.48-3.54 (m, 1H) 3.91 (br dd, J=14.2, 4.0 Hz, 1H) 4.55-4.61 (m, 1H) 6.70 (d, J=16.2 Hz, 1H) 7.07-7.26 (m, 4H) 7.33 (d, J=7.6 Hz, 1H) 7.43 (t, J=7.6 Hz, 1H) 7.79 (d, J=16.2 Hz, 1H) 7.96 (br t, J=7.3 Hz, 1H) 8.22 (br t, J=7.6 Hz, 1H) 12.65 (br s, 1H)

Compound (M27)

Major Rotamer (65%)

¹H NMR (500 MHz, DMSO-d₆) δ ppm 12.68 (br s, 1H) 8.24 (br t, J=6.5 Hz, 1H) 7.97 (br t, J=6.9 Hz, 1H) 7.79 (br d, J=16.1 Hz, 1H) 7.43 (br t, J=7.7 Hz, 1H) 6.86-7.37 (m, 6H) 6.71 (d, J=16.1 Hz, 1H) 5.60 (q, J=6.5 Hz, 1H) 3.82 (br dd, J=13.6, 3.8 Hz, 1H) 3.43-3.53 (m, 1H) 2.62-3.07 (m, 2H) 2.67-2.77 (m, 1H) 1.53 (br d, J=6.6 Hz, 3H) 1.23-1.41 (m, 4H)

Minor Rotamer (35%)

¹H NMR (500 MHz, DMSO-d₆) δ ppm 12.68 (br s, 1H) 8.24 (br t, J=6.5 Hz, 1H) 7.97 (br t, J=6.9 Hz, 1H) 7.79 (br d, J=16.1 Hz, 1H) 7.43 (br t, J=7.7 Hz, 1H) 7.04-7.30 (m, 6H) 6.71 (d, J=16.1 Hz, 1H) 5.60 (q, J=6.5 Hz, 1H) 4.97 (q, J=6.4 Hz, 1H) 4.51-4.60 (m, 1H) 2.62-3.07 (m, 3H) 1.56 (br d, J=6.9 Hz, 3H) 1.23-1.41 (m, 4H)

Compound (M28)

Major Rotamer (60%)

¹H NMR (500 MHz, DMSO-d₆) δ ppm 12.44-12.95 (m, 1H) 8.22 (td, J=7.4, 1.3 Hz, 1H) 7.92-8.01 (m, 1H) 7.78 (d, J=16.1 Hz, 1H) 7.42 (t, J=7.7 Hz, 1H) 7.16 (d, J=3.5 Hz, 1H) 6.86 (s, 1H) 6.70 (d, J=16.4 Hz, 1H) 3.98 (br d, J=13.6 Hz, 1H) 3.57-3.72 (m, 1H) 2.86-3.01 (m, 2H) 1.87-2.09 (m, 1H) 1.49-1.87 (m, 4H) 1.21-1.45 (m, 7H) 1.10 (d, J=6.3 Hz, 3H)

Minor Rotamer (40%)

¹H NMR (500 MHz, DMSO-d₆) δ ppm 12.44-12.95 (m, 1H) 8.22 (td, J=7.4, 1.3 Hz, 1H) 7.92-8.01 (m, 1H) 7.78 (d, J=16.1 Hz, 1H) 7.42 (t, J=7.7 Hz, 1H) 7.17 (d, J=3.5 Hz, 1H) 6.87 (s, 1H) 6.70 (d, J=16.4 Hz, 1H) 4.36-4.47 (m, 1H) 3.47 (br d, J=15.1 Hz, 1H) 2.86-3.16 (m, 2H) 1.87-2.09 (m, 1H) 1.49-1.87 (m, 4H) 1.21-1.45 (m, 7H) 1.14 (d, J=6.6 Hz, 3H)

Compound (N1)

Major Rotamer (60%)

¹H NMR (400 MHz, DMSO-d₆) δ ppm 8.21 (br t, J=8.0 Hz, 1H) 7.55-7.64 (m, 3H) 7.46 (d, J=15.7 Hz, 1H) 7.08-7.23 (m, 3H) 6.74 (d, J=16.0 Hz, 1H) 4.00 (br d, J=11.7 Hz, 1H) 3.47-3.78 (m, 1H) 2.78-3.26 (m, 3H) 1.88-2.12 (m, 1H) 1.53-1.84 (m, 4H) 1.42 (t, J=7.5 Hz, 3H) 1.22-1.35 (m, 3H) 1.10-1.19 (m, 3H)

Minor Rotamer (40%)

¹H NMR (400 MHz, DMSO-d₆) δ ppm 8.21 (br t, J=8.0 Hz, 1H) 7.55-7.64 (m, 3H) 7.46 (d, J=15.7 Hz, 1H) 7.08-7.23 (m, 3H) 6.74 (d, J=16.0 Hz, 1H) 4.37-4.50 (m, 1H) 3.47-3.78 (m, 1H) 2.78-3.26 (m, 3H) 1.88-2.12 (m, 1H) 1.53-1.84 (m, 4H) 1.42 (t, J=7.5 Hz, 3H) 1.22-1.35 (m, 3H) 1.10-1.19 (m, 3H)

Compound (O1)

Major Rotamer (60%)

¹H NMR (400 MHz, chloroform-d) δ ppm 8.16 (t, J=8.0 Hz, 1H) 7.17 (t, J=3.6 Hz, 1H) 6.90-7.07 (m, 3H) 4.25 (br d, J=13.2 Hz, 1H) 4.04 (br s, 1H) 2.81-3.30 (m, 4H) 2.61-2.70 (m, 1H) 2.08-2.20 (m, 1H) 1.66-2.02 (m, 7H) 1.33-1.55 (m, 6H) 1.25 (br t, J=7.0 Hz, 3H)

Minor Rotamer (40%)

¹H NMR (400 MHz, chloroform-d) δ ppm 8.16 (t, J=8.0 Hz, 1H) 7.17 (t, J=3.6 Hz, 1H) 6.90-7.07 (m, 3H) 4.60-4.73 (m, 1H) 3.89 (br d, J=15.6 Hz, 1H) 2.81-3.30 (m, 4H) 2.61-2.70 (m, 1H) 2.08-2.20 (m, 1H) 1.66-2.02 (m, 7H) 1.33-1.55 (m, 6H) 1.25 (br t, J=7.0 Hz, 3H)

Compound (O2):

Major Rotamer (60%)

¹H NMR (500 MHz, DMSO-d₆) δ ppm 1.12 (t, J=6.3 Hz 3H) 1.22-1.38 (m, 3H) 1.39-1.47 (m, 1H) 1.42 (t, J=7.6 Hz 3H) 1.50-2.11 (m, 7H) 2.41 (br s, 1H) 2.93 (br t, J=12.8 Hz, 1H) 3.24 (q, J=7.3 Hz 2H) 3.66-3.74 (m, 1H) 3.99 (br d, J=13.2 Hz, 1H) 7.06-7.11 (m, 2H) 7.13-7.23 (m, 2H) 8.05 (t, J=8.0 Hz, 1H) 12.6 (br s, 1H)

Minor Rotamer (40%)

¹H NMR (500 MHz, DMSO-d₆) δ ppm 1.15 (d, J=6.3 Hz 3H) 1.22-1.38 (m, 3H) 1.39-1.47 (m, 1H) 1.42 (t, J=7.6 Hz 3H) 1.50-2.11 (m, 7H) 2.41 (br s, 1H) 3.08-3.18 (m, 1H) 3.24 (q, J=7.3 Hz 2H) 3.53 (br d, J=14.2 Hz 1H) 4.40-4.48 (m, 1H) 7.06-7.11 (m, 2H) 7.13-7.23 (m, 2H) 8.05 (t, J=8.0 Hz, 1H) 12.6 (br s, 1H)

Compound (O3):

Major Rotamer 60%

¹H NMR (500 MHz, DMSO-d₆) δ ppm 1.11-1.18 (m, 3H) 1.21-1.38 (m, 3H) 1.40-1.49 (m, 2H) 1.55-1.61 (m, 1H) 1.63-1.83 (m, 3H) 1.84-1.98 (m, 3H) 2.00-2.10 (m, 1H) 2.12-2.24 (m, 1H) 2.32-2.47 (m, 3H) 2.52-2.60 (m, 3H) 2.93 (t, J=12.3 Hz, 1H) 3.70 (dt, J=9.8, 6.3 Hz, 1H) 4.00 (br d, J=13.6 Hz, 1H) 4.23-4.32 (m, 1H)) 7.10-7.11 (dd, J=7.9, 0.6 Hz, 1H) 7.12-7.15 (dd, J=7.9, 3.5 Hz, 1H) 7.18-7.21 (dt, J=7.6, 1.3 Hz, 1H) 7.27 (t, J=7.7 Hz, 1H) 7.98 (t, J=7.2 Hz, 1H)

Minor rotamer 40%

¹H NMR (500 MHz, DMSO-d₆) δ ppm 1.11-1.18 (m, 3H) 1.21-1.38 (m, 3H) 1.40-1.49 (m, 2H) 1.55-1.61 (m, 1H) 1.63-1.83 (m, 3H) 1.84-1.98 (m, 3H) 2.12-2.24 (m, 1H) 2.32-2.47 (m, 3H) 2.52-2.60 (m, 3H) 3.07-3.20 (m, 1H) 3.54 (br d, J=15.5 Hz, 1H) 4.23-4.32 (m, 1H) 4.45 (dt, J=12.1, 6.1 Hz, 1H) 7.10-7.11 (dd, J=7.9, 0.6 Hz, 1H) 7.12-7.15 (dd, J=7.9, 3.5 Hz, 1H) 7.18-7.21 (dt, J=7.6, 1.3 Hz, 1H) 7.27 (t, J=7.7 Hz, 1H) 7.98 (t, J=7.2 Hz, 1H)

Compound (W1):

Major Rotamer (60%)

¹H NMR (400 MHz, DMSO-d₆) δ ppm 1.12 (d, J=6.6 Hz, 3H) 1.20-1.36 (m, 3H) 1.40 (t, J=7.6 Hz, 3H) 1.54-1.83 (m, 4H) 1.85-1.99 (m, 1H) 2.92 (br t, J=12.4 Hz, 1H) 3.22 (q, J=7.6 Hz, 2H) 3.51-3.60 (m, 1H) 3.66-3.76 (m, 1H) 3.93-4.02 (m, 3H) 4.07-4.14 (m, 2H) 6.37-6.44 (m, 2H) 6.93 (t, J=4.7 Hz, 1H) 7.00 (d, J=7.2 Hz, 1H) 7.96 (t, J=8.7 Hz, 1H) 12.67 (br s, 1H)

Minor Rotamer (40%)

¹H NMR (400 MHz, DMSO-d₆) δ ppm 1.13 (d, J=6.6 Hz, 3H) 1.20-1.36 (m, 3H) 1.40 (t, J=7.6 Hz, 3H) 1.54-1.83 (m, 4H) 2.00-2.10 (m, 1H) 3.07-3.17 (m, 1H) 3.22 (q, J=7.6 Hz, 2H) 3.51-3.60 (m, 2H) 3.93-4.02 (m, 2H) 4.07-4.14 (m, 2H) 4.38-4.49 (m, 1H) 6.37-6.44 (m, 2H) 6.93 (t, J=4.7 Hz, 1H) 7.00 (d, J=7.2 Hz, 1H) 7.96 (t, J=8.7 Hz, 1H) 12.67 (br s, 1H Compound (W4)

Major Rotamer 60%

¹H NMR (500 MHz, DMSO-d₆) δ ppm 1.12 (d, J=6.1 Hz, 3H) 1.22-1.36 (m, 4H) 1.41 (t, J=7.4 Hz, 3H) 1.55-1.67 (m, 3H) 1.68-1.82 (m, 4H) 1.90-1.98 (m, 2H) 2.90-2.97 (m, 2H) 3.09-3.14 (m, 1H) 3.20-3.26 (m, 2H) 3.64-3.67 (br d, J=12.9 Hz, 1H) 3.68-3.73 (m, 1H) 3.80-3.84 (dd, J=9.8, 3.2 Hz, 1H) 3.98-4.01 (br d, J=12.9 Hz, 1H) 6.85-6.89 (dd, J=13.2, 2.2 Hz, 1H) 6.91-6.94 (dd, J=6.3, 2.3 Hz, 1H) 6.95-6.97 (m, 1H) 7.02 (d, J=8.5 Hz, 1H) 12.34-12.54 (m, 1H)

Minor rotamer 40%

¹H NMR (500 MHz, DMSO-d₆) δ ppm 1.15 (d, J=6.6 Hz, 3H) 1.22-1.36 (m, 4H) 1.41 (t, J=7.4 Hz, 3H) 1.55-1.67 (m, 3H) 1.68-1.82 (m, 4H) 1.90-1.98 (m, 1H) 2.00-2.10 (m, 1H) 2.90-2.97 (m, 2H) 3.09-3.14 (m, 1H) 3.20-3.26 (m, 2H) 3.52-3.56 (br d, J=15.1 Hz, 1H) 3.64-3.67 (br d, J=12.9 Hz, 1H) 3.80-3.84 (dd, J=9.8, 3.2 Hz, 1H) 4.42-4.47 (m, 1H) 6.85-6.89 (dd, J=13.2, 2.2 Hz, 1H) 6.91-6.94 (dd, J=6.3, 2.3 Hz, 1H) 6.95-6.97 (m, 1H) 7.02 (d, J=8.5 Hz, 1H) 12.34-12.54 (m, 1H)

Compound (W5)

Major Rotamer 60%

¹H NMR (400 MHz, DMSO-d₆) δ ppm 1.09-1.15 (m, 3H) 1.15-1.44 (m, 3H) 1.52 (t, J=7.6 Hz, 3H) 1.44-1.85 (m, 7H) 1.91-2.00 (m, 2H) 2.52-2.57 (m, 1H) 2.87-3.01 (m, 2H) 3.08-3.17 (m, 1H) 3.18-3.27 (q, J=7.6, 15.2 Hz, 2H) 3.50-4.04 (m, 4H) 6.83-7.02 (m, 4H) 7.97 (t, J=9.1 Hz, 1H) 12.17-12.46 (m, 1H)

Minor rotamer 40%

¹H NMR (400 MHz, DMSO-d₆) δ ppm 1.09-1.15 (m, 3H) 1.15-1.44 (m, 3H) 1.52 (t, J=7.6 Hz, 3H) 1.44-1.85 (m, 7H) 1.91-2.00 (m, 1H) 2.00-2.10 (m, 1H) 2.52-2.57 (m, 1H) 2.87-3.01 (m, 2H) 3.08-3.17 (m, 1H) 3.18-3.27 (q, J=7.6, 15.2 Hz, 2H) 3.50-4.04 (m, 3H) 4.39-4.49 (m, 1H) 6.83-7.02 (m, 4H) 7.97 (t, J=9.1 Hz, 1H) 12.17-12.46 (m, 1H)

Compound (W6)

Major Rotamer 60%

¹H NMR (500 MHz, DMSO-d₆) δ ppm 1.11-1.20 (m, 3H) 1.21-1.36 (m, 3H) 1.36-1.47 (m, 3H) 1.52-1.84 (m, 4H) 1.89-2.11 (m, 1H) 2.14-2.32 (m, 2H) 2.92 (br t, J=12.6 Hz, 1H) 3.18-3.28 (m, 3H) 3.36-3.42 (m, 2H) 3.44-3.57 (m, 2H) 3.66-3.74 (m, 1H) 3.99 (br d, J=12.9 Hz, 1H) 6.47 (br d, J=14.5 Hz, 1H) 6.54 (br d, J=8.5 Hz, 1H) 6.93 (br dd, J=7.3, 3.5 Hz, 1H) 7.00 (br d, J=8.5 Hz, 1H) 7.98 (br t, J=8.7 Hz, 1H) 12.58 (br s, 1H)

Minor rotamer 40%

¹H NMR (500 MHz, DMSO-d₆) δ ppm 1.11-1.20 (m, 3H) 1.21-1.36 (m, 3H) 1.36-1.47 (m, 3H) 1.52-1.84 (m, 4H) 1.89-2.11 (m, 1H) 2.14-2.32 (m, 2H) 3.12 (m, 1H) 3.18-3.28 (m, 3H) 3.36-3.42 (m, 2H) 3.44-3.57 (m, 3H) 4.44 (br d, J=6.0 Hz, 1H) 6.47 (br d, J=14.5 Hz, 1H) 6.54 (br d, J=8.5 Hz, 1H) 6.93 (br dd, J=7.3, 3.5 Hz, 1H) 7.00 (br d, J=8.5 Hz, 1H) 7.98 (br t, J=8.7 Hz, 1H) 12.58 (br s, 1H)

Compound (W7)

Major Rotamer 60%

¹H NMR (500 MHz, DMSO-d₆) δ ppm 1.11-1.20 (m, 3H) 1.21-1.36 (m, 3H) 1.36-1.47 (m, 3H) 1.52-1.84 (m, 4H) 1.89-2.11 (m, 1H) 2.14-2.32 (m, 2H) 2.92 (brt, J=12.6 Hz, 1H) 3.18-3.28 (m, 3H) 3.36-3.42 (m, 2H) 3.44-3.57 (m, 2H) 3.66-3.74 (m, 1H) 3.99 (br d, J=12.9 Hz, 1H) 6.47 (br d, J=14.5 Hz, 1H) 6.54 (br d, J=8.5 Hz, 1H) 6.93 (br dd, J=7.3, 3.5 Hz, 1H) 7.00 (br d, J=8.5 Hz, 1H) 7.98 (br t, J=8.7 Hz, 1H) 12.58 (br s, 1H)

Minor rotamer 40%

$^1$H NMR (500 MHz, DMSO-d$_6$) δ ppm 1.11-1.20 (m, 3H) 1.21-1.36 (m, 3H) 1.36-1.47 (m, 3H) 1.52-1.84 (m, 4H) 1.89-2.11 (m, 1H) 2.14-2.32 (m, 2H) 3.12 (m, 1H) 3.18-3.28 (m, 3H) 3.36-3.42 (m, 2H) 3.44-3.57 (m, 3H) 4.44 (br d, J=6.0 Hz, 1H) 6.47 (br d, J=14.5 Hz, 1H) 6.54 (br d, J=8.5 Hz, 1H) 6.93 (br dd, J=7.3, 3.5 Hz, 1H) 7.00 (br d, J=8.5 Hz, 1H) 7.98 (br t, J=8.7 Hz, 1H) 12.58 (br s, 1H)

Compound (W8)

Major Rotamer (60%)

$^1$H NMR (400 MHz, DMSO-d$_6$) δ ppm 12.76 (br s, 1H) 9.19 (s, 1H) 8.32 (t, J=8.6 Hz, 1H) 8.15 (s, 1H) 8.05 (dd, J=12.6, 2.0 Hz, 1H) 7.99 (dd, J=8.8, 2.3 Hz, 1H) 7.14 (d, J=3.0 Hz, 1H) 6.85 (s, 1H) 3.97 (br d, J=13.1 Hz, 1H) 3.58-3.71 (m, 1H) 2.85-3.03 (m, 2H) 1.85-2.13 (m, 1H) 1.49-1.85 (m, 4H) 1.22-1.44 (m, 7H) 1.10 (d, J=6.1 Hz, 3H)

Minor Rotamer (40%)

$^1$H NMR (400 MHz, DMSO-d$_6$) δ ppm 12.76 (br s, 1H) 9.19 (s, 1H) 8.32 (t, J=8.6 Hz, 1H) 8.15 (s, 1H) 8.05 (dd, J=12.6, 2.0 Hz, 1H) 7.99 (dd, J=8.8, 2.3 Hz, 1H) 7.16 (d, J=3.5 Hz, 1H) 6.85 (s, 1H) 4.36-4.47 (m, 1H) 3.47 (br d, J=14.7 Hz, 1H) 2.85-3.17 (m, 2H) 1.85-2.13 (m, 1H) 1.49-1.85 (m, 4H) 1.22-1.44 (m, 7H) 1.14 (d, J=6.6 Hz, 3H)

Compound (W9)

Major Rotamer (60%)

$^1$H NMR (500 MHz, DMSO-d$_6$) δ ppm 12.78 (br s, 1H) 9.19 (s, 1H) 8.30 (t, J=8.5 Hz, 1H) 8.16 (s, 1H) 7.90-8.09 (m, 2H) 7.05-7.22 (m, 2H) 4.30 (quin, J=8.7 Hz, 1H) 4.01 (br d, J=13.2 Hz, 1H) 3.66-3.83 (m, 1H) 2.94 (br t, J=12.5 Hz, 1H) 2.53-2.61 (m, 2H) 2.34-2.44 (m, 2H) 2.13-2.29 (m, 1H) 1.88-2.13 (m, 2H) 1.52-1.86 (m, 4H) 1.21-1.51 (m, 3H) 1.14 (d, J=6.3 Hz, 3H)

Minor Rotamer (40%)

$^1$H NMR (500 MHz, DMSO-d$_6$) δ ppm 12.78 (br s, 1H) 9.19 (s, 1H) 8.30 (t, J=8.5 Hz, 1H) 8.16 (s, 1H) 7.90-8.09 (m, 2H) 7.05-7.22 (m, 2H) 4.38-4.57 (m, 1H) 4.30 (quin, J=8.7 Hz, 1H) 3.54 (br d, J=15.4 Hz, 1H) 3.08-3.16 (m, 1H) 2.53-2.61 (m, 2H) 2.34-2.44 (m, 2H) 2.13-2.29 (m, 1H) 1.88-2.13 (m, 2H) 1.52-1.86 (m, 4H) 1.21-1.51 (m, 3H) 1.16 (d, J=6.3 Hz, 3H)

Compound (W10)

Major Rotamer (60%)

$^1$H NMR (500 MHz, DMSO-d$_6$) δ ppm 12.79 (br s, 1H) 9.20 (s, 1H) 8.31 (t, J=8.4 Hz, 1H) 8.17 (s, 1H) 8.05 (dd, J=12.5, 2.0 Hz, 1H) 8.00 (dd, J=8.5, 1.9 Hz, 1H) 7.18 (d, J=3.2 Hz, 1H) 7.08 (s, 1H) 3.99 (br d, J=13.2 Hz, 1H) 3.63-3.76 (m, 1H) 2.93 (br t, J=12.5 Hz, 1H) 1.90-2.11 (m, 1H) 1.54-1.85 (m, 7H) 1.20-1.50 (m, 5H) 1.13 (d, J=6.3 Hz, 3H) 1.00 (s, 2H)

Minor Rotamer (40%)

$^1$H NMR (500 MHz, DMSO-d$_6$) δ ppm 12.79 (br s, 1H) 9.20 (s, 1H) 8.31 (t, J=8.4 Hz, 1H) 8.17 (s, 1H) 8.05 (dd, J=12.5, 2.0 Hz, 1H) 8.00 (dd, J=8.5, 1.9 Hz, 1H) 7.20 (d, J=3.5 Hz, 1H) 7.09 (s, 1H) 4.38-4.43 (m, 1H) 3.51 (br d, J=15.4 Hz, 1H) 3.08-3.16 (m, 1H) 1.90-2.11 (m, 1H) 1.54-1.85 (m, 7H) 1.20-1.50 (m, 5H) 1.15 (d, J=6.3 Hz, 3H) 1.00 (s, 2H)

Compound (W11)

Major Rotamer 55%

$^1$H NMR (500 MHz, DMSO-d$_6$) δ ppm 1.13 (d, J=6.3 Hz, 3H) 1.21-1.35 (m, 3H) 1.41 (t, J=7.4 Hz, 3H) 1.54-1.66 (m, 2H) 1.68-1.84 (m, 3H) 1.92-1.99 (m, 1H) 2.43 (br s, 2H) 2.92 (brt, J=12.5 Hz, 1H) 3.19-3.26 (m, 2H) 3.50 (t, J=5.7 Hz, 2H) 3.67-3.75 (m, 1H) 3.99 (br d, J=2.8 Hz, 2H) 6.87-6.91 (m, 1H) 6.93 (br s, 1H) 6.96 (dt, J=7.1, 3.7 Hz, 2H) 7.02 (d, J=8.5 Hz, 1H) 8.01 (t, J=8.8 Hz, 1H) 12.4 (s, 1H)

Minor rotamer 45%

$^1$H NMR (500 MHz, DMSO-d$_6$) δ ppm 1.15 (d, J=6.3 Hz, 3H) 1.21-1.35 (m, 3H) 1.41 (t, J=7.4 Hz, 3H) 1.54-1.66 (m, 1H) 1.68-1.84 (m, 3H) 2.01-2.10 (m, 1H) 2.43 (br s, 2H) 3.09-3.17 (m, 1H) 3.19-3.26 (m, 2H) 3.50 (t, J=5.7 Hz, 2H) 3.54 (br d, J=15.5 Hz, 1H) 3.99 (br d, J=2.8 Hz, 2H) 4.44 (dt, J=12.0, 6.0 Hz, 1H) 6.87-6.91 (m, 1 H) 6.93 (br s, 1H) 6.96 (dt, J=7.1, 3.7 Hz, 2H) 7.02 (d, J=8.5 Hz, 1H) 8.01 (t, J=8.8 Hz, 1H) 12.4 (s, 1H)

Compound (W12)

Major Rotamer 60%

$^1$H NMR (400 MHz, DMSO-d$_6$) δ ppm 1.08-1.32 (m, 6H) 1.32-1.45 (m, 3H) 1.53-1.82 (m, 4H) 1.85-2.09 (m, 1H) 2.39-2.45 (m, 1H) 2.78 (dd, J=15.4, 4.8 Hz, 1H) 2.91 (t, J=12.6 Hz, 1H) 3.00-3.15 (m, 2H) 3.15-3.26 (m, 2H) 3.41-3.59 (m, 3H) 3.60-3.74 (m, 2H) 3.99 (br d, J=12.6 Hz, 1H) 6.47 (d, J=14.7 Hz, 1H) 6.55 (d, J=8.6 Hz, 1H) 6.60 (s, 1H) 6.86-6.94 (m, 1H) 6.98 (d, J=7.6 Hz, 1H) 7.96 (t, J=8.6 Hz, 1H) 12.15-12.44 (s, 1H)

Minor Rotamers 40%

$^1$H NMR (400 MHz, DMSO-d$_6$) δ ppm 1.08-1.32 (m, 6H) 1.32-1.45 (m, 3H) 1.53-1.82 (m, 4H) 1.85-2.09 (m, 1H) 2.39-2.45 (m, 1H) 2.78 (dd, J=15.4, 4.8 Hz, 1H) 2.91 (t, J=12.6 Hz, 1H) 3.00-3.15 (m, 2H) 3.15-3.26 (m, 2H) 3.41-3.59 (m, 3H) 3.60-3.74 (m, 2H) 4.39-4.48 (m, 1H) 6.47 (d, J=14.7 Hz, 1H) 6.55 (d, J=8.6 Hz, 1H) 6.60 (s, 1H) 6.86-6.94 (m, 1H) 6.98 (d, J=7.6 Hz, 1H) 7.96 (t, J=8.6 Hz, 1H) 12.15-12.44 (s, 1H)

Compound (X1):

Major Rotamer (60%)

$^1$H NMR (400 MHz, DMSO-d$_6$) δ ppm 1.13 (d, J=6.1 Hz, 3H) 1.09-1.51 (m, 4H) 1.43 (t, J=7.6 Hz, 3H) 1.55-1.83 (m, 4H) 1.89-1.99 (m, 1H) 2.93 (br t, J=12.6 Hz, 1H) 3.25 (d, J=7.6 Hz, 2H) 3.67-3.75 (m, 1H) 4.00 (br d, J=14.7 Hz, 1H) 6.74 (s, 1H) 7.13 (d, J=6.1 Hz, 1H) 7.20 (m, 1H) 7.79 (d, J=7.1 Hz, 1H) 7.87 (d, J=12.1 Hz, 1H) 8.30 (t, J=7.8 Hz, 1H) 11.57 (br s, 1H)

Minor Rotamer (40%)

$^1$H NMR (400 MHz, DMSO-d$_6$) δ ppm 1.15 (d, J=6.6 Hz, 3H) 1.09-1.51 (m, 4H) 1.43 (t, J=7.6 Hz, 3H) 1.55-1.83 (m, 4H) 2.02-2.10 (m, 1H) 3.10-3.20 (m, 1H) 3.25 (d, J=7.6 Hz, 2H) 3.50-3.57 (m, 1H) 4.41-4.48 (m, 1H) 6.74 (s, 1H) 7.13 (d, J=6.1 Hz, 1H) 7.20 (m, 1H) 7.79 (d, J=7.1 Hz, 1H) 7.87 (d, J=12.1 Hz, 1H) 8.30 (t, J=7.8 Hz, 1H) 11.57 (br s, 1H)

Compound (F41)

Major Rotamer (65%)

$^1$H NMR (500 MHz, DMSO-d$_6$) δ ppm 13.52 (br s, 1H) 9.19 (d, J=1.9 Hz, 1H) 8.39 (dd, J=8.2, 1.9 Hz, 1H) 8.30-8.35 (m, 1H) 8.26 (d, J=8.2 Hz, 1H) 8.17-8.23 (m, 2H) 7.21 (d, J=3.5 Hz, 1H) 7.14 (s, 1H)-4.01 (br d, J=13.2 Hz, 1H) 3.63-3.73 (m, 1H) 3.09-3.23 (m, 2H) 2.94 (br t, J=12.6 Hz, 1H) 2.43-2.48 (m, 1H) 1.90-1.99 (m, 1H) 1.50-1.86 (m, 4H) 1.22-1.49 (m, 3H) 1.12 (d, J=6.3 Hz, 3H) 0.97-1.04 (m, 6H)

Minor Rotamer (35%)

$^1$H NMR (500 MHz, DMSO-d$_6$) δ ppm 13.52 (br s, 1H) 9.19 (d, J=1.9 Hz, 1H) 8.39 (dd, J=8.2, 1.9 Hz, 1H) 8.30-8.35 (m, 1H) 8.26 (d, J=8.2 Hz, 1H) 8.17-8.23 (m, 2H) 7.22 (d, J=3.5 Hz, 1H) 7.16 (s, 1H) 4.41-4.49 (m, 1H) 3.54 (br d, J=15.8 Hz, 1H) 3.09-3.23 (m, 3H) 2.43-2.48 (m, 1H) 2.02-2.11 (m, 1H) 1.50-1.86 (m, 4H) 1.22-1.49 (m, 3H) 1.16 (d, J=6.3 Hz, 3H) 0.97-1.04 (m, 6H)

Compound (F42)
Major Rotamer (60%)
¹H NMR (500 MHz, DMSO-d₆) δ ppm 12.79 (br s, 1H) 7.58 (t, J=7.1 Hz, 1H) 7.01-7.13 (m, 3H) 4.39-4.50 (m, 1H) 4.30 (dd, J=10.7, 7.3 Hz, 1H) 3.99 (br d, J=12.9 Hz, 1H) 3.65-3.76 (m, 1H) 3.23 (q, J=7.3 Hz, 2H) 3.01-3.15 (m, 3H) 2.93 (br t, J=12.5 Hz, 1H) 1.89-1.99 (m, 1H) 1.53-1.86 (m, 4H) 1.41 (t, J=7.4 Hz, 3H) 1.19-1.38 (m, 3H) 1.12 (d, J=6.3 Hz, 3H)

Minor Rotamer (40%)
¹H NMR (500 MHz, DMSO-d₆) δ ppm 12.79 (br s, 1H) 7.58 (t, J=7.1 Hz, 1H) 7.01-7.13 (m, 3H) 4.39-4.50 (m, 2H) 4.30 (dd, J=10.7, 7.3 Hz, 1H) 3.54 (br d, J=14.5 Hz, 1H) 3.23 (q, J=7.3 Hz, 2H) 3.01-3.15 (m, 4H) 2.01-2.11 (m, 1H) 1.53-1.86 (m, 4H) 1.41 (t, J=7.4 Hz, 3H) 1.19-1.38 (m, 3H) 1.15 (d, J=6.3 Hz, 3H)

Compound (F43)
Major Rotamer 58%
¹H NMR (500 MHz, DMSO-d₆) δ ppm 1.14 (d, J=6.3 Hz, 3H) 1.21-1.38 (m, 3H) 1.43 (t, J=7.4 Hz, 3H) 1.54-1.80 (m, 4H) 1.94 (m, 1H) 2.94 (t, J=12.6 Hz, 1H) 3.22-3.30 (m, 2H) 3.67-3.74 (m, 1H) 4.00 (d, J=13.2 Hz, 1H) 7.14 (d, J=7.6 Hz, 1H) 7.22 (dd, J=8.2, 3.5 Hz, 1H) 8.02 (d, J=5.9 Hz, 1H) 8.04 (s, 1H) 8.34 (t, J=8.0 Hz, 1H) 8.48 (s, 1H) 13.75 (br s, 1H)

Minor rotamer 42%
¹H NMR (500 MHz, DMSO-d₆) δ ppm 1.16 (d, J=6.3 Hz, 3H) 1.21-1.38 (m, 3H) 1.43 (t, J=7.4 Hz, 3H) 1.54-1.80 (m, 4H) 2.00-2.10 (m, 1H) 3.08-3.18 (m, 1H) 3.22-3.30 (m, 2H) 3.54 (d, J=15.5 Hz, 1H) 4.44 (dt, J=12.0, 6.0 Hz, 1H) 7.14 (d, J=7.6 Hz, 1H) 7.22 (dd, J=8.2, 3.5 Hz, 1H) 8.02 (d, J=5.9 Hz, 1H) 8.04 (s, 1H) 8.34 (t, J=8.0 Hz, 1H) 8.48 (s, 1H) 13.75 (br s, 1H)

Compound (F44)
Major Rotamer 60%
¹H NMR (500 MHz, DMSO-d₆) δ ppm 1.14 (d, J=6.3 Hz, 3H) 1.24-1.40 (m, 3H) 1.44 (t, J=7.3 Hz, 3H) 1.55-1.85 (m, 4H) 1.95-2.11 (m, 1H) 2.94 (br t, J=12.6 Hz, 1H) 3.24-3.30 (q, J=7.25 Hz, 2H) 3.68-3.76 (m, 1H) 4.01 (br d, J=13.2 Hz, 1H) 7.12 (d, J=8.8 Hz, 1H) 7.20 (dd, J=7.9, 3.2 Hz, 1H) 7.76 (d, J=8.5 Hz, 1H) 7.86 (s, 1H) 8.30 (t, J=8.0 Hz, 1H) 13.79-14.01 (m, 1H)

Minor Rotamers 40%
¹H NMR (500 MHz, DMSO-d₆) δ ppm 1.17 (d, J=6.3 Hz, 3H) 1.24-1.40 (m, 3H) 1.44 (t, J=7.3 Hz, 3H) 1.55-1.85 (m, 4H) 1.95-2.11 (m, 1H) 3.10-3.18 (m, 1H) 3.24-3.30 (q, J=7.3 Hz, 2H) 3.52-3.59 (m, 1H) 4.42-4.49 (m, 1H) 7.12 (d, J=8.8 Hz, 1H) 7.20 (dd, J=7.9, 3.2 Hz, 1H) 7.76 (d, J=8.5 Hz, 1H) 7.86 (s, 1H) 8.30 (t, J=8.0 Hz, 1H) 13.79-14.01 (m, 1H)

Compound (F45)
Major Rotamer 60%
¹H NMR (400 MHz, DMSO-d₆) δ ppm 1.15 (d, J=6.6 Hz, 3H) 1.20-1.38 (m, 3H) 1.46 (br t, J=7.6 Hz, 3H) 1.54-1.85 (m, 4H) 1.89-2.14 (m, 1H) 2.89-3.01 (m, 1H) 3.22-3.37 (m, 2H) 3.67-3.84 (m, 1H) 3.94-4.10 (m, 1H) 7.15 (d, J=6.1 Hz, 1H) 7.38 (dd, J=8.1, 3.0 Hz, 1H) 8.03 (br d, J=8.6 Hz, 1H) 8.19 (d, J=8.6 Hz, 1H) 8.47 (br t, J=7.6 Hz, 1H) 8.62 (br d, J=8.6 Hz, 1H) 13.54 (br s, 1H)

Minor rotamer 40%
¹H NMR (400 MHz, DMSO-d₆) δ ppm 1.16 (d, J=6.6 Hz, 3H) 1.20-1.38 (m, 3H) 1.46 (br t, J=7.6 Hz, 3H) 1.54-1.85 (m, 4H) 1.89-2.14 (m, 1H) 3.09-3.20 (m, 1H) 3.22-3.37 (m, 2H) 3.53-3.64 (m, 1H) 4.38-4.56 (m, 1H) 7.15 (d, J=6.1 Hz, 1H) 7.38 (dd, J=8.1, 3.0 Hz, 1H) 8.03 (br d, J=8.6 Hz, 1H) 8.19 (d, J=8.6 Hz, 1H) 8.47 (br t, J=7.6 Hz, 1H) 8.62 (br d, J=8.6 Hz, 1H) 13.54 (br s, 1H)

Compound (F46)
Major Rotamer 60%
¹H NMR (500 MHz, DMSO-d₆) δ ppm 1.13 (d, J=6.5 Hz, 3H) 1.22-1.36 (m, 3H) 1.41 (t, J=7.4 Hz, 3H) 1.54-1.66 (m, 1H) 1.66-1.84 (m, 2H) 1.94-2.10 (m, 1H) 2.35-2.39 (m, 1H) 2.93 (t, J=12.6 Hz, 1H) 3.21-3.27 (m, 2H) 3.66-3.74 (m, 1H) 3.99 (br d, J=13.9 Hz, 1H) 5.04 (d, J=1.3 Hz, 2H) 6.93 (d, J=8.5 Hz, 1H) 7.07-7.10 (m, 2H) 7.55 (s, 1H) 8.06 (t, J=8.5 Hz, 1H) 13.10-13.30 (m, 1H)

Minor rotamer 40%
¹H NMR (500 MHz, DMSO-d₆) δ ppm 1.16 (d, J=6.5 Hz, 3H) 1.22-1.36 (m, 3H) 1.41 (t, J=7.4 Hz, 3H) 1.54-1.66 (m, 1H) 1.66-1.84 (m, 2H) 1.94-2.10 (m, 1H) 2.35-2.39 (m, 1H) 3.10-3.17 (m, 1H) 3.21-3.27 (m, 2H) 3.53 (br d, J=15.5 Hz, 1H) 4.44 (dt, J=11.7, 5.95 Hz, 1H) 5.04 (d, J=1.3 Hz, 2H) 6.93 (d, J=8.5 Hz, 1H) 7.07-7.10 (m, 2H) 7.55 (s, 1H) 8.06 (t, J=8.5 Hz, 1H) 13.10-13.30 (m, 1H)

Compound (F47)
Major Rotamer 65%
¹H NMR (500 MHz, DMSO-d₆) δ ppm 1.13 (d, J=6.3 Hz, 3H) 1.20-1.35 (m, 3H) 1.36-1.48 (m, 3H) 1.54-1.85 (m, 4H) 1.87-2.18 (m, 5H) 2.21-2.40 (m, 4H) 2.87-3.00 (m, 2H) 3.21-3.27 (m, 2H) 3.39-3.50 (m, 1H) 3.66-3.74 (m, 1H) 3.99 (br d, J=13.2 Hz, 1H) 7.05-7.11 (m, 2H) 7.18-7.24 (m, 2H) 8.07 (t, J=8.0 Hz, 1H) 11.91-12.80 (m, 1H)

Minor rotamer 45%
¹H NMR (500 MHz, DMSO-d₆) δ ppm 1.15 (d, J=6.3 Hz, 3H) 1.20-1.35 (m, 3H) 1.36-1.48 (m, 3H) 1.54-1.85 (m, 4H) 1.87-2.18 (m, 5H) 2.21-2.40 (m, 4H) 2.87-3.00 (m, 1H) 3.06-3.19 (m, 1H) 3.21-3.27 (m, 2H) 3.39-3.50 (m, 1H) 3.54 (br d, J=15.5 Hz, 1H) 4.40-4.50 (m, 1H) 7.05-7.11 (m, 2H) 7.18-7.24 (m, 2H) 8.07 (t, J=8.0 Hz, 1H) 11.91-12.80 (m, 1H)

Compound (F48)
Major Rotamer 60%
¹H NMR (400 MHz, DMSO-d₆) δ ppm 0.97 (s, 2H) 1.09-1.16 (m, 3H) 1.18-1.35 (m, 5H) 1.55-1.82 (m, 7H) 1.89-1.99 (m, 1H) 2.91 (br t, J=12.1 Hz, 1H) 3.64-3.75 (m, 1H) 3.98 (br d, J=13.6 Hz, 1H) 4.80 (s, 2H) 6.96-1.73 (m, 5H) 8.08 (t, J=8.8 Hz, 1H) 13.1 (br s, 1H)

Minor rotamer 40%
¹H NMR (400 MHz, DMSO-d₆) δ ppm 0.97 (s, 2H) 1.09-1.16 (m, 3H) 1.18-1.35 (m, 4H) 1.38-1.49 (m, 1H) 1.55-1.82 (m, 7H) 1.99-2.10 (m, 1H) 3.06-3.15 (m, 1H) 3.51 (br d, J=14.7 Hz, 1H) 4.38-4.47 (m, 1H) 4.80 (s, 2H) 6.96-1.73 (m, 5H) 8.08 (t, J=8.8 Hz, 1H) 13.1 (br s, 1H)

Compound (F49)
Major Rotamer 60%
¹H NMR (500 MHz, DMSO-d₆) δ ppm 1.06 (s, 2H) 1.17-1.23 (m, 3H) 1.26-1.44 (m, 4H) 1.46-1.55 (m, 1H) 1.64-1.73 (m, 4H) 1.75-1.88 (m, 3H) 1.94-2.06 (m, 1H) 3.00 (t, J=12.5 Hz, 1H) 3.73-3.80 (m, 1H) 4.05 (br d, J=7.6, 3.2 Hz, 1H) 7.20 (d, J=6.0 Hz, 1 H) 7.39 (dd, J=7.6, 3.2 Hz, 1H) 7.93 (d, J=8.5 Hz, 1H) 8.20 (t, J=7.1 Hz, 1H) 8.85 (s, 1H) 13.53 (br s, 1H)

Minor rotamer 40%
¹H NMR (500 MHz, DMSO-d₆) δ ppm 1.06 (s, 2H) 1.17-1.23 (m, 3H) 1.26-1.44 (m, 5H) 1.64-1.73 (m, 5H) 1.75-1.88 (m, 2H) 2.06-2.28 (m, 1H) 3.15-3.22 (m, 1H) 3.43-3.60 (m, 1H) 4.49 (dt, J=12.0, 6.0 Hz, 1H) 7.20 (d, J=6.0 Hz, 1H) 7.39 (dd, J=7.6, 3.2 Hz, 1H) 7.93 (d, J=8.5 Hz, 1H) 8.20 (t, J=7.1 Hz, 1H) 8.85 (s, 1H) 13.53 (br s, 1H)

Compound (F55)
Major Rotamer 65%
¹H NMR (400 MHz, DMSO-d₆) δ ppm 1.40-1.48 (m, 3H) 1.55 (d, J=6.6 Hz, 3H) 2.61-2.89 (m, 2H) 3.25-3.31 (m, 2H) 3.37-3.49 (m, 1H) 3.97 (br dd, J=13.4, 4.8 Hz, 1H) 5.70-5.77

(m, 1H) 6.85-6.89 (m, 1H) 7.18-7.24 (m, 1H) 7.27 (s, 1H) 7.37-7.45 (m, 1H) 8.17-8.40 (m, 5H) 9.19 (d, J=2.0 Hz, 1H) 13.5 (br s, 1H)

Minor rotamer 35%

$^1$H NMR (400 MHz, DMSO-$d_6$) δ ppm 1.40-1.48 (m, 3H) 1.61 (d, J=6.6 Hz, 3H) 2.61-2.89 (m, 2H) 3.16-3.25 (m, 1H) 3.25-3.31 (m, 2H) 4.63-4.70 (m, 1H) 5.19-5.26 (m, 1H) 6.85-6.89 (m, 1H) 7.18-7.24 (m, 1H) 7.27 (s, 1H) 7.37-7.45 (m, 1H) 8.17-8.40 (m, 5H) 9.19 (d, J=2.0 Hz, 1H) 13.5 (br s, 1H)

Compound (F56)

Major Rotamer 65%

$^1$H NMR (400 MHz, DMSO-$d_6$) δ ppm 1.41-1.49 (m, 3H) 1.49-1.54 (d, J=6.6 Hz, 3H) 3.25-3.30 (m, 2H) 3.67-3.80 (m, 1H) 3.86 (td, J=11.59, 3.63 Hz, 1H) 3.93-4.03 (m, 1H) 4.21 (br d, J=12.93 Hz, 1H) 5.66-5.73 (m, 1H) 6.06 (br d, J=3.15 Hz, 1H) 6.12 (d, J=3.47 Hz, 1H) 7.22-7.33 (m, 3H) 8.17-8.30 (m, 3H) 8.32-8.42 (m, 2H) 9.20 (s, 1H) 13.50 (br s, 1H)

Minor rotamer 35%

$^1$H NMR (400 MHz, DMSO-$d_6$) δ ppm 1.41-1.49 (m, 3H) 1.54-1.60 (d, J=6.31 Hz, 3H) 3.25-3.30 (m, 2H) 3.37-3.55 (m, 1H) 3.67-3.80 (m, 1H) 4.08-4.16 (m, 1H) 4.76 (br d, J=13.24 Hz, 1H) 5.22 (m, 1H) 5.85 (br d, J=3.5 Hz, 1H) 6.06 (br d, J=3.15 Hz, 1H) 7.22-7.33 (m, 3H) 8.17-8.30 (m, 3H) 8.32-8.42 (m, 2H) 9.20 (s, 1H) 13.50 (br s, 1H)

Compound (F57)

Major Rotamers 60%

$^1$H NMR (400 MHz, DMSO-$d_6$) δ ppm 1.17 (d, J=6.6 Hz, 1H) 1.22-1.38 (m, 4H) 1.41-1.54 (m, 5H) 1.61-1.89 (m, 3H) 2.27-2.32 (m, 1H) 2.66-2.75 (m, 1H) 3.49 (dd, J=11.9, 3.8 Hz, 1H) 3.58-3.63 (m, 1H) 3.95 (dd, J=12.4, 7.8 Hz, 1H) 4.10-4.16 (m, 1H) 7.21-7.27 (m, 2H) 8.15-8.23 (m, 2H) 8.25 (d, J=8.6 Hz, 1H) 8.31-8.40 (m, 2H) 9.18 (s, 1H) 13.35-13.57 (m, 1H)

Minor Rotamers 40%

$^1$H NMR (400 MHz, DMSO-$d_6$) δ ppm 1.17 (d, J=6.6 Hz, 1H) 1.22-1.38 (m, 4H) 1.41-1.54 (m, 5H) 1.61-1.89 (m, 3H) 2.27-2.32 (m, 1H) 2.75-2.83 (m, 1H) 3.49 (dd, J=11.9, 3.8 Hz, 1H) 3.58-3.63 (m, 1H) 3.95 (dd, J=12.4, 7.8 Hz, 1H) 4.19-4.25 (m, 1H) 7.21-7.27 (m, 2H) 8.15-8.23 (m, 2H) 8.25 (d, J=8.6 Hz, 1H) 8.31-8.40 (m, 2H) 9.18 (s, 1H) 13.35-13.57 (m, 1H)

Compound (F58)

Major Rotamer 65%

$^1$H NMR (500 MHz, DMSO-$d_6$) δ ppm 1.41-1.51 (m, 6H) 2.33 (s, 1H) 2.80-2.82 (m, 1H) 2.90-2.97 (m, 1H) 3.28-3.31 (q, 2H) 3.40-3.47 (m, 1H) 3.98-4.01 (dd, J=13.9, 4.7 Hz, 1H) 5.44-5.48 (q, J=12.9, 6.3 Hz, 1H), 6.70 (s 1H) 7.19-7.23 (m, 1H) 7.27-2.28 (m, 1H) 8.19-8.27 (m, 3H) 8.34-8.40 (m, 2H) 9.19 (d, J=1.9 Hz, 1H), 13.50-13.60 (br s, 1H)

Minor rotamer 35%

$^1$H NMR (500 MHz, DMSO-$d_6$) δ ppm 1.41-1.51 (m, 6H) 2.33 (s, 1H) 2.66 (m, 1H) 2.69 (m, 1H) 3.20-3.26 (m, 1H) 3.28-3.31 (q, 2H) 4.70-4.72 (m, 1H), 4.86-4.90 (q, J=14.2, 7.6 Hz, 1H) 6.67 (s, 1H) 7.19-7.23 (m, 1H) 7.27-2.28 (m, 1H) 8.19-8.27 (m, 3H) 8.34-8.40 (m, 2H) 9.19 (d, J=1.9 Hz, 1H), 13.50-13.60 (br s, 1H)

Compound (F59)

Major Rotamer 70%

$^1$H NMR (400 MHz, DMSO-$d_6$) δ ppm 1.40-1.47 (m, 3H) 1.56-1.65 (m, 3H) 1.68-1.78 (m, 1H) 1.84-2.01 (m, 1H) 3.24-3.31 (m, 2H) 3.64-3.76 (m, 1H) 4.09-4.22 (m, 2H) 5.66-5.78 (m, 1H) 5.90 (t, J=3.03 Hz, 1H) 6.03 (br s, 1H) 6.7 (br s, 1H) 7.18 (s, 1H) 7.22-7.29 (m, 1H) 8.16-8.28 (m, 3H) 8.29-8.43 (m, 2H) 9.18 (s, 1H) 13.42-13.69 (m, 1H)

Minor rotamer 30%

$^1$H NMR (400 MHz, DMSO-$d_6$) δ ppm 1.40-1.47 (m, 3H) 1.48-1.55 (m, 3H) 1.84-2.01 (m, 2H) 3.24-3.31 (m, 2H) 4.09-4.22 (m, 2H) 4.33-4.42 (m, 1H) 5.21 (m, 1H) 5.70 (br s, 1H) 5.82 (t, J=3.03 Hz, 1H) 6.68 (br s, 1H) 7.05 (s, 1H) 7.22-7.29 (m, 1H) 8.16-8.28 (m, 3H) 8.29-8.43 (m, 2H) 9.18 (s, 1H) 13.42-13.69 (m, 1H)

Compound (F60)

Major Rotamer 65%

$^1$H NMR (400 MHz, DMSO-$d_6$) δ ppm 1.39-1.45 (m, 3H) 1.45-1.50 (d, J=6.6 Hz, 3H) 2.76-3.04 (m, 2H) 3.25-3.29 (m, 2H) 3.41-3.50 (m, 1H) 4.03 (dd, J=13.6, 5.1 Hz, 1H) 5.54-5.60 (m, 1H) 7.03 (d, J=5.5 Hz, 1H) 7.19-7.28 (m, 2H) 7.39 (d, J=5.6 Hz, 1H) 8.17-8.28 (m, 3H) 8.32-8.40 (m, 2H) 9.19 (d, J=2.0 Hz, 1H) 13.36-13.60 (br s, 1H)

Minor rotamer 35%

$^1$H NMR (400 MHz, DMSO-$d_6$) δ ppm 1.39-1.50 (m, 3H) 1.54 (d, J=6.6 Hz, 3H) 1.91 (s, 1H) 2.76-3.04 (m, 2H) 3.25-3.29 (m, 2H) 4.70-4.78 (m, 1H) 4.96-5.01 (m, 1H) 6.80 (d, J=5.1 Hz, 1H) 7.19-7.28 (m, 2H) 7.30 (d, J=5.1 Hz, 1H) 8.17-8.28 (m, 3H) 8.32-8.40 (m, 2H) 9.19 (d, J=2.0 Hz, 1H) 13.36-13.60 (br s, 1H)

Compound (F61)

Major Rotamer 65%

$^1$H NMR (400 MHz, DMSO-$d_6$) δ ppm 1.39-1.45 (m, 3H) 1.49-1.55 (m, 3H) 3.21-3.27 (m, 2H) 3.62-3.72 (m, 1H) 3.98-3.96 (m, 1H) 4.00 (br d, J=6.1 Hz, 1H) 4.09-4.15 (m, 1H) 5.07 (d, J=1.0 Hz, 2H) 5.66-5.71 (m, 1H) 5.92-5.94 (m, 1H) 6.04 (t, J=3.0 Hz, 1H) 6.65 (s, 1H) 7.20 (d, J=3.5 Hz, 1H) 7.24 (s, 1H), 7.32 (d, J=8.1 Hz, 1H) 7.52 (s, 1H) 7.71 (t, J=6.8 Hz, 1H) 13.05 (br s, 1H)

Minor rotamer 35%

$^1$H NMR (400 MHz, DMSO-$d_6$) δ ppm 1.39-1.45 (m, 3H) 1.49-1.55 (m, 3H) 3.21-3.27 (m, 2H) 3.44-3.54 (m, 1H) 4.00 (br d, J=6.1 Hz, 1H) 4.09-4.15 (m, 1H) 4.65-4.69 (m, 1H) 5.07 (d, J=1.0 Hz, 2H) 5.19-5.24 (m, 1H) 5.71-5.74 (m, 1H) 6.04 (t, J=3.0 Hz, 1H) 6.65 (s, 1H) 7.20 (d, J=3.5 Hz, 1H) 7.24 (s, 1H), 7.32 (d, J=8.1 Hz, 1H) 7.52 (s, 1H) 7.71 (t, J=6.8 Hz, 1H) 13.05 (br s, 1H)

Compound (F62)

Major Rotamer 60%

$^1$H NMR (500 MHz, DMSO-$d_6$) δ ppm 1.01-1.13 (m, 3H) 1.13-1.45 (m, 3H) 1.46-1.78 (m, 4H) 1.84 (s, 3H) 1.86-2.03 (m, 1H) 2.87 (t, J=12.6 Hz, 1H) 3.60-3.72 (m, 1 H) 3.92 (br d, J=13.2 Hz, 1H) 4.60 (d, J=6.3 Hz, 2H) 4.99 (s, 2H) 5.02 (d, J=6.6 Hz, 2H) 6.99-7.18 (m, 2H) 7.24 (d, J=8.20 Hz, 1H) 7.45 (s, 1H) 7.56 (t, J=7.3 Hz, 1H) 13.03 (br s, 1H)

Minor rotamer 40%

$^1$H NMR (500 MHz, DMSO-$d_6$) δ ppm 1.01-1.13 (m, 3H) 1.13-1.45 (m, 3H) 1.46-1.78 (m, 4H) 1.84 (s, 3H) 1.86-2.03 (m, 1H) 3.02-3.15 (m, 1H) 3.47 (br d, J=15.1 Hz, 1H) 4.31-4.42 (m, 1H) 4.60 (d, J=6.30 Hz, 2H) 4.99 (s, 2H) 5.02 (d, J=6.6 Hz, 2H) 6.99-7.18 (m, 2H) 7.24 (d, J=8.2 Hz, 1H) 7.45 (s, 1H) 7.56 (t, J=7.3 Hz, 1H) 13.03 (br s, 1H)

Compound (F63)

Major Rotamer 65%

$^1$H NMR (400 MHz, DMSO-$d_6$) δ ppm 1.39-1.47 (m, 3H) 1.49 (d, J=7.1 Hz, 3H) 2.73-3.06 (m, 2H) 3.18-3.30 (m, 2H) 3.46 (br t, J=11.1 Hz, 1H) 3.96-4.09 (m, 1H) 5.50-5.62 (m, 1H) 7.03 (d, J=5.6 Hz, 1H) 7.23 (s, 1H) 7.25-7.29 (m, 1H) 7.39 (d, J=5.6 Hz, 1H) 8.14-8.30 (m, 3H) 8.30-8.42 (m, 2H) 9.19 (d, J=2.0 Hz, 1H) 13.49 (br s, 1H)

Minor rotamer 35%

$^1$H NMR (400 MHz, DMSO-$d_6$) δ ppm 1.39-1.47 (m, 3H) 1.54 (d, J=6.6 Hz, 3H) 2.73-3.06 (m, 2H) 3.18-3.30 (m, 2H) 3.96-4.09 (m, 1H) 4.73 (br d, J=11.6 Hz, 1H) 4.94-5.04 (m, 1H) 6.80 (d, J=5.6 Hz, 1H) 7.19 (s, 1H) 7.25-7.29 (m, 1H)

7.30 (d, J=5.1 Hz, 1H) 8.14-8.30 (m, 3H) 8.30-8.42 (m, 2H) 9.19 (d, J=2.0 Hz, 1H) 13.49 (br s, 1H)

Compound (F66)

Major Rotamer 65%

$^1$H NMR (500 MHz, DMSO-$d_6$) δ ppm 1.37-1.46 (m, 3H) 1.49 (d, J=6.6 Hz, 1H) 2.73-3.04 (m, 2H) 3.19-3.30 (m, 2H) 3.40-3.51 (m, 1H) 4.03 (br dd, J=14.0, 4.9 Hz, 1H) 5.08 (s, 2H) 5.50-5.62 (m, 1H) 7.04 (d, J=5.0 Hz, 1H) 7.16-7.25 (m, 2H) 7.34 (d, J=8.2 Hz, 1H) 7.40 (d, J=5.0 Hz, 1H) 7.54 (s, 1H) 7.64-7.79 (m, 1H) 12.71-13.25 (m, 1H)

Minor rotamer 35%

$^1$H NMR (500 MHz, DMSO-$d_6$) δ ppm 1.37-1.46 (m, 3H) 1.54 (d, J=6.6 Hz, 1H) 2.73-3.04 (m, 2H) 3.19-3.30 (m, 3H) 4.73 (br dd, J=12.5, 3.9 Hz, 1H) 4.94-5.02 (m, 1H) 5.08 (s, 2H) 6.81 (d, J=5.4 Hz, 1H) 7.16-7.25 (m, 2H) 7.31 (d, J=5.0 Hz, 1H) 7.34 (d, J=8.2 Hz, 1H) 7.54 (s, 1H) 7.64-7.79 (m, 1H) 12.71-13.25 (m, 1H)

Compound (F67)

Major Rotamer 60%

$^1$H NMR (400 MHz, DMSO-$d_6$) δ ppm 1.17-1.29 (m, 2H) 1.48 (d, J=6.6 Hz, 3H) 1.60-1.67 (m, 3H) 2.55-3.03 (m, 3H) 3.16-3.24 (m, 1H) 3.37-3.48 (m, 1H) 4.03 (br dd, J=14.2, 5.1 Hz, 1H) 5.08 (s, 2H) 5.52-5.58 (m, 1H) 7.02 (d, J=5.6 Hz, 1H) 7.12-7.21 (m, 2H) 7.28-7.39 (m, 2H) 7.53 (s, 1H) 7.73 (br t, J=7.3 Hz, 1H) 12.93-13.06 (m, 1H)

Minor rotamer 40%

$^1$H NMR (400 MHz, DMSO-$d_6$) δ ppm 1.17-1.29 (m, 2H) 1.53 (d, J=6.6 Hz, 3H) 1.60-1.67 (m, 3H) 2.55-3.03 (m, 3H) 3.16-3.24 (m, 1H) 3.33 (br s, 1H) 4.69-4.75 (m, 1H) 4.99 (br d, J=6.6 Hz, 1H) 5.08 (s, 2H) 6.80 (d, J=5.1 Hz, 1H) 7.12-7.21 (m, 2H) 7.28-7.39 (m, 2H) 7.53 (s, 1H) 7.73 (brt, J=7.3 Hz, 1H) 12.93-13.06 (m, 1H)

Compound (F68)

Major Rotamer 60%

$^1$H NMR (400 MHz, DMSO-$d_6$) δ ppm 1.17-1.29 (m, 2H) 1.48 (d, J=6.6 Hz, 3H) 1.60-1.67 (m, 3H) 2.55-3.03 (m, 3H) 3.16-3.24 (m, 1H) 3.37-3.48 (m, 1H) 4.03 (br dd, J=14.2, 5.1 Hz, 1H) 5.08 (s, 2H) 5.52-5.58 (m, 1H) 7.02 (d, J=5.6 Hz, 1H) 7.12-7.21 (m, 2H) 7.28-7.39 (m, 2H) 7.53 (s, 1H) 7.73 (br t, J=7.3 Hz, 1H) 12.93-13.06 (m, 1H)

Minor rotamer 40%

$^1$H NMR (400 MHz, DMSO-$d_6$) δ ppm 1.17-1.29 (m, 2H) 1.53 (d, J=6.6 Hz, 3H) 1.60-1.67 (m, 3H) 2.55-3.03 (m, 3H) 3.16-3.24 (m, 1H) 3.33 (br s, 1H) 4.69-4.75 (m, 1H) 4.99 (br d, J=6.6 Hz, 1H) 5.08 (s, 2H) 6.80 (d, J=5.1 Hz, 1H) 7.12-7.21 (m, 2H) 7.28-7.39 (m, 2H) 7.53 (s, 1H) 7.73 (brt, J=7.3 Hz, 1H) 12.93-13.06 (m, 1H)

Compound (M29)

Major Rotamer (60%)

$^1$H NMR (500 MHz, DMSO-$d_6$) δ ppm 12.67 (br s, 1H) 8.19 (t, J=6.8 Hz, 1H) 7.96 (t, J=6.8 Hz, 1H) 7.78 (d, J=16.1 Hz, 1H) 7.43 (t, J=7.9 Hz, 1H) 7.18 (d, J=3.5 Hz, 1H) 7.12 (s, 1H) 6.70 (d, J=16.1 Hz, 1H) 4.00 (br d, J=13.2 Hz, 1H) 3.63-3.73 (m, 1H) 3.04-3.21 (m, 2H) 2.90-2.98 (m, 1H) 2.40-2.47 (m, 1H) 1.89-1.99 (m, 1H) 1.21-1.87 (m, 7H) 1.11 (d, J=6.3 Hz, 3H) 0.96-1.01 (m, 6H)

Minor Rotamer (40%)

$^1$H NMR (500 MHz, DMSO-$d_6$) δ ppm 12.67 (br s, 1H) 8.19 (t, J=6.8 Hz, 1H) 7.96 (t, J=6.8 Hz, 1H) 7.78 (d, J=16.1 Hz, 1H) 7.43 (t, J=7.9 Hz, 1H) 7.19 (d, J=3.5 Hz, 1H) 7.15 (s, 1H) 6.70 (d, J=16.1 Hz, 1H) 4.39-4.50 (m, 1H) 3.53 (br d, J=15.4 Hz, 1H) 3.04-3.21 (m, 3H) 2.40-2.47 (m, 1H) 2.03-2.09 (m, 1H) 1.21-1.87 (m, 7H) 1.15 (d, J=6.3 Hz, 3H) 0.96-1.01 (m, 6H)

Compound (M30)

Major Rotamer (60%)

$^1$H NMR (500 MHz, DMSO-$d_6$) δ ppm 12.60 (br s, 1H) 9.23 (s, 1H) 8.73-8.81 (m, 1H) 8.44 (t, J=7.9 Hz, 1H) 7.85 (br d, J=12.3 Hz, 1H) 7.61-7.78 (m, 3H) 7.21 (d, 3.3 Hz, 1H) 6.72 (d, J=16.1 Hz, 1H) 4.06 (s, 3H) 3.97-4.14 (m, 1H) 3.68-3.76 (m, 1H), 2.95 (br t, J=12.5 Hz, 1H) 1.89-2.01 (m, 1H) 1.22-1.86 (m, 7H) 1.14 (br d, J=6.3 Hz, 3H)

Minor Rotamer (40%)

$^1$H NMR (500 MHz, DMSO-$d_6$) δ ppm 12.60 (br s, 1H) 9.23 (s, 1H) 8.73-8.81 (m, 1H) 8.44 (t, J=7.9 Hz, 1H) 7.85 (br d, J=12.3 Hz, 1H) 7.61-7.78 (m, 3H) 7.22 (d, 3.3 Hz, 1H) 6.72 (d, J=16.1 Hz, 1H) 4.42-4.52 (m, 1H) 4.06 (s, 3H) 3.56 (br d, J=15.1 Hz, 1H) 3.09-3.19 (m, 1H) 2.03-2.12 (m, 1H) 1.22-1.86 (m, 7H) 1.18 (br d, J=6.3 Hz, 3H)

Compound (M31)

Major Rotamer 60%

$^1$H NMR (400 MHz, DMSO-$d_6$) δ ppm 1.09-1.20 (m, 3H) 1.22-1.37 (m, 3H) 1.42 (t, J=7.5 Hz, 3H) 1.53-1.86 (m, 4H) 1.87-2.12 (m, 1H) 2.93 (t, J=12.1 Hz, 1H) 3.22-3.28 (m, 2H) 3.67-3.74 (m, 1H) 3.97-4.04 (m, 1H) 6.19 (d, J=12.1 Hz, 1H) 7.07-7.13 (m, 3H) 7.34 (t, J=7.8 Hz, 1H) 7.58 (t, J=6.8 Hz, 1H) 8.10 (t, J=7.5 Hz, 1H) 12.55 (br s, 1H)

Minor rotamer 40%

$^1$H NMR (400 MHz, DMSO-$d_6$) δ ppm 1.09-1.20 (m, 3H) 1.22-1.37 (m, 3H) 1.42 (t, J=7.5 Hz, 3H) 1.53-1.86 (m, 4H) 1.87-2.12 (m, 1H) 3.07-3.18 (m, 1H) 3.22-3.28 (m, 2H) 3.50-3.58 (m, 1H) 4.41-4.48 (m, 1H) 6.19 (d, J=12.1 Hz, 1H) 7.07-7.13 (m, 3H) 7.34 (t, J=7.8 Hz, 1H) 7.58 (t, J=6.8 Hz, 1H) 8.10 (t, J=7.5 Hz, 1H) 12.55 (br s, 1H)

Compound (M32)

Major Rotamer 60%

$^1$H NMR (400 MHz, DMSO-$d_6$) δ ppm 1.13 (d, J=6.6 Hz, 3H) 1.25-1.38 (m, 3H) 1.42 (t, J=7.1 Hz, 3H) 1.55-1.83 (m, 4H) 1.91-1.99 (m, 1H) 2.85-3.00 (m, 1H) 3.26 (q, J=7.6 Hz, 2H) 3.67-3.74 (m, 1H) 3.98 (d, J=1.0 Hz, 3H) 4.00-4.05 (m, 1H) 6.67 (d, J=16.2 Hz, 1H) 7.10-7.13 (m, 1H) 7.16-7.21 (m, 1H) 7.73-7.80 (m, 2H) 7.86-7.94 (m, 1H) 12.58 (br s, 1H)

Minor rotamer 40%

$^1$H NMR (400 MHz, DMSO-$d_6$) δ ppm 1.16 (d, J=6.6 Hz, 3H) 1.25-1.38 (m, 3H) 1.42 (t, J=7.1 Hz, 3H) 1.55-1.83 (m, 4H) 2.02-2.08 (m, 1H) 3.07-3.17 (m, 1H) 3.26 (q, J=7.6 Hz, 2H) 3.51-3.57 (m, 1H) 3.98 (d, J=1.0 Hz, 3H) 4.42-4.46 (m, 1H) 6.67 (d, J=16.2 Hz, 1H) 7.10-7.13 (m, 1H) 7.16-7.21 (m, 1H) 7.73-7.80 (m, 2H) 7.86-7.94 (m, 1H) 12.58 (br s, 1H)

Compound (M33)

Major Rotamer 60%

$^1$H NMR (500 MHz, DMSO-$d_6$) δ ppm 1.15 (d, J=6.3 Hz, 3H) 1.22-1.50 (m, 3H) 1.59-1.66 (m, 4H) 1.93 (3H) 1.90-2.1 (m, 1H) 2.95 (brt, J=12.5 Hz, 1H) 3.66-3.78 (m, 1H) 4.00 (br d, J=13.2 Hz, 1H) 4.69 (d, J=6.6 Hz, 2H) 5.10 (d, J=6.3 Hz, 2H) 6.66 (d, J=16.1 Hz, 1H) 7.15 (s, 1H) 7.20 (dd, J=3.2, 7.9 Hz, 1H) 7.39 (t, J=7.9 Hz, 1H) 7.64 (br d, J=16.4 Hz, 1H) 7.89 (br t, J=7.1 Hz, 1H) 8.08 (br t, J=6.9 Hz, 1H) 12.0-13.0 (m, 1H)

Minor Rotamers 40%

$^1$H NMR (500 MHz, DMSO-$d_6$) δ ppm 1.17 (d, J=6.3 Hz, 3H) 1.22-1.50 (m, 3H) 1.59-1.66 (m, 4H) 1.90-2.1 (m, 1H) 1.93 (s, 3H) 3.11-3.18 (m, 1H) 3.49-3.63 (m, 1H) 4.39-4.50 (m, 1H) 4.69 (d, J=6.6 Hz, 2H) 5.10 (d, J=6.3 Hz, 2H) 6.66 (d, J=16.1 Hz, 1H) 7.15 (s, 1H) 7.20 (dd, J=3.2, 7.9 Hz, 1H) 7.39 (t, J=7.9 Hz, 1H) 7.64 (br d, J=16.4 Hz, 1H) 7.89 (br t, J=7.1 Hz, 1H) 8.08 (br t, J=6.9 Hz, 1H) 12.0-13.0 (m, 1H)

Compound (M34)

Major Rotamer 60%

$^1$H NMR (400 MHz, DMSO-$d_6$) δ ppm 1.13 (d, J=6.6 Hz, 3H) 1.20-1.33 (m, 2H) 1.42 (t, J=7.6 Hz, 3H) 1.57-1.80 (m, 4H) 1.85-2.09 (m, 1H) 2.92 (t, J=12.4 Hz, 1H) 3.06-3.19 (m, 1H) 3.21-3.26 (m, 2H) 3.65-3.81 (m, 1H) 3.95-4.06 (m, 4H) 6.72 (d, J=16.2 Hz, 1H) 7.04-7.11 (m, 2H) 7.16 (d, J=8.6 Hz, 1H) 7.80 (d, J=16.7 Hz, 1H) 8.16 (t, J=8.6 Hz, 1H) 12.49 (br s, 1H)

Minor rotamer 40%

$^1$H NMR (400 MHz, DMSO-d$_6$) δ ppm 1.15 (d, J=6.6 Hz, 3H) 1.20-1.33 (m, 2H) 1.42 (t, J=7.6 Hz, 3H) 1.57-1.83 (m, 4H) 1.85-2.09 (m, 2H) 3.06-3.19 (m, 1H) 3.21-3.26 (m, 2H) 3.55 (m, 1H) 3.99 (s, 3H) 4.40-4.50 (m, 1H) 6.72 (d, J=16.2 Hz, 1H) 7.04-7.11 (m, 2H) 7.16 (d, J=8.6 Hz, 1H) 7.80 (d, J=16.7 Hz, 1H) 8.16 (t, J=8.6 Hz, 1H) 12.49 (br s, 1H)

Compound (M35)

Major Rotamer 53%

$^1$H NMR (500 MHz, DMSO-d$_6$) δ ppm 1.26 (d, J=6.8 Hz, 3H) 1.36-1.51 (m, 4H) 1.62-1.81 (m, 3H) 1.96 (br d, J=16.7 Hz, 1H) 2.20-2.44 (m, 3H) 3.17-3.30 (m, 3H) 3.49-3.56 (m, 1H) 4.38 (br d, J=14.2 Hz, 1H) 5.54 (br d, J=18.3 Hz, 1H) 5.67 (br s, 1H) 6.70 (d, J=15.8 Hz, 1H) 7.10 (d, J=4.7 Hz, 1H) 7.15-7.21 (dd, J=3.5 Hz, 24.9 Hz, 1H) 7.64 (d, J=16.1 Hz, 1H) 7.71 (d, J=8.2 Hz, 1H) 7.81 (d, J=12.3 Hz, 1H) 8.20 (td, J=7.9, 1.9 Hz, 1H) 12.57 (br s, 1H)

Minor rotamer 47%

$^1$H NMR (500 MHz, DMSO-d$_6$) δ ppm 1.28 (d, J=6.8 Hz, 3H) 1.36-1.51 (m, 4H) 1.62-1.81 (m, 3H) 2.12 (d, J=16.4 Hz, 1H) 2.20-2.44 (m, 3H) 2.89-2.97 (m, 1H) 3.17-3.30 (m, 2H) 3.63 (q, J=6.5 Hz, 1H) 4.62 (q, J=6.9 Hz, 1H) 5.54 (br d, J=18.3 Hz, 1H) 5.67 (br s, 1H) 6.70 (d, J=15.8 Hz, 1H) 7.10 (d, J=4.7 Hz, 1H) 7.15-7.21 (dd, J=3.5 Hz, 24.9 Hz, 1H) 7.64 (d, J=16.1 Hz, 1H) 7.71 (d, J=8.2 Hz, 1H) 7.81 (d, J=12.3 Hz, 1H) 8.20 (td, J=7.9, 1.9 Hz, 1H) 12.57 (br s, 1H)

Compound (M44)

Major Rotamer (65%)

$^1$H NMR (500 MHz, DMSO-d$_6$) δ ppm 12.58 (br s, 1H) 8.22 (t, J=8.0 Hz, 1H) 7.82 (dd, J=12.3, 0.9 Hz, 1H) 7.71 (dd, J=8.4, 1.4 Hz, 1H) 7.64 (d, J=15.8 Hz, 1H) 7.20-7.28 (m, 2H) 6.71 (d, J=16.1 Hz, 1H) 6.64-6.68 (m, 1H) 6.05 (t, J=3.2 Hz, 1H) 5.94 (d, J=3.2 Hz, 1H) 5.69 (q, J=6.7 Hz, 1H) 4.07-4.18 (m, 1H) 3.97-4.06 (m, 1H) 3.62-3.74 (m, 1H) 3.22-3.31 (m, 3H) 1.50 (d, J=6.6 Hz, 3H) 1.40-1.47 (m, 3H)

Minor Rotamer (35%)

$^1$H NMR (500 MHz, DMSO-d$_6$) δ ppm 12.58 (br s, 1H) 8.22 (t, J=8.0 Hz, 1H) 7.82 (dd, J=12.3, 0.9 Hz, 1H) 7.71 (dd, J=8.4, 1.4 Hz, 1H) 7.64 (d, J=15.8 Hz, 1H) 7.20-7.28 (m, 2H) 6.71 (d, J=16.1 Hz, 1H) 6.64-6.68 (m, 1H) 5.99 (t, J=3.2 Hz, 1H) 5.73 (br s, 1H) 5.21 (q, J=6.6 Hz, 1H) 4.64-4.71 (m, 1H) 4.07-4.18 (m, 1H) 3.93 (td, J=12.1, 3.9 Hz, 1H) 3.45-3.54 (m, 1H) 3.22-3.31 (m, 2H) 1.54 (d, J=6.6 Hz, 3H) 1.40-1.47 (m, 3H)

Compound (M45)

Major Rotamer 65%

$^1$H NMR (400 MHz, DMSO-d$_6$) δ ppm 1.40-1.45 (m, 3H) 1.49-1.55 (m, 3H) 3.24-3.26 (m, 2H) 3.64-3.72 (m, 1H) 3.90-3.97 (m, 1H) 3.98-4.01 (m, 1H) 4.09-4.15 (m, 1H) 5.68-5.74 (m, 1H) 5.94 (br s, 1H) 5.99-6.05 (m, 1H) 6.67 (d, J=8.6 Hz, 1H) 6.72 (s, 1H) 7.21-7.25 (m, 2H) 7.43 (t, J=7.8 Hz, 1H) 7.79 (d, J=16.2 Hz, 1H) 7.96 (br t, J=7.1 Hz, 1H) 8.21 (br t, J=7.6 Hz, 1H) 12.6 (br s, 1H)

Minor rotamer 35%

$^1$H NMR (400 MHz, DMSO-d$_6$) δ ppm 1.40-1.45 (m, 3H) 1.49-1.55 (m, 3H) 3.24-3.27 (m, 2H) 3.44-3.53 (m, 1H) 3.90-3.97 (m, 1H) 3.98-4.01 (m, 1H) 4.09-4.15 (m, 1H) 4.65-4.71 (m, 1H) 5.22 (br d, J=7.1 Hz, 1H) 5.94 (br s, 1H) 6.67 (d, J=8.6 Hz, 1H) 6.72 (s, 1H) 7.21-7.25 (m, 2H) 7.43 (t, J=7.8 Hz, 1H) 7.79 (d, J=16.2 Hz, 1H) 7.96 (br t, J=7.1 Hz, 1H) 8.21 (br t, J=7.6 Hz, 1H) 12.6 (br s, 1H)

Compound (M46)

Major Rotamer 65%

$^1$H NMR (500 MHz, DMSO-d$_6$) δ ppm 1.27-1.37 (m, 4H) 1.47 (d, J=6.9 Hz, 3H) 2.74-3.00 (m, 3H) 3.37-3.48 (m, 1H) 3.94 (br dd, J=13.6, 4.7 Hz, 1H) 5.55 (q, J=6.5 Hz, 1H) 6.71 (d, J=16.1 Hz, 1H) 6.91-6.96 (m, 1H) 7.03 (d, J=5.4 Hz, 1H) 7.22 (s, 1H) 7.39 (d, J=5.0 Hz, 1H) 7.44 (t, J=7.6 Hz, 1H) 7.80 (d, J=16.08 Hz, 1H) 7.97 (br t, J=7.1 Hz, 1H) 8.21-8.27 (m, 1H) 12.68 (br s, 1H)

Minor Rotamer 35%

$^1$H NMR (500 MHz, DMSO-d$_6$) δ ppm 1.27-1.37 (m, 4H) 1.51 (d, J=6.9 Hz, 3H) 2.74-3.00 (m, 3H) 3.20-3.25 (m, 1H) 4.72 (br dd, J=13.1, 5.2 Hz, 1H) 4.91 (q, J=6.3 Hz, 1H) 6.71 (d, J=16.1 Hz, 1H) 6.80 (d, J=5.4 Hz, 1H) 6.91-6.96 (m, 1H) 7.22 (m, 1H) 7.30 (d, J=5.0 Hz, 1H) 7.44 (t, J=7.57 Hz, 1H) 7.80 (d, J=16.1 Hz, 1H) 7.97 (br t, J=7.1 Hz, 1H) 8.21-8.27 (m, 1H) 12.68 (br s, 1H)

Compound (M47)

Major Rotamer 60%

$^1$H NMR (400 MHz, DMSO-d$_6$) δ ppm 0.95-1.02 (m, 2H) 1.18-1.30 (m, 2H) 1.47 (d, J=6.6 Hz, 3H) 1.65 (s, 3H) 2.74-2.84 (m, 1H) 2.85-3.03 (m, 2H) 3.34-3.48 (m, 1H) 4.02 (br dd, J=13.1, 4.6 Hz, 1H) 5.52-5.59 (m, 1H) 6.70 (d, J=16.2 Hz, 1H) 7.02 (d, J=5.1 Hz, 1H) 7.12-7.18 (m, 1H) 7.23 (d, J=3.5 Hz, 1H) 7.38 (d, J=5.1 Hz, 1H) 7.45 (t, J=7.6 Hz, 1H) 7.80 (d, J=16.2 Hz, 1H) 7.96 (t, J=7.1 Hz, 1H) 8.23 (br t, J=7.3 Hz, 1H) 12.60 (br s, 1H)

Minor rotamer 40%

$^1$H NMR (400 MHz, DMSO-d$_6$) δ ppm 0.95-1.02 (m, 2H) 1.18-1.30 (m, 2H) 1.53 (d, J=6.6 Hz, 3H) 1.64 (s, 3H) 2.85-3.03 (m, 2H) 3.14-3.25 (m, 1H) 4.68-4.76 (m, 1H) 4.99 (br d, J=7.1 Hz, 1H) 6.70 (d, J=16.2 Hz, 1H) 6.80 (d, J=5.1 Hz, 1H) 7.12-7.18 (m, 1H) 7.23 (d, J=3.5 Hz, 1H) 7.29 (d, J=5.1 Hz, 1H) 7.45 (t, J=7.6 Hz, 1H) 7.80 (d, J=16.2 Hz, 1H) 7.96 (t, J=7.1 Hz, 1H) 8.23 (br t, J=7.3 Hz, 1H) 12.60 (br s, 1H)

Compound (M48)

Major Rotamer 60%

$^1$H NMR (400 MHz, DMSO-d$_6$) δ ppm 1.39-1.47 (m, 3H) 1.48 (d, J=6.6 Hz, 3H) 2.73-2.84 (m, 1H) 2.84-3.07 (m, 1H) 3.27 (q, J=7.6 Hz, 2H) 3.36-3.53 (m, 1H) 4.02 (br dd, J=13.9, 4.8 Hz, 1H) 5.57 (q, J=6.6 Hz, 1H) 6.70 (d, J=15.7 Hz, 1H) 7.03 (d, J=5.1 Hz, 1H) 7.17-7.25 (m, 2H) 7.38 (d, J=5.1 Hz, 1H) 7.43 (t, J=8.1 Hz, 1H) 7.79 (d, J=16.2 Hz, 1H) 7.96 (t, J=6.6 Hz, 1H) 8.21 (t, J=6.6 Hz, 1H) 12.63 (br s, 1H)

Minor rotamer 40%

$^1$H NMR (400 MHz, DMSO-d$_6$) δ ppm 1.39-1.47 (m, 3H) 1.53 (d, J=6.6 Hz, 3H) 2.84-3.07 (m, 2H) 3.22-3.30 (m, 3H) 4.70-4.77 (m, 1H) 4.94-5.05 (m, 1H) 6.70 (d, J=15.7 Hz, 1H) 6.80 (d, J=5.6 Hz, 1H) 7.17-7.25 (m, 2H) 7.30 (d, J=5.6 Hz, 1H) 7.43 (t, J=8.1 Hz, 1H) 7.79 (d, J=16.2 Hz, 1H) 7.96 (t, J=6.6 Hz, 1H) 8.21 (t, J=6.6 Hz, 1H) 12.63 (br s, 1H)

Compound (M49)

Major Rotamer 60%

$^1$H NMR (400 MHz, DMSO-d$_6$) δ ppm 1.39-1.47 (m, 3H) 1.48 (d, J=6.6 Hz, 3H) 2.73-2.84 (m, 1H) 2.84-3.07 (m, 1H) 3.27 (q, J=7.6 Hz, 2H) 3.36-3.53 (m, 1H) 4.02 (br dd, J=13.9, 4.8 Hz, 1H) 5.57 (q, J=6.6 Hz, 1H) 6.70 (d, J=15.7 Hz, 1H) 7.03 (d, J=5.1 Hz, 1H) 7.17-7.25 (m, 2H) 7.38 (d, J=5.1 Hz, 1H) 7.43 (t, J=8.1 Hz, 1H) 7.79 (d, J=16.2 Hz, 1H) 7.96 (t, J=6.6 Hz, 1H) 8.21 (t, J=6.6 Hz, 1H) 12.63 (br s, 1H)

Minor rotamer 40%

$^1$H NMR (400 MHz, DMSO-d$_6$) δ ppm 1.39-1.47 (m, 3H) 1.53 (d, J=6.6 Hz, 3H) 2.84-3.07 (m, 2H) 3.22-3.30 (m, 3H) 4.70-4.77 (m, 1H) 4.94-5.05 (m, 1H) 6.70 (d, J=15.7 Hz, 1H) 6.80 (d, J=5.6 Hz, 1H) 7.17-7.25 (m, 2H) 7.30 (d, J=5.6 Hz, 1H) 7.43 (t, J=8.1 Hz, 1H) 7.79 (d, J=16.2 Hz, 1H) 7.96 (t, J=6.6 Hz, 1H) 8.21 (t, J=6.6 Hz, 1H) 12.63 (br s, 1H)

Compound (M51)

Major Rotamer 70%

$^1$H NMR (500 MHz, DMSO-d$_6$) δ ppm 1.30 (d, J=6.6 Hz, 3H) 1.43 (t, J=7.4 Hz, 3H) 1.48-1.66 (m, 4H) 1.77-2.01 (m, 4H) 2.08-2.33 (m, 2H) 3.24-3.30 (m, 1H) 3.26 (q, J=7.6 Hz, 2H) 3.72 (br dd, J=13.1, 5.5 Hz, 1H) 4.62 (br d, J=6.3 Hz, 1H) 6.71 (d, J=16.1 Hz, 1H) 7.13-7.18 (m, 1H) 7.22 (d, J=2.8 Hz, 1H) 7.43 (t, J=7.7 Hz, 1H) 7.79 (d, J=16.1 Hz, 1H) 7.97 (br t, J=7.3 Hz, 1H) 8.22 (br t, J=7.3 Hz, 1H) 12.68 (br s, 1H)

Minor rotamer 30%

$^1$H NMR (500 MHz, DMSO-d$_6$) δ ppm 1.37 (d, J=6.6 Hz, 3H) 1.43 (t, J=7.41 Hz, 3H) 1.48-1.66 (m, 4H) 1.77-2.01 (m, 4H) 2.08-2.33 (m, 2H) 3.02-3.09 (m, 1H) 3.26 (q, J=7.6 Hz, 2H) 3.99-4.06 (m, 1H) 4.47 (br dd, J=13.1, 6.2 Hz, 1H) 6.71 (d, J=16.1 Hz, 1H) 7.13-7.18 (m, 1H) 7.22 (d, J=2.8 Hz, 1H) 7.43 (t, J=7.7 Hz, 1H) 7.79 (d, J=16.1 Hz, 1H) 7.97 (br t, J=7.3 Hz, 1H) 8.22 (br t, J=7.3 Hz, 1H) 12.68 (br s, 1H)

Compound (O5)

Major Rotamer (60%)

$^1$H NMR (400 MHz, DMSO-d$_6$) δ ppm 1.21-1.38 (m, 5H) 1.43-1.56 (m, 5H) 1.92-2.02 (m, 1H) 2.66-2.74 (m, 1H) 2.85-3.05 (m, 2H) 3.34-3.50 (m, 1H) 3.76-3.84 (m, 1H) 5.59 (q, J=6.9 Hz, 1H) 6.85-6.92 (m, 1H) 7.06-7.26 (m, 6H) 7.32 (d, J=7.6 Hz, 1H) 8.09 (t, J=7.9 Hz, 1H) 12.27-12.48 (m, 1H)

Minor Rotamer (40%)

$^1$H NMR (400 MHz, DMSO-d$_6$) δ ppm 1.21-1.38 (m, 5H) 1.43-1.56 (m, 5H) 1.92-2.02 (m, 1H) 2.42-2.44 (m, 1H) 2.85-3.05 (m, 2H) 3.22-3.25 (m, 1H) 4.52-4.58 (m, 1H) 4.96 (d, J=6.6 Hz, 1H) 6.85-6.92 (m, 1H) 7.06-7.26 (m, 7H) 8.09 (t, J=7.9 Hz, 1H) 12.27-12.48 (m, 1H)

Compound (O7)

Major Rotamer 60%

$^1$H NMR (500 MHz, DMSO-d$_6$) δ ppm 1.10 (d, J=6.3 Hz, 3H) 1.20-1.40 (m, 7H) 1.42-1.56 (m, 3H) 1.59-1.82 (m, 3H) 1.89-1.98 (m, 2H) 2.43-2.55 (m, 1H) 2.87-2.97 (m, 2H) 3.57-3.67 (m, 1H) 3.98 (br d, J=13.6 Hz, 1H) 6.82 (d, J=2.2 Hz, 1H) 7.06 (dd, J=7.9, 3.5 Hz, 1H) 7.20 (dd, J=8.2, 1.6 Hz, 1H) 7.24 (dd, J=12.9, 1.6 Hz, 1H) 8.08 (t, J=8.0 Hz, 1H) 12.41 (br s, 1H)

Minor rotamer 40%

$^1$H NMR (500 MHz, DMSO-d$_6$) δ ppm 1.14 (d, J=6.3 Hz, 3H) 1.20-1.40 (m, 7H) 1.42-1.56 (m, 3H) 1.59-1.82 (m, 3H) 1.89-1.98 (m, 2H) 1.98-2.08 (m, 1H) 2.43-2.55 (m, 1 H) 2.87-2.97 (m, 1H) 3.06-3.26 (m, 1H) 3.43-3.51 (br d, J=15.4 Hz, 1H) 4.42 (dt, J=11.9, 6.2 Hz, 1H) 6.82 (d, J=2.2 Hz, 1H) 7.06 (dd, J=7.9, 3.5 Hz, 1H) 7.20 (dd, J=8.2, 1.6 Hz, 1H) 7.24 (dd, J=12.9, 1.6 Hz, 8.08 (t, J=8.0 Hz, 1H) 12.41 (br s, 1H)

Compound (O17)

Major Rotamer 60%

$^1$H NMR (500 MHz, DMSO-d$_6$) δ ppm 1.15 (t, J=5.7 Hz, 3H) 1.17-1.85 (m, 9H) 1.91 (s, 3H) 1.92-2.11 (m, 2H) 2.94 (brt, J=12.6 Hz, 1H) 3.10-3.29 (m, 1H) 3.68-3.76 (m, 1H) 3.99 (br d, J=13.2 Hz, 1H) 4.43 (m 1H) 4.67 (d, J=6.3 Hz, 2H) 5.09 (br d, J=6.6 Hz, 2H) 7.09 (br dd, J=7.4 Hz, 3.5 Hz, 1H) 7.12 (s, 1H) 7.19 (br d, J=8.2 Hz, 1H) 7.23 (br d, J=12.6 Hz, 1H) 7.98 (t, J=8.0 Hz, 1H) 12.46 (s, 1H)

Minor rotamer 40%

$^1$H NMR (500 MHz, DMSO-d$_6$) δ ppm 1.15 (t, J=5.7 Hz, 3H) 1.17-1.85 (m, 9H) 1.91 (s, 3H) 1.92-2.11 (m, 2H) 3.10-3.17 (m, 1H) 3.54 (br d, J=6.3 Hz, 1H) 3.99 (br d, J=13.2 Hz, 1H) 4.43 (m 1H) 4.67 (br d, J=6.3 Hz, 2H) 5.09 (br d, J=6.6 Hz, 2H) 7.09 (br dd, J=7.4 Hz, 3.5 Hz, 1H) 7.12 (s, 1H) 7.19 (br d, J=8.2 Hz, 1H) 7.23 (br d, J=12.6 Hz, 1H) 7.98 (t, J=8.0 Hz, 1H) 12.46 (s, 1H)

Compound (O18)

Major Rotamer 60%

$^1$H NMR (500 MHz, DMSO-d$_6$) δ ppm 1.13 (d, J=6.6 Hz, 3H) 1.22-1.38 (m, 4H) 1.42 (t, J=7.6 Hz, 1H) 1.52-1.85 (m, 5H) 2.45-2.50 (m, 1H) 2.90-2.09 (m, 1H) 2.93 (br t, J=12.6 Hz, 1H) 3.20-3.30 (dd, J=14.5, 7.3 Hz, 1H) 3.36-3.46 (m, 1H) 3.61-3.67 (m, 1H) 3.67-3.74 (m, 1H) 4.00 (br d, J=13.6 Hz, 1H) 7.09-7.15 (m, 2H) 7.40 (br d, J=8.2 Hz, 1H) 7.48 (br d, J=12.6 Hz, 1H) 8.14 (t, J=8.2 Hz, 1H) 13.37 (s, 1H)

Minor rotamer 40%

$^1$H NMR (500 MHz, DMSO-d$_6$) δ ppm 1.15 (d, J=6.6 Hz, 3H) 1.22-1.38 (m, 4H) 1.42 (t, J=7.6 Hz, 1H) 1.52-1.85 (m, 5H) 2.45-2.50 (m, 1H) 2.90-2.09 (m, 1H) 3.10-3.19 (m, 1H) 3.20-3.30 (dd, J=14.5, 7.3 Hz, 1H) 3.36-3.46 (m, 1H) 3.49-3.57 (m, 1H) 3.61-3.67 (m, 1H) 4.41-4.47 (m, 1H) 7.09-7.15 (m, 2H) 7.40 (br d, J=8.2 Hz, 1H) 7.48 (br d, J=12.6 Hz, 1H) 8.14 (t, J=8.2 Hz, 1H) 13.30-13.43 (m, 1H)

Compound (O19)

Major Rotamer 67%

$^1$H NMR (500 MHz, DMSO-d$_6$) δ ppm 1.39-1.56 (m, 8H) 1.91-2.03 (m, 1H) 3.22-3.31 (m, 2H) 3.62-3.72 (m, 1H) 3.90-4.04 (m, 2H) 4.07-4.17 (m, 1H) 4.65-4.71 (m, 1H) 5.66-5.74 (m, 1H) 5.95 (m, 1H), 6.05 (t, J=3.0 Hz, 1H) 6.66 (s, 1H) 7.15 (d, J=3.5 Hz, 1H) 7.19-7.27 (m, 3H) 8.08 (t, J=8.0 Hz, 1H) 12.44 (br s, 1H)

Minor rotamer 33%

$^1$H NMR (500 MHz, DMSO-d$_6$) δ ppm 1.39-1.56 (m, 8H) 1.91-2.03 (m, 1H) 3.22-3.31 (m, 2H) 3.42-3.52 (m, 1H) 3.90-4.04 (m, 2H) 4.07-4.17 (m, 1H) 4.70 (m, 1H), 5.18-5.23 (m, 1H) 5.73 (m, 1H), 5.99 (t, J=3.0 Hz, 1H) 6.66 (s, 1H) 7.15 (d, J=3.5 Hz, 1H) 7.19-7.27 (m, 3H) 8.08 (t, J=8.0 Hz, 1H) 12.44 (br s, 1H)

Compound (O20)

Major Rotamer 60%

$^1$H NMR (400 MHz, DMSO-d$_6$) δ ppm 1.21-1.39 (m, 5H) 1.42-1.53 (m, 5H) 1.91-1.99 (m, 1H) 2.70-2.80 (m, 1H) 2.83-3.01 (m, 2H) 3.36-3.45 (m, 1H) 3.92 (br dd, J=13.4, 4.8 Hz, 1H) 5.54 (q, J=7.1 Hz, 1H) 6.87-6.90 (m, 1H) 7.02 (d, J=5.6 Hz, 1H) 7.08-7.12 (m, 1H) 7.18-7.27 (m, 2H) 7.38 (d, J=5.6 Hz, 1H) 8.09 (td, J=8.1, 2.5 Hz, 1H) 12.40 (s, 1H)

Minor rotamer 40%

$^1$H NMR (400 MHz, DMSO-d$_6$) δ ppm 1.21-1.39 (m, 5H) 1.42-1.53 (m, 5H) 1.91-1.99 (m, 1H) 2.83-3.01 (m, 3H) 3.17-3.29 (m, 1H) 4.68-4.73 (m, 1H) 4.90 (q, J=7.1 Hz, 1H) 6.79 (d, J=5.1 Hz, 1H) 6.87-6.90 (m, 1H) 7.08-7.12 (m, 1H) 7.18-7.27 (m, 2H) 7.29 (d, J=5.6 Hz, 1H) 8.09 (td, J=8.1, 2.5 Hz, 1H) 12.40 (s, 1H)

Compound (O21)

Major Rotamer 60%

$^1$H NMR (400 MHz, DMSO-d$_6$) δ ppm 0.93-1.01 (m, 2H) 1.15-1.30 (m, 3H) 1.43-1.55 (m, 5H) 1.60-1.66 (m, 3H) 1.93-2.01 (m, 1H) 2.71-2.82 (m, 1H) 2.84-3.02 (m, 1H) 3.34-3.46 (m, 1H) 3.96-4.04 (m, 1H) 5.51-5.58 (m, 1H) 7.02 (d, J=5.6 Hz, 1H) 7.10-7.15 (m, 2H) 7.20-7.27 (m, 2H) 7.38 (d, J=5.1 Hz, 1H) 8.08 (t, J=7.9 Hz, 1H) 12.41 (s, 1H)

Minor rotamer 40%

$^1$H NMR (400 MHz, DMSO-d$_6$) δ ppm 0.93-1.01 (m, 2H) 1.15-1.30 (m, 2H) 1.43-1.55 (m, 6H) 1.60-1.66 (m, 3H) 1.93-2.01 (m, 1H) 2.84-3.02 (m, 2H) 3.19-3.30 (m, 1H) 4.68-4.74 (m, 1H) 4.94-5.01 (m, 1H) 6.79 (d, J=5.6 Hz, 1H) 7.10-7.15 (m, 2H) 7.20-7.27 (m, 2H) 7.29 (d, J=5.1 Hz, 1H) 8.08 (t, J=7.9 Hz, 1H) 12.41 (s, 1H)

Compound (O22)
Major Rotamer 62%
¹H NMR (400 MHz, DMSO-d₆) δ 1.38-1.54 (m, 9H) 1.93-1.98 (m, 1H) 2.74-2.82 (m, 1H) 2.84-3.03 (m, 1H) 3.20-3.30 (m, 2H) 3.38-3.49 (m, 1H) 4.01 (dd, J=14.4, 5.3 Hz, 1H) 5.53-5.59 (m, 1H) 7.03 (d, J=5.6 Hz, 1H) 7.12-7.30 (m, 4H) 7.39 (d, J=5.1 Hz, 1H) 8.07 (t, J=7.9 Hz, 1H) 12.30-12.50 (br s, 1H)
Minor rotamer 38%
¹H NMR (400 MHz, DMSO-d₆) δ ppm 1.38-1.54 (m, 9H) 1.93-1.98 (m, 1H) 2.84-3.03 (m, 2H) 3.20-3.30 (m, 3H) 4.69-4.76 (m, 1H) 4.97 (q, J=6.6 Hz, 1H) 6.79 (d, J=5.1 Hz, 1H) 7.12-7.30 (m, 4H) 7.29 (d, J=5.1 Hz, 1H) 8.07 (t, J=7.9 Hz, 1H) 12.30-12.50 (br s, 1H)

Compound (O23)
Major Rotamer 60%
¹H NMR (500 MHz, DMSO-d₆) δ ppm 1.14 (d, 6.3 Hz, 3H) 1.22-1.38 (m, 3H) 1.43-1.52 (m, 2H) 1.56-1.82 (m, 5H) 1.89-2.10 (m, 2H) 2.94 (brt, J=12.6 Hz, 1H) 3.10-3.24 (m, 4H) 3.65-3.72 (m, 1H) 4.00 (br d, J=12.9 Hz, 1H) 4.10 (quin, J=8.8 Hz, 1H) 7.12 (dd, J=8.2, 3.2 Hz, 1H) 7.19-7.25 (m, 2H) 7.28 (s, 1H), 8.09 (t, J=8.0 Hz, 1H) 12.43 (br s, 1H)
Minor Rotamer 40%
¹H NMR (500 MHz, DMSO-d₆) δ ppm 1.17 (d, 6.3 Hz, 3H) 1.22-1.38 (m, 3H) 1.43-1.52 (m, 3H) 1.56-1.82 (m, 4H) 1.89-2.00 (m, 2H) 3.10-3.24 (m, 5H) 3.52 (br d, J=15.1 Hz, 1H) 4.10 (quin, J=8.8 Hz, 1H) 4.45 (dt, J=11.7, 5.8 Hz, 1H) 7.12 (dd, J=8.2, 3.2 Hz, 1H) 7.19-7.25 (m, 2H) 7.28 (s, 1H), 8.09 (t, J=8.0 Hz, 1H) 12.43 (br s, 1H)

Compound (O24)
Major Rotamer 60%
¹H NMR (400 MHz, DMSO-d₆) δ ppm 0.87 (s, 3H) 1.09-1.17 (m, 3H) 1.32 (s, 3H) 1.26-1.36 (m, 2H) 1.38-1.51 (m, 1H) 1.41 (t, J=7.3 Hz, 3H) 1.53-1.86 (m, 4H) 1.93 (br d, J=5.1 Hz, 1H) 1.96-2.12 (m, 1H) 2.38 (br d, J=5.6 Hz, 1H) 2.92 (br t, J=12.9 Hz, 1H) 3.19-3.28 (m, 2H) 3.63-3.76 (m, 1H) 3.92-4.06 (m, 1H) 7.04-7.11 (m, 2H) 7.12-7.21 (m, 2H) 8.04 (t, J=7.8 Hz, 1H) CO₂H (not visible)
Minor rotamer 40%
¹H NMR (400 MHz, DMSO-d₆) δ ppm 0.87 (s, 3H) 1.09-1.17 (m, 3H) 1.32 (s, 3H) 1.26-1.36 (m, 2H) 1.38-1.51 (m, 1H) 1.41 (t, J=7.3 Hz, 3H) 1.53-1.86 (m, 4H) 1.93 (br d, J=5.1 Hz, 1H) 1.96-2.12 (m, 1H) 2.38 (br d, J=5.6 Hz, 1H) 3.04-3.17 (m, 1H) 3.19-3.28 (m, 2H) 3.49-3.59 (m, 1H) 3.35-4.52 (m, 1H) 7.04-7.11 (m, 2H) 7.12-7.21 (m, 2H) 8.04 (t, J=7.8 Hz, 1H) CO₂H (not visible)

Compound (W2)
Major Diastereomer (60%)
1H NMR (500 MHz, DMSO-d₆) δ ppm 1.14 (d, J=6.3 Hz, 3H) 1.22-1.39 (m, 3H) 1.44 (t, J=7.4 Hz, 3H) 1.55-1.85 (m, 4H) 1.91-2.10 (m, 1H) 2.94 (t, J=12.6 Hz, 1H) 3.27 (q, J=7.6 Hz, 2H) 3.67-3.75 (m, 1H) 4.00 (br d, J=13.2 Hz, 1H) 7.13 (d, J=7.9 Hz, 1H) 7.19 (d, J=7.8 Hz, 1H) 8.00 (dd, J=8.5, 1.6 Hz, 1H) 8.06 (dd, J=12.3, 1.6 Hz, 1H) 8.17 (s, 1H) 8.32 (t, J=8.45 Hz, 1H) 9.20 (s, 1H) 12.69-12.87 (m, 1H)
Minor Diastereomer (40%)
1H NMR (500 MHz, DMSO-d₆) δ ppm 1.17 (dd, J=6.3 Hz, 3H) 1.22-1.39 (m, 3H) 1.44 (t, J=7.4 Hz, 3H) 1.55-1.85 (m, 4H) 1.91-2.10 (m, 1H) 3.13-3.17 (m, 1H) 3.27 (q, J=7.6 Hz, 2H) 3.55 (br d, J=15.1 Hz, 1H) 4.45 (m, 1H) 7.13 (d, J=7.9 Hz, 1H) 7.19 (d, J=7.8 Hz, 1H) 8.00 (dd, J=8.5, 1.6 Hz, 1H) 8.06 (dd, J=12.3, 1.6 Hz, 1H) 8.17 (s, 1H) 8.32 (t, J=8.4 Hz, 1H) 9.20 (s, 1H) 12.69-12.87 (m, 1H)

Compound (W13):
Major Rotamer (60%)
¹H NMR (500 MHz, DMSO-d₆) δ ppm 12.79 (br s, 1H) 9.20 (s, 1H) 8.29 (t, J=8.4 Hz, 1H) 8.16 (s, 1H) 8.05 (dd, J=12.3, 2.2 Hz, 1H) 7.99 (dd, J=8.7, 2.0 Hz, 1H) 7.17 (d, J=3.5 Hz, 1H) 7.13 (s, 1H) 4.00 (br d, J=13.2 Hz, 1H) 3.63-3.76 (m, 1H) 3.06-3.23 (m, 2H) 2.93 (t, J=12.5 Hz, 1H) 2.41-2.48 (m, 1H) 1.89-1.99 (m, 1H) 1.22-1.85 (m, 7H) 1.12 (d, J=6.6 Hz, 3H) 0.97-1.03 (m, 6H)
Minor Rotamer (40%)
¹H NMR (500 MHz, DMSO-d₆) δ ppm 12.79 (br s, 1H) 9.20 (s, 1H) 8.29 (t, J=8.4 Hz, 1H) 8.16 (s, 1H) 8.05 (dd, J=12.3, 2.2 Hz, 1H) 7.99 (dd, J=8.7, 2.0 Hz, 1H) 7.18 (d, J=3.5 Hz, 1H) 7.15 (s, 1H) 4.37-4.50 (m, 1H) 3.53 (br d, J=15.1 Hz, 1H) 3.06-3.23 (m, 3H) 2.41-2.48 (m, 1H) 2.02-2.12 (m, 1H) 1.22-1.85 (m, 7H) 1.15 (d, J=6.3 Hz, 3H) 0.97-1.03 (m, 6H)

Compound (W14)
Major Rotamer (60%)
¹H NMR (500 MHz, DMSO-d₆) δ ppm 12.58 (br s, 1H) 7.96 (t, J=8.8 Hz, 1H) 6.99 (s, 1H) 6.91 (d, J=3.5 Hz, 1H) 6.55 (br d, J=8.8 Hz, 1H) 6.47 (br d, J=14.5 Hz, 1H) 3.99 (br d, J=13.2 Hz, 1H) 3.60-3.73 (m, 1H) 3.36-3.57 (m, 3H) 3.24 (quin, J=7.0 Hz, 1H) 3.02-3.17 (m, 2H) 2.92 (br t, J=12.6 Hz, 1H) 2.39-2.47 (m, 1H) 2.13-2.30 (m, 2H) 1.89-1.97 (m, 1H) 1.22-1.85 (m, 8H) 1.11 (br d, J=6.3 Hz, 3H) 0.94-1.04 (m, 6H)
Minor Rotamer (40%)
¹H NMR (500 MHz, DMSO-d₆) δ ppm 12.58 (br s, 1H) 7.96 (t, J=8.8 Hz, 1H) 7.02 (s, 1H) 6.92 (d, J=3.8 Hz, 1H) 6.55 (br d, J=8.8 Hz, 1H) 6.47 (br d, J=14.5 Hz, 1H) 4.39-4.49 (m, 1H) 3.36-3.57 (m, 4H) 3.24 (quin, J=7.0 Hz, 1H) 3.02-3.17 (m, 3H) 2.39-2.47 (m, 1H) 2.13-2.30 (m, 2H) 2.01-2.08 (m, 1H) 1.22-1.85 (m, 8H) 1.15 (br d, J=6.3 Hz, 3H) 0.94-1.04 (m, 6H)

Compound (W15)
Major Rotamer (60%)
¹H NMR (500 MHz, DMSO-d₆) δ ppm 7.96 (br t, J=8.5 Hz, 1H) 6.85-7.03 (m, 3H) 6.51 (br d, J=8.2 Hz, 1H) 6.43 (br d, J=14.2 Hz, 1H) 4.00 (br d, J=12.6 Hz, 1H) 3.70-3.80 (m, 1H) 3.27-3.43 (m, 3H) 3.08-3.19 (m, 2H) 2.92 (br t, J=12.5 Hz, 1H) 1.89-2.26 (m, 9H) 1.19-1.87 (m, 7H) 1.06-1.18 (m, 3H)
Minor Rotamer (40%)
¹H NMR (500 MHz, DMSO-d₆) δ ppm 7.96 (br t, J=8.5 Hz, 1H) 6.85-7.03 (m, 3H) 6.51 (br d, J=8.2 Hz, 1H) 6.43 (br d, J=14.2 Hz, 1H) 4.39-4.51 (m, 1H) 3.60 (br d, J=14.5 Hz, 1H) 3.27-3.43 (m, 4H) 3.08-3.19 (m, 2H) 1.89-2.26 (m, 9H) 1.19-1.87 (m, 7H) 1.06-1.18 (m, 3H)

Compound (W16)
Major Rotamer (60%)
¹H NMR (500 MHz, DMSO-d₆) δ ppm 12.52 (br s, 1H) 7.88 (t, J=8.7 Hz, 1H) 7.16 (s, 1H) 6.99 (s, 1H) 6.90 (d, J=3.5 Hz, 1H) 6.58 (dd, J=8.7, 1.7 Hz, 1H) 6.44 (dd, J=14.2, 1.6 Hz, 1H) 3.98 (br d, J=13.2 Hz, 1H) 3.66-3.77 (m, 1H) 3.21 (q, J=7.3 Hz, 2H) 2.92 (br t, J=12.6 Hz, 1H) 1.89-1.98 (m, 1H) 1.53-1.86 (m, 4H) 1.46-1.52 (m, 2H) 1.40 (t, J=7.4 Hz, 3H) 1.21-1.35 (m, 3H) 1.12 (d, J=6.3 Hz, 3H) 1.04-1.09 (m, 2H)
Minor Rotamer (40%)
¹H NMR (500 MHz, DMSO-d₆) δ ppm 12.52 (br s, 1H) 7.88 (t, J=8.7 Hz, 1H) 7.16 (s, 1H) 7.01 (s, 1H) 6.91 (d, J=3.5 Hz, 1H) 6.58 (dd, J=8.7, 1.7 Hz, 1H) 6.44 (dd, J=14.2, 1.6 Hz, 1H) 4.37-4.48 (m, 1H) 3.54 (br d, J=15.4 Hz, 1H) 3.21 (q, J=7.3 Hz, 2H) 3.07-3.15 (m, 1H) 2.01-2.11 (m, 1H) 1.53-1.86 (m, 4H) 1.46-1.52 (m, 2H) 1.40 (t, J=7.4 Hz, 3H) 1.21-1.35 (m, 3H) 1.14 (d, J=6.3 Hz, 3H) 1.04-1.09 (m, 2H)

Compound (W17)
Major Rotamer (60%)
¹H NMR (500 MHz, DMSO-d₆) δ ppm 12.64 (br s, 1H) 7.97 (t, J=8.8 Hz, 1H) 6.98 (s, 1H) 6.91 (d, J=3.5 Hz, 1H)

6.51 (dd, J=8.8, 1.9 Hz, 1H) 6.44 (br d, J=14.8 Hz, 1H) 3.99 (br d, J=13.2 Hz, 1H) 3.64-3.77 (m, 2H) 3.36-3.46 (m, 2H) 3.15-3.28 (m, 3H) 2.92 (brt, J=12.6 Hz, 1H) 2.37-2.43 (m, 1H) 1.86-2.11 (m, 2H) 1.53-1.85 (m, 4H) 1.41 (t, J=7.4 Hz, 3H) 1.34 (s, 3H) 1.21-1.31 (m, 3H) 1.12 (d, J=6.3 Hz, 3H)

Minor Rotamer (40%)

$^1$H NMR (500 MHz, DMSO-d$_6$) δ ppm 12.64 (br s, 1H) 7.97 (t, J=8.8 Hz, 1H) 7.00 (s, 1H) 6.92 (d, J=3.5 Hz, 1H) 6.51 (dd, J=8.8, 1.9 Hz, 1H) 6.44 (br d, J=14.8 Hz, 1H) 4.38-4.49 (m, 1H) 3.64-3.77 (m, 1H) 3.54 (br d, J=15.4 Hz, 1H) 3.36-3.46 (m, 2H) 3.15-3.28 (m, 3H) 3.04-3.15 (m, 1H) 2.37-2.43 (m, 1H) 1.86-2.11 (m, 2H) 1.53-1.85 (m, 4H) 1.41 (t, J=7.4 Hz, 3H) 1.34 (s, 3H) 1.21-1.31 (m, 3H) 1.14 (d, J=6.3 Hz, 3H)

Compound (W18)

Major Rotamer (60%)

$^1$H NMR (500 MHz, DMSO-d$_6$) δ ppm 11.63-13.30 (m, 1H) 7.95 (t, J=8.8 Hz, 1H) 6.97 (s, 1H) 6.89 (d, J=3.5 Hz, 1H) 6.50 (dd, J=8.8, 1.9 Hz, 1H) 6.42 (br d, J=14.5 Hz, 1H) 3.97 (br d, J=13.2 Hz, 1H) 3.55-3.73 (m, 4H) 3.34-3.42 (m, 4H) 3.20 (q, J=7.6 Hz, 2H) 2.90 (brt, J=12.6 Hz, 1H) 2.22-2.31 (m, 1H) 1.87-2.07 (m, 2H) 1.49-1.83 (m, 4H) 1.39 (t, J=7.4 Hz, 3H) 1.16-1.37 (m, 3H) 1.10 (d, J=6.3 Hz, 3H)

Minor Rotamer (40%)

$^1$H NMR (500 MHz, DMSO-d$_6$) δ ppm 11.63-13.30 (m, 1H) 7.95 (t, J=8.8 Hz, 1H) 6.98 (s, 1H) 6.91 (d, J=3.5 Hz, 1H) 6.50 (dd, J=8.8, 1.9 Hz, 1H) 6.42 (br d, J=14.5 Hz, 1H) 4.31-4.49 (m, 1H) 3.55-3.73 (m, 3H) 3.52 (br d, J=15.4 Hz, 1H) 3.34-3.42 (m, 4H) 3.20 (q, J=7.6 Hz, 2H) 3.05-3.15 (m, 1H) 2.22-2.31 (m, 1H) 1.87-2.07 (m, 2H) 1.49-1.83 (m, 4H) 1.39 (t, J=7.4 Hz, 3H) 1.16-1.37 (m, 3H) 1.12 (d, J=6.3 Hz, 3H)

Compound (W19)

Major Rotamer (60%)

$^1$H NMR (500 MHz, DMSO-d$_6$) δ ppm 7.87 (br t, J=9.0 Hz, 1H) 6.95 (s, 1H) 6.84-6.91 (m, 1H) 6.51 (br d, J=8.5 Hz, 1H) 6.37 (br d, J=15.4 Hz, 1H) 3.98 (br d, J=12.9 Hz, 1H) 3.66-3.75 (m, 1H) 3.57 (s, 2H) 3.17-3.28 (m, 2H) 2.98 (s, 3H) 2.91 (br t, J=12.3 Hz, 1H) 1.89-1.99 (m, 1H) 1.54-1.83 (m, 4H) 1.40 (br t, J=7.4 Hz, 3H) 1.20-1.35 (m, 3H) 1.13 (br d, J=6.3 Hz, 3H)

Minor Rotamer (40%)

$^1$H NMR (500 MHz, DMSO-d$_6$) δ ppm 7.87 (br t, J=9.0 Hz, 1H) 6.97 (s, 1H) 6.84-6.91 (m, 1H) 6.51 (br d, J=8.5 Hz, 1H) 6.37 (br d, J=15.4 Hz, 1H) 4.34-4.49 (m, 1H) 3.57 (s, 2H) 3.47-3.56 (m, 1H) 3.06-3.28 (m, 3H) 2.98 (s, 3H) 2.01-2.09 (m, 1H) 1.54-1.83 (m, 4H) 1.40 (br t, J=7.4 Hz, 3H) 1.20-1.35 (m, 3H) 1.14 (br d, J=6.3 Hz, 3H)

Compound (W20)

Major Rotamer (60%)

$^1$H NMR (500 MHz, DMSO-d$_6$) δ ppm 12.73 (br s, 1H) 8.74 (d, J=1.9 Hz, 1H) 8.21 (br t, J=8.4 Hz, 1H) 7.96 (dd, J=8.8, 1.9 Hz, 1H) 7.49 (br d, J=12.6 Hz, 1H) 7.38 (br d, J=8.2 Hz, 1H) 7.09-7.18 (m, 2H) 6.82 (d, J=8.8 Hz, 1H) 4.00 (br d, J=13.9 Hz, 1H) 3.66-3.77 (m, 1H) 3.54 (s, 3H) 3.26 (q, J=7.3 Hz, 2H) 2.94 (br t, J=12.6 Hz, 1H) 1.89-2.02 (m, 1H) 1.53-1.88 (m, 4H) 1.43 (t, J=7.4 Hz, 3H) 1.22-1.38 (m, 3H) 1.12-1.20 (m, 3H)

Minor Rotamer (40%)

$^1$H NMR (500 MHz, DMSO-d$_6$) δ ppm 12.73 (br s, 1H) 8.74 (d, J=1.9 Hz, 1H) 8.21 (br t, J=8.4 Hz, 1H) 7.96 (dd, J=8.8, 1.9 Hz, 1H) 7.49 (br d, J=12.6 Hz, 1H) 7.38 (br d, J=8.2 Hz, 1H) 7.09-7.18 (m, 2H) 6.82 (d, J=8.8 Hz, 1H) 4.41-4.50 (m, 1H) 3.55-3.59 (m, 1H) 3.54 (s, 3H) 3.26 (q, J=7.3 Hz, 2H) 3.10-3.19 (m, 1H) 2.02-2.11 (m, 1H) 1.53-1.88 (m, 4H) 1.43 (t, J=7.4 Hz, 3H) 1.22-1.38 (m, 3H) 1.12-1.20 (m, 3H)

Compound (W21)

Major Rotamer (60%)

$^1$H NMR (500 MHz, DMSO-d$_6$) δ ppm 8.69 (br s, 1H) 7.97 (br t, J=8.5 Hz, 1H) 6.97 (s, 1H) 6.91 (br d, J=3.2 Hz, 1H) 6.79 (br d, J=8.8 Hz, 1H) 6.69 (br d, J=13.2 Hz, 1H) 6.54 (s, 1H) 3.92 (br d, J=13.6 Hz, 1H) 3.73 (s, 3H) 3.71 (s, 3H) 3.58-3.67 (m, 1H) 3.16 (q, J=7.1 Hz, 2H) 2.86 (br t, J=12.6 Hz, 1H) 1.82-1.92 (m, 1H) 1.47-1.81 (m, 4H) 1.34 (t, J=7.4 Hz, 3H) 1.11-1.29 (m, 3H) 1.06 (br d, J=6.3 Hz, 3H)

Minor Rotamer (40%)

$^1$H NMR (500 MHz, DMSO-d$_6$) δ ppm 8.69 (br s, 1H) 7.97 (br t, J=8.5 Hz, 1H) 6.98 (s, 1H) 6.92 (br d, J=3.2 Hz, 1H) 6.79 (br d, J=8.8 Hz, 1H) 6.69 (br d, J=13.2 Hz, 1H) 6.54 (s, 1H) 4.32-4.43 (m, 1H) 3.73 (s, 3H) 3.71 (s, 3H) 3.43-3.51 (m, 1H) 3.16 (q, J=7.1 Hz, 2H) 3.00-3.10 (m, 1H) 1.93-2.05 (m, 1H) 1.47-1.81 (m, 4H) 1.34 (t, J=7.4 Hz, 3H) 1.11-1.29 (m, 3H) 1.08 (br d, J=6.6 Hz, 3H)

Compound (W22)

Major Rotamer (60%)

$^1$H NMR (500 MHz, chloroform-d) δ ppm 8.05 (t, J=8.8 Hz, 1H) 7.04-7.08 (m, 1H) 6.85 (s, 1H) 6.63 (dd, J=8.7, 2.4 Hz, 1H) 6.51 (dd, J=14.5, 2.2 Hz, 1H) 4.45 (quin, J=8.0 Hz, 1H) 4.23 (br d, J=13.9 Hz, 1H) 3.96-4.11 (m, 1H) 3.28 (q, J=7.5 Hz, 2H) 3.01-3.14 (m, 1H) 2.93 (s, 3H) 2.80-2.91 (m, 1H) 2.61-2.73 (m, 2H) 2.45-2.58 (m, 2H) 1.97-2.06 (m, 1H) 1.64-1.96 (m, 4H) 1.49 (t, J=7.4 Hz, 3H) 1.32-1.45 (m, 3H) 1.22 (d, J=6.3 Hz, 3H)

Minor Rotamer (40%)

$^1$H NMR (500 MHz, chloroform-d) δ ppm 8.05 (t, J=8.8 Hz, 1H) 7.04-7.08 (m, 1H) 6.89 (s, 1H) 6.63 (dd, J=8.7, 2.4 Hz, 1H) 6.51 (dd, J=14.5, 2.2 Hz, 1H) 4.62-4.71 (m, 1H) 4.45 (quin, J=8.0 Hz, 1H) 3.89 (br d, J=14.8 Hz, 1H) 3.28 (q, J=7.5 Hz, 2H) 3.01-3.14 (m, 2H) 2.93 (s, 3H) 2.61-2.73 (m, 2H) 2.45-2.58 (m, 2H) 2.08-2.17 (m, 1H) 1.64-1.96 (m, 4H) 1.49 (t, J=7.4 Hz, 3H) 1.32-1.45 (m, 3H) 1.24 (d, J=6.3 Hz, 3H)

Compound (W23)

Major Rotamer (60%)

$^1$H NMR (500 MHz, DMSO-d$_6$) δ ppm 12.28 (br s, 1H) 7.96 (t, J=9.0 Hz, 1H) 7.00 (s, 1H) 6.93 (d, J=3.5 Hz, 1H) 6.75 (dd, J=9.0, 2.0 Hz, 1H) 6.68 (br d, J=15.1 Hz, 1H) 4.21 (quin, J=8.4 Hz, 1H) 3.99 (br d, J=13.2 Hz, 1H) 3.66-3.75 (m, 1H) 3.22 (q, J=7.4 Hz, 2H) 2.85-2.96 (m, 4H) 2.71-2.81 (m, 1H) 2.51-2.56 (m, 2H, partially obscured by solvent peak) 2.22-2.33 (m, 2H) 1.88-1.98 (m, 1H) 1.52-1.86 (m, 4H) 1.41 (t, J=7.4 Hz, 3H) 1.20-1.37 (m, 3H) 1.12 (d, J=6.3 Hz, 3H)

Minor Rotamer (40%)

$^1$H NMR (500 MHz, DMSO-d$_6$) δ ppm 12.28 (br s, 1H) 7.96 (t, J=9.0 Hz, 1H) 7.02 (s, 1H) 6.92 (d, J=3.5 Hz, 1H) 6.75 (dd, J=9.0, 2.0 Hz, 1H) 6.68 (br d, J=15.1 Hz, 1H) 4.32-4.43 (m, 1H) 4.21 (quin, J=8.4 Hz, 1H) 3.53 (br d, J=15.1 Hz, 1H) 3.22 (q, J=7.4 Hz, 2H) 3.05-3.16 (m, 1H) 2.89 (s, 3H) 2.71-2.81 (m, 1H) 2.51-2.56 (m, 2H, partially obscured by solvent peak) 2.22-2.33 (m, 2H) 1.98-2.11 (m, 1H) 1.52-1.86 (m, 4H) 1.41 (t, J=7.4 Hz, 3H) 1.20-1.37 (m, 3H) 1.14 (d, J=6.3 Hz, 3H)

Compound (W24)

Major Rotamer (60%)

$^1$H NMR (500 MHz, DMSO-d$_6$) δ ppm 12.71 (br s, 2H) 9.15 (s, 1H) 8.25 (t, J=8.5 Hz, 1H) 8.13 (s, 1H) 7.84-8.04 (m, 2H) 6.41 (br s, 1H) 5.13-5.42 (m, 1H) 3.92 (br d, J=12.9 Hz, 1H) 3.76-3.85 (m, 1H) 2.71-3.11 (m, 1H) 1.90-2.05 (m, 1H) 1.34-1.84 (m, 4H) 1.17-1.32 (m, 3H) 1.08 (br d, J=5.7 Hz, 3H)

Minor Rotamer (40%)

¹H NMR (500 MHz, DMSO-d₆) δ ppm 12.71 (br s, 2H) 9.15 (s, 1H) 8.25 (t, J=8.5 Hz, 1H) 8.13 (s, 1H) 7.84-8.04 (m, 2H) 6.41 (br s, 1H) 5.13-5.42 (m, 1H) 4.28-4.59 (m, 1H) 3.57-3.70 (m, 1H) 2.71-3.11 (m, 1H) 1.90-2.05 (m, 1H) 1.34-1.84 (m, 4H) 1.17-1.32 (m, 3H) 1.08 (br d, J=5.7 Hz, 3H)

Compound (W25)

Major Rotamer 60%

¹H NMR (500 MHz, DMSO-d₆) δ ppm 1.13 (d, J=6.3 Hz, 3H) 1.21-1.38 (m, 3H) 1.43 (t, J=7.4 Hz, 3H) 1.57 (br s, 1H) 1.60-1.83 (m, 3H) 1.93-1.99 (m, 1H) 2.44-2.47 (s, 3H) 2.93 (br t, J=12.6 Hz, 1H) 3.22-3.31 (m, 2H) 3.66-3.74 (m, 1H) 3.99 (br d, J=13.2 Hz, 1H) 7.11 (d, J=7.9 Hz, 1H) 7.16 (d, J=7.7 Hz, 1H) 7.94 (d, J=8.4 Hz, 1H) 7.98-8.01 (d, J=12.6 Hz, 1H) 8.27 (t, J=8.4 Hz, 1H) 9.08 (s, 1H) 12.60 (m, 1H)

Minor rotamer 40%

¹H NMR (500 MHz, DMSO-d₆) δ ppm 1.16 (d, J=6.3 Hz, 3H) 1.21-1.38 (m, 3H) 1.43 (t, J=7.4 Hz, 3H) 1.57 (br s, 1H) 1.60-1.83 (m, 3H) 2.06 (m, 1H) 2.44-2.47 (s, 3H) 3.09-3.18 (m, 1H) 3.22-3.31 (m, 2H) 3.54 (br d, J=15.1 Hz, 1H) 4.44 (dt, J=12.0, 6.0 Hz, 1H) 7.11 (d, J=7.9 Hz, 1H) 7.16 (dd, J=7.9 Hz, 1H) 7.94 (d, J=8.4 Hz, 1H) 7.98-8.01 (d, J=12.6 Hz, 1H) 8.27 (t, J=8.4 Hz, 1H) 9.08 (s, 1H) 12.60 (m, 1H)

Compound (W33)

Major Rotamer 63%

¹H NMR (500 MHz, DMSO-d₆) δ ppm 1.21-1.41 (m, 4H) 1.53 (d, J=6.6 Hz, 3H) 2.70-2.75 (m, 1H) 2.86-3.06 (m, 2H) 3.45-3.51 (m, 1H) 3.73-3.91 (m, 1H) 5.60 (q, J=6.6 Hz, 1H) 6.90-6.96 (m, 1H) 7.08-7.34 (m, 5H) 7.99-8.10 (m, 2H) 8.17 (s, 1H) 8.35 (br t, J=8.5 Hz, 1H) 9.21 (s, 1H) 12.79 (br s, 1H)

Minor Rotamer 37%

¹H NMR (500 MHz, DMSO-d₆) δ ppm 1.21-1.41 (m, 4H) 1.56 (d, J=6.6 Hz, 3H) 2.70-2.75 (m, 1H) 2.86-3.06 (m, 2H) 3.45-3.51 (m, 1H) 4.55-4.58 (m, 1H) 4.97 (q, J=6.9 Hz, 1H) 6.90-6.96 (m, 1H) 7.08-7.34 (m, 5H) 7.99-8.10 (m, 2H) 8.17 (s, 1H) 8.35 (br t, J=8.5 Hz, 1H) 9.21 (s, 1H) 12.79 (br s, 1H)

Compound (W35)

Major Rotamer 60%

¹H NMR (400 MHz, DMSO-d₆) δ ppm 1.13 (d, J=6.6 Hz, 3H) 1.20-1.38 (m, 3H) 1.43 (t, J=7.3 Hz, 3H) 1.52-1.87 (m, 4H) 1.92-2.13 (m, 1H) 2.93 (t, J=12.1 Hz, 1H) 3.21-3.30 (m, 2H) 3.64-3.78 (m, 1H) 3.95-4.05 (m, 1H) 7.11 (s, 1H) 7.17 (d, J=3.5 Hz, 1H) 7.94 (dd, J=8.6, 2.0 Hz, 1H) 8.03 (dd, J=12.4, 2.3 Hz, 1H) 8.31 (t, J=8.34 Hz, 1H) 9.27 (s, 1H) 13.08 (br s, 1H)

Minor rotamer 40%

¹H NMR (400 MHz, DMSO-d₆) δ ppm 1.15 (d, J=6.6 Hz, 3H) 1.20-1.38 (m, 3H) 1.43 (t, J=7.3 Hz, 3H) 1.52-1.87 (m, 4H) 1.92-2.13 (m, 1H) 3.08-3.16 (m, 1H) 3.21-3.30 (m, 2H) 3.49-3.60 (m, 1H) 4.39-4.53 (m, 1H) 7.13 (s, 1H) 7.19 (d, J=3.5 Hz, 1H) 7.94 (dd, J=8.6, 2.0 Hz, 1H) 8.03 (dd, J=12.4, 2.3 Hz, 1H) 8.31 (t, J=8.3 Hz, 1H) 9.27 (s, 1H) 13.08 (br s, 1H)

Compound (W36)

Major Rotamer 60%

¹H NMR (500 MHz, DMSO-d₆) δ ppm 1.07-1.11 (m, 3H) 1.13-1.43 (m, 3H) 1.46-1.78 (m, 4H) 1.87 (s, 3H) 1.89-2.03 (m, 1H) 2.88 (br t, J=12.6 Hz, 1H) 3.60-3.76 (m, 1H) 3.93 (br d, J=14.2 Hz, 1H) 4.63 (br d, J=6.3 Hz, 2H) 5.04 (d, J=6.6 Hz, 2H) 7.09 (s, 1H) 7.13 (dd, J=7.9, 3.2 Hz, 1H) 7.90 (dd, J=8.7, 1.7 Hz, 1H) 7.94-8.00 (m, 1H) 8.09 (s, 1H) 8.16 (t, J=8.2 Hz, 1H) 9.12 (s, 1H) 12.72 (br s, 1H)

Minor rotamer 40%

¹H NMR (500 MHz, DMSO-d₆) δ ppm 1.07-1.11 (m, 3H) 1.13-1.43 (m, 3H) 1.46-1.78 (m, 4H) 1.87 (s, 3H) 1.89-2.03 (m, 1H) 3.02-3.15 (m, 1H) 3.47 (br d, J=16.1 Hz, 1H) 4.32-4.41 (m, 1H) 4.63 (br d, J=6.3 Hz, 2H) 5.04 (d, J=6.6 Hz, 2H) 7.09 (s, 1H) 7.13 (dd, J=7.9, 3.2 Hz, 1H) 7.90 (dd, J=8.7, 1.7 Hz, 1H) 7.94-8.00 (m, 1H) 8.09 (s, 1H) 8.16 (t, J=8.2 Hz, 1H) 9.12 (s, 1H) 12.72 (br s, 1H)

Compound (W37)

Major Rotamer 65%

¹H NMR (500 MHz, DMSO-d₆) δ 1.25-1.35 (m, 5H) 1.46 (d, J=6.6 Hz, 3H) 2.14-2.33 (m, 2H) 2.75 (br d, J=15.5 Hz, 1H) 2.81-3.00 (m, 2H) 3.17-3.29 (m, 1H) 3.36-3.57 (m, 4H) 3.93 (br dd, J=13.9, 5.0 Hz, 1H) 5.53 (q, J=6.7 Hz, 1H) 6.48 (br d, J=14.8 Hz, 1H) 6.55 (br d, J=8.8 Hz, 1H) 6.77-6.83 (m, 1H) 6.91-6.98 (m, 1H) 7.02 (d, J=5.0 Hz, 1H) 7.39 (d, J=5.0 Hz, 1H) 8.01 (t, J=8.3 Hz, 1H) 12.50-12.72 (m, 1H)

Minor rotamer 35%

¹H NMR (500 MHz, DMSO-d₆) δ ppm 1.25-1.35 (m, 5H) 1.51 (d, J=6.6 Hz, 3H) 2.14-2.33 (m, 2H) 2.81-3.00 (m, 2H) 3.17-3.29 (m, 2H) 3.36-3.57 (m, 4H) 4.71 (br dd, J=12.6, 4.7 Hz, 1H) 4.90 (br d, J=6.3 Hz, 1H) 6.48 (br d, J=14.8 Hz, 1H) 6.55 (br d, J=8.83 Hz, 1H) 6.77-6.83 (m, 2H) 6.91-6.98 (m, 1H) 7.30 (d, J=5.0 Hz, 1H) 8.01 (t, J=8.32 Hz, 1H) 12.50-12.72 (m, 1H)

Compound (W38)

Major Rotamer 60%

¹H NMR (400 MHz, DMSO-d₆) δ ppm 1.20-1.38 (m, 4H) 1.52 (d, J=6.6 Hz, 3H) 2.13-2.34 (m, 2H) 2.52-2.55 (m, 1H) 2.65-2.76 (m, 1H) 2.83-3.06 (m, 2H) 3.17-3.29 (m, 1H) 3.33-3.57 (m, 4H) 3.81 (br dd, J=13.4, 4.8 Hz, 1H) 5.58 (q, J=6.6 Hz, 1H) 6.48 (d, J=14.7 Hz, 2.20 Hz, 1H) 6.54 (d, J=9.1 Hz, 1.52 Hz, 1H) 6.76-6.83 (m, 1H) 6.91-6.96 (m, 1H) 7.06-7.34 (m, 4H) 8.00 (t, J=8.8 Hz, 1H) 12.55 (br s, 1H)

Minor rotamer 40%

¹H NMR (400 MHz, DMSO-d₆) δ ppm 1.20-1.38 (m, 4H) 1.55 (d, J=7.1 Hz, 3H) 2.13-2.34 (m, 2H) 2.52-2.55 (m, 1H) 2.65-2.76 (m, 1H) 2.83-3.06 (m, 2H) 3.17-3.29 (m, 1H) 3.33-3.57 (m, 4H) 4.51-4.58 (m, 1H) 4.96 (d, J=6.6 Hz, 1H) 6.48 (d, J=14.7 Hz, 2.2 Hz, 1H) 6.54 (d, J=9.1 Hz, 1.52 Hz, 1H) 6.76-6.83 (m, 1H) 6.91-6.96 (m, 1H) 7.06-7.34 (m, 4H) 8.00 (t, J=8.8 Hz, 1H) 12.55 (br s, 1H)

Compound (W39)

Major Rotamer 60%

¹H NMR (400 MHz, DMSO-d₆) δ ppm 0.94-1.05 (m, 2H) 1.16-1.31 (m, 2H) 1.48 (d, J=6.6 Hz, 3H) 1.63-1.68 (m, 3H) 2.72-3.05 (m, 2H) 3.31-3.48 (m, 1H) 4.02 (br dd, J=13.4, 4.8 Hz, 1H) 5.56 (d, J=6.6 Hz, 1H) 7.02 (d, J=5.1 Hz, 1H) 7.13-7.18 (m, 1H) 7.23 (d, J=3.5 Hz, 1H) 7.38 (d, J=5.1 Hz, 1H) 7.98-8.07 (m, 2H) 8.16 (s, 1H) 8.32 (t, J=8.2 Hz, 1H) 9.18 (s, 1H) 12.73 (br s, 1H)

Minor rotamer 40%

¹H NMR (400 MHz, DMSO-d₆) δ ppm 0.94-1.05 (m, 2H) 1.16-1.31 (m, 2H) 1.54 (d, J=6.6 Hz, 3H) 1.63-1.68 (m, 3H) 2.72-3.05 (m, 2H) 4.68-4.77 (m, 1H) 4.99 (d, J=6.6 Hz, 1H) 5.56 (d, J=6.6 Hz, 1H) 6.80 (d, J=5.6 Hz, 1H) 7.13-7.18 (m, 1H) 7.23 (d, J=3.5 Hz, 1H) 7.30 (d, J=5.1 Hz, 1H) 7.98-8.07 (m, 2H) 8.16 (s, 1H) 8.32 (t, J=8.2 Hz, 1H) 9.18 (s, 1H) 12.73 (br s, 1H)

Compound (W40)

Major Rotamer 60%

¹H NMR (400 MHz, DMSO-d₆) δ ppm 1.39-1.56 (m, 6H) 2.75-3.04 (m, 2H) 3.21-3.30 (m, 2H) 3.45 (br t, J=10.6 Hz, 1H) 3.98-4.07 (m, 1H) 5.54-5.60 (m, 1H) 7.03 (d, J=5.6 Hz, 1H) 7.17-7.25 (m, 2H) 7.39 (d, J=4.6 Hz, 1H) 7.96-8.09 (m, 2H) 8.15 (s, 1H) 8.32 (br t, J=8.3 Hz, 1H) 9.19 (s, 1H) 12.75 (br s, 1H)

Minor rotamer 40%

¹H NMR (400 MHz, DMSO-d₆) δ ppm 1.39-1.56 (m, 6H) 2.75-3.04 (m, 3H) 3.21-3.30 (m, 2H) 4.73 (br d, J=10.1 Hz, 1H) 4.98 (br d, J=7.1 Hz, 1H) 6.80 (d, J=5.1 Hz, 1H)

7.17-7.25 (m, 2H) 7.30 (d, J=5.6 Hz, 1H) 7.96-8.09 (m, 2H) 8.15 (s, 1H) 8.32 (br t, J=8.3 Hz, 1H) 9.19 (s, 1H) 12.75 (br s, 1H)

Compound (W43)
Major Rotamer 60%
$^1$H NMR (400 MHz, DMSO-$d_6$) δ ppm 1.35-1.45 (m, 3H) 1.47 (d, J=7.1 Hz, 3H) 2.15-2.31 (m, 2H) 2.73-2.81 (m, 1H) 2.84-3.03 (m, 1H) 3.19-3.27 (m, 3H) 3.32-3.56 (m, 5H) 3.98-4.06 (m, 1H) 5.52-5.58 (m, 1H) 6.45-6.57 (m, 2H) 6.95-6.98 (m, 1H) 7.02 (d, J=5.6 Hz, 1H) 7.05-7.11 (m, 1H) 7.38 (d, J=5.1 Hz, 1H) 7.99 (t, J=8.8 Hz, 1H) 12.54 (br s, 1H)
Minor rotamer 40%
$^1$H NMR (400 MHz, DMSO-$d_6$) δ ppm 1.35-1.45 (m, 3H) 1.52 (d, J=6.6 Hz, 3H) 2.15-2.31 (m, 2H) 2.84-3.03 (m, 2H) 3.19-3.27 (m, 4H) 3.32-3.56 (m, 4H) 4.69-4.76 (m, 1H) 4.94-5.01 (m, 1H) 6.45-6.57 (m, 2H) 6.80 (d, J=5.6 Hz, 1H) 6.95-6.98 (m, 1H) 7.05-7.11 (m, 1H) 7.29 (d, J=5.1 Hz, 1H) 7.99 (t, J=8.8 Hz, 1H) 12.54 (br s, 1H)

Compound (W44)
Major Rotamer 60%
$^1$H NMR (500 MHz, DMSO-$d_6$) δ ppm 0.93-1.01 (m, 2H) 1.16-1.30 (m, 3H) 1.47 (d, J=6.6 Hz, 3H) 1.59-1.69 (m, 3H) 2.15-2.32 (m, 2H) 2.74-2.81 (m, 1H) 2.92-3.04 (m, 1H) 3.17-3.31 (m, 1H) 3.36-3.57 (m, 4H) 4.01 (br dd, J=13.4, 4.6 Hz, 1H) 5.55 (q, J=6.6 Hz, 1H) 6.49 (br d, J=14.5 Hz, 1H) 6.58 (br d, J=9.1 Hz, 1H) 6.97-7.07 (m, 3H) 7.39 (d, J=5.0 Hz, 1H) 8.01 (t, J=8.8 Hz, 1H) 12.58 (br s, 1H)
Minor rotamer 40%
$^1$H NMR (500 MHz, DMSO-$d_6$) δ ppm 0.93-1.01 (m, 2H) 1.16-1.30 (m, 3H) 1.54 (d, J=6.6 Hz, 3H) 1.59-1.69 (m, 3H) 2.15-2.32 (m, 2H) 2.83-2.92 (m, 2H) 3.17-3.31 (m, 2H) 3.36-3.57 (m, 3H) 4.72 (br dd, J=12.8, 4.3, 1H) 4.97 (q, J=6.6 Hz, 1H) 6.49 (br d, J=14.5 Hz, 1H) 6.58 (br d, J=9.1 Hz, 1H) 6.80 (d, J=5.4 Hz, 1H) 6.97-7.07 (m, 2H) 7.30 (d, J=5.0 Hz, 1H) 8.01 (t, J=8.8 Hz, 1H) 12.58 (br s, 1H)

Compound (W46)
Major Rotamer 60%
$^1$H NMR (500 MHz, DMSO-$d_6$) δ ppm 1.13 (d, 6.3 Hz, 3H) 1.22-1.38 (m, 2H) 1.62-1.83 (m, 4H) 1.89-1.99 (m, 1H) 2.14-2.30 (m, 2H) 2.93 (brt, J=12.6 Hz, 1H) 3.09-3.27 (m, 6H) 3.35-3.42 (m, 2H) 3.46-3.57 (m, 2H) 3.65-3.72 (m, 1H) 3.99 (br d, J=13.2 Hz, 1H) 4.09 (q, J=8.7 Hz, 1H) 6.45-6.50 (m, 1H) 6.54 (d, J=8.6 Hz, 1H) 6.96 (dd, J=7.9, 3.5 Hz, 1H) 7.19 (s, 1H) 8.00 (t, J=8.8 Hz, 1H) 12.58 (br s, 1H)
Minor rotamer 40%
$^1$H NMR (500 MHz, DMSO-$d_6$) δ ppm 1.15 (d, 6.3 Hz, 3H) 1.22-1.48 (m, 4H) 1.62-1.83 (m, 4H) 2.00-2.10 (m, 1H) 2.14-2.30 (m, 2H) 3.09-3.27 (m, 5H) 3.35-3.42 (m, 2H) 3.46-3.57 (m, 3H) 4.09 (quin, J=8.7 Hz, 1H) 4.41-4.48 (m, 1H) 6.45-6.50 (m, 1H) 6.54 (d, J=8.6 Hz, 1H) 6.96 (dd, J=7.9, 3.5 Hz, 1H) 7.19 (s, 1H) 8.00 (t, J=8.8 Hz, 1H) 12.58 (br s, 1H)

Compound (W47)
Major Rotamer 60%
$^1$H NMR (500 MHz, DMSO-$d_6$) δ ppm 1.31-1.46 (m, 6H) 1.54 (d, J=6.6 Hz, 3H) 1.87-1.97 (m, 1H) 2.37-2.44 (m, 1H) 2.75 (br d, J=16.4 Hz, 1H) 3.10-3.09 (m, 1H) 3.16-3.30 (m, 3H) 3.36-3.53 (m, 3H) 3.74 (br d, J=9.8 Hz, 1H) 3.91 (br dd, J=12.9, 3.8 Hz, 1H) 5.61 (br q, J=6.9 Hz, 1H) 6.46 (br d, J=14.2 Hz, 1H) 6.53 (br d, J=8.8 Hz, 1H) 6.94-7.00 (m, 1H) 7.05-7.26 (m, 4H) 7.34 (d, J=7.3 Hz, 1H) 7.99 (br t, J=8.7 Hz, 1H) 12.64 (br s, 1H)
Minor rotamer 40%
$^1$H NMR (500 MHz, DMSO-$d_6$) δ ppm 1.31-1.46 (m, 6H) 1.58 (d, J=6.6 Hz, 3H) 1.87-1.97 (m, 1H) 2.37-2.44 (m, 1H) 2.82-2.99 (m, 2H) 3.16-3.30 (m, 3H) 3.36-3.53 (m, 3H) 3.74 (br d, J=9.8 Hz, 1H) 4.58 (br d, J=15.8 Hz, 1H) 5.04 (br q, J=6.3 Hz, 1H) 6.46 (br d, J=14.2 Hz, 1H) 6.53 (br d, J=8.8 Hz, 1H) 6.94-7.00 (m, 1H) 7.05-7.26 (m, 5H) 7.99 (br t, J=8.7 Hz, 1H) 12.64 (br s, 1H)

Compound (W48)
Major Rotamer 63%
$^1$H NMR (500 MHz, DMSO-$d_6$) δ ppm 1.35 (s, 3H) 1.38-1.45 (m, 3H) 1.48 (d, J=6.6 Hz, 3H) 1.88-2.03 (m, 1H) 2.32-2.46 (m, 1H) 2.75-3.03 (m, 2H) 3.18 (d, J=9.8 Hz, 1H) 3.21-3.28 (m, 2H) 3.36-3.47 (m, 3H) 3.74 (d, J=9.8 Hz, 1H) 4.02 (br dd, J=13.4, 4.9 Hz, 1H) 5.56 (q, J=6.6 Hz, 1H) 6.46 (br d, J=14.8 Hz, 1H) 6.53 (br d, J=8.8 Hz, 1H) 6.96-6.98 (m, 1H) 7.03 (d, J=5.0 Hz, 1H) 7.11 (s, 1H) 7.39 (d, J=5.0 Hz, 1H) 7.99 (td, J=8.8, 2.4 Hz, 1H) 12.63 (br s, 1H)
Minor rotamer 37%
$^1$H NMR (500 MHz, DMSO-$d_6$) δ ppm 1.35 (s, 3H) 1.38-1.45 (m, 3H) 1.53 (d, J=6.6 Hz, 3H) 1.88-2.03 (m, 1H) 2.32-2.46 (m, 1H) 2.75-3.03 (m, 2H) 3.18 (d, J=9.8 Hz, 1H) 3.21-3.28 (m, 2H) 3.36-3.47 (m, 3H) 3.74 (d, J=9.8 Hz, 1H) 4.73 (br dd, J=12.8, 4.3 Hz, 1H) 4.97 (q, J=6.6 Hz, 1H) 6.46 (br d, J=14.8 Hz, 1H) 6.53 (br d, J=8.8 Hz, 1H) 6.81 (d, J=5.0 Hz, 1H) 6.96-6.98 (m, 1H) 7.07 (s, 1H) 7.30 (d, J=5.0 Hz, 1H) 7.99 (td, J=8.8, 2.4 Hz, 1H) 12.63 (br s, 1H)

Compound (W49)
Major Rotamer 60%
$^1$H NMR (500 MHz, DMSO-$d_6$) δ ppm 1.11-1.32 (m, 5H) 1.35 (s, 3H) 1.41 (br t, J=7.41 Hz, 3H) 1.46-2.21 (m, 7H) 2.39-2.44 (m, 1H) 2.92 (br t, J=12.77 Hz, 1H) 3.10-3.30 (m, 3H) 3.36-3.46 (m, 2H) 3.66-3.77 (m, 2H) 3.95-4.03 (m, 1H) 6.45 (br d, J=15.13 Hz, 1H) 6.52 (br d, J=8.51 Hz, 1H) 6.92 (dd, J=7.25, 3.47 Hz, 1H) 7.00 (br d, J=8.51 Hz, 1H) 7.97 (br t, J=8.83 Hz, 1H) 12.63 (br s, 1H)
Minor rotamer 40%
$^1$H NMR (500 MHz, DMSO-$d_6$) δ ppm 1.11-1.32 (m, 5H) 1.35 (s, 3H) 1.41 (br t, J=7.41 Hz, 3H) 1.46-2.21 (m, 7H) 2.39-2.44 (m, 1H) 3.10-3.30 (m, 4H) 3.36-3.46 (m, 2H) 3.49-3.62 (m, 1H) 3.66-3.77 (m, 1H) 4.40-4.48 (m, 1H) 6.45 (br d, J=15.13 Hz, 1H) 6.52 (br d, J=8.51 Hz, 1H) 6.92 (dd, J=7.25, 3.47 Hz, 1H) 7.00 (br d, J=8.51 Hz, 1H) 7.97 (br t, J=8.83 Hz, 1H) 12.63 (br s, 1H)

Compound (W41)
Major Diastereomer (65%)
1H NMR (500 MHz, DMSO-d6) δ ppm 1.22-1.40 (m, 4H) 1.47 (d, J=6.6 Hz, 3H) 2.76 (dd, J=15.5, 1.9 Hz, 1H) 2.83-3.03 (m, 2H) 3.43 (m, 1H) 3.94 (br dd, J=13.6, 5.0 Hz, 1H) 5.55 (q, J=6.6 Hz, 1H) 6.94 (s, 1H) 7.03 (d, J=5.0 Hz, 1H) 7.20 (m, 1H) 7.39 (d, J=5.4 Hz, 1H) 8.01 (d, J=8.4 Hz, 1H) 8.07 (d, J=12.6 Hz 1H) 8.17 (s, 1H) 8.35 (td, J=8.4, 3.5 Hz, 1H) 9.21 (s, 1H) 12.75 (br s, 1H)
Minor Diastereomer (35%)
1H NMR (500 MHz, DMSO-d6) δ ppm 1.22-1.40 (m, 4H) 1.51 (d, J=6.6 Hz, 3H) 2.83-3.03 (m, 3H) 3.23 (td, J=12.3, 4.4 Hz, 1H) 4.72 (br dd, J=12.6, 4.7 Hz, 1H) 4.91 (q, J=6.6 Hz, 1H) 6.80 (d, J=5.0 Hz, 1H) 6.92 (s, 1H) 7.20 (m, 1H) 7.31 (d, J=5.0 Hz, 1H) 8.01 (d, J=8.4 Hz, 1H) 8.07 (d, J=12.6 Hz 1H) 8.17 (s, 1H) 8.35 (td, J=8.4, 3.5 Hz, 1H) 9.21 (s, 1H) 12.75 (br s, 1H)

Compound (W50)
Major Rotamer 60%
$^1$H NMR (500 MHz, DMSO-$d_6$) δ ppm 1.11-1.32 (m, 5H) 1.35 (s, 3H) 1.41 (br t, J=7.4 Hz, 3H) 1.46-2.21 (m, 7H) 2.39-2.44 (m, 1H) 2.92 (br t, J=12.8 Hz, 1H) 3.10-3.30 (m, 3H) 3.36-3.46 (m, 2H) 3.66-3.77 (m, 2H) 3.95-4.03 (m, 1H) 6.45 (br d, J=15.1 Hz, 1H) 6.52 (br d, J=8.5 Hz, 1H) 6.92 (dd, J=7.3, 3.5 Hz, 1H) 7.00 (br d, J=8.5 Hz, 1H) 7.97 (br t, J=8.8 Hz, 1H) 12.63 (br s, 1H)

Minor rotamer 40%

$^1$H NMR (500 MHz, DMSO-d$_6$) δ ppm 1.11-1.32 (m, 5H) 1.35 (s, 3H) 1.41 (br t, J=7.4 Hz, 3H) 1.46-2.21 (m, 7H) 2.39-2.44 (m, 1H) 3.10-3.30 (m, 4H) 3.36-3.46 (m, 2H) 3.49-3.62 (m, 1H) 3.66-3.77 (m, 1H) 4.40-4.48 (m, 1H) 6.45 (br d, J=15.1 Hz, 1H) 6.52 (br d, J=8.5 Hz, 1H) 6.92 (dd, J=7.3, 3.5 Hz, 1H) 7.00 (br d, J=8.5 Hz, 1H) 7.97 (br t, J=8.83 Hz, 1H) 12.63 (br s, 1H)

Compound (W51)

Major Rotamer (60%)

$^1$H NMR (500 MHz, DMSO-d$_6$) δ ppm 12.59 (br s, 1H) 7.99 (t, J=8.8 Hz, 1H) 6.89 (d, J=3.5 Hz, 1H) 6.72 (s, 1H) 6.54 (br d, J=8.8 Hz, 1H) 6.48 (br d, J=14.8 Hz, 1H) 3.96 (br d, J=13.2 Hz, 1H) 3.45-3.57 (m, 3H) 3.36-3.41 (m, 2H) 3.23 (quin, J=7.2 Hz, 1H) 2.85-2.98 (m, 2H) 2.12-2.32 (m, 2H) 1.87-1.99 (m, 1H) 1.50-1.84 (m, 4H) 1.20-1.47 (m, 7H) 1.09 (d, J=6.3 Hz, 3H)

Minor Rotamer (40%)

$^1$H NMR (500 MHz, DMSO-d$_6$) δ ppm 12.59 (br s, 1H) 7.99 (t, J=8.8 Hz, 1H) 6.91 (d, J=3.5 Hz, 1H) 6.73 (s, 1H) 6.54 (br d, J=8.8 Hz, 1H) 6.48 (br d, J=14.8 Hz, 1H) 4.36-4.45 (m, 1H) 3.42-3.69 (m, 2H) 3.36-3.41 (m, 2H) 3.23 (quin, J=7.2 Hz, 1H) 3.05-3.13 (m, 1H) 2.85-2.98 (m, 2H) 2.12-2.32 (m, 2H) 2.00-2.10 (m, 1H) 1.50-1.84 (m, 4H) 1.20-1.47 (m, 7H) 1.13 (d, J=6.3 Hz, 3H)

Melting Points

For a number of compounds, melting points (m.p.) were determined with a DSC 1 (Mettler Toledo). Melting points were measured with a temperature gradient of 10° C./minute. Maximum temperature was 350° C. The reported values are peak values.

Values are obtained with experimental uncertainties that are commonly associated with this analytical method.

LC/MS

For LCMS-characterization of the compounds of the present invention, the following methods were used:

Instrument Configuration: Shimadzu Analytical HPLC SCL10Avp, Auto Sampler Gilson 215, ELSD (evaporative light scattering detector) Sedex 75, Mass Spectrometr PE SCIEX API 150, Analyst 1.3.1

Column: Waters XBridge C18 3.5 u, 4.6×100 mm

Gradient Flow Rate: 0.9 ml/min

Mobile Phase: A: Water with 0.05% TFA

B: Acetonitrile 0.05% TFA

Gradient: 0.01 min—controller start;
8.00 min—pump B %—90.0;
10.05 min—pump B %—90.0;
10.10 min—pump B %—5.0;
10.15 min—controller stop;

Sample Injection: 3.0-5.0 (1 mg/ml CH$_3$CN/H$_2$

MS Detection: electrospray +ive ion (100-1100 range)

UV detection wave-length: nm: 220, 254.

TABLE melting point and LC/MS date (retention time, theoretical molecular weight (MW theor) and (MH)$^+$ peak)

| Co. No. | mp° C. | Rt min | MW theor | MH$^+$ | Co. No. | mp° C. | Rt min | MW theor | MH$^+$ |
|---|---|---|---|---|---|---|---|---|---|
| A1 | 110-120 | 2.95 | 368.167 | 369.1 | F3 | 185 | 3 | 440.232 | 441.55 |
| A2 | 193-194 | 2.72 | 405.253 | 406.4 | F4 | 167-168 | 6.27 | 457.228 | 458.2 |
| A3 | 135-136 | 3.08 | 396.172 | 397.1 | F5 | 75-76 | 7.4 | 446.223 | 447.6 |
| A4 | 120-125 | 2.96 | 380.201 | 381.4 | F6 | oil | 7.76 | 446.223 | 447.5 |
| A5 | oil | 3.38 | 368.258 | 369.2 | F7 | 95-96 | 8.67 | 475.218 | 476.5 |
| A6 | 84 | 3.66 | 423.243 | 424.3 | F8 | 86-87 | 8.73 | 475.218 | 476.5 |
| A7 | 195-197 | 3.3 | 401.222 | 402.2 | F9 | 65-67 | 7.81 | 460.239 | 461.5 |
| A8 | 230-235 | 6.37 | 417.216 | 418.3 | F10 | 118-119 | 6.14 | 474.254 | 475.5 |
| A9 | 225-230 | 7.03 | 431.232 | 432.3 | F11 | oil | 5.69 | 474.254 | 475.6 |
| A10 | 155 | 2.84 | 417.55 | 418.7 | F12 | oil | 8.51 | 486.254 | 487.6 |
| A11 | 170-175 | 2.23 | 413.56 | 414.4 | F13 | oil | 6.05 | 460.239 | 461.5 |
| A12 | 195-200 | 5.37 | 427.237 | 428.3 | F14 | 245-250 | 8.16 | 501.218 | 502.4 |
| A13 | 145-150 | 5.07 | 402.217 | 403.2 | F15 | 181-182 | 8.19 | 501.218 | 502.4 |
| A14 | 115 | 5.21 | 416.232 | 417.5 | F16 | oil | 5.95 | 446.223 | 447.5 |
| A15 | 175 | 6.63 | 429.216 | 430.5 | F17 | 140-145 | 8.4 | 472.239 | 473.6 |
| A16 | oil | 3.24 | 382.217 | 383.5 | F18 | 165-170 | 9.01 | 521.19 | 522.4 |
| A17 | oil | 3.28 | 382.217 | 383.5 | G1 | 195-200 | 7.31 | 424.208 | 425.4 |
| A18 | 125-130 | 3.28 | 394.217 | 395.5 | H1 | 219-220 | 7.03 | 406.192 | 407.3 |
| A19 | 207-208 | 2.02 | 446.279 | 447.3 | H2 | 194-195 | 7.43 | 420.207 | 421.2 |
| A20 | oil | 3.03 | 448.264 | 449 | H4 | 96 | 8.44 | 405.196 | 406.3 |
| A21 | 155-160 | 2.5 | 392.221 | 393.3 | H5 | 95 | 2.79 | 405.196 | 406.5 |
| A22 | — | 2.78 | 442.225 | 443.3 | I1 | 180 | 2.86 | 423.207 | 424.2 |
| A24 | 145-150 | 6.9 | 431.212 | 432.4 | I2 | 170 | 2.25 | 423.207 | 424.5 |
| A25 | 155-160 | 2.26 | 405.216 | 406.4 | I3 | 165 | 6.5 | 423.207 | 424.4 |
| A26 | 160-165 | 2.72 | 405.216 | 406.3 | I4 | 186 | 2.64 | 409.191 | 410.2 |
| A27 | 160-165 | 2.47 | 391.201 | 392.2 | I5 | 145 | 2.77 | 423.207 | 424.2 |
| A28 | 140-145 | 2.63 | 393.216 | 394.2 | I6 | 153 | 2.73 | 411.207 | 412 |
| A29 | 170-175 | 2.29 | 419.232 | 420.6 | I7 | 235-240 | 5.83 | 425.186 | 426.3 |
| A30 | 165-170 | 2.32 | 419.232 | 420.3 | I9 | 205-210 | 6.07 | 481.212 | 481.9 |
| A31 | 185-190 | 7.41 | 465.197 | 466.1 | I10 | 160-165 | 5.76 | 479.233 | 480 |
| A32 | 122 | 7.66 | 438.207 | 439.4 | I11 | 185-190 | 7.07 | 457.191 | 458.4 |
| B1 | 140 | 2.73 | 522.275 | 523.5 | I12 | 235-240 | 7.08 | 457.191 | 458.2 |
| B2 | 180-185 | 2.5 | 510.275 | 511.2 | I13 | 140-145 | 5.29 | 437.186 | 438.4 |
| B3 | 195-200 | 3.03 | 536.291 | 537.3 | I14 | 180-185 | 6.73 | 459.188 | 460.5 |
| B4 | 123 | 2.43 | 518.3 | 519.7 | I16 | 218 | 5.21 | 425.186 | 426 |
| B5 | 205 | 2.47 | 504.285 | 505.4 | I17 | 195 | 6.48 | 437.223 | 438.5 |
| B6 | 260-265 | 2.88 | 514.249 | 515.3 | I19 | 205 | 6.47 | 423.207 | 424.5 |
| B7 | 175-180 | 2.27 | 490.269 | 491.3 | I20 | 275-280 | 7.85 | 463.238 | 464.5 |
| B8 | 240-245 | 2.38 | 460.259 | 461.5 | I21 | 165-170 | 7.45 | 435.207 | 436.6 |
| B9 | 165-170 | 2.51 | 474.274 | 475.5 | I22 | 155-160 | 5.83 | 437.186 | 438.3 |
| B10 | 228-230 | 2.13 | 546.319 | 546.2 | I23 | 245-249 | 7.46 | 443.176 | 444.7 |

TABLE-continued melting point and LC/MS date (retention time, theoretical molecular weight (MW theor) and (MH)+ peak)

| Co. No. | mp° C. | Rt min | MW theor | MH+ | Co. No. | mp° C. | Rt min | MW theor | MH+ |
|---|---|---|---|---|---|---|---|---|---|
| B11 | 168-171 | 2.37 | 560.335 | 560.5 | I24 | 242-243 | 7.82 | 485.223 | 486.5 |
| B12 | 181-182 | 2.53 | 588.366 | 588.5 | I27 | 160-165 | 6.43 | 441.198 | 442.4 |
| B13 | 210-215 | 2.84 | 538.253 | 539.5 | I28 | 174-175 | 6.7 | 406.49 | 407.5 |
| B14 | 220-222 | 3.22 | 494.63 | 495.3 | I29 | 179-181 | 5.06 | 424.202 | 425.3 |
| B16 | 160-165 | 3.02 | 546.65 | 547.4 | I30 | 215-216 | 5.33 | 438.218 | 439.3 |
| B17 | 225-230 | 3.04 | 502.59 | 503.3 | I31 | 238-240 | 6.91 | 463.163 | 464.1 |
| B18 | 222-223 | 2.83 | 484.6 | 485.3 | I32 | 274-276 | 2 | 446.243 | 447.3 |
| C1 | 160-165 | 2.84 | 523.259 | 524.8 | I33 | 165-170 | 6.02 | 481.212 | 482.2 |
| C3 | 165-170 | 3.26 | 497.244 | 498.5 | I34 | 205-210 | 6.56 | 459.188 | 460.5 |
| C3 | oil | 2.49 | 522.275 | 523.6 | J1 | 173 | 6.63 | 441.198 | 442.4 |
| C4 | 175-180 | 2.91 | 483.228 | 484.1 | J2 | 195-200 | 2.88 | 423.207 | 424.1 |
| C5 | 165-170 | 2.49 | 536.291 | 537.2 | K1 | 165-170 | 8.21 | 458.175 | 459.5 |
| C6 | 176-178 | 2.85 | 465.55 | 466.3 | K2 | 210 | 2.9 | 424.191 | 425.3 |
| C7 | 195-200 | 2.69 | 449.243 | 450.4 | K3 | 150-155 | 8.17 | 458.175 | 459.5 |
| D1 | 135-140 | 2.52 | 473.19 | 474.6 | K4 | 133-134 | 8.16 | 438.207 | 439.5 |
| D'1 | 120-130 | 2.68 | 551.167 | 552.7 | K5 | 148 | 7.24 | 424.191 | 425.5 |
| D2 | oil | 2.69 | 499.205 | 500.7 | K6 | 235-240 | 8.44 | 486.207 | 487.5 |
| D3 | 195-200 | 7.62 | 487.205 | 488.2 | K8 | 105-110 | 8.08 | 472.191 | 473.6 |
| D4 | 210-212 | 7.25 | 491.18 | 492.2 | L1 | 196 | 3.13 | 463.238 | 464.3 |
| E1 | 210-215 | 3.3 | 503.244 | 504.1 | L2 | 178 | 2.27 | 494.281 | 495.6 |
| E2 | 195-200 | 2.47 | 514.249 | 515.2 | L3 | 188 | 3.32 | 465.254 | 466.3 |
| E3 | 155-160 | 2.41 | 503.244 | 504.1 | L4 | 174 | 2.22 | 508.26 | 509.4 |
| E4 | 175-180 | 3.41 | 465.254 | 466.3 | L5 | 177 | 2.7 | 467.233 | 468.3 |
| E5 | 170-175 | 3.31 | 463.238 | 464.2 | L6 | 180 | 6.04 | 439.202 | 440.3 |
| E6 | 245-250 | 3.07 | 462.218 | 463.1 | L7 | 168 | 3.32 | 503.233 | 504.2 |
| E7 | 175-180 | 3.12 | 481.249 | 482.3 | L8 | 156 | 3.49 | 519.21 | 520.5 |
| E8 | 225-230 | 2.97 | 477.58 | 478.5 | L9 | 140 | 6.27 | 492.265 | 493.3 |
| E9 | 255-260 | 2.33 | 544.316 | 545.5 | L10 | 194 | 3 | 501.185 | 502.4 |
| E10 | 225-230 | 7.85 | 463.238 | 464.2 | L11 | 165-170 | 7.5 | 529.212 | 530.3 |
| E11 | 145 | 2.91 | 463.238 | 464.2 | M1 | 205-210 | 8.25 | 450.207 | 451.5 |
| E12 | — | 2.74 | 463.238 | 464.5 | M3 | 198-200 | 6.55 | 451.202 | 452.2 |
| E13 | 245-250 | 3.23 | 497.199 | 498.4 | M4 | 173-175 | 6.85 | 465.218 | 466.3 |
| E14 | 265-270 | 2.52 | 445.248 | 446.4 | M6 | 152-153 | 8.42 | 500.161 | 503.3 |
| E15 | 260-265 | 2.62 | 431.232 | 432.4 | M7 | — | 7.95 | 450.2 | 451 |
| E16 | 223 | 2.64 | 459.263 | 460.5 | M8 | 268-269 | 6.8 | 485.186 | 486.4 |
| E17 | 282-284 | 2.17 | 487.282 | 487.6 | M10 | 243-245 | 7.07 | 499.202 | 500.6 |
| E18 | 299-300 | 2.58 | 500.29 | 501.7 | M11 | 225-230 | 8.06 | 484.191 | 485.2 |
| E19 | 261-262 | 2.77 | 528.321 | 529.6 | M12 | 197-199 | 6.41 | 482.183 | 483.2 |
| E20 | 268-270 | 3.24 | 447.263 | 448.2 | M13 | oil | 7.47 | 464.54 | 465.2 |
| E21 | 243-244 | 3.21 | 445.56 | 446.2 | N1 | 140-145 | 7.08 | 449.223 | 450.5 |
| E22 | 196-198 | 3.12 | 485.254 | 486.3 | O1 | — | 8.048 | 464.222 | 465.3 |
| E23 | 232-234 | 2.29 | 496.61 | 497.5 | P1 | 120 | 3.22 | 487.205 | 488.2 |
| E24 | 225-230 | 2.86 | 495.228 | 496.5 | P2 | 229 | 2.29 | 459.174 | 460.4 |
| E25 | 155-160 | 2.65 | 494.244 | 495.4 | P3 | 116 | 2.94 | 473.19 | 474.2 |
| E26 | 190-195 | 3.01 | 477.218 | 478.1 | Q1 | 125-130 | 7.89 | 452.222 | 453.3 |
| E27 | 215-220 | 2.75 | 508.26 | 509.2 | R1 | 95-100 | 7.04 | 451.238 | 452.4 |
| E28 | 180-185 | 2.92 | 522.275 | 523.4 | S1 | 162-163 | 2.43 | 369.162 | 370.4 |
| E29 | 204-205 | 6.04 | 490.269 | 491.3 | T1 | 210-215 | 2.37 | 464.234 | 465.5 |
| E30 | 277-279 | 2.4 | 452.199 | 453.3 | U1 | 185-190 | 2.19 | 523.271 | 524.8 |
| F1 | 150-151 | 2.14 | 425.222 | 426.3 | V1 | 215-220 | 5.66 | 424.202 | 425.1 |
| F2 | oil | 2.37 | 439.237 | 440.3 | | | | | |
| F19 | 160° C. | 2.22 | 519.2 | 520.3 | M19 | 150° C. | 2.46 | 476.2 | 477.3 |
| F20 | 150° C. | 2.4 | 519.2 | 520.3 | O2 | — | 2.38 | 464.2 | 465.4 |
| F21 | 172° C. | 2.24 | 513.2 | 514.3 | W1 | 240.93° C. | 2.3 | 450.2 | 451.1 |
| F22 | — | 2.4 | 535.2 | 536.2 | W2 | 240.87° C. | 2.32 | 484.2 | 485.2 |
| F23 | 170° C. | 2.19 | 535.2 | 536.4 | X1 | 178.37° C. | 2.23 | 479.2 | 480.3 |
| F24 | 114.73° C. | 2.28 | 501.2 | 502.2 | Y1 | 215.31° C. | 2.66 | 463.2 | 464.3 |
| F25 | 183.69° C. | 2.26 | 501.2 | 502.3 | Z1 | 238.19° C. | 2.37 | 474.2 | 475.1 |
| M14 | 165° C. | 1.93 | 485.2 | 486.4 | Z2 | 168.55° C. | 2.3 | 478.2 | 479.3 |
| M15 | 135.05° C. | 2.4 | 484.2 | 485.1 | Z3 | 131.54° C. | 3.33 | 431.2 | 432.2 |
| M16 | 187° C. | 2.4 | 525.2 | 526.3 | Z4 | 202.06° C. | 3.11 | 465.2 | 466.5 |
| M17 | 145° C. | 2.3 | 498.2 | 499.4 | Z5 | — | 2.62 | 504.3 | 505.3 |
| M18 | — | 2.44 | 498.2 | 499.2 | | | | | |
| F31 | 257.89 | 2.45 | 527.23 | 528.3 | M24 | 213.66 | 2.09 | 466.2 | 467.1 |
| F32 | — | 2.47 | 527.2 | 528.3 | M27 | 202.04 | 2.4 | 496.2 | 497.2 |
| F33 | — | 2.19 | 475.2 | 476.2 | M28 | — | 2.29 | 462.2 | 463.2 |
| F34 | 198.45 | 2.48 | 508.2 | 509.2 | O3 | — | 2.62 | 490.2 | 491.2 |
| F35 | 268.78 | 2.18 | 502.2 | 503.1 | W2 | — | 2.26 | 490.2 | 491.2 |
| F36 | 274.48 | 2.4 | 474.2 | 475.3 | W3 | 207.63 | 2.23 | 490.2 | 491.3 |
| F37 | — | 2.83 | 506.3 | 507.3 | W4 | — | 2.52 | 507.3 | 508.4 |
| F38 | — | 2.28 | 490.2 | 491.2 | W5 | — | 2.52 | 507.3 | 508.3 |
| F39 | 230.94 | 2.44 | 504.2 | 505.2 | W6 | 214.84 | 2.41 | 493.2 | 494.2 |
| F40 | 213.87 | 2.26 | 464.2 | 465.1 | W7 | 205.80 | 2.41 | 493.2 | 494.2 |
| M19 | | 2.46 | 476.2 | 477.3 | W8 | 232.32 | 2.25 | 502.2 | 503.2 |
| M20 | 228.12 | 2.19 | 476.2 | 477.6 | W9 | 142.16 | 2.41 | 516.2 | 517.2 |

TABLE-continued melting point and LC/MS date (retention time, theoretical molecular weight (MW theor) and (MH)⁺ peak)

| Co. No. | mp° C. | Rt min | MW theor | MH⁺ | Co. No. | mp° C. | Rt min | MW theor | MH⁺ |
|---|---|---|---|---|---|---|---|---|---|
| M21 | 128.89 | 2.29 | 462.2 | 463.2 | W10 | 239.85 | 2.39 | 516.2 | 517.2 |
| M22 | 214.14 | 2.45 | 476.2 | 477.2 | W11 | 277.45 | 2.48 | 505.2 | 506.3 |
| M23 | 231.54 | 2.49 | 476.2 | 477.1 | W12 | 252.19 | 2.63 | 531.3 | 532.3 |
| F41 | 197.2 | 2.5 | 529.249 | 530.3 | O10 | 333.75 | 2.49 | 490.238 | 491.3 |
| F42 | 189.39 | 2.25 | 480.217 | 481.1 | O11 | 249.19 | 2.52 | 490.238 | 491.2 |
| F43 | 177.53 | 2.32 | 507.174 | 508.1 | O12 | 204.71 | 2.19 | 465.218 | 466.2 |
| F44 | — | 2.21 | 464.186 | 465.2 | O13 | — | 2.46 | 466.238 | 467.2 |
| F45 | — | 2.2 | 475.202 | 476.1 | O14 | — | 2.46 | 466.238 | 467.2 |
| F46 | 282.17 | 2.31 | 478.202 | 479.2 | O15 | — | 2.53 | 498.207 | 499.3 |
| F47 | — | 2.97 | 518.269 | 519.3 | O16 | 333.46 | 2.58 | 464.222 | 465.2 |
| F48 | 204.93 | 2.28 | 480.217 | 481.3 | O17 | 219.7 | 2.3 | 506.233 | 507.2 |
| F49 | 218.14 | 2.31 | 518.196 | 519.2 | O18 | — | 2.39 | 500.203 | 501.2 |
| F50 | — | 2.45 | 539.233 | 540.3 | O19 | — | 2.34 | 487.202 | 488.2 |
| F51 | 261.88 | 2.42 | 504.217 | 505.2 | O20 | 252.97 | 2.48 | 516.163 | 517.2 |
| F52 | — | 2.8 | 504.254 | 505.3 | O21 | 207.61 | 2.65 | 530.179 | 531.3 |
| F53 | 175.52 | 2.33 | 518.196 | 519.3 | O22 | 228.98 | 2.5 | 504.163 | 505.2 |
| F54 | 256.44 | 2.49 | 512.186 | 513.3 | O23 | 239.3 | 2.43 | 526.219 | 527.4 |
| F55 | — | 2.42 | 541.158 | 542.3 | O24 | — | 2.68 | 492.254 | 493.5 |
| F56 | — | 2.51 | 558.158 | 559.3 | O5 | 222.18 | 2.52 | 510.207 | 511.3 |
| F57 | — | 2.42 | 513.218 | 514.4 | O6 | — | 2.38 | 476.222 | 477.2 |
| F58 | — | 2.55 | 555.174 | 556.4 | O7 | 245.75 | 2.35 | 476.222 | 477.2 |
| F59 | — | 2.28 | 538.213 | 539.3 | O8 | — | 2.58 | 524.222 | 525.3 |
| F60 | 270.54 | 2.41 | 541.158 | 542.2 | O9 | — | 2.54 | 490.238 | 491.3 |
| F61 | — | 2.26 | 501.181 | 502.1 | W13 | 215.1 | 2.43 | 518.244 | 519.3 |
| F62 | — | 2.24 | 520.212 | 521.2 | W14 | 199.65 | 2.69 | 521.28 | 522.3 |
| F63 | 255.4 | 2.43 | 541.158 | 542.2 | W15 | 189.89 | 2.56 | 519.265 | 520.3 |
| F64 | 195.6 | 2.3 | 480.217 | 481.2 | W16 | — | 2.38 | 479.233 | 480.2 |
| F65 | 186.2 | 2.29 | 480.217 | 481.2 | W17 | 172.28 | 2.64 | 507.265 | 508.3 |
| F66 | 256.54 | 2.45 | 518.142 | 519.3 | W18 | 276.58 | 2.35 | 523.26 | 524.3 |
| F67 | | 2.47 | 544.158 | 545.2 | W19 | — | 2.3 | 467.233 | 468.2 |
| F68 | 203.36 | 2.5 | 567.174 | 568.3 | W20 | 132 | 2.43 | 530.244 | 531.3 |
| F69 | 176.26 | 2.84 | 504.254 | 505.3 | W21 | — | 3.22 | 533.255 | 534.3 |
| I35 | 242 | 6.32 | 446.187 | 446.9 | W22 | — | 2.62 | 507.265 | 508.3 |
| I36 | 165-170 | 6.92 | 460.202 | 461.3 | W23 | 182.69 | 2.58 | 507.265 | 508.3 |
| I37 | 250-255 | 5.51 | 447.182 | 448.5 | W24 | — | 1.59 | 478.177 | 479.1 |
| I38 | 205-210 | 7.21 | 496.202 | 497.7 | W25 | — | 2.46 | 504.228 | 505.3 |
| K9 | 155-160 | 7.46 | 447.171 | 448.4 | W26 | 238.58 | 2.48 | 550.213 | 551.3 |
| M29 | 176 | 2.52 | 478.238 | 479.2 | W27 | 144.43 | 2.36 | 524.197 | 525.2 |
| M30 | 163 | 2.17 | 502.213 | 503.2 | W28 | 218.99 | 2.33 | 527.233 | 528.5 |
| M31 | — | 2.2 | 450.207 | 451.2 | W29 | — | 2.18 | 490.213 | 491.2 |
| M32 | — | 2.3 | 480.217 | 481.2 | W30 | — | 2.63 | 519.265 | 520.3 |
| M33 | — | 2.22 | 492.217 | 493.2 | W31 | — | 2.41 | 519.265 | 520.6 |
| M34 | 238.95 | 2.37 | 480.217 | 481.2 | W32 | 268.79 | 2.18 | 491.208 | 492.2 |
| M35 | 206.72 | 2.45 | 488.222 | 489.3 | W33 | 257.75 | 2.41 | 536.197 | 537.2 |
| M36 | 199.02 | 2.53 | 510.207 | 511.3 | W34 | 162.08 | 2.71 | 553.249 | 554.4 |
| M37 | 200.99 | 2.33 | 477.218 | 478.2 | W35 | 145.75 | 2.42 | 524.174 | 525.2 |
| M38 | 195.53 | 2.29 | 438.207 | 439.2 | W36 | 223.2 | 2.23 | 532.223 | 533.2 |
| M39 | 230.29 | 2.47 | 488.222 | 489.2 | W37 | 231.1 | 2.52 | 545.19 | 546.2 |
| M40 | 104.88 | 2.18 | 451.202 | 452.1 | W38 | 214 | 2.54 | 539.233 | 540.3 |
| M41 | 225-230 | 6.67 | 474.182 | 475.4 | W39 | 265.13 | 2.43 | 556.169 | 557.2 |
| M42 | 240-245 | 8.05 | 487.202 | 488.3 | W40 | 168.11 | 2.33 | 530.154 | 531.1 |
| M43 | 255-260 | 4.42 | 473.186 | 474.1 | W41 | 257.83 | 2.38 | 542.154 | 543.2 |
| M44 | 127.94 | 2.24 | 473.186 | 474.1 | W43 | 252.56 | 2.31 | 533.19 | 534.5 |
| M45 | 227.94 | 2.26 | 473.186 | 474.1 | W44 | — | 2.69 | 559.205 | 560.3 |
| M46 | 265.43 | 2.42 | 502.147 | 503.1 | W46 | 223.0 | 2.58 | 555.246 | 556.3 |
| M47 | 225.94 | 2.52 | 516.163 | 517.2 | W47 | — | 2.73 | 541.249 | 542.3 |
| M48 | 255.50 | 2.37 | 490.147 | 491.1 | W48 | 227.9 | 2.69 | 547.205 | 548.3 |
| M49 | 262.19 | 2.38 | 490.147 | 491.2 | W49 | 179.2 | 2.64 | 507.265 | 508.3 |
| M50 | 184.15 | 2.61 | 490.238 | 491.2 | W50 | 110.2 | 2.65 | 507.265 | 508.3 |
| M51 | 227.14 | 2.71 | 488.222 | 489.2 | W51 | 203.3 | 2.45 | 506.2 | 505.2 |

Optical Rotation

The optical rotation was measured using a polarimeter with light at the wavelength of the D-line of sodium (589 nm) at a temperature of 20° C. in DMF as solvent.

| Co. No. | $[\alpha]_D^{20}$ | c (w/v %) |
|---|---|---|
| A26 | −17.19 | 0.3664 |
| A27 | −9.53 | 0.3673 |
| E10 | −14.88 | 0.3764 |
| F15 | −12.89 | 0.38 |
| H4 | −20.05 | 0.3891 |
| I1 | −16.5 | 0.3818 |
| I4 | −3.36 | 0.3873 |
| I19 | −6.1 | 0.3773 |
| K5 | −18.75 | 0.32 |
| M3 | −5.89 | 0.3736 |
| M4 | −22.59 | 0.3718 |

| Co. No. | $[\alpha]_D^{20}$ | c (w/v %) |
| --- | --- | --- |
| M7 | −18.31 | 0.344 |
| M12 | −12.51 | 0.3436 |
| S1 | −12.77 | 0.3836 |

| Co. No. | $[\alpha]_D^{20}$ | c (w/v %) |
| --- | --- | --- |
| F19 | −12.63 | 0.246 |
| F20 | −14.4 | 0.250 |
| F21 | −15.03 | 0.273 |
| F23 | −22.46 | 0.285 |
| F24 | −6.72 | 0.238 |
| F25 | −12.26 | 0.310 |
| M14 | −25.85 | 0.182 |
| M15 | −27.04 | 0.233 |
| M16 | −30.54 | 0.203 |
| M19 | −22.73 | 0.220 |
| O2 | +150.87 | 0.269 |
| W1 | −14 | 0.250 |
| W2 | −20 | 0.280 |
| X1 | −15.83 | 0.278 |
| Y1 | −17.45 | 0.2636 |
| Z1 | −4.56 | 0.241 |
| Z2 | −12.63 | 0.246 |
| Z3 | −7.51 | 0.226 |
| Z5 | −17.19 | 0.320 |

| Co. No. | $[\alpha]_D^{20}$ | c (w/v %) |
| --- | --- | --- |
| F31 | −12.96° | 0.27 |
| F32 | −13.58° | 0.265 |
| F33 | −27.62° | 0.21 |
| F34 | −11.2° | 0.25 |
| F36 | −7.97° | 0.251 |
| F37 | −22.96° | 0.27 |
| F39 | −13.33° | 0.3 |
| F40 | −17.54° | 0.217 |
| M19 | −29.1° | 0.244 |
| M20 | −11.42° | 0.289 |
| M21 | −21.2° | 0.25 |
| M22 | −9.86° | 0.233 |
| M23 | −10.91° | 0.183 |
| M24 | −22.86° | 0.175 |
| M27 | −25.83° | 0.24 |
| O3 | −64.22° | 0.237 |
| W2 | −12.64° | 0.261 |
| W3 | −7.49° | 0.427 |
| W4 | −102.73° | 0.22 |
| W5 | +47.22° | 0.324 |
| W6 | −27.59° | 0.261 |
| W7 | +28.62° | 0.29 |
| W8 | −20.17° | 0.238 |
| W9 | −20.37° | 0.27 |
| W10 | −78.26° | 0.23 |
| W11 | −20.87° | 0.115 |
| W12 | −15.38° | 0.26 |

| Co. No. | $[\alpha]_D^{20}$ | c (w/v %) |
| --- | --- | --- |
| F41 | −24.17° | 0.24 |
| F43 | −11.79° | 0.28 |
| F44 | −12.13° | 0.231 |
| F45 | −10° | 0.3 |
| F46 | −6.4° | 0.25 |
| F47 | −17.67° | 0.3 |
| F48 | −23.56° | 0.225 |
| F49 | +28.57° | 0.28 |
| F51 | −8.96° | 0.201 |
| F53 | −5.4° | 0.278 |
| F54 | −19.69° | 0.325 |
| F62 | −8.75° | 0.32 |
| F63 | −29.31° | 0.29 |
| F64 | −10.88° | 0.239 |
| F65 | −30.84° | 0.227 |
| F66 | −27.22° | 0.36 |
| M29 | −13.48° | 0.23 |
| M30 | −11.9° | 0.21 |
| M31 | −19.94° | 0.261 |
| M32 | −17.07° | 0.217 |
| M33 | −6.09° | 0.23 |
| M34 | −10.14° | 0.178 |
| M36 | −24° | 0.208 |
| M44 | −36.73° | 0.226 |
| M46 | −32.85° | 0.274 |
| M49 | −31.86° | 0.242 |
| O10 | +169.34° | 0.168 |
| O11 | +170.26° | 0.237 |
| O15 | +157.19° | 0.278 |
| O16 | −22.5° | 0.28 |
| O17 | +166.15° | 0.26 |
| O19 | +134.78° | 0.276 |
| O20 | +94.33° | 0.3 |
| O21 | +145.17° | 0.29 |
| O22 | +147.24° | 0.29 |
| O5 | +156.37° | 0.259 |
| O6 | −70° | 0.25 |
| O7 | +180.44° | 0.238 |
| O8 | +167.6° | 0.233 |
| W13 | −12.75° | 0.212 |
| W14 | +37.5° | 0.24 |
| W15 | +33.8° | 0.213 |
| W25 | −14.62° | 0.26 |
| W26 | −25.65° | 0.242 |
| W27 | −25° | 0.32 |
| W28 | −65.2° | 0.25 |
| W30 | +33.67° | 0.199 |
| W31 | −62.46° | 0.285 |
| W33 | −27.59° | 0.29 |
| W34 | +26.79° | 0.28 |
| W35 | −16.21° | 0.29 |
| W36 | −12.26° | 0.31 |
| W37 | +16.04° | 0.293 |
| W38 | +15° | 0.3 |
| W41 | −33.87° | 0.31 |
| W43 | −76.15° | 0.26 |
| W44 | +16.21° | 0.29 |
| W46 | +27.56° | 0.254 |
| W48 | −28.57° | 0.259 |
| W49 | −65.6° | 0.25 |
| W50 | +31.29° | 0.278 |
| W51 | +30.67° | 0.225 |

E. Pharmacological Examples

E.1 Antiviral Activity

Black 384-well clear-bottom microtiter plates (Corning, Amsterdam, The Netherlands) were filled via acoustic drop ejection using the echo liquid handler (Labcyte, Sunnyvale, Calif.). 200 nL of compound stock solutions (100% DMSO) were transferred to the assay plates. 9 serial 4-fold dilutions of compound were made, creating per quadrant the same compound concentration. The assay was initiated by adding 10 µL of culture medium to each well (RPMI medium without phenol red, 10% FBS-heat inactivated, 0.04% gentamycin (50 mg/mL). All addition steps are done by using a multidrop dispenser (Thermo Scientific, Erembodegem, Belgium). Next, rgRSV224 virus (MOI=1) diluted in culture medium was added to the plates. rgRSV224 virus is an engineered virus that includes an additional GFP gene (Hallak L K, Spillmann D, Collins P L, Peeples M E. Glycosaminoglycan sulfation requirements for respiratory syncytial virus infection; Journal of virology (2000), 74(22), 10508-13) and was in-licensed from the NIH (Bethesda, Md., USA). Finally, 20 µL of a HeLa cell suspension (3,000 cells/well) were plated. Medium, virus- and mock-infected controls were included in each test. The wells contain 0.05% DMSO per volume. Cells were incubated at 37° C. in a 5% $CO_2$ atmosphere. Three days post-virus exposure, viral replication was quantified by measuring GFP expression in the cells by an in house developed MSM laser microscope (Tibotec, Beerse, Belgium). The EC50 was defined as the 50% inhibitory concentration for GFP expression. In parallel, compounds were incubated for three days in a set of white 384-well microtiter plates (Corning) and the cytotoxicity of compounds in HeLa cells was determined by measuring the ATP content of the cells using the ATPlite kit (Perkin Elmer, Zaventem, Belgium) according to the manufacturer's instructions. The CC50 was defined as the 50% concentration for cytotoxicity.

TABLE antiviral data

| Co. No. | RSV HELA pEC50 | TOX HELA pCC50 |
|---|---|---|
| A1 | 5.30 | <4.30 |
| A2 | 5.52 | <4.60 |
| A3 | 5.45 | 4.40 |
| A4 | 5.99 | 4.34 |
| A5 | 5.32 | 4.48 |
| A6 | 6.14 | 4.24 |
| A7 | 6.23 | <4.60 |
| A8 | 6.19 | <4.60 |
| A9 | 6.27 | <4.60 |
| A10 | 5.68 | <4.60 |
| A11 | 6.19 | <4.60 |
| A12 | 6.06 | <4.60 |
| A13 | 6.48 | <4.60 |
| A14 | 6.40 | <4.60 |
| A15 | 6.47 | <4.60 |
| A16 | 5.57 | 4.45 |
| A17 | 5.82 | 4.39 |
| A18 | 6.45 | <4.00 |
| A19 | 5.34 | 4.42 |
| A20 | 5.20 | <4.60 |
| A21 | 6.05 | <4.00 |
| A22 | 6.22 | <4.60 |
| A24 | 6.52 | <4.60 |
| A25 | 6.26 | <4.00 |
| A26 | 6.71 | <4.60 |
| A27 | 6.06 | <4.60 |
| A28 | 6.10 | <4.60 |
| A29 | 6.81 | <4.60 |
| A30 | 6.08 | <4.00 |
| A31 | 6.20 | <4.60 |
| A32 | 5.97 | <4.60 |
| B1 | 6.89 | <4.00 |
| B2 | 6.39 | <4.00 |
| B3 | 7.10 | <4.60 |
| B4 | 6.59 | 4.26 |
| B5 | 6.78 | <4.00 |
| B6 | 6.13 | <4.00 |
| B7 | 6.20 | <4.00 |
| B8 | 6.62 | 4.77 |
| B9 | 6.30 | <4.00 |
| B10 | 6.50 | <4.00 |
| B11 | 6.55 | <4.00 |
| B12 | 6.72 | <4.00 |
| B13 | 6.40 | <4.60 |
| B14 | 6.36 | <4.60 |
| B16 | 6.23 | <4.60 |
| B17 | 6.39 | <4.60 |
| B18 | 5.94 | <4.60 |
| C1 | 6.46 | <4.00 |
| C3 | 6.78 | <4.60 |
| C3 | 6.55 | 4.89 |
| C4 | 6.96 | <4.60 |
| C5 | 6.75 | 4.86 |
| C6 | 6.27 | <4.60 |
| C7 | 5.86 | <4.00 |
| D1 | 6.54 | 4.29 |
| D'1 | 6.68 | <4.00 |
| D2 | 6.22 | <4.30 |
| D3 | 6.84 | <4.60 |
| D4 | 6.31 | <4.60 |
| E1 | 6.21 | <4.60 |
| E2 | 7.03 | <4.60 |
| E3 | 6.88 | 5.19 |
| E4 | 6.74 | <4.60 |
| E5 | 6.86 | <4.60 |
| E6 | 6.78 | <4.60 |
| E7 | 6.93 | <4.60 |
| E8 | 6.33 | <4.60 |
| E9 | 6.77 | <4.60 |
| E10 | 7.04 | <4.60 |
| E11 | 6.20 | <4.60 |
| E12 | 6.35 | 4.22 |
| E13 | 5.83 | <4.60 |
| E14 | 6.51 | <4.30 |
| E15 | 6.08 | <4.017 |
| E16 | 5.88 | <5.00 |
| E17 | 6.29 | <4.30 |
| E18 | 5.90 | <4.60 |
| E19 | 6.27 | <4.00 |
| E20 | 6.16 | <4.60 |
| E21 | 6.22 | <4.60 |
| E22 | 5.77 | 4.66 |
| E23 | 6.19 | <4.60 |
| E24 | 6.55 | <4.60 |
| E25 | 7.21 | <4.60 |
| E26 | 6.39 | <4.60 |
| E27 | 6.93 | <4.60 |
| E28 | 6.93 | <4.60 |
| E29 | 6.34 | <4.60 |
| E30 | 5.74 | <4.60 |
| F1 | 6.06 | 4.42 |
| F2 | 5.53 | 4.41 |
| F3 | 6.08 | <4.00 |
| F4 | 6.14 | <4.60 |
| F5 | 6.51 | <4.60 |
| F6 | 6.45 | <4.60 |
| F7 | 5.68 | <4.60 |
| F8 | 5.63 | <4.60 |
| F9 | 6.18 | <4.60 |
| F10 | 6.16 | <4.60 |
| F11 | 5.87 | <4.60 |
| F12 | 5.86 | <4.60 |
| F13 | 6.25 | <4.60 |
| F14 | 6.74 | <4.60 |
| F15 | 6.92 | <4.60 |
| F16 | 6.84 | <4.60 |
| F17 | 6.19 | <4.60 |
| F18 | 6.70 | <4.60 |
| G1 | 6.55 | <4.60 |
| H1 | 6.25 | <4.60 |
| H2 | 6.04 | <4.60 |
| H4 | 6.18 | <4.60 |
| H5 | 6.09 | <4.60 |
| I1 | 7.27 | <4.60 |
| I2 | 7.25 | <4.30 |
| I3 | 5.65 | <4.60 |
| I4 | 6.51 | <4.60 |
| I5 | 5.23 | <4.60 |
| I6 | 6.38 | <4.60 |
| I7 | 5.99 | <4.60 |
| I9 | 5.87 | <5.00 |
| I10 | 6.64 | <4.60 |
| I11 | 6.55 | <4.60 |
| I12 | 7.52 | <4.60 |
| I13 | 6.12 | <4.60 |
| I14 | 6.47 | <4.60 |
| I16 | 5.61 | <4.60 |
| I17 | 5.58 | <4.60 |
| I19 | 6.60 | <4.60 |
| I20 | 5.10 | <4.60 |
| I21 | 6.09 | <4.60 |
| I22 | 6.16 | <4.60 |
| I23 | 5.26 | <4.60 |
| I24 | 6.10 | 4.76 |
| I27 | 6.60 | <4.60 |
| I28 | 5.75 | <4.60 |
| I29 | 6.53 | <4.60 |
| I30 | 6.62 | <4.60 |
| I31 | 6.85 | <4.60 |
| I32 | 6.35 | <4.60 |
| I33 | 7.06 | <4.60 |
| I34 | 6.64 | <4.60 |

TABLE-continued antiviral data

| Co. No. | pEC50 | pCC50 |
|---|---|---|
| J1 | 6.83 | <4.60 |
| J2 | 6.58 | <4.60 |
| K1 | 6.80 | <4.60 |
| K2 | 6.25 | <4.60 |
| K3 | 5.96 | <4.60 |
| K4 | 6.56 | <4.60 |
| K5 | 6.51 | <4.60 |
| K6 | 5.62 | <4.60 |
| K8 | 6.36 | <4.60 |
| L1 | 6.89 | <4.60 |
| L2 | 6.26 | <4.60 |
| L3 | 6.62 | <4.60 |
| L4 | 6.63 | <4.60 |
| L5 | 6.80 | <4.60 |
| L6 | 6.83 | 4.69 |
| L7 | 6.62 | <4.60 |
| L8 | 6.49 | <4.60 |
| L9 | 6.43 | <4.60 |
| L10 | 5.57 | <4.60 |
| L11 | 6.20 | <4.60 |
| M1 | 6.76 | <4.60 |
| M3 | 6.60 | <4.60 |
| M4 | 6.80 | <4.60 |
| M6 | 6.84 | <4.60 |
| M7 | 7.00 | <4.60 |
| M8 | 7.31 | <4.60 |
| M10 | 7.32 | 4.70 |
| M11 | 7.42 | <4.60 |
| M12 | 5.39 | <4.60 |
| M13 | 6.65 | <4.60 |
| N1 | 6.89 | <4.60 |
| O1 | 6.91 | <4.60 |
| P1 | 5.55 | <4.60 |
| P2 | 6.19 | <4.60 |
| P3 | 6.16 | <4.60 |
| Q1 | 6.27 | <4.60 |
| R1 | 6.60 | <4.60 |
| S1 | 6.08 | <4.00 |
| T1 | 6.26 | <4.00 |
| U1 | 6.28 | <4.00 |
| V1 | 5.72 | <4.60 |

| Co. No. | RSV HELA pEC50 | TOX HELA pCC50 |
|---|---|---|
| F31 | 7.31 | 4.49 |
| F32 | 7.55 | 4.49 |
| F33 | 7.04 | 4.18 |
| F34 | 7.46 | 4.17 |
| F35 | 6.79 | <4 |
| F36 | 7.33 | <4 |
| F37 | 6.74 | 4.42 |
| F38 | 7.29 | 4.44 |
| F39 | 7.41 | 4.35 |
| F40 | 6.88 | 4.28 |
| M19 | 7.52 | 4.41 |
| M20 | 7.49 | 4.44 |
| M21 | 7.16 | 4.34 |
| M22 | 7.34 | 4.05 |
| M23 | 7.35 | <4 |
| M24 | 6.42 | <4 |
| M27 | 7.93 | — |
| M28 | 7.03 | 4.75 |
| O3 | 7.06 | 4.22 |
| W2 | 7.21 | <4.60 |
| W3 | 6.97 | 4.22 |
| W4 | 6.98 | 4.05 |
| W5 | 7.05 | 4.02 |
| W6 | 7.09 | 4.16 |
| W7 | 7.32 | 4.15 |
| W8 | 7.11 | 4.26 |
| W9 | 7.33 | 4.29 |
| W10 | 7.51 | 4.28 |
| W11 | 6.63 | 4.23 |
| W12 | 6.69 | 4.20 |

| Co. No. | RSV HELA pEC50 | TOX HELA pCC50 |
|---|---|---|
| F19 | 7.01 | 4.44 |
| F20 | 7.07 | 4.30 |
| F21 | 7.28 | 4.37 |
| F22 | 7.45 | 5.16 |
| F23 | 7.39 | <4.60 |
| F24 | 7.16 | 4.90 |
| F25 | 7.36 | 4.87 |
| M14 | 7.62 | 4.80 |
| M15 | 7.82 | <4.69 |
| M16 | 7.88 | 4.78 |
| M17 | 7.20 | 4.76 |
| M18 | 7.11 | <4.60 |
| M19 | 7.72 | 4.49 |
| O2 | 7.23 | <4.60 |
| W1 | 7.19 | <4.60 |
| W2 | 7.91 | 4.31 |
| X1 | 7.03 | <4.60 |
| Y1 | 7.19 | <4.60 |
| Z1 | 7.22 | <4.60 |
| Z2 | 7.26 | <4.60 |
| Z3 | 7.02 | <4.60 |
| Z4 | 7.11 | <4.60 |
| Z5 | 7.19 | 4.36 |

| Co. No. | pEC50 | pCC50 |
|---|---|---|
| F41 | 7.44 | 4.65 |
| F42 | 7.16 | <4 |
| F43 | 7.21 | 4.37 |
| F44 | 6.40 | 4.25 |
| F45 | 7.36 | 4.04 |
| F46 | 7.31 | <4 |
| F47 | 6.61 | 4.33 |
| F48 | 6.36 | <4 |
| F49 | 7.58 | 4.24 |
| F50 | 6.49 | 4.22 |
| F51 | 7.56 | 4.24 |
| F52 | 6.81 | 4.22 |
| F53 | 7.44 | 4.22 |
| F54 | 8.59 | 4.75 |
| F55 | 6.92 | <4 |
| F56 | 6.81 | <4 |
| F57 | 6.69 | 4.52 |
| F58 | 6.77 | 4.58 |
| F59 | 6.72 | <4.60 |
| F60 | 7.34 | <4.60 |
| F61 | 7.34 | <4 |
| F62 | 7.24 | <4.60 |
| F63 | 7.34 | 4.35 |
| F64 | 7.12 | <4 |
| F65 | 6.85 | <4 |
| F66 | 8.15 | 4.81 |
| F67 | 7.40 | 4.17 |
| F68 | 7.36 | 4.29 |
| F69 | 6.71 | <4.6 |
| I35 | 7.36 | <4.60 |
| I36 | 6.58 | <4.60 |
| I37 | 6.24 | <4.60 |
| I38 | 5.75 | <4.60 |
| K9 | 6.28 | <4.60 |
| M29 | 7.41 | 4.17 |
| M30 | 7.39 | 4.55 |
| M31 | 6.13 | <4 |
| M32 | 6.75 | 4.18 |
| M33 | 6.99 | <4 |
| M34 | 7.04 | <4 |
| M35 | 6.70 | 4.37 |
| M36 | 7.99 | 4.26 |
| M37 | 7.10 | <4 |
| M38 | 6.65 | <4 |
| M39 | 6.19 | <4 |
| M40 | 6.37 | <4 |
| M41 | 6.10 | <4.60 |
| M42 | 6.72 | <4.60 |
| M43 | 7.32 | <4.60 |

TABLE-continued antiviral data

| | | |
|---|---|---|
| M44 | 7.74 | <4.60 |
| M45 | 7.54 | <4 |
| M46 | 8.30 | 4.17 |
| M47 | 7.87 | 4.07 |
| M48 | 7.89 | <4.60 |
| M49 | 8.00 | 4.38 |
| M50 | 6.72 | 4.33 |
| M51 | 6.79 | 4.18 |
| O5 | 7.96 | 4.26 |
| O6 | 6.83 | 4.01 |
| O7 | 7.40 | 4.34 |
| O8 | 7.93 | 4.31 |
| O9 | 6.96 | 4.05 |
| O10 | 7.54 | 4.34 |
| O11 | 7.52 | 4.32 |
| O12 | 6.76 | <4 |
| O13 | 6.85 | 4.34 |
| O14 | 6.66 | 4.18 |
| O15 | 7.91 | 4.32 |
| O16 | 6.77 | <4 |
| O17 | 7.29 | 4.11 |
| O18 | 6.72 | 4.27 |
| O19 | 7.51 | 4.04 |
| O20 | 8.09 | 4.28 |
| O21 | 7.96 | 4.26 |
| O22 | 8.16 | 4.32 |
| W13 | 7.45 | 4.38 |
| W14 | 7.53 | 4.29 |
| W15 | 7.29 | 4.24 |
| W16 | 6.57 | <4 |
| W17 | 7.66 | 4.23 |
| W18 | 7.09 | <4 |
| W19 | 6.58 | <4 |
| W20 | 6.45 | 4.20 |
| W21 | 5.99 | 4.66 |
| W22 | 7.34 | 4.06 |
| W23 | 7.12 | 4.10 |
| W25 | 7.03 | 4.18 |
| W26 | 7.63 | <4 |
| W27 | 7.40 | 4.33 |
| W28 | 8.37 | 4.29 |
| W29 | 6.44 | <4 |
| W30 | 7.76 | 4.30 |
| W31 | 7.90 | 4.31 |
| W32 | 6.66 | <4 |
| W33 | 7.79 | 4.24 |
| W34 | 7.95 | 4.36 |
| W35 | 6.72 | <4.6 |
| W36 | 6.82 | <4.60 |
| W37 | 8.25 | 4.34 |
| W38 | 8.24 | 4.33 |
| W39 | 7.55 | 4.26 |
| W40 | 7.66 | 4.44 |
| W41 | 7.88 | <4.6 |
| W43 | 8.56 | 4.31 |
| W44 | 8.06 | 4.31 |
| W49 | 7.36 | 4.27 |
| W50 | 7.35 | 4.13 |
| W51 | 7.41 | 4.16 |

F. Prophetic Composition Examples

"Active ingredient" as used throughout these examples relates to a final compound of Formula (I), the pharmaceutically acceptable salts thereof, the solvates and the stereochemically isomeric forms and the tautomers thereof.

Typical examples of recipes for the formulation of the invention are as follows:

F.1. Tablets

| | |
|---|---|
| Active ingredient | 5 to 50 mg |
| Di calcium phosphate | 20 mg |
| Lactose | 30 mg |
| Talcum | 10 mg |
| Magnesium stearate | 5 mg |
| Potato starch | ad 200 mg |

In this Example, active ingredient can be replaced with the same amount of any of the compounds according to the present invention, in particular by the same amount of any of the exemplified compounds.

F.2. Suspension

An aqueous suspension is prepared for oral administration so that each 1 milliliter contains 1 to 5 mg of one of the active compounds, 50 mg of sodium carboxymethyl cellulose, 1 mg of sodium benzoate, 500 mg of sorbitol and water ad 1 ml.

F.3. Injectable

A parenteral composition is prepared by stirring 1.5% by weight of active ingredient of the invention in 10% by volume propylene glycol in water.

F.4. Ointment

| | |
|---|---|
| Active ingredient | 5 to 1000 mg |
| Stearyl alcohol | 3 g |
| Lanoline | 5 g |
| White petroleum | 15 g |
| Water | ad 100 g |

In this Example, active ingredient can be replaced with the same amount of any of the compounds according to the present invention, in particular by the same amount of any of the exemplified compounds.

Reasonable variations are not to be regarded as a departure from the scope of the invention. It will be obvious that the thus described invention may be varied in many ways by those skilled in the art.

The invention claimed is:

1. A pharmaceutical composition comprising a compound having the chemical structure:

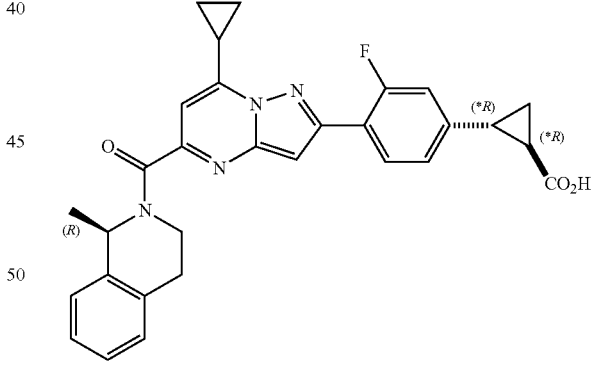

or a pharmaceutically acceptable salt thereof, and a pharmaceutically acceptable carrier.

2. The pharmaceutical composition of claim 1, wherein *R has the S stereochemical configuration.

3. The pharmaceutical composition of claim 1, wherein said compound has the (+) specific rotation measured in DMF as solvent.

4. The pharmaceutical composition of claim 3, wherein the compound has a specific optical rotation of $[\alpha]^D_{20}$= +156.37° at a concentration of 0.259 (w/v %).

5. The pharmaceutical composition of claim 1 being an oral dosage form.

6. The pharmaceutical composition of claim 5, wherein the oral dosage form is liquid.

7. The pharmaceutical composition of claim 5, wherein the oral dosage form is a tablet.

8. A method of treating a respiratory syncytial virus (RSV) infection comprising administering to a subject in need thereof a therapeutically effective amount of a compound having the chemical structure:

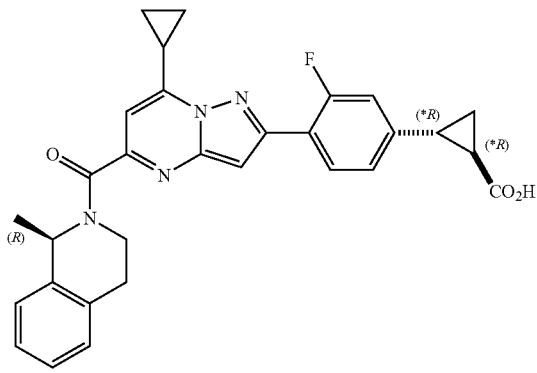

or a pharmaceutically acceptable salt thereof.

9. The method of claim 8, wherein *R has the S stereochemical configuration.

10. The method of claim 8, wherein said compound has the (+) specific rotation measured in DMF as solvent.

11. The method as claimed in claim 10, wherein said compound has a specific optical rotation of $[\alpha]^D_{20}$= +156.37° at a concentration of 0.259 (w/v %).

12. The method of claim 8, wherein the compound is orally administered to the subject in need thereof.

13. The method of claim 8, wherein the compound is in a pharmaceutical composition with a pharmaceutically acceptable carrier.

14. The method of claim 13, wherein the pharmaceutical composition is an oral dosage form.

15. The method of claim 14, wherein the oral dosage form is liquid.

16. The method of claim 14, wherein the oral dosage form is a tablet.

* * * * *